US011390665B2

(12) United States Patent
Smider et al.

(10) Patent No.: US 11,390,665 B2
(45) Date of Patent: *Jul. 19, 2022

(54) ULTRALONG COMPLEMENTARITY DETERMINING REGIONS AND USES THEREOF

(71) Applicant: The Scripps Research Institute, La Jolla, CA (US)

(72) Inventors: Vaughn Smider, San Diego, CA (US); Omar A. Bazirgan, San Diego, CA (US); Hongyuan Helen Mao, San Diego, CA (US); Peter Schultz, La Jolla, CA (US); Feng Wang, Beijing (CN); Yong Zhang, Los Angeles, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/742,759

(22) Filed: Jan. 14, 2020

(65) Prior Publication Data

US 2020/0181241 A1  Jun. 11, 2020

Related U.S. Application Data

(62) Division of application No. 13/737,910, filed on Jan. 9, 2013, now Pat. No. 10,774,132.

(60) Provisional application No. 61/584,680, filed on Jan. 9, 2012, provisional application No. 61/671,629, filed on Jul. 13, 2012.

(51) Int. Cl.
| | |
|---|---|
| C12N 15/62 | (2006.01) |
| C12N 15/09 | (2006.01) |
| C12N 15/10 | (2006.01) |
| C12N 5/00 | (2006.01) |
| C07K 16/46 | (2006.01) |
| C07K 16/10 | (2006.01) |
| C07K 16/00 | (2006.01) |
| C07K 14/53 | (2006.01) |
| C12N 15/63 | (2006.01) |

(52) U.S. Cl.
CPC .............. *C07K 16/10* (2013.01); *C07K 14/53* (2013.01); *C07K 16/00* (2013.01); *C07K 16/46* (2013.01); *C07K 2317/20* (2013.01); *C07K 2317/50* (2013.01); *C07K 2317/55* (2013.01); *C07K 2317/565* (2013.01); *C07K 2317/569* (2013.01); *C07K 2317/73* (2013.01); *C07K 2317/76* (2013.01); *C07K 2317/94* (2013.01); *C07K 2318/00* (2013.01); *C07K 2319/00* (2013.01); *C07K 2319/30* (2013.01); *C07K 2319/50* (2013.01); *C07K 2319/55* (2013.01); *C12N 5/00* (2013.01); *C12N 15/09* (2013.01); *C12N 15/62* (2013.01); *C12N 15/63* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 6,294,654 B1 | 9/2001 | Bogen et al. |
| 6,372,716 B1 | 4/2002 | Bush et al. |
| 6,498,020 B1 | 12/2002 | Walker et al. |
| 6,566,329 B1 | 5/2003 | Meyn et al. |
| 6,685,940 B2 | 2/2004 | Andya et al. |
| 6,740,747 B2 | 5/2004 | Kaushik et al. |

(Continued)

FOREIGN PATENT DOCUMENTS

| | | |
|---|---|---|
| EP | 2194066 A1 | 6/2010 |
| EP | 2322228 A1 | 5/2011 |

(Continued)

OTHER PUBLICATIONS

Vargas et al. Vm24, a natural immunosuppressive peptide, potently and selectively blocks Kv1.3 potassium channels of human T cells. Molecular Pharmacology vol. 82/No. 3:372-382 (Sep. 2012)(published online May 23, 2012). (Year: 2012).*
Bhattacharya et al. Impact of genetic variation on three dimensional structure and function of proteins; PLOS One 12(3): e0171355, pp. 1-22 (Mar. 2017). (Year: 2017).*
Almagro et al. Characterization of a High-Affinity Human Antibody with a Disulfide bridge in the Third Complementarity-Determining Region of the Heavy Chain. Journal of Molecular Recognition, vol. 25, pp. 125-135 (2012).
Almagro, Juan C., Fransson, Johan. Humanization of antibodies. Frontiers in Bioscience 13:1619-1633 (Jan. 1, 2008).

(Continued)

*Primary Examiner* — Elizabeth C. Kemmerer
*Assistant Examiner* — Regina M DeBerry
(74) *Attorney, Agent, or Firm* — Wilson Sonsini Goodrich & Rosati

(57) ABSTRACT

Disclosed herein are immunoglobulin constructs comprising at least one immunoglobulin domain or fragment thereof; and a therapeutic polypeptide or derivative or variant thereof attached to or inserted into said immunoglobulin domain. Also provided are immunoglobulin constructs comprising a mammalian immunoglobulin heavy chain comprising at least a portion of a knob domain in the complementarity-determining region 3 (CDR3H) or fragment thereof; and a therapeutic polypeptide attached to or inserted into said knob domain of the CDR3H. Also provided are immunoglobulin constructs comprising a mammalian immunoglobulin heavy chain comprising at least a portion of a stalk domain in the complementarity-determining region 3 (CDR3H) or fragment thereof; and a therapeutic polypeptide attached to or inserted into said stalk domain of the CDR3H. Also described herein are methods and compositions comprising the immunoglobulin constructs described herein for treatment and prevention of a disease or condition in a subject.

12 Claims, 36 Drawing Sheets

Specification includes a Sequence Listing.

(56) References Cited

U.S. PATENT DOCUMENTS

| | | | |
|---|---|---|---|
| 7,112,660 B1* | 9/2006 | Domingues | C07K 14/5406 530/351 |
| 7,166,697 B1 | 1/2007 | Galanis et al. | |
| 7,196,185 B2 | 3/2007 | Kaushik et al. | |
| 7,575,893 B2 | 8/2009 | Simmons | |
| 7,592,010 B2 | 9/2009 | Rosen et al. | |
| 7,736,652 B2 | 6/2010 | Penichet et al. | |
| 7,977,071 B2 | 7/2011 | Nuttal et al. | |
| 9,644,021 B2 | 5/2017 | Wang et al. | |
| 10,259,863 B2 | 4/2019 | Wang et al. | |
| 2003/0045474 A1* | 3/2003 | Sailer | A61P 19/00 514/8.8 |
| 2003/0088074 A1 | 5/2003 | Hamers et al. | |
| 2003/0166196 A1* | 9/2003 | Better | C07K 14/415 435/188.5 |
| 2003/0170646 A1 | 9/2003 | Kaushik et al. | |
| 2003/0215880 A1 | 11/2003 | Burton et al. | |
| 2003/0232395 A1 | 12/2003 | Hufton | |
| 2006/0160995 A1 | 7/2006 | Baker et al. | |
| 2006/0182751 A1 | 8/2006 | Gazzard et al. | |
| 2006/0275254 A1 | 12/2006 | Kim et al. | |
| 2007/0065430 A1 | 3/2007 | Ellis et al. | |
| 2007/0160617 A1 | 7/2007 | Ma et al. | |
| 2008/0152586 A1 | 6/2008 | Hudson et al. | |
| 2009/0148455 A1 | 6/2009 | Fischer et al. | |
| 2009/0286964 A1 | 11/2009 | Gegg et al. | |
| 2009/0304580 A1 | 12/2009 | Goldenberg et al. | |
| 2010/0136032 A1 | 6/2010 | Weinberg et al. | |
| 2010/0311119 A1 | 12/2010 | Hermans et al. | |
| 2011/0039761 A1 | 2/2011 | Eckert et al. | |
| 2011/0172125 A1 | 7/2011 | Ladner | |
| 2011/0189690 A1 | 8/2011 | Shibasaki et al. | |
| 2011/0269938 A1 | 11/2011 | Nuttall et al. | |
| 2011/0288102 A1* | 11/2011 | Samatar | G01N 33/57407 514/252.18 |
| 2011/0293513 A1 | 12/2011 | Govindan et al. | |
| 2012/0128672 A1 | 5/2012 | Keer | |
| 2012/0302737 A1 | 11/2012 | Christensen et al. | |
| 2012/0328612 A1* | 12/2012 | Grosse-Hovest | A61P 35/02 424/133.1 |
| 2014/0022767 A1 | 1/2014 | Martinez | |
| 2014/0050720 A1 | 2/2014 | Smider et al. | |
| 2014/0086871 A1 | 3/2014 | Smider et al. | |
| 2014/0227267 A1 | 8/2014 | Wang et al. | |
| 2015/0011431 A1 | 1/2015 | Smider et al. | |
| 2015/0192971 A1 | 7/2015 | Shah | |
| 2016/0159920 A1 | 6/2016 | Wang et al. | |
| 2016/0168231 A1 | 6/2016 | De Los Rios et al. | |
| 2016/0237156 A1 | 8/2016 | Wang et al. | |

FOREIGN PATENT DOCUMENTS

| | | |
|---|---|---|
| JP | 2005522197 A | 7/2005 |
| JP | 2010006788 A | 1/2010 |
| WO | WO-8907142 A1 | 8/1989 |
| WO | WO-9320210 A1 | 10/1993 |
| WO | WO-9418221 A1 | 8/1994 |
| WO | WO-9420069 A1 | 9/1994 |
| WO | WO-9622377 A1 | 7/1996 |
| WO | WO-0103737 A1 | 1/2001 |
| WO | WO-0222809 A2 | 3/2002 |
| WO | WO-03030821 A2 | 4/2003 |
| WO | WO-03085086 A2 | 10/2003 |
| WO | WO-2005007809 A2 | 1/2005 |
| WO | WO-2005082353 A3 | 11/2005 |
| WO | WO-2008135557 A1 | 11/2008 |
| WO | WO-2009132876 A1 | 11/2009 |
| WO | WO-2010028791 A1 | 3/2010 |
| WO | WO-2010108048 A2 | 9/2010 |
| WO | WO-2010119249 A1 | 10/2010 |
| WO | WO-2011044542 A1 | 4/2011 |
| WO | WO-2012007167 A1 | 1/2012 |
| WO | WO-2012169822 A2 | 12/2012 |
| WO | WO-2012170977 A1 | 12/2012 |
| WO | WO-2013106485 A2 | 7/2013 |
| WO | WO-2013106489 A1 | 7/2013 |
| WO | WO-2015006744 A1 | 1/2015 |
| WO | WO-2015017146 A2 | 2/2015 |
| WO | WO-2015105741 A1 | 7/2015 |

OTHER PUBLICATIONS

Altschul et al. Basic Local Alignment Search Tool. J. Mol. Biol. 215: 403-410 (1990).

Apostolovic, B. et al. Coiled Coils: attractive protein folding motifs for the fabrication of self-assembled, responsive and bioactive materials, Chem. Soc. Rev. 39:3541-3575 (2010).

Baca et al. Antibody humanization using monovalent phage display. J Biol Chem 272(16):10678-10684 (1997).

Barbas, C.F. et al. Molecular Profile of an Antibody Response to HIV-1 as Probed by Combinatorial Libraries. Journal of Molecular Biology, 230(3):812-823 (Apr. 5, 1993).

Barthelemy, et al. Comprehensive Analysis of the Factor Contributing to the Stability and Solubility of Autonomous Human VH Domains. The Journal of Biological Chemistry, 283(6):3639-3654 (Feb. 8, 2008).

Beiboer, Sigrid H. et al. Guided Selection of a Pan Carcinoma Specific Antibody Reveals Similar Binding Characteristics yet Structural Divergence Between the Original Murine Antibody and its Human Equivalent. J. Mol. Biol. 296:833-849 (2000).

Berens, et al. Use of a single VH family and long CDR3s in the variable region of cattle Ig heavy chains. International Immunology, vol. 9, No. 1, pp. 189-199, (1997).

Brumeanu et al. Efficient loading of identical viral peptide onto class II molecules by antigenized immunoglobulin and influenza virus. J. Exp. Med. 178:1795-1799 (Nov. 1, 1993).

Burkhard, P. et al. Coiled coils: a highly versatile protein folding motif, TRENDS in Cell Biology, 11.2 (Feb. 2001): 82-88.

Casset et al. A peptide mimetic of an anti-CD4 monoclonal antibody by rational design. Biochemical and Biophysical Research Communication 307:198-205 (2003).

Chain H., Crystal Structure Of Bovine Antibody Blv5b8 With Ultralong Cdr H3.Accessed PDB: 4K3E-H NCBI Feb. 12, 2016 http://www.ncbi.nlm.nih.gov/protein/4K3E_H.

Chen et al.Selection and analysis of an Optimized Anti-VEGF Antibody: Crystal Structure of an Affinity-matured Fab in Complex with Antigen Journal of Molecular Biology, vol. 293, pp. 865-881(1999).

Choi, Yoonjoo et al. Predicting antibody complementarity determining region structures without classification. Mol. BioSyst. 7:3327-3334 (2011).

Collis et al. Analysis of the Antigen Combining Site: Correlations Between Length and Sequence Composition of the Hypervariable Loops and the Nature of the Antigen. Journal of Molecular Biology, vol. 325, pp. 337-354 (2003).

Conway, S. P. et al. Pharmacokinetics and safety of itraconazole in patients with cystic fibrosis. Journal of Antimicrobial Chemotherapy, Mar. 24, 2004, vol. 53, No. 5, pp. 841-847.

DeGenst, Erwin et al., Antibody repertoire development in camelids. Developmental and Comparative Immunology, 2006 ;30(1-2): 187-98.

Edgar. Muscle: multiple sequence alignment with high accuracy and high throughput. Nucleic Acids Res. 32(5): 1792-1797 (2004).

Ekiert et al. Cross-Neutralization of Influenza A viruses mediated by a Single Antibody Loop. Nature, vol. 489, pp. 526-532 (2012).

Elsik et al. The Genome Sequence of Taurine Cattle: A window to ruminant biology and evolution. Science, vol. 324, No. 5926, pp. 522-528 Apr. 24, 2009.

European Application No. 13735853 Office Action dated Sep. 7, 2017.

European Application No. 14737834.3 Extended European Sear Report dated May 4, 2016.

Gazi, A.D. et al. Coiled-coils in type III secretion systems: structural flexibility, disorder and biological implications, Cellular Microbiology 11(5):719-729 (2009).

(56) References Cited

OTHER PUBLICATIONS

Glaser, et al. Novel antibody hinge regions for efficient production of CH2 domain-deleted antibodies.The Journal of Biological Chemistry, vol. 280, No. 50, pp. 41494-41503 (2005).
Goldenberg, M. Trastuzumab, a recombinant DNA-derived humanized monoclonal antibody, a novel agent for the treatment of metastatic breast cancer. Clinical Therapeutics, 21(2):309-318 (1999).
Griffiths, Andrew et al. Human anti-self antibodies with high specificity from phage display libraries. The EMBO Journal, 12(2):725-734 (1993).
Hadley, EB et al. An Antiparalallel a-Helical Coiled-Coil Model System for Rapid Assessment of Side-Chain Recognition at the Hydrophobic Interface, J. Am. Chem. Soc. 128:16444-16445 (2006).
Harbury, P.B et al. A Switch Between Two, Three, and Four-Stranded Coiled Coils in GCN4 Leucine Zipper Mutants, Science, New Series, 262(5138);1401-1407 (Nov. 26, 1993).
Henderson et al. Structure of an IgNAR-AMA1 Complex: Targeting a Conserved Hydrophobic Cleft Broadens Malarial Strain Recognition. Structure, vol. 15, pp. 1452-1466 (2007).
Hill, R.B. et al. De Novo Design of Helical Bundles as Models for Understanding Protein Folding and Function, Acc. Chem. Res. 33(11):745-754 (Nov. 2011).
Hosseini, et al. Duplicated copies of the bovine JH locus contribute to the Ig repertoire International Immunology, vol. 16, No. 6, pp. 843-852, May 4, 2004.
Immunoglobulin heavy chain variable region, partial [Bos taurus]. Accessed from GenBank: AAC71038.1. NCBI on Feb. 12, 2016 http://ncbi.nlm.nig.gov/protein/AAC71038.1.
Immunoglobulin light chain variable region, partial [Bos taurus] GenBank: AAB81517.1 Accessed via NCBI Feb. 12, 2016 http://ncbi.nlm.nih.gov/protein/2555151.
Immunoglobulin light chain variable region, partial [Bos taurus]. Accessed Feb. 12, 2016 via NCBI GenBank: AAB66580.1 http://ncbi.nlm.nih.gov/protein/2323408.
Inoue, Hidetoshi et al. Affinity transfer to a human protein by CDR3 grafting of camelid VHH, Protein Science: A Publication of the Protein Society. vol. 20, No. 12. Dec. 2011, pp. 1971-1981.
International Application No. PCT/US2014/046429 International Search Report and Written Opinion dated Nov. 3, 2014.
Karlin et al. Applications and statistics for multiple high-scoring segments in molecular sequences. PNAS USA 90:5873-5877 (1993).
Karlin et al. Methods for assessing the statistical significance of molecular sequence features by using general scoring schemes. PNAS USA 87: 2264-2268 (1990).
Kaushik, et al. Novel Insight into Antibody diversification from Cattle. Veterinary Immunology and Immunopathology, vol. 87, pp. 347-350 (2002).
Kaushik, et al., Somatic hypermutations and isotype restricted exceptionally long CDR3H contribute to antibody diversification in cattle. Veterinary Immunology and Immunopathology, vol. 127, pp. 106-113 (2009).
Klimka, A. et al. Human anti-CD30 recombinant antibodies by guided phage antibody selection using cell panning. British Journal of Cancer 83(2):252-260 (2000).
Koti, et al. Novel atypical nucleotide insertions specifically at VH-DH junction generate exceptionally long CDR3H in cattle antibodies. Mol Immunol. Jul. 2010;47(11-12):2119-2128.
Koti et al. Organization of DH-Gene Locus is Distinct in Cattle Developments in biologicals (Basel), vol. 132, pp. 307-313 (2008).
Krause et al., An insertion mutation that distorts antibody binding site architecture enhances function of a human antibody. mBio 2(1):e00345-10 (2011).
Li, Tengfei et al. Cell-penetrating anti-GFAP VHH and corresponding fluorescent fusion protein VHH-GFP spontaneously cross the blood-brain barrier and specifically recognize astrocytes: application to brain imaging. The FASEB Journal 26:1-11 (Oct. 2012).
Lopez et al., A Single Vh Family and long CDR3 are the targets for Hypermutation in Bovine Immunoglobulin Heavy Chains. Immunological Reviews. 162: 55-66 (1998).

Marsden, H.R. et al. Self-Assembly of Coiled Coils in Synthetic Biology: Inspiration and Progress, Angew. Chem. Int. Ed. (2010) 49:2988-3005.
McLellan et al., Structure of HIV-1 gp120 V1/V2 domain with broadly neutralizign antibody PG9. Nature 480 (7377): 336-343 (2011).
NCBI, GenBank Accession No. DM113215.1, Jun. 18, 2009.
NCBI, PDB accession No. 4K3D_H (Jul. 3, 2013).
Ngo, J. Thomas et al. Computational Complexity, Protein Structure Prediction, and the Levinthal Paradox, Birkhauser, pp. 433-440, 492-495, 1994.
Nuttall et al., Design and expression of soluble CTLA-4 variable domain as a scaffold for the display of functional polypeptides. Proteins: Strucutre, Function and Genetics. 36: 217-227 (1999).
Nuttall et al. Selection and affinity maturation of IgNAR variable domains targeting Plasmodium falciparum AMA1.Protein: Structure, Function and Bioinformatics. vol. 55, Issue Apr. 1, 2004, pp. 187-197.
Oakley, M.G. et al. The design of antiparallel coiled coils, Current Opinion in Structural Biology, 11:450-457 (2011).
Paul, W.E. Fundamental Immunology, Third Edition (textbook). "Fv Structure and Diversity in Three Dimensions" pp. 292-295; Raven Press, New York (1993).
PCT/US2013/020903 International Search Report and Written Opinion dated Jun. 25, 2013.
PCT/US2014/011043 Search Report and Written Opinion dated May 1, 2014.
Peckman, M. Coiled coils and SAH domains in cytoskeletal molecular motors, Biochemical Society Transactions 39(5):1142-1148 (2011).
Pejchal et al., Structure and Function of Broadly Reactive Antibody PG16 Reveal an H3 Subdomain that Mediates Potent Neutralization of HIV-1. PNAS, 107(25): 11483-11488 (2010).
Pistillo, MP et al. Molecular Characterization and Applications of Recombinant scFv Antibodies to CD152 Co-Stimulatory Molecule, Tissue Antigens, Munksgaard, Copenhagen, DK, vol. 55, No. 3, Mar. 1, 2000, pp. 229-238.
Qin W. et al. Fusion protein of CDR mimetic peptide with Fc inhibit TNF-alpha induced cytotoxicity, Molecular Immunology, 43(6); 660-666 (Feb. 1, 2006).
Ramsland, PA et al. Incorporation of long CDR3s into V domains: implications for the structural evolution of the antibody-combining site, Experimental and Clinical Immunogenetics, S. Karger, Basel, CH, vol. 18, No. 4, Jan. 1, 2001, pp. 176-198.
Roche, JR et al. Invited review: Body condition score and its association with dairy cow productivity, health, and welfare Journal of Dairy Science, vol. 92, No. 12, 5769-5801 (Aug. 2009).
Saini et al., Bovine IgM Antibodies with Exceptionally Long complementarity—Determining Region 3 of the Heavy Chain Share Unique Structural Properties Conferring Restricted Vh +Vλ pairings. International Immunology. 15(7): 845-853 (2003).
Saini, et al. Exceptionally long CDR3H region with multiple cysteine residues in functional bovine IgM antibodies. Eur J Immunol. Aug. 1999;29(8):2420-2426.
Saini, et al. Extensive CDR3H length heterogeneity exists in bovine foetal VDJ rearrangements. Scand J Immunol. Feb. 2002;55(2):140-148.
Saphire et al., Crystal Structure of a Neutralizing Human IgG Against HIV-1: A Template for Vaccine Deisgn, Science 293: 1155-1159 (2001).
Shojaei, et al., Unusually long Germline Dh Genes Contribue to Large Sized CDR3H in Bovine Antibodies. Molecular Immunology 40: 61-67 (2003).
Simmons et al. Shark IgNAR antibody mimotopes target a murine immunoglobulin through extended CDR3 loop structures.Proteins: Structure, Function and Bioinformatics vol. 71, Issue Apr. 1, 2008, pp. 119-130.
Steltsov, Victor A. et al. Crystal Structure of the Amyloid-p3 Fragment Provides a Model for Oligomer Formation in Alzheimer's Disease. The Journal of Neuroscience 31(4);1419-1426 (Jan. 26, 2011).

(56) References Cited

OTHER PUBLICATIONS

Streltsov et al. Crystal Structure of the Amyloid p3 Fragment Provides a Model for Oligomer Formation in Alzheimers Disease The Journal of Neuroscience, Jan. 26, 2011, 31(4):1419-1426, 1419 (with Supplemental Data).
U.S. Appl. No. 13/737,910 Final Office Action dated Feb. 17, 2017.
U.S. Appl. No. 13/737,910 Non-Final Office Action dated Aug. 7, 2018.
U.S. Appl. No. 13/737,910 Non-Final Office Action dated Jan. 18, 2018.
U.S. Appl. No. 13/737,910 Office Action dated Aug. 22, 2016.
U.S. Appl. No. 13/737,913 Office Action dated Jan. 27, 2017.
U.S. Appl. No. 13/737,913 Office Action dated Jun. 21, 2016.
U.S. Appl. No. 14/152,441 Final Office Action dated Nov. 18, 2015.
"U.S. Appl. No. 14/152,441 Office Action dated Jun. 1, 2015".
U.S. Appl. No. 14/152,441 Office Action dated May 18, 2016.
U.S. Appl. No. 14/152,441 Office Action dated Nov. 30, 2016.
U.S. Appl. No. 14/760,115 Advisory Office Action dated Aug. 25, 2017.
U.S. Appl. No. 14/760,115 Advisory Office Action dated Jul. 10, 2018.
U.S. Appl. No. 14/760,115 Final Office Action dated Jun. 22, 2017.
U.S. Appl. No. 14/760,115 Final Office Action dated May 2, 2018.
U.S. Appl. No. 14/760,115 Non-final Office Action dated Feb. 10, 2017.
U.S. Appl. No. 14/760,115 Non-Final Office Action dated Nov. 24, 2017.
U.S. Appl. No. 14/903,489 Non-Final Office Action dated Jan. 12, 2018.
Wang, et al., Reshaping Antibody Diversity. Cell 153: 1379-1393 (2013).
Ward, E. Sally et al. Binding activities of a repertoire of single immunoglobulin variable domains secreted from *Escherichia coli*. Nature, Letters to the Editor, 341:544-546 (Oct. 12, 1989).
Wells, James A. Additivity of Mutational Effects in Proteins, vol. 29, No. 37, pp. 8509-8517 (Sep. 18, 1990).
Woolfson et al. The Design of Coiled-Coil Structures and Assemblies, Advances in Protein Chemistry, 70 (2005): 79-112.
Wynne et al. Oxyntomodulin increases energy expenditure in addition to decreasing energy intake in overweight and obese humans: a randomised controlled trial International Journal of Obesity, vol. 30, 1729-1736, 2006.
Xiao-Qing; Qiu et al., "Xiao-Qing Qiu, et al. Small antibody mimetics comprising two complementarity-determining regions and a framework region for tumor targeting", Nature Biotechnology, Aug. 2007, vol. 25, No. 8, pp. 921-929.
Yang Xi et al. The three complementarity-determining region-like loops in the second extracellular domain of human Fc alpha/mu receptor contribute to its binding of IgA and Igm. Immunobiology,Urban Und Fischer Verlag, DE, 218(5); 798-809 (Oct. 4, 2012).
Zaghouani, et al. Engineered immunoglobulin molecules as vehicles for T cell epitopes. Int Rev Immunol. 1993;10(2-3):265-78.
Zhang, et al. An Antibody CDR3-Erythropoietin Fusion Protein. ACS Chem. Biolo. 8:2117-2121 (2013).
Zhang, et al. An Antibody with a Variable-Region Coiled-Coil Knob: Domain. Angew. Chem. Int. Ed. 53: 132-135 (2014).
Zhang, et al., Functional Antibody CDR3 fusion proteins with enhanced pharmacological properties. Angew. Chem. Int. Ed. 52: 8295-8298 (2013).
Zhao et al., The Bovine Antibody Repertoire. Developmental and Comparative Immunology 30: 175-186 (2006).
Zhong et al., Small antibody fusion proteins with complementarity-determining regions and lidamycin for tumor targeting therapy. Onoclogy Letters. 5: 1183-188 (2013).

* cited by examiner

FIG. 2A
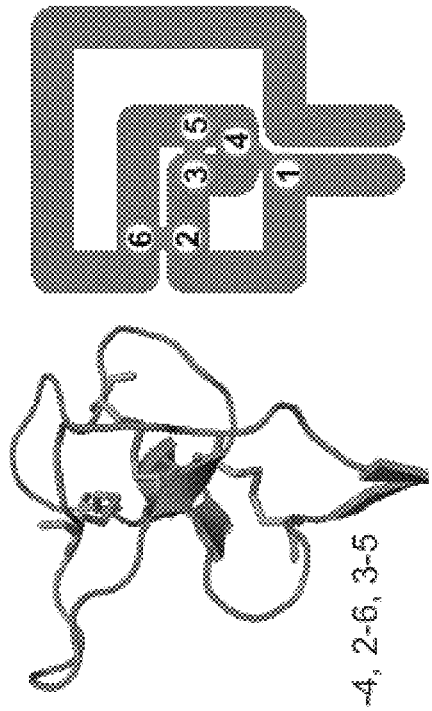
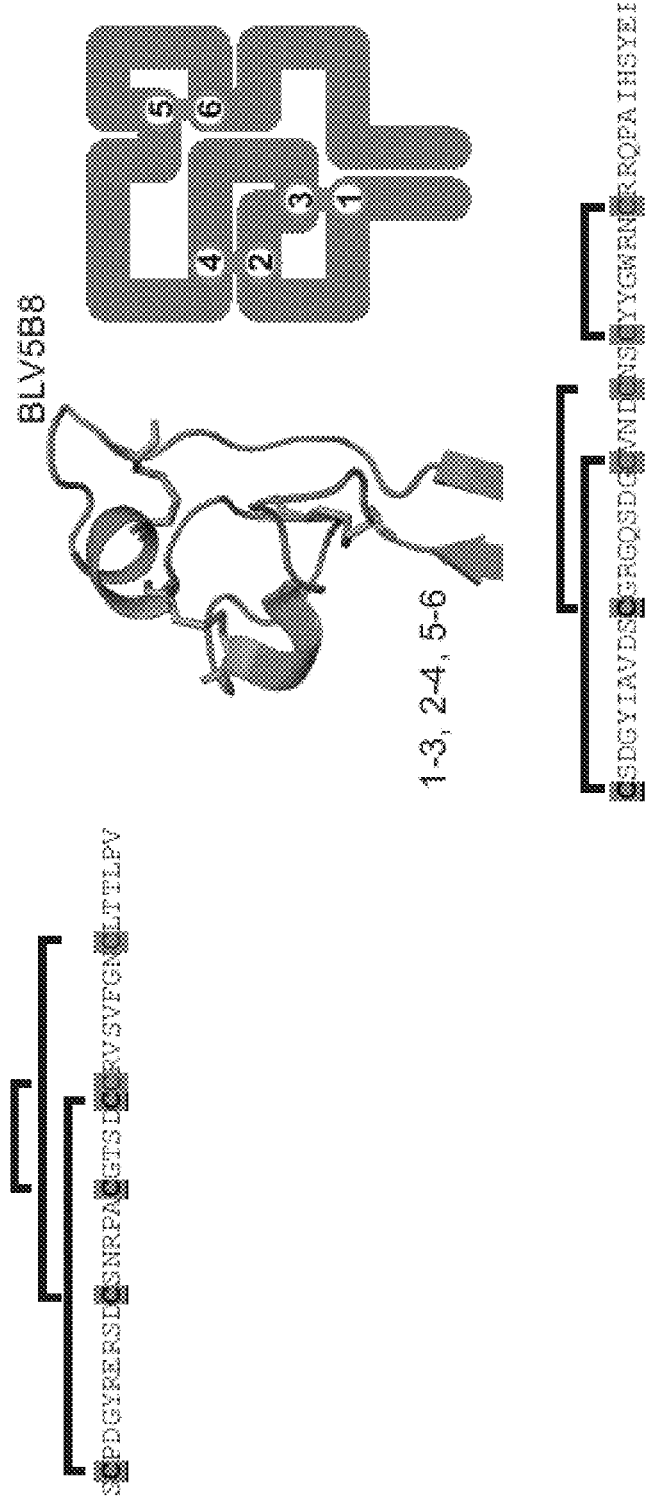

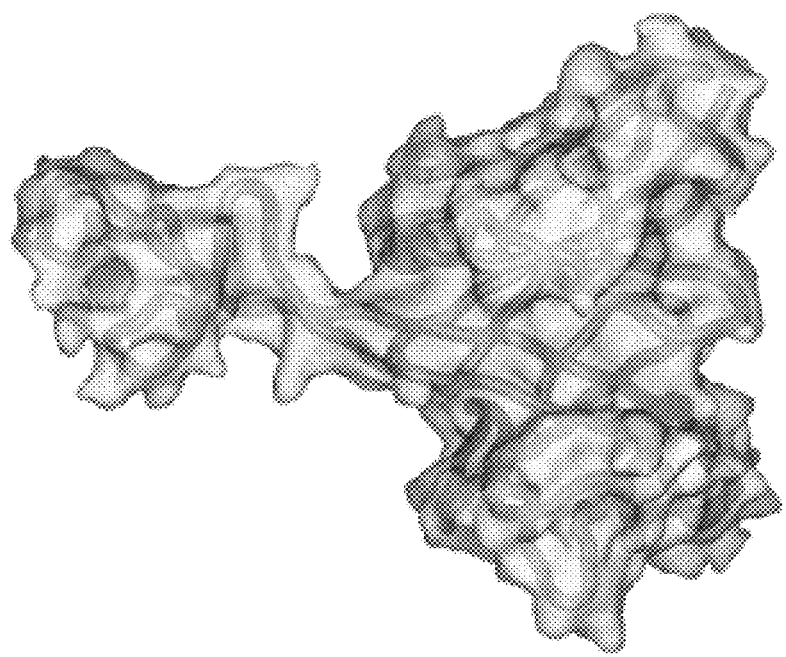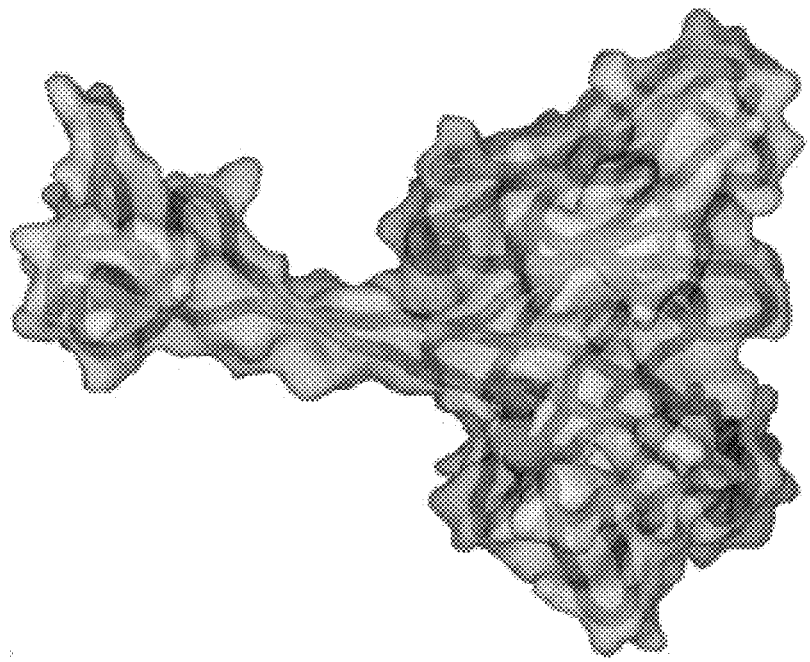
FIG. 2C

FIG. 3A

```
L K R L V G V V T L I C S K M P L M T
tgaggagctgtggagtggtggtactctcatcctgctctgcaagatgccactggacccc L L F V L S A P R G
cccctcttcgtgctctcagcccccagaggtgagtgggtcctctctgggtcaggcacgtgg
                                                      V L S Q V Q L R E S G P S L V K P S Q T L S L
caggtgcagctgcgggagtcgggaccctcactcgtcaagcctctcagaccctgtctctc T C T A S G F S L S D K A V G W V R Q A
acctgcactgcctctggattctcattgagcgacaaggctgtaggctgggtccgccaggct P G K A L E W L G G I D T G G S T G Y N
ccagggaaggcgctggagtggctgggaggcatagacactggtggaagcacaggctataac P G L K S R L S I T K D M S K S Q V S L
ccaggcctgaaatcccggctcagcatcactaaggacacctccaagagccaagtctccctg S V S S V T E D S A T Y Y C A R Q
tcagtgagcagtgtgacagagacagccacatactactgtgcgagccagtgtaccgg
```

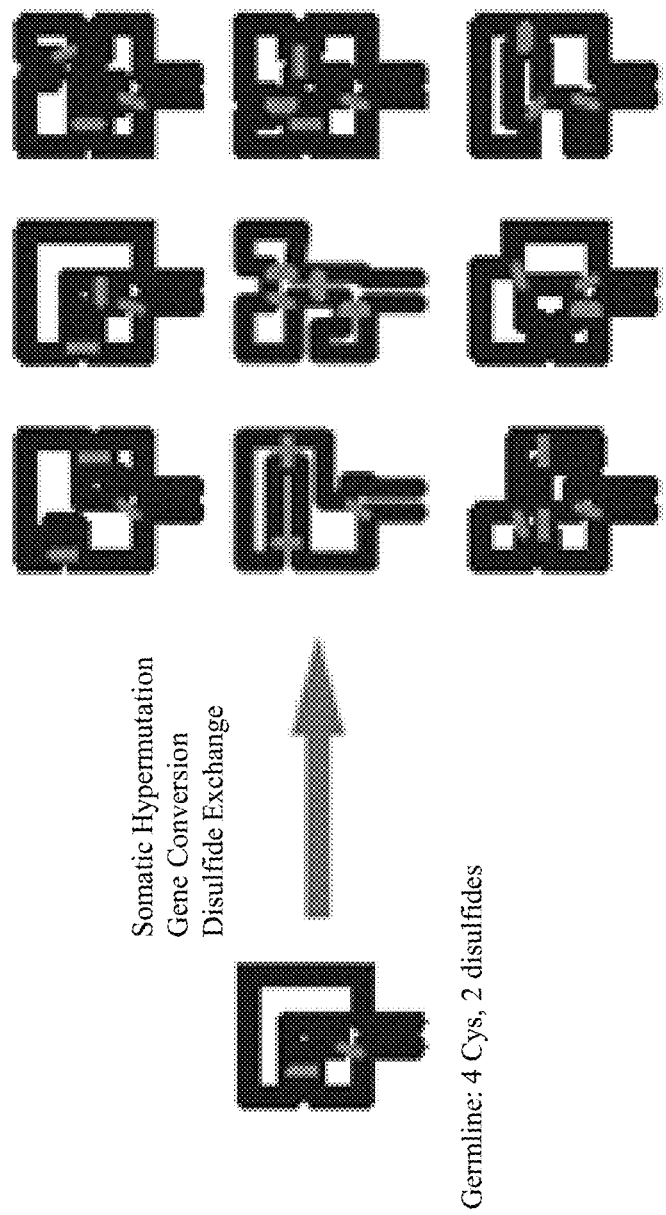

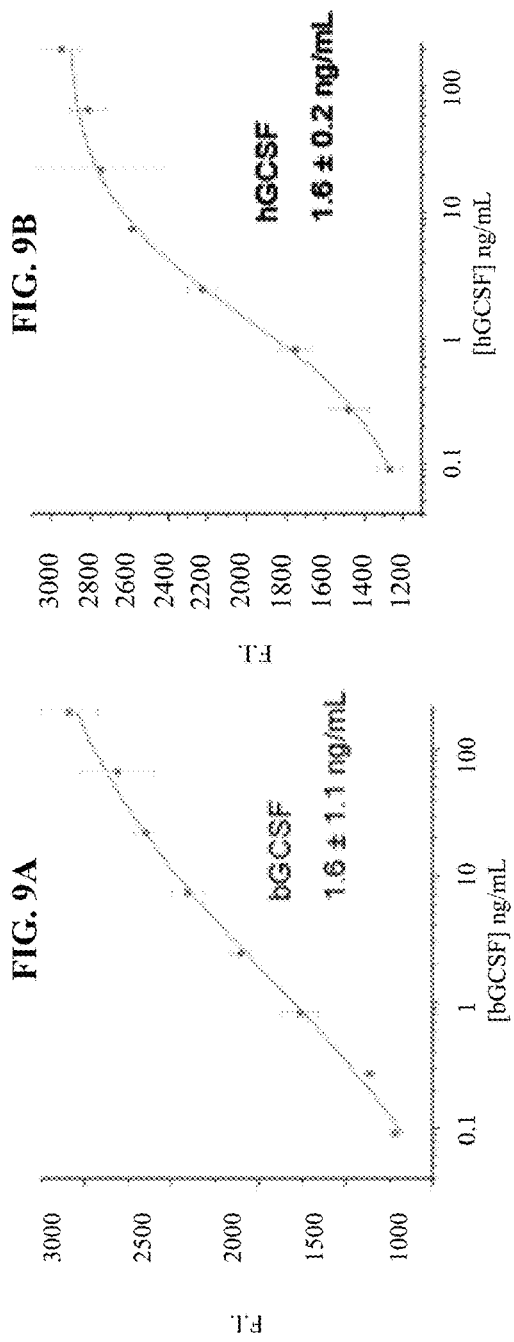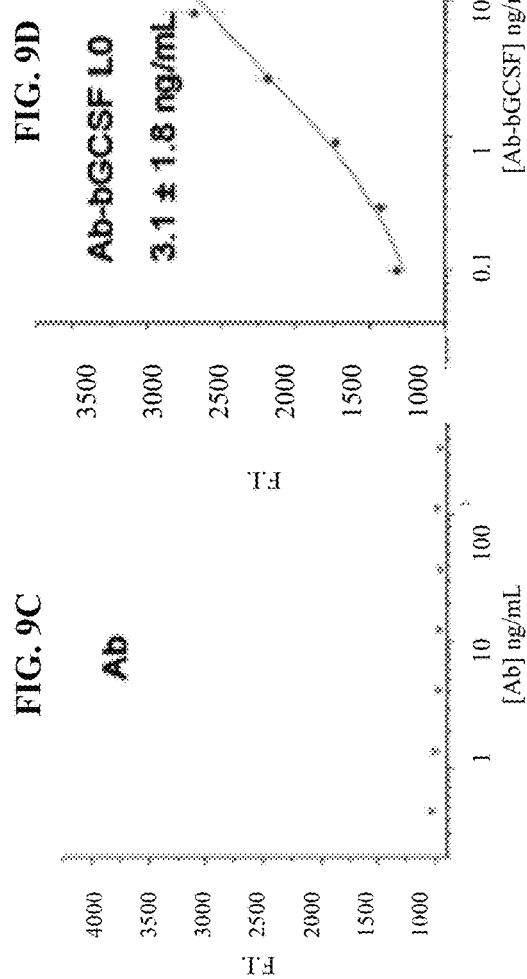

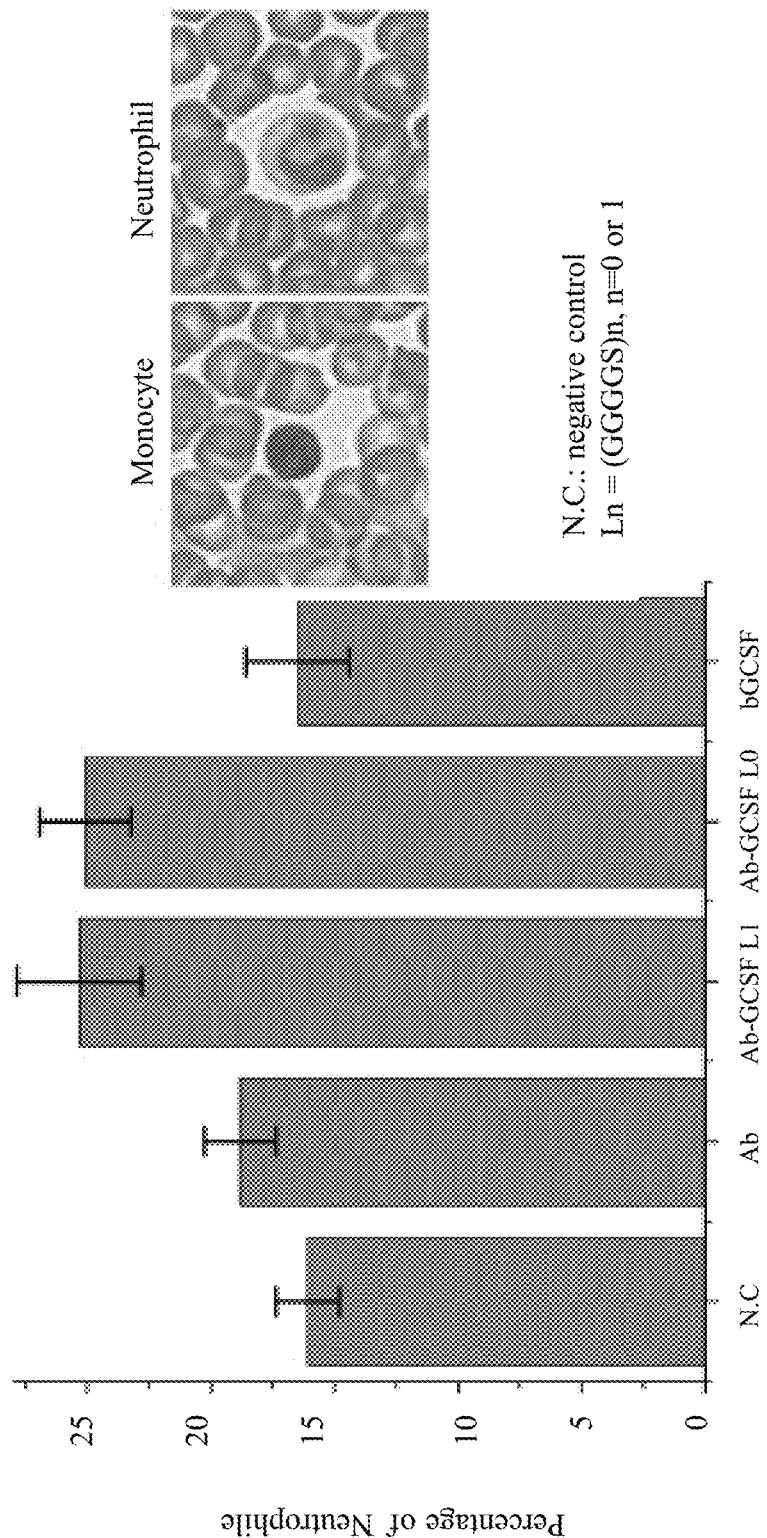

SDS-PAGE gel of the purified Ab-bGCSF fusion proteins expressed in Pichia
Yield: ~ 70 ug per 100 mL culture Western blot of post-induction of Ab-bGCSF fusion proteins expression NR: non-reducing; R: reducing
Ln = (GGGGS)n, n =0 or 1 pFUSE-BLV1H12-bGCSF-hIgG1Fc
5424 bp

BLV1H12-bGCSF L1
Ln=(GGGGS)n, n=0 or 1 pFUSE-BLV1H12-Light chain
4141 bp

BLV1H12 antibody light chain pFUSE-BLV1H12-bGCSF-hIgG1Fc
5394 bp

BLV1H12-bGCSF L0

FIG. 15B

Protoxin
R  N

R: reduced condition; N: non-reduced condition

NR: non-reducing condition;
R: reducing condition
Ln = (GGGGS)n, n = 0 or 1

Other Representative sequences:

| | | | |
|---|---|---|---|
| UL-58 | CTTYRQ QTRATR | RCPXXYRDNYACXSNYGCSABGCCRWDPGSGACTCATYTSPYEW | YVDAN 57 |
| UL-59 | CAAVHQ RTMOQQ | SCPDAYLEFRVCPYRMYRCIGWDCCRCSDGRDMYIMTYSTEP | HVEVR 56 |
| UL-60 | CTTVHQ ETKTES | GCPIKYKSCCYNGWSBSCRPNDCSTYGEVBSLSRSCTTWNTEP | YVDAN 55 |
| UL-61 | CGTTYQ HYKEIK | TCPIKYKYRDVFTYCPVTCPGWDCQRNDCQRTRYVAYSAL | HVDVR 54 |
| UL-62 | CTTVYQ ETMOOR | GCPAGTOVVDCGFTQDCCRTSYVCQPLTCGNTATRNTQW | YVDAN 53 |
| UL-63 | CTTVYQ KTEK | KCPDIGYTDNHEDNTCRNPDCSNEGLRCLCSAYTRAYEF | HVDAN 51 |
| UL-64 | CTTVVQ QRK | SCPNYASYDCASPDTRRCSSCRSCTRKCAPTAPYIYTYQF | YVDAN 50 |
| UL-65 | CTTVHQ ETQRT | RCPTYNSTLCRMIGCSGDECQNTGRVECTSTYWTHRF | HVDAN 49 |
| UL-66 | CATVHQ KDX | SCPSGWTYCNCRNGDGCYRPSQLCGAYVAVTRTYEF | YVDAN 49 |
| UL-67 | CAAVHQ QTTENGE | HCPAGYRSGTLCRMIGCSGDCQNTDRVECTNYDYTNRF | HVETR 48 |
| UL-68 | CSTVRQ KTTTV | TCPFRSRDMSTECBDDRYYPNRYSDYYYYTYEN | HVETH 47 |
| UL-69 | CSTVHQ ETMTQR | TCIRPTVRCTCGRRRGCCYDPRCSTTYRGTYTTDP | YVDAN 46 |
| UL-70 | CGTVHQ KTBK | TCPDACDYTGDNCKVRRMGWCGRASKTDTYDF | YVDAN 45 |
| UL-71 | CTTVYC KTSX | SCPENYARTCYCMCGSWRCGYGSTTELIVSYKW | RVDAN 44 |
| UL-72 | CTTVHQ RTRT | GCPDSYTHMSGSCCRGSICTNGLPRNTYTYEF | YVDSH 43 |
| UL-73 | CTTYYQ KTTTTK | NCPGGFPNORRCTMGLGDLRDYTYPNRYEW | YYETK 43 |
| UL-74 | CSTVYQ KTSO | RCLDSTDDRGAYCTDSVRGLMSWTYKYVTEW | RVDTH 42 |
| UL-75 | CTNVHQ MTIK | TCPSGGSYGWYWPTCYCGNGGVSATYTYEF | YVDAN 41 |
| UL-76 | CTTYYQ KTESVR | SCPDRSMDOWRCRLGTMRWIYSNTTEF | YVDAN 40 |

ULTRALONG COMPLEMENTARITY DETERMINING REGIONS AND USES THEREOF

CROSS-REFERENCE TO RELATED APPLICATIONS

This application is a Divisional of U.S. application Ser. No. 13/737,910, filed Jan. 9, 2013, which claims the benefit of U.S. Provisional Application No. 61/584,680 filed Jan. 9, 2012, and U.S. Provisional Application No. 61/671,629, filed Jul. 13, 2012, all of which are incorporated by reference herein in their entirety.

STATEMENT AS TO FEDERALLY SPONSORED RESEARCH

This invention was made with government support under grant number GM062159 awarded by The National Institutes of Health. The government has certain rights in the invention.

SEQUENCE LISTING

The instant application contains a Sequence Listing which has been submitted in ASCII format via EFS-Web and hereby incorporated by reference in its entirety. Said ASCII copy, created on Apr. 4, 2013, is named 36271-701-601_SL.txt and is 353,533 bites in size.

FIELD

Described herein are immunoglobulin constructs comprising at least a portion of an ultralong CDR3, methods of making such constructs, pharmaceutical compositions and medicaments comprising such constructs, and methods of using such constructs and compositions to prevent, inhibit, and/or treat a disease or condition in a subject.

BACKGROUND

Antibodies are natural proteins that the vertebrate immune system forms in response to foreign substances (antigens), primarily for defense against infection. For over a century, antibodies have been induced in animals under artificial conditions and harvested for use in therapy or diagnosis of disease conditions, or for biological research. Each individual antibody producing cell produces a single type of antibody with a chemically defined composition, however, antibodies obtained directly from animal serum in response to antigen inoculation actually comprise an ensemble of non-identical molecules (e.g., polyclonal antibodies) made from an ensemble of individual antibody producing cells.

Some bovine antibodies have unusually long VH CDR3 sequences compared to other vertebrates. For example, about 10% of IgM contains "ultralong" CDR3 sequences, which can be up to 61 amino acids long. These unusual CDR3s often have multiple cysteines. Functional VH genes form through a process called V(D)J recombination, wherein the D-region encodes a significant proportion of CDR3. A unique D-region encoding an ultralong sequence has been identified in cattle. Ultralong CDR3s are partially encoded in the cattle genome, and provide a unique characteristic of their antibody repertoire in comparison to humans. Kaushik et al. (U.S. Pat. Nos. 6,740,747 and 7,196,185) disclose several bovine germline D-gene sequences unique to cattle stated to be useful as probes and a bovine VDJ cassette stated to be useful as a vaccine vector.

SUMMARY

The present disclosure provides antibodies that comprise an utralong CDR3 including, libraries that comprise an ultralong CDR3, and uses thereof.

The present disclosure also provides a library of antibodies or binding fragments thereof, wherein the antibodies or binding fragments thereof comprise an ultralong CDR3.

In some embodiments of each or any of the above or below mentioned embodiments, the ultralong CDR3 is 35 amino acids in length or longer, 40 amino acids in length or longer, 45 amino acids in length or longer, 50 amino acids in length or longer, 55 amino acids in length or longer, or 60 amino acids in length or longer.

In some embodiments of each or any of the above or below mentioned embodiments, the ultralong CDR3 is 35 amino acids in length or longer.

In some embodiments of each or any of the above or below mentioned embodiments, the ultralong CDR3 comprises 3 or more cysteine residues, 4 or more cysteine residues, 5 or more cysteine residues, 6 or more cysteine residues, 7 or more cysteine residues, 8 or more cysteine residues, 9 or more cysteine residues, 10 or more cysteine residues, 11 or more cysteine residues, or 12 or more cysteine residues.

In some embodiments of each or any of the above or below mentioned embodiments, the ultralong CDR3 comprises 3 or more cysteine residues.

In some embodiments of each or any of the above or below mentioned embodiments, the antibodies or binding fragments thereof comprise a cysteine motif.

In some embodiments of each or any of the above or below mentioned embodiments, the cysteine motif is selected from the group consisting of SEQ ID NOS: 45-156. In some embodiments of each or any of the above or below mentioned embodiments, the cysteine motif is selected from the group consisting of SEQ ID NOS: 45-99. In some embodiments of each or any of the above or below mentioned embodiments, the cysteine motif is selected from the group consisting of SEQ ID NOS: 45-135. In some embodiments of each or any of the above or below mentioned embodiments, the cysteine motif is selected from the group consisting of SEQ ID NOS: 100-135. In some embodiments of each or any of the above or below mentioned embodiments, the cysteine motif is selected from the group consisting of SEQ ID NOS: 136-156.

In some embodiments of each or any of the above or below mentioned embodiments, the ultralong CDR3 comprises a non-human DH or a derivative thereof.

In some embodiments of each or any of the above or below mentioned embodiments, the ultralong CDR3 comprises a JH sequence or a derivative thereof.

In some embodiments of each or any of the above or below mentioned embodiments, the ultralong CDR3 comprises: a non-human VH sequence or a derivative thereof, a non-human DH sequence or a derivative thereof; and/or a JH sequence or derivative thereof.

In some embodiments of each or any of the above or below mentioned embodiments, the ultralong CDR3 comprises an additional amino acid sequence comprising two to six amino acid residues or more positioned between the VH sequence and the DH sequence.

In some embodiments of each or any of the above or below mentioned embodiments, the ultralong CDR3 comprises a non-bovine sequence.

In some embodiments of each or any of the above or below mentioned embodiments, the non-bovine sequence is a non-antibody or a human sequence.

In some embodiments of each or any of the above or below mentioned embodiments, the non-bovine sequence replaces at least a portion of the ultralong CDR3.

In some embodiments of each or any of the above or below mentioned embodiments, the non-bovine sequence is a hormone, lymphokine, interleukin, chemokine, cytokine, toxin, or combination thereof.

In some embodiments of each or any of the above or below mentioned embodiments, the non-bovine sequence is a cytokine.

In some embodiments of each or any of the above or below mentioned embodiments, the cytokine is granulocyte colony-stimulating factor (G-CSF).

In some embodiments of each or any of the above or below mentioned embodiments, the ultralong CDR3 comprises an additional sequence that is a linker.

In some embodiments of each or any of the above or below mentioned embodiments, the linker is linked to a C-terminus, a N-terminus, or both C-terminus and N-terminus of the non-antibody sequence.

In some embodiments of each or any of the above or below mentioned embodiments, the linker is (GGGGS)$_n$ (SEQ ID NO: 339), where n is an integer between 0 and 5. Alternatively, or additionally, the linker is (GSG)n (SEQ ID NO: 342), GGGSGGGGS (SEQ ID NO: 337) or GGGGSGGGS (SEQ ID NO: 338)

In some embodiments of each or any of the above or below mentioned embodiments, the ultralong CDR3 comprises a $X^1X^2X^3X^4X^5X_n$ motif (SEQ ID NO: 494), wherein $X_1$ is threonine (T), glycine (G), alanine (A), serine (S), or valine (V), wherein $X_2$ is serine (S), threonine (T), proline (P), isoleucine (I), alanine (A), valine (V), or asparagine (N), wherein $X_3$ is valine (V), alanine (A), threonine (T), or aspartic acid (D), wherein $X_4$ is histidine (H), threonine (T), arginine (R), tyrosine (Y), phenylalanine (F), or leucine (L), wherein $X_5$ is glutamine (Q), and wherein n is 27-54.

In some embodiments of each or any of the above or below mentioned embodiments, the $X^1X^2X^3X^4X^5$ motif (SEQ ID NO: 495) is TTVHQ (SEQ ID NO: 159) or TSVHQ (SEQ ID NO: 160).

In some embodiments of each or any of the above or below mentioned embodiments, the ultralong CDR3 further comprises a $(X^aX^b)_z$ motif (SEQ ID NO: 496), wherein $X^a$ is an aromatic amino acid selected from the group consisting of: tyrosine (Y), phenylalanine (F), tryptophan (W), and histidine (H), $X^b$ is any amino acid residue, and wherein z is 1-4.

In some embodiments of each or any of the above or below mentioned embodiments, the $(X^aX^b)_z$ motif (SEQ ID NO: 496) is YXYXYX (SEQ ID NO: 298).

In some embodiments of each or any of the above or below mentioned embodiments, the ultralong CDR3 comprises a $X^1X^2X^3X^4X^5X_x(X^aX^b)_z$ motif (SEQ ID NO: 497), wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q), wherein $X^a$ is an aromatic amino acid selected from the group consisting of: tyrosine (Y), phenylalanine (F), tryptophan (W), and histidine (H), $X^b$ is any amino acid residue, wherein n is 27-54, and wherein z is 1-4.

In some embodiments of each or any of the above or below mentioned embodiments, the $X^1X^2X^3X^4X^5$ motif (SEQ ID NO: 495) is TTVHQ (SEQ ID NO: 159) or TSVHQ (SEQ ID NO: 160), and wherein the $(X^aX^b)_z$ motif (SEQ ID NO: 496) is YXYXYX (SEQ ID NO: 298).

In some embodiments of each or any of the above or below mentioned embodiments, the ultralong CDR3 comprises TSVHQETKKYQ (SEQ ID NO.157).

In some embodiments of each or any of the above or below mentioned embodiments, the ultralong CDR3 comprises VHQETKKYQ (SEQ ID NO: 158).

In some embodiments of each or any of the above or below mentioned embodiments, the ultralong CDR3 comprises CTTVHQXn (SEQ ID NO. 223).

In some embodiments of each or any of the above or below mentioned embodiments, the ultralong CDR3 comprises $CTSVHQX_n$ (SEQ ID NO. 224), wherein n is 1-8.

In some embodiments of each or any of the above or below mentioned embodiments, the ultralong CDR3 comprises TTVHQ (SEQ ID NO. 159).

In some embodiments of each or any of the above or below mentioned embodiments, the ultralong CDR3 comprises TSVHQ (SEQ ID NO. 160).

In some embodiments of each or any of the above or below mentioned embodiments, the ultralong CDR3 comprises VHQ (SEQ ID NO: 225).

In some embodiments of each or any of the above or below mentioned embodiments, the ultralong CDR3 comprises KKQ (SEQ ID NO: 226).

In some embodiments of each or any of the above or below mentioned embodiments, the ultralong CDR3 comprises VYQ (SEQ ID NO: 227).

In some embodiments of each or any of the above or below mentioned embodiments, the ultralong CDR3 comprises $CX^1X^2X^3X^4Q$ (SEQ ID NO: 228), wherein $X^1$ is T, S, A, or G, wherein $X^2$ is T, S, A, P, or I, wherein $X^3$ is V or K, and wherein $X^4$ is H, K, or Y.

In some embodiments of each or any of the above or below mentioned embodiments, the ultralong CDR3 comprises $CX^1X^2VHQ$ (SEQ ID NO: 230), wherein $X^1$ is T, S, A, or G, and wherein $X^2$ is T, S, A, P, or I.

In some embodiments of each or any of the above or below mentioned embodiments, the ultralong CDR3 comprises $CX^1X^2VX^3Q$ (SEQ ID NO: 232), wherein $X^1$ is T, S, A, or G, wherein $X^2$ is T, S, A, P, or I, and wherein $X^3$ is H, Y, or K.

In some embodiments of each or any of the above or below mentioned embodiments, the ultralong CDR3 comprises $CX^1X^2KKQ$ (SEQ ID NO: 234), wherein $X^1$ is T, S, A, or G, and wherein $X^2$ is T, S, A, P, or I.

In some embodiments of each or any of the above or below mentioned embodiments, the ultralong CDR3 comprises YTYNYEW (SEQ ID NO: 235).

In some embodiments of each or any of the above or below mentioned embodiments, the ultralong CDR3 comprises $YX^1YX^2$ (SEQ ID NO: 296), wherein $X^2$ is E or D.

In some embodiments of each or any of the above or below mentioned embodiments, the ultralong CDR3 comprises $YX^1YX^2Y$ (SEQ ID NO: 297).

In some embodiments of each or any of the above or below mentioned embodiments, the ultralong CDR3 comprises YEX (SEQ ID NO: 300), wherein X is H, W, N, F, I or Y.

In some embodiments of each or any of the above or below mentioned embodiments, the ultralong CDR3 comprises YDX (SEQ ID NO: 301), wherein X is H, W, N, F, I or Y.

In some embodiments of each or any of the above or below mentioned embodiments, the ultralong CDR3 comprises XYE (SEQ ID NO: 302), wherein X is T, S, N or I.

In some embodiments of each or any of the above or below mentioned embodiments, the ultralong CDR3 comprises XYD (SEQ ID NO: 303), wherein X is T, S, N or I.

In some embodiments of each or any of the above or below mentioned embodiments, the ultralong CDR3 comprises Y(E/D)X$^1$X$_n$W (SEQ ID NO: 498 with specific embodiments disclosed as SEQ ID NOS: 304-305), wherein X$^1$ is H, W, N, F, I or Y, and wherein n is 1-4.

In some embodiments of each or any of the above or below mentioned embodiments, the antibodies or binding fragments thereof are chimeric, human engineered, or humanized.

In some embodiments of each or any of the above or below mentioned embodiments, the ultralong CDR3 is a ruminant CDR3.

In some embodiments of each or any of the above or below mentioned embodiments, the ruminant is a cow.

The present disclosure also provides a library of polynucleotides encoding for antibodies or binding fragments thereof, wherein the encoded antibodies or binding fragments thereof comprise an ultralong CDR3.

In some embodiments of each or any of the above or below mentioned embodiments, the ultralong CDR3 is 35 amino acids in length or longer, 40 amino acids in length or longer, 45 amino acids in length or longer, 50 amino acids in length or longer, 55 amino acids in length or longer, or 60 amino acids in length or longer.

In some embodiments of each or any of the above or below mentioned embodiments, the ultralong CDR3 is 35 amino acids in length or longer.

In some embodiments of each or any of the above or below mentioned embodiments, the ultralong CDR3 comprises 3 or more cysteine residues, 4 or more cysteine residues, 5 or more cysteine residues, 6 or more cysteine residues, 7 or more cysteine residues, 8 or more cysteine residues, 9 or more cysteine residues, 10 or more cysteine residues, 11 or more cysteine residues, or 12 or more cysteine residues.

In some embodiments of each or any of the above or below mentioned embodiments, the ultralong CDR3 comprises 3 or more cysteine residues.

In some embodiments of each or any of the above or below mentioned embodiments, the antibodies or binding fragments thereof comprise a cysteine motif.

In some embodiments of each or any of the above or below mentioned embodiments, the cysteine motif is selected from the group consisting of SEQ ID NOS: 45-156. In some embodiments of each or any of the above or below mentioned embodiments, the cysteine motif is selected from the group consisting of SEQ ID NOS: 45-99. In some embodiments of each or any of the above or below mentioned embodiments, the cysteine motif is selected from the group consisting of SEQ ID NOS: 45-135. In some embodiments of each or any of the above or below mentioned embodiments, the cysteine motif is selected from the group consisting of SEQ ID NOS: 100-135. In some embodiments of each or any of the above or below mentioned embodiments, the cysteine motif is selected from the group consisting of SEQ ID NOS: 136-156.

In some embodiments of each or any of the above or below mentioned embodiments, the ultralong CDR3 comprises a non-human DH or a derivative thereof.

In some embodiments of each or any of the above or below mentioned embodiments, the ultralong CDR3 comprises a JH sequence or a derivative thereof.

In some embodiments of each or any of the above or below mentioned embodiments, the ultralong CDR3 comprises: a non-human VH sequence or a derivative thereof, a non-human DH sequence or a derivative thereof; and/or a JH sequence or derivative thereof.

In some embodiments of each or any of the above or below mentioned embodiments, the ultralong CDR3 comprises an additional amino acid sequence comprising two to six amino acid residues or more positioned between the VH sequence and the DH sequence.

In some embodiments of each or any of the above or below mentioned embodiments, the ultralong CDR3 comprises a non-bovine sequence.

In some embodiments of each or any of the above or below mentioned embodiments, the non-bovine sequence is a non-antibody or a human sequence.

In some embodiments of each or any of the above or below mentioned embodiments, the non-bovine sequence replaces at least a portion of the ultralong CDR3.

In some embodiments of each or any of the above or below mentioned embodiments, the non-antibody sequence is a hormone, lymphokine, interleukin, chemokine, cytokine, toxin, or combination thereof.

In some embodiments of each or any of the above or below mentioned embodiments, the non-bovine sequence is a cytokine.

In some embodiments of each or any of the above or below mentioned embodiments, the cytokine is granulocyte colony-stimulating factor (G-CSF).

In some embodiments of each or any of the above or below mentioned embodiments, the ultralong CDR3 comprises an additional sequence that is a linker.

In some embodiments of each or any of the above or below mentioned embodiments, the linker is linked to a C-terminus, a N-terminus, or both C-terminus and N-terminus of the non-antibody sequence.

In some embodiments of each or any of the above or below mentioned embodiments, the linker is (GGGGS)$_n$ (SEQ ID NO: 339), where n is an integer between 0 and 5. Alternatively, the linker is (GSG)n (SEQ ID NO: 342), GGGSGGGGS (SEQ ID NO: 337) or GGGGSGGGS (SEQ ID NO: 338).

In some embodiments of each or any of the above or below mentioned embodiments, the ultralong CDR3 comprises a X$^1$—X$^2$—X$^3$—X$^4$—X$^5$ motif (SEQ ID NO: 495), wherein X$^1$ is threonine (T), glycine (G), alanine (A), serine (S), or valine (V), wherein X$^2$ is serine (S), threonine (T), proline (P), isoleucine (I), alanine (A), valine (V), or asparagine (N), wherein X$_3$ is valine (V), alanine (A), threonine (T), or aspartic acid (D), wherein X$^4$ is histidine (H), threonine (T), arginine (R), tyrosine (Y), phenylalanine (F), or leucine (L), and wherein X$_5$ is glutamine (Q).

In some embodiments of each or any of the above or below mentioned embodiments, the X$^1$X$^2$X$^3$X$^4$X$^5$ motif (SEQ ID NO: 495) is TTVHQ (SEQ ID NO:159) or TSVHQ (SEQ ID NO: 160).

In some embodiments of each or any of the above or below mentioned embodiments, the ultralong CDR3 further comprises a (X$^a$X$^b$)$_z$ motif (SEQ ID NO: 496), wherein X$^a$ is an aromatic amino acid selected from the group consisting of: tyrosine (Y), phenylalanine (F), tryptophan (W), and histidine (H), wherein $X^b$ is any amino acid residue, and wherein z is 1-4.

In some embodiments of each or any of the above or below mentioned embodiments, the $(X^a X^b)_z$ motif (SEQ ID NO: 496) is YXYXYX (SEQ ID NO: 298).

In some embodiments of each or any of the above or below mentioned embodiments, the ultralong CDR3 comprises a $X^1 X^2 X^3 X^4 X^5 X_n (X^a X^b)_z$ motif (SEQ ID NO: 497), wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q), wherein $X^a$ is an aromatic amino acid selected from the group consisting of: tyrosine (Y), phenylalanine (F), tryptophan (W), and histidine (H), $X^b$ is any amino acid residue, wherein n is 27-54, and wherein z is 1-4.

In some embodiments of each or any of the above or below mentioned embodiments, the $X^1 X^2 X^3 X^4 X^5$ motif (SEQ ID NO: 495) is TTVHQ (SEQ ID NO: 159) or TSVHQ (SEQ ID NO: 160), and wherein the $(X^a-X^b)_z$ motif (SEQ ID NO: 496) is YXYXYX (SEQ ID NO: 298).

In some embodiments of each or any of the above or below mentioned embodiments, the ultralong CDR3 comprises TSVHQETKKYQ (SEQ ID NO. 157).

In some embodiments of each or any of the above or below mentioned embodiments, the ultralong CDR3 comprises VHQETKKYQ (SEQ ID NO: 158).

In some embodiments of each or any of the above or below mentioned embodiments, the ultralong CDR3 comprises CTTVHQXn (SEQ ID NO: 223).

In some embodiments of each or any of the above or below mentioned embodiments, the ultralong CDR3 comprises CTSVHQXn (SEQ ID NO: 224), wherein n is 1-8.

In some embodiments of each or any of the above or below mentioned embodiments, the ultralong CDR3 comprises TTVHQ (SEQ ID NO. 159).

In some embodiments of each or any of the above or below mentioned embodiments, the ultralong CDR3 comprises TSVHQ (SEQ ID NO. 160).

In some embodiments of each or any of the above or below mentioned embodiments, the ultralong CDR3 comprises VHQ (SEQ ID NO: 225).

In some embodiments of each or any of the above or below mentioned embodiments, the ultralong CDR3 comprises KKQ (SEQ ID NO: 226).

In some embodiments of each or any of the above or below mentioned embodiments, the ultralong CDR3 comprises VYQ (SEQ ID NO: 227).

In some embodiments of each or any of the above or below mentioned embodiments, the ultralong CDR3 comprises $CX^1 X^2 X^3 X^4 Q$ (SEQ ID NO: 228), wherein $X^1$ is T, S, A, or G, wherein $X^2$ is T, S, A, P, or I, wherein $X^3$ is V or K, and wherein $X^4$ is H, K, or Y.

In some embodiments of each or any of the above or below mentioned embodiments, the ultralong CDR3 comprises $CX^1 X^2 VHQ$ (SEQ ID NO: 230), wherein $X^1$ is T, S, A, or G, and wherein $X^2$ is T, S, A, P, or I.

In some embodiments of each or any of the above or below mentioned embodiments, the ultralong CDR3 comprises $CX^1 X^2 VX^3 Q$ (SEQ ID NO: 232), wherein $X^1$ is T, S, A, or G, wherein $X^2$ is T, S, A, P, or I, and wherein $X^3$ is H, Y, or K.

In some embodiments of each or any of the above or below mentioned embodiments, the ultralong CDR3 comprises $CX^1 X^2 KKQ$ (SEQ ID NO: 234), wherein $X^1$ is T, S, A, or G, and wherein $X^2$ is T, S, A, P, or I.

In some embodiments of each or any of the above or below mentioned embodiments, the ultralong CDR3 comprises YTYNYEW (SEQ ID NO: 235).

In some embodiments of each or any of the above or below mentioned embodiments, the ultralong CDR3 comprises $YX^1 YX^2$ (SEQ ID NO: 296), wherein $X^2$ is E or D.

In some embodiments of each or any of the above or below mentioned embodiments, the ultralong CDR3 comprises $YX^1 YX^2 Y$ (SEQ ID NO: 297).

In some embodiments of each or any of the above or below mentioned embodiments, the ultralong CDR3 comprises YEX (SEQ ID NO: 300), wherein X is H, W, N, F, I or Y.

In some embodiments of each or any of the above or below mentioned embodiments, the ultralong CDR3 comprises YDX (SEQ ID NO: 301), wherein X is H, W, N, F, I or Y.

In some embodiments of each or any of the above or below mentioned embodiments, the ultralong CDR3 comprises XYE (SEQ ID NO: 302), wherein X is T, S, N or I.

In some embodiments of each or any of the above or below mentioned embodiments, the ultralong CDR3 comprises XYD (SEQ ID NO: 303), wherein X is T, S, N or I.

In some embodiments of each or any of the above or below mentioned embodiments, the ultralong CDR3 comprises $Y(E/D)X^1 X_n W$ (SEQ ID NO: 498), wherein $X^1$ is H, W, N, F, I or Y, and wherein n is 1-4.

In some embodiments of each or any of the above or below mentioned embodiments, the antibodies or binding fragments thereof are chimeric, human engineered, or humanized.

In some embodiments of each or any of the above or below mentioned embodiments, the ultralong CDR3 is a ruminant CDR3.

In some embodiments of each or any of the above or below mentioned embodiments, the ruminant is a cow.

In some embodiments of each or any of the above or below mentioned embodiments, the antibodies or binding fragments thereof are present in a spatially addressed format.

In some embodiments of each or any of the above or below mentioned embodiments, the polynucleotides coding for the antibodies or binding fragments thereof are present in a spatially addressed format.

The present disclosure also provides a library of vectors comprising any of the library of polynucleotides disclosed herein.

The present disclosure also provides a library of host cells comprising the any library of vectors disclosed herein.

In some embodiments of each or any of the above or below mentioned embodiments, the cell is a bacteria, virus, or bacteriophage.

In some embodiments of each or any of the above or below mentioned embodiments, the antibodies or binding fragments thereof are displayed on the cell surface.

In some embodiments of each or any of the above or below mentioned embodiments, the antibodies or binding fragments thereof are secreted from the cell.

In some embodiments of each or any of the above or below mentioned embodiments, the antibodies or binding fragments thereof are present in a spatially addressed format.

The present disclosure also provides an antibody or binding fragment thereof comprising an ultralong CDR3, wherein the ultralong CDR3 comprises a non-bovine sequence.

In some embodiments of each or any of the above or below mentioned embodiments, the ultralong CDR3 is 35 amino acids in length or longer, 40 amino acids in length or longer, 45 amino acids in length or longer, 50 amino acids in length or longer, 55 amino acids in length or longer, or 60 amino acids in length or longer.

In some embodiments of each or any of the above or below mentioned embodiments, the ultralong CDR3 is 35 amino acids in length or longer.

In some embodiments of each or any of the above or below mentioned embodiments, the ultralong CDR3 comprises 3 or more cysteine residues, 4 or more cysteine residues, 5 or more cysteine residues, 6 or more cysteine residues, 7 or more cysteine residues, 8 or more cysteine residues, 9 or more cysteine residues, 10 or more cysteine residues, 11 or more cysteine residues, or 12 or more cysteine residues.

In some embodiments of each or any of the above or below mentioned embodiments, the ultralong CDR3 comprises 3 or more cysteine residues.

In some embodiments of each or any of the above or below mentioned embodiments, the antibodies or binding fragments thereof comprise a cysteine motif.

In some embodiments of each or any of the above or below mentioned embodiments, the cysteine motif is selected from the group consisting of SEQ ID NOS: 45-156. In some embodiments of each or any of the above or below mentioned embodiments, the cysteine motif is selected from the group consisting of SEQ ID NOS: 45-99. In some embodiments of each or any of the above or below mentioned embodiments, the cysteine motif is selected from the group consisting of SEQ ID NOS: 45-135. In some embodiments of each or any of the above or below mentioned embodiments, the cysteine motif is selected from the group consisting of SEQ ID NOS: 100-135. In some embodiments of each or any of the above or below mentioned embodiments, the cysteine motif is selected from the group consisting of SEQ ID NOS: 136-156.

In some embodiments of each or any of the above or below mentioned embodiments, the non-bovine sequence is a non-antibody sequence or a human sequence.

In some embodiments of each or any of the above or below mentioned embodiments, the ultralong CDR3 comprises a non-human DH or a derivative thereof.

In some embodiments of each or any of the above or below mentioned embodiments, the ultralong CDR3 comprises a JH sequence or a derivative thereof.

In some embodiments of each or any of the above or below mentioned embodiments, the ultralong CDR3 comprises: a non-human VH sequence or a derivative thereof, a non-human DH sequence or a derivative thereof and/or a JH sequence or derivative thereof.

In some embodiments of each or any of the above or below mentioned embodiments, the ultralong CDR3 comprises an additional amino acid sequence comprising two to six amino acid residues or more positioned between the VH sequence and the DH sequence.

In some embodiments of each or any of the above or below mentioned embodiments, the non-bovine sequence replaces at least a portion of the ultralong CDR3.

In some embodiments of each or any of the above or below mentioned embodiments, the non-bovine sequence is a hormone, lymphokine, interleukin, chemokine, cytokine, toxin, or combination thereof.

In some embodiments of each or any of the above or below mentioned embodiments, the non-bovine sequence is a cytokine.

In some embodiments of each or any of the above or below mentioned embodiments, the cytokine is granulocyte colony-stimulating factor (G-CSF).

In some embodiments of each or any of the above or below mentioned embodiments, the antibodies or binding fragments thereof are chimeric, human engineered, or humanized.

In some embodiments of each or any of the above or below mentioned embodiments, the ultralong CDR3 is a ruminant CDR3.

In some embodiments of each or any of the above or below mentioned embodiments, the ruminant is a cow.

The present disclosure also provides a polynucleotide encoding for any antibody or binding fragment thereof disclosed herein.

The present disclosure also provides a vector comprising any polynucleotide encoding for the antibody or binding fragment thereof disclosed herein.

The present disclosure also provides a host cell comprising any vector disclosed herein.

In some embodiments of each or any of the above or below mentioned embodiments, the cell is a bacteria, virus, or bacteriophage.

In some embodiments of each or any of the above or below mentioned embodiments, the antibody or binding fragment thereof is displayed on the surface of the cell.

In some embodiments of each or any of the above or below mentioned embodiments, the antibody or binding fragment thereof is secreted from the cell.

The present disclosure also provides a method of producing an antibody or binding fragment thereof comprising an ultralong CDR3 or fragment thereof comprising culturing a host cell comprising a polynucleotide encoding any of the antibodies disclosed herein under conditions wherein the polynucleotide sequence is expressed and the antibody or binding fragment thereof comprising an ultralong CDR3 or fragment thereof is produced.

In some embodiments of each or any of the above or below mentioned embodiments, the methods further comprise recovering the antibody or binding fragment thereof comprising an ultralong CDR3 or fragment thereof from the host cell culture.

The present disclosure also provides a pharmaceutical composition comprising any antibody or binding fragment thereof disclosed herein.

The present disclosure also provides a method of treating a mammal in need thereof comprising administering to the mammal an amount of any antibody disclosed herein.

In some embodiments of each or any of the above or below mentioned embodiments, the mammal is a human.

In some embodiments is a recombinant antibody or fragment thereof, wherein at least a portion of the recombinant antibody or fragment thereof is based on or derived from at least a portion of an ultralong CDR3.

In some embodiments is an antibody or fragment thereof comprising at least a portion of an ultralong CDR3 sequence and at least a portion of a non-bovine sequence.

In some embodiments is an antibody or fragment thereof comprising (a) a first antibody sequence, wherein at least a portion of the first antibody sequence is derived from at least a portion of an ultralong CDR3; (b) a non-antibody sequence; and (c) optionally, a second antibody sequence, wherein at least a portion of the second antibody sequence is derived from at least a portion of an ultralong CDR3.

The antibodies disclosed herein may be a chimeric, human engineered, or humanized antibody. The antibodies disclosed herein may be a bovine engineered, bovinized, or fully bovine antibody. The antibodies disclosed herein may comprise a Fab, a scFv, dsFv, diabody, (dsFv)$_2$, minibody, flex minibody or bi-specific fragment. The antibodies disclosed herein may be an isolated antibody.

The antibodies disclosed herein may further comprise a non-antibody sequence. The non-antibody sequence may be derived from a mammal. The mammal may be a bovine, human, or non-bovine mammal. The antibodies disclosed herein may comprise a non-antibody sequence derived from a non-bovine animal. The non-bovine animal may be a scorpion. The non-bovine animal may be a lizard. The lizard may be a gila monster. The non-antibody sequence may be a derived from a growth factor. The growth factor may be a GCSF, GMCSF or FGF21. The GCSF may be a bovine GCSF. Alternatively, the GCSF may be a human GCSF. The GMCSF and/or the FGF21 may be from a human. The non-antibody sequence may be a derived from a cytokine. The cytokine may be a beta-interferon. The non-antibody sequence may be a derived from a hormone. The hormone may be an exendin-4, GLP-1, somatostatin, or erythropoietin. The GLP-1 and/or erythropoietin may be from a human. The non-antibody sequence may be a derived from a toxin. The toxin may be a Moka1, VM-24, ziconotide, chlorotoxin, or protoxin2 (ProTxII). The non-antibody sequence may be IL8, ziconotide, somatostatin, chlorotoxin, SDF1(alpha), or IL21. The non-antibody sequence may comprise an amino acid sequence based on or derived from any of SEQ ID NOS: 317-332. The non-antibody sequence may replace at least a portion of the ultralong CDR3. The non-antibody sequence may be inserted into the sequence of the ultralong CDR3. The non-antibody sequence may be conjugated to at least a portion of the antibody (e.g., ultralong CDR3, variable region, heavy chain, light chain). The non-antibody sequence may be attached to the ultralong CDR3, linker, cleavage site, non-bovine sequence, non-ultralong CDR3 antibody sequence, or combination thereof. The non-antibody sequence may be adjacent to the ultralong CDR3, linker, cleavage site, non-bovine sequence, non-ultralong CDR3 antibody sequence, or combination thereof.

The antibodies disclosed herein may comprise an ultralong CDR3 may be based on or derived from a cow ultralong CDR3. At least a portion of the antibodies disclosed herein may be from a mammal. At least a portion of the first antibody sequence and/or at least a portion of the second antibody sequence of the antibodies disclosed herein may be from a mammal. The mammal may be a bovine, human or non-bovine mammal.

The antibodies disclosed herein may comprise 3 or more amino acids in length. The antibodies disclosed herein may comprise a sequence that may be based on or derived from an ultralong CDR3 disclosed herein. The antibodies disclosed herein may comprise 1 or more amino acid residues based on or derived from a stalk domain of the ultralong CDR3. The antibodies disclosed herein may comprise 1 or more amino acid residues based on or derived from a knob domain of the ultralong CDR3.

At least a portion of the antibodies disclosed herein may be based on or derived from at least a portion of an ultralong CDR3 disclosed herein. The portion of the antibody based on or derived from at least a portion of the ultralong CDR3 may be 20 or fewer amino acids in length. The portion of the antibody based on or derived from at least a portion of the ultralong CDR3 may be 3 or more amino acids in length The antibodies disclosed herein may comprise 1 or more conserved motifs derived from a stalk domain of the ultralong CDR3. The 1 or more conserved motifs derived from the stalk domain of the ultralong CDR3 may comprise any of the stalk domain conserved motifs disclosed herein.

The portion of the ultralong CDR3s disclosed herein may comprise at least a portion of a stalk domain of the ultralong CDR3, at least a portion of the knob domain of the ultralong CDR3, or a combination thereof.

The antibodies disclosed herein may comprise a sequence selected from any one of SEQ ID NOS: 157-307 and SEQ ID NOS: 333-336. The antibodies disclosed herein may comprise a sequence that may be 50% or more homologous to a sequence selected from any one of SEQ ID NOS: 157-224 and 235-295.

A portion of any of the antibodies disclosed herein may be based on or derived from at least a portion of a single ultralong CDR3 sequence. A portion of the antibodies disclosed herein may be based on or derived from at least a portion of two or more different ultralong CDR3 sequences.

In any of the embodiments disclosed herein, the portion of the ultralong CDR3 is based on or derived from a BLV1H12 ultralong CDR3 sequence. The portion of the ultralong CDR3 may be based on or derived from a sequence that may be 50% or more homologous to a BLV1H12 ultralong CDR3 sequence. The portion of the ultralong CDR3 may be based on or derived from a BLV5B8, BLVCV1, BLV5D3, BLV8C11, BF1H1, or F18 ultralong CDR3 sequence. The portion of the ultralong CDR3 may be based on or derived from a sequence that may be 50% or more homologous to a BLV5B8, BLVCV1, BLV5D3, BLV8C11, BF1H1, or F18 ultralong CDR3 sequence.

The antibodies disclosed herein may comprise a first and/or second antibody sequence that comprises 3 or more amino acids in length. A portion of the first antibody sequence derived from at least a portion of the ultralong CDR3 and/or the portion of the second antibody sequence derived from at least a portion of the ultralong CDR3 may be 20 or fewer amino acids in length. A portion of the first antibody sequence derived from at least a portion of the ultralong CDR3 and/or the portion of the second antibody sequence derived from at least a portion of the ultralong CDR3 may be 3 or more amino acids in length.

In any of the embodiments disclosed herein, the first and/or second antibody sequences comprise one or more amino acid residues based on or derived from a stalk domain of the ultralong CDR3. The first and/or second antibody sequences may comprise one or more amino acid residues based on or derived from a knob domain of the ultralong CDR3. The one or more amino acid residues derived from the knob domain of the ultralong CDR3 may be a serine and/or cysteine residue. The first and/or second antibody sequences may comprise one or more conserved motifs derived from a stalk domain of the ultralong CDR3. The one or more conserved motifs derived from the stalk domain of the ultralong CDR3 may comprise a sequence selected from any one of SEQ ID NOS: 157-307 and SEQ ID NOS: 333-336.

In any of the embodiments disclosed herein, the portion of the first antibody sequence derived from at least a portion of the ultralong CDR3 and/or the portion of the second antibody sequence derived from at least a portion of the ultralong CDR3 comprises a sequence selected from any one of SEQ ID NOS: 157-307 and SEQ ID NOS: 333-336. The portion of the first antibody sequence derived from at least a portion of the ultralong CDR3 and/or the portion of the second antibody sequence derived from at least a portion of the ultralong CDR3 may comprise a sequence that may be 50% or more homologous to a sequence selected from any one of SEQ ID NOS: 157-224 and 235-295. The portion of the first antibody sequence derived from at least a portion of the ultralong CDR3 may comprise a sequence selected from any one of SEQ ID NOS: 157-234. The portion of the first antibody sequence derived from at least a portion of the ultralong CDR3 may comprise a sequence that may be 50% or more homologous to a sequence selected from any one of SEQ ID NOS: 157-224.

In any of the embodiments disclosed herein, the portion of the second antibody sequence derived from at least a portion of the ultralong CDR3 comprises a sequence selected from any one of SEQ ID NOS: 235-307 and SEQ ID NOS: 333-336. The portion of the second antibody sequence derived from at least a portion of the ultralong CDR3 may comprise a sequence that may be 50% or more homologous to a sequence selected from any one of SEQ ID NOS: 235-295. The portion of the first antibody sequence derived from at least a portion of the ultralong CDR3 and the portion of the second antibody sequence derived from at least a portion of the ultralong CDR3 may be derived from the same ultralong CDR3 sequence.

In any of the embodiments disclosed herein, the portion of the first antibody sequence derived from at least a portion of the ultralong CDR3 and the portion of the second antibody sequence derived from at least a portion of the ultralong CDR3 is derived from two or more different ultralong CDR3 sequences. The portions of the ultralong CDR3 of the first and/or second antibody sequences may be based on or derived from a BLV1H12 ultralong CDR3 sequence. The portions of the ultralong CDR3 of the first and/or second antibody sequences may be based on or derived from a sequence that may be 50% or more homologous to a BLV1H12 ultralong CDR3 sequence. The portions of the ultralong CDR3 of the first and/or second antibody sequences may be based on or derived from a BLV5B8, BLVCV1, BLV5D3, BLV8C11, BF1H1, or F18 ultralong CDR3 sequence. The portions of the ultralong CDR3 of the first and/or second antibody sequences may be based on or derived from a sequence that may be 50% or more homologous to a BLV5B8, BLVCV1, BLV5D3, BLV8C11, BF1H1, or F18 ultralong CDR3 sequence.

In any of the embodiments disclosed herein, the ultralong CDR3 is based on or derived from an ultralong CDR3 that may be 35 or more amino acids in length. The ultralong CDR3 may be based on or derived from an ultralong CDR3 comprising 3 or more cysteine residues.

In any of the embodiments disclosed herein, the ultralong CDR3 is based on or derived from an ultralong CDR3 may comprise one or more cysteine motifs. The one or more cysteine motifs may be selected from the group consisting of SEQ ID NOS: 45-156. In some embodiments of each or any of the above or below mentioned embodiments, the cysteine motif is selected from the group consisting of SEQ ID NOS: 45-99. In some embodiments of each or any of the above or below mentioned embodiments, the cysteine motif is selected from the group consisting of SEQ ID NOS: 45-135. In some embodiments of each or any of the above or below mentioned embodiments, the cysteine motif is selected from the group consisting of SEQ ID NOS: 100-135. In some embodiments of each or any of the above or below mentioned embodiments, the cysteine motif is selected from the group consisting of SEQ ID NOS: 136-156.

The antibodies disclosed herein may be based on or derived from an ultralong CDR3 that may be 35 or more amino acids in length. The antibodies disclosed herein may be based on or derived from an ultralong CDR3 comprising 3 or more cysteine residues. The antibodies disclosed herein may be based on or derived from an ultralong CDR3 may comprise 1 or more cysteine motifs.

The antibodies disclosed herein may comprise an ultralong CDR3 that is 35 or more amino acids in length. The antibodies disclosed herein may comprise an ultralong CDR3 comprising 3 or more cysteine residues. The antibodies disclosed herein may comprise an ultralong CDR3 comprising one or more cysteine motifs.

In any of the embodiments disclosed herein, the ultralong CDR3 may be a heavy chain CDR3. The ultralong CDR3 may comprise an amino acid sequence derived from or based on a non-human DH sequence. The ultralong CDR3 may comprise an amino acid sequence derived from or based on a JH sequence. The ultralong CDR3 may comprise an amino acid sequence derived from or based on a non-human VH sequence; an amino acid sequence derived from or based on a non-human DH sequence; and/or an amino acid sequence derived from or based on a JH sequence. The ultralong CDR3 may comprise an additional amino acid sequence comprising at least about two amino acid residues positioned between the VH derived amino acid sequence and the DH derived amino acid sequence.

Any of the antibodies disclosed herein may comprise a sequence based on or derived from a sequence selected from SEQ ID NOS: 24-44, the antibody or binding fragment thereof encoded by a DNA sequence based on or derived from the DNA of SEQ ID NOS: 2-22. Any of the antibodies disclosed herein may comprise a sequence based on or derived from a sequence selected from SEQ ID NO: 23, the antibody or binding fragment thereof encoded by a DNA sequence based on or derived from the DNA of SEQ ID NO: 1.

Any of the ultralong CDR3s disclosed herein may comprise a sequence based on or derived from a sequence selected from SEQ ID NOS: 24-44. Any of the antibodies disclosed herein may comprise a sequence based on or derived from a sequence selected from SEQ ID NO: 23. Any of the ultralong CDR3s disclosed herein may be encoded by a DNA sequence that may be derived from or based on SEQ ID NOS: 2-22. Any of the antibodies disclosed herein may comprise a portion encoded by a DNA sequence that may be derived from or based on SEQ ID NO: 1.

Any of the antibodies disclosed herein may comprise one or more linkers. Any of the antibodies disclosed herein may comprise a first linker sequence. Any of the antibodies disclosed herein may comprise a second linker sequence. The first and second linker sequences may comprise the same sequence. The first and second linker sequences may comprise different sequences. The first and/or second linker sequences may be the same length. The first and/or second linker sequences may be different lengths. The first and/or second linker sequences may be 3 or more amino acids in length.

The first and/or second linker sequence may attach the non-antibody sequence to the portion based on or derived from the portion of the ultralong CDR3. The first and/or second linker sequences may attach the non-antibody sequence to the first antibody sequence. The first and/or second linker sequences may attach the non-antibody sequence to the second antibody sequence. The first and/or second linker sequences may be adjacent to a non-antibody sequence, a portion of an ultralong CDR3 sequence, a cleavage site sequence, a non-bovine sequence, an antibody sequence, or a combination thereof.

The first and/or second linker sequences may comprise one or more glycine residues. The first and/or second linker sequences may comprise two or more consecutive glycine residues. The first and/or second linker sequences may comprise one or more serine residues. The first and/or second linker sequence may comprise one or more polar amino acid residues. The one or more polar amino acid residues may be selected from serine, threonine, asparagine, or glutamine. The the polar amino acid residues may comprise uncharged side chains. The first and/or second linker sequences may comprise the sequence (GGGGS)$_n$, wherein n=1 to 5 (SEQ ID NO: 499); the sequence GGGSGGGGS (SEQ ID NO: 337); the sequence GGGGSGGGS (SEQ ID NO: 338); the sequence of (GSG)n (SEQ ID NO: 342), wherein n is greater than or equal to one; or a combination thereof.

Any of the antibodies disclosed herein may comprise one or more cleavage sites. The one or more cleavage sites may comprise a recognition site for a protease. The protease may be a Factor Xa or thrombin. The one or more cleavage sites may comprise an amino acid sequence of IEGR (SEQ ID NO: 510).

The one or more cleavage site may be between a first antibody sequence and the non-antibody sequence. The one or more cleavage sites may be between a second antibody sequence and the non-antibody sequence. The one or more cleavage sites may be between the one or more linkers and the non-antibody sequence. The one or more cleavage sites may be between a first antibody sequence and the one or more linkers. The one or more cleavage sites may be between a second antibody sequence and the one or more linkers. The one or more cleavage sites may be adjacent to a non-antibody sequence, a portion of an ultralong CDR3 sequence, a linker sequence, an antibody sequence, or a combination thereof.

In some embodiments is library of antibodies or binding fragments thereof, wherein the antibodies or binding fragments thereof may comprise an ultralong CDR3.

In some embodiments is library of antibodies or binding fragments thereof, wherein the antibodies or binding fragments thereof may comprise any of the antibodies disclosed herein.

In some embodiments is nucleic acid library comprising a plurality of polynucleotides comprising sequences coding for antibodies or binding fragments thereof, wherein the antibodies or binding fragments thereof may comprise an ultralong CDR3.

In some embodiments is nucleic acid library comprising a plurality of polynucleotides comprising sequences coding for antibodies or binding fragments thereof, wherein the antibodies or binding fragments thereof may comprise any of the antibodies disclosed herein.

In some embodiments is polynucleotide comprising a nucleic acid sequence that encodes a variable region, wherein the variable region may comprise an ultralong CDR3.

In some embodiments is vector comprising a polynucleotide, wherein the polynucleotide comprises a nucleic acid sequence that encodes a variable region, wherein the variable region may comprise an ultralong CDR3.

In some embodiments is host cell comprising a polynucleotide, wherein the polynucleotide comprises a nucleic acid sequence that encodes a variable region, wherein the variable region may comprise an ultralong CDR3.

In some embodiments is polynucleotide comprising a nucleic acid sequence that encodes the antibody or binding fragment thereof of any of the antibodies disclosed herein.

In some embodiments is vector comprising a polynucleotide, wherein the polynucleotide comprises a nucleic acid sequence that encodes the antibody or binding fragment thereof of any of the antibodies disclosed herein.

In some embodiments is host cell comprising a polynucleotide, wherein the polynucleotide comprises a nucleic acid sequence that encodes the antibody or binding fragment thereof of any of the antibodies disclosed herein.

In some embodiments is method of producing an antibody or binding fragment thereof comprising an ultralong CDR3 or fragment thereof comprising culturing a host cell comprising a polynucleotide, wherein the polynucleotide may comprise a nucleic acid sequence that encodes the antibody or binding fragment thereof of any of the antibodies disclosed herein under conditions wherein the polynucleotide sequence may be expressed and the antibody or binding fragment thereof comprising an ultralong CDR3 or fragment thereof may be produced. The method may comprise recovering the antibody or binding fragment thereof comprising the ultralong CDR3 or fragment thereof from the host cell culture.

In some embodiments is pharmaceutical composition comprising any of the antibodies disclosed herein. The pharmaceutical compostion may comprise two or more antibodies, wherein at least one of the two or more antibodies comprises at least a portion of an ultralong CDR3.

In some embodiments is pharmaceutical composition comprising (a) an antibody or fragment thereof comprising sequence based on or derived from at least a portion of an ultralong CDR3; and (b) a pharmaceutically acceptable excipient.

In some embodiments is method of treating a disease or condition in a subject in need thereof comprising administering to the mammal a therapeutically effective amount of any of the antibodies disclosed herein. In some instances, the antibodies disclosed herein comprise an ultralong CDR3 sequence and a non-antibody sequence. In some instances, the non-antibody sequence is selected from the group comprising Moka1, Vm24, human GLP-1, Exendin-4, beta-interferon, human EPO, human FGF21, human GMCSF, human interferon-beta, bovine GCSF, human GCSF, be IL8, ziconotide, somatostatin, chlorotoxin, SDF1(alpha), IL21 and a derivative or variant thereof. The non-antibody sequence may comprise an amino acid sequence based on or derived from any of SEQ ID NOS: 317-332.

The disease or condition may be selected from the group comprising autoimmune disease, heteroimmune disease or condition, inflammatory disease, pathogenic infection, thromboembolic disorder, respiratory disease or condition, metabolic disease, central nervous system (CNS) disorder, bone disease, cancer, blood disorder, obesity, diabetes, osteoporosis, anemia, or pain.

The disease or condition would benefit from the modulation of an ion channel. The ion channel may be selected from the group comprising a potassium ion channel, sodium ion channel, or acid sensing ion channel. The ion channel may be selected from the group comprising Kv1.3 ion channel, Nav1.7 ion channel and acid sensing ion channel (ASIC).

The disease or condition would benefit from the modulation of a receptor. The receptor may be selected from the group comprising GLP1R, GCGR, EPO receptor, FGFR, FGF21R, CSFR, GMCSFR, IL8R, IL21R and GCSFR.

The disease or condition may be mastitis.

The subject may be a mammal. The mammal may be a bovine or human.

In some embodiments are crystals based on or derived from the antibodies disclosed herein. The crystals may have a space group $P2_12_12_1$. In some instances, the crystal has the unit cell dimensions of "a" between about 40 to 80 angstroms, between 45 to about 75 angstroms, or between about 50 to about 75 angstroms; "b" between about 40 to 140 angstroms, between about 50 to about 130 angstroms, between about 55 to about 130 angstroms; and "c" between 100 to about 350 angstroms, between 120 to about 340 angstroms, or between about 125 to about 330 angstroms. The crystal may comprise a bovine antibody or portion thereof. The crystal may comprise a Fab fragment based on or derived from a bovine antibody. The crystal may be an isolated crystal.

In some embodiments, is an isolated crystal comprising a bovine antibody Fab fragment comprising SEQ ID NO: 24 and SEQ ID NO: 23, wherein the crystal has a space group $P2_12_12_1$ and unit cell dimensions of a=71.4 angstroms, b=127.6 angstroms and c=127.9 angstroms.

In some embodiments, is an isolated crystal comprising a bovine antibody Fab fragment comprising SEQ ID NO: 340 and SEQ ID NO: 341, wherein the crystal has a space group $P2_12_12_1$ and unit cell dimensions of a=54.6 angstroms, b=53.7 angstroms and c=330.5 angstroms.

In any or all of the above or below disclosure (e.g., antibodies, uses, or methods) or embodiments utilizing an antibody comprising an ultralong CDR3, any antibody comprising an ultralong CDR3 may be used including, for example, any of the above mentioned antibodies comprising an ultralong CDR3.

BRIEF DESCRIPTION OF THE DRAWINGS

The foregoing summary, as well as the following detailed description of the disclosure, will be better understood when read in conjunction with the appended figures. For the purpose of illustrating the disclosure, shown in the figures are embodiments which are presently preferred. It should be understood, however, that the disclosure is not limited to the precise arrangements, examples and instrumentalities shown.

FIG. 1A shows a comparison of CDR H3 length amongst murine, human, and bovine repertoires. An ultralong subset of over 60 amino acids is uniquely found in bovine heavy chains. FIG. 1B shows sequences (SEQ ID NOS 343-359, respectively, in order of appearance) of representative CDR H3 from murine (mu), human (hu), or bovine sequences from the literature along with six bovine sequences (B-S1 to B-S4, and B-L1 and B-L2) from our deep sequencing results. The conserved cysteine of framework 3 and tryptophan of framework 4 that define CDR H3 boundaries in all antibody variable regions are shaded in grey for reference. The lengths of the CDR H3s are indicated at the right. The murine antibodies include D44.1, an anti-HEL antibody, 93F3, an aldolase, and OKT3, a therapeutic antibody targeting human CD3. This antibody is unusual in having a free cysteine in CDR H3. The human antibodies include Yvo, a cryoglobulin, CR6261, an anti-influenza A hemaglutinin, and PG9, an anti-HIV antibody which has one of the longest human CDR H3s. The bovine antibodies represent the ultralong sequences in the literature, and short sequences for comparison. BLV5B8 and BLV1H12 (indicated in bold) were used in our structure determinations. Relatively conserved TTVHQ (SEQ ID NO: 159) and CPDG (SEQ ID NO: 500) motifs are in bold. FIG. 1C shows crystal structures of BLV1H12 (left) and BLV5B8 (middle) Fabs compared to the 93F3 Fab with a "normal" CDR H3 (right). A superlong, two β-stranded stalk protrudes from each bovine VH immunoglobulin domain and terminates in an unusual three disulfide-linked knob domain.

FIGS. 2A-2C present the structural diversity in ultralong bovine antibodies. FIG. 2A shows a comparison of the structure of the two knobs showing differences in disulfide patterns. Close up views of the knobs of BLV1H12 (left) and BLV5H8 (right) are shown, in addition to a two-dimensional representation of the knob and its disulfide pattern. Disulfides are in numbered and circled. The sequences of the knob regions are shown below (SEQ ID NOS 360 and 361, respectively), with cysteines conserved with the $D_H2$ germline gene segment underlined. The disulfide pattern is indicated above each sequence. FIG. 2B shows an overlay of the variable regions of BLV1H12 and BLV5B8 shows structural homology in the variable regions except the upper part of the stalk and knob, which are significantly divergent. FIG. 2C shows surface and charge density representation of BLV1H12 (left) and BLV5B8 (right) showing different shapes and charge in the knob region.

FIGS. 3A-3C present the genetic basis for ultralong antibody formation. FIG. 3A shows the identification of $V_HBUL$ (SEQ ID NOS 362 and 363, respectively, in order of appearance), a germline variable region used in ultralong antibodies. The leader sequence is in light grey, coding sequence is indicated with the amino acid translation above, the intron is in italics, and the unique TTVHQ extension (SEQ ID NO: 159), which forms a portion of the ascending strand of the stalk is in bold. The recombination signal sequence heptamer and nonamer are underlined. FIG. 3B shows the $V_HBUL$ region is found on chromosome 21. Partial cattle metaphase spread (left) and enlarged chromosome 21 (top right) showing the location of $V_HBUL$ region in BTA21q24 by two-color FISH with BAC clones 318H2 and 14-74H6. International nomenclature for BTA21 is depicted at the bottom. FIG. 3C shows a schematic of the bovine immunoglobulin loci depicting $V_HBUL$, $D_H2$, and $V_\lambda 1x$, which are preferentially used in ultralong antibodies. The process of V(D)J recombination assembles the gene segments to form functional ultralong heavy and light chain genes. (bottom left) The V-D-J regions mapped onto the BLV1H12 Fab structure. $V_HBUL$ is unique in encoding CDR H1 and CDR H2 residues that interact with the stalk, as well as a TTVHQ motif (SEQ ID NO: 159) that initiates the ascending β-strand. Similarly, the $V_\lambda 1x$ light chain encodes CDR L1 and CDR L2 residues that interact with the stalk. Arrows indicate areas of potential junctional diversity. Relatively long V-D insertions are indicated in purple. It is unclear whether this sequence results from N-additions, gene conversion, or another mechanism. "CPDG" and "YXYXY" disclosed as SEQ ID NOS 500 and 297, respectively. (bottom right) A detailed depiction of the interactions of CDR H1, H2, L1, and L2 with the stalk of BLV1H12, as well as the location of the YxYxY motif (SEQ ID NO: 297) of the descending strand.

FIG. 4A shows the distribution of the number of cysteines in bovine ultralong CDR H3s of IgM and IgG. FIG. 4B shows the length distribution of ultralong CDR H3s. Note that clonal sequences selected during an immune response can bias the proportion at any given length. FIG. 4C shows representative sequences of ultralong bovine VH CDR H3s (SEQ ID NOS 364-366, 358, and 368-388, respectively, in order of appearance). The terminal portion of the V$_H$BUL region is shown, along with junctional diversity at the V-D joint, D$_H$2 and JH (top). The sequences of BLVH12 and BLV5B8 are shown for comparison, followed by 20 ultralong CDR H3 sequences (bottom). Cysteines conserved with D$_H$2 are underlined. The conserved cysteine and tryptophan that define the CDR H3 boundaries in all antibody variable regions are highlighted in grey for reference. The CPDG motif (SEQ ID NO: 500) is underlined in grey and the region of the descending strand encoding a YxYxY motif (SEQ ID NO: 297) is underlined in grey.

FIG. 5A shows that the consensus of ultralong CDR H3 deep sequences aligns with D$_H$2 (alignment discloses SEQ ID NOS 389-393, respectively, in order of appearance). A consensus sequence for three deep sequencing runs (from two cows) were determined, and aligned with one another and with D$_H$2. The consensus aligns well except for some areas of insertions/deletions. Thus, either a single DH gene, or highly related genes, produce the diversity of sequences in ultralong CDR H3 antibodies. FIG. 5B shows that the D$_H$2 gene region analysis showing residues that can readily mutate to cysteine, including SH hotspots. The nucleotide sequence is above and translated amino-acid sequence below (SEQ ID NOS 394 and 395, respectively). RGYW hotspots, which are recognized by AID for SH and/or gene conversion, are boxed. Nucleotides at positions 3, 15, 19, 21, 25, 27, 31, 33, 39, 43, 45, 49, 51, 57, 60, 64, 73, 75, 79, 81, 84, 88, 90, 93, 97, 102, 106, 112, 117, 121, 123, 127, 129, 133, 139, and 145 in (B) can be altered in a single mutation to a cysteine-encoding codon. FIG. 5C shows affinity maturation groups show mutation to and from cysteine. Several groups of clonally related sequences were identified and analyzed for somatic hypermutation. Three groups are shown as examples (labeled 1 to 3 on the left). Sequence differences from cysteine are highlighted in grey. The number of times each sequence is represented in the cluster is shown at the right. FIG. 5C discloses SEQ ID NOS 396-410, respectively, in order of appearance.

FIG. 6A shows immunization experimental scheme for identifying antigen-specific, ultralong CDR H3 antibodies. Heavy chain variable region mRNA was isolated, amplified by RT PCR, and paired with the invariant light chain to produce a small library of IgG produced in HEK293 cells. FIG. 6B shows ELISA of 132 ultralong CDR H3 antibodies against BVDV (left), and binding activity of the "hits" B8, B9, and H12 in a titration assay (right). FIG. 6C shows the sequences of B8, H9, and H12 in comparison to BLV1H12 and the germline D$_H$2 region. Lengths (L) of the CDR H3 are indicated at the right. Cysteines conserved with D$_H$2 are underlined. FIG. 6C discloses SEQ ID NOS 411-415, respectively, in order of appearance. FIG. 6D shows that H12 binds NS2-3 on cells. A flag-tagged BVDV NS2-3 protein construct was transfected into HEK293A cells and stained with anti-Flag as a positive control (left), the H12 antibody (middle), and B8 (right). Binding assays with untransfected cells are shown on the bottom.

FIGS. 7A-7B depict a model for ultralong CDR H3 diversification into novel minifolds. FIG. 7A shows a schematic of the D$_H$2 knob with 4 cysteines is shown on the left, with SH and/or gene conversion leading to a multitude of new cysteine patterns and new loops on the right. FIG. 7B shows mechanisms for generating antibody diversity. In humans and mice (left), combinatorial diversity through V(D)J recombination and V$_H$-V$_L$ pairing creates a multitude of different binding sites, which are further optimized following antigen exposure by somatic hypermutation. In cows (right), combinatorial diversity is severely limited; however, somatic mutation to and from cysteines can reshape the "knob" region, creating substantial structural diversity in ultralong CDR H3s. These antibodies may be further optimized through SH and may bind unique targets such as pores or channels.

FIG. 8A shows a ribbon diagram of a heavy chain region and light chain region of bovine BLV1H12 antibody. The boxed region highlights the extended region of the ultralong CDR3 comprising the stalk and knob domain. FIG. 8B shows a ribbon diagram of a growth factor (e.g., bovine G-CSF) inserted into or replacing a portion of the knob domain of a heavy chain region of a bovine BLV1H12 antibody. FIG. 8C shows a ribbon diagram of a toxin (e.g., Moka1, VM-24) inserted into or replacing a portion of the knob domain of a heavy chain region of a bovine BLV1H12 antibody. FIG. 8D shows a ribbon diagram of a receptor ligand (e.g., GLP-1, exendin-4) inserted into or replacing a portion of the knob domain of a heavy chain region of a bovine BLV1H12 antibody. FIG. 8E shows a ribbon diagram of a hormone (e.g., erythropoietin) inserted into or replacing a portion of the knob domain of a heavy chain region of a bovine BLV1H12 antibody. FIG. 8F shows a cartoon depicting a heavy chain region and light chain region of bovine BLV1H12 antibody. FIG. 8G shows a cartoon of a growth factor (e.g., bovine G-CSF) inserted into or replacing a portion of the knob domain of a heavy chain region of a bovine BLV1H12 antibody. FIG. 8H shows a cartoon of a toxin (e.g., Moka1, VM-24) inserted into or replacing a portion of the knob domain of a heavy chain region of a bovine BLV1H12 antibody. FIG. 8I shows a cartoon of a receptor ligand (e.g., GLP-1, exendin-4) inserted into or replacing a portion of the knob domain of a heavy chain region of a bovine BLV1H12 antibody. The left panel shows both ends of the receptor ligand inserted into or replacing a portion of the knob domain; the right panel shows the N-terminus of the receptor ligand released from the knob domain after treatment with a protease. FIG. 8J shows a cartoon of a hormone (e.g., erythropoietin) inserted into or replacing a portion of the knob domain of a heavy chain region of a bovine BLV1H12 antibody. Said attachment of the growth factor, toxin, receptor ligand, and hormone can be by means of a polypeptide linker of sequence GGGGS (SEQ ID NO: 501) (Ab-peptide L1) or GGGSGGGGS (SEQ ID NO: 337) and GGGGSGGGS (SEQ ID NO: 338) (Ab-peptide L2). Another construct (Ab-peptide L0) in which attachment is not by means of a linker is not shown in this cartoon.

FIGS. 9A-9E present illustrative mouse NFS-60 cell proliferative activity for the Ab-bGCSF fusion proteins. FIGS. 9A-9B depict proliferative activity of bovine G-CSF and human G-CSF respectively. FIG. 9C depicts the lack of proliferative activity for bovine BLV1H12 antibody in the absence of G-CSF. FIG. 9D depicts proliferative activity of bovine G-CSF inserted into or replacing a portion of the knob domain in the absence of a linker (Ab-bGCSF L0). FIG. 9E depicts proliferative activity of bovine G-CSF inserted into or replacing a portion of the knob domain by means of a polypeptide linker of sequence GGGGS (SEQ ID NO: 501) (Ab-bGCSF L1). Figure discloses SEQ ID NO: 509.

FIG. 10A depicts proliferative activity of bovine G-CSF. FIG. 10B depicts proliferative activity of human G-CSF. FIG. 10C depicts the lack of proliferative activity for bovine BLV1H12 antibody (Ab) in the absence of G-CSF. FIG. 10D depicts proliferative activity of bovine G-CSF inserted into or replacing a portion of the knob domain in the absence of a linker (Ab-bGCSF L0). FIG. 10E depicts proliferative activity of bovine G-CSF inserted into or replacing a portion of the knob domain, said attachment by disclosed herein further comprise a cleavage site. A portion of the antibodies and fragments disclosed herien may be based on or derived from an antibody sequence from a different animal or specie from with the ultralong CDR3 is derived. For example, the ultralong CDR3 may be derived from or based on a bovine antibody sequence and the additional and another portion of the antibody sequence may be derived from or based on a non-bovine antibody sequence. Further details of the antibodies and fragments thereof are described herein.

Ultralong CDR3 Proteins

Figure 1A:
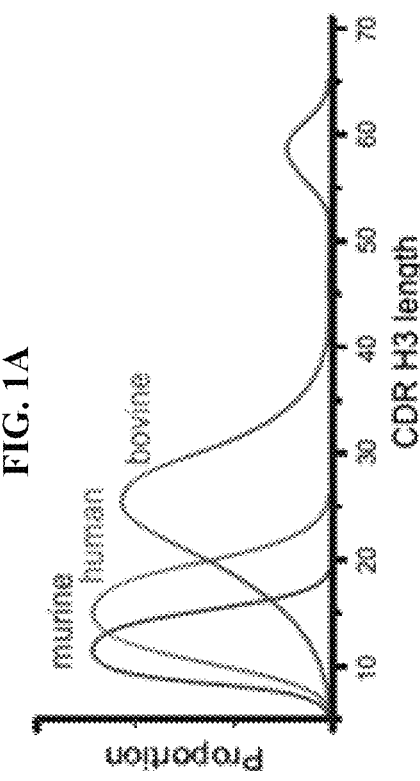
FIGS. 1A-1C present the identification of a new structural domain in bovine antibodies.

The present disclosure provides antibodies or immunoglobulin constructs comprising ultralong CDR3 sequences or portions thereof.

In an embodiment, the present disclosure provides an antibody comprising an ultralong CDR3. The ultralong CDR3 may be 35 amino acids in length or more (e.g., 40 or more, 45 or more, 50 or more, 55 or more, 60 or more). The ultralong CDR3 may comprise at least a portion of a knob domain of a CDR3, at least a portion of a stalk domain of a CDR3, or a combination thereof. The portion of the knob domain of the CDR3 may comprise one or more conserved motifs derived from the knob domain of the ultralong CDR3. The portion of the stalk domain of the CDR3 may comprise one or more conserved motis derived from the stalk domain of the ultralong CDR3. Such an antibody may comprise at least 3 cysteine residues or more (e.g., 4 or more, 6 or more, 8 or more) within the ultralong CDR3. The antibody may comprise one or more cysteine motifs. The antibody may comprise a non-antibody sequence within the ultralong CDR3. Alternatively, or additionally, the antibody comprises a non-bovine sequence. The non-bovine sequence can be linked to the ultralong CDR3 sequence. The antibody may further comprise a linker. The linker can comprise an amino acid sequence of (GGGGS)$_n$ wherein n=1 to 5 (SEQ ID NO: 499). Alternatively, the linker comprises an amino acids sequence of (GSG)n (SEQ ID NO: 342), GGGSGGGGS (SEQ ID NO: 337) or GGGGSGGGS (SEQ ID NO: 338). The antibody may comprise a non-bovine sequence within the ultralong CDR3. The antibody may further comprise an antibody sequence, wherein the antibody sequence does not comprise an ultralong CDR3 sequence. The antibody may further comprise an antibody sequence, wherein the amino acid sequence identity of the antibody peptide sequence to the ultralong CDR3 peptide sequence is about 40% or less (e.g., about 35% or less, about 30% or less, about 25% or less, about 20% or less, about 15% or lress, 10% or less, about 5% or less, about 3% or less, about 1% or less). The antibody may comprise a cytotoxic agent or therapeutic polypeptide. The cytotoxic agent or therapeutic polypeptide may be conjugated to the ultralong CDR3. The antibody may bind to a target. The target may be a protein target. The protein target may be a transmembrane protein target. The antibody may comprise at least a portion of a BLV1H12 and/or BLVCV1 antibody. Alternatively, or additionally, the antibody comprises at least a portion of a BLV5D3, BLV8C11, BF1H1, BLV5B8 and/or F18 antibody. The antibody may comprise at least a portion of a human antibody. The antibody may be a chimeric, recombinant, engineered, synthetic, humanized, fully human, or human engineered antibody. The antibody may comprise antibody sequences from two or more different antibodies. The two or more different antibodies may be from the same species. For example, the specie may be a bovine specie, human specie, or murine specie. The two or more different antibodies may be from the same type of animal. For example the two or more different antibodies may be from a cow. The two or more different antibodies may be from a human. Alternatively, the two or more different antibodies are from different species. For example, the two or more different antibodies are from a human specie and bovine specie. In another example, the two or more diffent antibodies are from a bovine specie and a non-bovine specie. In another example, the two or more different antibodies are from a human specie and a non-human specie.

In another embodiment, the present disclosure provides an antibody comprising an ultralong CDR3, wherein the CDR3 is 35 amino acids in length or more and is derived from or based on a non-human sequence. The ultralong CDR3 sequence may be derived from any species that naturally produces ultralong CDR3 antibodies, including ruminants such as cattle (Bos taurus). The antibody may comprise at least a portion of a BLV1H12 and/or BLVCV1 antibody. Alternatively, or additionally, the antibody comprises at least a portion of a BLV5D3, BLV8C11, BF1H1, BLV5B8 and/or F18 antibody. Alternatively, the ultralong CDR3 sequence may be derived from a camelid or shark CDR3 sequence.

In another embodiment, the present disclosure provides an antibody comprising an ultralong CDR3, wherein the CDR3 comprises a non-antibody sequence. The non-antibody sequence may be derived from any protein family including, but not limited to, chemokines, growth factors, peptides, cytokines, cell surface proteins, serum proteins, toxins, extracellular matrix proteins, clotting factors, secreted proteins, etc. The non-antibody sequence may be derived from a therapeutic polypeptide. The non-antibody sequence may be of human or non-human origin. The non-antibody sequence may comprise a synthetic sequence. The non-antibody sequence may comprise a portion of a non-antibody protein such as a peptide or domain. The non-antibody sequence of an ultralong CDR3 may contain mutations from its natural sequence, including amino acid changes (e.g., substitutions), insertions or deletions. Engineering additional amino acids at the junction between the non-antibody sequence may be done to facilitate or enhance proper folding of the non-antibody sequence within the antibody. The CDR3 may be 35 amino acids in length or more. The ultralong CDR3 may comprise at least a portion of a knob domain of a CDR3, at least a portion of a stalk domain of a CDR3, or a combination thereof. The portion of the knob domain of the CDR3 may comprise one or more conserved motifs derived from the knob domain of the ultralong CDR3. The portion of the stalk domain of the CDR3 may comprise one or more conserved motis derived from the stalk domain of the ultralong CDR3. Alternatively, or additionally, the antibody comprises at least 3 cysteine residues or more. The antibody can comprise one or more cysteine motifs. The antibody may comprise at least a portion of a BLV1H12 and/or BLVCV1 antibody. Alternatively, or additionally, the antibody comprises at least a portion of a BLV5D3, BLV8C11, BF1H1, BLV5B8 and/or F18 antibody.

In another embodiment, the present disclosure provides an antibody comprising an ultralong CDR3 and a non-bovine sequence. The ultralong CDR3 can be derived from a ruminant. The ruminant can be a bovine. The non-bovine sequence can be derived from or based on a non-bovine mammal sequence. For example, the non-bovine sequence can be derived from or based on a human, mouse, rat, sheep, dog, and/or goat sequence. The ultralong CDR3 sequence can comprise the non-bovine sequence. Alternatively, the non-bovine sequence is linked to the ultralong CDR3 sequence. The non-bovine sequence can be derived from or based on at least a portion of an antibody sequence. The antibody sequence can encode a variable region, constant region or a combination thereof. The CDR3 may be 35 amino acids in length or more. The ultralong CDR3 may comprise at least a portion of a knob domain of a CDR3, at least a portion of a stalk domain of a CDR3, or a combination thereof. The portion of the knob domain of the CDR3 may comprise one or more conserved motifs derived from the knob domain of the ultralong CDR3. The portion of the stalk domain of the CDR3 may comprise one or more conserved motis derived from the stalk domain of the ultralong CDR3. Alternatively, or additionally, the antibody comprises at least 3 cysteine residues or more. The antibody can comprise one or more cysteine motifs.

In another embodiment, the present disclosure provides an antibody comprising an ultralong CDR3, wherein the CDR3 is 35 amino acids in length or more and comprises at least 3 cysteine residues or more, including, for example, 4 or more, 6 or more, and 8 or more.

In another embodiment, the present disclosure provides for an antibody comprising an ultralong CDR3 wherein the CDR3 is 35 amino acids in length or more and comprises at least 3 cysteine residues or more and wherein the ultralong CDR3 is a component of a multispecific antibody. The multispecific antibody may be bispecific or comprise greater valencies.

In another embodiment, the present disclosure provides an antibody comprising an ultralong CDR3, wherein the CDR3 is 35 amino acids in length or more and comprises at least 3 cysteine residues or more, wherein the ultralong CDR3 is a component of an immunoconjugate.

In another embodiment, the present disclosure provides an antibody comprising an ultralong CDR3, wherein the CDR3 is 35 amino acids in length or more and comprises at least 3 cysteine residues or more, wherein the antibody comprising an ultralong CDR3 binds to a transmembrane protein target. Such transmembrane targets may include, but are not limited to, GPCRs, ion channels, transporters, and cell surface receptors.

In another embodiment, the present disclosure provides an antibody comprising an ultralong CDR3, wherein the antibody comprising an ultralong CDR3 binds to a transmembrane protein target. Such transmembrane targets may include, but are not limited to, GPCRs, ion channels, transporters, and cell surface receptors. The CDR3 may be 35 amino acids in length or more. The ultralong CDR3 may comprise at least a portion of a knob domain of a CDR3, at least a portion of a stalk domain of a CDR3, or a combination thereof. The portion of the knob domain of the CDR3 may comprise one or more conserved motifs derived from the knob domain of the ultralong CDR3. The portion of the stalk domain of the CDR3 may comprise one or more conserved motis derived from the stalk domain of the ultralong CDR3. Alternatively, or additionally, the antibody comprises at least 3 cysteine residues or more. The antibody can comprise one or more cysteine motifs.

Provided herein is an immunoglobulin construct comprising a mammalian immunoglobulin heavy chain comprising at least a portion of complementarity-determining region 3 (CDR3H); and a therapeutic polypeptide, wherein the therapeutic polypeptide is inserted into or replaces at least a portion of the CDR3H. The immunoglobulin construct may comprise one or more linkers. The one or more linkers can connect the therapeutic polypeptide to the heavy chain. In some embodiments, the linker comprises an amino acid sequence of (GGGGS)n wherein n=1 to 5 (SEQ ID NO: 499). Alternatively, or additionally, the linker comprises an amino acid sequence of (GSG)n (SEQ ID NO: 342), GGGSGGGGS (SEQ ID NO: 337) or GGGGSGGGS (SEQ ID NO: 338). In some embodiments provided are immunoglobulin constructs described herein, wherein the therapeutic polypeptide is selected from a hormone, a lymphokine, an interleukin, a chemokines, a cytokine and combinations thereof. In certain embodiments, the therapeutic polypeptide is a cytokine. In some embodiments, the therapeutic polypeptide is a colony stimulating factor polypeptide. In certain embodiments, the colony stimulating factor is macrophage colony-stimulating factor (M-CSF), Granulocyte-macrophage colony-stimulating factor (GM-CSF), Granulocyte colony-stimulating factor (G-CSF) or fragment, or variant thereof. In an embodiment, the colony stimulating factor is mammalian G-CSF or derivative or variant thereof. In a certain embodiment, the colony stimulating factor is bovine G-CSF or derivative or variant thereof. In other instances, the therapeutic polypeptide is Moka1, Vm24, human GLP-1, Exendin-4, human EPO, human FGF21, human GMCSF, or human interferon-beta. Provided herein are immunoglobulin constructs comprising a mammalian immunoglobulin heavy chain comprising a knob domain in the complementarity-determining region 3 (CDR3H) or fragment thereof; and a therapeutic polypeptide attached to said knob domain of the CDR3H, wherein said mammalian immunoglobulin is a bovine immunoglobulin. In some embodiments, the bovine immunoglobulin is a BLV1H12 antibody. In some embodiments of the immunoglobulin constructs described herein, at least a portion of the knob domain is replaced by the therapeutic polypeptide. The knob domain of the CDR3H may comprise one or more conserved motifs derived from the knob domain of the ultralong CDR3H. The immunoglobulin construct may further comprise at least a portion of a stalk domain in the CDR3H. The portion of the stalk domain of the CDRH3 may comprise one or more conserved motis derived from the stalk domain of the ultralong CDR33H.

Further provided herein are antibodies or fragments thereof comprising a stalk domain in the complementarity-determining region 3 (CDR3H) or fragment thereof; and a therapeutic polypeptide. In some instances, the complementarity-determining region 3 (CDR3H) is derived from a bovine ultralong CDR3H. The therapeutic polypeptide can be any of the therapeutic polypeptides disclosed herein. For example, the therapeutic polypeptide is Moka1, Vm24, GLP-1, Exendin-4, human EPO, human FGF21, human GMCSF, or human interferon-beta. The therapeutic polypeptide can be attached to the stalk domain. In some instances, the antibody or fragment thereof further comprises a linker. The linker can attach the therapeutic polypeptide to the stalk domain. Alternatively, or additionally, the antibody or fragment thereof further comprises at least a portion of a knob domain in the CDR3H. In some instances, the linker attaches the therapeutic polypeptide to the knob domain. In some instances, the knob domain is attached to the stalk domain. The portion of the knob domain of the CDR3 may comprise one or more conserved motifs derived from the knob domain of the ultralong CDR3. The stalk domain of the CDR3 may comprise one or more conserved motis derived from the stalk domain of the ultralong CDR3.

In some instances, an antibody or fragment thereof is provided herein. The antibody or fragment thereof can comprise at least one immunoglobulin domain or fragment thereof and a therapeutic polypeptide or derivative or variant thereof. The therapeutic polypeptide, or derivative or variant thereof can be attached to the immunoglobulin domain. In some instances, the therapeutic polypeptide is Moka1, Vm24, GLP-1, Exendin-4, human EPO, human FGF21, human GMCSF, human interferon-beta, or derivative or variant thereof. In some embodiments, the immunoglobulin domain is an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. In some instances, the immunoglobulin domain is from an engineered antibody or recombinant antibody. In other instances, the immunoglobulin domain is from a humanized, human engineered or fully human antibody. In certain embodiments, the mammalian antibody is a bovine antibody. In other instances, the mammalin antibody is a human antibody. In other instances, the mammalian antibody is a murine antibody. In some instances, the immunoglobulin domain is a heavy chain region comprising a knob domain in the complementarity-determining region 3 (CDR3H) or fragment thereof. The therapeutic polypeptide can be attached to the knob domain. Alternatively, or additionally, the immunoglobulin domain is a heavy chain region comprising a stalk domain in the complementarity-determining region 3 (CDR3H) or fragment thereof. In some instances, the therapeutic polypeptide is attached to the stalk domain. In some instances, the antibody or fragment thereof further comprises a linker. The linker can attach the therapeutic polypeptide to the immunoglobulin domain or fragment thereof. The knob domain of the CDR3 may comprise one or more conserved motifs derived from the knob domain of the ultralong CDR3. The stalk domain of the CDR3 may comprise one or more conserved motis derived from the stalk domain of the ultralong CDR3.

Provided herein is an immunoglobulin construct comprising at least one immunoglobulin domain or fragment thereof; and a G-CSF polypeptide or derivative or variant thereof attached to said immunoglobulin domain. In some embodiments, the immunoglobulin domain is an immunoglobulin A, an immunoglobulin D, an immunoglobulin E, an immunoglobulin G, or an immunoglobulin M. In some embodiments, the immunoglobulin domain is an immunoglobulin heavy chain region or fragment thereof. In an embodiment, the immunoglobulin domain is from a mammalian or chimeric antibody. In other instances, the immunoglobulin domain is from a humanized, human engineered or fully human antibody. In certain embodiments, the mammalian antibody is a bovine antibody. In some instances, the mammalian antibody is a human antibody. In other instances, the mammalian antibody is a murine antibody. In an embodiment, the immunoglobulin domain is a heavy chain region comprising a knob domain in the complementarity-determining region 3 (CDR3H) or fragment thereof. In an embodiment, the G-CSF polypeptide is attached to the knob domain. The immunoglobulin domain may be a heavy chain region comprising a stalk domain in the complementarity-determining region 3 (CDR3H) or fragment thereof. The G-CSF polypeptide may be attached to the stalk domain. The knob domain of the CDR3 may comprise one or more conserved motifs derived from the knob domain of the ultralong CDR3. The stalk domain of the CDR3 may comprise one or more conserved motis derived from the stalk domain of the ultralong CDR3.

In certain embodiments, provided is an immunoglobulin construct comprising at least one immunoglobulin domain or fragment thereof; and a G-CSF polypeptide or derivative or variant thereof attached to said immunoglobulin domain, wherein said G-CSF polypeptide is a bovine G-CSF polypeptide or derivative or variant thereof. In certain embodiments provided herein is a pharmaceutical composition comprising an immunoglobulin construct provided herein, and a pharmaceutically acceptable carrier. In certain embodiments is provided a method of preventing or treating a disease in a mammal in need thereof comprising administering a pharmaceutical composition described herein to said mammal. The immunoglobulin domain may be a heavy chain region comprising a knob domain in the complementarity-determining region 3 (CDR3H) or fragment thereof. The G-CSF polypeptide may be attached to the knob domain. The immunoglobulin domain may be a heavy chain region comprising a stalk domain in the complementarity-determining region 3 (CDR3H) or fragment thereof. The G-CSF polypeptide may be attached to the stalk domain. The knob domain of the CDR3 may comprise one or more conserved motifs derived from the knob domain of the ultralong CDR3. The stalk domain of the CDR3 may comprise one or more conserved motis derived from the stalk domain of the ultralong CDR3.

In some embodiments is an antibody or fragment thereof comprising: (a) a first antibody sequence, wherein at least a portion of the first antibody sequence is derived from at least a portion of an ultralong CDR3; and (b) a non-antibody sequence. The antibody or fragment thereof may further comprise a second antibody sequence, wherein at least a portion of the second antibody sequence is derived from at least a portion of an ultralong CDR3. The ultralong CDR3 from which the first antibody sequence and/or second antibody sequence may be derived from a ruminant. The ruminant can be a cow. At least a portion of the first antibody sequence and/or at least a portion of the second antibody sequence can be derived from a mammal. The mammal may be a bovine. Alternatively, the mammal is a non-bovine mammal, such as a human. The first and/or second antibody sequences may be 3 or more amino acids in length. The amino acids may be consecutive amino acids. Alternatively, the amino acids are non-consecutive amino acids. The first and/or second antibody sequences may comprise a bovine antibody sequence comprising 3 or more amino acids in length. The bovine antibody may be a BLVH12, BLV5B8, BLVCV1, BLV5D3, BLV8C11, BF1H1, or F18 antibody. The first and/or second antibody sequences may comprise a human antibody sequence comprising 3 or moreore amino acids in length. The portion of the first antibody sequence derived from at least a portion of the ultralong CDR3 and/or the portion of the second antibody sequence derived from at least a portion of the ultralong CDR3 can be 20 or fewer amino acids in length. The portion of the first antibody sequence derived from at least a portion of the ultralong CDR3 and/or the portion of the second antibody sequence derived from at least a portion of the ultralong CDR3 may be 3 or more amino acids in length. The first and/or second antibody sequences can comprise 1 or more, 2 or more, 3 or more, 4 or more, 5 or more, 6 or more, 7 or more, 8 or more, 9 or more, 10 or more, 15 or more, 20 or more, 30 or more, or 40 or more amino acid residues derived from a knob domain of the ultralong CDR3. The 1 or more amino acid residues derived from the knob domain of the ultralong CDR3 may be a serine and/or cysteine residue. The first and/or second antibody sequences may comprise 1 or more, 2 or more, 3 or more, 4 or more, 5 or more, 6 or more, 7 or more, 8 or more, 9 or more, or 10 or more amino acid residues derived from a stalk domain of the ultralong CDR3. The first and/or second antibody sequences may comprise 1 or more, 2 or more, 3 or more, 4 or more, or 5 or more conserved motifs derived from a stalk domain of the ultralong CDR3. The one or more conserved motifs derived from the stalk domain of the ultralong CDR3 may comprise a sequence selected from any one of SEQ ID NOS: 157-307 and SEQ ID NOS: 333-336. The portion of the first antibody sequence derived from at least a portion of the ultralong CDR3 and/or the portion of the second antibody sequence derived from at least a portion of the ultralong CDR3 may comprise a sequence selected from any one of SEQ ID NOS: 157-307 and SEQ ID NOS: 333-336. The portion of the first antibody sequence derived from at least a portion of the ultralong CDR3 and/or the portion of the second antibody sequence derived from at least a portion of the ultralong CDR3 may comprise a sequence that is 50% or more homologous to a sequence selected from any one of SEQ ID NOS: 157-224 and 235-295. The portion of the first antibody sequence derived from at least a portion of the ultralong CDR3 may comprise a sequence selected from any one of SEQ ID NOS: 157-234. The portion of the first antibody sequence derived from at least a portion of the ultralong CDR3 may comprise a sequence that is 50% or more homologous to a sequence selected from any one of SEQ ID NOS: 157-224. The portion of the first antibody sequence derived from at least a portion of the ultralong CDR3 may comprise a sequence that is 50% or more homologous to a sequence selected from any one of SEQ ID NOS: 225-227. The portion of the second antibody sequence derived from at least a portion of the ultralong CDR3 may comprise a sequence selected from any one of SEQ ID NOS: 235-307 and SEQ ID NOS: 333-336. The portion of the second antibody sequence derived from at least a portion of the ultralong CDR3 may comprise a sequence that may be 50% or more homologous to a sequence selected from any one of SEQ ID NOS: 235-295. The portion of the first antibody sequence derived from at least a portion of the ultralong CDR3 and the portion of the second antibody sequence derived from at least a portion of the ultralong CDR3 may be derived from the same ultralong CDR3 sequence. The portion of the first antibody sequence derived from at least a portion of the ultralong CDR3 and the portion of the second antibody sequence derived from at least a portion of the ultralong CDR3 may be derived from two or more different ultralong CDR3 sequences. The portions of the ultralong CDR3 of the first and/or second antibody sequences may be based on or derived from a BLV1H12 ultralong CDR3 sequence. The portions of the ultralong CDR3 of the first and/or second antibody sequences may be based on or derived from a BLV5B8, BLVCV1, BLV5D3, BLV8C11, BF1H1, or F18 ultralong CDR3 sequence. The antibody may further comprise one or more linker sequences.

The present disclosure also provides antibodies that comprise a heavy chain polypeptide, wherein the heavy chain polypeptide comprises at least a portion of an ultralong CDR3 sequence. The heavy chain polypeptide may comprise a polypeptide sequence based on or derived from a polypeptide sequence of any one of SEQ ID NOS: 24-44. The heavy chain polypeptide may comprise a polypeptide sequence encoded by a DNA sequence based on or derived from the DNA sequence of any one of SEQ ID NOS: 2-22. Also provided are antibodies comprising a heavy chain polypeptide, wherein the heavy chain polypeptide comprises an ultralong CDR3 sequence and the heavy chain polypeptide sequences are substantially similar to those polypeptide sequences provided by any one of SEQ ID NOS: 24-44. A heavy chain polypeptide sequence may be considered substantially similar to a polypeptide sequence provided by any one of SEQ ID NOS: 24-44 where the heavy chain polypeptide sequence shares 60%, 70%, 80%, 90%, 95%, 99%, or more nucleic acid identity to a nucleotide sequence provided by any one of SEQ ID NOS: 24-44. The antibodies may further comprise a light chain polypeptide. The light chain polypeptide may comprise a polypeptide sequence based on or derived from a polypeptide sequence of SEQ ID NO: 23. The light chain polypeptide may comprise a polypeptide sequence encoded by a DNA sequence based on or derived from the DNA sequence of SEQ ID NO: 1. Also provided are antibodies further comprising a light chain polypeptide, wherein the light chain polypeptide comprises an ultralong CDR3 sequence and the light chain polypeptide sequences are substantially similar to those polypeptide sequences provided by SEQ ID NO: 23. A light chain polypeptide sequence may be considered substantially similar to a polypeptide sequence provided by SEQ ID NO: 1 where the light chain polypeptide sequence shares 60%, 70%, 80%, 90%, 95%, 99%, or more nucleic acid identity to a nucleotide sequence provided by any one of SEQ ID NO: 1. The antibody may have therapeutic activity in an animal. The antibody can have therapeutic activity in infectious disease in a subject. The antibody may comprise a monoclonal antibody, polyclonal antibody, chimeric antibody, recombinant antibody, engineered antibody, or synthetic antibody. The antibody may comprise a mammalian antibody. The antibody may comprise a bovine antibody. The antibody may comprise a G-CSF polypeptide, or derivative or variant thereof. The antibody may comprise a mammalian G-CSF polypeptide, or derivative or variant thereof. The antibody may comprise a bovine G-CSF, or derivative or variant thereof. In some embodiments, a pharmaceutical composition of therapeutic formulation comprises an antibody described herein and a pharmaceutically acceptable carrier. In certain embodiments, the antibody is used in a method of treating a subject in need thereof, with a therapeutically effective amount of the antibody or a pharmaceutical composition described herein. In some embodiments, a nucleic acid molecule or a complement therof encodes a therapeutic immunoglobulin described herein.

Genetic Sequences

The present disclosure provides genetic sequences (e.g., genes, nucleic acids, polynucleotides) encoding antibodies comprising ultralong CDR3 sequences or portions thereof. The present disclosure provides genetic sequences (e.g., genes, nucleic acids, polynucleotides) encoding antibodies comprising the knob domain and/or knob domain of ultralong CDR3 sequences. In another embodiment, the present disclosure provides genetic sequences encoding an antibody or immunoglobulin construct described herein.

The present disclosure also provides genetic sequences (e.g., genes, nucleic acids, polynucleotides) encoding an ultralong CDR3 or portion thereof. The present disclosure also provides genetic sequences (e.g., genes, nucleic acids, polynucleotides) encoding the knob domain and/or knob domain of an ultralong CDR3.

In an embodiment, the present disclosure provides genetic sequences encoding an antibody comprising an ultralong CDR3. The ultralong CDR3 may be 35 amino acids in length or more (e.g., 40 or more, 45 or more, 50 or more, 55 or more, 60 or more). The ultralong CDR3 may comprise at least a portion of a knob domain of a CDR3, at least a portion of a stalk domain of a CDR3, or a combination thereof. Such an antibody may comprise at least 3 cysteine residues or more (e.g., 4 or more, 6 or more, 8 or more) within the ultralong CDR3. The antibody may comprise one or more cysteine motifs. The antibody may comprise a non-antibody sequence within the ultralong CDR3. Alternatively, or additionally, the antibody comprises a non-bovine sequence. The antibody may further comprise an antibody sequence. The antibody may comprise a cytotoxic agent or therapeutic polypeptide. The cytotoxic agent or therapeutic polypeptide may be conjugated to the ultralong CDR3. The antibody may bind to a target. The target may be a protein target, such as a transmembrane protein target.

In another embodiment, the present disclosure provides genetic sequences encoding an antibody comprising an ultralong CDR3, wherein the CDR3 is 35 amino acids in length or more and is derived from or based on a non-human sequence. The genetic sequences encoding the ultralong CDR3 may be derived from any species that naturally produces ultralong CDR3 antibodies, including ruminants such as cattle (Bos taurus). Alternatively, the ultralong CDR3 sequence may be derived from a camelid or shark CDR3 sequence.

In another embodiment, the present disclosure provides genetic sequences encoding an antibody comprising an ultralong CDR3, wherein the CDR3 comprises a non-antibody protein sequence. The genetic sequences encoding the non-antibody protein sequences may be derived from any protein family including, but not limited to, chemokines, growth factors, peptides, cytokines, cell surface proteins, serum proteins, toxins, extracellular matrix proteins, clotting factors, secreted proteins, etc. The non-antibody sequence may be derived from a therapeutic polypeptide. The non-antibody protein sequence may be of human or non-human origin. The non-antibody sequence may comprise a synthetic sequence. The non-antibody sequencemay comprise a portion of a non-antibody protein such as a peptide or domain. The non-antibody protein sequence of an ultralong CDR3 may contain mutations from its natural sequence, including amino acid changes (e.g., substitutions), insertions or deletions. Engineering additional amino acids at the junction between the non-antibody sequence may be done to facilitate or enhance proper folding of the non-antibody sequence within the antibody. The CDR3 may be 35 amino acids in length or more. The ultralong CDR3 may comprise at least a portion of a knob domain of a CDR3, at least a portion of a stalk domain of a CDR3, or a combination thereof. Alternatively, or additionally, the antibody comprises at least 3 cysteine residues or more. The antibody can comprise one or more cysteine motifs.

In another embodiment, the present disclosure provides genetic sequences encoding an antibody comprising an ultralong CDR3 and a non-bovine sequence. The ultralong CDR3 can be derived from a ruminant. The ruminant can be a bovine. The non-bovine sequence can be derived from or based on a non-bovine mammal sequence. For example, the non-bovine sequence can be derived from or based on a human, mouse, rat, sheep, dog, and/or goat sequence. The non-bovine sequence can be within the ultralong CDR3. Alternatively, the non-bovine sequence is linked or attached to the ultralong CDR3 sequence. The non-bovine sequence can be derived from or based on at least a portion of an antibody sequence. The antibody sequence can encode a variable region, constant region or a combination thereof. The CDR3 may be 35 amino acids in length or more. The ultralong CDR3 may comprise at least a portion of a knob domain of a CDR3, at least a portion of a stalk domain of a CDR3, or a combination thereof. Alternatively, or additionally, the antibody comprises at least 3 cysteine residues or more. The antibody can comprise one or more cysteine motifs.

In another embodiment, the present disclosure provides genetic sequences encoding an antibody comprising an ultralong CDR3, wherein the CDR3 is 35 amino acids in length or more and comprises at least 3 cysteine residues or more, including, for example, 4 or more, 6 or more, and 8 or more.

In another embodiment, the present disclosure provides genetic sequences encoding an antibody comprising an ultralong CDR3 wherein the CDR3 is 35 amino acids in length or more and comprises at least 3 cysteine residues or more and wherein the ultralong CDR3 is a component of a multispecific antibody. The multispecific antibody may be bispecific or comprise greater valencies.

In another embodiment, the present disclosure provides genetic sequences encoding an antibody comprising an ultralong CDR3, wherein the CDR3 is 35 amino acids in length or more and comprises at least 3 cysteine residues or more, wherein the ultralong CDR3 is a component of an immunoconjugate.

In another embodiment, the present disclosure provides genetic sequences encoding an antibody comprising an ultralong CDR3 wherein the CDR3 is 35 amino acids in length or more and comprises at least 3 cysteine residues or more and wherein the antibody comprising an ultralong CDR3 binds to a transmembrane protein target. Such transmembrane targets may include, but are not limited to, GPCRs, ion channels, transporters, and cell surface receptors.

In another embodiment, the present disclosure provides genetic sequences encoding an antibody comprising an ultralong CDR3, wherein the antibody comprising an ultralong CDR3 binds to a transmembrane protein target. Such transmembrane targets may include, but are not limited to, GPCRs, ion channels, transporters, and cell surface receptors. The CDR3 may be 35 amino acids in length or more. The ultralong CDR3 may comprise at least a portion of a knob domain of a CDR3, at least a portion of a stalk domain of a CDR3, or a combination thereof. Alternatively, or additionally, the antibody comprises at least 3 cysteine residues or more. The antibody can comprise one or more cysteine motifs.

In another embodiment, the present disclosure provides genetic sequences encoding an antibody or fragment thereof comprising: (a) a first antibody sequence, wherein at least a portion of the first antibody sequence is derived from at least a portion of an ultralong CDR3; and (b) a non-antibody sequence. The antibody or fragment thereof may further comprise a second antibody sequence, wherein at least a portion of the second antibody sequence is derived from at least a portion of an ultralong CDR3. The ultralong CDR3 from which the first antibody sequence and/or second antibody sequence may be derived from a ruminant. The ruminant can be a cow. At least a portion of the first antibody sequence and/or at least a portion of the second antibody sequence can be derived from a mammal. The mammal may be a bovine. Alternatively, the mammal is a non-bovine mammal, such as a human. The first and/or second antibody sequences may be 3 or more amino acids in length. The amino acids may be consecutive amino acids. Alternatively, the amino acids are non-consecutive amino acids. The first and/or second antibody sequences may comprise a bovine antibody sequence comprising 3 or more amino acids in length. The bovine antibody may be a BLVH12, BLV5B8, BLVCV1, BLV5D3, BLV8C11, BF1H1, or F18 antibody. The first and/or second antibody sequences may comprise a human antibody sequence comprising 3 or more, 4 or more, 5 or more, 6 or more, 7 or more, 8 or more, 9 or more, 10 or more, 15 or more, 20 or more, 30 or more, 40 or more, 50 or more, 60 or more, or 70 or more amino acids in length.

The portion of the first antibody sequence derived from at least a portion of the ultralong CDR3 and/or the portion of the second antibody sequence derived from at least a portion of the ultralong CDR3 can be 20 or fewer amino acids in length. The portion of the first antibody sequence derived from at least a portion of the ultralong CDR3 and/or the portion of the second antibody sequence derived from at least a portion of the ultralong CDR3 may be 3 or more amino, 4 or more, 5 or more, 6 or more, 7 or more, 8 or more, 9 or more, 10 or more, 15 or more, or 20 or more acids in length. The first and/or second antibody sequences can comprise 1 or more, 2 or more, 3 or more, 4 or more, 5 or more, 6 or more, 7 or more, 8 or more, 9 or more, 10 or more, 15 or more, 20 or more, 30 or more, or 40 or more amino acid residues derived from a knob domain of the ultralong CDR3. The 1 or more amino acid residues derived from the knob domain of the ultralong CDR3 may be a serine and/or cysteine residue. The first and/or second antibody sequences may comprise 1 or more, 2 or more, 3 or more, 4 or more, 5 or more, 6 or more, 7 or more, 8 or more, 9 or more, or 10 or more amino acid residues derived from a stalk domain of the ultralong CDR3. The first and/or second antibody sequences may comprise 1 or more, 2 or more, 3 or more, 4 or more, or 5 or more conserved motifs derived from a stalk domain of the ultralong CDR3. The one or more conserved motifs derived from the stalk domain of the ultralong CDR3 may comprise a sequence selected from any one of SEQ ID NOS: 157-307 and SEQ ID NOS: 333-336. The portion of the first antibody sequence derived from at least a portion of the ultralong CDR3 and/or the portion of the second antibody sequence derived from at least a portion of the ultralong CDR3 may comprise a sequence selected from any one of SEQ ID NOS: 157-307 and SEQ ID NOS: 333-336. The portion of the first antibody sequence derived from at least a portion of the ultralong CDR3 and/or the portion of the second antibody sequence derived from at least a portion of the ultralong CDR3 may comprise a sequence that is 50% or more homologous to a sequence selected from any one of SEQ ID NOS: 157-224 and 235-295. The portion of the first antibody sequence derived from at least a portion of the ultralong CDR3 may comprise a sequence selected from any one of SEQ ID NOS: 157-234. The portion of the first antibody sequence derived from at least a portion of the ultralong CDR3 may comprise a sequence that is 50% or more homologous to a sequence selected from any one of SEQ ID NOS: 157-224. The portion of the first antibody sequence derived from at least a portion of the ultralong CDR3 may comprise a sequence that is 50% or more homologous to a sequence selected from any one of SEQ ID NOS: 225-227. The portion of the second antibody sequence derived from at least a portion of the ultralong CDR3 may comprise a sequence selected from any one of SEQ ID NOS: 235-307 and SEQ ID NOS: 333-336. The portion of the second antibody sequence derived from at least a portion of the ultralong CDR3 may comprise a sequence that may be 50% or more homologous to a sequence selected from any one of SEQ ID NOS: 235-295. The portion of the first antibody sequence derived from at least a portion of the ultralong CDR3 and the portion of the second antibody sequence derived from at least a portion of the ultralong CDR3 may be derived from the same ultralong CDR3 sequence. The portion of the first antibody sequence derived from at least a portion of the ultralong CDR3 and the portion of the second antibody sequence derived from at least a portion of the ultralong CDR3 may be derived from two or more different ultralong CDR3 sequences. The portions of the ultralong CDR3 of the first and/or second antibody sequences may be based on or derived from a BLV1H12 ultralong CDR3 sequence. The portions of the ultralong CDR3 of the first and/or second antibody sequences may be based on or derived from a BLV5B8, BLVCV1, BLV5D3, BLV8C11, BF1H1, or F18 ultralong CDR3 sequence. The antibody may further comprise one or more linker sequences.

The present disclosure also provides isolated genetic sequences (e.g., genes, nucleic acids, polynucleotides, oligonucleotides) such as genetic sequences encoding antibodies that comprise an ultralong CDR sequence including, for example, a CDR3 sequence as provided by any one of SEQ ID NOS: 2-22. Also provided are ultralong CDR3 nucleic acid sequences that are substantially similar to those CDR3 sequences provided by any one of SEQ ID NOS: 2-22. A CDR3 sequence may be considered substantially similar to a CDR3 sequence provided by any one of SEQ ID NOS: 2-22 where the CDR3 sequence shares 80%, 85%, 90%, 95%, 99%, or more, nucleic acid sequence identity to a CDR3 sequence provided by any one of SEQ ID NOS: 2-22 or hybridizes to any one of SEQ ID NOS: 2-22 under stringent hybridization conditions.

The present disclosure also provides isolated genetic sequences (e.g., genes, nucleic acids, polynucleotides, oligonucleotides) such as genetic sequences encoding antibodies that comprise a heavy chain polypeptide, wherein the heavy chain polypeptide comprises at least a portion of an ultralong CDR3 sequence. The heavy chain polypeptide may comprise a polypeptide sequence of any one of SEQ ID NOS: 24-44. The heavy chain polypeptide may comprise a polypeptide sequence encoded by the DNA of any one of SEQ ID NOS: 2-22. Also provided are isolated genetic sequences (e.g., genes, nucleic acids, polynucleotides, oligonucleotides) such as genetic sequences encoding antibodies comprising a heavy chain polypeptide, wherein the heavy chain polypeptide comprises an ultralong CDR3 sequence and the heavy chain polypeptide sequences are substantially similar to those polypeptide sequences provided by any one of SEQ ID NOS: 24-44. A heavy chain polypeptide sequence may be considered substantially similar to a polypeptide sequence provided by any one of SEQ ID NOS: 24-44 where the heavy chain polypeptide sequence shares 60%, 70%, 80%, 90%, 95%, 99%, or more nucleic acid identity to a nucleotide sequence provided by any one of SEQ ID NOS: 24-44 or hybridizes to any one of SEQ ID NOS: 24-44 under stringent hybridization conditions. The isolated genetic sequences (e.g., genes, nucleic acids, polynucleotides, oligonucleotides) such as genetic sequences encoding antibodies may further comprise a light chain polypeptide. The light chain polypeptide may comprise a polypeptide sequence of SEQ ID NO: 23. The light chain polypeptide may comprise a polypeptide sequence encoded by the DNA of SEQ ID NO: 1. Also provided are isolated genetic sequences (e.g., genes, nucleic acids, polynucleotides, oligonucleotides) such as genetic sequences encoding antibodies further comprising a light chain polypeptide, wherein the light chain polypeptide comprises an ultralong CDR3 sequence and the light chain polypeptide sequences are substantially similar to those polypeptide sequences provided by SEQ ID NO: 23. A light chain polypeptide sequence may be considered substantially similar to a polypeptide sequence provided by SEQ ID NO: 1 where the light chain polypeptide sequence shares 60%, 70%, 80%, 90%, 95%, 99%, or more nucleic acid identity to a nucleotide sequence provided by any one of SEQ ID NO: 1 or hybridizes to SEQ ID NOS: 1 under stringent hybridization conditions.

Libraries and Arrays

The present disclosure provides collections, libraries and arrays of antibodies comprising ultralong CDR3 sequences. In some embodiments, members of the collections, libraries, or arrays may exhibit sequence diversity.

In an embodiment, the present disclosure provides a library or an array of antibodies comprising ultralong CDR3 sequences wherein at least two members of the library or array differ in the positions of at least one of the cysteines in the ultralong CDR3 sequence. Structural diversity may be enhanced through different numbers of cysteines in the ultralong CDR3 sequence (e.g., at least 3 or more cysteine residues such as 4 or more, 6 or more and 8 or more) and/or through different disulfide bond formation, and hence different loop structures.

In another embodiment, the present disclosure provides for a library or an array of antibodies comprising ultralong CDR3 sequences wherein at least two members of the library or the array differ in at least one amino acid located between cysteines in the ultralong CDR3. In this regard, members of the library or the array can contain cysteines in the same positions of CDR3, resulting in similar overall structural folds, but with fine differences brought about through different amino acid side chains. Such libraries or arrays may be useful for affinity maturation.

In another embodiment, the present disclosure provides libraries or arrays of antibodies comprising ultralong CDR3 sequences wherein at least two of the ultralong CDR3 sequences differ in length (e.g., 35 amino acids in length or more such as 40 or more, 45 or more, 50 or more, 55 or more and 60 or more). The amino acid and cysteine content may or may not be altered between the members of the library or the array. Different lengths of ultralong CDR3 sequences may provide for unique binding sites, including, for example, due to steric differences, as a result of altered length.

In another embodiment, the present disclosure provides libraries or arrays of antibodies comprising ultralong CDR3 sequences wherein at least two members of the library differ in the human framework used to construct the antibody comprising an ultralong CDR3.

In another embodiment, the present disclosure provides libraries or arrays of antibodies comprising ultralong CDR3 sequences wherein at least two members of the library or the array differ in having a non-antibody protein sequence that comprises a portion of the ultralong CDR3. Such libraries or arrays may contain multiple non-antibody protein sequences, including for chemokines, growth factors, peptides, cytokines, cell surface proteins, serum proteins, toxins, extracellular matrix proteins, clotting factors, secreted proteins, viral or bacterial proteins, etc. The non-antibody protein sequence may be of human or non-human origin and may be comprised of a portion of a non-antibody protein such as a peptide or domain. The non-antibody protein sequence of the ultralong CDR3 may contain mutations from its natural sequence, including amino acid changes (e.g., substitutions), or insertions or deletions. Engineering additional amino acids at the junction between the non-antibody sequence within the ultralong CDR3 may be done to facilitate or enhance proper folding of the non-antibody sequence within the antibody.

In another embodiment, the present disclosure provides libraries or arrays of antibodies comprising ultralong CDR3 sequences wherein at least two members of the library or the array differ in having a non-bovine sequence. The non-bovine sequence can be derived from or based on a non-bovine mammal sequence. For example, the non-bovine sequence can be derived from or based on a human, mouse, rat, sheep, dog, and/or goat sequence. The non-bovine sequence can be within the ultralong CDR3. Alternatively, the non-bovine sequence is linked or attached to the ultralong CDR3 sequence. The non-bovine sequence can be derived from or based on at least a portion of an antibody sequence. The antibody sequence can encode a variable region, constant region or a combination thereof.

In another embodiment, the present disclosure provides libraries or arrays of antibodies comprising ultralong CDR3 sequences wherein at least two members of the library or array differ in having a cytoxic agent or therapeutic polypeptide that is conjugated to the ultralong CDR3. The cytoxic agent or therapeutic polypeptide may include, but is not limited to, a chemotherapeutic agent, a drug, a growth inhibitory agent, a toxin (e.g., an enzymatically active toxin of bacterial, fungal, plant, or animal origin, or fragments thereof), or a radioactive isotope (e.g., a radioconjugate). The cytotoxic agent or therapeutic polypeptide can be encoded by a non-antibody sequence.

In another embodiment, the present disclosure provides libraries or arrays of antibodies comprising ultralong CDR3 sequences wherein at least two members of the library or array differ in binding to targets. The target can be a protein target. The protein target can be a transmembrane protein target. Such transmembrane targets may include, but are not limited to, GPCRs, ion channels, transporters, and cell surface receptors.

The libraries or the arrays of the present disclosure may be in several formats well known in the art. The library or the array may be an addressable library or an addressable array. The library or array may be in display format, for example, the antibody sequences may be expressed on phage, ribosomes, mRNA, yeast, or mammalian cells.

Cells

The present disclosure provides cells comprising genetic sequences encoding antibodies comprising ultralong CDR3 sequences or portions thereof. The present disclosure provides cells comprising genetic sequences encoding antibodies comprising at least a portion of a knob domain or at least a portion of a knob domain of an ultralong CDR3 sequence.

The present disclosure provides cells comprising genetic sequences (e.g., genes, nucleic acids, polynucleotides) encoding an ultralong CDR3 or portion thereof. The present disclosure also provides cells comprising genetic sequences (e.g., genes, nucleic acids, polynucleotides) encoding the knob domain and/or knob domain of an ultralong CDR3.

In an embodiment, the present disclosure provides cells expressing an antibody comprising an ultralong CDR3. The cells may be prokaryotic or eukaryotic, and an antibody comprising an ultralong CDR3 may be expressed on the cell surface or secreted into the media. When displayed on the cell surface an antibody preferentially contains a motif for insertion into the plasmid membrane such as a membrane spanning domain at the C-terminus or a lipid attachment site. For bacterial cells, an antibody comprising an ultralong CDR3 may be secreted into the periplasm. When the cells are eukaryotic, they may be transiently transfected with genetic sequences encoding an antibody comprising an ultralong CDR3. Alternatively, a stable cell line or stable pools may be created by transfecting or transducing genetic sequences encoding an antibody comprising an ultralong CDR3 by methods well known to those of skill in the art. Cells can be selected by fluorescence activated cell sorting (FACS) or through selection for a gene encoding drug resistance. Cells useful for producing antibodies comprising ultralong CDR3 sequences include prokaryotic cells like *E.* coli, eukaryotic cells like the yeasts *Saccharomyces cerevisiae* and *Pichia pastoris*, insect cells (e.g., Sf9, Hi5), chinese hamster ovary (CHO) cells, monkey cells like COS-1, or human cells like HEK-293, HeLa, SP-1.

Library Methods

The present disclosure provides methods for making libraries comprising antibodies comprising ultralong CDR3 sequences. Methods for making libraries of spatially addressed libraries are described in WO 2010/054007. Methods of making libraries in yeast, phage, *E. coli*, or mammalian cells are well known in the art.

The present disclosure also provides methods of screening libraries of antibodies comprising ultralong CDR3 sequences.

Definitions

The terms "a," "an," "the" and similar referents used in the context of describing the exemplary embodiments (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the exemplary embodiments and does not pose a limitation on the scope of the exemplary embodiments otherwise claimed. No language in the specification should be construed as indicating any non-claimed element essential to the practice of the exemplary embodiments.

An "ultralong CDR3" or an "ultralong CDR3 sequence", used interchangeably herein, comprises a CDR3 or CDR3 sequence that is not derived from a human antibody sequence. An ultralong CDR3 may be 35 amino acids in length or longer, for example, 40 amino acids in length or longer, 45 amino acids in length or longer, 50 amino acids in length or longer, 55 amino acids in length or longer, or 60 amino acids in length or longer. The length of the ultralong CDR3 may include a non-antibody sequence. An ultralong CDR3 may comprise at least a portion of a knob domain and/or knob domain. An ultralong CDR3 may comprise a non-antibody sequence, including, for example, a cytokine, chemokine, growth factor or hormone sequence. Preferably, the ultralong CDR3 is a heavy chain CDR3 (CDR-H3 or CDRH3). Preferably, the ultralong CDR3 is a sequence derived from or based on a ruminant (e.g., bovine) sequence. An ultralong CDR3 may comprise at least 3 or more cysteine residues, for example, 4 or more cysteine residues, 6 or more cysteine residues, or 8 or more cysteine residues. An ultralong CDR3 may comprise one or more cysteine motifs. An ultralong CDR3 may comprise an amino acid sequence that is derived from or based on SEQ ID NOS: 23-44 or is encoded by a DNA sequence that is derived from or based on SEQ ID NOS: 2-22. A variable region that comprises an ultralong CDR3 may include an amino acid sequence that is derived from or based on SEQ ID NOS: 23-44 or is encoded by a DNA sequence that is derived from or based on SEQ ID NOS: 2-22. Such a sequence may be derived from or based on a bovine germline VH gene sequence. An ultralong CDR3 may comprise a sequence derived from or based on a non-human DH gene sequence (see, e.g., Koti, et al. (2010) *Mol. Immunol.* 47: 2119-2128). An ultralong CDR3 may comprise a sequence derived from or based on a JH sequence, (see e.g., Hosseini, et al. (2004) *Int. Immunol.* 16: 843-852). In an embodiment, an ultralong CDR3 may comprise a sequence derived from or based on a non-human $V_H$ sequence and/or a sequence derived from or based on a non-human DH sequence and/or a sequence derived from or based on a JH sequence, and optionally an additional sequence comprising two to six amino acids or more such as, for example, between the VH derived sequence and the DH derived sequence. In another embodiment, an ultralong CDR3 may comprise a sequence that is about 50% or more homologous to a sequence derived from or based on SEQ ID NOS: 23-44. For example, the ultralong CDR3 may comprise a sequence that is about 60%, 70%, 80%, 85%, 90%, 95%, 97% or more homologous to a sequence derived from or based on SEQ ID NOS: 23-44. In another embodiment, an ultralong CDR3 may comprise a sequence that aligns to 5 or more amino acids to a sequence derived from or based SEQ ID NOS: 23-44. For example, the ultralong CDR3 may comprise a sequence that aligns to 5, 10, 15, 20, 25, 30, 35, 40, 45, 50, 55, 60 or more amino acids to a sequence derived from or based SEQ ID NOS: 23-44. In another embodiment, an ultralong CDR3 may comprise a sequence that comprises 5 or more consecutive amino acids to a sequence derived from or based SEQ ID NOS: 23-44. For example, the ultralong CDR3 may comprise a sequence that comprises 5, 10, 15, 20, 25, 30, 35, 40, 45, 50, 55, 60 or more consecutive amino acids to a sequence derived from or based SEQ ID NOS: 23-44. In another embodiment, an ultralong CDR3 may comprise a sequence that is about 50% or more homologous to a DNA sequence that is derived from or based on a SEQ ID NOS: 2-22. For example, the ultralong CDR3 may comprise a sequence that is about 60%, 70%, 80%, 85%, 90%, 95%, 97% or more homologous to a DNA sequence that is derived from or based on SEQ ID NOS: 2-22. In another embodiment, an ultralong CDR3 may comprise a sequence that aligns to 5 or more nucleic acids to a DNA sequence that is derived from or based SEQ ID NOS: 2-22. For example, the ultralong CDR3 may comprise a sequence that aligns to 5, 10, 15, 20, 25, 30, 35, 40, 45, 50, 55, 60, 80, 100, 120, 140, 150, 175, 200, 225, 250, 275, 300, 350, 400, 450, 500, 550, 600 or more nucleic acids to a DNA sequence that is derived from or based SEQ ID NOS: 2-22. In another embodiment, an ultralong CDR3 may comprise a sequence that comprises 5 or more consecutive nucleic acids to a DNA sequence that is derived from or based SEQ ID NOS: 2-22. For example, the ultralong CDR3 may comprise a sequence that comprises 5, 10, 15, 20, 25, 30, 35, 40, 45, 50, 55, 60, 80, 100, 120, 140, 150, 175, 200, 225, 250, 275, 300, 350, 400, 450, 500, 550, 600 or more consecutive amino acids to a DNA sequence that is derived from or based SEQ ID NOS: 2-22. In another embodiment, an ultralong CDR3 may comprise a sequence that is about 50% or more homologous to a sequence derived from or based on a knob domain sequence. For example, the ultralong CDR3 may comprise a sequence that is about 60%, 70%, 80%, 85%, 90%, 95%, 97% or more homologous to a sequence derived from or based on a knob domain sequence. In another embodiment, an ultralong CDR3 may comprise a sequence that aligns to 5 or more amino acids to a sequence derived from or based a knob domain sequence. For example, the ultralong CDR3 may comprise a sequence that aligns to 5, 10, 15, 20, 25, 30, 35, 40, 45, 50, 55, 60 or more amino acids to a sequence derived from or based a knob domain sequence In another embodiment, an ultralong CDR3 may comprise a sequence that comprises 5 or more consecutive amino acids to a sequence derived from or based a knob domain sequence For example, the ultralong CDR3 may comprise a sequence that comprises 5, 10, 15, 20, 25, 30, 35, 40, 45, 50, 55, 60 or more consecutive amino acids to a sequence derived from or based a knob domain sequence. In another embodiment, an ultralong CDR3 may comprise a sequence that is about 50% or more homologous to a sequence derived from or based on a knob domain sequence. For example, the ultralong CDR3 may comprise a sequence that is about 60%, 70%, 80%, 85%, 90%, 95%, 97% or more homologous to a sequence derived from or based on a knob domain sequence. In another embodiment, an ultralong CDR3 may comprise a sequence that aligns to 5 or more amino acids to a sequence derived from or based a knob domain sequence For example, the ultralong CDR3 may comprise a sequence that aligns to 5, 10, 15, 20, 25, 30, 35, 40, 45, 50, 55, 60 or more amino acids to a sequence derived from or based a knob domain sequence In another embodiment, an ultralong CDR3 may comprise a sequence that comprises 5 or more consecutive amino acids to a sequence derived from or based a stalk domain sequence For example, the ultralong CDR3 may comprise a sequence that comprises 5, 10, 15, 20, 25, 30, 35, 40, 45, 50, 55, 60 or more consecutive amino acids to a sequence derived from or based a stalk domain sequence. The antibodies disclosed herein may comprise at least a portion of an ultralong CDR3 derived from or based on a sequence of any of the ultralong CDR3s disclosed herein. The sequence of the ultralong CDR3 or a portion thereof may be modified or altered to contain one or more non-bovine antibody-based nucleotides and/or amino acids. The modifications and/or alterations in the sequence of the ultralong CDR3 or portion therof may improve one or more features of the expressed antibody. For example, the modifications and/or alterations may improve expression, folding, half-life, activity and/or solubility of the antibody.

An "isolated" biological molecule, such as the various polypeptides, polynucleotides, and antibodies disclosed herein, refers to a biological molecule that has been identified and separated and/or recovered from at least one component of its natural environment.

"Antagonist" refers to any molecule that partially or fully blocks, inhibits, or neutralizes an activity (e.g., biological activity) of a polypeptide. Also encompassed by "antagonist" are molecules that fully or partially inhibit the transcription or translation of mRNA encoding the polypeptide. Suitable antagonist molecules include, e.g., antagonist antibodies or antibody fragments; fragments or amino acid sequence variants of a native polypeptide; peptides; antisense oligonucleotides; small organic molecules; and nucleic acids that encode polypeptide antagonists or antagonist antibodies. Reference to "an" antagonist encompasses a single antagonist or a combination of two or more different antagonists.

"Agonist" refers to any molecule that partially or fully mimics a biological activity of a polypeptide. Also encompassed by "agonist" are molecules that stimulate the transcription or translation of mRNA encoding the polypeptide. Suitable agonist molecules include, e.g., agonist antibodies or antibody fragments; a native polypeptide; fragments or amino acid sequence variants of a native polypeptide; peptides; antisense oligonucleotides; small organic molecules; and nucleic acids that encode polypeptides agonists or antibodies. Reference to "an" agonist encompasses a single agonist or a combination of two or more different agonists.

An "isolated" antibody refers to one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody (e.g., as determined by the Lowry method), and preferably to more than 99% by weight, (2) to a degree sufficient to obtain at least 15 residues of N-terminal or internal amino acid sequence (e.g., by use of a spinning cup sequenator), or (3) to homogeneity by SDS-PAGE under reducing or nonreducing conditions (e.g., using Coomassie™ blue or, preferably, silver stain). Isolated antibody includes the antibody in situ within recombinant cells since at least one component of the antibody's natural environment will not be present. Similarly, isolated antibody includes the antibody in medium around recombinant cells. An isolated antibody may be prepared by at least one purification step.

An "isolated" nucleic acid molecule refers to a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that express an antibody where, for example, the nucleic acid molecule is in a chromosomal location different from that of natural cells.

Variable domain residue numbering as in Kabat or amino acid position numbering as in Kabat, and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (e.g., residue 52a according to Kabat) after residue 52 of H2 and inserted residues (e.g., residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence.

"Substantially similar," or "substantially the same", refers to a sufficiently high degree of similarity between two numeric values (generally one associated with an antibody disclosed herein and the other associated with a reference/comparator antibody) such that one of skill in the art would consider the difference between the two values to be of little or no biological and/or statistical significance within the context of the biological characteristic measured by said values (e.g., Kd values). The difference between said two values is preferably less than about 50%, preferably less than about 40%, preferably less than about 30%, preferably less than about 20%, preferably less than about 10% as a function of the value for the reference/comparator antibody.

"Binding affinity" generally refers to the strength of the sum total of noncovalent interactions between a single binding site of a molecule (e.g., an antibody) and its binding partner (e.g., an antigen). Unless indicated otherwise, "binding affinity" refers to intrinsic binding affinity which reflects a 1:1 interaction between members of a binding pair (e.g., antibody and antigen). The affinity of a molecule X for its partner Y can generally be represented by the dissociation constant. Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure.

An "on-rate" or "rate of association" or "association rate" or "$k_{on}$," can be determined with a surface plasmon resonance technique such as Biacore (e.g., Biacore A100, Biacore™-2000, Biacore™-3000, Biacore, Inc., Piscataway, N.J.) carboxymethylated dextran biosensor chips (C1\45, Biacore Inc.) and according to the supplier's instructions.

"Vector" refers to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. Accordingly, "plasmid" and "vector" may, at times, be used interchangeably as the plasmid is a commonly used form of vector.

"Gene" refers to a nucleic acid (e.g., DNA) sequence that comprises coding sequences necessary for the production of a polypeptide, precursor, or RNA (e.g., mRNA, rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns can contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. In addition to containing introns, genomic forms of a gene can also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region can contain regulatory sequences such as promoters and enhancers that control or influence the transcription of the gene. The 3' flanking region can contain sequences that direct the termination of transcription, post transcriptional cleavage and polyadenylation.

"Polynucleotide," or "nucleic acid," as used interchangeably herein, refers to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and a basic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide" refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

"Stringent hybridization conditions" refer to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

"Recombinant" when used with reference to a cell, nucleic acid, protein, antibody or vector indicates that the cell, nucleic acid, protein or vector has been modified by the introduction of a heterologous nucleic acid or protein, the alteration of a native nucleic acid or protein, or that the cell is derived from a cell so modified. For example, recombinant cells express genes that are not found within the native (non-recombinant) form of the cell or express native genes that are overexpressed or otherwise abnormally expressed such as, for example, expressed as non-naturally occurring fragments or splice variants. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this disclosure. It is understood that once a recombinant nucleic acid is made and introduced into a host cell or organism, it will replicate non-recombinantly, e.g., using the in vivo cellular machinery of the host cell rather than in vitro manipulations; however, such nucleic acids, once produced recombinantly, although subsequently replicated non-recombinantly, are still considered recombinant for the purposes disclosed herein. Similarly, a "recombinant protein" is a protein made using recombinant techniques, e.g., through the expression of a recombinant nucleic acid as depicted herein.

"Percent (%) amino acid sequence identity" with respect to a peptide or polypeptide sequence refers to the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MegAlign (DNASTAR) software. Those skilled in the art can determine appropriate parameters for measuring alignment, including any algorithms needed to achieve maximal alignment over the full length of the sequences being compared.

"Polypeptide," "peptide," "protein," and "protein fragment" may be used interchangeably to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

"Amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, e.g., an alpha carbon that is bound to a hydrogen, a carboxyl group, an amino group, and an R group, e.g., homoserine, norleucine, methionine sulfoxide, methionine methyl sulfonium. Such analogs can have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

"Conservatively modified variants" applies to both amino acid and nucleic acid sequences. "Amino acid variants" refers to amino acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated (e.g., naturally contiguous) sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, silent variations of a nucleic acid which encodes a polypeptide is implicit in a described sequence with respect to the expression product, but not with respect to actual probe sequences. As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" including where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles disclosed herein. Typically conservative substitutions include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

"Antibodies" (Abs) and "immunoglobulins" (Igs) are glycoproteins having similar structural characteristics. While antibodies may exhibit binding specificity to a specific antigen, immunoglobulins may include both antibodies and other antibody-like molecules which generally lack antigen specificity. Polypeptides of the latter kind are, for example, produced at low levels by the lymph system and at increased levels by myelomas.

"Antibody", "immunoglobulin" and "immunoglobulin construct" are used interchangeably in the broadest sense and include monoclonal antibodies (e.g., full length or intact monoclonal antibodies), polyclonal antibodies, multivalent antibodies, multi specific antibodies (e.g., bispecific antibodies so long as they exhibit the desired biological activity) and may also include certain antibody fragments (as described in greater detail herein). The term "antibody" can refer to a full length antibody or a portion thereof. An antibody can refer to a peptide comprising at least one antibody sequence. The antibody sequence can comprise 5 or more amino acids of an antibody sequence. For example the antibody sequence can comprise 6, 7, 8, 9, 10, 11, 12, 13, 14, 15, 16, 17, 18, 19, 20 or more amino acids of an antibody sequence. The 5 or more amino acids may be consecutive amino acids of an antibody sequence. Alternatively, the 5 or more amino acids are non-consecutive amino acids of an antibody sequence. For example, the 5 or more amino acids may comprise a conserved motif within the antibody sequence. For example, the 5 or more amino acids may comprise a conserved motif within an ultralong CDR3 sequence. An antibody can be human, humanized, fully human and/or affinity matured. An antibody can be a chimeric antibody. An antibody can be a recombinant, engineered, or synthetic antibody. An antibody may be a bovine, bovine engineered, fully bovine and/or affinity matured. The bovine engineered antibody may comprise one or more nucleotides or peptides derived from a bovine antibody sequence. A fully bovine antibody may comprise replacing one or more nucleotides or peptides from a non-bovine antibody sequence with one or more nucleotides or peptides based on a bovine antibody sequence. An antibody may refer to immunoglobulins and immunoglobulin portions, whether natural or partially or wholly synthetic, such as recombinantly produced, including any portion thereof containing at least a portion of the variable region of the immunoglobulin molecule that is sufficient to form an antigen binding site. Hence, an antibody or portion thereof includes any protein having a binding domain that is homologous or substantially homologous to an immunoglobulin antigen binding site. For example, an antibody may refer to an antibody that contains two heavy chains (which can be denoted H and H') and two light chains (which can be denoted L and L'), where each heavy chain can be a full-length immunoglobulin heavy chain or a portion thereof sufficient to form an antigen binding site (e.g. heavy chains include, but are not limited to, VH, chains VH-CH1 chains and VH-CH1-CH2-CH3 chains), and each light chain can be a full-length light chain or a thereof sufficient to form an antigen binding site (e.g. light chains include, but are not limited to, VL chains and VL-CL chains). Each heavy chain (H and H') pairs with one light chain (L and L', respectively). Typically, antibodies minimally include all or at least a portion of the variable heavy (VH) chain and/or the variable light (VL) chain. The antibody also can include all or a portion of the constant region. For example, a full-length antibody is an antibody having two full-length heavy chains (e.g. VH-CH1-CH2-CH3 or VH-CH1-CH2-CH3-CH4) and two full-length light chains (VL-CL) and hinge regions, such as antibodies produced by antibody secreting B cells and antibodies with the same domains that are produced synthetically. Additionally, an "antibody" refers to a protein of the immunoglobulin family or a polypeptide comprising fragments of an immunoglobulin that is capable of noncovalently, reversibly, and in a specific manner binding a corresponding antigen. An exemplary antibody structural unit comprises a tetramer. Each tetramer is composed of two identical pairs of polypeptide chains, each pair having one "light" (about 25 kD) and one "heavy" chain (about 50-70 kD), connected through a disulfide bond. The recognized immunoglobulin genes include the $\kappa$, $\lambda$, $\alpha$, $\gamma$, $\delta$, $\epsilon$, and $\mu$ constant region genes, as well as the myriad immunoglobulin variable region genes. Light chains are classified as either $\kappa$ or $\lambda$. Heavy chains are classified as $\gamma$, $\mu$, $\alpha$, $\delta$, or $\epsilon$, which in turn define the immunoglobulin classes, IgG, IgM, IgA, IgD, and IgE, respectively. The N-terminus of each chain defines a variable region of about 100 to 110 or more amino acids primarily responsible for antigen recognition. The terms variable light chain (VL) and variable heavy chain (VH) refer to these regions of light and heavy chains respectively. In some instances, the antibodies provided herein comprise at least one immunoglobulin domain from an avian antibody, reptilian antibody, amphibian antibody, insect antibody, or chimeric combinations thereof. The antibodies can comprise at least one immunoglobulin domain from a chimeric antibody. The chimeric antibody can be derived from two or more different species (e.g., mouse and human, bovine and human). The antibodies can comprise at least one immunoglobulin domain from an engineered, recombinant or synthetic antibody. In some instances, engineered, recombinant or synthetic antibodies are created using antibody genes made in a laboratory or taken from cells. The antibody genes can be derived from one or more mammals. For example, the antibody genes are derived from a human. The antibody genes may be derived from a bovine. Alternatively, or additionally, the antibodies disclosed herein comprise at least one immunoglobulin domain from a humanized, human engineered or fully human antibody. The antibody may comprise antibody sequences from two or more different antibodies. The two or more different antibodies may be from the same species. For example, the specie may be a bovine specie, human specie, or murine specie. The two or more different antibodies may be from the same type of animal. For example the two or more different antibodies may be from a cow. The two or more different antibodies may be from a human. Alternatively, the two or more different antibodies are from different species. For example, the two or more different antibodies are from a human specie and bovine specie. In another example, the two or more diffent antibodies are from a bovine specie and a non-bovine specie. In another example, the two or more different antibodies are from a human specie and a non-human specie. The two or more different antibodies may be from different animals. For example, the two different animals are a human and a cow. The different animals may be from the same specie. For example, the different animals may be a cow and a water buffalo.

"Variable" refers to the fact that certain portions of the variable domains (also referred to as variable regions) differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions (HVRs) both in the light-chain and the heavy-chain variable domains. CDRs include those specified as Kabat, Chothia, and IMGT as shown herein within the variable region sequences. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" refers to an antibody fragment which contains an antigen-recognition and antigen-binding site. In a two-chain Fv species, this region consists of a dimer of one heavy and one light chain variable domain in non-covalent association. In a single chain Fv (scFv) species, one heavy chain and one light chain variable domain can be covalently linked by a flexible peptide linker such that the light and heavy chains can associate in a "dimeric" structure analogous to that in a two-chain Fv (scFv) species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CHl) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., IgG$_1$, IgG$_2$, IgG$_3$, IgG$_4$, IgA$_1$, and IgA$_2$. The heavy-chain constant domains that correspond to the different classes of immunoglobulins are called α, δ, ε, γ, and μ, respectively. The subunit structures and three-dimensional configurations of different classes of immunoglobulins are well known.

"Antibody fragments" comprise only a portion of an intact antibody, wherein the portion preferably retains at least one, preferably most or all, of the functions normally associated with that portion when present in an intact antibody. Examples of antibody fragments include Fab, Fab', F(ab')2, single-chain Fvs (scFv), Fv, dsFv, diabody (e.g., (ds Fv)$_2$), Fd and Fd' fragments Fab fragments, Fd fragments, scFv fragments, linear antibodies, single-chain antibody molecules, minibodies, flex minibodies, bispecific fragments, and multispecific antibodies formed from antibody fragments (see, for example, Methods in Molecular Biology, Vol 207: Recombinant Antibodies for Cancer Therapy Methods and Protocols (2003); Chapter 1; p 3-25, Kipriyanov). Other known fragments include, but are not limited to, scFab fragments (Hust et al., BMC Biotechnology (2007), 7:14). In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For example, such an antibody fragment may comprise on antigen binding arm linked to an Fc sequence capable of conferring in vivo stability to the fragment. For another example, an antibody fragment or antibody portion refers to any portion of a full-length antibody that is less than full length but contains at least a portion of the variable region of the antibody sufficient to form an antigen binding site (e.g. one or more CDRs) and thus retains the a binding specificity and/or an activity of the full-length antibody; antibody fragments include antibody derivatives produced by enzymatic treatment of full-length antibodies, as well as synthetically, e.g. recombinantly produced derivatives.

A "dsFv" refers to an Fv with an engineered intermolecular disulfide bond, which stabilizes the VH-VL pair.

A "Fd fragment" refers to a fragment of an antibody containing a variable domain (VH) and one constant region domain (CH1) of an antibody heavy chain.

A "Fab fragment" refers to an antibody fragment that contains the portion of the full-length antibody that would results from digestion of a full-length immunoglobulin with papain, or a fragment having the same structure that is produced synthetically, e.g. recombinantly. A Fab fragment contains a light chain (containing a VL and CL portion) and another chain containing a variable domain of a heavy chain (VH) and one constant region domain portion of the heavy chain (CH1); it can be recombinantly produced.

A "F(ab')2 fragment" refers to an antibody fragment that results from digestion of an immunoglobulin with pepsin at pH 4.0-4.5, or a synthetically, e.g. recombinantly, produced antibody having the same structure. The F(ab')2 fragment contains two Fab fragments but where each heavy chain portion contains an additional few amino acids, including cysteine residues that form disulfide linkages joining the two fragments; it can be recombinantly produced.

A "Fab' fragment" refers to a fragment containing one half (one heavy chain and one light chain) of the F(ab')2 fragment.

A "Fd' fragment refers to a fragment of an antibody containing one heavy chain portion of a F(ab')2 fragment.

A "Fv' fragment" refers to a fragment containing only the VH and VL domains of an antibody molecule.

A "scFv fragment" refers to an antibody fragment that contains a variable light chain (VL) and variable heavy chain (VH), covalently connected by a polypeptide linker in any order. The linker is of a length such that the two variable domains are bridged without substantial interference. Exemplary linkers are (Gly-Ser)n residues with some Glu or Lys residues dispersed throughout to increase solubility.

Diabodies are dimeric scFv; diabodies typically have shorter peptide linkers than scFvs, and they preferentially dimerize.

"HsFv" refers to antibody fragments in which the constant domains normally present in a Fab fragment have been substituted with a heterodimeric coiled-coil domain (see, e.g., Arndt et al. (2001) J Mol Biol. 7:312:221-228).

"Hypervariable region", "HVR", or "HV", as well as "complementary determing region" or "CDR", may refer to the regions of an antibody variable domain which are hypervariable in sequence and/or form structurally defined loops. Generally, antibodies comprise six hypervariable or CDR regions; three in the VH (H1, H2, H3), and three in the VL (L1, L2, L3). A number of hypervariable region or CDR delineations are in use and are encompassed herein. The Kabat Complementarity Determining Regions (Kabat CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk, J. Mol. Biol. 196:901-917 (1987)). The AbM hypervariable regions represent a compromise between the Kabat CDRs and Chothia structural loops, (Chothia "CDRs") and are used by Oxford Molecular's AbM antibody modeling software. The "contact" hypervariable regions are based on an analysis of the available complex crystal structures. The residues from each of these hypervariable regions are noted below. (See also, for example, FIGS. 1A-1C and bold, italicized text for Kabat CDRs and underlined text for Chothia CDRs for 12.3 ICI antibody).

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |

| Loop | Kabat | AbM | Chothia | Contact |
|---|---|---|---|---|
| (Kabat Numbering) | | | | |
| H1 | H31-H35 | H26-H35 | H26-H32 | H30-H35 |
| (Chothia Numbering) | | | | |
| H2 | H50-H65 | H50-H58 | H53-H55 | H47-H58 |
| H3 | H95-H102 | H95-H102 | H96-H101 | H93-H101 |

IMGT referes to the international ImMunoGeneTics Information System, as described by Lefrace et al., Nucl. Acids, Res. 37; D1006-D1012 (2009), including for example, IMGT designated CDRs for antibodies (see also, for example, FIGS. 1A-1C and bracketed text for 12.3 ICI antibody).

Hypervariable regions may comprise "extended hypervariable regions" as follows: 24-36 or 24-34 (L1), 46-56 or 50-56 (L2) and 89-97 (L3) in the VL and 26-35 (H1), 50-65 or 49-65 (H2) and 93-102, 94-102 or 95-102 (H3) in the VH. The variable domain residues are numbered according to Kabat et al., Supra for each of these definitions.

"Framework" or "FR" residues are those variable domain residues other than the hypervariable region residues as herein defined. "Framework regions" (FRs) are the domains within the antibody variable region domains comprising framework residues that are located within the beta sheets; the FR regions are comparatively more conserved, in terms of their amino acid sequences, than the hypervariable regions.

"Monoclonal antibody" refers to an antibody from a population of substantially homogeneous antibodies, that is, for example, the individual antibodies comprising the population are identical and/or bind the same epitope(s), except for possible variants that may arise during production of the monoclonal antibody, such variants generally being present in minor amounts. Such monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones or recombinant DNA clones. It should be understood that the selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this disclosure. In contrast to polyclonal antibody preparations which typically include different antibodies directed against different determinants (e.g., epitopes), each monoclonal antibody of a monoclonal antibody preparation is directed against a single determinant on an antigen. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by a variety of techniques, including, for example, the hybridoma method (e.g., Kohler et al., Nature, 256:495 (1975); Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681, (Elsevier, N.Y., 1981)), recombinant DNA methods (see, e.g., U.S. Pat. No. 4,816,567), phage display technologies (see, e.g., Clackson et al., Nature, 352:624-628 (1991); Marks et al., J. Mol. Biol., 222:581-597 (1991); Sidhu et al., J. Mol. Biol. 338(2):299-310 (2004); Lee et al., J. Mol. Biol. 340(5):1073-1093 (2004); Fellouse, Proc. Nat. Acad. Sci. USA 101(34):12467-12472 (2004); and Lee et al. J. Immunol. Methods 284(1-2):119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806; 5,569,825; 5,591,669; 5,545,807; WO 1997/17852; U.S. Pat. Nos. 5,545,807; 5,545,806; 5,569,825; 5,625,126; 5,633,425; and 5,661,016; Marks et al., Bio/Technology, 10: 779-783 (1992); Lonberg et al., Nature, 368: 856-859 (1994); Morrison, Nature, 368: 812-813 (1994); Fishwild et al., Nature Biotechnology, 14: 845-851 (1996); Neuberger, Nature Biotechnology, 14: 826 (1996); and Lonberg and Huszar, Intern. Rev. Immunol., 13: 65-93 (1995)).

"Humanized" or "Human engineered" forms of non-human (e.g., murine, bovine) antibodies are chimeric antibodies that contain amino acids represented in human immunoglobulin sequences, including, for example, wherein minimal sequence is derived from non-human immunoglobulin. For example, humanized antibodies may be human antibodies in which some hypervariable region residues and possibly some FR residues are substituted by residues from analogous sites in non-human (e.g., rodent) antibodies. Alternatively, humanized or human engineered antibodies may be non-human (e.g., rodent) antibodies in which some residues are substituted by residues from analogious sites in human antibodies (see, e.g., U.S. Pat. No. 5,766,886). Humanized antibodies include human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody, including, for example non-antibody sequences such as a chemokine, growth factor, peptide, cytokine, cell surface protein, serum protein, toxin, extracellular matrix protein, clotting factor, or secreted protein sequence. These modifications may be made to further refine antibody performance. Humanized antibodies include human engineered antibodies, for example, as described by U.S. Pat. No. 5,766,886, including methods for preparing modified antibody variable domains. A humanized antibody may comprise substantially all of at least one, and typically two, variable domains, in which all or substantially all of the hypervariable loops correspond to those of a non-human immunoglobulin and all or substantially all of the FRs are those of a human immunoglobulin sequence. A humanized antibody optionally may also comprise at least a portion of an immunoglobulin constant region (Fc), typically that of a human immunoglobulin. For further details, see Jones et al., Nature 321:522-525 (1986); Riechmann et al., Nature 332: 323-329 (1988); and Presta, Curr. Op. Struct. Biol. 2:593-596 (1992). See also the following review articles and references cited therein: Vaswani and Hamilton, Ann. Allergy, Asthma & Immunol. 1: 105-115 (1998); Harris, Biochem. Soc. Transactions 23:1035-1038 (1995); Hurle and Gross, Curr. Op. Biotech. 5:428-433 (1994).

"Hybrid antibodies" refer to immunoglobulin molecules in which pairs of heavy and light chains from antibodies with different antigenic determinant regions are assembled together so that two different epitopes or two different antigens can be recognized and bound by the resulting tetramer.

"Chimeric" antibodies (immunoglobulins) have a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see e.g., Morrison et al., Proc. Natl. Acad. Sci. USA 81:6851-6855 (1984)). Humanized antibody refers to a subset of chimeric antibodies.

"Single-chain Fv" or "scFv" antibody fragments may comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see e.g., Pluckthun, in The Pharmacology of Monoclonal Antibodies, vol. 113, Rosenburg and Moore eds., Springer-Verlag, New York, pp. 269-315 (1994).

An "antigen" refers to a predetermined antigen to which an antibody can selectively bind. The target antigen may be polypeptide, carbohydrate, nucleic acid, lipid, hapten or other naturally occurring or synthetic compound. Preferably, the target antigen is a polypeptide.

"Epitope" or "antigenic determinant", used interchangeably herein, refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation. Antibodies may bind to the same or a different epitope on an antigen. Antibodies may be characterized in different epitope bins. Whether an antibody binds to the same or different epitope as another antibody (e.g., a reference antibody or benchmark antibody) may be determined by competition between antibodies in assays (e.g., competitive binding assays).

Competition between antibodies may be determined by an assay in which the immunoglobulin under test inhibits specific binding of a reference antibody to a common antigen. Numerous types of competitive binding assays are known, for example: solid phase direct or indirect radioimmunoassay (RIA), solid phase direct or indirect enzyme immunoassay (EIA or enzyme-linked immunosorbent assay (EIA or ELISA), sandwich competition assay including an ELISA assay (see Stahli et al., Methods in Enzymology 9:242-253 (1983)); solid phase direct biotin-avidin EIA (see Kirkland et al., J. Immunol. 137:3614-3619 (1986)); solid phase direct labeled assay, solid phase direct labeled sandwich assay (see Harlow and Lane, "Antibodies, A Laboratory Manual," Cold Spring Harbor Press (1988)); solid phase direct label RIA using I-125 label (see Morel et al., Molec. Immunol. 25(1): 7-15 (1988)); solid phase direct biotin-avidin EIA (Cheung et al., Virology 176:546-552 (1990)); and direct labeled RIA (Moldenhauer et al., Scand. J. Immunol., 32:77-82 (1990)). Competition binding assays may be performed using Surface Plasmon Resonance (SPR), for example, with a Biacore® instrument for kinetic analysis of binding interactions. In such an assay, an antibody comprising an ultralong CDR3 of unknown epitope specificity may be evaluated for its ability to compete for binding against a comparator antibody (e.g., a BA1 or BA2 antibody as described herein). An assay may involve the use of purified antigen bound to a solid surface or cells bearing either of these, an unlabeled test immunoglobulin and a labeled reference immunoglobulin. Competitive inhibition may be measured by determining the amount of label bound to the solid surface or cells in the presence of the test immunoglobulin. Usually the test immunoglobulin is present in excess. An assay (competing antibodies) may include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50%, or at least about 70%, or at least about 80%, or at least about 90%, or at least about 95%, or at least about 99% or about 100% for a competitor antibody.

That an antibody "selectively binds" or "specifically binds" means that the antibody reacts or associates more frequently, more rapidly, with greater duration, with greater affinity, or with some combination of the above to an antigen or an epitope than with alternative substances, including unrelated proteins. "Selectively binds" or "specifically binds" may mean, for example, that an antibody binds to a protein with a $K_D$ of at least about 0.1 mM, or at least about 1 µM or at least about 0.1 µM or better, or at least about 0.01 µM or better. Because of the sequence identity between homologous proteins in different species, specific binding can include an antibody that recognizes a given antigen in more than one species.

"Non-specific binding" and "background binding" when used in reference to the interaction of an antibody and a protein or peptide refer to an interaction that is not dependent on the presence of a particular structure (e.g., the antibody is binding to proteins in general rather that a particular structure such as an epitope).

"Diabodies" refer to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et. al., Proc. Natl. Acad. Sci. USA, 90:6444-6448 (1993).

A "human antibody" refers to one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody refers to one with one or more alterations in one or more CDRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al., Bio/Technology 10:779-783 (1992) describes affinity maturation by VH and VL domain shuffling. Random mutagenesis of CDR and/or framework residues is described by: Barbas et al., Proc Nat. Acad. Sci. USA 91:3809-3813 (1994); Schier et al., Gene 169:147-155 (1995); Yelton et al., J. Immunol. 155:1994-2004 (1995); Jackson et al., J. Immunol. 154(7):3310-9 (1995); and Hawkins et al., J. Mol. Biol. 226:889-896 (1992).

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g. B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. Proc. Natl. Acad. Sci. USA 95:652-656 (1998).

"Effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g., from blood.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daeron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)) and regulates homeostasis of immunoglobulins. For example, antibody variants with improved or diminished binding to FcRs have been described (see, e.g., Shields et al. J. Biol. Chem. 9(2): 6591-6604 (2001)).

Methods of measuring binding to FcRn are known (see, e.g., Ghetie 1997, Hinton 2004). Binding to human FcRn in vivo and serum half life of human FcRn high affinity binding polypeptides can be assayed, e.g., in transgenic mice or transfected human cell lines expressing human FcRn, or in primates administered with the Fc variant polypeptides.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, for example, as described in Gazzano-Santoro et al., J. Immunol. Methods 202:163 (1996), may be performed.

Polypeptide variants with altered Fc region amino acid sequences and increased or decreased C1q binding capability have been described (e.g., see, also, Idusogie et al. J. Immunol. 164: 4178-4184 (2000)).

"Fc region-comprising polypeptide" refers to a polypeptide, such as an antibody or immunoadhesin (see definitions below), which comprises an Fc region. The C-terminal lysine (residue 447 according to the EU numbering system) of the Fc region may be removed, for example, during purification of the polypeptide or by recombinant engineering the nucleic acid encoding the polypeptide.

"Blocking" antibody or an "antagonist" antibody refers to one which inhibits or reduces biological activity of the antigen it binds. Preferred blocking antibodies or antagonist antibodies substantially or completely inhibit the biological activity of the antigen.

"Agonist" antibody refers to an antibody which mimics (e.g., partially or fully) at least one of the functional activities of a polypeptide of interest.

"Acceptor human framework" refers to a framework comprising the amino acid sequence of a VL or VH framework derived from a human immunoglobulin framework, or from a human consensus framework. An acceptor human framework "derived from" a human immunoglobulin framework or human consensus framework may comprise the same amino acid sequence thereof, or may contain pre-existing amino acid sequence changes. Where pre-existing amino acid changes are present, preferably no more than 5 and preferably 4 or less, or 3 or less, pre-existing amino acid changes are present.

A "human consensus framework" refers to a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

"Disorder" or "disease" refers to any condition that would benefit from treatment with a substance/molecule (e.g., an antibody comprising an ultralong CDR3 as disclosed herein) or method disclosed herein. This includes chronic and acute disorders or diseases including those pathological conditions which predispose the mammal to the disorder in question.

"Treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies disclosed herein are used to delay development of a disease or disorder.

"Individual" (e.g., a "subject") refers to a vertebrate, preferably a mammal, more preferably a human. Mammals include, but are not limited to, farm animals (such as cows), sport animals, pets (such as cats, dogs and horses), primates, mice and rats.

"Mammal" for purposes of treatment refers to any animal classified as a mammal, including humans, rodents (e.g., mice and rats), and monkeys; domestic and farm animals; and zoo, sports, laboratory, or pet animals, such as dogs, cats, cattle, horses, sheep, pigs, goats, rabbits, etc. In some embodiments, the mammal is selected from a human, rodent, or monkey.

"Pharmaceutically acceptable" refers to approved or approvable by a regulatory agency of the Federal or a state government or listed in the U.S. Pharmacopeia or other generally recognized pharmacopeia for use in animals, including humans.

"Pharmaceutically acceptable salt" refers to a salt of a compound that is pharmaceutically acceptable and that possesses the desired pharmacological activity of the parent compound.

"Pharmaceutically acceptable excipient, carrier or adjuvant" refers to an excipient, carrier or adjuvant that can be administered to a subject, together with at least one antibody of the present disclosure, and which does not destroy the pharmacological activity thereof and is nontoxic when administered in doses sufficient to deliver a therapeutic amount of the compound.

"Pharmaceutically acceptable vehicle" refers to a diluent, adjuvant, excipient, or carrier with which at least one antibody of the present disclosure is administered.

"Providing a prognosis", "prognostic information", or "predictive information" refer to providing information, including for example the presence of cancer cells in a subject's tumor, regarding the impact of the presence of cancer (e.g., as determined by the diagnostic methods of the present disclosure) on a subject's future health (e.g., expected morbidity or mortality, the likelihood of getting cancer, and the risk of metastasis).

Terms such as "treating" or "treatment" or "to treat" or "alleviating" or "to alleviate" refer to both 1) therapeutic measures that cure, slow down, lessen symptoms of, and/or halt progression of a diagnosed pathologic condition or disorder and 2) prophylactic or preventative measures that prevent and/or slow the development of a targeted pathologic condition or disorder. Thus those in need of treatment include those already with the disorder; those prone to have the disorder; and those in whom the disorder is to be prevented.

"Providing a diagnosis" or "diagnostic information" refers to any information, including for example the presence of cancer cells, that is useful in determining whether a patient has a disease or condition and/or in classifying the disease or condition into a phenotypic category or any category having significance with regards to the prognosis of or likely response to treatment (either treatment in general or any particular treatment) of the disease or condition. Similarly, diagnosis refers to providing any type of diagnostic information, including, but not limited to, whether a subject is likely to have a condition (such as a tumor), whether a subject's tumor comprises cancer stem cells, information related to the nature or classification of a tumor as for example a high risk tumor or a low risk tumor, information related to prognosis and/or information useful in selecting an appropriate treatment. Selection of treatment can include the choice of a particular chemotherapeutic agent or other treatment modality such as surgery or radiation or a choice about whether to withhold or deliver therapy.

A "human consensus framework" refers to a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

An "acceptor human framework" for the purposes herein refers to a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Antigen-binding site" refers to the interface formed by one or more complementary determining regions. An antibody molecule has two antigen combining sites, each containing portions of a heavy chain variable region and portions of a light chain variable region. The antigen combining sites can contain other portions of the variable region domains in addition to the CDRs.

An "antibody light chain" or an "antibody heavy chain" refers to a polypeptide comprising the VL or VH, respectively. The VL is encoded by the minigenes V (variable) and J (junctional), and the VH by minigenes V, D (diversity), and J. Each of VL or VH includes the CDRs as well as the framework regions. In this application, antibody light chains and/or antibody heavy chains may, from time to time, be collectively referred to as "antibody chains." These terms encompass antibody chains containing mutations that do not disrupt the basic structure of VL or VH, as one skilled in the art will readily recognize.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide bonded. From N- to C-terminus, each heavy chain has a variable region (V H), also called a variable heavy domain or a heavy chain variable domain, followed by three constant domains (CH1, CH2, and CH3). Similarly, from N- to C-terminus, each light chain has a variable region (V L), also called a variable light domain or a light chain variable domain, followed by a constant light (CL) domain. The light chain of an antibody may be assigned to one of two types, called kappa (K) and lambda (K), based on the amino acid sequence of its constant domain.

"Combinatorial library" refers to collections of compounds formed by reacting different combinations of interchangeable chemical "building blocks" to produce a collection of compounds based on permutations of the building blocks. For an antibody combinatorial library, the building blocks are the component V, D and J regions (or modified forms thereof) from which antibodies are formed. For purposes herein, the terms "library" or "collection" are used interchangeably.

A "combinatorial antibody library" refers to a collection of antibodies (or portions thereof, such as Fabs), where the antibodies are encoded by nucleic acid molecules produced by the combination of V, D and J gene segments, particularly human V, D and J germline segments. The combinatorial libraries herein typically contain at least 50 different antibody (or antibody portions or fragment) members, typically at or about 50, 100, 500, 103, 1×103, 2×103, 3×103, 4×103, 5×103, 6×103, 7×103, 8×103, 9×103, 1×104, 2×104, 3×104, 4×104, 5×104, 6×104, 7×104, 8×104, 9×104, 1×105, 2×105, 3×105, 4×105, 5×105, 6×105, 7×105, 8×105, 9×105, 106, 107, 108, 109, 1010, or more different members. The resulting libraries or collections of antibodies or portions thereof, can be screened for binding to a target protein or modulation of a functional activity.

A "human combinatorial antibody library" refers to a collection of antibodies or portions thereof, whereby each member contains a VL and VH chains or a sufficient portion thereof to form an antigen binding site encoded by nucleic acid containing human germline segments produced as described herein.

A "variable germline segment" refers to V, D and J groups, subgroups, genes or alleles thereof. Gene segment sequences are accessible from known database (e.g., National Center for Biotechnology Information (NCBI), the international ImMunoGeneTics information System® (IMGT), the Kabat database and the Tomlinson's VBase database (Lefranc (2003) Nucleic Acids Res., 31:307-310; Martin et al., Bioinformatics Tools for Antibody Engineering in Handbook of Therapeutic Antibodies, Wiley-VCH (2007), pp. 104-107). Tables 3-5 list exemplary human variable germline segments. Sequences of exemplary VH, DH, JH, Vκ, Jκ, Vλ and or Jλ, germline segments are set forth in SEQ ID NOS: 10-451 and 868. For purposes herein, a germline segment includes modified sequences thereof, that are modified in accord with the rules of sequence compilation provided herein to permit practice of the method. For example, germline gene segments include those that contain one amino acid deletion or insertion at the 5' or 3' end compared to any of the sequences of nucleotides set forth in SEQ ID NOS:10-451, 868.

"Compilation," "compile," "combine," "combination," "rearrange," "rearrangement," or other similar terms or grammatical variations thereof refers to the process by which germline segments are ordered or assembled into nucleic acid sequences representing genes. For example, variable heavy chain germline segments are assembled such that the VH segment is 5' to the DH segment which is 5' to the JH segment, thereby resulting in a nucleic acid sequence encoding a VH chain. Variable light chain germline segments are assembled such that the VL segment is 5' to the JL segment, thereby resulting in a nucleic acid sequence encoding a VL chain. A constant gene segment or segments also can be assembled onto the 3' end of a nucleic acid encoding a VH or VL chain.

"Linked," or "linkage" or other grammatical variations thereof with reference to germline segments refers to the joining of germline segments. Linkage can be direct or indirect. Germline segments can be linked directly without additional nucleotides between segments, or additional nucleotides can be added to render the entire segment in-frame, or nucleotides can be deleted to render the resulting segment in-frame. It is understood that the choice of linker nucleotides is made such that the resulting nucleic acid molecule is in-frame and encodes a functional and productive antibody.

"In-frame" or "linked in-frame" with reference to linkage of human germline segments means that there are insertions and/or deletions in the nucleotide germline segments at the joined junctions to render the resulting nucleic acid molecule in-frame with the 5' start codon (ATG), thereby producing a "productive" or functional full-length polypeptide. The choice of nucleotides inserted or deleted from germline segments, particularly at joints joining various VD, DJ and VJ segments, is in accord with the rules provided in the method herein for V(D)J joint generation. For example, germline segments are assembled such that the VH segment is 5' to the DH segment which is 5' to the JH segment. At the junction joining the VH and the DH and at the junction joining the DH and JH segments, nucleotides can be inserted or deleted from the individual VH, DH or JH segments, such that the resulting nucleic acid molecule containing the joined VDJ segments are in-frame with the 5' start codon (ATG).

A portion of an antibody includes sufficient amino acids to form an antigen binding site.

A "reading frame" refers to a contiguous and non-overlapping set of three-nucleotide codons in DNA or RNA. Because three codons encode one amino acid, there exist three possible reading frames for given nucleotide sequence, reading frames 1, 2 or 3. For example, the sequence ACTGGTCA will be ACT GGT CA for reading frame 1, A CTG GTC A for reading frame 2 and AC TGG TCA for reading frame 3. Generally for practice of the method described herein, nucleic acid sequences are combined so that the V sequence has reading frame 1.

A "stop codon" refers to a three-nucleotide sequence that signals a halt in protein synthesis during translation, or any sequence encoding that sequence (e.g. a DNA sequence encoding an RNA stop codon sequence), including the amber stop codon (UAG or TAG)), the ochre stop codon (UAA or TAA)) and the opal stop codon (UGA or TGA)). It is not necessary that the stop codon signal termination of translation in every cell or in every organism. For example, in suppressor strain host cells, such as amber suppressor strains and partial amber suppressor strains, translation proceeds through one or more stop codon (e.g. the amber stop codon for an amber suppressor strain), at least some of the time.

A "variable heavy" (VH) chain or a "variable light" (VL) chain (also termed VH domain or VL domain) refers to the polypeptide chains that make up the variable domain of an antibody. For purposes herein, heavy chain germline segments are designated as VH, DH and JH, and compilation thereof results in a nucleic acid encoding a VH chain. Light chain germline segments are designated as VL or JL, and include kappa and lambda light chains (Vκ and Jκ; Vλ and Jλ.) and compilation thereof results in a nucleic acid encoding a VL chain. It is understood that a light chain is either a kappa or lambda light chain, but does not include a kappa/lambda combination by virtue of compilation of a Vκ and Jλ.

A "degenerate codon" refers to three-nucleotide codon that specifies the same amino acid as a codon in a parent nucleotide sequence. One of skill in the art is familiar with degeneracy of the genetic code and can identify degenerate codons.

"Diversity" with respect to members in a collection refers to the number of unique members in a collection. Hence, diversity refers to the number of different amino acid sequences or nucleic acid sequences, respectively, among the analogous polypeptide members of that collection. For example, a collection of polynucleotides having a diversity of 104 contains 104 different nucleic acid sequences among the analogous polynucleotide members. In one example, the provided collections of polynucleotides and/or polypeptides have diversities of at least at or about 102, 103, 104, 105, 106, 107, 108, 109, 1010 or more.

"Sequence diversity" refers to a representation of nucleic acid sequence similarity and is determined using sequence alignments, diversity scores, and/or sequence clustering. Any two sequences can be aligned by laying the sequences side-by-side and analyzing differences within nucleotides at every position along the length of the sequences. Sequence alignment can be assessed in silico using Basic Local Alignment Search Tool (BLAST), an NCBI tool for comparing nucleic acid and/or protein sequences. The use of BLAST for sequence alignment is well known to one of skill in the art. The Blast search algorithm compares two sequences and calculates the statistical significance of each match (a Blast score). Sequences that are most similar to each other will have a high Blast score, whereas sequences that are most varied will have a low Blast score.

A "polypeptide domain" refers to a part of a polypeptide (a sequence of three or more, generally 5 or 7 or more amino acids) that is a structurally and/or functionally distinguishable or definable. Exemplary of a polypeptide domain is a part of the polypeptide that can form an independently folded structure within a polypeptide made up of one or more structural motifs (e.g. combinations of alpha helices and/or beta strands connected by loop regions) and/or that is recognized by a particular functional activity, such as enzymatic activity or antigen binding. A polypeptide can have one, typically more than one, distinct domains. For example, the polypeptide can have one or more structural domains and one or more functional domains. A single polypeptide domain can be distinguished based on structure and function. A domain can encompass a contiguous linear sequence of amino acids. Alternatively, a domain can encompass a plurality of non-contiguous amino acid portions, which are non-contiguous along the linear sequence of amino acids of the polypeptide. Typically, a polypeptide contains a plurality of domains. For example, each heavy chain and each light chain of an antibody molecule contains a plurality of immunoglobulin (Ig) domains, each about 110 amino acids in length.

An "Ig domain" refers to a domain, recognized as such by those in the art, that is distinguished by a structure, called the Immunoglobulin (Ig) fold, which contains two beta-pleated sheets, each containing anti-parallel beta strands of amino acids connected by loops. The two beta sheets in the Ig fold are sandwiched together by hydrophobic interactions and a conserved intra-chain disulfide bond. Individual immunoglobulin domains within an antibody chain further can be distinguished based on function. For example, a light chain contains one variable region domain (VL) and one constant region domain (CL), while a heavy chain contains one variable region domain (VH) and three or four constant region domains (CH). Each VL, CL, VH, and CH domain is an example of an immunoglobulin domain.

A "variable domain" with reference to an antibody refers to a specific Ig domain of an antibody heavy or light chain that contains a sequence of amino acids that varies among different antibodies. Each light chain and each heavy chain has one variable region domain (VL, and, VH). The variable domains provide antigen specificity, and thus are responsible for antigen recognition. Each variable region contains CDRs that are part of the antigen binding site domain and framework regions (FRs).

A "constant region domain" refers to a domain in an antibody heavy or light chain that contains a sequence of amino acids that is comparatively more conserved among antibodies than the variable region domain. Each light chain has a single light chain constant region (CL) domain and each heavy chain contains one or more heavy chain constant region (CH) domains, which include, CH1, CH2, CH3 and CH4. Full-length IgA, IgD and IgG isotypes contain CH1, CH2 CH3 and a hinge region, while IgE and IgM contain CH1, CH2 CH3 and CH4. CH1 and CL domains extend the Fab arm of the antibody molecule, thus contributing to the interaction with antigen and rotation of the antibody arms. Antibody constant regions can serve effector functions, such as, but not limited to, clearance of antigens, pathogens and toxins to which the antibody specifically binds, e.g. through interactions with various cells, biomolecules and tissues.

An "antibody or portion thereof that is sufficient to form an antigen binding site" means that the antibody or portion thereof contains at least 1 or 2, typically 3, 4, 5 or all 6 CDRs of the VH and VL sufficient to retain at least a portion of the binding specificity of the corresponding full-length antibody containing all 6 CDRs. Generally, a sufficient antigen binding site at least requires CDR3 of the heavy chain (CDRH3). It typically further requires the CDR3 of the light chain (CDRL3). As described herein, one of skill in the art knows and can identify the CDRs based on Kabat or Chothia numbering (see, e.g., Kabat, E. A. et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917). For example, based on Kabat numbering, CDR-L1 corresponds to residues L24-L34; CDR-L2 corresponds to residues L50-L56; CDR-L3 corresponds to residues L89-L97; CDR-H1 corresponds to residues H31-H35, 35a or 35b depending on the length; CDR-H2 corresponds to residues H50-H65; and CDR-H3 corresponds to residues H95-H102.

A "peptide mimetic" refers to a peptide that mimics the activity of a polypeptide. For example, an erythropoietin (EPO) peptide mimetic is a peptide that mimics the activity of Epo, such as for binding and activation of the EPO receptor.

An "address" refers to a unique identifier for each locus in a collection whereby an addressed member (e.g. an antibody) can be identified. An addressed moiety is one that can be identified by virtue of its locus or location. Addressing can be effected by position on a surface, such as a well of a microplate. For example, an address for a protein in a microwell plate that is F9 means that the protein is located in row F, column 9 of the microwell plate. Addressing also can be effected by other identifiers, such as a tag encoded with a bar code or other symbology, a chemical tag, an electronic, such RF tag, a color-coded tag or other such identifier.

An "array" refers to a collection of elements, such as antibodies, containing three or more members.

A "spatial array" refers to an array where members are separated or occupy a distinct space in an array. Hence, spatial arrays are a type of addressable array. Examples of spatial arrays include microtiter plates where each well of a plate is an address in the array. Spacial arrays include any arrangement wherein a plurality of different molecules, e.g., polypeptides, are held, presented, positioned, situated, or supported. Arrays can include microtiter plates, such as 48-well, 96-well, 144-well, 192-well, 240-well, 288-well, 336-well, 384-well, 432-well, 480-well, 576-well, 672-well, 768-well, 864-well, 960-well, 1056-well, 1152-well, 1248-well, 1344-well, 1440-well, or 1536-well plates, tubes, slides, chips, flasks, or any other suitable laboratory apparatus. Furthermore, arrays can also include a plurality of sub-arrays. A plurality of sub-arrays encompasses an array where more than one arrangement is used to position the polypeptides. For example, multiple 96-well plates could constitute a plurality of sub-arrays and a single array.

An "addressable library" or "spatially addressed library" refers to a collection of molecules such as nucleic acid molecules or protein agents, such as antibodies, in which each member of the collection is identifiable by virtue of its address.

An "addressable array" refers to one in which the members of the array are identifiable by their address, the position in a spatial array, such as a well of a microtiter plate, or on a solid phase support, or by virtue of an identifiable or detectable label, such as by color, fluorescence, electronic signal (i.e. RF, microwave or other frequency that does not substantially alter the interaction of the molecules of interest), bar code or other symbology, chemical or other such label. Hence, in general the members of the array are located at identifiable loci on the surface of a solid phase or directly or indirectly linked to or otherwise associated with the identifiable label, such as affixed to a microsphere or other particulate support (herein referred to as beads) and suspended in solution or spread out on a surface.

"An addressable combinatorial antibody library" refers to a collection of antibodies in which member antibodies are identifiable and all antibodies with the same identifier, such as position in a spatial array or on a solid support, or a chemical or RF tag, bind to the same antigen, and generally are substantially the same in amino acid sequence. For purposes herein, reference to an "addressable arrayed combinatorial antibody library" means that the antibody members are addressed in an array.

"In silico" refers to research and experiments performed using a computer. In silico methods include, but are not limited to, molecular modeling studies, biomolecular docking experiments, and virtual representations of molecular structures and/or processes, such as molecular interactions. For purposes herein, the antibody members of a library can be designed using a computer program that selects component V, D and J germline segments from among those input into the computer and joins them in-frame to output a list of nucleic acid molecules for synthesis. Thus, the recombination of the components of the antibodies in the collections or libraries provided herein, can be performed in silico by combining the nucleotide sequences of each building block in accord with software that contains rules for doing so. The process could be performed manually without a computer, but the computer provides the convenience of speed.

A "database" refers to a collection of data items. For purposes herein, reference to a database is typically with reference to antibody databases, which provide a collection of sequence and structure information for antibody genes and sequences. Exemplary antibody databases include, but are not limited to, IMGT®, the international ImMunoGeneTics information system (imgt.cines.fr; see e.g., Lefranc et al. (2008) Briefings in Bioinformatics, 9:263-275), National Center for Biotechnology Information (NCBI), the Kabat database and the Tomlinson's VBase database (Lefranc (2003) Nucleic Acids Res., 31:307-310; Martin et al., Bioinformatics Tools for Antibody Engineering in Handbook of Therapeutic Antibodies, Wiley-VCH (2007), pp. 104-107). A database also can be created by a user to include any desired sequences. The database can be created such that the sequences are inputted in a desired format (e.g., in a particular reading frame; lacking stop codons; lacking signal sequences). The database also can be created to include sequences in addition to antibody sequences.

"Screening" refers to identification or selection of an antibody or portion thereof from a collection or library of antibodies and/or portions thereof, based on determination of the activity or property of an antibody or portion thereof. Screening can be performed in any of a variety of ways, including, for example, by assays assessing direct binding (e.g. binding affinity) of the antibody to a target protein or by functional assays assessing modulation of an activity of a target protein.

"Activity towards a target protein" refers to binding specificity and/or modulation of a functional activity of a target protein, or other measurements that reflects the activity of an antibody or portion thereof towards a target protein.

A "target protein" or "protein target" refers to candidate proteins or peptides that are specifically recognized by an antibody or portion thereof and/or whose activity is modulated by an antibody or portion thereof. Modulating the activity can comprise increasing, decreasing, stimulating, or preventing the activity or expression of the target protein. A target protein includes any peptide or protein that contains an epitope for antibody recognition. Target proteins include proteins involved in the etiology of a disease or disorder by virtue of expression or activity. Exemplary target proteins are described herein. In some instances, the target protein is a transmembrane protein target. Transmembrane protein targets include, but are not limited to, GPCRs, ion channels, transporters, and cell surface receptors. Ion channels may be potassium ion channels, sodium ion channels, calcium ion channels, and voltage gated channels. In some instances, the antibodies disclosed herein modulate a Kv1.3 ion channel, Nav1.7 ion channel, or acid sensing ion channel (ASIC). The antibodies disclosed herein may modulate cell surface receptors such as GLP1R, GCGR, EPO receptor, FGFR, FGF21R, CSFR, GMCSFR, and GCSFR. Additional target proteins include, but are not limited to, cytokines, kinases, interferons, hormones, and growth factors. The target proteins can be from a mammal or non-mammal. The target proteins can be from a human. Alternatively, the target proteins are from a bovine.

"Hit" refers to an antibody or portion thereof identified, recognized or selected as having an activity in a screening assay.

"Iterative" with respect to screening means that the screening is repeated a plurality of times, such as 2, 3, 4, 5 or more times, until a "Hit" is identified whose activity is optimized or improved compared to prior iterations.

"High-throughput" refers to a large-scale method or process that permits manipulation of large numbers of molecules or compounds, generally tens to hundreds to thousands of compounds. For example, methods of purification and screening can be rendered high-throughput. High-throughput methods can be performed manually. Generally, however, high-throughput methods involve automation, robotics or software.

Basic Local Alignment Search Tool (BLAST) is a search algorithm developed by Altschul et al. (1990) to separately search protein or DNA databases, for example, based on sequence identity. For example, blastn is a program that compares a nucleotide query sequence against a nucleotide sequence database (e.g. GenBank). BlastP is a program that compares an amino acid query sequence against a protein sequence database.

A BLAST bit score is a value calculated from the number of gaps and substitutions associated with each aligned sequence. The higher the score, the more significant the alignment.

A "human protein" refers to a protein encoded by a nucleic acid molecule, such as DNA, present in the genome of a human, including all allelic variants and conservative variations thereof. A variant or modification of a protein is a human protein if the modification is based on the wildtype or prominent sequence of a human protein.

"Naturally occurring amino acids" refer to the 20 L-amino acids that occur in polypeptides. The residues are those 20 α-amino acids found in nature which are incorporated into protein by the specific recognition of the charged tRNA molecule with its cognate mRNA codon in humans.

"Non-naturally occurring amino acids" refer to amino acids that are not genetically encoded. For example, a non-natural amino acid is an organic compound that has a structure similar to a natural amino acid but has been modified structurally to mimic the structure and reactivity of a natural amino acid. Non-naturally occurring amino acids thus include, for example, amino acids or analogs of amino acids other than the 20 naturally-occurring amino acids and include, but are not limited to, the D-isostereomers of amino acids. Exemplary non-natural amino acids are known to those of skill in the art.

"Nucleic acids" include DNA, RNA and analogs thereof, including peptide nucleic acids (PNA) and mixtures thereof. Nucleic acids can be single or double-stranded. When referring to probes or primers, which are optionally labeled, such as with a detectable label, such as a fluorescent or radiolabel, single-stranded molecules are contemplated. Such molecules are typically of a length such that their target is statistically unique or of low copy number (typically less than 5, generally less than 3) for probing or priming a library. Generally a probe or primer contains at least 14, 16 or 30 contiguous nucleotides of sequence complementary to or identical to a gene of interest. Probes and primers can be 10, 20, 30, 50, 100 or more nucleic acids long.

A "peptide" refers to a polypeptide that is from 2 to 40 amino acids in length.

The amino acids which occur in the various sequences of amino acids provided herein are identified according to their known, three-letter or one-letter abbreviations (Table 1). The nucleotides which occur in the various nucleic acid fragments are designated with the standard single-letter designations used routinely in the art.

An "amino acid" is an organic compound containing an amino group and a carboxylic acid group. A polypeptide contains two or more amino acids. For purposes herein, amino acids include the twenty naturally-occurring amino acids, non-natural amino acids and amino acid analogs (i.e., amino acids wherein the α-carbon has a side chain).

"Amino acid residue" refers to an amino acid formed upon chemical digestion (hydrolysis) of a polypeptide at its peptide linkages. The amino acid residues described herein are presumed to be in the "L" isomeric form. Residues in the "D" isomeric form, which are so designated, can be substituted for any L-amino acid residue as long as the desired functional property is retained by the polypeptide. NH2 refers to the free amino group present at the amino terminus of a polypeptide. COOH refers to the free carboxy group present at the carboxyl terminus of a polypeptide. In keeping with standard polypeptide nomenclature described in J. Biol. Chem., 243: 3552-3559 (1969), and adopted 37 C.F.R. □§§ 1.821-1.822, abbreviations for amino acid residues are shown below:

| SYMBOL | | |
|---|---|---|
| 1-Letter | 3-Letter | AMINO ACID |
| Y | Tyr | Tyrosine |
| G | Gly | Glycine |
| F | Phe | Phenylalanine |
| M | Met | Methionine |
| A | Ala | Alanine |
| S | Ser | Serine |
| I | Ile | Isoleucine |
| L | Leu | Leucine |
| T | Thr | Threonine |
| V | Val | Valine |
| P | Pro | Proline |
| K | Lys | Lysine |
| H | His | Histidine |
| Q | Gln | Glutamine |
| E | Glu | Glutamic acid |
| Z | Glx | Glu and/or Gln |
| W | Trp | Tryptophan |
| R | Arg | Arginine |
| D | Asp | Aspartic acid |
| N | Asn | Asparagine |
| B | Asx | Asn and/or Asp |
| C | Cys | Cysteine |
| X | Xaa | Unknown or other |

It should be noted that all amino acid residue sequences represented herein by formulae have a left to right orientation in the conventional direction of amino-terminus to carboxyl-terminus. In addition, the phrase "amino acid residue" is broadly defined to include the amino acids listed in the Table of Correspondence (Table 1) and modified and unusual amino acids, such as those referred to in 37 C.F.R. §§ 1.821-1.822, and incorporated herein by reference. Furthermore, it should be noted that a dash at the beginning or end of an amino acid residue sequence indicates a peptide bond to a further sequence of one or more amino acid residues, to an amino-terminal group such as NH2 or to a carboxyl-terminal group such as COOH. The abbreviations for any protective groups, amino acids and other compounds, are, unless indicated otherwise, in accord with their common usage, recognized abbreviations, or the IUPAC-IUB Commission on Biochemical Nomenclature (see, (1972) Biochem. 11:1726). Each naturally occurring L-amino acid is identified by the standard three letter code (or single letter code) or the standard three letter code (or single letter code) with the prefix "L-"; the prefix "D-" indicates that the stereoisomeric form of the amino acid is D.

An "immunoconjugate" refers to an antibody conjugated to one or more heterologous molecule(s), including but not limited to a cytotoxic agent, non-antibody peptide or therapeutic polypeptide. An immunoconjugate may include non-antibody sequences. The non-antibody sequence can be conjugated to the antibody. Alternatively, the non-antibody sequence can be within the antibody sequence.

A "non-antibody peptide" refers to a peptide encoded by a non-antibody antibody sequence. For example, a non-antibody peptide may be a hormone, a lymphokine, an interleukin, a chemokines, a cytokine or a peptide toxin.

As used herein, the terms "therapeutic polypeptide," "therapeutic peptides," and therapeutic immunoglobulin construct" mean one or more peptides having demonstrated or potential use in treating, preventing, or ameliorating one or more diseases, disorders, or conditions in a subject in need thereof, as well as related peptides. Therapeutic peptides include peptides found to have use in treating, preventing, or ameliorating one or more diseases, disorders, or conditions after the time of filing of this application. Related peptides include fragments of therapeutic peptides, therapeutic peptide variants, and therapeutic peptide derivatives that retain some or all of the therapeutic activities of the therapeutic peptide. As will be known to one of skill in the art, as a general principle, modifications may be made to peptides that do not alter, or only partially abrogate, the properties and activities of those peptides. In some instances, modifications result in an increase in therapeutic activities. The terms "therapeutic polypeptide" or "therapeutic peptides" encompass modifications to the therapeutic peptides defined and/or disclosed herein. In certain embodiments, the therapeutic polypeptide is selected from a hormone, a lymphokine, an interleukin, a chemokines, a cytokine, a peptide toxin, and combinations thereof. Therapeutic polypeptides can be peptides encoded by non-antibody sequences.

A derivative or a variant of a polypeptide is said to share "homology" or be "homologous" with the peptide if the amino acid sequences of the derivative or variant has at least 50% identity with the original peptide. In certain embodiments, the derivative or variant is at least 75% the same as that of either the peptide or a fragment of the peptide having the same number of amino acid residues as the derivative. In certain embodiments, the derivative or variant is at least 85% the same as that of either the peptide or a fragment of the peptide having the same number of amino acid residues as the derivative. In certain embodiments, the amino acid sequence of the derivative is at least 90% the same as the peptide or a fragment of the peptide having the same number of amino acid residues as the derivative. In some embodiments, the amino acid sequence of the derivative is at least 95% the same as the peptide or a fragment of the peptide having the same number of amino acid residues as the derivative. In certain embodiments, the derivative or variant is at least 99% the same as that of either the peptide or a fragment of the peptide having the same number of amino acid residues as the derivative.

Groupings of alternative elements or embodiments disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the exemplary embodiments. Of course, variations on these described embodiments will become apparent to those of ordinary skill in the art upon reading the foregoing description. The inventor expects skilled artisans to employ such variations as appropriate, and the inventors intend for the embodiments to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Furthermore, numerous references have been made to patents and printed publications. Each of the above-cited references is individually incorporated herein by reference in their entirety.

Specific embodiments disclosed herein can be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Exemplary embodiments so claimed are inherently or expressly described and enabled herein.

In closing, it is to be understood that the exemplary embodiments disclosed herein are illustrative of the principles of the present disclosure. Other modifications that can be employed are within the scope of the disclosure. Thus, by way of example, but not of limitation, alternative configurations of the present exemplary embodiments can be utilized in accordance with the teachings herein. Accordingly, the present exemplary embodiments are not limited to that precisely as shown and described.

General Techniques

The present disclosure relies on routine techniques in the field of recombinant genetics. Basic texts disclosing the general methods of use in this present disclosure include Sambrook and Russell, Molecular Cloning: A Laboratory Manual 3d ed. (2001); Kriegler, Gene Transfer and Expression: A Laboratory Manual (1990); and Ausubel et al., Current Protocols in Molecular Biology (1994).

For nucleic acids, sizes are given in either kilobases (Kb) or base pairs (bp). These are estimates derived from agarose or polyacrylamide gel electrophoresis, from sequenced nucleic acids, or from published DNA sequences. For proteins, sizes are given in kilo-Daltons (kD) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage and Caruthers, Tetrahedron Letters, 22:1859-1862 (1981), using an automated synthesizer, as described in Van Devanter et al., Nucleic Acids Res., 12:6159-6168 (1984). Purification of oligonucleotides is by either native polyacrylamide gel electrophoresis or by anion-exchange chromatography as described in Pearson & Reanier, J. Chrom., 255:137-149 (1983). The sequence of the cloned genes and synthetic oligonucleotides can be verified after cloning using, e.g., the chain termination method for sequencing double-stranded templates of Wallace et al., Gene, 16:21-26 (1981).

The nucleic acids encoding recombinant polypeptides of the present disclosure may be cloned into an intermediate vector before transformation into prokaryotic or eukaryotic cells for replication and/or expression. The intermediate vector may be a prokaryote vector such as a plasmid or shuttle vector.

Antibodies with Ultralong CDR3 Sequences

To date, cattle are the only species where ultralong CDR3 sequences have been identified. However, other species, for example other ruminants, may also possess antibodies with ultralong CDR3 sequences.

Exemplary antibody variable region sequences comprising an ultralong CDR3 sequence identified in cattle include those designated as: BLV1H12 (see, SEQ ID NO: 22), BLV5B8 (see, SEQ ID NO: 23), BLV5D3 (see, SEQ ID NO: 24) and BLV8C11 (see, SEQ ID NO: 25) (see, e.g., Saini, et al. (1999) Eur. J. Immunol. 29: 2420-2426; and Saini and Kaushik (2002) Scand. J. Immunol. 55: 140-148); BF4E9 (see, SEQ ID NO: 26) and BF1H1 (see, SEQ ID NO: 27) (see, e.g., Saini and Kaushik (2002) Scand. J. Immunol. 55: 140-148); and F18 (see, SEQ ID NO: 28) (see, e.g., Berens, et al. (1997) Int. Immunol. 9: 189-199).

In an embodiment, bovine antibodies are identified and/or produced. Multiple techniques exist to identify and/or produce antibodies.

Antibodies of the present disclosure may be isolated by screening including, high-throughput screening, of combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in Methods in Molecular Biology 178:1-37 (O'Brien et al., ed., Human Press, Totowa, N.J., 2001) and further described, e.g., in the McCafferty et al., Nature 348:552-554; Clackson et al., Nature 352: 624-628 (1991); Marks et al., J. Mol. Biol. 222: 581-597 (1992); Marks and Bradbury, in Methods in Molecular Biology 248:161-175 (Lo, ed., Human Press, Totowa, N.J., 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004). Such screening may be iterative until a hit is obtained.

In certain phage display methods, repertoires of VH and VL genes are separately cloned by polymerase chain reaction (PCR) and recombined randomly in phage libraries, which can then be screened for antigen-binding phage as described in Winter et al., Ann. Rev. Immunol., 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Phage display libraries of bovine antibodies may be a source of bovine antibody gene sequences, including ultralong CDR3 sequences.

Typically, a non-human antibody is humanized to reduce imrnunogenicity to humans, while retaining the specificity and affinity of the parental non-human antibody. Generally, a humanized antibody comprises one or more variable domains in which CDRs (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the CDR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing SDR (a-CDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005); Klimka et al., Br. J. Cancer, 83:252-260 (2000) (describing the "guided selection" approach to FR shuffling); and Studnicka et al., U.S. Pat. No. 5,766,886.

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., Biol. Chem. 272:10678-10684 (1997) and Rosok et al., J. Biol. Chem. 271:22611-22618 (1996)).

Antibodies with ultralong CDR3 sequences may also include non-antibody sequences, such as cytokines, therapeutic polypeptides or growth factors, into the CDR3 region. The resultant antibody can be effective in treating or preventing a disease or condition. For example, an antibody comprising an ultralong CDR3 inhibits tumor metastasis. In some embodiments, the cytokine, therapeutic polypeptide or growth factor may be shown to have an antiproliferative effect on at least one cell population. Alternatively, or additionally, the resultant antibody modulates the expression or activity of a target (e.g., protein target, transmembrane protein target). For example, an antibody comprising an ultralong CDR3 inhibits or blocks an ion channel. The non-antibody sequence may be a hormone, a lymphokine, an interleukin, a chemokines, a cytokine, a peptide toxin, and combinations thereof. Such cytokines, therapeutic polypeptides, toxins, lymphokines, growth factors, or other hematopoietic factors include Granulocyte colony-stimulating factor (G-CSF), macrophage colony-stimulating factor (M-CSF), Granulocyte-macrophage colony-stimulating factor (GM-CSF), Meg-CSF, TNF, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IFN (e.g., α-interferon, β-interferon, a λ-interferon), TNF-alpha, TNF1, TNF2, thrombopoietin, stem cell factor, and erythropoietin (EPO). Additional growth factors for use in the antibodies and/or pharmaceutical compositions of the present disclosure include: angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor, cytokine-induced neutrophil chemotactic factor 1, cytokine-induced neutrophil, chemotactic factor 2, cytokine-induced neutrophil chemotactic factor 2, endothelial cell growth factor, endothelin 1, epidermal growth factor, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor 21 (FGF21) fibroblast growth factor acidic, fibroblast growth factor basic, glial cell line-derived neutrophic factor receptor-1, glial cell line-derived neutrophic factor receptor-2, growth related protein, growth related protein-1, growth related protein-2, growth related protein-3, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor-1, nerve growth factor nerve growth factor receptor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor-1, platelet derived growth factor receptor-2, pre-B cell growth stimulating factor, stem cell factor, stem cell factor receptor, transforming growth factor-1, transforming growth factor-2, transforming growth factor-1, transforming growth factor-1.2, transforming growth factor-2, transforming growth factor-3, transforming growth factor-S, latent transforming growth factor-1, transforming growth factor-1 binding protein I, transforming growth factor-1 binding protein II, transforming growth factor-1 binding protein III, tumor necrosis factor receptor type I, tumor necrosis factor receptor type II, urokinase-type plasminogen activator receptor, vascular endothelial growth factor, and chimeric proteins and biologically or immunologically active fragments thereof. In some embodiments, the therapeutic polypeptide is a mammalian G-CSF, a growth hormone, a leptin, a α-interferon, a β-interferon, a λ-interferon, a GM-CSF, a IL-11, a IL-10, a moka1 (e.g., Moka, moka-toxin-1), or a VM-24. In some embodiments, the therapeutic polypeptide is a glucagon-like peptide 1 (GLP-1), exendin-4 (Ex-4), erythropoietin (EPO), fibroblast growth factor (FGF21), IL8, ziconotide, somatostatin, chlorotoxin, SDF1 (alpha), IL21, or derivative or variant thereof. The G-CSF may be a bovine G-CSF. The G-CSF, GM-CSF, EPO, FGF21, β-interferon and GLP-1 may be from a human.

The non-antibody sequence may comprise an amino acid sequence based on or derived from any of SEQ ID NOS: 317-332. The non-antibody sequence may comprise an amino acid sequence that is 50%, 60%, 70% 80%, 90%, 95%, 97%, 99% identical to any of SEQ ID NOS: 317-332. The non-antibody sequence may comprise an amino acid sequence that comprises 5, 6, 7, 8, 9, 10, 11, 12, 13, 14, 15, 16, 17, 18, 19, 20, or more amino acid residues of SEQ ID NOS: 317-332. The amino acid residues may be consecutive. Alternatively, the amino acid residues are non-consecutive. The non-antibody sequence may comprise at least a portion of any of SEQ ID NOS: 317-332.

The antibodies disclosed herein may comprise one or more sequences based on or derived from a mammalian, avian, reptilian, amphibian, fish, insect, bug, or arachnid sequence. Mammals include, but are not limited to, cows, bison, buffalo, humans, mice, dogs, cats, sheep, goats, or rabbits. Avians include, but are not limited to, chicken, geese, doves, eagles, sparrows, and pidgeons. Reptiles include, but are not limited to, lizards, gators, snakes, and turtles. Amphibians include, but are not limited to, frogs, salamanders, toads, and newts. Fish include, but are not limited to, tuna, salmon, whales, and sharks. Insects, bugs, and arachnids include, but are not limited to, flies, mosquitos, spiders, and scorpions. The non-antibody sequence may be based on or derived from a bovine or human sequence. Alternatively, the non-antibody sequence is based on or derived from a lizard, snail, snake or scorpion sequence. The lizard may be a gila monster. The snail may be a cone snail.

In some embodiments, the non-antibody sequence is linked to an end of an ultralong CDR3 sequence. For example, the non-antibody sequence can be linked to the 5' end or 3' end of the ultralong CDR3 nucleotide sequence. In another example, the non-antibody sequence can be linked to the N-terminus or C-terminus of the ultralong CDR3 peptide sequence.

In another embodiment, the non-antibody sequence is inserted within an ultralong CDR3 sequence. For example, the non-antibody sequence is inserted between the stalk domain of an ultralong CDR3 sequence. The non-antibody sequence can be inserted within the stalk domain of an ultralong CDR3 sequence. In another example, the non-antibody sequence is inserted between the stalk domain and the knob domain of an ultralong CDR3 sequence. Alternatively, the non-antibody sequence is inserted within the knob domain of an ultralong CDR3 sequence.

In some embodiments, the non-antibody sequence replaces at least a portion of an ultralong CDR3 sequence. The non-antibody sequence can replace about 1 or more, 2 or more, 3 or more, 4 or more, 5 or more, 10 or more, 15 or more, 20 or more, 25 or more, 30 or more, 35 or more, 40 or more, 45 or more, 50 or more, 55 or more amino acids of the ultralong CDR3 peptide sequence. The non-antibody sequence can replace about 10% or more, 20% or more, 30% or more, 40% or more, 50% or more, 55% or more, 60% or more, 65% or more, 70% or more, 75% or more, 80% or more, 85% or more, 90% or more, 95% or more of the ultralong CDR3 peptide sequence. The non-antibody sequence can replace at least a portion of a knob domain of an ultralong CDR3. The non-antibody sequence can replace about 5 or more, 10 or more, 15 or more, 20 or more, 25 or more, 30 or more, 35 or more, 40 or more, 45 or more amino acids of the knob domain of an ultralong CDR3 peptide sequence. The non-antibody sequence can replace about 10% or more, 20% or more, 30% or more, 40% or more, 50% or more, 55% or more, 60% or more, 65% or more, 70% or more, 75% or more, 80% or more, 85% or more, 90% or more, 95% or more of the knob domain of the ultralong CDR3 peptide sequence. The non-antibody sequence can replace at least a portion of a stalk domain of an ultralong CDR3. The non-antibody sequence can replace about 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more amino acids of the stalk domain of an ultralong CDR3 peptide sequence. The non-antibody sequence can replace about 10% or more, 20% or more, 30% or more, 40% or more, 50% or more, 55% or more, 60% or more, 65% or more, 70% or more, 75% or more, 80% or more, 85% or more, 90% or more, 95% or more of the stalk domain of the ultralong CDR3 peptide sequence. The amino acids may be consecutive amino acids. Alternatively, the amino acids are non-consecutive amino acids. The ultralong CDR3 may comprise one or more conserved motifs. The conserved motifs may be stalk domain conserved motifs as disclosed herein. Alternatively, the conserved motifs may be knob domain conserved motifs as disclosed herein.

In some embodiments, the non-antibody sequence replaces at least a portion of an ultralong CDR3 sequence. The non-antibody sequence can replace about 5 or more, 10 or more, 15 or more, 20 or more, 25 or more, 30 or more, 40 or more, 50 or more, 55 or more, 60 or more, 70 or more, 80 or more, 90 or more, 100 or more, 110 or more, 120 or more, 130 or more, 140 or more, 150 or more, 160 or more, 170 or more nucleotides of the ultralong CDR3 nucleotide sequence. The non-antibody sequence can replace about 10% or more, 20% or more, 30% or more, 40% or more, 50% or more, 55% or more, 60% or more, 65% or more, 70% or more, 75% or more, 80% or more, 85% or more, 90% or more, 95% or more of the ultralong CDR3 nucleotide sequence. The non-antibody sequence can replace at least a portion of a knob domain of an ultralong CDR3. The non-antibody sequence can replace about 5 or more, 10 or more, 15 or more, 20 or more, 25 or more, 30 or more, 40 or more, 50 or more, 55 or more, 60 or more, 70 or more, 80 or more, 90 or more, 100 or more, 110 or more, 120 or more, 130 or more, 140 or more nucleotides of the knob domain of an ultralong CDR3 nucleotide sequence. The non-antibody sequence can replace about 10% or more, 20% or more, 30% or more, 40% or more, 50% or more, 55% or more, 60% or more, 65% or more, 70% or more, 75% or more, 80% or more, 85% or more, 90% or more, 95% or more of the knob domain of the ultralong CDR3 nucleotide sequence. The non-antibody sequence can replace at least a portion of a stalk domain of an ultralong CDR3. The non-antibody sequence can replace about 5 or more, 10 or more, 15 or more, 20 or more, 25 or more, 30 or more, 35 or more, 40 or more, 45 or more, 50 or more, 55 or more, 60 or more, 65 or more, 70 or more nucleotides of the stalk domain of an ultralong CDR3 nucleotide sequence. The non-antibody sequence can replace about 10% or more, 20% or more, 30% or more, 40% or more, 50% or more, 55% or more, 60% or more, 65% or more, 70% or more, 75% or more, 80% or more, 85% or more, 90% or more, 95% or more of the stalk domain of the ultralong CDR3 nucleotide sequence. The nucleotides may be consecutive nucleotides. Alternatively, the nucleotides are non-consecutive nucleotides. The ultralong CDR3 may comprise one or more conserved motifs. The conserved motifs may be stalk domain conserved motifs as disclosed herein. Alternatively, the conserved motifs may be knob domain conserved motifs as disclosed herein.

An antibody comprising an ultralong CDR3 sequence and a non-antibody sequence may further comprise one or more cleavage sites between the ultralong CDR3 sequence and the non-antibody sequence. The one or more cleavage sites may be in front of the N-terminus of the non-antibody peptide sequence. For example, a cleavage site is inserted at the N-terminus of the non-antibody peptide sequence and at the C-terminus of the ultralong CDR3 peptide sequence. Alternatively, the one or more cleave sites are behind the C-terminus of the non-antibody peptide sequence. For example the cleavage site is inserted at the C-terminus of the non-antibody peptide sequence and at the N-terminus of the ultralong CDR3 peptide sequence. The one or more cleavage sites may flank both the N-terminus and the C-terminus of the non-antibody peptide sequence. The one or more cleavage sites may be upstream of the non-antibody nucleotide sequence. For example, the one or more cleavage sites may be at the 5' end of the non-antibody nucleotide sequence and at the 3' end of the ultralong CDR3 nucleotide sequence. The one or more cleavage sites may be downstream of the non-antibody nucleotide sequence. For example, the one or more cleavage sites may be at the 3' end of the non-antibody nucleotide sequence and at the 5' end of the ultralong CDR3 nucleotide sequence. The one or more cleavage sites may flank both the 5' end and the 3' end of the non-antibody nucleotide sequence. The one or more cleavage sites may directly flank the non-antibody sequence. For example, there are zero nucleotides or amino acids between the cleavage site sequence and the non-antibody sequence. Alternatively, the one or more cleavage sites may indirectly flank the non-antibody sequence. For example, there are one or more nucleotides between the cleavage site nucleotide sequence and the non-antibody nucleotide sequence. There may be 2 or more, 3 or more, 4 or more, 5 or more, 6 or more, 7 or more, 8 or more, 9 or more, 10 or more, 12 or more, 15 or more, 20 or more nucleotides between the cleavage site nucleotide sequence and the non-antibody nucleotide sequence. In another example, there are one or more amino acids between the cleavage site peptide sequence and the non-antibody peptide sequence. There may be 2 or more, 3 or more, 4 or more, 5 or more, 6 or more, 7 or more, 8 or more, 9 or more, 10 or more, 12 or more, 15 or more, 20 or more amino acids between the cleavage site peptide sequence and the non-antibody peptide sequence. The cleavage site may be adjacent to the sequence based on or derived from the ultralong CDR3 sequence, linker sequence, non-antibody sequence, non-bovine sequence, or a combination thereof. The cleavage site may be between the sequence based on or derived from the ultralong CDR3 sequence and the linker sequence. The cleavage site may be between the sequence based on or derived from the ultralong CDR3 sequence and the non-antibody sequence. The cleavage site may be between the linker sequence and the non-antibody sequence. The cleavage site may be for a protease. The protease may be a serine protease, threonine protease, cysteine protease, aspartate protease, or metalloprotease. The protease may include, but is not limited to, Factor Xa protease, chymotrypsin-like protease, trypsin-like protease, elastase-like protease, subtilisin-like protease, actinidain, bromelain, calpains, caspases, cathepsins, Mir1-CP, papain, HIV-1 protease, chymosin, renin, cathepsin D, pepsin, plasmepsin, nepenthesin, metalloexopeptidases, and metalloendopeptidases. The cleavage site may be a cleavage site for Factor Xa or thrombin. For example, the cleavage site may comprise the amino acid sequence of IEGR (SEQ ID NO: 510). Alternatively, the cleavage site is for a nuclease. The antibody comprising the ultralong CDR3 sequence and non-antibody sequence may be cleaved by one or more proteases. Cleavage of the antibody by the one or more protease can result in release of one or more ends of the non-antibody peptide from the ultralong CDR3 region of the antibody. For example, cleavage of the antibody results in release of the N-terminus of the non-antibody peptide from the ultralong CDR3 region. Alternatively, cleavage of the antibody results in release of the C-terminus of the non-antibody peptide from the ultralong CDR3 region.

The non-antibody sequence may be linked to the ultralong CDR3 sequence via one or more linkers. The non-antibody sequence may be inserted with an ultralong CDR3 sequence. In some instances, two or more linkers are used to link the non-antibody sequence to the ultralong CDR3 sequence. The two or more linkers may comprise the same sequence. Alternatively, the two or more linkers comprise different sequences. The one or more linker sequences may be the same length. The one or more linker sequences may be different lengths. The one or more linker sequences may be 3 or more, 4 or more, 5 or more, 6 or more, 7 or more, 8 or more, 9 or more or 10 or more amino acids in length. The one or more linker sequences may comprise 1 or more, 2 or more, 3 or more, 4 or more, 5 or more, 6 or more, 7 or more, 8 or more, 9 or more, or 10 or more glycine residues. The one or more linker sequences may comprise 2 or more, 3 or more, 4 or more, or 5 or more consecutive glycine residues. The one or more linker sequences may comprise 1 or more serine residues. The one or more linker sequences may comprise 1 or more, 2 or more, 3 or more, 4 or more, or 5 or more polar amino acid residues. The polar amino acid residues may be selected from serine, threonine, asparagine, or glutamine. The polar amino acid residues may comprise uncharged side chains. The linkers may be attached to the N-terminal, C-terminal, or both N- and C-termini of the non-antibody peptide sequence. The linkers may be attached to the 5'-end, 3'-end, or both the 5'- and 3'ends of the non-antibody nucleotide sequence. In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Alternatively, the linker comprises an amino acid sequence of (GGGGS)$_n$ (SEQ ID NO: 499) wherein n=1 to 5. The linker may comprise an amino acid sequence of GGGSGGGGS (SEQ ID NO: 337) or GGGGSGGGS (SEQ ID NO: 338). Amino acid residues which comprise an amino acid linker component include those occurring naturally, as well as minor amino acids and non-naturally occurring amino acids including analogs, such as citrulline. Amino acid linker components can be designed and optimized in their selectivity for enzymatic cleavage by a particular enzymes, for example, a tumor-associated protease, cathepsin B, C and D, or a plasmin protease.

The ultralong CDR3 may be based on or derived from a single ultralong CDR3 sequence. Alternatively, the ultralong CDR3 is based on or derived from two or more ultralong CDR3 sequences. The two or more ultralong CDR3 sequences may be from the same animal. Alternatively, the two or more ultralong CDR3 sequences are from two or more different animals.

The ultralong CDR3 may comprise at least a portion of a stalk domain of an ultralong CDR3. The antibodies disclosed herein may comprise 1 or more, 2 or more, 3 or more, 4 or more, 5 or more, 6 or more 7 or more, 8 or more, 9 or more, or 10 or more amino acids derived from or based on the stalk domain of the ultralong CDR3. The antibodies disclosed herien may comprise 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, or 2 or fewer amino acids derived from or based the stalk domain of the ultralong CDR3. The amino acids may be consecutive amino acids. Alternatively, the amino acids are non-consecutive amino acids. The antibodies disclosed herein may comprise a sequence that is 50% or more, 60% or more, 70% or more, 80% or more, 85% or more, 90% or more, 95% or more, 97% or more, 99% or more, or 100% homologous the sequence of the stalk domain of the ultralong CDR3. The ultralong CDR3 may comprise one or more conserved motifs derived from or based on a stalk domain of the ultralong CDR3. The antibodies disclosed herein may comprise 1 or more, 2 or more, 3 or more, 4 or more, or 5 or more conserved motifs derived from or based on the stalk domain of the ultralong CDR3. The one or more conserved motifs derived from or based on the stalk domain of the ultralong CDR3 may comprise a sequence selected from any one of SEQ ID NOS: 157-307 and SEQ ID NOS: 333-336. The antibodies disclosed herein may comprise a sequence that is 50% or more, 60% or more, 70% or more, 80% or more, 85% or more, 90% or more, 95% or more, 97% or more, 99% or more, or 100% homologous to a sequence selected from any one of SEQ ID NOS: 157-224 and 235-295. The antibodies disclosed herein may comprise a sequence that is 50% or more, 60% or more, 70% or more, 80% or more, 85% or more, 90% or more, 95% or more, 97% or more, 99% or more, or 100% homologous to a sequence selected from any one of SEQ ID NOS: 225-227.

The one or more conserved motifs derived from or based on the stalk domain of the ultralong CDR3 may comprise a CT(T/S)VHQ motif (SEQ ID NO: 502). Alternatively, the one or more conserved motifs derived from or based on the stalk domain of the ultralong CDR3 comprise a CT(T/S)VHQX$_n$ motif (SEQ ID NO: 503). In some instances, n is between 1 to 8, between 1 to 7, between 1 to 6, between 1 to 5, between 1 to 4, or between 1 to 3. The one or more conserved motifs derived from or based on the stalk domain of the ultralong CDR3 may comprise a CX$^1$X$^2$X$^3$X$^4$Q motif (SEQ ID NO: 228). X$^1$ may be a T, S, A, or G residue. X$^2$ may be a T, S, A, P, or I residue. X$^3$ may be a V or K residue. X$^4$ may be an H, K, or Y residue. The one or more conserved motifs derived from or based on the stalk domain of the ultralong CDR3 may comprise an X$^1$X$^2$VHQ motif (SEQ ID NO: 229). X$^1$ may be a T, S, A, or G residue. X$^2$ may be a T, S, A, P or I residue. The one or more conserved motifs derived from or based on the stalk domain of the ultralong CDR3 may comprise a CX$^1$X$^2$VHQ motif (SEQ ID NO: 230). X$^1$ may be a T, S, A, or G residue. X$^2$ may be a T, S, A, P or I residue. The one or more conserved motifs derived from or based on the stalk domain of the ultralong CDR3 may comprise an X$^1$X$^2$VX$^3$Q motif (SEQ ID NO: 231). X$^1$ may be a T, S, A, or G residue. X$^2$ may be a T, S, A, P or I residue. X$^3$ may be an H, Y or K residue. The one or more conserved motifs derived from or based on the stalk domain of the ultralong CDR3 may comprise a CX$^1$X$^2$VX$^3$Q motif (SEQ ID NO: 232). X$^1$ may be a T, S, A, or G residue. X$^2$ may be a T, S, A, P or I residue. X$^3$ may be an H, Y or K residue. The one or more conserved motifs derived from or based on the stalk domain of the ultralong CDR3 may comprise an X$^1$X$^2$KKQ motif (SEQ ID NO: 233). X$^1$ may be a T, S, A, or G residue. X$^2$ may be a T, S, A, P or I residue. The one or more conserved motifs derived from or based on the stalk domain of the ultralong CDR3 may comprise a CX$^1$X$^2$KKQ motif (SEQ ID NO: 234). X$^1$ may be a T, S, A, or G residue. X$^2$ may be a T, S, A, P or I residue.

The one or more conserved motifs derived from or based on the stalk domain of the ultralong CDR3 may comprise an YX$^1$YX$^2$ motif (SEQ ID NO: 296). X$^1$ may be a T, S, N, or I residue. X$^2$ may be an E or D residue. The one or more conserved motifs derived from or based on the stalk domain of the ultralong CDR3 may comprise an YX$^1$YX$^2$Y motif (SEQ ID NO: 297). X$^1$ may be an L, S, T, or R residue. X$^2$ may be a T, S, N or I residue. The one or more conserved motifs derived from or based on the stalk domain of the ultralong CDR3 may comprise an YX$^1$YX$^2$YX$^3$ motif (SEQ ID NO: 298). X$^1$ may be an L, S, T, or R residue. X$^2$ may be a T, S, N or I residue. X$^3$ may be an E or D residue. The one or more conserved motifs derived from or based on the stalk domain of the ultralong CDR3 may comprise an YX$^1$YX$^2$YX$^3$X$^4$ motif (SEQ ID NO: 299). X$^1$ may be an L, S, T, or R residue. X$^2$ may be a T, S, N or I residue. X$^3$ may be an E or D residue. X$^4$ may be an H, W, N, F, I or Y residue. The one or more conserved motifs derived from or based on the stalk domain of the ultralong CDR3 may comprise an Y(E/D)X motif (SEQ ID NO: 504). X may be an H, W, N, F, I or Y residue. The one or more conserved motifs derived from or based on the stalk domain of the ultralong CDR3 may comprise an XY(E/D) motif (SEQ ID NO: 505). X may be a T, S, N or I residue. The one or more conserved motifs derived from or based on the stalk domain of the ultralong CDR3 may comprise an Y(E/D)X$^1$X$_n$W motif (SEQ ID NO: 498). X$^1$ may be an H, W, N, F, I or Y residue. In some instances, n is between 1 to 4, between 1 to 3, or between 1 to 2. The one or more conserved motifs derived from or based on the stalk domain of the ultralong CDR3 may comprise an Y(E/D)X$^1$X$^2$X$^3$X$^4$X$^5$W motif (SEQ ID NO: 506). X$^1$ may be an H, W, N, F, I or Y residue. X$^2$ may be an Y, H, G, or N residue. X$_3$ may be a V, I, or A residue. X$^4$ may be a D, N, T, or E residue. X$^5$ may be an A, V, S, or T residue.

The antibodies disclosed herein may comprise a first conserved motif derived from or based on the stalk domain of the ultralong CDR3 selected from any of SEQ ID NOS: 157-234 and a second conserved motif derived from or based on the stalk domain of the ultralong CDR3 selected from any of SEQ ID NOS: 235-307 and SEQ ID NOS: 333-336. The antibodies disclosed herein may comprise a first conserved motif derived from or based on the stalk domain of the ultralong CDR3 selected from a group comprising CT(T/S)VHQX$_n$ (SEQ ID NO: 503), CX$^1$X$^2$X$^3$X$^4$Q (SEQ ID NO: 228), X$^1$X$^2$VHQ (SEQ ID NO: 229), CX$^1$X$^2$VHQ (SEQ ID NO: 230), X$^1$X$^2$VX$^3$Q (SEQ ID NO: 231), CX$^1$X$^2$VX$^3$Q (SEQ ID NO: 232), X$^1$X$^2$KKQ (SEQ ID NO: 233), and CX$^1$X$^2$KKQ (SEQ ID NO: 234) and a second conserved motif derived from or based on the stalk domain of the ultralong CDR3 selected from the group comprising YX$^1$YX$^2$ (SEQ ID NO: 296), YX$^1$YX$^2$Y (SEQ ID NO: 297), YX$^1$YX$^2$YX$^3$ (SEQ ID NO: 298), YX$^1$YX$^2$YX$^3$X$^4$ (SEQ ID NO: 299), Y(E/D)X (SEQ ID NO: 504), XY(E/D) (SEQ ID NO: 505), Y(E/D)X$^1$X$_n$W (SEQ ID NO: 498), and Y(E/D)X$^1$X$^2$X$^3$X$^4$X$^5$W (SEQ ID NO: 506).

The ultralong CDR3 may comprise at least a portion of a knob domain of an ultralong CDR3. The antibodies disclosed herein may comprise 1 or more, 2 or more, 3 or more, 4 or more, 5 or more, 6 or more 7 or more, 8 or more, 9 or more, or 10 or more amino acids derived from or based on the knob domain of the ultralong CDR3. The antibodies disclosed herien may comprise 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, or 2 or fewer amino acids derived from or based the knob domain of the ultralong CDR3. The amino acids may be consecutive amino acids. Alternatively, the amino acids are non-consecutive amino acids. The antibodies disclosed herein may comprise a sequence that is 50% or more, 60% or more, 70% or more, 80% or more, 85% or more, 90% or more, 95% or more, 97% or more, 99% or more, or 100% homologous the sequence of the knob domain of the ultralong CDR3. The ultralong CDR3 may comprise one or more conserved motifs derived from or based on a knob domain of the ultralong CDR3. The antibodies disclosed herein may comprise 1 or more, 2 or more, 3 or more, 4 or more, or 5 or more conserved motifs derived from or based on the knob domain of the ultralong CDR3. The one or more conserved motifs derived from or based on the knob domain may comprise a cysteine motif as disclosed herein. Alternatively, or additionally, one or more conserved motifs derived from or based on the knob domain comprises a C(P/S)DG motif (SEQ ID NO: 507).

The antibodies disclosed herein may comprise a sequence based on or derived from a mammal. The mammal may be a bovine. Alternatively, the mammal is a non-bovine mammal, such as a human. The antibody sequences may be 3 or more, 4 or more, 5 or more, 6 or more, 7 or more, 8 or more, 9 or more, 10 or more, 11 or more, 12 or more, 15 or more, 20 or more, 25 or more, 30 or more, 35 or more, 40 or more 45 or more, 50 or more, 55 or more, 60 or more, 65 or more 70 or more, 80 or more, 90 or more, 100 or more, 110 or more, 120 or more, 130 or more, 140 or more, 150 or more, 160 or more, 170 or more, 180 or more 190 or more, 200 or more, 220 or more, 230 or more, 240 or more 250 or more 260 or more, 270 or more, 280 or more, 290 or more or 300 or more amino acids in length. The amino acids may be consecutive amino acids. Alternatively, the amino acids are non-consecutive amino acids.

The antibody sequences may comprise a bovine antibody sequence comprising 3 or more, 4 or more, 5 or more, 6 or more, 7 or more, 8 or more, 9 or more, 10 or more, 11 or more, 12 or more, 15 or more, 20 or more, 25 or more, 30 or more, 35 or more, 40 or more 45 or more, 50 or more, 55 or more, 60 or more, 65 or more 70 or more, 80 or more, 90 or more, 100 or more, 110 or more, 120 or more, 130 or more, 140 or more, 150 or more, 160 or more, 170 or more, 180 or more 190 or more, 200 or more, 220 or more, 230 or more, 240 or more 250 or more 260 or more, 270 or more, 280 or more, 290 or more or 300 or more amino acids in length. The bovine antibody may be a BLVH12, BLV5B8, BLVCV1, BLV5D3, BLV8C11, BF1H1, or F18 antibody. The antibody sequences may comprise a human antibody sequence comprising 3 or more, 4 or more, 5 or more, 6 or more, 7 or more, 8 or more, 9 or more, 10 or more, 11 or more, 12 or more, 15 or more, 20 or more, 25 or more, 30 or more, 35 or more, 40 or more 45 or more, 50 or more, 55 or more, 60 or more, 65 or more 70 or more, 80 or more, 90 or more, 100 or more, 110 or more, 120 or more, 130 or more, 140 or more, 150 or more, 160 or more, 170 or more, 180 or more 190 or more, 200 or more, 220 or more, 230 or more, 240 or more 250 or more 260 or more, 270 or more, 280 or more, 290 or more or 300 or more amino acids in length. The amino acids may be consecutive amino acids. Alternatively, the amino acids are non-consecutive amino acids.

The antibody sequence based on or derived from at least a portion of the ultralong CDR3 can be 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, or 5 or fewer amino acids in length. The antibody sequence based on or derived from at least a portion of the ultralong CDR3 may be 3 or more, 4 or more, 5 or more, 6 or more, 7 or more, 8 or more, 9 or more, 10 or more, 11 or more, 12 or more, 13 or more, 14 or more, or 15 or more amino acids in length. The amino acids may be consecutive amino acids. Alternatively, the amino acids are non-consecutive amino acids.

The antibody sequence based on or derived from at least a portion of the ultralong CDR3 can contain 1 or more, 2 or more, 3 or more, 4 or more, 5 or more, 6 or more, 7 or more, 8 or more, 9 or more, 10 or more, 15 or more, 20 or more, 25 or more, 30 or more, 35 or more, 40 or more, 50 or more, 60 or more, 70 or more, 80 or more, 90 or more, or 100 or more nucleic acid modifications or alterations in the nucleotide sequence of the ultralong CDR3 from which it is based on or derived from. The modifications and/or alterations may comprise substitutions, deletions, and/or insertions. Substitutions may comprise replacing one nucleic acid with another nucleic acid. The nucleic acid may be a natural nucleic acid or a non-natural nucleic acid.

The antibody sequence based on or derived from at least a portion of the ultralong CDR3 can contain 1 or more, 2 or more, 3 or more, 4 or more, 5 or more, 6 or more, 7 or more, 8 or more, 9 or more, 10 or more, 15 or more, 20 or more, 25 or more, 30 or more, 35 or more, 40 or more, 50 or more, or 60 or more amino acid modifications or alterations in the peptide sequence of the ultralong CDR3 from which it is based on or derived from. The modifications and/or alterations may comprise substitutions, deletions, and/or insertions. Substitutions may comprise replacing one amino acid with another amino acid. The amino acids to be substituted may contain one or more similar features to the amino acid by which it is replaced. The features may include, but are not limited to, size, polarity, hydrophobicity, acidity, side chain, and bond formations. The amino acid may be a natural amino acid or a non-natural amino acid.

In certain embodiments, the half-life of an antibody described herein is greater than the half-life of the un-conjugated therapeutic peptide or un-conjugated non-antibody peptide that is incorporated in the antibody. In some embodiments, the half-life of an antibody provided herein is greater than 4 hours when administered to a subject. In certain embodiments, the half-life of an antibody provided herein is greater than 4 hours, greater than 6 hours, greater than 12 hours, greater than 24 hours, greater than 36 hours, greater than 2 days, greater than 3 days, greater than 4 days, greater than 5 days, greater than 6 days, greater than 7 days, greater than 8 days, greater than 9 days, greater than 10 days, greater than 11 days, greater than 12 days, greater than 13 days, or greater than 14 days when administered to a subject. In some instances, the subject is a mammal. In some embodiments, the subject is a mouse or a bovine. In other instances, the subject is a human. In certain embodiments, a pharmaceutical composition comprising the antibody is administered to the subject once a day, every two days, every three days, every 4 days, every 7 days, every 10 days, every 14 days, every 21 days, every 28 days, every 2 months, or every three months.

The antibodies may be modified or altered to reduce immunogenicity. For example, the sequence of a partially bovine or non-bovine antibody may be modified or altered to reduce immunogenicity to humans. A non-human antibody may be humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

The antibodies comprising an ultralong CDR3 as disclosed herein are preferably monoclonal. Also encompassed within the scope of the disclosure are Fab, Fab', Fab'-SH and F(ab')$_2$ fragments of the antibodies comprising an ultralong CDR3 as provided herein. These antibody fragments can be created by traditional means, such as enzymatic digestion, or may be generated by recombinant techniques. Such antibody fragments may be chimeric or humanized. These fragments are useful for the diagnostic and therapeutic purposes set forth below.

Monoclonal antibodies are obtained from a population of substantially homogeneous antibodies, e.g., the individual antibodies comprising the population are identical except for possible naturally occurring mutations that may be present in minor amounts. Thus, the modifier "monoclonal" indicates the character of the antibody as not being a mixture of discrete antibodies.

The antibodies comprising an ultralong CDR3 as disclosed herein can be made using a hybridoma cell-based method first described by Kohler et al., Nature, 256:495 (1975), or may be made by recombinant DNA methods.

Hybridoma cells can be generated by fusing B cells producing a desired antibody with an immortalized cell line, usually a myeloma cell line, so that the resulting fusion cells will be an immortalized cell line that secrets a particular antibody. By the same principle, myeloma cells can be first transfected with a nucleic acid encoding a germline antibody V region and can be screened for the expression of the germline V region. Those myeloma cells with highest level of proteolytic light chain expression can be subsequently fused with B cells that produce an antibody with desired target protein specificity. The fusion cells will produce two types of antibodies: one is a heterologous antibody containing an endogenous antibody chain (either heavy or light) operably joined to the recombinant germline V region (either heavy or light), and the other is the same antibody that the parental B cells would secrete (e.g. both endogenous heavy and light chains). The operably joined heterologous heavy and light chains can be isolated by conventional methods such as chromatography and identification can be confirmed by target protein binding assays, assays identifying a unique tag of the germline polypeptide, or endopeptidase activity assays described in other sections of this disclosure. In some cases, where the heterologous antibody is the predominant type in quantity among the two types of antibodies, such isolation may not be needed.

The hybridoma cells may be seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, myeloma cell lines may be murine myeloma lines, such as those derived from MOPC-21 and MPC-11 mouse tumors available from the Salk Institute Cell Distribution Center, San Diego, Calif. USA, and SP-2 or X$_{63}$-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, pp. 51-63 (Marcel Dekker, Inc., New York, 1987)).

Culture medium in which hybridoma cells are growing is assayed for production of antibodies comprising an ultralong CDR3. For example, the binding specificity of monoclonal antibodies produced by hybridoma cells may be determined by immunoprecipitation or by an in vitro binding assay, such as an enzyme-linked immunoadsorbent assay (ELISA).

The binding affinity of the monoclonal antibody can, for example, be determined by the Scatchard analysis of Munson et al., Anal. Biochem., 107:220 (1980).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

The antibodies comprising an ultralong CDR3 as disclosed herein may be made by using combinatorial libraries to screen for synthetic antibody clones with the desired activity or activities. For example, synthetic antibody clones are selected by screening phage libraries containing phage that display various fragments of antibody variable regions (e.g., scFv or Fab) fused to phage coat protein. Such phage libraries may be panned, for example, by affinity chromatography against the desired antigen. Clones expressing antibody fragments capable of binding to the desired antigen may be adsorbed to the antigen and thus separated from the non-binding clones in the library. The binding clones may then be eluted from the antigen, and can be further enriched by additional cycles of antigen adsorption/elution. Any of the antibodies comprising an ultralong CDR3 as disclosed herein may be obtained by designing a suitable antigen screening procedure to select for the phage clone of interest followed by construction of a full length antibody comprising an ultralong CDR3 clone using the VH and VL (e.g., from scFv or Fab) sequences from the phage clone of interest and suitable constant region (Fc) sequences described in Kabat et al., Sequences of Proteins of Immunological Interest, Fifth Edition, NIH Publication 91-3242, Bethesda Md. (1991), vols. 1-3.

The antigen-binding domain of an antibody is formed from two variable (V) regions, one each from the light (VL) and heavy (VH) chains, that both present three hypervariable loops or complementarity-determining regions (CDRs). Variable domains may be displayed functionally on phage, either as single-chain Fv (scFv, also referred to as single-chain antibody (SCA)) fragments, in which VH and VL are covalently linked through a short, flexible peptide, or as Fab fragments, in which they are each fused to a constant domain and interact non-covalently, as described in Winter et al., Ann. Rev. Immunol., 12: 433-455 (1994). scFv or SCA encoding phage clones and Fab encoding phage clones may be separately or collectively referred to as "Fv phage clones" or "Fv clones".

Repertoires of VH and VL genes may be separately cloned by polymerase chain reaction (PCR) and recombined randomly in phage libraries, which can then be searched for antigen-binding clones as described in Winter et al., Ann. Rev. Immunol., 12: 433-455 (1994). Libraries from immunized sources provide high-affinity antibodies to the immunogen without the requirement of constructing hybridomas. Alternatively, the naive repertoire may be cloned to provide a single source of human antibodies to a wide range of non-self and also self antigens without any immunization as described by Griffiths et al., EMBO J. 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, J. Mol. Biol., 227: 381-388 (1992).

Filamentous phage is used to display antibody fragments by fusion to the minor coat protein pIII. Protein pIII may include truncated forms of pIII. The antibody fragments can be displayed as single chain Fv fragments, in which VH and VL domains are connected on the same polypeptide chain by a flexible polypeptide spacer, (e.g., as described by Marks et al., J. Mol. Biol., 222: 581-597 (1991)), or as Fab fragments, in which one chain is fused to pIII (e.g., a truncated pIII) and the other is secreted into the bacterial host cell periplasm where assembly of a Fab-coat protein structure which becomes displayed on the phage surface by displacing some of the wild type coat proteins, (e.g., as described in Hoogenboom et al., Nucl. Acids Res., 19: 4133-4137 (1991)).

Nucleic acid encoding antibody variable gene segments (including VH and VL segments) are recovered from the cells of interest and and may be amplified or copies made by recombinant DNA techniques (e.g., Kunkel mutagenesis). For example, in the case of rearranged $V_H$ and VL gene libraries, the desired DNA may be obtained by isolating genomic DNA or mRNA from lymphocytes followed by polymerase chain reaction (PCR) with primers matching the 5' and 3' ends of rearranged VH and VL genes as described in Orlandi et al., Proc. Natl. Acad. Sci. (USA), 86: 3833-3837 (1989), thereby making diverse V gene repertoires for expression. The V genes may be amplified from cDNA and genomic DNA, with back primers at the 5' end of the exon encoding the mature V-domain and forward primers based within the J-segment as described in Orlandi et al. (1989) and in Ward et al., Nature, 341: 544-546 (1989). For amplifying from cDNA, back primers can also be based in the leader exon as described in Jones et al., Biotechnol., 9: 88-89 (1991), and forward primers within the constant region as described in Sastry et al., Proc. Natl. Acad. Sci. (USA), 86: 5728-5732 (1989). To enhance or maximize complementarity, degeneracy may be incorporated in the primers as described in Orlandi et al. (1989) or Sastry et al. (1989). Library diversity may be enhanced or maximized by using PCR primers targeted to each V-gene family in order to amplify available VH and VL arrangements present in the immune cell nucleic acid sample, for example, as described in the method of Marks et al., J. Mol. Biol., 222: 581-597 (1991) or as described in the method of Orum et al., Nucleic Acids Res., 21: 4491-4498 (1993). For cloning of the amplified DNA into expression vectors, rare restriction may can be introduced within the PCR primer as a tag at one end as described in Orlandi et al. (1989), or by further PCR amplification with a tagged primer as described in Clackson et al., Nature, 352: 624-628 (1991).

Repertoires of synthetically rearranged V genes may be derived in vitro from V gene segments. Most of the human VH-gene segments have been cloned and sequenced (e.g., reported in Tomlinson et al., J. Mol. Biol., 227: 776-798 (1992)), and mapped (e.g., reported in Matsuda et al., Nature Genet., 3: 88-94 (1993); these cloned segments (including all the major conformations of the H1 and H2 loop) may be used to generate diverse VH gene repertoires with PCR primers encoding H3 loops of diverse sequence and length as described in Hoogenboom and Winter, J. Mol. Biol., 227: 381-388 (1992). VH repertoires may also be made with all the sequence diversity focused in a long H3 loop of a single length as described in Barbas et al., Proc. Natl. Acad. Sci. USA, 89: 4457-4461 (1992). Human Vκ and Vλ segments have been cloned and sequenced (reported in Williams and Winter, Eur. J. Immunol., 23: 1456-1461 (1993)) and can be used to make synthetic light chain repertoires. Synthetic V gene repertoires, based on a range of VH and VL folds, and L3 and H3 lengths, will encode antibodies of considerable structural diversity. Following amplification of V-gene encoding DNAs, germline V-gene segments can be rearranged in vitro according to the methods of Hoogenboom and Winter, J. Mol. Biol., 227: 381-388 (1992).

Repertoires of antibody fragments may be constructed by combining VH and VL gene repertoires together in several ways. Each repertoire may be created in different vectors, and the vectors recombined in vitro, for example, as described in Hogrefe et al., Gene, 128: 119-126 (1993), or in vivo by combinatorial infection, for example, the loxP system described in Waterhouse et al., Nucl. Acids Res., 21: 2265-2266 (1993). The in vivo recombination approach exploits the two-chain nature of Fab fragments to overcome the limit on library size imposed by E. coli transformation efficiency. Naive VH and VL repertoires are cloned separately, one into a phagemid and the other into a phage vector. The two libraries are then combined by phage infection of phagemid-containing bacteria so that each cell contains a different combination and the library size is limited only by the number of cells present (about $10^{12}$ clones). Both vectors contain in vivo recombination signals so that the VH and VL genes are recombined onto a single replicon and are co-packaged into phage virions. These large libraries may provide large numbers of diverse antibodies of good affinity ($K_d^{-1}$ of about $10^{-8}$ M).

Alternatively, the repertoires may be cloned sequentially into the same vector, for example, as described in Barbas et al., Proc. Natl. Acad. Sci. USA, 88: 7978-7982 (1991), or assembled together by PCR and then cloned, for example, as described in Clackson et al., Nature, 352: 624-628 (1991). PCR assembly may also be used to join VH and VL DNAs with DNA encoding a flexible peptide spacer to form single chain Fv (scFv) repertoires. In yet another technique, "in cell PCR assembly" may be used to combine VH and VL genes within lymphocytes by PCR and then clone repertoires of linked genes as described in Embleton et al., Nucl. Acids Res., 20: 3831-3837 (1992).

The antibodies produced by naive libraries (either natural or synthetic) can be of moderate affinity ($K_d^{-1}$ of about $10^6$ to $10^7 M^{-1}$), but affinity maturation may also be mimicked in vitro by constructing and reselecting from secondary libraries as described in Winter et al. (1994), supra. For example, mutation can be introduced at random in vitro by using error-prone polymerase (reported in Leung et al., Technique, 1: 11-15 (1989)) in the method of Hawkins et al., J. Mol. Biol., 226: 889-896 (1992) or in the method of Gram et al., Proc. Natl. Acad. Sci. USA, 89: 3576-3580 (1992). Additionally, affinity maturation may be performed by randomly mutating one or more CDRs, for example, using PCR with primers carrying random sequence spanning the CDR of interest, in selected individual Fv clones and screening for higher affinity clones. WO 9607754 described a method for inducing mutagenesis in a complementarity determining region of an immunoglobulin light chain to create a library of light chain genes. Another effective approach is to recombine the VH or VL domains selected by phage display with repertoires of naturally occurring V domain variants obtained from unimmunized donors and screen for higher affinity in several rounds of chain reshuffling as described in Marks et al., Biotechnol., 10: 779-783 (1992). This technique allows the production of antibodies and antibody fragments with affinities in the $10^{-9}$ M range.

The phage library samples are contacted with an immobilized protein under conditions suitable for binding of at least a portion of the phage particles with the adsorbent. Normally, the conditions, including pH, ionic strength, temperature and the like are selected to mimic physiological conditions. The phages bound to the solid phase are washed and then eluted by acid, e.g., as described in Barbas et al., Proc. Natl. Acad. Sci. USA, 88: 7978-7982 (1991), or by alkali, (e.g., as described in Marks et al., J. Mol. Biol., 222: 581-597 (1991)), or by antigen competition, (e.g., in a procedure similar to the antigen competition method of Clackson et al., Nature, 352: 624-628 (1991)). Phages may be enriched 20-1,000-fold in a single round of selection. Moreover, the enriched phages may be grown in bacterial culture and subjected to further rounds of selection.

The efficiency of selection depends on many factors, including the kinetics of dissociation during washing, and whether multiple antibody fragments on a single phage can simultaneously engage with antigen. Antibodies with fast dissociation kinetics (and weak binding affinities) may be retained by use of short washes, multivalent phage display and high coating density of antigen in solid phase. The high density not only stabilizes the phage through multivalent interactions, but favors rebinding of phage that has dissociated. The selection of antibodies with slow dissociation kinetics (and good binding affinities) may be promoted by use of long washes and monovalent phage display as described in Bass et al., Proteins, 8: 309-314 (1990) and in WO 92/09690, and a low coating density of antigen as described in Marks et al., Biotechnol., 10: 779-783 (1992).

DNA encoding the hybridoma-derived monoclonal antibodies or phage display Fv clones disclosed herein is readily isolated and sequenced using conventional procedures (e.g., by using oligonucleotide primers designed to specifically amplify the heavy and light chain coding regions of interest from hybridoma or phage DNA template). Once isolated, the DNA can be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of the desired monoclonal antibodies in the recombinant host cells. Recombinant expression in bacteria of antibody-encoding DNA has been described by Better et al., U.S. Pat. No. 6,204,023 (see also, e.g., Skerra et al., Curr. Opinion in Immunol., 5: 256 (1993) and Pluckthun, Immunol. Revs, 130: 151 (1992)).

DNA encoding Fv clones as disclosed herein may be combined with known DNA sequences encoding heavy chain and/or light chain constant regions (e.g., the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions may be obtained from any human or animal species. A Fv clone derived from the variable domain DNA of one animal (such as human) species and then fused to constant region DNA of another animal species to form coding sequence(s) for "hybrid", full length heavy chain and/or light chain is included in the definition of "chimeric" and "hybrid" antibody as used herein. In a preferred Fv clone embodiment, a Fv clone derived from human variable DNA is fused to human constant region DNA to form coding sequence(s) for all human, full or partial length heavy and/or light chains.

DNA encoding an antibody comprising an ultralong CDR3 derived from a hybridoma disclosed herein may also be modified, for example, by substituting the coding sequence for human heavy- and light-chain constant domains in place of homologous murine sequences derived from the hybridoma clone (e.g., as in the method of Morrison et al., Proc. Natl. Acad. Sci. USA, 81: 6851-6855 (1984)). DNA encoding a hybridoma or Fv clone-derived antibody or fragment can be further modified by covalently joining to the immunoglobulin coding sequence all or part of the coding sequence for a non-immunoglobulin polypeptide. In this manner, "chimeric" or "hybrid" antibodies are prepared that have the binding specificity of the Fv clone or hybridoma clone-derived antibodies disclosed herein.

Antibody Genes and Proteins

The present disclosure provides antibody genes and proteins including, for example, chimeric, recombinant, engineered, synthetic, hybrid, bovine, fully bovine, bovinized, human, fully human or humanized antibody genes or proteins that comprise an ultralong CDR3 sequence. The antibodies disclosed herein may selectively or specifically bind to an epitope of a target protein. In some embodiments, the antibody may be an antagonist (e.g., blocking) antibody or an agonist antibody.

The variable region of the heavy and light chains are encoded by multiple germline gene segments separated by non-coding regions, or introns, and often are present on different chromosomes. For example, the genes for the human immunoglobulin heavy chain region contains approximately 65 variable (VH;) genes, 27 Diversity (DH) genes, and 6 Joining (JH) genes. The human kappa (κ) and lambda (λ) light chains are also each encoded by a similar number of VL and JL gene segments, but do not include any D gene segments. Exemplary VH, DH, JH and VL (Vκ or Vλ) and JL (Jκ or Jλ) germline gene segments are set forth in WO 2010/054007.

During B cell differentiation germline DNA is rearranged whereby one DH and one JH gene segment of the heavy chain locus are recombined, which is followed by the joining of one $V_H$ gene segment forming a rearranged VDJ gene that encodes a VH chain. The rearrangement occurs only on a single heavy chain allele by the process of allelic exclusion. Allelic exclusion is regulated by in-frame or "productive" recombination of the VDJ segments, which occurs in only about one-third of VDJ recombinations of the variable heavy chain. When such productive recombination events first occur in a cell, this result in production of a μ heavy chain that gets expressed on the surface of a pre-B cell and transmits a signal to shut off further heavy chain recombination, thereby preventing expression of the allelic heavy chain locus. The surface-expressed μ heavy chain also acts to activate the kappa (κ) locus for rearrangement. The lambda (λ) locus is only activated for rearrangement if the κ recombination is unproductive on both loci. The light chain rearrangement events are similar to the heavy chain, except that only the VL and JL segments are recombined. Before primary transcription of each, the corresponding constant chain gene is added. Subsequent transcription and RNA splicing leads to mRNA that is translated into an intact light chain or heavy chain.

The variable regions of antibodies confer antigen binding and specificity due to recombination events of individual germline V, D and J segments, whereby the resulting recombined nucleic acid sequences encoding the variable region domains differ among antibodies and confer antigen-specificity to a particular antibody. The variation, however, is limited to three complementarity determining regions (CDR1, CDR2, and CDR3) found within the N-terminal domain of the heavy (H) and (L) chain variable regions. The CDRs are interspersed with regions that are more conserved, termed "framework regions" (FR). The extent of the framework region and CDRs has been precisely defined (see e.g., Kabat, E. A. et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917). Each VH and VL is typically composed of three CDRs and four FRs arranged from the amino terminus to carboxy terminus in the following order: FR1, CDR1, FR2, CDR2, FR3, CDR3 and FR4. Sequence variability among VL and VH domains is generally limited to the CDRs, which are the regions that form the antigen binding site. For example, for the heavy chain, generally, VH genes encode the N-terminal three framework regions, the first two complete CDRs and the first part of the third CDR), the DH gene encodes the central portion of the third CDR, and the JH gene encodes the last part of the third CDR and the fourth framework region. For the light chain, the VL genes encode the first CDR and second CDR. The third CDR (CDRL3) is formed by the joining of the VL and JL gene segments. Hence, CDRs 1 and 2 are exclusively encoded by germline V gene segment sequences. The VH and VL chain CDR3s form the center of the Ag-binding site, with CDRs 1 and 2 form the outside boundaries; the FRs support the scaffold by orienting the H and L CDRs. On average, an antigen binding site typically requires at least four of the CDRs make contact with the antigen's epitope, with CDR3 of both the heavy and light chain being the most variable and contributing the most specificity to antigen binding (see, e.g., Janis Kuby, Immunology, Third Edition, New York, W.H. Freeman and Company, 1998, pp. 115-118). CDRH3, which includes all of the D gene segment, is the most diverse component of the Ab-binding site, and typically plays a critical role in defining the specificity of the Ab. In addition to sequence variation, there is variation in the length of the CDRs between the heavy and light chains.

The constant regions, on the other hand, are encoded by sequences that are more conserved among antibodies. These domains confer functional properties to antibodies, for example, the ability to interact with cells of the immune system and serum proteins in order to cause clearance of infectious agents. Different classes of antibodies, for example IgM, IgD, IgG, IgE and IgA, have different constant regions, allowing them to serve distinct effector functions.

These natural recombination events of V, D, and J, can provide nearly $2 \times 10^7$ different antibodies with both high affinity and specificity. Additional diversity is introduced by nucleotide insertions and deletions in the joining segments and also by somatic hypermutation of V regions. The result is that there are approximately $10^{10}$ antibodies present in an individual with differing antigen specificities.

Antibody Fragments

The present disclosure encompasses antibody fragments. In certain circumstances there are advantages of using antibody fragments, rather than whole antibodies. The smaller size of the fragments allows for rapid clearance, and may lead to improved access to solid tumors. Antibody fragments include, but are not limited to, Fab, Fab', Fab'-SH, F(ab')2, Fv, Fv', Fd, Fd', scFv, hsFv fragments, and diabodies, and other fragments described below. For a review of certain antibody fragments, see Hudson et al. Nat. Med. 9:129-134 (2003). For a review of scFv fragments, see, e.g., Pluckthun, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9: 129134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516). Antibody fragments can be made by various techniques, including but not limited to proteolytic digestion of an intact antibody as well as production by recombinant host cells (e.g. E. coli or phage), as described herein.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E. coli, thus allowing the facile production of large amounts of these fragments (see, e.g., U.S. Pat. No. 6,204,023). Antibody fragments can be isolated from antibody phage libraries as discussed above. Alternatively, Fab'-SH fragments can be directly recovered from E. coli and chemically coupled to form F(ab')2 fragments (see, e.g., Carter et al., Bio/Technology 10: 163-167 (1992)). According to another approach, F(ab')$_2$ fragments can be isolated directly from recombinant host cell culture. Fab and F(ab')$_2$ fragment with increased in vivo half-life comprising a salvage receptor binding epitope residues (see, e.g., in U.S. Pat. No. 5,869,046). Other techniques for the production of antibody fragments will be apparent to the skilled practitioner. In other embodiments, the antibody of choice is a single chain Fv fragment (scFv or single chain antibody (SCA)). See WO 93/16185; U.S. Pat. Nos. 5,571,894; and 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, Supra. The antibody fragment may also be a "linear antibody", for example, as described in U.S. Pat. No. 5,641,870. Such linear antibody fragments may be monospecific or bispecific.

Humanized Antibodies

The present disclosure provides humanized antibodies comprising an ultralong CDR3. Humanized antibodies may include human engineered antibodies (see, e.g., Studnicka et al. (1994) Protein Eng. 7(6) 805-814; and U.S. Pat. No. 5,766,886). Various methods for humanizing non-human antibodies are known in the art. For example, a humanized antibody can have one or more amino acid residues introduced into it from a source which is human or non-human. Humanization may be performed following the method of Studnicka (see, e.g., Studnicka et al. (1994) Protein Eng. 7(6) 805-814; and U.S. Pat. No. 5,766,886), including the preparation of modified antibody variable domains. Humanization may alternatively be performed following the method of Winter and co-workers (Jones et al. (1986) Nature 321:522-525; Riechmann et al. (1988) Nature 332:323-327; Verhoeyen et al. (1988) Science 239:1534-1536), by substituting hypervariable region sequences for the corresponding sequences of a human antibody. Accordingly, such "humanized" or "human engineered" antibodies are chimeric antibodies, including wherein substantially less than an intact human variable domain has been substituted by or incorporated into the corresponding sequence from a non-human species. For example, humanized antibodies may be human antibodies in which some hypervariable region residues and possibly some FR residues are substituted by residues from analogous sites in rodent antibodies. Alternatively, humanized or human engineered antibodies may be non-human (e.g, rodent) antibodies in which some residues are substituted by residues from analogious sites in human antibodies (see, e.g., Studnicka et al. (1994) Protein Eng. 7(6) 805-814; and U.S. Pat. No. 5,766,886).

The choice of human variable domains, both light and heavy, to be used in making the humanized antibodies is important to reduce antigenicity. For example, to the so-called "best-fit" method, the sequence of the variable domain of a rodent antibody is screened against the entire library of known human variable-domain sequences. The human sequence which is closest to that of the rodent is then accepted as the human framework for the humanized antibody (Sims et al. (1993) J. Immunol. 151:2296; Chothia et al. (1987) J. Mol. Biol. 196:901). Another method uses a particular framework derived from the consensus sequence of all human antibodies of a particular subgroup of light or heavy chains. The same framework may be used for several different humanized antibodies (Carter et al. (1992) Proc. Natl. Acad. Sci. USA, 89:4285; Presta et al. (1993) J. Immunol., 151:2623).

It is further important that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, e.g., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

In some embodiments, the humanized antibodies comprising an ultralong CDR3 may be deimmunized. Methods of deimmunizing an antibody or protein are well known in the art. The immunogenicity of therapeutic proteins such as antibodies is thought to result from the presence of T-cell epitopes which can bind MHC class II molecules and generate a proliferative and cytokine response in CD4+ helper T-cells. These CD4+ helper cells then collaborate with B-cells to generate an antibody response against the therapeutic protein. Removal of the T-cell epitopes are thought to be key steps in deimmunizing a recombinant protein. T-cell epitopes can be predicted by in silico algorithms that identify residues required for binding MHC. Alternatively, epitopes can be identified directly by utilizing peripheral blood mononuclear cells from panels of human donors and measuring their response against the therapeutic protein when incubated with antigen presenting cells. Such in silico and in vitro systems are well known in the art [Jones T D, Crompton L J Carr F J, Baker M P. Methods Mol Biol. 2009; 525:405-23, Deimmunization of monoclonal antibodies; and Baker M, and Jones T D. The identification and removal of immunogenicity in therapeutic proteins. *Curr. Opin. Drug Discovery Dev.* 2007; (2007); 10(2): 219-227]. When peptides are identified that bind MHC II or otherwise stimulate CD4+ cell activation, the residues of the peptide can be mutated one by one and tested for T-cell activation until a mutation is found which disrupts MHC II binding and T-cell activation. Such mutations, when found in an individual peptide, can be encoded directly in the recombinant therapeutic protein. Incubation of the whole protein with antigen presenting cells will not induce a significant CD4+ response, indicating successful deimmunization.

Bovine Antibodies

The present disclosure provides for bovine antibodies comprising an ultralong CDR3. The bovine antibodies may be recombinant antibodies, engineered antibodies, synthetic antibodies, bovinized antibodies, or fully bovine antibodies. Bovinized antibodies may include bovine engineered antibodies. Methods for producing a bovinized antibody may comprise introducing one or more amino acid residues into it from a source which is a bovine. In some instances, methods for producing a bovinized antibody may comprise introducing one or more amino acid residues into it from a source which is a non-bovine. Bovinization may be performed by preparing a modified antibody variable domains. Alternatively, bovinization may be performed by substituting hypervariable region sequences for the corresponding sequences of a bovine antibody. Accordingly, such "bovinized" or "bovine engineered" antibodies are chimeric antibodies. Chimeric antibodies may include antibodies wherein substantially less than an intact bovine variable domain has been substituted by or incorporated into the corresponding sequence from a non-bovine species. Bovinized or bovine engineered antibodies may be bovine antibodies in which some hypervariable region residues and constant region residues are substituted by residues from analogous sites in non-bovine antibodies. Alternatively, bovinized, bovine engineered or fully bovine antibodies may be non-bovine (e.g, human) antibodies in which some residues are substituted by residues from analogious sites in bovine antibodies. For example, a bovine immunoglobuline region can be used to replace a non-bovine (e.g., human, rodent) immunoglobulin region to produce a fully bovine, bovinized or bovine engineered antibody.

Bispecific Antibodies

Bispecific antibodies are monoclonal, preferably human or humanized, antibodies that have binding specificities for at least two different antigens. For example, one of the binding specificities may be for a first antigen and the other may be for any other antigen. Exemplary bispecific antibodies may bind to two different epitopes of the same protein. Bispecific antibodies may also be used to localize cytotoxic agents to cells which express a particular protein. These antibodies possess a binding arm specific for the particular protein and an arm which binds the cytotoxic agent (e.g., saporin, anti-interferon-α, vinca alkaloid, ricin A chain, methotrexate or radioactive isotope hapten). Bispecific antibodies may be prepared as full length antibodies or antibody fragments (e.g., F(ab')$_2$ bispecific antibodies).

Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature, 305: 537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829, and in Traunecker et al., EMBO J., 10: 3655 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are not of particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure may facilitate the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach, the interface between a pair of antibody molecules may can be engineered to maximize the percentage of heterodimers which are recovered from recombinant cell culture. The preferred interface comprises at least a part of the $C_{H3}$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate may be coupled to avidin, the other to biotin. Such antibodies have, for example, been proposed to target immune system cells to unwanted cells (U.S. Pat. No. 4,676,980), and for treatment of HIV infection (WO 91/00360, WO 92/00373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies may be prepared using chemical linkage. Brennan et al., Science, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced may be used as agents for the selective immobilization of enzymes.

Recent progress has facilitated the direct recovery of Fab'-SH fragments from *E. coli*, which can be chemically coupled to form bispecific antibodies. Shalaby et al., J. Exp. Med., 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. See, e.g., Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See, Gruber et al., J. Immunol., 152:5368 (1994).

Antibodies with more than two valencies are contemplated. For example, tri specific antibodies can be prepared. See, e.g., Tutt et al. J. Immunol. 147: 60 (1991).

Multivalent Antibodies

A multivalent antibody may be internalized (and/or catabolized) faster than a bivalent antibody by a cell expressing an antigen to which the antibodies bind. The antibodies of the present disclosure may be multivalent antibodies (which are other than of the IgM class) with three or more antigen binding sites (e.g., tetravalent antibodies), which may be produced by recombinant expression of nucleic acid encoding the polypeptide chains of the antibody. The multivalent antibody may comprise a dimerization domain and three or more antigen binding sites. A preferred dimerization domain may comprise (or consist of) an Fc region or a hinge region. In this scenario, the antibody will comprise an Fc region and three or more antigen binding sites amino-terminal to the Fe region. A preferred multivalent antibody may comprise (or consist of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. A multivalent antibody may preferably further comprises at least two (and preferably four) light chain variable domain polypeptides. A multivalent antibody may, for instance, comprise from about two to about eight light chain variable domain polypeptides. The light chain variable domain polypeptides may comprise a light chain variable domain and, optionally, further comprise a CL domain.

Antibody Variants

In some embodiments, amino acid sequence modification(s) of the antibodies comprising an ultralong CDR3 as described herein are contemplated. For example, it may be desirable to improve the binding affinity and/or other biological properties of the antibody. Amino acid sequence variants including, for example, conservatively modified variants, of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) Science, 244: 1081-1085. Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme (e.g., for ADEPT) or a polypeptide which increases the serum half-life of the antibody.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, the carbohydrate attached thereto may be altered. For example, antibodies with a mature carbohydrate structure that lacks fucose attached to an Fc region of the antibody have been described (see, e.g., US 2003/0157108, US 2004/0093621. Antibodies with a bisecting N-acetylglucosamine (GlcNAc) in the carbohydrate attached to an Fc region of the antibody have been described (see, e.g., WO 2003/011878, and U.S. Pat. No. 6,602,684). Antibodies with at least one galactose residue in the oligosaccharide attached to an Fc region of the antibody WO 1997/30087; see, also, WO 1998/58964 and WO 1999/22764 concerning antibodies with altered carbohydrate attached to the Fc region thereof). Antigen-binding molecules with modified glycosylation have been described (see, e.g., WO 99/54342, U.S. Pat. Nos. 6,602,684 and 7,517,670, and US 2004/0072290; see also, e.g., U.S. Pat. Nos. 7,214,775 and 7,682,610).

The preferred glycosylation variant herein comprises an Fc region, wherein a carbohydrate structure attached to the Fc region lacks fucose. Such variants have improved ADCC function. Optionally, the Fc region further comprises one or more amino acid substitutions therein which further improve ADCC, for example, substitutions at positions 298, 333, and/or 334 of the Fc region (Eu numbering of residues). Examples of publications related to "defucosylated" or "fucose-deficient" antibodies include: US 2003/0157108; WO 2000/61739; WO 2001/29246; US 2003/0115614 (now U.S. Pat. No. 6,946,292) US 2002/0164328 (now U.S. Pat. No. 7,064,191); US 2004/0093621; US 2004/0132140; US 2004/0110704; US 2004/0110282 (now U.S. Pat. No 7,749, 753); US 2004/0109865; WO 2003/085119; WO 2003/084570; WO 2005/035586; WO 2005/035778; WO2005/053742; Okazaki et al. J. Mol. Biol. 336:1239-1249 (2004); Yamane-Ohnuki et al. Biotech. Bioeng. 87: 614 (2004). Examples of cell lines producing defucosylated antibodies include Lec13 CHO cells deficient in protein fucosylation (Ripka et al. Arch. Biochem. Biophys. 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (Yamane-Ohnuki et al. Biotech. Bioeng. 87: 614 (2004)).

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in Table 2 under the heading of "preferred substitutions". If such substitutions result in a change in biological activity, then more substantial changes, denominated "exemplary substitutions", or as further described below in reference to amino acid classes, may be introduced and the products screened.

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring amino acids are divided into groups based on common side-chain properties: (1) hydrophobic: norleucine, met, ala, val, leu, ile; (2) neutral hydrophilic: Cys, Ser, Thr, Asn, Gln; (3) acidic: asp, glu; (4) basic: his, lys, arg; (5) residues that influence chain orientation: gly, pro; and (6) aromatic: trp, tyr, phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino acid substitutions at each site. The antibodies thus generated are displayed from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of the immunoglobulin polypeptides disclosed herein, thereby generating a Fc region variant. The Fc region variant may comprise a human Fc region sequence (e.g., a human IgG1, IgG2, IgG3 or IgG4 Fc region) comprising an amino acid modification (e.g., a substitution) at one or more amino acid positions including that of a hinge cysteine.

In accordance with this description and the teachings of the art, it is contemplated that in some embodiments, an antibody used in methods disclosed herein may comprise one or more alterations as compared to the wild type counterpart antibody, e.g., in the Fc region. These antibodies would nonetheless retain substantially the same characteristics required for therapeutic utility as compared to their wild type counterpart. For example, it is thought that certain alterations can be made in the Fc region that would result in altered (e.g., either improved or diminished) C1q binding and/or Complement Dependent Cytotoxicity (CDC), e.g., as described in WO99/51642. See also Duncan & Winter Nature 322:738-40 (1988); U.S. Pat. Nos. 5,648,260; 5,624, 821; and WO94/29351 concerning other examples of Fc region variants. WO00/42072 and WO 2004/056312 describe antibody variants with improved or diminished binding to FcRs. See, also, Shields et al. J. Biol. Chem. 9(2): 6591-6604 (2001). Antibodies with increased half lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/

0014934 (Hinton et al.). These antibodies comprise an Fc reg on with one or more substitutions therein which improve binding of the Fc region to FcRn. Polypeptide variants with altered Fc region amino acid sequences and increased or decreased C1q binding capability are described in U.S. Pat. No. 6,194,551, WO99/51642. See, also, Idusogie et al. J. Immunol. 164:4178-4184 (2000).

In certain embodiments, the present disclosure contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII FcR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g. Hellstrom, I. et al. Proc. Nat'! Acad. Sci. USA 83:7059-7063 (1986)) and Hellstrom, I et al., Proc. Nat'l Acad. Sci. USA 82:1499-1502 (1985); 5,821,337 (see, Bruggemann, M. et al., Exp. Med. 166:1351-1361 (1987)). Alternatively, non-radioactive assays methods may be employed (see, for example, ACTITM non-radioactive cytotoxicity assay for flow cytometry (CellTecl1r1ology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. Proc. Nat'l Acad. Sci. USA 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., Immunol. Methods 202: 163 (1996); Cragg, M. S. et al., Blood 101:1045-1052 (2003); and Cragg, M. S, and M. J. Glennie, Blood 103: 27382743 (2004)). FcRn binding and in vivo clearance/half life determinations can also be performed using methods known in the art (see, e.g., Petkova, S. B. et al., Int'l Immunol. 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., Biol. Chem. 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. Immunol. 164: 41784184 (2000).

Antibodies with increased half lives and improved binding to the neonatal Fc receptor (FcRn), which is responsible for the transfer of maternal IgGs to the fetus (Guyer et al., Immunol. 117:587 (1976) and Kim et al., Immunol. 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, Nature 322:738-40 (1988); U.S. Pat. Nos. 5,648,260; 5,624,821; and WO 94/29351 concerning other examples of Fc region variants.

Antibody Derivatives

The antibodies comprising an ultralong CDR3 as disclosed herein may be further modified to contain additional nonproteinaceous moieties that are known in the art and readily available. Preferably, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymers are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

Vectors, Host Cells and Recombinant Methods

For recombinant production of an antibody or fragment thereof as disclosed herein, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). In an exemplary embodiment, nucleic acid encoding an antibody comprising an ultralong CDR3, a variable region comprising an ultralong CDR3, or an ultralong CDR3, is isolated and inserted into a replicable vector for further cloning (amplification of the DNA) or for expression. Many vectors are available. The choice of vector depends in part on the host cell to be used. Generally, preferred host cells are of either prokaryotic or eukaryotic (generally mammalian) origin. It will be appreciated that constant regions of any isotype can be used for this purpose, including IgG, IgM, IgA, IgD, and IgE constant regions, and that such constant regions can be obtained from any human or animal species.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase and dihydrofolate reductase. Alternatively, high yield expression systems not involving gene amplification are also suitable, such as using a baculovirus vector in insect cells, with a nucleic acid sequence encoding a partially human ultralong CDR3 antibody chain under the direction of the polyhedrin promoter or other strong baculovirus promoters.

a. Generating Antibodies Using Prokaryotic or Eukaryotic Host Cells:

i. Vector Construction

Polynucleotide sequences encoding polypeptide components of the antibodies disclosed herein can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present disclosure. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence. Additionally, V regions comprising an ultralong CDR3 may optionally be fused to a C-region to produce an antibody comprising constant regions.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies have been described (see, e.g., U.S. Pat. No. 5,648,237).

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as *E. coli* LE392.

The expression vectors disclosed herein may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g., the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector disclosed herein. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include: an ara B promoter, a PhoA promoter, β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (e.g., Siebenlist et al. (1980) Cell 20: 269) using linkers or adaptors to supply any required restriction sites.

Suitable bacterial promoters are well known in the art and fully described in scientific literature such as Sambrook and Russell, supra, and Ausubel et al, supra. Bacterial expression systems for expressing antibody chains of the recombinant catalytic polypeptide are available in, e.g., *E. coli, Bacillus* sp., and *Salmonella* (Palva et al., Gene, 22:229-235 (1983); Mosbach et al., Nature, 302:543-545 (1983)).

In one aspect disclosed herein, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence should be one that is recognized and processed (e.g., cleaved by a signal peptidase) by the host cell. For prokaryotic host cells that do not recognize and process the signal sequences native to the heterologous polypeptides, the signal sequence is substituted by a prokaryotic signal sequence selected, for example PelB, OmpA, alkaline phosphatase, penicillinase, lpp, or heat-stable enterotoxin II (STII) leaders, LamB, PhoE, and MBP. In one embodiment disclosed herein, the signal sequences used in both cistrons of the expression system are STII signal sequences or variants thereof.

In another aspect, the production of the immunoglobulins according to the disclosure can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the *E. coli* trxB-strains) provide cytoplasm conditions that are favorable for disulfide bond formation, thereby permitting proper folding and assembly of expressed protein subunits (see e.g., Proba and Pluckthun Gene, 159:203 (1995)).

Suitable host cells for cloning or expression of antibody-encoding vectors include prokaryotic or eukaryotic cells described herein. In one embodiment, the host cell is eukaryotic, e.g. a Chinese Hamster Ovary (CHO) cell, Human Embryonic Kidney (HEK) cell or lymphoid cell (e.g., YO, NSO, Sp20 cell). For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified. In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gemgross, Nat. Biotech. 22: 1409-1414 (2004), and Li et al., Nat. Biotech. 24:210-215 (2006). Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, *E. coli, Serratia*, or *Salmonella* species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

Plant cell cultures can also be utilized as hosts. See, e.g. U.S. Pat. Nos. 5,959,177, 6,040,498, 6,420,548, 7,125, 978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., Gen VII'01. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (V ERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TR1 cells, as described, e.g., in Mather et al., Annals NI'. Acad. Sci. 383:44-68 (1982); MRC 5 cells; and FS4 cells. Other useful mammalian host cell lines include Chinese hamster ovary (CHO) cells, including DHFR' CHO cells (Urlaub et al., Proc. Natl. Acad. Sci. USA 77:4216 (1980)); and myeloma cell lines such as YO, NSO and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.].), pp. 255-268 (2003).

In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody.

ii. Antibody Production

For recombinant production of a partially human ultralong CDR3 antibody, nucleic acid encoding an antibody comprising an ultralong CDR3 is inserted into one or more expression vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody). Host cells are transformed with such expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides disclosed herein are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector disclosed herein, protein expression is induced under conditions suitable for the activation of the promoter. For example, an ara B or phoA promoter may be used for controlling transcription of the polypeptides. A variety of inducers may be used, according to the vector construct employed, as is known in the art.

The expressed polypeptides of the present disclosure are secreted into and recovered from the periplasm of the host cells or transported into the culture media. Protein recovery from the periplasm typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins that are transported into the culture media may be isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

Antibody production may be conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (a preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides disclosed herein, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) may be used to co-transform the host prokaryotic cells. The chaperone proteins have been demonstrated to facilitate the proper folding and solubility of heterologous proteins produced in bacterial host cells. (see e.g., Chen et al. (1999) J Bio Chem 274:19601-19605; U.S. Pat. Nos. 6,083,715; 6,027,888; Bothmann and Pluckthun (2000) J. Biol. Chem. 275:17100-17105; Ramm and Pluckthun (2000) J. Biol. Chem. 275:17106-17113; Arie et al. (2001) Mol. Microbiol. 39:199-210).

To minimize proteolysis of expressed heterologous proteins (especially those that are proteolytically sensitive), certain host strains deficient for proteolytic enzymes can be used for the present disclosure. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available (see, e.g., Joly et al. (1998), supra; U.S. Pat. Nos. 5,264,365; 5,508,192; Hara et al., Microbial Drug Resistance, 2:63-72 (1996)).

*E. coli* strains deficient for proteolytic enzymes and transformed with plasmids overexpressing one or more chaperone proteins may be used as host cells in the expression systems disclosed herein.

iii. Antibody Purification

Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the full length antibody products disclosed herein. Protein A is a 41 kD cell wall protein from *Staphylococcus aureas* which binds with a high affinity to the Fc region of antibodies (see, e.g., Lindmark et al (1983) J. Immunol. Meth. 62:1-13). The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants.

As the first step of purification, the preparation derived from the cell culture as described above is applied onto the Protein A immobilized solid phase to allow specific binding of the antibody of interest to Protein A. The solid phase is then washed to remove contaminants non-specifically bound to the solid phase. Finally the antibody of interest is recovered from the solid phase by elution.

b. Generating Antibodies Using Eukaryotic Host Cells:

The vector components generally include, but are not limited to, one or more of the following: a signal sequence, an origin of replication, one or more marker genes, an enhancer element, a promoter, and a transcription termination sequence.

(i) Signal Sequence Component

A vector for use in a eukaryotic host cell may also contain a signal sequence or other polypeptide having a specific cleavage site at the N-terminus of the mature protein or polypeptide of interest. The heterologous signal sequence selected preferably is one that is recognized and processed (e.g., cleaved by a signal peptidase) by the host cell. In mammalian cell expression, mammalian signal sequences as well as viral secretory leaders, for example, the herpes simplex gD signal, are available.

The DNA for such precursor region is ligated in reading frame to DNA encoding the antibody.

(ii) Origin of Replication

Generally, an origin of replication component is not needed for mammalian expression vectors. For example, the SV40 origin may be used only because it contains the early promoter.

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

(iv) Promoter Component

Expression and cloning vectors usually contain a promoter that is recognized by the host organism and is operably linked to the antibody polypeptide nucleic acid. Promoter sequences are known for eukaryotes. Virtually alleukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Antibody polypeptide transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. Alternatively, the Rous Sarcoma Virus long terminal repeat can be used as the promoter.

(v) Enhancer Element Component

Transcription of DNA encoding the antibody polypeptide of this disclosure by higher eukaryotes is often increased by inserting an enhancer sequence into the vector. Many enhancer sequences are now known from mammalian genes (globin, elastase, albumin, α-fetoprotein, and insulin). An enhancer from a eukaryotic cell virus may also be used. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the antibody polypeptide-encoding sequence, but is preferably located at a site 5' from the promoter.

(vi) Transcription Termination Component

Expression vectors used in eukaryotic host cells will typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA, or other foreign genetic material into a host cell (see, e.g., Sambrook and Russell, supra). It is only necessary that the particular genetic engineering procedure used be capable of successfully introducing at least both genes into the host cell capable of expressing germline antibody polypeptide.

Host cells are transformed with the above-described expression or cloning vectors for antibody production and cultured in conventional nutrient media modified as appropriate for inducing promoters, selecting transformants, or amplifying the genes encoding the desired sequences.

(viii) Culturing the Host Cells

The host cells used to produce an antibody of this disclosure may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. No. Reissue 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Purification of Antibody

When using recombinant techniques, the antibody can be produced intracellularly, or directly secreted into the medium. If the antibody is produced intracellularly, as a first step, the particulate debris, either host cells or lysed fragments, are removed, for example, by centrifugation or ultrafiltration. Where the antibody is secreted into the medium, supernatants from such expression systems are generally first concentrated using a commercially available protein concentration filter, for example, an Amicon or Millipore Pellicon® ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Meth. 62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Soluble forms of antibody or fragment present either in the cytoplasm or released from the periplasmic space may be further purified using methods known in the art, for example Fab fragments are released from the bacterial periplasmic space by osmotic shock techniques.

If inclusion bodies comprising an antibody or fragment have formed, they can often bind to the inner and/or outer cellular membranes and thus will be found primarily in the pellet material after centrifugation. The pellet material can then be treated at pH extremes or with chaotropic agent such as a detergent, guanidine, guanidine derivatives, urea, or urea derivatives in the presence of a reducing agent such as dithiothreitol at alkaline pH or tris carboxyethyl phosphine at acid pH to release, break apart, and solubilize the inclusion bodies. The soluble antibody or fragment can then be analyzed using gel electrophoresis, immunoprecipitation or the like. If it is desired to isolate a solublized antibody or antigen binding fragment isolation may be accomplished using standard methods such as those set forth below and in Marston et al. (Meth. Enz., 182:264-275 (1990)).

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25 M salt).

In some cases, an antibody or fragment may not be biologically active upon isolation. Various methods for "refolding" or converting a polypeptide to its tertiary structure and generating disulfide linkages, can be used to restore biological activity. Such methods include exposing the solubilized polypeptide to a pH usually above 7 and in the presence of a particular concentration of a chaotrope. The selection of chaotrope is very similar to the choices used for inclusion body solubilization, but usually the chaotrope is used at a lower concentration and is not necessarily the same as chaotropes used for the solubilization. In most cases the refolding/oxidation solution will also contain a reducing agent or the reducing agent plus its oxidized form in a specific ratio to generate a particular redox potential allowing for disulfide shuffling to occur in the formation of the protein's cysteine bridge(s). Some of the commonly used redox couples include cysteine/cystamine, glutathione (GSH)/dithiobis GSH, cupric chloride, dithiothreitol (DTT)/dithiane DTT, and 2-mercaptoethanol (bME)/di-thio-b(ME). In many instances, a cosolvent may be used to increase the efficiency of the refolding, and common reagents used for this purpose include glycerol, polyethylene glycol of various molecular weights, arginine and the like.

Immunoconjugates

The disclosure also provides immunoconjugates (interchangeably termed "antibody-drug conjugates" or "ADC"), comprising any of the antibodies comprising an ultralong CDR3 as described herein conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (e.g., a radioconjugate). Alternatively, the immunoconjugate comprises any of the antibodies comprising an ultralong CDR3 as described herein conjugated to a peptide. The peptide may be a non-antibody peptide, therapeutic polypeptide, cytokine, hormone or growth factor. The peptide may be encoded by a non-antibody sequence.

The antibody-drug conjugates may be used for the local delivery of cytotoxic or cytostatic agents. For example, drugs to kill or inhibit tumor cells in the treatment of cancer (Syrigos and Epenetos (1999) Anticancer Research 19:605-614; Niculescu-Duvaz and Springer (1997) Adv. Drg Del. Rev. 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986):603-05; Thorpe, (1985) "Antibody Carriers Of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (Rowland et al., (1986) Supra). Toxins used in antibody-toxin conjugates include bacterial toxins such as diphtheria toxin, plant toxins such as ricin, small molecule toxins such as geldanamycin (Mandler et al (2000) Jour. of the Nat. Cancer Inst. 92(19):1573-1581; Mandler et al (2000) Bioorganic & Med. Chem. Letters 10: 1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins may effect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and $^{111}$In or $^{90}$Y radioisotope bound by a thiourea linker-chelator (Wiseman et al (2000) Eur. Jour. Nucl. Med. 27(7):766-77; Wiseman et al (2002) Blood 99(12):4336-42; Witzig et al (2002) J. Clin. Oncol. 20(10): 2453-63; Witzig et al (2002) J. Clin. Oncol. 20(15):3262-69). Although ZEVALIN has activity against B-cell non-Hodgkin's Lymphoma (NHL), administration results in severe and prolonged cytopenias in most patients. MYLOTARG™ (gemtuzumab ozogamicin, Wyeth Pharmaceuticals), an antibody drug conjugate composed of a hu CD33 antibody linked to calicheamicin, was approved in 2000 for the treatment of acute myeloid leukemia by injection (Drugs of the Future (2000) 25(7):686; U.S. Pat. Nos. 4,970,198; 5,079,233; 5,585,089; 5,606,040; 5,693,762; 5,739,116; 5,767,285; 5,773,001). Cantuzumab mertansine (Immunogen, Inc.), an antibody drug conjugate composed of the huC242 antibody linked via the disulfide linker SPP to the maytansinoid drug moiety, DM1, is advancing into Phase II trials for the treatment of cancers that express CanAg, such as colon, pancreatic, gastric, and others. MLN-2704 (Millennium Pharm., BZL Biologics, Immunogen Inc.), an antibody drug conjugate composed of the anti-prostate specific membrane antigen (PSMA) monoclonal antibody linked to the maytansinoid drug moiety, DM1, is under development for the potential treatment of prostate tumors. The auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al (2003) Nature Biotechnology 21(7):778-784) and are under therapeutic development.

Chemotherapeutic agents useful in the generation of immunoconjugates are described herein. Enzymatically active toxins and fragments thereof that can be used include diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin may be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, dolastatins, aurostatins, a trichothecene, and CC1065, and the derivatives of these toxins that have toxin activity, are also contemplated herein.

a. Maytansine and Maytansinoids

In some embodiments, the immunoconjugate comprises an antibody (full length or fragments) comprising an ultralong CDR3 as disclosed herein conjugated to one or more maytansinoid molecules.

Maytansinoids are mitotetic inhibitors which act by inhibiting tubulin polymerization. Maytansine was first isolated from the east African shrub Maytenus serrata (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Immunoconjugates containing maytansinoids, methods of making same, and their therapeutic use are disclosed, for example, in U.S. Pat. Nos. 5,208,020, 5,416,064 and EP 0 425 235. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansinoid conjugate was tested in vitro on the human breast cancer cell line SK-BR-3, which expresses $3 \times 10^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-maytansinoid conjugates are prepared by chemically linking an antibody to a maytansinoid molecule without significantly diminishing the biological activity of either the antibody or the maytansinoid molecule. See, e.g., U.S. Pat. No. 5,208,020. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. Nos. 5,208,020, 6,441, 163, or EP Patent 0 425 235, Chari et al., Cancer Research 52:127-131 (1992). Antibody-maytansinoid conjugates comprising the linker component SMCC may be prepared. The linking groups include disulfide groups, thioether groups, acid labile groups, photolabile groups, peptidase labile groups, or esterase labile groups, as disclosed in the above-identified patents; disulfide and thioether groups being preferred. Additional linking groups are described and exemplified herein.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al., Biochem. J. 173:723-737 (1978)) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

b. Auristatins and Dolastatins

In some embodiments, the immunoconjugate comprises an antibody disclosed herein conjugated to dolastatins or dolostatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, (see, e.g., U.S. Pat. No. 7,498,298).

Typically, peptide-based drug moieties can be prepared by forming a peptide bond between two or more amino acids and/or peptide fragments. Such peptide bonds can be prepared, for example, according to the liquid phase synthesis method (see, e.g., E. Schroder and K. Lubke, "The Peptides", volume 1, pp 76-136, 1965, Academic Press) that is well known in the field of peptide chemistry. The auristatin/dolastatin drug moieties may be prepared according to the methods of: U.S. Pat. Nos. 5,635,483; 5,780,588; Pettit et al (1989) J. Am. Chem. Soc. 111:5463-5465; Pettit et al. (1998) Anti-Cancer Drug Design 13:243-277; Pettit, G. R., et al. Synthesis, 1996, 719-725; and Pettit et al. (1996) J. Chem. Soc. Perkin Trans. 1 5:859-863. See also Doronina (2003) Nat Biotechnol 21(7):778-784; U.S. Pat. No. 7,498,289, (disclosing, linkers and methods of preparing monomethylvaline compounds such as MMAE and MMAF conjugated to linkers).

c. Calicheamicin

In other embodiments, the immunoconjugate comprises an antibody disclosed herein conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296. Structural analogues of calicheamicin which may be used include, but are not limited to, $\gamma_1^I$, $\alpha_2^I$, $\alpha_3^I$, N-acetyl-$\gamma_1^I$, PSAG and $\theta^I_1$ (see, e.g., Hinman et al., Cancer Research 53:3336-3342 (1993), Lode et al., Cancer Research 58:2925-2928 (1998) and the aforementioned U.S. patents). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

d. Other Cytotoxic Agents

Other antitumor agents that can be conjugated to the antibodies disclosed herein include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, for example, WO 93/21232 published Oct. 28, 1993.

The present disclosure further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radiolabels or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57) can be used to incorporate iodine-123. "Monoclonal Antibodies in Immunoscintigraphy" (Chatal, CRC Press 1989) describes other methods.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HC1), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The compounds disclosed herein expressly contemplate, but are not limited to, ADC prepared with cross-linker reagents: BMPS, EMCS, GMBS, HBVS, LC-SMCC, MBS, MPBH, SBAP, SIA, SLAB, SMCC, SMPB, SMPH, sulfo-EMCS, sulfo-GMBS, sulfo-KMUS, sulfo-MBS, sulfo-SLAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

e. Preparation of Antibody Drug Conjugates

In the antibody drug conjugates (ADC) disclosed herein, an antibody (Ab) is conjugated to one or more drug moieties (D), e.g., about 1 to about 20 drug moieties per antibody, through a linker (L). An ADC of Formula I [Ab-(L-D)$_p$] may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody. Additional methods for preparing ADC are described herein.

The linker may be composed of one or more linker components. Exemplary linker components include 6-maleimidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio) pentanoate ("SPP"), N-Succinimidyl 4-(N-maleimidomethyl)cyclohexane-1 carboxylate ("SMCC"), and N-Succinimidyl (4-iodo-acetyl)aminobenzoate ("SIAB"). Additional linker components are known in the art and some are disclosed herein (see, e.g., U.S. Pat. No. 7,498,298).

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acids including analogs, such as citrulline. Amino acid linker components can be designed and optimized in their selectivity for enzymatic cleavage by a particular enzymes, for example, a tumor-associated protease, cathepsin B, C and D, or a plasmin protease.

Nucleophilic groups on antibodies include, but are not limited to: (i) N-terminal amine groups, (ii) side chain amine groups, e.g., lysine, (iii) side chain thiol groups, e.g., cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, e.g., cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Antibody drug conjugates disclosed herein may also be produced by modification of the antibody to introduce electrophilic moieties, which can react with nucleophilic substituents on the linker reagent or drug. The sugars of glycosylated antibodies may be oxidized, e.g., with periodate oxidizing reagents, to form aldehyde or ketone groups which may react with the amine group of linker reagents or drug moieties. The resulting imine Schiff base groups may form a stable linkage, or may be reduced, e.g., by borohydride reagents to form stable amine linkages. In one embodiment, reaction of the carbohydrate portion of a glycosylated antibody with either glactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

Engineered Hybridomas

Hybridoma cells can be generated by fusing B cells producing a desired antibody with an immortalized cell line, usually a myeloma cell line, so that the resulting fusion cells will be an immortalized cell line that secrets a particular antibody. By the same principle, myeloma cells can be first transfected with a nucleic acid encoding a germline antibody V region and can be screened for the expression of the germline V region. Those myeloma cells with highest level of proteolytic light chain expression can be subsequently fused with B cells that produce an antibody with desired target protein specificity. The fusion cells will produce two types of antibodies: one is a heterologous antibody containing an endogenous antibody chain (either heavy or light) operably joined to the recombinant germline V region (either heavy or light), and the other is the same antibody that the parental B cells would secrete (e.g. both endogenous heavy and light chains). The operably joined heterologous heavy and light chains can be isolated by conventional methods such as chromatography and identification can be confirmed by target protein binding assays, assays identifying a unique tag of the germline polypeptide, or endopeptidase activity assays described in other sections of this disclosure. In some cases, where the heterologous antibody is the predominant type in quantity among the two types of antibodies, such isolation may not be needed. Hybridomas. Including bovine hybridomas, may be a source of bovine antibody gene sequences, including ultralong CDR3 sequences.

Transgenic Mammals

A nucleic acid sequence encoding a germline antibody polypeptide of the present disclosure can be introduced into a non-human mammal to generate a transgenic animal that expresses the germline antibody polypeptide. Unlike the transgenic animal models more commonly seen, the transgene expressed by the transgenic mammals of the present disclosure need not replace at least one allele of the endogenous coding sequence responsible for the variable regions of antibody chains following somatic recombination. Due to allelic exclusion, the presence of an exogenous, post-somatic rearrangement version of the germline V region DNA will inhibit the endogenous alleles of pre-somatic rearrangement V minigenes from undergoing somatic rearrangement and contributing to the makeup of antibody chains this mammal may produce. Thus, when exposed to a particular antigen, the mammal will generate heterologous antibodies comprising one endogenously rearranged antibody chain, and one transgenic gene which was rearranged a priori. Such heterologous antibodies are invaluable in research and in treating certain conditions in live subjects. On the other hand, a method that directs the integration of the transgene to the locus of an endogenous allele will fully serve the purpose of practicing the present disclosure as well.

The general methods of generating transgenic animals have been well established and frequently practiced. For reviews and protocols for generating transgenic animals and related methods for genetic manipulations, see, e.g., Mansour et al., Nature 336:348-352 (1988); Capecchi et al., Trends Genet. 5:70-76 (1989); Capecchi, Science 244:1288-1292 (1989); Capecchi et al., Current Communications in Molecular Biology, pp 45-52, Capecchi, M. R. (ed.), Cold Spring Harbor Press, Cold Spring Harbor, N.Y. (1989); Frohman et al., Cell 56: 145-147 (1989); Brinster et al., Proc. Natl. Acad. Sci. USA 82:4438-4442 (1985); Evans et. al., Nature 292:154-156 (1981); Bradley et al., Nature 309:255-258 (1984); Gossler et al., Proc. Natl. Acad. Sci. USA 83:9065-9069 (1986); Robertson et al., Nature 322: 445-448 (1986); Jaenisch Science 240:1468-1474 (1988); and Siedel, G. E., Jr., "Critical review of embryo transfer procedures with cattle" in Fertilization and Embryonic Development in Vitro, page 323, L. Mastroianni, Jr. and J. D. Biggers, ed., Plenum Press, New York, N.Y. (1981).

An exemplary transgenic animal of the present disclosure is mouse, whereas a number of other transgenic animals can also be produced using the same general method. These animals include, but are not limited to: rabbits, sheep, cattle, and pigs (Jaenisch Science 240:1468-1474 (1988); Hammer et al., J. Animal. Sci. 63:269 (1986); Hammer et al. Nature 315:680 (1985); Wagner et al., Theriogenology 21:29 (1984)).

Pharmaceutical Compositions

Antibodies comprising an ultralong CDR3, antibody fragments, nucleic acids, or vectors disclosed herein can be formulated in compositions, especially pharmaceutical compositions. Such compositions with antibodies comprising an ultralong CDR3 comprise a therapeutically or prophylactically effective amount of antibodies comprising an ultralong CDR3, antibody fragment, nucleic acid, or vector disclosed herein in admixture with a suitable carrier, e.g., a pharmaceutically acceptable agent. Typically, antibodies comprising an ultralong CDR3, antibody fragments, nucleic acids, or vectors disclosed herein are sufficiently purified for administration before formulation in a pharmaceutical composition.

Pharmaceutically acceptable salts, excipients, or vehicles for use in the present pharmaceutical compositions include carriers, excipients, diluents, antioxidants, preservatives, coloring, flavoring and diluting agents, emulsifying agents, suspending agents, solvents, fillers, bulking agents, buffers, delivery vehicles, tonicity agents, cosolvents, wetting agents, complexing agents, buffering agents, antimicrobials, and surfactants.

Neutral buffered saline or saline mixed with serum albumin are exemplary appropriate carriers. The pharmaceutical compositions may include antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics, or polyethylene glycol (PEG). Also by way of example, suitable tonicity enhancing agents include alkali metal halides (preferably sodium or potassium chloride), mannitol, sorbitol, and the like. Suitable preservatives include benzalkonium chloride, thimerosal, phenethyl alcohol, methylparaben, propylparaben, chlorhexidine, sorbic acid and the like. Hydrogen peroxide also may be used as preservative. Suitable cosolvents include glycerin, propylene glycol, and PEG. Suitable complexing agents include caffeine, polyvinylpyrrolidone, beta-cyclodextrin or hydroxy-propyl-beta-cyclodextrin. Suitable surfactants or wetting agents include sorbitan esters, polysorbates such as polysorbate 80, tromethamine, lecithin, cholesterol, tyloxapal, and the like. The buffers may be conventional buffers such as acetate, borate, citrate, phosphate, bicarbonate, or Tris-HCl. Acetate buffer may be about pH 4-5.5, and Tris buffer can be about pH 7-8.5. Additional pharmaceutical agents are set forth in Remington's Pharmaceutical Sciences, 18th Edition, A. R. Gennaro, ed., Mack Publishing Company, 1990.

The composition may be in liquid form or in a lyophilized or freeze-dried form and may include one or more lyoprotectants, excipients, surfactants, high molecular weight structural additives and/or bulking agents (see, for example, U.S. Pat. Nos. 6,685,940, 6,566,329, and 6,372,716). In one embodiment, a lyoprotectant is included, which is a non-reducing sugar such as sucrose, lactose or trehalose. The amount of lyoprotectant generally included is such that, upon reconstitution, the resulting formulation will be isotonic, although hypertonic or slightly hypotonic formulations also may be suitable. In addition, the amount of lyoprotectant should be sufficient to prevent an unacceptable amount of degradation and/or aggregation of the protein upon lyophilization. Exemplary lyoprotectant concentrations for sugars (e.g., sucrose, lactose, trehalose) in the pre-lyophilized formulation are from about 10 mM to about 400 mM. In another embodiment, a surfactant is included, such as for example, nonionic surfactants and ionic surfactants such as polysorbates (e.g., polysorbate 20, polysorbate 80); poloxamers (e.g., poloxamer 188); poly(ethylene glycol) phenyl ethers (e.g., Triton); sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl ofeyl-taurate; and the MONAQUAT™. series (Mona Industries, Inc., Paterson, N.J.), polyethyl glycol, polypropyl glycol, and copolymers of ethylene and propylene glycol (e.g., Pluronics, PF68 etc). Exemplary amounts of surfactant that may be present in the pre-lyophilized formulation are from about 0.001-0.5%. High molecular weight structural additives (e.g., fillers, binders) may include for example, acacia, albumin, alginic acid, calcium phosphate (dibasic), cellulose, carboxymethylcellulose, carboxymethylcellulose sodium, hydroxyethylcellulose, hydroxypropylcellulose, hydroxypropylmethylcellulose, microcrystalline cellulose, dextran, dextrin, dextrates, sucrose, tylose, pregelatinized starch, calcium sulfate, amylose, glycine, bentonite, maltose, sorbitol, ethylcellulose, disodium hydrogen phosphate, disodium phosphate, disodium pyrosulfite, polyvinyl alcohol, gelatin, glucose, guar gum, liquid glucose, compressible sugar, magnesium aluminum silicate, maltodextrin, polyethylene oxide, polymethacrylates, povidone, sodium alginate, tragacanth microcrystalline cellulose, starch, and zein. Exemplary concentrations of high molecular weight structural additives are from 0.1% to 10% by weight. In other embodiments, a bulking agent (e.g., mannitol, glycine) may be included.

Compositions may be suitable for parenteral administration. Exemplary compositions are suitable for injection or infusion into an animal by any route available to the skilled worker, such as intraarticular, subcutaneous, intravenous, intramuscular, intraperitoneal, intracerebral (intraparenchymal), intracerebroventricular, intramuscular, intraocular, intraarterial, or intralesional routes. A parenteral formulation typically will be a sterile, pyrogen-free, isotonic aqueous solution, optionally containing pharmaceutically acceptable preservatives.

Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringers' dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, anti-microbials, anti-oxidants, chelating agents, inert gases and the like. See generally, Remington's Pharmaceutical Science, 16th Ed., Mack Eds., 1980.

Pharmaceutical compositions described herein may be formulated for controlled or sustained delivery in a manner that provides local concentration of the product (e.g., bolus, depot effect) and/or increased stability or half-life in a particular local environment. The compositions can include the formulation of antibodies comprising an ultralong CDR3, antibody fragments, nucleic acids, or vectors disclosed herein with particulate preparations of polymeric compounds such as polylactic acid, polyglycolic acid, etc., as well as agents such as a biodegradable matrix, injectable microspheres, microcapsular particles, microcapsules, bioerodible particles beads, liposomes, and implantable delivery devices that provide for the controlled or sustained release of the active agent which then can be delivered as a depot injection. Techniques for formulating such sustained- or controlled-delivery means are known and a variety of polymers have been developed and used for the controlled release and delivery of drugs. Such polymers are typically biodegradable and biocompatible. Polymer hydrogels, including those formed by complexation of enantiomeric polymer or polypeptide segments, and hydrogels with temperature or pH sensitive properties, may be desirable for providing drug depot effect because of the mild and aqueous conditions involved in trapping bioactive protein agents (e.g., antibodies comprising an ultralong CDR3). See, for example, the description of controlled release porous polymeric microparticles for the delivery of pharmaceutical compositions in WO 93/15722.

Suitable materials for this purpose include polylactides (see, e.g., U.S. Pat. No. 3,773,919), polymers of poly-(a-hydroxycarboxylic acids), such as poly-D-(–)-3-hydroxybutyric acid (EP 133,988A), copolymers of L-glutamic acid and gamma ethyl-L-glutamate (Sidman et al., Biopolymers, 22: 547-556 (1983)), poly(2-hydroxyethyl-methacrylate) (Langer et al., J. Biomed. Mater. Res., 15: 167-277 (1981), and Langer, Chem. Tech., 12: 98-105 (1982)), ethylene vinyl acetate, or poly-D(–)-3-hydroxybutyric acid. Other biodegradable polymers include poly(lactones), poly(acetals), poly(orthoesters), and poly(orthocarbonates). Sustained-release compositions also may include liposomes, which can be prepared by any of several methods known in the art (see, e.g., Eppstein et al., Proc. Natl. Acad. Sci. USA, 82: 3688-92 (1985)). The carrier itself, or its degradation products, should be nontoxic in the target tissue and should not further aggravate the condition. This can be determined by routine screening in animal models of the target disorder or, if such models are unavailable, in normal animals.

Microencapsulation of recombinant proteins for sustained release has been performed successfully with human growth hormone (rhGH), interferon-(rhIFN-), interleukin-2, and MN rgp120. Johnson et al., Nat. Med., 2:795-799 (1996); Yasuda, Biomed. Ther., 27:1221-1223 (1993); Hora et al., Bio/Technology. 8:755-758 (1990); Cleland, "Design and Production of Single Immunization Vaccines Using Polylactide Polyglycolide Microsphere Systems," in Vaccine Design: The Subunit and Adjuvant Approach, Powell and Newman, eds, (Plenum Press: New York, 1995), pp. 439-462; WO 97/03692, WO 96/40072, WO 96/07399; and U.S. Pat. No. 5,654,010. The sustained-release formulations of these proteins were developed using poly-lactic-coglycolic acid (PLGA) polymer due to its biocompatibility and wide range of biodegradable properties. The degradation products of PLGA, lactic and glycolic acids can be cleared quickly within the human body. Moreover, the degradability of this polymer can be depending on its molecular weight and composition. Lewis, "Controlled release of bioactive agents from lactide/glycolide polymer," in: M. Chasin and R. Langer (Eds.), Biodegradable Polymers as Drug Delivery Systems (Marcel Dekker: New York, 1990), pp. 1-41. Additional examples of sustained release compositions include, for example, EP 58,481A, U.S. Pat. No. 3,887,699, EP 158,277A, Canadian Patent No. 1176565, U. Sidman et al., Biopolymers 22, 547 [1983], R. Langer et al., Chem. Tech. 12, 98 [1982], Sinha et al., J. Control. Release 90, 261 [2003], Zhu et al., Nat. Biotechnol. 18, 24 [2000], and Dai et al., Colloids Surf B Biointerfaces 41, 117 [2005].

Bioadhesive polymers are also contemplated for use in or with compositions of the present disclosure. Bioadhesives are synthetic and naturally occurring materials able to adhere to biological substrates for extended time periods. For example, Carbopol and polycarbophil are both synthetic cross-linked derivatives of poly(acrylic acid). Bioadhesive delivery systems based on naturally occurring substances include for example hyaluronic acid, also known as hyaluronan. Hyaluronic acid is a naturally occurring mucopolysaccharide consisting of residues of D-glucuronic and N-acetyl-D-glucosamine. Hyaluronic acid is found in the extracellular tissue matrix of vertebrates, including in connective tissues, as well as in synovial fluid and in the vitreous and aqueous humor of the eye. Esterified derivatives of hyaluronic acid have been used to produce microspheres for use in delivery that are biocompatible and biodegradable (see, for example, Cortivo et al., Biomaterials (1991) 12:727-730; EP 517,565; WO 96/29998; Illum et al., J. Controlled Rel. (1994) 29:133-141). Exemplary hyaluronic acid containing compositions of the present disclosure comprise a hyaluronic acid ester polymer in an amount of approximately 0.1% to about 40% (w/w) of an antibody comprising an ultralong CDR3 to hyaluronic acid polymer.

Both biodegradable and non-biodegradable polymeric matrices may be used to deliver compositions of the present disclosure, and such polymeric matrices may comprise natural or synthetic polymers. Biodegradable matrices are preferred. The period of time over which release occurs is based on selection of the polymer. Typically, release over a period ranging from between a few hours and three to twelve months is most desirable. Exemplary synthetic polymers which may be used to form the biodegradable delivery system include: polymers of lactic acid and glycolic acid, polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyanhydrides, polyurethanes and co-polymers thereof, poly(butic acid), poly(valeric acid), alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly (ethylene glycol), poly(ethylene oxide), poly(ethylene terephthalate), poly(vinyl alcohols), polyvinyl acetate, poly vinyl chloride, polystyrene and polyvinylpyrrolidone. Exemplary natural polymers include alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The polymer optionally is in the form of a hydrogel (see, for example, WO 04/009664, WO 05/087201, Sawhney, et al., Macromolecules, 1993, 26, 581-587) that can absorb up to about 90% of its weight in water and further, optionally is cross-linked with multi-valent ions or other polymers.

Delivery systems also include non-polymer systems that are lipids including sterols such as cholesterol, cholesterol esters and fatty acids or neutral fats such as mono-di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the product is contained in a form within a matrix such as those described in U.S. Pat. Nos. 4,452,775, 4,675,189 and 5,736,152 and (b) diffusional systems in which a product permeates at a controlled rate from a polymer such as described in U.S. Pat. Nos. 3,854,480, 5,133,974 and 5,407,686. Liposomes containing the product may be prepared by methods known methods, such as for example (DE 3,218,121; Epstein et al., Proc. Natl. Acad. Sci. USA, 82: 3688-3692 (1985); Hwang et al., Proc. Natl. Acad. Sci. USA, 77: 4030-4034 (1980); EP 52,322; EP 36,676; EP 88,046; EP 143,949; EP 142,641; JP 83-118008; U.S. Pat. Nos. 4,485,045 and 4,544,545; and EP 102,324).

Alternatively or additionally, the compositions may be administered locally via implantation into the affected area of a membrane, sponge, or other appropriate material on to which an antibody comprising an ultralong CDR3, antibody fragment, nucleic acid, or vector disclosed herein has been absorbed or encapsulated. Where an implantation device is used, the device may be implanted into any suitable tissue or organ, and delivery of an antibody comprising an ultralong CDR3 antibody fragment, nucleic acid, or vector disclosed herein can be directly through the device via bolus, or via continuous administration, or via catheter using continuous infusion.

A pharmaceutical composition comprising an antibody comprising an ultralong CDR3, antibody fragment, nucleic acid, or vector disclosed herein may be formulated for inhalation, such as for example, as a dry powder. Inhalation solutions also may be formulated in a liquefied propellant for aerosol delivery. In yet another formulation, solutions may be nebulized. Additional pharmaceutical composition for pulmonary administration include, those described, for example, in WO 94/20069, which discloses pulmonary delivery of chemically modified proteins. For pulmonary delivery, the particle size should be suitable for delivery to the distal lung. For example, the particle size may be from 1 µm to 5 µm; however, larger particles may be used, for example, if each particle is fairly porous.

Certain formulations containing antibodies comprising an ultralong CDR3, antibody fragments, nucleic acids, or vectors disclosed herein may be administered orally. Formulations administered in this fashion may be formulated with or without those carriers customarily used in the compounding of solid dosage forms such as tablets and capsules. For example, a capsule can be designed to release the active portion of the formulation at the point in the gastrointestinal tract when bioavailability is maximized and pre-systemic degradation is minimized. Additional agents may be included to facilitate absorption of a selective binding agent. Diluents, flavorings, low melting point waxes, vegetable oils, lubricants, suspending agents, tablet disintegrating agents, and binders also can be employed.

Another preparation may involve an effective quantity of an antibody comprising an ultralong CDR3, antibody fragment, nucleic acid, or vector disclosed herein in a mixture with non-toxic excipients which are suitable for the manufacture of tablets. By dissolving the tablets in sterile water, or another appropriate vehicle, solutions may be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Suitable and/or preferred pharmaceutical formulations may be determined in view of the present disclosure and general knowledge of formulation technology, depending upon the intended route of administration, delivery format, and desired dosage. Regardless of the manner of administration, an effective dose may be calculated according to patient body weight, body surface area, or organ size. Further refinement of the calculations for determining the appropriate dosage for treatment involving each of the formulations described herein are routinely made in the art and is within the ambit of tasks routinely performed in the art. Appropriate dosages may be ascertained through use of appropriate dose-response data.

In some embodiments, antibodies comprising an ultralong CDR3 or fragments thereof are provided with a modified Fc region where a naturally-occurring Fc region is modified to increase the half-life of the antibody or fragment in a biological environment, for example, the serum half-life or a half-life measured by an in vitro assay. Methods for altering the original form of a Fc region of an IgG also are described in U.S. Pat. No. 6,998,253.

In certain embodiments, it may be desirable to modify the antibody or fragment in order to increase its serum half-life, for example, adding molecules such as PEG or other water soluble polymers, including polysaccharide polymers, to antibody fragments to increase the half-life. This may also be achieved, for example, by incorporation of a salvage receptor binding epitope into the antibody fragment (e.g., by mutation of the appropriate region in the antibody fragment or by incorporating the epitope into a peptide tag that is then fused to the antibody fragment at either end or in the middle, e.g., by DNA or peptide synthesis) (see, International Publication No. WO96/32478). Salvage receptor binding epitope refers to an epitope of the Fc region of an IgG molecule (e.g., IgG1, IgG2, IgG3, or IgG4) that is responsible for increasing the in vivo serum half-life of the IgG molecule.

A salvage receptor binding epitope may include a region wherein any one or more amino acid residues from one or two loops of a Fc domain are transferred to an analogous position of the antibody fragment. Even more preferably, three or more residues from one or two loops of the Fc domain are transferred. Still more preferred, the epitope is taken from the CH2 domain of the Fc region (e.g., of an IgG) and transferred to the CH1, CH3, or VH region, or more than one such region, of the antibody. Alternatively, the epitope is taken from the CH2 domain of the Fc region and transferred to the $C_L$ region or $V_L$ region, or both, of the antibody fragment. See also WO 97/34631 and WO 96/32478 which describe Fc variants and their interaction with the salvage receptor.

Mutation of residues within Fc receptor binding sites may result in altered effector function, such as altered ADCC or CDC activity, or altered half-life. Potential mutations include insertion, deletion or substitution of one or more residues, including substitution with alanine, a conservative substitution, a non-conservative substitution, or replacement with a corresponding amino acid residue at the same position from a different IgG subclass (e.g., replacing an IgG1 residue with a corresponding IgG2 residue at that position).

For example, it has been reported that mutating the serine at amino acid position 241 in IgG4 to proline (found at that position in IgG1 and IgG2) led to the production of a homogeneous antibody, as well as extending serum half-life and improving tissue distribution compared to the original chimeric IgG4. (Angal et al., Mol. Immunol. 30:105-8, 1993).

In some embodiments is a pharmaceutical composition comprising an antibody comprising an ultralong CDR3; and a pharmaceutically acceptable carrier. The antibody may comprise a therapeutic polypeptide, or derivative or variant thereof. The therapeutic polypeptide may be a non-antibody sequence. The therapeutic polypeptide, or derivative or variant thereof can be within the ultralong CDR3. In some instances, the therapeutic polypeptide is Moka1, Vm24, GLP-1, Exendin-4, human EPO, human FGF21, human GMCSF, human interferon-beta, human GCSF, bovine GCSF or derivative or variant thereof. Alternatively, the antibody is an immunoconjugate as described herein. The antibody can comprise one or more immunoglobulin domains. In some embodiments, the immunoglobulin domain is an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. In some instances, the immunoglobulin domain is from an engineered antibody or recombinant antibody. In other instances, the immunoglobulin domain is from a humanized, human engineered or fully human antibody. The mammalian antibody may be a bovine antibody. The mammalin antibody may be a human antibody. In other instances, the mammalian antibody is a murine antibody. The ultralong CDR3 can comprise at least a portion of a knob domain in the CDR3. The therapeutic polypeptide can be attached to the knob domain. Alternatively, or additionally, the ultralong CDR3 comprises at least a portion of a stalk domain in the CDR3. The therapeutic polypeptide may be attached to the stalk domain. In some instances, the antibody further comprises a linker. The linker can be within the ultralong CDR3. The linker can attach the therapeutic polypeptide to the immunoglobulin domain or fragment thereof. In other instances, the linker attaches the therapeutic polypeptide to the knob domain or stalk domain. In certain embodiments is a method of preventing or treating a disease in a subject in need thereof comprising administering this pharmaceutical composition to the subject. In some embodiments, the pharmaceutical composition comprising an immunoglobulin construct comprising a heavy chain polypeptide comprising a sequence based on or derived from a sequence selected from any one of SEQ ID NOS: 24-44 and the polypeptide sequence encoded by the DNA any one of SEQ ID NOS: 2-22; and a light chain polypeptide comprising a sequence selected from SEQ ID NO: 23 and a polypeptide sequence encoded by the DNA of SEQ ID NO: 1; and a pharmaceutically acceptable carrier. In certain embodiments is a method of preventing or treating a disease in a mammal in need thereof comprising administering this phartmaceutical composition to the mammal. In some embodiments, the disease is an infectious disease such as mastitis. In certain embodiments, the mammal in need is a dairy animal selected from a list comprising cow, camel, donkey, goat, horse, reindeer, sheep, water buffalo, moose and yak. In some embodiments, the mammal in need is bovine.

In some embodiments, the pharmaceutical compositions disclosed herein may be useful for providing prognostic or providing diagnostic information.

Kits/Articles of Manufacture

As an additional aspect, the present disclosure includes kits which comprise one or more compounds or compositions packaged in a manner which facilitates their use to practice methods of the present disclosure. In one embodiment, such a kit includes a compound or composition described herein (e.g., a composition comprising an antibody comprising an ultralong CDR3 alone or in combination with a second agent), packaged in a container with a label affixed to the container or a package insert that describes use of the compound or composition in practicing the method. Suitable containers include, for example, bottles, vials, syringes, etc. The containers may be formed from a variety of materials such as glass or plastic. The container may have a sterile access port (for example the container may be an intravenous solution bag or a vial having a stopper pierceable by a hypodermic injection needle). The article of manufacture may comprise (a) a first container with a composition contained therein, wherein the composition comprises an antibody comprising an ultralong CDR3 as disclosed herein; and (b) a second container with a composition contained therein, wherein the composition comprises a further therapeutic agent. The article of manufacture in this embodiment disclosed herein may further comprise a package insert indicating that the first and second compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes. Preferably, the compound or composition is packaged in a unit dosage form. The kit may further include a device suitable for administering the composition according to a specific route of administration or for practicing a screening assay. Preferably, the kit contains a label that describes use of the antibody comprising an ultralong CDR3 composition.

In certain embodiments, the composition comprising the antibody is formulated in accordance with routine procedures as a pharmaceutical composition adapted for intravenous administration to mammals, such as humans, bovines, felines, canines, and murines. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The amount of the composition described herein which will be effective in the treatment, inhibition and prevention of a disease or disorder associated with aberrant expression and/or activity of a Therapeutic protein can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses are extrapolated from dose-response curves derived from in vitro or animal model test systems.

The following are examples of the methods and compositions of the disclosure. It is understood that various other embodiments may be practiced, given the general description provided above.

Methods of Treatment

Further disclosed herein are methods of preventing or treating a disease or condition in a subject in need thereof comprising administering a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is Moka1, Vm24, human GLP-1, Exendin-4, human EPO, human FGF21, human GMCSF, human interferon-beta, or derivative or variant thereof. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalin antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The one or more cysteine motifs may be based on or derived from SEQ ID NOS: 45-156. The one or more cysteine motifs may be based on or derived from SEQ ID NOS: 45-99. The one or more cysteine motifs may be based on or derived from SEQ ID NOS: 100-135. The one or more cysteine motifs may be based on or derived from SEQ ID NOS: 136-156. The ultralong CDR3 can comprise at least a portion of a knob domain. The knob domain may comprise a conserved motif within the knob domain of an ultralong CDR3. For example, the knob domain may comprise a cysteine motif disclosed herein. The therapeutic polypeptide can be attached to the knob domain. Alternatively, or additionally, the ultralong CDR3 comprises at least a portion of a stalk domain. The stalk domain may comprise a conserved motif within the stalk domain of an ultralong CDR3. The conserved motif within the stalk domain of the ultralong CDR3 may comprise a polypeptide sequence based on or derived from SEQ ID NOS: 157-307 and SEQ ID NOS: 333-336. The conserved motif with the stalk domain of the ultralong CDR3 may comprise a polypeptide sequence based on or derived from SEQ ID NOS: 157-224. The conserved motif with the stalk domain of the ultralong CDR3 may comprise a polypeptide sequence based on or derived from SEQ ID NOS: 157-161. The conserved motif with the stalk domain of the ultralong CDR3 may comprise a polypeptide sequence based on or derived from SEQ ID NOS: 223-234. The conserved motif with the stalk domain of the ultralong CDR3 may comprise a polypeptide sequence based on or derived from SEQ ID NOS: 235-239. The conserved motif with the stalk domain of the ultralong CDR3 may comprise a polypeptide sequence based on or derived from SEQ ID NOS: 296-299. The conserved motif with the stalk domain of the ultralong CDR3 may comprise a polypeptide sequence based on or derived from SEQ ID NOS: 300-303. The conserved motif with the stalk domain of the ultralong CDR3 may comprise a polypeptide sequence based on or derived from a first sequence selected from the derived from SEQ ID NOS: 300-303. The conserved motif with the stalk domain of the ultralong CDR3 may comprise a polypeptide sequence basegroup comprising SEQ ID NOS: 157-234 and a second sequence selected from the group comprising SEQ ID NOS: 235-307 and SEQ ID NOS: 333-336. The antibodies disclosed herein may comprise 2 or more, 3 or more, 4 or more, 5 or more sequences based on or derived from SEQ ID NOS: 157-307 and SEQ ID NOS: 333-336. The conserved motif with the stalk domain of the ultralong CDR3 may comprise a polypeptide sequence based on or derived from SEQ ID NOS: 304-307 AND SEQ ID NOS: 333-336. For example, the stalk domain may comprise a T(S/T)VHQ motif (SEQ ID NO: 508). The therapeutic polypeptide can be attached to the stalk domain. In some instances, the antibody, antibody fragment or immunoglobulin construct further comprises a linker. The linker can attach the therapeutic polypeptide to the immunoglobulin domain or fragment thereof. In other instances, the linker attaches the therapeutic polypeptide to the knob domain or stalk domain. In some instances, the disease or condition is an autoimmune disease, heteroimmune disease or condition, inflammatory disease, pathogenic infection, thromboembolic disorder, respiratory disease or condition, metabolic disease, central nervous system (CNS) disorder, bone disease or cancer. In other instances, the disease or condition is a blood disorder. In some instances, the disease or condition is obesity, diabetes, osteoporosis, anemia, or pain.

In some embodiments is a method of preventing or treating a disease or condition in a subject in need thereof comprising administering to the subject a composition comprising: an immunoglobulin construct comprising a heavy chain polypeptide comprising a sequence that is substantially similar to a sequence selected from SEQ ID NOS: 24-44; and a light chain polypeptide comprising the sequence that is substantially similar to a sequence of SEQ ID NO: 23. The heavy chain polypeptide sequence may share 50%, 60%, 70%, 80%, 85%, 90%, 95%, 97%, 99%, or more amino acid sequence identity to a heavy chain sequence provided by any one of SEQ ID NOS: 24-44. The light chain polypeptide sequence may share 50%, 60%, 70%, 80%, 85%, 90%, 95%, 97%, 99%, or more amino acid sequence identity to a light chain sequence provided by SEQ ID NO: 23. In some instances, the disease or condition is an autoimmune disease, heteroimmune disease or condition, inflammatory disease, pathogenic infection, thromboembolic disorder, respiratory disease or condition, metabolic disease, central nervous system (CNS) disorder, bone disease or cancer. In other instances, the disease or condition is a blood disorder. In some instances, the disease or condition is obesity, diabetes, osteoporosis, anemia, or pain.

In an embodiment is provided a method of preventing or treating a disease or condition in a subject in need thereof comprising administering to the subject a composition comprising: an immunoglobulin construct comprising a heavy chain polypeptide comprising a polypeptide sequence encoded by a DNA sequence that is substantially similar to a sequence selected from SEQ ID NOS: 2-22; and a light chain polypeptide comprising a polypeptide sequence encoded by a DNA sequence that is substantially similar to a sequence of SEQ ID NO: 1. The heavy chain nucleotide sequence may share 50%, 60%, 70%, 80%, 85%, 90%, 95%, 97%, 99%, or more homology to a heavy chain sequence provided by any one of SEQ ID NOS: 2-22. The light chain nucleotide sequence may share 50%, 60%, 70%, 80%, 85%, 90%, 95%, 97%, 99%, or more homology to a light chain sequence provided by SEQ ID NO: 1. In some instances, the disease or condition is an autoimmune disease, heteroimmune disease or condition, inflammatory disease, pathogenic infection, thromboembolic disorder, respiratory disease or condition, metabolic disease, central nervous system (CNS) disorder, bone disease or cancer. In other instances, the disease or condition is a blood disorder. In some instances, the disease or condition is obesity, diabetes, osteoporosis, anemia, or pain.

Disclosed herein in some embodiments is a method of preventing or treating an autoimmune disease in a subject in need thereof comprising administering a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is Moka1, VM-24 or beta-interferon or derivative or variant thereof. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalin antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The one or more cysteine motifs may be based on or derived from SEQ ID NOS: 45-156. The one or more cysteine motifs may be based on or derived from SEQ ID NOS: 45-99. The one or more cysteine motifs may be based on or derived from SEQ ID NOS: 100-135. The one or more cysteine motifs may be based on or derived from SEQ ID NOS: 136-156. The ultralong CDR3 comprises at least a portion of a knob domain. The knob domain may comprise a conserved motif within the knob domain of an ultralong CDR3. For example, the knob domain may comprise a cysteine motif disclosed herein. The Moka1, VM-24, beta-interferon, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. The conserved motif within the stalk domain of the ultralong CDR3 may comprise a polypeptide sequence based on or derived from SEQ ID NOS: 157-307 and SEQ ID NOS: 333-336. The conserved motif with the stalk domain of the ultralong CDR3 may comprise a polypeptide sequence based on or derived from SEQ ID NOS: 157-224. The conserved motif with the stalk domain of the ultralong CDR3 may comprise a polypeptide sequence based on or derived from SEQ ID NOS: 157-161. The conserved motif with the stalk domain of the ultralong CDR3 may comprise a polypeptide sequence based on or derived from SEQ ID NOS: 223-234. The conserved motif with the stalk domain of the ultralong CDR3 may comprise a polypeptide sequence based on or derived from SEQ ID NOS: 235-239. The conserved motif with the stalk domain of the ultralong CDR3 may comprise a polypeptide sequence based on or derived from SEQ ID NOS: 296-299. The conserved motif with the stalk domain of the ultralong CDR3 may comprise a polypeptide sequence based on or derived from SEQ ID NOS: 300-303. The conserved motif with the stalk domain of the ultralong CDR3 may comprise a polypeptide sequence based on or derived from a first sequence selected from the derived from SEQ ID NOS: 300-303. The conserved motif with the stalk domain of the ultralong CDR3 may comprise a polypeptide sequence base-group comprising SEQ ID NOS: 157-234 and a second sequence selected from the group comprising SEQ ID NOS: 235-307 and SEQ ID NOS: 333-336. The antibodies disclosed herein may comprise 2 or more, 3 or more, 4 or more, 5 or more sequences based on or derived from SEQ ID NOS: 157-307 and SEQ ID NOS: 333-336. The conserved motif with the stalk domain of the ultralong CDR3 may comprise a polypeptide sequence based on or derived from SEQ ID NOS: 304-307 AND SEQ ID NOS: 333-336. For example, the stalk domain may comprise a T(S/T)VHQ motif (SEQ ID NO: 508). The Moka1, VM-24, beta-interferon, or a derivative or variant thereof can be attached to the stalk domain. In some instances, the antibody, antibody fragment or immunoglobulin construct further comprises a linker. The linker can attach Moka1, VM-24, beta-interferon, or a derivative or variant thereof to the immunoglobulin domain or fragment thereof. In other instances, the linker attaches Moka1, VM-24, beta-interferon, or a derivative or variant thereof to the knob domain or stalk domain. In some instances, the autoimmune disease is a T-cell mediated autoimmune disease. T-cell mediated autoimmune diseases include, but are not limited to, multiple sclerosis, type-1 diabetes, and psoriasis. In other instances, the autoimmune disease lupus, Sjogren's syndrome, scleroderma, rheumatoid arthritis, dermatomyositis, Hasmimoto's thyroiditis, Addison's disease, celiac disease, Crohn's disease, pernicious anemia, pemphigus vulgaris, vitiligo, autoimmune hemolytic anemia, idiopathic thrombocytopenic purpura, myasthenia gravis, Ord's thyroiditis, Graves' disease, Guillain-Barre syndrome, acute disseminated encephalomyelitis, opsoclonus-myoclonus syndrome, ankylosing spondylitisis, antiphospholipid antibody syndrome, aplastic anemia, autoimmune hepatitis, Goodpasture's syndrome, Reiter's syndrome, Takayasu's arteritis, temporal arteritis, Wegener's granulomatosis, alopecia universalis, Behcet's disease, chronic fatigue, dysautonomia, endometriosis, interstitial cystitis, neuromyotonia, scleroderma, and vulvodynia. Lupus can include, but is not limited to, acute cutaneous lupus erythematosus, subacute cutaneous lupus erythematosus, chronic cutaneous lupus erythematosus, discoid lupus erythematosus, childhood discoid lupus erythematosus, generalized discoid lupus erythematosus, localized discoid lupus erythematosus, chilblain lupus erythematosus (hutchinson), lupus erythematosus-lichen planus overlap syndrome, lupus erythematosus panniculitis (lupus erythematosus profundus), tumid lupus erythematosus, verrucous lupus erythematosus (hypertrophic lupus erythematosus), complement deficiency syndromes, drug-induced lupus erythematosus, neonatal lupus erythematosus, and systemic lupus erythematosus.

Further disclosed herein is a method of preventing or treating a disease or condition which would benefit from the modulation of a potassium voltage-gated channel in a subject in need thereof comprising administering a composition comprising one or more antibodies comprising an ultralong CDR3 as disclosed herein to said subject. The composition can further comprise a pharmaceutically acceptable carrier. In some instances, the potassium voltage-gated channel is a KCNA3 or $K_v1.3$ channel. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is Moka1, VM-24, or derivative or variant thereof. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalin antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The one or more cysteine motifs may be based on or derived from SEQ ID NOS: 45-156. The one or more cysteine motifs may be based on or derived from SEQ ID NOS: 45-99. The one or more cysteine motifs may be based on or derived from SEQ ID NOS: 100-135. The one or more cysteine motifs may be based on or derived from SEQ ID NOS: 136-156. The ultralong CDR3 comprises at least a portion of a knob domain. The knob domain may comprise a conserved motif within the knob domain of an ultralong CDR3. For example, the knob domain may comprise a cysteine motif disclosed herein. The Moka1, VM-24, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. The conserved motif within the stalk domain of the ultralong CDR3 may comprise a polypeptide sequence based on or derived from SEQ ID NOS: 157-307 and SEQ ID NOS: 333-336. The conserved motif with the stalk domain of the ultralong CDR3 may comprise a polypeptide sequence based on or derived from SEQ ID NOS: 157-224. The conserved motif with the stalk domain of the ultralong CDR3 may comprise a polypeptide sequence based on or derived from SEQ ID NOS: 157-161. The conserved motif with the stalk domain of the ultralong CDR3 may comprise a polypeptide sequence based on or derived from SEQ ID NOS: 223-234. The conserved motif with the stalk domain of the ultralong CDR3 may comprise a polypeptide sequence based on or derived from SEQ ID NOS: 235-239. The conserved motif with the stalk domain of the ultralong CDR3 may comprise a polypeptide sequence based on or derived from SEQ ID NOS: 296-299. The conserved motif with the stalk domain of the ultralong CDR3 may comprise a polypeptide sequence based on or derived from SEQ ID NOS: 300-303. The conserved motif with the stalk domain of the ultralong CDR3 may comprise a polypeptide sequence based on or derived from a first sequence selected from the derived from SEQ ID NOS: 300-303. The conserved motif with the stalk domain of the ultralong CDR3 may comprise a polypeptide sequence basegroup comprising SEQ ID NOS: 157-234 and a second sequence selected from the group comprising SEQ ID NOS: 235-307 and SEQ ID NOS: 333-336. The antibodies disclosed herein may comprise 2 or more, 3 or more, 4 or more, 5 or more sequences based on or derived from SEQ ID NOS: 157-307 and SEQ ID NOS: 333-336. The conserved motif with the stalk domain of the ultralong CDR3 may comprise a polypeptide sequence based on or derived from SEQ ID NOS: 304-307 AND SEQ ID NOS: 333-336. For example, the stalk domain may comprise a T(S/T)VHQ motif (SEQ ID NO: 508). The Moka1, VM-24, or a derivative or variant thereof can be attached to the stalk domain. In some instances, the antibody, antibody fragment or immunoglobulin construct further comprises a linker. The linker can attach Moka1, VM-24, or a derivative or variant thereof to the immunoglobulin domain or fragment thereof. In other instances, the linker attaches Moka1, VM-24, beta-interferon, or a derivative or variant thereof to the knob domain or stalk domain. In some instances, the disease or condition is an autoimmune disease. The autoimmune disease can be a T-cell mediated autoimmune disease. In some instances, modulating a potassium voltage-gated channel comprises inhibiting or blocking a potassium voltage-gated channel. In some instances, the disease or condition is episodic ataxia, seizure, or neuromyotonia.

Provided herein is a method of preventing or treating a metabolic disease or condition in a subject in need thereof comprising administering a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is GLP-1, Exendin-4, FGF21, or derivative or variant thereof. The GLP-1 may be a human GLP-1. In some instances, the FGF21 is a human FGF21. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalin antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The one or more cysteine motifs may be based on or derived from SEQ ID NOS: 45-156. The one or more cysteine motifs may be based on or derived from SEQ ID NOS: 45-99. The one or more cysteine motifs may be based on or derived from SEQ ID NOS: 100-135. The one or more cysteine motifs may be based on or derived from SEQ ID NOS: 136-156. The ultralong CDR3 comprises at least a portion of a knob domain. The knob domain may comprise a conserved motif within the knob domain of an ultralong CDR3. For example, the knob domain may comprise a cysteine motif disclosed herein. The GLP-1, Exendin-4, FGF21, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. The conserved motif within the stalk domain of the ultralong CDR3 may comprise a polypeptide sequence based on or derived from SEQ ID NOS: 157-307 and SEQ ID NOS: 333-336. The conserved motif with the stalk domain of the ultralong CDR3 may comprise a polypeptide sequence based on or derived from SEQ ID NOS: 157-224. The conserved motif with the stalk domain of the ultralong CDR3 may comprise a polypeptide sequence based on or derived from SEQ ID NOS: 157-161. The conserved motif with the stalk domain of the ultralong CDR3 may comprise a polypeptide sequence based on or derived from SEQ ID NOS: 223-234. The conserved motif with the stalk domain of the ultralong CDR3 may comprise a polypeptide sequence based on or derived from SEQ ID NOS: 235-239. The conserved motif with the stalk domain of the ultralong CDR3 may comprise a polypeptide sequence based on or derived from SEQ ID NOS: 296-299. The conserved motif with the stalk domain of the ultralong CDR3 may comprise a polypeptide sequence based on or derived from SEQ ID NOS: 300-303. The conserved motif with the stalk domain of the ultralong CDR3 may comprise a polypeptide sequence based on or derived from a first sequence selected from the derived from SEQ ID NOS: 300-303. The conserved motif with the stalk domain of the ultralong CDR3 may comprise a polypeptide sequence basegroup comprising SEQ ID NOS: 157-234 and a second sequence selected from the group comprising SEQ ID NOS: 235-307 and SEQ ID NOS: 333-336. The antibodies disclosed herein may comprise 2 or more, 3 or more, 4 or more, 5 or more sequences based on or derived from SEQ ID NOS: 157-307 and SEQ ID NOS: 333-336. The conserved motif with the stalk domain of the ultralong CDR3 may comprise a polypeptide sequence based on or derived from SEQ ID NOS: 304-307 AND SEQ ID NOS: 333-336. For example, the stalk domain may comprise a T(S/T)VHQ motif (SEQ ID NO: 508). The GLP-1, Exendin-4, FGF21, or a derivative or variant thereof can be attached to the stalk domain. In some instances, the antibody, antibody fragment or immunoglobulin construct further comprises a linker. The linker can attach GLP-1, Exendin-4, FGF21, or a derivative or variant thereof to the immunoglobulin domain or fragment thereof. In other instances, the linker attaches GLP-1, Exendin-4, FGF21, or a derivative or variant thereof to the knob domain or stalk domain. Metabolic diseases and/or conditions can include disorders of carbohydrate metabolism, amino acid metabolism, organic acid metabolism (organic acidurias), fatty acid oxidation and mitochondrial metabolism, porphyrin metabolism, purine or pyrimidine metabolism, steroid metabolism, mitochondrial function, peroxisomal function, urea cycle disorder, urea cycle defects or lysosomal storage disorders. In some instances, the metabolic disease or condition is diabetes. In other instances, the metabolic diese or condition is glycogen storage disease, phenylketonuria, maple syrup urine disease, glutaric acidemia type 1, Carbamoyl phosphate synthetase I deficiency, alcaptonuria, Medium-chain acyl-coenzyme A dehydrogenase deficiency (MCADD), acute intermittent porphyria, Lesch-Nyhan syndrome, lipoid congenital adrenal hyperplasia, congenital adrenal hyperplasia, Kearns-Sayre syndrome, Zellweger syndrome, Gaucher's disease, or Niemann Pick disease.

Provided herein is a method of preventing or treating a central nervous system (CNS) disorder in a subject in need thereof comprising administering a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is GLP-1, Exendin-4, or derivative or variant thereof. The GLP-1 may be a human GLP-1. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The one or more cysteine motifs may be based on or derived from SEQ ID NOS: 45-156. The one or more cysteine motifs may be based on or derived from SEQ ID NOS: 45-99. The one or more cysteine motifs may be based on or derived from SEQ ID NOS: 100-135. The one or more cysteine motifs may be based on or derived from SEQ ID NOS: 136-156. The ultralong CDR3 comprises at least a portion of a knob domain. The knob domain may comprise a conserved motif within the knob domain of an ultralong CDR3. For example, the knob domain may comprise a cysteine motif disclosed herein. The GLP-1, Exendin-4, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. The conserved motif within the stalk domain of the ultralong CDR3 may comprise a polypeptide sequence based on or derived from SEQ ID NOS: 157-307 and SEQ ID NOS: 333-336. The conserved motif with the stalk domain of the ultralong CDR3 may comprise a polypeptide sequence based on or derived from SEQ ID NOS: 157-224. The conserved motif with the stalk domain of the ultralong CDR3 may comprise a polypeptide sequence based on or derived from SEQ ID NOS: 157-161. The conserved motif with the stalk domain of the ultralong CDR3 may comprise a polypeptide sequence based on or derived from SEQ ID NOS: 223-234. The conserved motif with the stalk domain of the ultralong CDR3 may comprise a polypeptide sequence based on or derived from SEQ ID NOS: 235-239. The conserved motif with the stalk domain of the ultralong CDR3 may comprise a polypeptide sequence based on or derived from SEQ ID NOS: 296-299. The conserved motif with the stalk domain of the ultralong CDR3 may comprise a polypeptide sequence based on or derived from SEQ ID NOS: 300-303. The conserved motif with the stalk domain of the ultralong CDR3 may comprise a polypeptide sequence based on or derived from a first sequence selected from the derived from SEQ ID NOS: 300-303. The conserved motif with the stalk domain of the ultralong CDR3 may comprise a polypeptide sequence basegroup comprising SEQ ID NOS: 157-234 and a second sequence selected from the group comprising SEQ ID NOS: 235-307 and SEQ ID NOS: 333-336. The antibodies disclosed herein may comprise 2 or more, 3 or more, 4 or more, 5 or more sequences based on or derived from SEQ ID NOS: 157-307 and SEQ ID NOS: 333-336. The conserved motif with the stalk domain of the ultralong CDR3 may comprise a polypeptide sequence based on or derived from SEQ ID NOS: 304-307 AND SEQ ID NOS: 333-336. For example, the stalk domain may comprise a T(S/T)VHQ motif (SEQ ID NO: 508). The GLP-1, Exendin-4, or a derivative or variant thereof can be attached to the stalk domain. In some instances, the antibody, antibody fragment or immunoglobulin construct further comprises a linker. The linker can attach GLP-1, Exendin-4, or a derivative or variant thereof to the immunoglobulin domain or fragment thereof. In other instances, the linker attaches GLP-1, Exendin-4, or a derivative or variant thereof to the knob domain or stalk domain.

In some instances, the CNS disorder is Alzheimer's disease (AD). Additional CNS disorders include, but are not limited to, encephalitis, meningitis, tropical spastic paraparesis, arachnoid cysts, Huntington's disease, locked-in syndrome, Parkinson's disease, Tourette's, and multiple sclerosis.

Provided herein is a method of preventing or treating a disease or condition which benefits from a GLP-1R and/or glucagon receptor (GCGR) agonist in a subject in need thereof comprising administering a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is GLP-1, Exendin-4, or derivative or variant thereof. The GLP-1 may be a human GLP-1. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalin antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The one or more cysteine motifs may be based on or derived from SEQ ID NOS: 45-156. The one or more cysteine motifs may be based on or derived from SEQ ID NOS: 45-99. The one or more cysteine motifs may be based on or derived from SEQ ID NOS: 100-135. The one or more cysteine motifs may be based on or derived from SEQ ID NOS: 136-156. The ultralong CDR3 comprises at least a portion of a knob domain. The knob domain may comprise a conserved motif within the knob domain of an ultralong CDR3. For example, the knob domain may comprise a cysteine motif disclosed herein. The GLP-1, Exendin-4, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. The conserved motif within the stalk domain of the ultralong CDR3 may comprise a polypeptide sequence based on or derived from SEQ ID NOS: 157-307 and SEQ ID NOS: 333-336. The conserved motif with the stalk domain of the ultralong CDR3 may comprise a polypeptide sequence based on or derived from SEQ ID NOS: 157-224. The conserved motif with the stalk domain of the ultralong CDR3 may comprise a polypeptide sequence based on or derived from SEQ ID NOS: 157-161. The conserved motif with the stalk domain of the ultralong CDR3 may comprise a polypeptide sequence based on or derived from SEQ ID NOS: 223-234. The conserved motif with the stalk domain of the ultralong CDR3 may comprise a polypeptide sequence based on or derived from SEQ ID NOS: 235-239. The conserved motif with the stalk domain of the ultralong CDR3 may comprise a polypeptide sequence based on or derived from SEQ ID NOS: 296-299. The conserved motif with the stalk domain of the ultralong CDR3 may comprise a polypeptide sequence based on or derived from SEQ ID NOS: 300-303. The conserved motif with the stalk domain of the ultralong CDR3 may comprise a polypeptide sequence based on or derived from a first sequence selected from the derived from SEQ ID NOS: 300-303. The conserved motif with the stalk domain of the ultralong CDR3 may comprise a polypeptide sequence basegroup comprising SEQ ID NOS: 157-234 and a second sequence selected from the group comprising SEQ ID NOS: 235-307 and SEQ ID NOS: 333-336. The antibodies disclosed herein may comprise 2 or more, 3 or more, 4 or more, 5 or more sequences based on or derived from SEQ ID NOS: 157-307 and SEQ ID NOS: 333-336. The conserved motif with the stalk domain of the ultralong CDR3 may comprise a polypeptide sequence based on or derived from SEQ ID NOS: 304-307 AND SEQ ID NOS: 333-336. For example, the stalk domain may comprise a T(S/T)VHQ motif (SEQ ID NO: 508). The GLP-1, Exendin-4, or a derivative or variant thereof can be attached to the stalk domain. In some instances, the antibody, antibody fragment or immunoglobulin construct further comprises a linker. The linker can attach GLP-1, Exendin-4, or a derivative or variant thereof to the immunoglobulin domain or fragment thereof. In other instances, the linker attaches GLP-1, Exendin-4, or a derivative or variant thereof to the knob domain or stalk domain. The disease or condition can be a metabolic disease or disorder. In some instances, the disease or condition is diabetes. In other instances, the disease or condition is obesity. Additional diseases and/or conditions which benefit from a GLP-1R and/or GCGR agonist include, but are not limited to, dyslipidemia, cardiovascular and fatty liver diseases.

Provided herein is a method of preventing or treating a blood disorder in a subject in need thereof comprising administering a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is erythropoietin, GMCSF, or derivative or variant thereof. The erythropoietin may be a human erythropoietin. The GMCSF may be a human GMCSF. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalin antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The one or more cysteine motifs may be based on or derived from SEQ ID NOS: 45-156. The one or more cysteine motifs may be based on or derived from SEQ ID NOS: 45-99. The one or more cysteine motifs may be based on or derived from SEQ ID NOS: 100-135. The one or more cysteine motifs may be based on or derived from SEQ ID NOS: 136-156. The ultralong CDR3 comprises at least a portion of a knob domain. The knob domain may comprise a conserved motif within the knob domain of an ultralong CDR3. For example, the knob domain may comprise a cysteine motif disclosed herein. The erythropoietin, GMCSF, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. The conserved motif within the stalk domain of the ultralong CDR3 may comprise a polypeptide sequence based on or derived from SEQ ID NOS: 157-307 and SEQ ID NOS: 333-336. The conserved motif with the stalk domain of the ultralong CDR3 may comprise a polypeptide sequence based on or derived from SEQ ID NOS: 157-224. The conserved motif with the stalk domain of the ultralong CDR3 may comprise a polypeptide sequence based on or derived from SEQ ID NOS: 157-161. The conserved motif with the stalk domain of the ultralong CDR3 may comprise a polypeptide sequence based on or derived from SEQ ID NOS: 223-234. The conserved motif with the stalk domain of the ultralong CDR3 may comprise a polypeptide sequence based on or derived from SEQ ID NOS: 235-239. The conserved motif with the stalk domain of the ultralong CDR3 may comprise a polypeptide sequence based on or derived from SEQ ID NOS: 296-299. The conserved motif with the stalk domain of the ultralong CDR3 may comprise a polypeptide sequence based on or derived from SEQ ID NOS: 300-303. The conserved motif with the stalk domain of the ultralong CDR3 may comprise a polypeptide sequence based on or derived from a first sequence selected from the derived from SEQ ID NOS: 300-303. The conserved motif with the stalk domain of the ultralong CDR3 may comprise a polypeptide sequence basegroup comprising SEQ ID NOS: 157-234 and a second sequence selected from the group comprising SEQ ID NOS: 235-307 and SEQ ID NOS: 333-336. The antibodies disclosed herein may comprise 2 or more, 3 or more, 4 or more, 5 or more sequences based on or derived from SEQ ID NOS: 157-307 and SEQ ID NOS: 333-336. The conserved motif with the stalk domain of the ultralong CDR3 may comprise a polypeptide sequence based on or derived from SEQ ID NOS: 304-307 AND SEQ ID NOS: 333-336. For example, the stalk domain may comprise a T(S/T)VHQ motif (SEQ ID NO: 508). The erythropoietin, GMCSF, or a derivative or variant thereof can be attached to the stalk domain. In some instances, the antibody, antibody fragment or immunoglobulin construct further comprises a linker. The linker can attach erythropoietin, GMCSF, or a derivative or variant thereof to the immunoglobulin domain or fragment thereof. In other instances, the linker attaches erythropoietin, GMCSF, or a derivative or variant thereof to the knob domain or stalk domain. In some instances, the blood disorder is anemia. Examples of anemia include, but are not limited to, herditary xerocytosis, congenital dyserythropoietic anemia, Rh null disease, infectious mononucleosis related anemia, drugs-related anemia, aplastic anemia, microcytic anemia, macrocytic anemia, normocytic anemia, hemolytic anemia, poikilocytic anemia, spherocytic anemia, drepanocytic anemia, normochromic anemia, hyperchromic anemia, hypochromic anemia, macrocytic-normochromic anemia, microcytic-hypochromic anemia, normocytic-normochromic anemia, iron-deficiency anemia, pernicious anemia, folate-deficiency anemia, thalassemia, sideroblastic anemia, posthemorrhagic anemia, sickle cell anemia, chronic anemia, achrestic anemia, autoimmune haemolytic anemia, Cooley's anemia, drug-induced immune haemolytic anemia, erythroblastic anemia, hypoplastic anemia, Diamond-Blackfan anemia, Pearson's anemia, transient anemia, Fanconi's anemia, Lederer's anemia, myelpathic anemia, nutritional anemia, spur-cell anemia, Von Jaksh's anemia, sideroblatic anemia, sideropenic anemia, alpha thalassemia, beta thalassemia, hemoglobin h disease, acute acquired hemolytic anemia, warm autoimmune hemolytic anemia, cold autoimmune hemolytic anemia, primary cold autoimmune hemolytic anemia, secondary cold autoimmune hemolytic anemia, secondary autoimmune hemolytic anemia, primary autoimmune hemolytic anemia, x-linked sideroblastic anemia, pyridoxine-responsive anemia, nutritional sideroblastic anemia, pyridoxine deficiency-induced sideroblastic anemia, copper deficiency-induced sideroblastic anemia, cycloserine-induced sideroblastic anemia, chloramphenicol-induced sideroblastic anemia, ethanol-induced sideroblastic anemia, isoniazid-induced sideroblastic anemia, drug-induced sideroblastic anemia, toxin-induced sideroblastic anemia, microcytic hyperchromic anemia, macrocytic hyperchromic anemia, megalocytic-normochromic anemia, drug-induced immune hemolytic anemia, non-hereditary spherocytic anemia, inherited spherocytic anemia, and congenital spherocytic anemia. In other instances, the blood disorder is malaria. Alternatively, the blood disorder is lymphoma, leukemia, multiple myeloma, or myelodysplastic syndrome. In some instances, the blood disorder is neutropenia, Shwachmann-Daimond syndrome, Kostmann syndrome, chronic granulomatous disease, leukocyte adhesion deficiency, meyloperoxidase deficiency, or Chediak Higashi syndrome.

Provided herein is a method of preventing or treating a disease or disorder which benefitis from stimulating or increasing white blood cell production in a subject in need thereof comprising administering a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is GMCSF, or derivative or variant thereof. The GMCSF may be a human GMCSF. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalin antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The one or more cysteine motifs may be based on or derived from SEQ ID NOS: 45-156. The one or more cysteine motifs may be based on or derived from SEQ ID NOS: 45-99. The one or more cysteine motifs may be based on or derived from SEQ ID NOS: 100-135. The one or more cysteine motifs may be based on or derived from SEQ ID NOS: 136-156. The ultralong CDR3 comprises at least a portion of a knob domain. The knob domain may comprise a conserved motif within the knob domain of an ultralong CDR3. For example, the knob domain may comprise a cysteine motif disclosed herein. The GMCSF, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. The conserved motif within the stalk domain of the ultralong CDR3 may comprise a polypeptide sequence based on or derived from SEQ ID NOS: 157-307 and SEQ ID NOS: 333-336. The conserved motif with the stalk domain of the ultralong CDR3 may comprise a polypeptide sequence based on or derived from SEQ ID NOS: 157-224. The conserved motif with the stalk domain of the ultralong CDR3 may comprise a polypeptide sequence based on or derived from SEQ ID NOS: 157-161. The conserved motif with the stalk domain of the ultralong CDR3 may comprise a polypeptide sequence based on or derived from SEQ ID NOS: 223-234. The conserved motif with the stalk domain of the ultralong CDR3 may comprise a polypeptide sequence based on or derived from SEQ ID NOS: 235-239. The conserved motif with the stalk domain of the ultralong CDR3 may comprise a polypeptide sequence based on or derived from SEQ ID NOS: 296-299. The conserved motif with the stalk domain of the ultralong CDR3 may comprise a polypeptide sequence based on or derived from SEQ ID NOS: 300-303. The conserved motif with the stalk domain of the ultralong CDR3 may comprise a polypeptide sequence based on or derived from a first sequence selected from the derived from SEQ ID NOS: 300-303. The conserved motif with the stalk domain of the ultralong CDR3 may comprise a polypeptide sequence basegroup comprising SEQ ID NOS: 157-234 and a second sequence selected from the group comprising SEQ ID NOS: 235-307 and SEQ ID NOS: 333-336. The antibodies disclosed herein may comprise 2 or more, 3 or more, 4 or more, 5 or more sequences based on or derived from SEQ ID NOS: 157-307 and SEQ ID NOS: 333-336. The conserved motif with the stalk domain of the ultralong CDR3 may comprise a polypeptide sequence based on or derived from SEQ ID NOS: 304-307 AND SEQ ID NOS: 333-336. For example, the stalk domain may comprise a T(S/T)VHQ motif (SEQ ID NO: 508). The GMCSF, or a derivative or variant thereof can be attached to the stalk domain. In some instances, the antibody, antibody fragment or immunoglobulin construct further comprises a linker. The linker can attach GMCSF, or a derivative or variant thereof to the immunoglobulin domain or fragment thereof. In other instances, the linker attaches GMCSF, or a derivative or variant thereof to the knob domain or stalk domain. In some instances, the disese or disorder is neutropenia, Shwachmann-Daimond syndrome, Kostmann syndrome, chronic granulomatous disease, leukocyte adhesion deficiency, meyloperoxidase deficiency, or Chediak Higashi syndrome.

Provided herein is a method of preventing or treating a disease or disorder which benefits from stimulating or increasing red blood cell production in a subject in need thereof comprising administering a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is erythropoietin, or derivative or variant thereof. The erythropoietin may be a human erythropoietin. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalin antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The one or more cysteine motifs may be based on or derived from SEQ ID NOS: 45-156. The one or more cysteine motifs may be based on or derived from SEQ ID NOS: 45-99. The one or more cysteine motifs may be based on or derived from SEQ ID NOS: 100-135. The one or more cysteine motifs may be based on or derived from SEQ ID NOS: 136-156. The ultralong CDR3 comprises at least a portion of a knob domain. The knob domain may comprise a conserved motif within the knob domain of an ultralong CDR3. For example, the knob domain may comprise a cysteine motif disclosed herein. The erythropoietin, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. The conserved motif within the stalk domain of the ultralong CDR3 may comprise a polypeptide sequence based on or derived from SEQ ID NOS: 157-307 and SEQ ID NOS: 333-336. The conserved motif with the stalk domain of the ultralong CDR3 may comprise a polypeptide sequence based on or derived from SEQ ID NOS: 157-224. The conserved motif with the stalk domain of the ultralong CDR3 may comprise a polypeptide sequence based on or derived from SEQ ID NOS: 157-161. The conserved motif with the stalk domain of the ultralong CDR3 may comprise a polypeptide sequence based on or derived from SEQ ID NOS: 223-234. The conserved motif with the stalk domain of the ultralong CDR3 may comprise a polypeptide sequence based on or derived from SEQ ID NOS: 235-239. The conserved motif with the stalk domain of the ultralong CDR3 may comprise a polypeptide sequence based on or derived from SEQ ID NOS: 296-299. The conserved motif with the stalk domain of the ultralong CDR3 may comprise a polypeptide sequence based on or derived from SEQ ID NOS: 300-303. The conserved motif with the stalk domain of the ultralong CDR3 may comprise a polypeptide sequence based on or derived from a first sequence selected from the derived from SEQ ID NOS: 300-303. The conserved motif with the stalk domain of the ultralong CDR3 may comprise a polypeptide sequence basegroup comprising SEQ ID NOS: 157-234 and a second sequence selected from the group comprising SEQ ID NOS: 235-307 and SEQ ID NOS: 333-336. The antibodies disclosed herein may comprise 2 or more, 3 or more, 4 or more, 5 or more sequences based on or derived from SEQ ID NOS: 157-307 and SEQ ID NOS: 333-336. The conserved motif with the stalk domain of the ultralong CDR3 may comprise a polypeptide sequence based on or derived from SEQ ID NOS: 304-307 AND SEQ ID NOS: 333-336. For example, the stalk domain may comprise a T(S/T)VHQ motif (SEQ ID NO: 508). The erythropoietin, or a derivative or variant thereof can be attached to the stalk domain. In some instances, the antibody, antibody fragment or immunoglobulin construct further comprises a linker. The linker can attach erythropoietin, or a derivative or variant thereof to the immunoglobulin domain or fragment thereof. In other instances, the linker attaches erythropoietin, or a derivative or variant thereof to the knob domain or stalk domain. In some instances, the disease or disorder is anemia.

Provided herein is a method of preventing or treating obesity in a subject in need thereof comprising administering a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is GLP-1, Exendin-4, FGF21, or derivative or variant thereof. The GLP-1 may be a human GLP-1. In some instances, the FGF21 is a human FGF21. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalin antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The one or more cysteine motifs may be based on or derived from SEQ ID NOS: 45-156. The one or more cysteine motifs may be based on or derived from SEQ ID NOS: 45-99. The one or more cysteine motifs may be based on or derived from SEQ ID NOS: 100-135. The one or more cysteine motifs may be based on or derived from SEQ ID NOS: 136-156. The ultralong CDR3 comprises at least a portion of a knob domain. The knob domain may comprise a conserved motif within the knob domain of an ultralong CDR3. For example, the knob domain may comprise a cysteine motif disclosed herein. The GLP-1, Exendin-4, FGF21, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. The conserved motif within the stalk domain of the ultralong CDR3 may comprise a polypeptide sequence based on or derived from SEQ ID NOS: 157-307 and SEQ ID NOS: 333-336. The conserved motif with the stalk domain of the ultralong CDR3 may comprise a polypeptide sequence based on or derived from SEQ ID NOS: 157-224. The conserved motif with the stalk domain of the ultralong CDR3 may comprise a polypeptide sequence based on or derived from SEQ ID NOS: 157-161. The conserved motif with the stalk domain of the ultralong CDR3 may comprise a polypeptide sequence based on or derived from SEQ ID NOS: 223-234. The conserved motif with the stalk domain of the ultralong CDR3 may comprise a polypeptide sequence based on or derived from SEQ ID NOS: 235-239. The conserved motif with the stalk domain of the ultralong CDR3 may comprise a polypeptide sequence based on or derived from SEQ ID NOS: 296-299. The conserved motif with the stalk domain of the ultralong CDR3 may comprise a polypeptide sequence based on or derived from SEQ ID NOS: 300-303. The conserved motif with the stalk domain of the ultralong CDR3 may comprise a polypeptide sequence based on or derived from a first sequence selected from the derived from SEQ ID NOS: 300-303. The conserved motif with the stalk domain of the ultralong CDR3 may comprise a polypeptide sequence basegroup comprising SEQ ID NOS: 157-234 and a second sequence selected from the group comprising SEQ ID NOS: 235-307 and SEQ ID NOS: 333-336. The antibodies disclosed herein may comprise 2 or more, 3 or more, 4 or more, 5 or more sequences based on or derived from SEQ ID NOS: 157-307 and SEQ ID NOS: 333-336. The conserved motif with the stalk domain of the ultralong CDR3 may comprise a polypeptide sequence based on or derived from SEQ ID NOS: 304-307 AND SEQ ID NOS: 333-336. For example, the stalk domain may comprise a T(S/T)VHQ motif (SEQ ID NO: 508). The GLP-1, Exendin-4, FGF21, or a derivative or variant thereof can be attached to the stalk domain. In some instances, the antibody, antibody fragment or immunoglobulin construct further comprises a linker. The linker can attach GLP-1, Exendin-4, FGF21, or a derivative or variant thereof to the immunoglobulin domain or fragment thereof. In other instances, the linker attaches GLP-1, Exendin-4, FGF21, or a derivative or variant thereof to the knob domain or stalk domain.

Provided herein is a method of preventing or treating a pain in a subject in need thereof comprising administering a composition comprising one or more antibodies, antibody fragments, or immunoglobulin constructs described herein to said subject. In some instances, the subject is a mammal. In certain instances, the mammal is a human. Alternatively, the mammal is a bovine. In some instances, the one or more antibodies, antibody fragments, or immunoglobulin constructs comprise a protoxin2 or a derivative or variant thereof. Alternatively, or additionally, the one or more antibodies, antibody fragments, or immunoglobulin constructs comprise at least a portion of a CDR3H. The portion of the CDR3H can be a stalk domain or knob domain in the CDR3H. In some instances, the one or more antibodies, antibody fragments, or immunoglobulin constructs further comprise a linker. The linker can attach the protoxin2 or a derivative or variant thereof to the portion of the CDR3H.

Provided herein is a method of preventing or treating a disease or condition which benefits from modulating a sodium ion channel in a subject in need thereof comprising administering a composition comprising one or more antibodies, antibody fragments, or immunoglobulin constructs described herein to said subject. In some instances, the subject is a mammal. In certain instances, the mammal is a human. Alternatively, the mammal is a bovine. In some instances, the one or more antibodies, antibody fragments, or immunoglobulin constructs comprise a protoxin2 or a derivative or variant thereof. Alternatively, or additionally, the one or more antibodies, antibody fragments, or immunoglobulin constructs comprise at least a portion of a CDR3H. The portion of the CDR3H can be a stalk domain or knob domain in the CDR3H. In some instances, the one or more antibodies, antibody fragments, or immunoglobulin constructs further comprise a linker. The linker can attach the protoxin2 or a derivative or variant thereof to the portion of the CDR3H. In some instances, the sodium ion channel is a Na, channel. In some instances, the Na, channel is a $Na_v1.7$ channel. In some instances, modulating a sodium ion channel comprises inhibiting or blocking a sodium ion channel. In some instances, the disease or condition is Dravet Syndrome, generalized epilepsy with febrile seizures plus (GEFS+), paramyotonia congenital or erythromelalgia. In some instances, the disease or condition is pain.

Provided herein is a method of preventing or treating a disease or condition which benefits from modulating an acid sensing ion channel (ASIC) in a subject in need thereof comprising administering a composition comprising one or more antibodies, antibody fragments, or immunoglobulin constructs described herein to said subject. In some instances, the subject is a mammal. In certain instances, the mammal is a human. Alternatively, the mammal is a bovine. In some instances, the one or more antibodies, antibody fragments, or immunoglobulin constructs comprise a protoxin2 or a derivative or variant thereof. Alternatively, or additionally, the one or more antibodies, antibody fragments, or immunoglobulin constructs comprise at least a portion of a CDR3H. The portion of the CDR3H can be a stalk domain or knob domain in the CDR3H. In some instances, the one or more antibodies, antibody fragments, or immunoglobulin constructs further comprise a linker. The linker can attach the protoxin2 or a derivative or variant thereof to the portion of the CDR3H. In some instances, modulating an ASIC comprises inhibiting or blocking the ASIC. In some instances, the disease or condition is a central nervous system disorder. In other instances, the disease or condition is pain.

Provided herein is a method of preventing or treating a pathogenic infection in a subject in need thereof comprising administering a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is beta-interferon, or derivative or variant thereof. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalin antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The one or more cysteine motifs may be based on or derived from SEQ ID NOS: 45-156. The one or more cysteine motifs may be based on or derived from SEQ ID NOS: 45-99. The one or more cysteine motifs may be based on or derived from SEQ ID NOS: 100-135. The one or more cysteine motifs may be based on or derived from SEQ ID NOS: 136-156. The ultralong CDR3 comprises at least a portion of a knob domain. The knob domain may comprise a conserved motif within the knob domain of an ultralong CDR3. For example, the knob domain may comprise a cysteine motif disclosed herein. The beta-interferon, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. The conserved motif within the stalk domain of the ultralong CDR3 may comprise a polypeptide sequence based on or derived from SEQ ID NOS: 157-307 and SEQ ID NOS: 333-336. The conserved motif with the stalk domain of the ultralong CDR3 may comprise a polypeptide sequence based on or derived from SEQ ID NOS: 157-224. The conserved motif with the stalk domain of the ultralong CDR3 may comprise a polypeptide sequence based on or derived from SEQ ID NOS: 157-161. The conserved motif with the stalk domain of the ultralong CDR3 may comprise a polypeptide sequence based on or derived from SEQ ID NOS: 223-234. The conserved motif with the stalk domain of the ultralong CDR3 may comprise a polypeptide sequence based on or derived from SEQ ID NOS: 235-239. The conserved motif with the stalk domain of the ultralong CDR3 may comprise a polypeptide sequence based on or derived from SEQ ID NOS: 296-299. The conserved motif with the stalk domain of the ultralong CDR3 may comprise a polypeptide sequence based on or derived from SEQ ID NOS: 300-303. The conserved motif with the stalk domain of the ultralong CDR3 may comprise a polypeptide sequence based on or derived from a first sequence selected from the derived from SEQ ID NOS: 300-303. The conserved motif with the stalk domain of the ultralong CDR3 may comprise a polypeptide sequence basegroup comprising SEQ ID NOS: 157-234 and a second sequence selected from the group comprising SEQ ID NOS: 235-307 and SEQ ID NOS: 333-336. The antibodies disclosed herein may comprise 2 or more, 3 or more, 4 or more, 5 or more sequences based on or derived from SEQ ID NOS: 157-307 and SEQ ID NOS: 333-336. The conserved motif with the stalk domain of the ultralong CDR3 may comprise a polypeptide sequence based on or derived from SEQ ID NOS: 304-307 AND SEQ ID NOS: 333-336. For example, the stalk domain may comprise a T(S/T)VHQ motif (SEQ ID NO: 508). The beta-interferon, or a derivative or variant thereof can be attached to the stalk domain. In some instances, the antibody, antibody fragment or immunoglobulin construct further comprises a linker. The linker can attach beta-interferon, or a derivative or variant thereof to the immunoglobulin domain or fragment thereof. In other instances, the linker attaches beta-interferon, or a derivative or variant thereof to the knob domain or stalk domain. In some instances, the pathogenic infection is a viral, bacterial, fungal, or parasitic infection. In some instances, the viral infection is a herpes virus.

Provided herein is a method of preventing or treating a cancer in a subject in need thereof comprising administering a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is beta-interferon, or derivative or variant thereof. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalin antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The one or more cysteine motifs may be based on or derived from SEQ ID NOS: 45-156. The one or more cysteine motifs may be based on or derived from SEQ ID NOS: 45-99. The one or more cysteine motifs may be based on or derived from SEQ ID NOS: 100-135. The one or more cysteine motifs may be based on or derived from SEQ ID NOS: 136-156. The ultralong CDR3 comprises at least a portion of a knob domain. The knob domain may comprise a conserved motif within the knob domain of an ultralong CDR3. For example, the knob domain may comprise a cysteine motif disclosed herein. The beta-interferon, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. The conserved motif within the stalk domain of the ultralong CDR3 may comprise a polypeptide sequence based on or derived from SEQ ID NOS: 157-307 and SEQ ID NOS: 333-336. The conserved motif with the stalk domain of the ultralong CDR3 may comprise a polypeptide sequence based on or derived from SEQ ID NOS: 157-224. The conserved motif with the stalk domain of the ultralong CDR3 may comprise a polypeptide sequence based on or derived from SEQ ID NOS: 157-161. The conserved motif with the stalk domain of the ultralong CDR3 may comprise a polypeptide sequence based on or derived from SEQ ID NOS: 223-234. The conserved motif with the stalk domain of the ultralong CDR3 may comprise a polypeptide sequence based on or derived from SEQ ID NOS: 235-239. The conserved motif with the stalk domain of the ultralong CDR3 may comprise a polypeptide sequence based on or derived from SEQ ID NOS: 296-299. The conserved motif with the stalk domain of the ultralong CDR3 may comprise a polypeptide sequence based on or derived from SEQ ID NOS: 300-303. The conserved motif with the stalk domain of the ultralong CDR3 may comprise a polypeptide sequence based on or derived from a first sequence selected from the derived from SEQ ID NOS: 300-303. The conserved motif with the stalk domain of the ultralong CDR3 may comprise a polypeptide sequence basegroup comprising SEQ ID NOS: 157-234 and a second sequence selected from the group comprising SEQ ID NOS: 235-307 and SEQ ID NOS: 333-336. The antibodies disclosed herein may comprise 2 or more, 3 or more, 4 or more, 5 or more sequences based on or derived from SEQ ID NOS: 157-307 and SEQ ID NOS: 333-336. The conserved motif with the stalk domain of the ultralong CDR3 may comprise a polypeptide sequence based on or derived from SEQ ID NOS: 304-307 AND SEQ ID NOS: 333-336. For example, the stalk domain may comprise a T(S/T)VHQ motif (SEQ ID NO: 508). The beta-interferon, or a derivative or variant thereof can be attached to the stalk domain. In some instances, the antibody, antibody fragment or immunoglobulin construct further comprises a linker. The linker can attach beta-interferon, or a derivative or variant thereof to the immunoglobulin domain or fragment thereof. In other instances, the linker attaches beta-interferon, or a derivative or variant thereof to the knob domain or stalk domain. In some instances, the cancer is a hematological malignancy. The hematological malignancy can be a leukemia or lymphoma. In some instances, the hematological malignancy is a B-cell lymphoma, T-cell lymphoma, follicular lymphoma, marginal zone lymphoma, hairy cell leukemia, chronic myeloid leukemia, mantle cell lymphoma, nodular lymphoma, Burkitt's lymphoma, cutaneous T-cell lymphoma, chronic lymphocytic leukemia, or small lymphocytic leukemia.

Provided herein is a method of preventing or treating a disease in a mammal in need thereof comprising administering a pharmaceutical composition described herein to said mammal. In some embodiments, the disease is an infectious disease. In certain embodiments, the infectious disease is mastitis. In some embodiments, the infectious disease is a respiratory disease. In certain embodiments, the respiratory disease is bovine respiratory disease of shipping fever. In certain embodiments, the mammal in need is a dairy animal selected from a list comprising cow, camel, donkey, goat, horse, reindeer, sheep, water buffalo, moose and yak. In some embodiments, the mammal in need is bovine.

Provided is a method of preventing or treating mastitis in a dairy animal, comprising providing to said dairy animal an effective amount of a composition comprising: an immunoglobulin construct comprising a heavy chain polypeptide comprising a sequence selected from SEQ ID NO: 25 and SEQ ID NO: 26; and a light chain polypeptide comprising the sequence of SEQ ID NO: 23. In an embodiment is provided a method of preventing or treating mastitis in a dairy animal, comprising providing to said dairy animal an effective amount of a composition comprising: an immunoglobulin construct comprising a heavy chain polypeptide comprising a polypeptide sequence encoded by the DNA selected from SEQ ID NO: 4 and SEQ ID NO: 5; and a light chain polypeptide comprising a polypeptide sequence encoded by the DNA of SEQ ID NO: 1. In some embodimetns, the dairy animal is a cow or a water buffalo. Provided are methods of treatment, inhibition and prevention by administration to a subject of an effective amount of an antibody or pharmaceutical composition described herein. The antibody may be substantially purified (e.g., substantially free from substances that limit its effect or produce undesired side-effects). The subject can be an animal, including but not limited to animals such as cows, pigs, sheep, goats, rabbits, horses, chickens, cats, dogs, mice, etc. The subject can be a mammal. In some instances, the subject is a human. Alternatively, the subject is a bovine.

Various delivery systems are known and can be used to administer an antibody formulation described herein, e.g., encapsulation in liposomes, microparticles, microcapsules, recombinant cells capable of expressing the compound, receptor-mediated endocytosis (see, e.g., Wu and Wu, J. Biol. Chem. 262:4429-4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, in certain embodiments, it is desirable to introduce the heteromultimer compositions described herein into the central nervous system by any suitable route, including intraventricular and intrathecal injection; intraventricular injection may be facilitated by an intraventricular catheter, for example, attached to a reservoir, such as an Ommaya reservoir.

In a specific embodiment, it is desirable to administer the antibody, or compositions described herein locally to the area in need of treatment; this may be achieved by, for example, and not by way of limitation, local infusion, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the antibody or pharmaceutical composition is delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the heteromultimers or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, e.g., the brain, thus requiring only a fraction of the systemic dose (see, e.g., Goodson, in Medical Applications of Controlled Release, supra, vol. 2, pp. 115-138 (1984)). Other controlled release systems are discussed in the review by Langer (Science 249:1527-1533 (1990)).

In a specific embodiment comprising a nucleic acid encoding a antibody decribed herein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864-1868 (1991)), etc. Alternatively, a nucleic acid can be introduced intracellularly and incorporated within host cell DNA for expression, by homologous recombination.

In some embodiments are crystals based on or derived from the antibodies disclosed herein. The crystals may have a space group P212121. In some instances, the crystal has the unit cell dimensions of "a" between about 40 to 80 angstroms, between 45 to about 75 angstroms, or between about 50 to about 75 angstroms; "b" between about 40 to 140 angstroms, between about 50 to about 130 angstroms, between about 55 to about 130 angstroms; and "c" between 100 to about 350 angstroms, between 120 to about 340 angstroms, or between about 125 to about 330 angstroms. Alternatively, the crystal has the unit cell dimensions of "a" greater than or equal to 40, 50, 60, 70, or 80 angstroms; "b" greater than or equal to 40, 50, 60, 70, 80, 90, 100, 110, 120, or 130 angstroms; and "c" greater than or equal to 100, 110, 120, 130, 140, 150, 160, 170, 180, 190, 200, 210, 220, 230, 240, 250, 260, 270, 280, 290, 300, 310, 320, 330, or 340 angstroms.

The crystal may comprise a bovine antibody or portion thereof. The crystal may comprise a Fab fragment based on or derived from a bovine antibody. The crystal may comprise a non-antibody sequence, linker, cleave site, non-bovine sequence, or a combination thereof. The crystal may be an isolated crystal. The antibody may be based on or derived from the peptide sequence of any of SEQ ID NOS: 1-44. The antibody may comprise at least a portion of a heavy chain. The portion of the heavy chain may comprise the peptide sequence of any of SEQ ID NOS: 24-44. The antibody may comprise at least a portion of a heavy chain. The portion of the heavy chain may be encoded by a DNA sequence based on or derived from the DNA sequence of any of SEQ ID NOS: 2-22. The antibody may comprise at least a portion of a light chain. The portion of the light chain may comprise the peptide sequence of SEQ ID NO: 23. The antibody may comprise at least a portion of a heavy chain. The portion of the heavy chain may be encoded by a DNA sequence based on or derived from the DNA sequence of SEQ ID NOS: 1.

In some embodiments, is an isolated crystal comprising a bovine antibody Fab fragment comprising SEQ ID NO: 24 and SEQ ID NO: 23, wherein the crystal has a space group $P2_12_12_1$ and unit cell dimensions of a=71.4 angstroms, b=127.6 angstroms and c=127.9 angstroms.

In some embodiments, is an isolated crystal comprising a bovine antibody Fab fragment comprising SEQ ID NO: 340 and SEQ ID NO: 341, wherein the crystal has a space group $P2_12_12_1$ and unit cell dimensions of a=54.6 angstroms, b=53.7 angstroms and c=330.5 angstroms.

Example 1

Purification and Crystallization of Antibodies Comprising an Ultralong CDR3

An antibody that comprises an ultralong CDR3 including, for example, an antibody generated by any of the examples described herein, may be purified and subsequently crystallized to determine the structure of the antibody.

A. Purification:

Genes encoding the heavy and light chain Fab regions of BLV1H12 and BLV5B8 were generated by gene synthesis (GenScript, Piscataway, N.J.). A DNA fragment derived from the promoter region of pFastBacDual (Invitrogen) was fused to the gp67 and the honey bee mellitin (HBM) signal peptides by overlap PCR, yielding a fragment with head-to-head p10 and polyhedrin promoters upstream of the HBM and gp67 signal peptides, respectively (i.e., HBM-p10-pPolyH-gp67). Bovine Fab heavy and light chain regions were fused to the promoter-signal peptide cassette by overlap PCR (heavy chain downstream of pPolyH-gp67 and light chain downstream of p10-HBM), and ligated into the SfiI sites of pDCE361, a derivative of pFastBacDual. Next, a His6-tag (SEQ ID NO: 511) was introduced at the C-terminus of the heavy chain to facilitate purification. The resulting baculovirus transfer vectors were used to generate recombinant bacmids using the Bac-to-Bac system (Invitrogen) and virus was rescued by transfecting purified bacmid DNA into Sf9 cells using Cellfectin II (Invitrogen). Both Fab proteins were produced by infecting suspension cultures of Sf9 cells with recombinant baculovirus at an MOI of 5-10 and incubating at 28° C. with shaking at 110 RPM. After 72 hours, the cultures were clarified by two rounds of centrifugation at 2000 g and 10,000 g at 4° C. The supernatant, containing secreted, soluble Fab were then concentrated and buffer exchanged into 1×PBS, pH 7.4. After metal affinity chromatography using Ni-NTA resin, Fabs were purified by protein G affinity chromatography (GE Healthcare), cation exchange chromatography (MonoS, GE healthcare), and gel filtration (Superdex200, GE Healthcare).

B. Crystallization and Structure Determination

Gel filtration fractions containing the bovine Fabs were concentrated to ~10 mg/mL in 10 mM Tris, pH 8.0 and 50 mM NaCl. Initial crystallization trials were set up using the automated Rigaku Crystalmation robotic system at the Joint Center for Structural Genomics. Several hits were obtained for BLV1H12 and BLV5B8, and crystals used for data collection were grown by the sitting drop vapor diffusion method with a reservoir solution (100 µL) containing 0.27 M potassium citrate and 22% PEG 3350 (BLV1H12) and 0.2 M di-sodium tartrate and 20% PEG 3350 (BLV5B8). Drops consisting of 100 nL protein+100 nL precipitant were set up at 20° C., and crystals appeared within 3-7 days. The resulting crystals were cryoprotected using well solution supplemented with 15% ethylene glycol then flash cooled and stored in liquid nitrogen until data collection.

Diffraction data were then collected on the GM/CA-CAT 23ID-D beamline at the Advanced Photon Source at Argonne National Laboratory (BLV1H12) and the 11-1 beamline at the Stanford Synchrotron Radiation Lightsource for BLV5B8. Both datasets were indexed in spacegroup P212121, integrated, scaled, and merged using HKL2000 (BLV5B8; HKL Research) or XPREP (BLV1H12; Bruker). The BLV1H12 structure was solved by molecular replacement to 1.88 Å resolution using Phaser (McCoy et al., 2007). Fab variable domains from 1BVK and constant domains from 2FB4 were used as search models and two complete BLV1H12 Fabs were found in the asymmetric unit. The BLV5B8 dataset was also solved by molecular replacement (to 2.20 Å), using the refined BLV1H12 coordinates as a model. Rigid body refinement, simulated annealing and restrained refinement (including TLS refinement, with one group for each Ig domain and one for each CDR H3) were carried out in Phenix (Adams et al. (2010) *Acta Crystallogr D Biol Crystallogr* 66:213-221). Riding hydrogens were used during refinement and are included in the final model.

Between rounds of refinement, the model was built and adjusted using Coot. Waters were built automatically using the "ordered solvent" modeling function in Phenix (Adams et al. (2010) *Acta Crystallogr D Biol Crystallogr* 66:213-221). Structures were validated using the JCSG QC Server (publicly available at http://smb.slac.stanford.edu/jcsg/QC/), which includes Molprobity (Chen et al. (2010) *Acta Crystallogr D Biol Crystallogr* 66:12-21) Table 1

TABLE 1

Data collection and refinement statistics

| Data collection | BLV1H12 Fab | BLV5B8 Fab |
|---|---|---|
| Beamline | APS 231D-D | SSRL 11-1 |
| Wavelength (Å) | 1.033 | 0.979 |
| Space group | P2₁2₁2₁ | P2₁2₁2₁ |
| Unit cell parameters (Å, °) | a = 71.4, b = 127.6, c = 127.9, α = β = γ = 90 | A = 54.6, b = 53.7, c = 330.5, α = β = γ = 90 |
| Resolution (Å) | 50-1.88 (1.92-1.88) | 50-2.20 (2.28-2.20) |
| Observations | 638,900 | 313,175 |
| Unique Reflections | 96,353 | 49,527 |
| Redundancy | 6.2 (4.9) | 6.3 (3.5) |
| Completeness (%) | 97.3 (98.2) | 96.7 (75.4) |

TABLE 1-continued

Data collection and refinement statistics

| Data collection | BLV1H12 Fab | BLV5B8 Fab |
|---|---|---|
| $<I/\sigma_I>^a$ | 14.7 (2.5) | 17.8 (2.3) |
| $R_{sym}{}^b$ | 0.09 (0.76) | 0.10 (0.45) |
| $Z_a{}^c$ | 2 | 2 |
| Refinement statistics | | |
| Resolution (Å) | 50-1.88 | 50-2.20 |
| Reflections (work) | 89,254 | 46,900 |
| Reflections (test) | 4,704 | 2,441 |
| $R_{cryst}(\%)^d/R_{free}(\%)^e$ | 20.8/23.9 | 2.07/24.8 |
| Average B (Å²) | 43.0 | 42.7 |
| Wilson B (Å²) | 32.5 | 32.0 |
| Protein atoms | 6,724 | 6,939 |
| Carbohydrate atoms | 0 | 0 |
| Waters | 501 | 474 |
| Other | 1 | 0 |
| RMSD from ideal geometry | | |
| Bond length (Å) | 0.014 | 0.003 |
| Bond angles (°) | 1.12 | 0.79 |
| Ramachandran statistics (%)$^f$ | | |
| Favored | 96.9 | 95.2 |
| Outliers | 0.1 | 0.5 |
| PDB Code $^g$ | wwww | Xxxx |

$^a$Numbers in parentheses refer to the highest resoution shell.
$^b R_{sym} = \Sigma_{hkl}\Sigma_i \mid I_{hkl, i} - <I_{hkl}> \mid / \Sigma_{hkl}\Sigma_i I_{hkl, i}$ and $R_{pim} = \Sigma_{hkl} (1/(n-1))^{1/2}\Sigma_i \mid I_{hkl, i} - <I_{hkl}> \mid / \Sigma_{hkl}\Sigma_i I_{hkl, i}$, where $I_{hkl, i}$ is the scaled intensity of the $i^{th}$ measurement of relection h, k, l, $<I_{hkl}>$ is the average intensity for that reflection, and n is the redundancy (Emsley et al. (2010) *Acta Crystallogr D Biol Crystallogr* 66: 486-501).
$^c Z_a$ is the number of Fabs per crystallographic asymmetric unit.
$^d R_{cryst} = \Sigma_{hkl} \mid F_o - F_c \mid / \Sigma_{hkl} \mid F_o \mid \times 100$
$^e R_{free}$ was calculated as for $R_{cryst}$, but on a test set comprising 5% of the data excluded from refinement.
$^f$Calculated using Molprobity (Chen et al. (2010) *Acta Crystallogr D Biol Crystallogr* 66: 12-21).
$^g$ Coordinates and structure factors will be deposited in the PDB prior to publication and be available immediately on publication.

Example 2

Generation of Libraries of Polynucleotides Encoding Antibodies Comprising an Ultralong CDR3

Bovine spleen and lymph nodes were obtained from Animal Technologies (Tyler, Tex.), or from Texas A&M University. Total RNA was isolated from bovine tissues from three different cows (MID1, MID10, and MID 11) using TRIzol reagent (Invitrogen, Carlsbad, Calif., USA) followed by on column digestion of DNA using the RNeasy Mini Kit (Qiagen, Valencia, Calif., USA). Next, RNA quantity and quality were assessed with Nanodrop (Thermal Scientific), Qubit RNA and Agilent 2100 Bioanalyzer (Agilent, Santa Clara, Calif., USA), following the manufacturer's protocols. Total RNA was used as a template for cDNA synthesis catalyzed by Superscript II (Invitrogen).

The library of amplified antibody variable regions were then subjected to deep sequencing. Briefly, bar-coded primers (Table 2) for each of the three cows (MID 1, MID10, and MID11) were used to amplify VH from bovine spleen cDNA.

TABLE 2

Bar-coded primers for deep sequencing

| Description | SEQ ID NO: | Isotype | Primers |
|---|---|---|---|
| MID1 FW | 308 | IgG | CCTATCCCCTGTGTGCCTTGGCAGTCTCAGAC GAGTGCGTTTGAGCGACAAGGCTGTAGGCTG |

TABLE 2-continued

Bar-coded primers for deep sequencing

| Description | SEQ ID NO: | Isotype | Primers |
|---|---|---|---|
| MID1 RV | 309 | IgG | CCATCTCATCCCTGCGTGTCTCCGACTCAGAC GAGTGCGTCTTTCGGGGCTGTGGTGGAGGC |
| MID10 FW | 310 | IgM | CCTATCCCCTGTGTGCCTTGGCAGTCTCAGTC TCTATGCGTTGAGCGACAAGGCTGTAGGCTG |
| MID10 RV | 311 | IgM | CCATCTCATCCCTGCGTGTCTCCGACTCAGTC TCTATGCGAGTGAAGACTCTCGGGTGTGATT CAC |
| MID11 FW | 312 | IgM | CCTATCCCCTGTGTGCCTTGGCAGTCTCAGTG ATACGTCTTTGAGCGACAAGGCTGTAGGCTG |
| MID11 RV | 313 | IgM | CCATCTCATCCCTGCGTGTCTCCGACTCAGTG ATACGTCTAGTGAAGACTCTCGGGTGTGATT CAC |
| Primer A | 314 | | TTGAGCGACAAGGCTGTAGGCTG |
| Primer B | 315 | | CTTTCGGGGCTGTGGTGG-AGGC |
| Primer C | 316 | | AGATCCAAGCTGTGACCGGC |

Next, the amplicons of VH were purified from 2% agarose gels and deep sequenced according to Roche 454 GS FLX instructions. Multiple alignments were performed with the MUSCLE algorithm (Edgar (2004) Nucleic Acids Research 32:1792-1797). MUSCLE was executed to generate multiple long CDR H3 nucleotide alignments with relatively high gap open (−20.0) and gap extend (−10.0) penalties due to the large amount of heterogeneity observed in the sequences. Local alignment was executed using the Smith-Waterman algorithm with the following settings, match score=2.0, mismatch penalty=−1.0, gap opening penalty=−2.0, and gap extension penalty=−0.5. CDR H3s were defined by the third residue following the conserved cysteine in framework 3 to the residue immediately preceding the conserved tryptophan in framework 4. $V_H$BUL was identified by BLAST searching the bovine genome (assembly Btau_4.6.1) with multiple ultralong VH sequences identified by deep sequencing. The deep sequencing identified a total of 11,728 ultralong CDR3 sequences with having a length between 44 and 69 amino acid residues. The results of the deep sequencing are summarized in Table 3 below.

TABLE 3

Summary of deep sequencing results from bovine spleen

| | Source (Bar code) | | |
|---|---|---|---|
| | Cow#1 (MID1) | Cow#1 (MID10) | Cow#2 (MID11) |
| Ig Class | IgG | IgM | IgM |
| CDR H3 length range | 44-66 | 44-68 | 44-69 |
| Number of unique cysteine patterns | 655 | 449 | 847 |
| Total number of unique long CDR H3 sequences | 5633 | 1639 | 4456 |

The results of the deep sequencing also revealed that ultralong CDR3 comprise a cysteine motif (e.g., a pattern of cysteine residues) that comprises between 3 and 12 cysteine residues. Representative examples of cysteine patterns are shown for the deep sequencing run for three different cows (MID1, MID10, and MID11) as well as their abundance in the run (Table 4-6; SEQ ID NOS: 45-156). The cysteines in the ultralong CDR3 regions are symbolized as "C". The amino acids between two cysteines are symbolized as "$X_n$". Additional exemplary cysteine motifs are shown in the ultralong CDR3 sequences set forth in Table 23.

TABLE 4

Cysteine patterns identified in ultralong CDR3s from MID1

| Cysteine pattern (MID1) | SEQ ID NO: | Abundance (%) |
|---|---|---|
| $CX_{10}CX_5CX_5CXCX_7C$ | 45 | 10.44% |
| $CX_{10}CX_6CX_5CXCX_{15}C$ | 46 | 8.11% |
| $CX_{11}CXCX_5C$ | 47 | 5.22% |
| $CX_{11}CX_5CX_5CXCX_7C$ | 48 | 2.56% |
| $CX_{10}CX_6CX_5CXCX_{13}C$ | 49 | 1.47% |
| $CX_{10}CX_5CXCX_4CX_8C$ | 50 | 1.19% |
| $CX_{10}CX_6CX_6CXCX_7C$ | 51 | 1.08% |
| $CX_{10}CX_4CX_7CXCX_8C$ | 52 | 1.05% |
| $CX_{10}CX_4CX_7CXCX_7C$ | 53 | 0.91% |
| $CX_{13}CX_8CX_8C$ | 54 | 0.91% |
| $CX_{10}CX_6CX_5CXCX_7C$ | 55 | 0.59% |
| $CX_{10}CX_5CX_5C$ | 56 | 0.57% |
| $CX_{10}CX_5CX_6CXCX_7C$ | 57 | 0.50% |
| $CX_{10}CX_6CX_5CX_7CX_9C$ | 58 | 0.43% |
| $CX_9CX_7CX_5CXCX_7C$ | 59 | 0.41% |
| $CX_{10}CX_6CX_5CXCX_9C$ | 60 | 0.36% |
| $CX_{10}CXCX_4CX_5CX_{11}C$ | 61 | 0.32% |
| $CX_7CX_3CX_6CX_5CXCX_5CX_{10}C$ | 62 | 0.32% |
| $CX_{10}CXCX_4CX_5CXCX_2CX_3C$ | 63 | 0.30% |
| $CX_{16}CX_5CXC$ | 64 | 0.23% |

TABLE 5

Cysteine patterns identified in ultralong CDR3s from MID10

| Cysteine pattern (MID10) | SEQ ID NO: | Abundance (%) |
|---|---|---|
| $CX_{10}CXCX_4CX_5CXCX_2CX_3C$ | 63 | 2.87% |
| $CX_{10}CX_5CX_5C$ | 56 | 0.73% |
| $CX_{10}CXCX_4CX_5CX_{11}C$ | 61 | 0.67% |
| $CX_6CX_4CXCX_4CX_5C$ | 65 | 0.61% |
| $CX_{11}CX_4CX_5CX_6CX_3C$ | 66 | 0.55% |
| $CX_8CX_2CX_6CX_5C$ | 67 | 0.43% |
| $CX_{10}CX_5CX_5CXCX_{10}C$ | 68 | 0.37% |
| $CX_{10}CXCX_6CX_4CXC$ | 69 | 0.31% |
| $CX_{10}CX_5CX_5CXCX_2C$ | 70 | 0.31% |
| $CX_{14}CX_2CX_3CXCXC$ | 71 | 0.31% |
| $CX_{15}CX_5CXC$ | 72 | 0.31% |
| $CX_4CX_6CX_9CX_2CX_{11}C$ | 73 | 0.31% |
| $CX_6CX_4CX_5CX_5CX_{12}C$ | 74 | 0.31% |
| $CX_7CX_3CXCXCX_4CX_5CX_9C$ | 75 | 0.31% |
| $CX_{10}CX_6CX_5C$ | 76 | 0.24% |
| $CX_7CX_3CX_5CX_5CX_9C$ | 77 | 0.24% |
| $CX_7CX_5CXCX_2C$ | 78 | 0.24% |
| $CX_{10}CXCX_6C$ | 79 | 0.18% |
| $CX_{10}CX_3CX_3CX_5CX_7CXCX_6C$ | 80 | 0.18% |
| $CX_{10}CX_4CX_5CX_{12}CX_2C$ | 81 | 0.18% |

TABLE 6

Cysteine patterns identified in ultralong CDR3s from MID11

| Cysteine pattern (MID11) | SEQ ID NO: | Abundance (%) |
|---|---|---|
| $CX_{12}CX_4CX_5CXCXCX_9CX_3C$ | 82 | 1.19% |
| $CX_{12}CX_4CX_5CX_{12}CX_2C$ | 83 | 0.96% |
| $CX_{10}CX_6CX_5CXCX_{11}C$ | 84 | 0.92% |
| $CX_{16}CX_5CXCXCX_{14}C$ | 85 | 0.70% |
| $CX_{10}CX_5CXCX_8CX_6C$ | 86 | 0.52% |
| $CX_{12}CX_4CX_5CX_8CX_2C$ | 87 | 0.49% |
| $CX_{12}CX_5CX_5CXCX_8C$ | 88 | 0.47% |
| $CX_{10}CX_6CX_5CXCX_4CXCX_9C$ | 89 | 0.45% |
| $CX_{11}CX_4CX_5CX_8CX_2C$ | 90 | 0.45% |

TABLE 6-continued

Cysteine patterns identified in ultralong CDR3s from MID11

| Cysteine pattern (MID11) | SEQ ID NO: | Abundance (%) |
|---|---|---|
| $CX_{10}CX_6CX_5CX_8CX_2C$ | 91 | 0.43% |
| $CX_{10}CX_6CX_5CXCX_8C$ | 92 | 0.36% |
| $CX_{10}CX_6CX_5C$ | 76 | 0.31% |
| $CX_{10}CX_6CX_5CXCX_3CX_8CX_2C$ | 93 | 0.29% |
| $CX_{10}CX_6CX_5CX_3CX_8C$ | 95 | 0.29% |
| $CX_{10}CX_6CX_5CXCX_2CX_6CX_5C$ | 94 | 0.25% |
| $CX_7CX_6CX_3CX_3CX_9C$ | 96 | 0.25% |
| $CX_9CX_8CX_5CX_6CX_5C$ | 97 | 0.22% |
| $CX_{10}CX_2CX_2CX_7CXCX_{11}CX_5C$ | 98 | 0.20% |
| $CX_{10}CX_6CX_5CXCX_{13}C$ | 49 | 0.20% |
| $CX_{10}CX_6CX_5CXCX_2CX_8CX_4C$ | 99 | 0.20% |

Bovine VH regions were amplified from cDNA prepared in example 9 using primers 5'-TTGAGCGACAAGGCTGTAGGCTG-3' (SEQ ID NO: 314) and 5'-CTTTCGGGGCTGTGGTGG-AGGC-3' (SEQ ID NO: 315) producing a library of antibody variable region cDNA biased for ultralong CDRs. Next, the mixture of VH regions was assembled by overlap PCR with bovine $C_H1$ and human IgG Fc. Briefly, EcoRI and NheI sites were incorporated for ligation into pFUSE expression vector, to afford a full-length heavy chain library ready for expression in mammalian cells. The ligation product was transformed into E. coli and 500 single E. coli transformants were picked. Each transformant was then grown overnight in a separate vessel and DNA from each colony was extracted using Qiagen minprep kits (Qiagen, Inc.) and sequenced by BATJ, Inc. (San Diego, Calif.) using the oligo 5'-AGATCCAAGCTGTGACCGGC-3' (SEQ ID NO: 316). Sequences were analyzed using VectorNTI (Invitrogen, Inc. Carlsbad, Calif.). Duplicative sequences, sequences with no insert, and sequences encoding a CDR shorter than 35 residues were excluded. 132 clones containing unique long CDR heavy chain sequences were selected. Each heavy chain in the 132 member library was then co-transfected in parallel with pFUSE expression vector encoding the invariant bovine light chain (SEQ ID NO: N) into 293T cells, to generate a small spatially addressed library (Mao et al. (2010) Nat Biotech 28:1195-1202). 130,000 293T cells per well were plated in 24 well plates and grown overnight in 500 ul DMEM media (Invitrogen) with 10% FBS (Invitrogen), and Penicillin/streptomycin/glutamine (Invitrogen) at 37° C. and 5% $CO_2$. 0.5 μg of Hc-encoding pFuse vector and 0.5 μg of Lc-encoding pFuse vector were added to 25 μl of optimem (Invitrogen). 1 μl of Lipofectamine 2000 or 293Fectin transfection reagent (Invitrogen) was added to 25 μl of optimem, and incubated 5 minutes. Next, the DNA-optimem mix and transfection reagent-optimem mix were combined and incubated 15 minutes, added to 293T cells, and allowed to incubate on cells 4-6 hours. Then media was then aspirated from wells and replaced with fresh media, and cells were allowed to grow and secrete IgG into the media for 4 days. Cell-culture supernatants containing IgG were harvested in 96 well format for further testing. The chimeric antibodies were quantified by sandwich ELISA detecting human $F_c$ and screened for binding to BVDV by ELISA.

Antibodies were then secreted into culture media and harvested in a 96 well format to generate a small spatially addressed library for further testing including, screening for binding to BVDV by ELISA. For example, an ELISA was conducted to screen the antibody library for binding to BVDV. Briefly, killed BVDV (0.2 μg) in 100 μL DPBS was coated on 96-well MaxiSorp ELISA plates (Nunc) for 1 hour at 37° C. Next, the plates were blocked with 200 μL 3% BSA solution in DPBST, Dulbecco's phosphate buffered saline, 0.25% Tween 20) for 1 hour at 37° C. Samples were then incubated with 3% BSA in DPBST for 1 hour at 37° C. Subsequently, wells were washed 5 times with 200 μL DPBST. Next, Goat Anti-Human IgG (Fc)—HRP conjugated antibody (KPL Inc.) was added at a 1:1,000 dilution in blocking solution and incubated for 1 hour at 37° C. Wells were then washed 10 times with 200 μL DPBST. A 100 μL working solution of QuantaBlu (Pierce) was added to each well and incubated for 5 minutes at room temperature before plates were read in a SpectraMax M5 plate reader at ex325/em420 nm. Several candidate binders were identified (FIG. 1B, left). Clone H12 has a 63-residue CDR3 with 6 cysteine residues and was able to strongly bind BVDV in a dose dependent fashion (FIG. 1B, right; and FIG. 1C).

Additionally, binding of the chimeric recombinant antibodies to BVDV antigens was evaluated by immunocytometric analysis of transfected human embryonic kidney (HEK) 293A cells (Invitrogen), as previously described (see, e.g., Njongmeta et al. (2012) Vaccine 30:1624-1635). Briefly, HEK 293A monolayers grown in 6-well tissue culture plates were transfected with 2 μg/well of plasmid (pCDNA3.3, Invitrogen) encoding BVDV antigens ($N^{pro}$, E2, or non-structural proteins NS2-3) using Lipofectamine 2000 reagent (Invitrogen), and incubated for 48 hr at 37° C. with 5% $CO_2$. The monolayers were fixed with ice-cold 100% methanol for 10 minutes, rinsed with PBS, and after blocking for 1 hr with PBS containing 5% fetal bovine serum (blocking buffer), the monolayers were incubated at room temperature for 1 hr with 10 μg/ml of a mouse anti-FLAG M2-alkaline phosphatase (AP)-conjugate (Sigma) in blocking buffer or 10 μg/ml of the chimeric recombinant antibodies (H12 or B8). Monolayers transfected with empty vector were similarly reacted to serve as negative controls and, following washes in blocking buffer, the monolayers probed with the chimeric recombinant antibodies were incubated with a 1/200 dilution of AP-conjugated goat anti-Human IgG (Fc specific) mAb (Sigma) in blocking buffer for 1 hr. Following washes in blocking buffer, the AP activity in all the wells was detected using Fast Red AS-MX substrate (Sigma). Stained cells were visualized and photographed using an IS70 inverted optical microscope (Olympus, Japan) equipped with a camera. H12 strongly binds HEK293A cells transfected with the NS2-3 non-structural proteins of BVDV but weakly bound to untransfected cells while B8 had weak binding to both HEK293A cells transfected with the NS2-3 non-structural proteins of BVDV and untransfected cells.

Example 3

Generation and Testing of Libraries of Antibodies Comprising an Ultralong CDR3

Figure 1B:
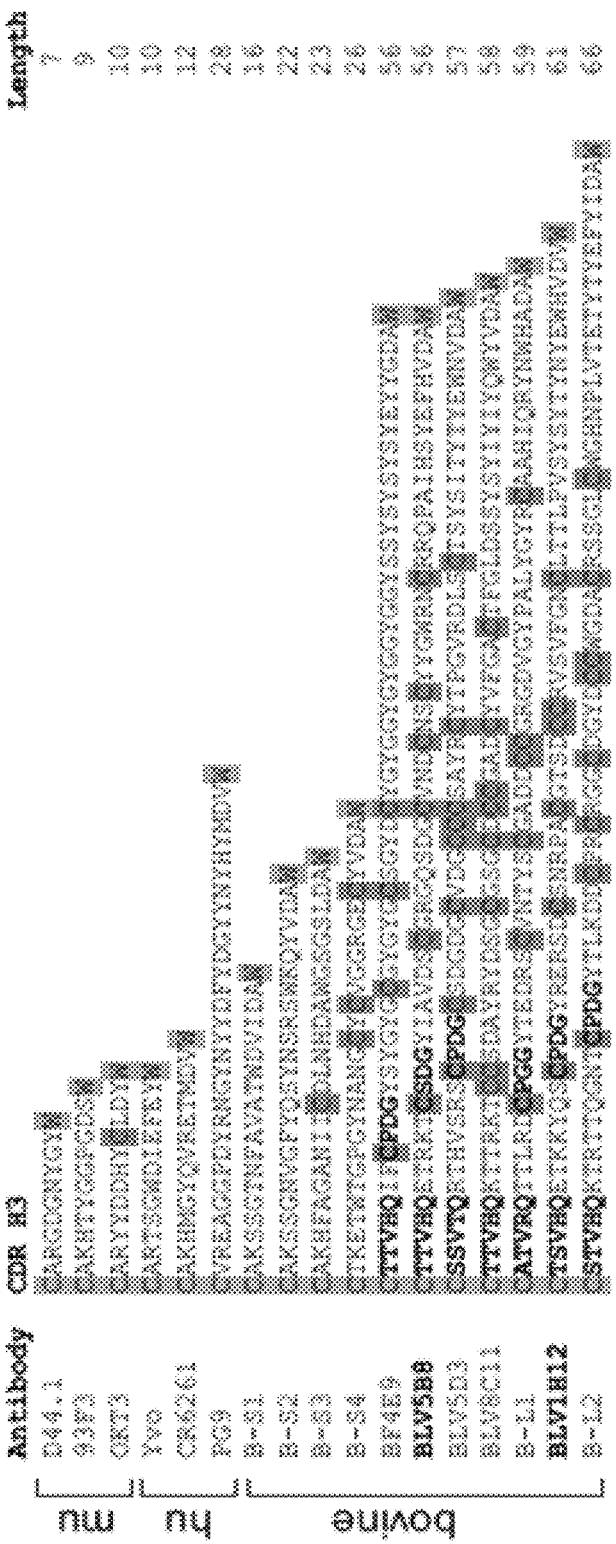
Figure 1C:
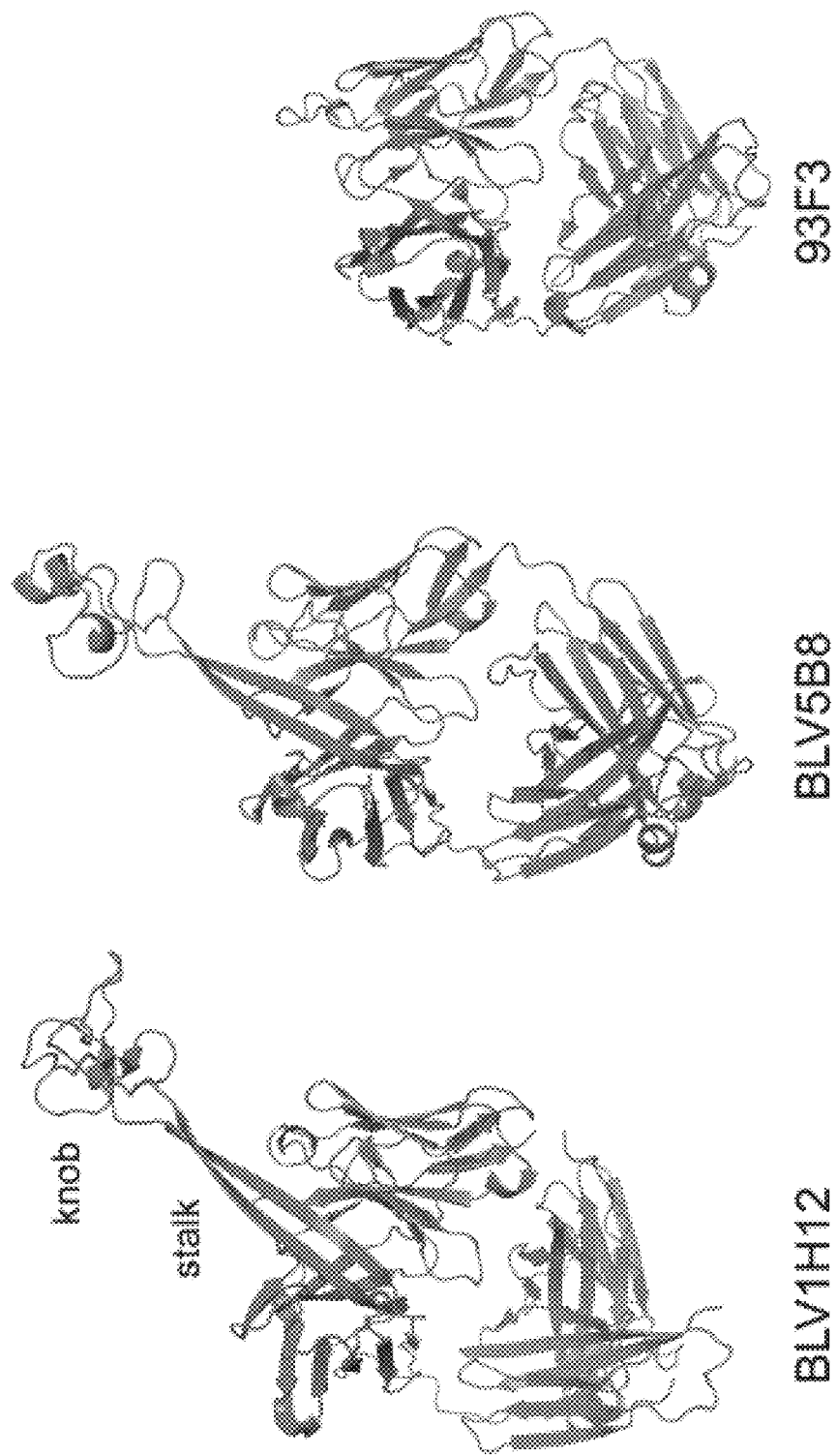
Figure 2B:
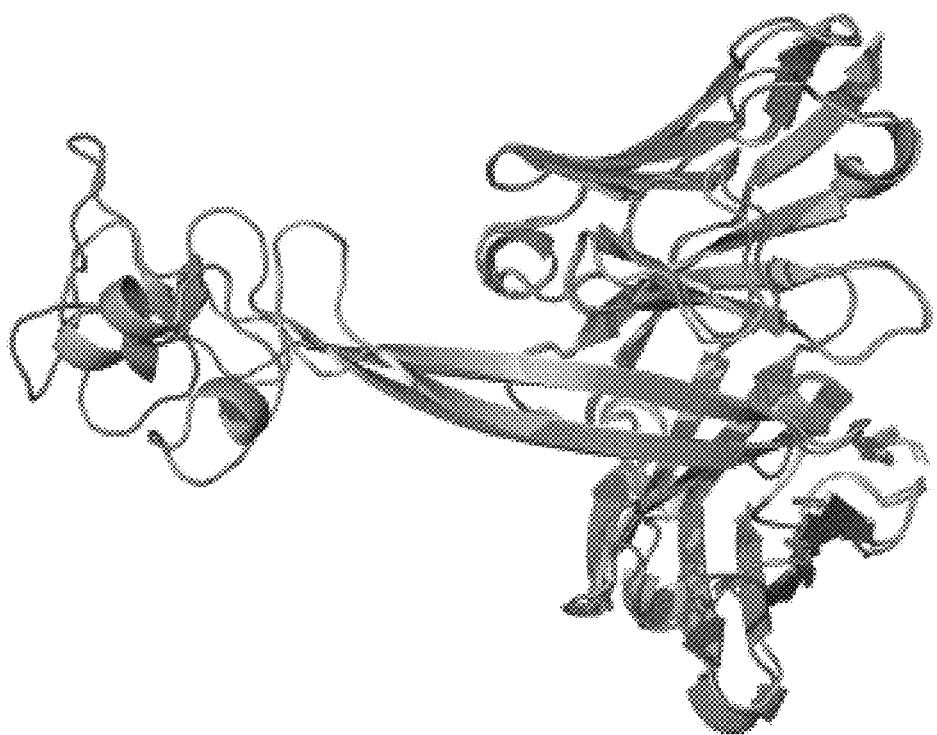
Figure 3B:
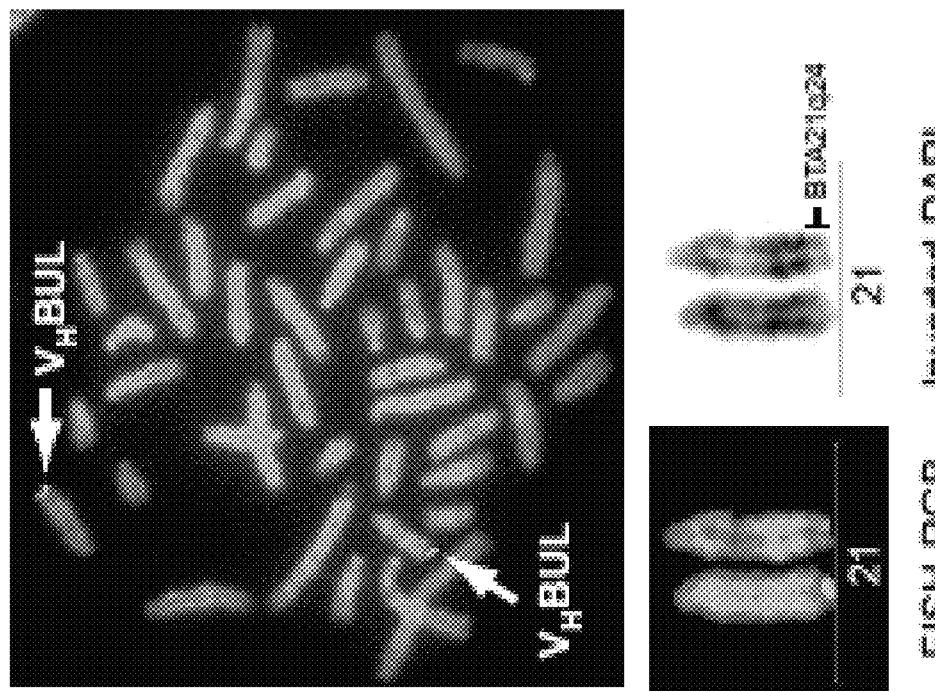
Figure 3C:
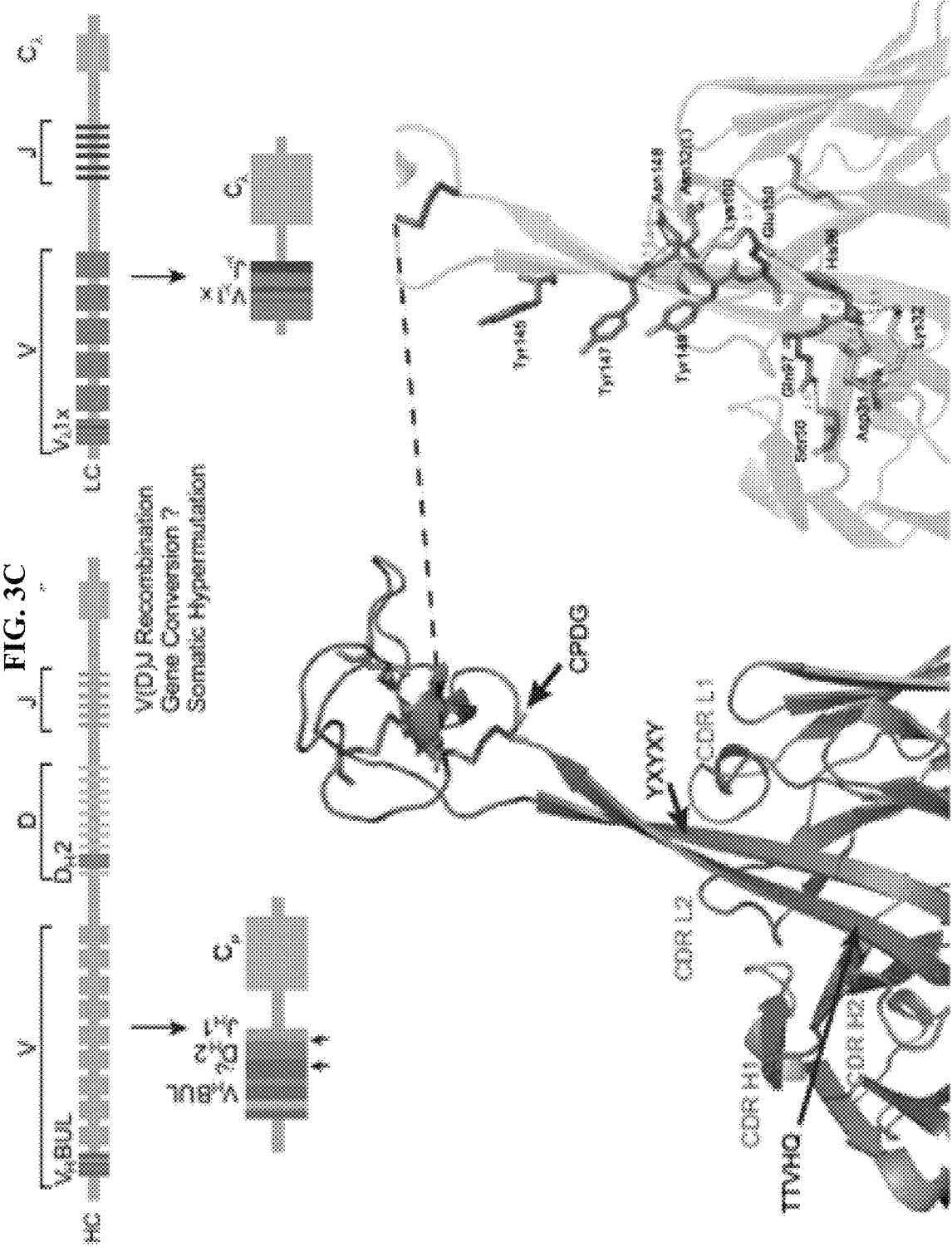
Figure 4A:
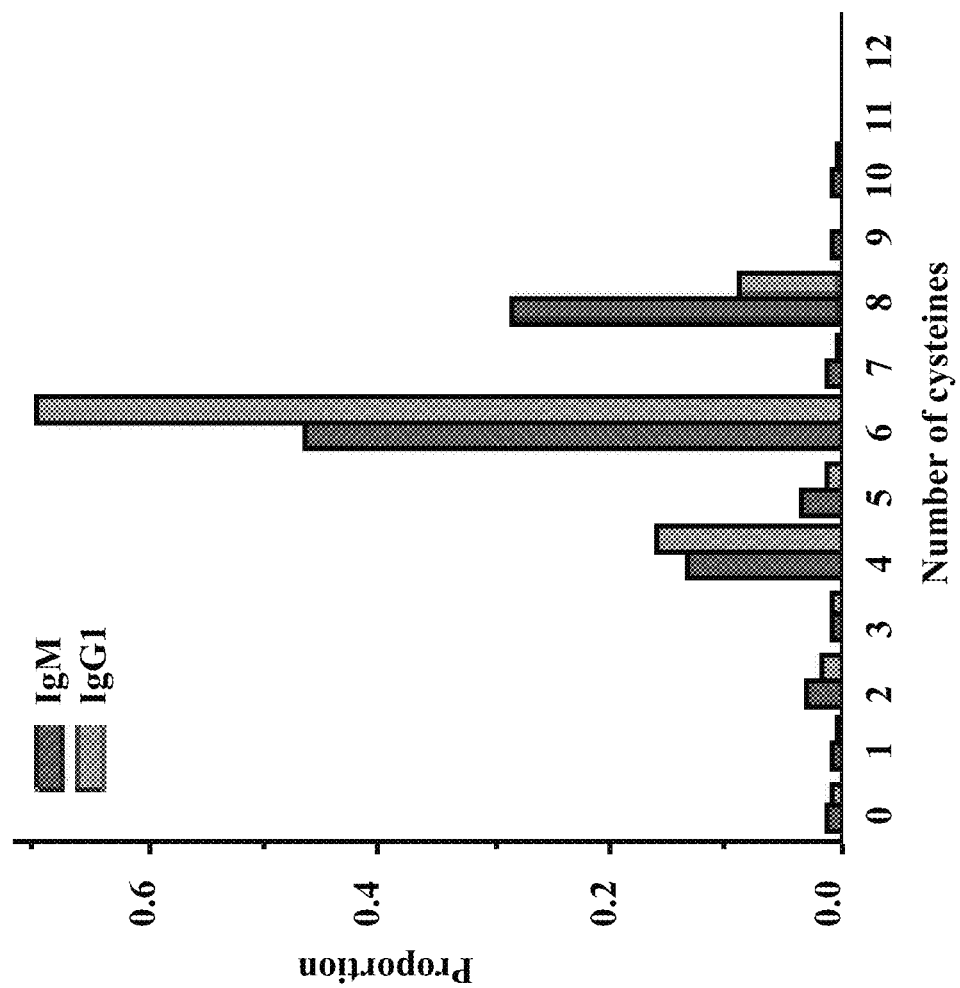
FIGS. 4A-4C depict deep sequence diversity of bovine ultralong VH CDR H3s.
Figure 4B:
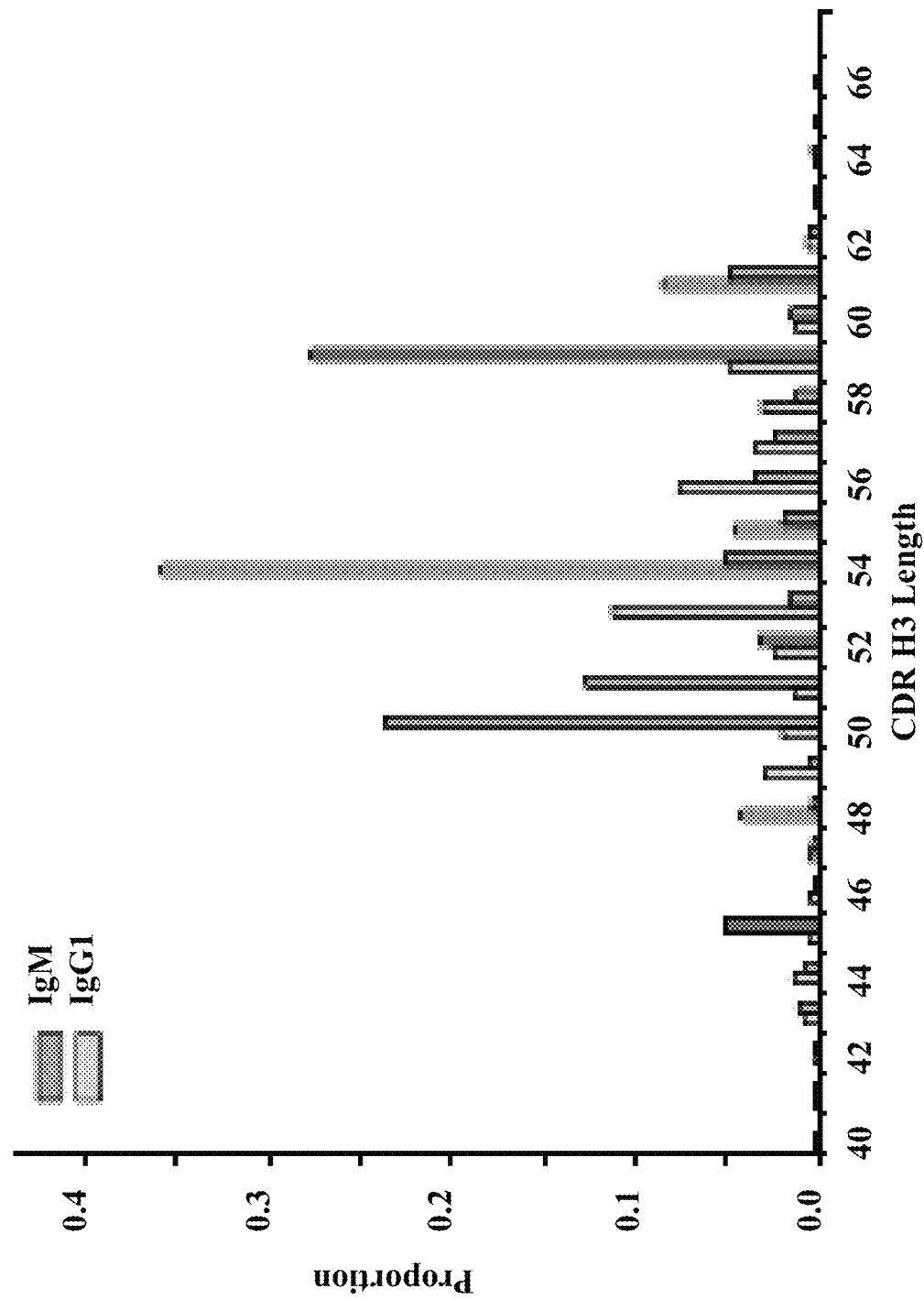
Figure 4C:
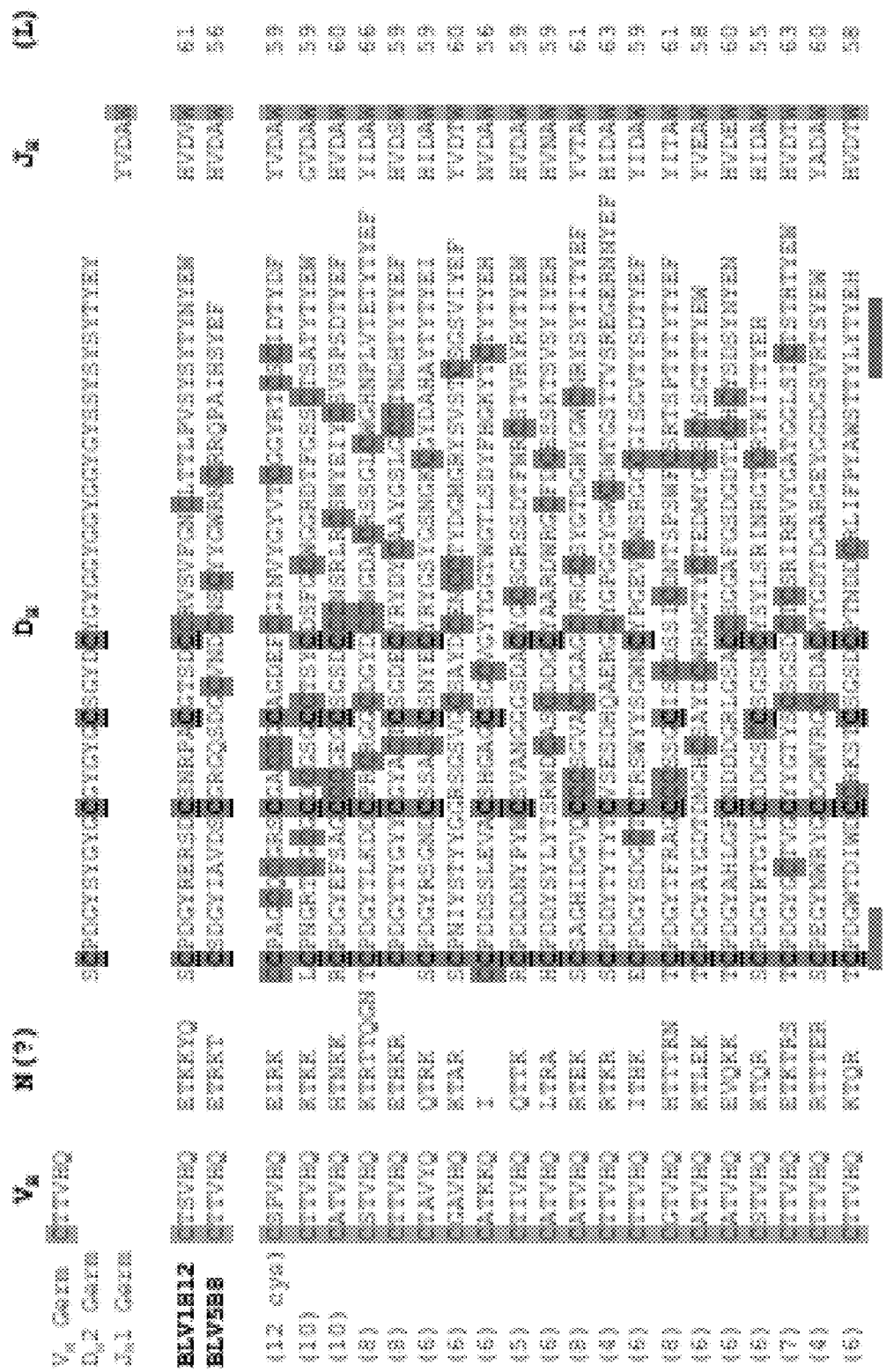
Figure 5A:
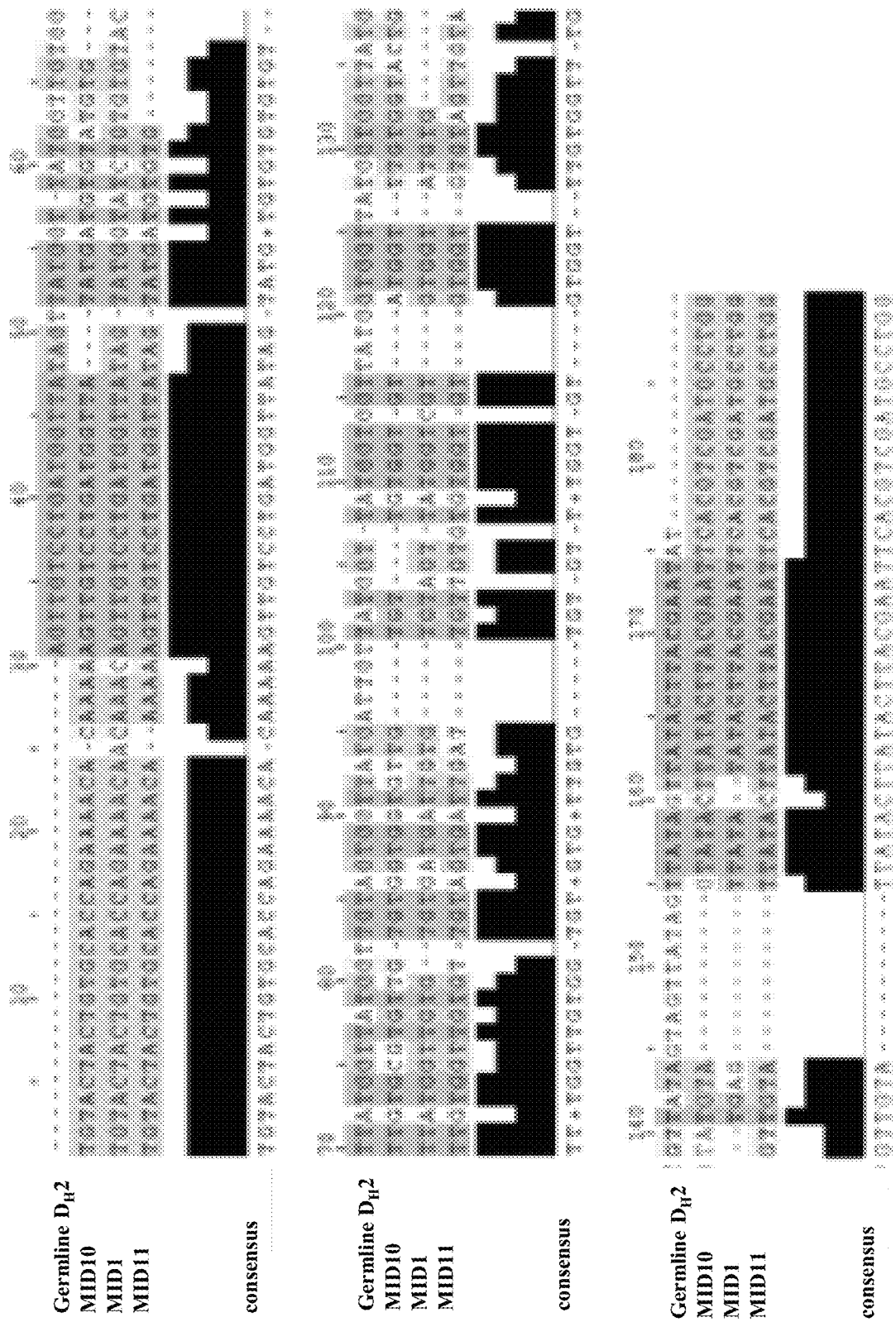
FIGS. 5A-5C show that cysteine mutations contribute to ultralong CDR H3 diversity.
Figure 5B:
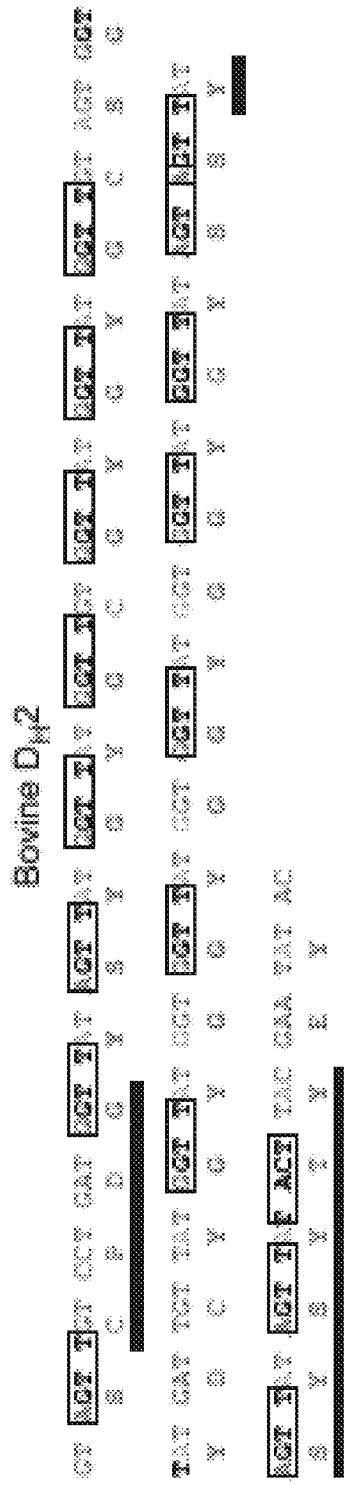
Figure 5C:
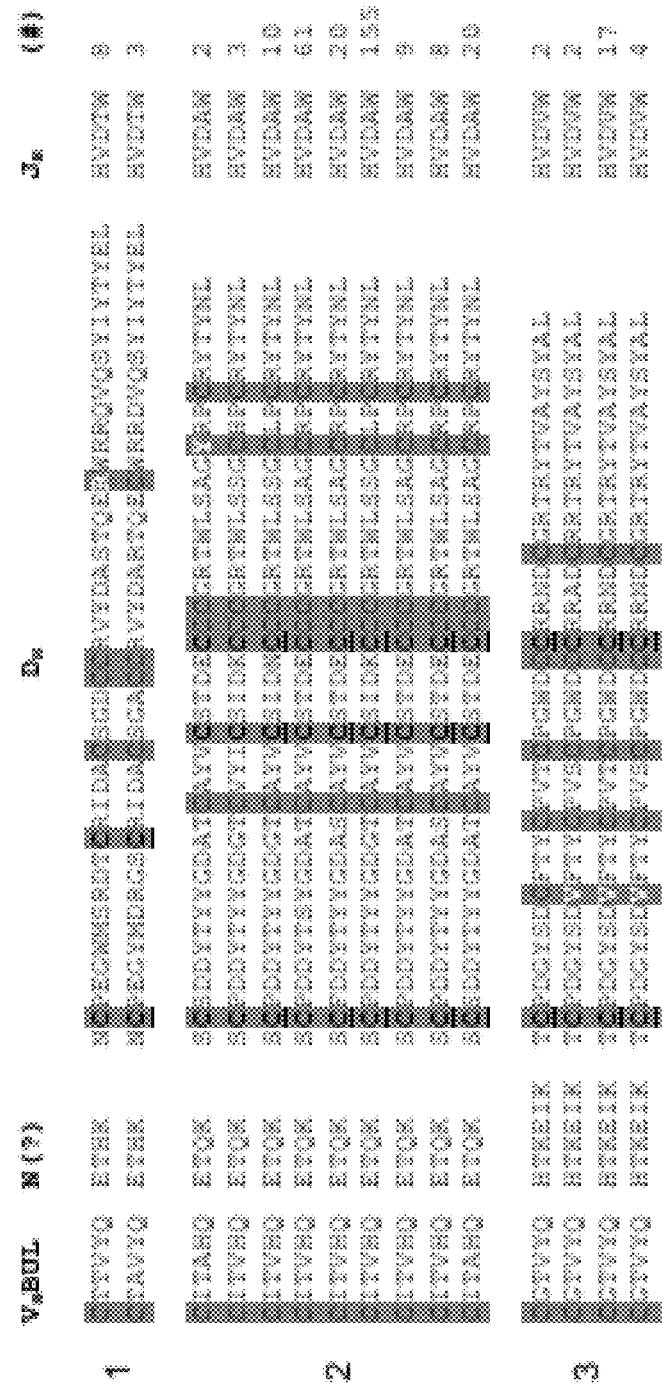
Figure 6A:
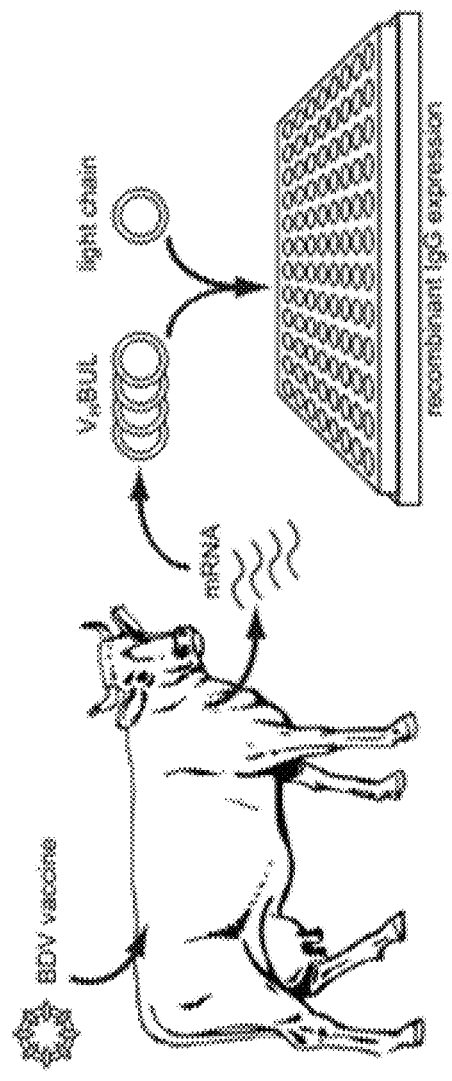
FIGS. 6A-6D show bovine antibodies with ultralong CDR H3s bind antigen.
Figure 6B:
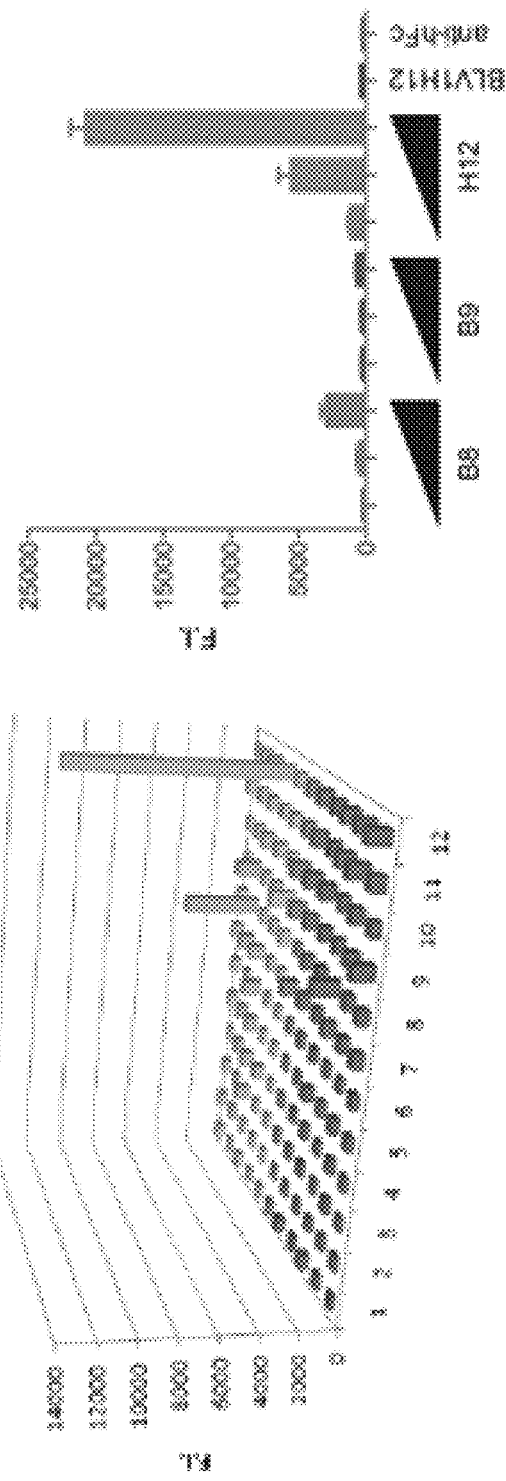
Figure 6C:
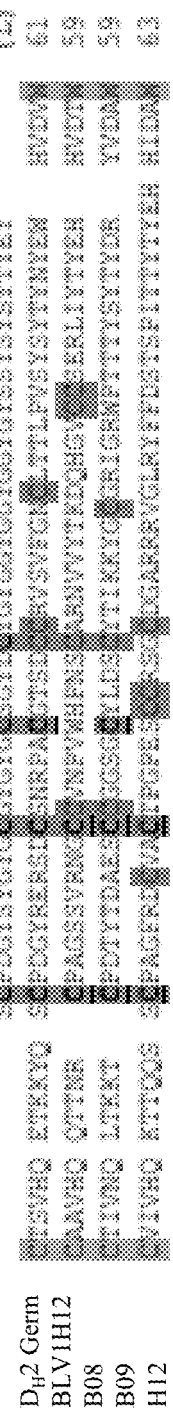
Figure 6D:
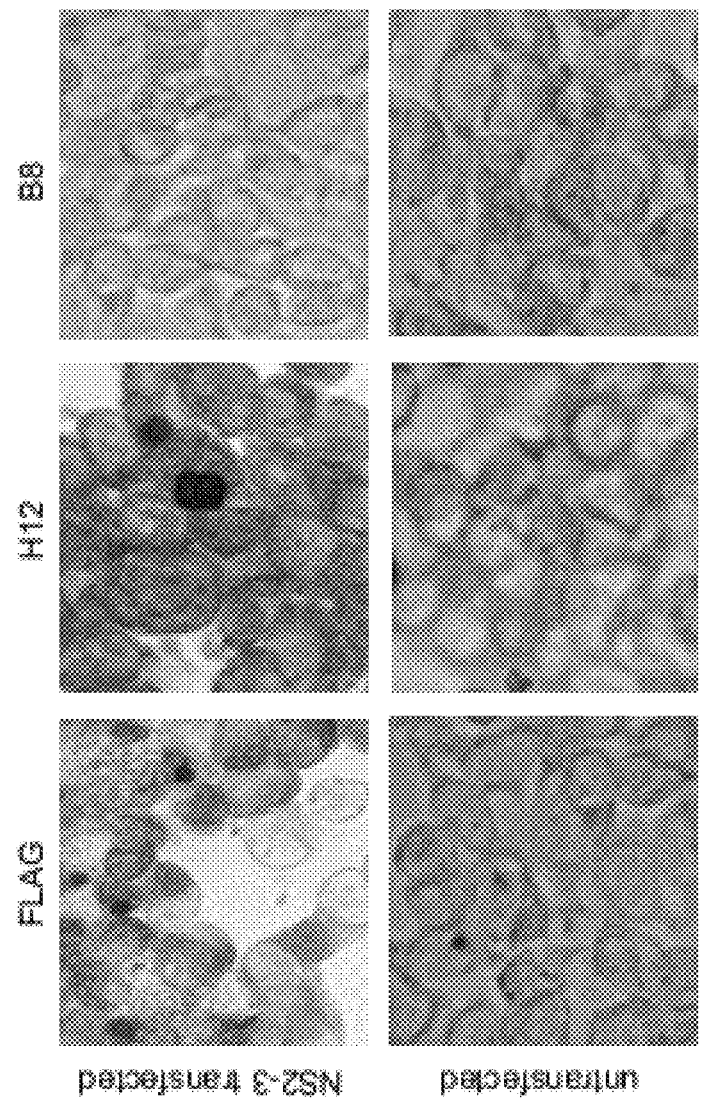
Figure 7B:
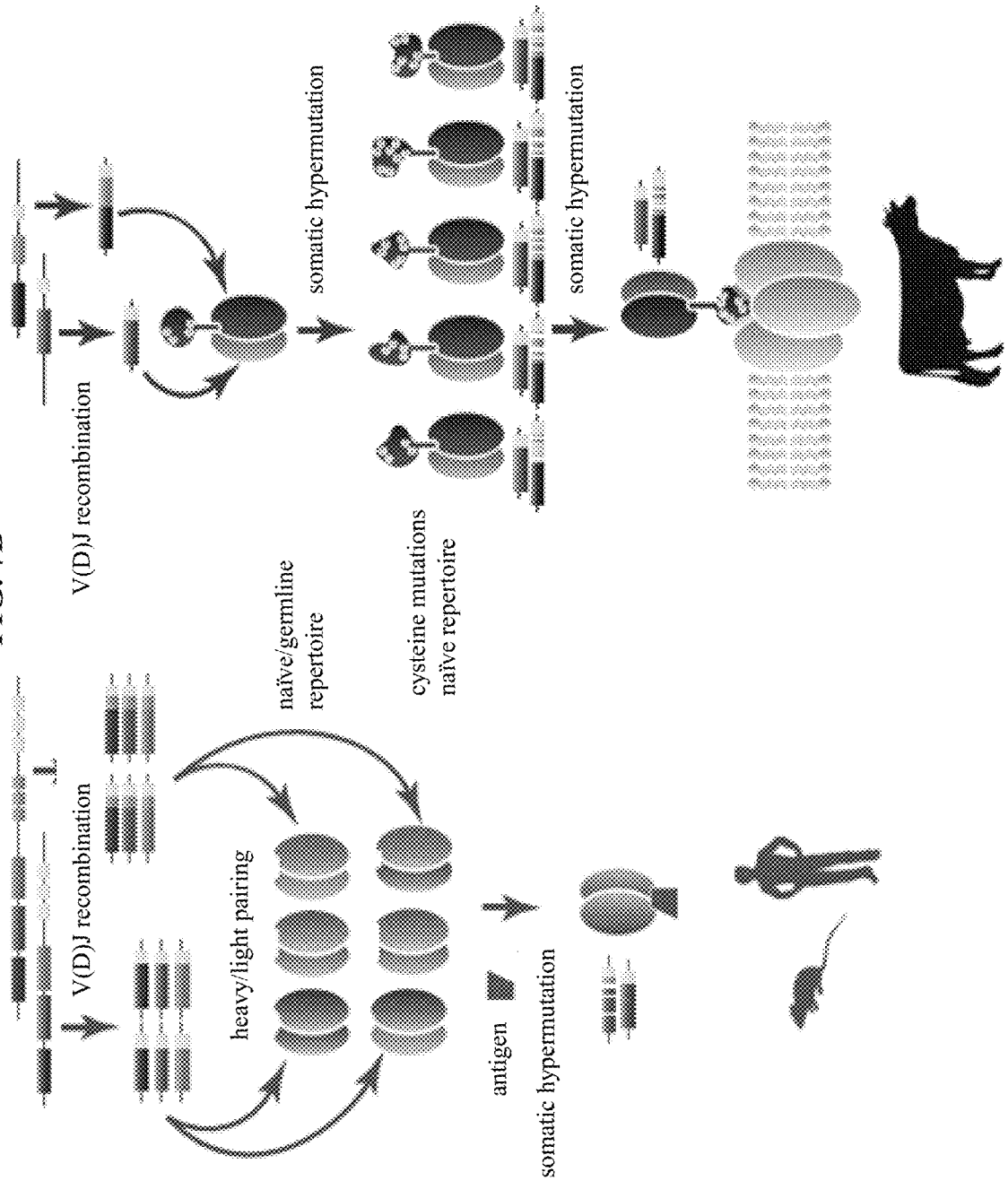

A library of polynucleotides coding for antibodies that comprise an ultralong CDR3 is generated by immunization of cattle with whole killed bovine viral diarrhea virus (BVDV) (FIG. 1A). Briefly, a four month-old Holstein steer was immunized by intradermal inoculation of a mixture of heat killed BVDV-1 and BVDV-2 (100 μg of each). The inactivated virus mixture was suspended in 500 μl PBS and emulsified in 500 μl Freund's Complete Adjuvant by repeated passage through a double barrel needle. Next, the immunogen was inoculated intradermally (200 IA/injection) at the neck region using a 26×1½ G needle. The steer was then boosted three times at monthly intervals with the same amount of antigen but formulated in Freund's Incomplete Adjuvant. Sero-conversion was tested by ELISA using plates coated with the inactivated virus and by immunocytometric analysis of MDBK cells infected with either BVDV-1 or BVDV-2. The steer was then bled from the jugular vein and blood was collected in heparin. Lymphocytes were purified through Lymphocyte Separation Media (Mediatech) centrifugation and stored in RNAlater. A cDNA library was then made from the plurality of lymphocyte RNA as described in Example 2.

Example 4

Constructing Vectors of BLV1H12-bGCSF Fusion Proteins for Expression in Mammalian Cells A gene encoding bovine G-CSF (bGCSF) was synthesized by Genscript (NJ, USA) and amplified by polymerase chain reaction (PCR). To optimize the folding and stability of the immunoglobulin constructs, flexible linkers of (GGGGS)n (SEQ ID NO: 509) (n=0, 1) were added on both ends of the bGCSF fragment. Subsequently, PCR fragments of bGCSF with varied lengths of linkers were grafted into the complementarity determining region 3 of the heavy chain (CDR3H) of BLV1H12 antibody by exploiting overlap extension PCR, to replace the 'knob' domain as shown in the crystal structure of BLV1H12. The expression vectors of BLV1H12-bGCSF fusion proteins were generated by in-frame ligation of the amplified BLV1H12-bGCSF fusion genes to the pFuse-hIgG1-Fc backbone vector (InvivoGen, CA). Similarly, the gene encoding the light chain of BLV1H12 antibody was cloned into the pFuse vector without hIgG1 Fc fragment. The obtained expression vectors were confirmed by sequencing. FIGS. 8F-8G provide depictions of the bovine G-CSF inserted into or replacing at least a portion of the knob domain of a heavy chain region of bovine BLV1H12 antibody. FIGS. 14A-14C shows vectors for expression of the BLV1H12-bGCSF fusion protein. DNA sequences encoding the heavy and light chain immunoglobulin constructs Ab-bGCSF L0 (n=0) (SEQ ID NO: 4) and Ab-bGCSF L1 (n=1) (SEQ ID NO: 5) are shown in Table 19. Amino acid sequences encoding the heavy and light chain immunoglobulin constructs Ab-bGCSF L0 and Ab-bGCSF L1 are shown in Table 21.

Example 5

Expression and Purification of BLV1H12-bGCSF Fusion Antibodies

BLV1H12-bGCSF fusion antibodies were expressed through transient transfections of free style HEK 293 cells with vectors encoding BLV1H12-bGCSF fusion heavy chain and BLVH1H12 light chain. Expressed BLV1H12-bGCSF fusion antibodies were secreted into the culture medium and harvested at 48 hours and 96 hours after transfection. The BLV1H12-bGCSF fusion antibodies were purified by Protein A/G chromatography (Thermo Fisher Scientific, IL), and analyzed by SDS-PAGE gel. FIG. 15A shows SDS-PAGE gel of purified Ab-bGCSF L0 and Ab-bGCSF L1 fusion antibodies from HEK 293 cells.

Example 6

In Vitro Study of Proliferative Activities of the BLV1H12-bGCSF Fusion Antibodies on Mouse NFS-60 Cells Mouse NFS-60 cells were obtained from American Type Culture Collection (ATCC), VA, and cultured in RPMI-1640 medium supplemented with 10% fetal bovine serum (FBS), 0.05 mM 2-mercapoethanol and 62 ng/ml human macrophage colony stimulating factor (M-CSF). For proliferation assay, mouse NFS-60 cells were washed three times with RPMI-1640 medium and resuspended in RPMI-1640 medium with 10% FBS and 0.05 mM 2-mercapoethanol at a density of $1.5\times10^5$ cells/ml. In 96-well plates, 100 μl of cell suspension was added into each well, followed by the addition of varied concentrations of bGCSF, BLV1H12 antibody, and the immunoglobulin constructs described herein, Equal volume of PBS buffer was added into the control wells. The plates were incubated at 37° C. in a 5% CO2 incubator for 72 hours. Cells were then treated with AlamarBlue (Invitrogen) (1/10 volume of cell suspension) for 4 hours at 37° C. Fluorescence at 595 nm for each well was read to indicate the cell viability. As seen in FIGS. 9A-9E and Tables 7-8, the immunoglobulin constructs Ab-bGCSF L0 and Ab-bGCSF L1 display similar activity as the bovine G-CSF and human G-CSF.

TABLE 7

| bGCSF (ng/mL) | F.I. | hGCSF (ng/mL) | F.I. | Ab (ng/mL) | F.I. |
|---|---|---|---|---|---|
| 0.09145 | 1213.67567 | 0.09145 | 1266.554 | 0.45725 | 1039.57933 |
| 0.27435 | 1360.925 | 0.27435 | 1478.287 | 1.37174 | 1009.55533 |
| 0.82305 | 1761.00533 | 0.82305 | 1752.216 | 4.11523 | 983.27867 |
| 2.46914 | 2100.51733 | 2.46914 | 2224.028 | 12.34568 | 971.84967 |
| 7.40741 | 2405.09667 | 7.40741 | 2587.222 | 37.03704 | 960.54933 |
| 22.22222 | 2646.24067 | 22.22222 | 2751.249 | 111.11111 | 991.83 |
| 66.66667 | 2812.098 | 66.66667 | 2815.37 | 333.33333 | 964.798 |
| 200 | 3087.144 | 200 | 2948.509 | | |

TABLE 8

| Ab-bGCSF (ng/mL) | F.I. | Ab-bGCSF L1 (ng/mL) | F.I. |
|---|---|---|---|
| 0.09876 | 1327.94667 | 0.09808 | 1412.387 |
| 0.29627 | 1435.92467 | 0.29424 | 1654.776 |
| 0.88881 | 1734.765 | 0.88272 | 2082.718 |
| 2.66642 | 2188.50333 | 2.64816 | 2550.674 |
| 7.99927 | 2680.08167 | 7.94449 | 2997.807 |
| 23.9978 | 2899.28333 | 23.83346 | 3277.812 |
| 71.9934 | 2920.56767 | 71.50039 | 3308.383 |
| 215.9802 | 3416.20433 | 214.50117 | 3868.075 |

Example 7

In Vitro Study of Proliferative Activities of BLV1H12-bGCSF Fusion Antibodies on Human Granulocyte Progenitors Human mPB $CD34^+$ cells were purchased from AllCells. Cells were resuspended in HSC expansion medium (StemSpan SFEM, StemCell Technologies) supplemented with 1× antibiotics and the following recombinant human cytokines: thrombopoietin, IL6, Flt3 ligand, and stem cell factor (100 ng/mL, R & D Systems), then plated in 96-well plates (1000 cells per well), with varied concentrations of BLV1H12-bGCSF fusion antibodies. Cells were cultured for 7 days at 37° C. in a 5% $CO_2$ incubator, then analyzed by flow cytometry to measure cell number and expression of CD45ra and CD41. Cells were stained in staining medium (HBSS supplemented with 2% FBS and 2 mM EDTA) at 4° C. for 1 h with PECy7 anti-CD45ra and eFluor 450 anti-CD41 (eBiosciences), then washed with staining medium and analyzed. Multicolor analysis for cell phenotyping was performed on a LSR II flow cytometer (Becton Dickinson). FIGS. 10A-10E and Tables 9-10 show the human granulocyte progenitor cell proliferative activities of the Ab-GCSF fusion antibodies.

TABLE 9

| bGCSF (ng/mL) | Number of CD45RA−CD41− | hGCSF (ng/mL) | Number of CD45RA−CD41− | Ab (ng/mL) | Number of CD45RA−CD41− |
|---|---|---|---|---|---|
| 0.55886 | 7354 | 0.05081 | 4175 | 0.28959 | 3666 |
| 1.67657 | 9776 | 0.15242 | 3651 | 0.86877 | 3839 |
| 5.02972 | 12700 | 0.45725 | 3671 | 2.60631 | 3852 |
| 15.08916 | 13200 | 1.37174 | 4299 | 23.45679 | 3519 |
| 45.26749 | 13700 | 4.11523 | 5900 | 70.37037 | 3541 |
| 135.80247 | 13300 | 12.34568 | 7784 | 211.11111 | 3606 |
| 407.40741 | 13700 | 37.03704 | 10500 | 5700 | 4100 |
| 1222.22222 | 14100 | 111.11111 | 12200 | | |
| 3666.66667 | 13100 | 333.33333 | 14100 | | |
| 11000 | 13800 | 1000 | 13900 | | |

TABLE 10

| Ab-bGCSF (ng/mL) | Number of CD45RA−CD41− | Ab-bGCSF L1 (ng/mL) | Number of CD45RA−CD41− |
|---|---|---|---|
| 0.14225 | 2601 | 0.30483 | 4070 |
| 0.42676 | 2253 | 0.91449 | 3601 |
| 1.28029 | 4155 | 2.74348 | 4303 |
| 3.84088 | 4399 | 8.23045 | 6404 |
| 11.52263 | 7262 | 24.69136 | 9122 |
| 34.5679 | 9902 | 74.07407 | 11200 |
| 103.7037 | 11500 | 222.22222 | 11000 |
| 311.11111 | 11500 | 666.66667 | 11400 |
| 933.33333 | 11900 | 2000 | 11400 |
| 2800 | 12100 | 6000 | 13200 |

Example 8

Pharmacokinetics of BLV1H12-bGCSF Fusion Antibodies in Mice

Figure 11A:
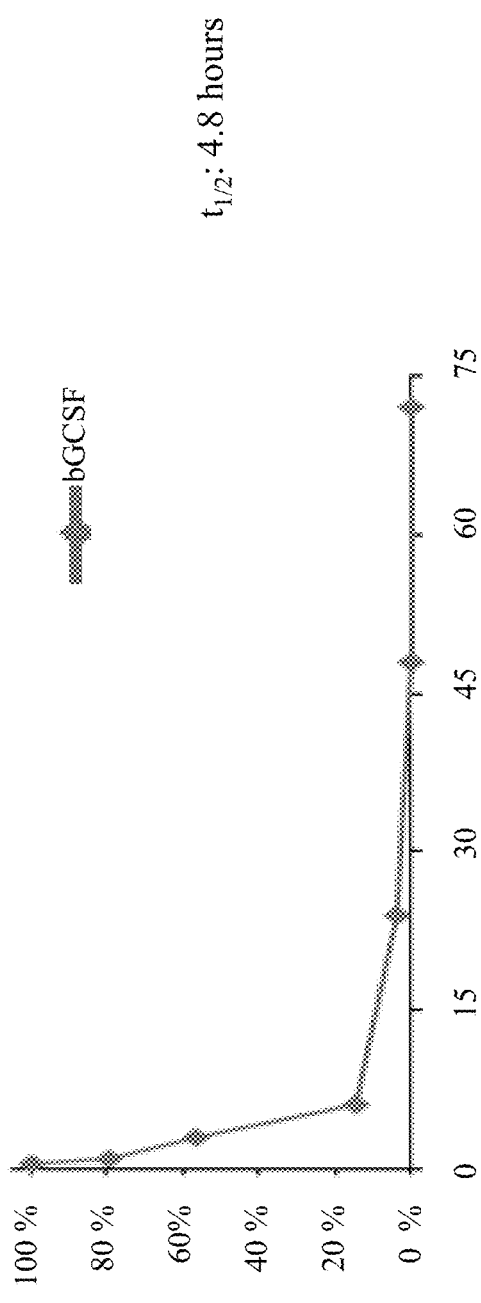
Figure 11B:
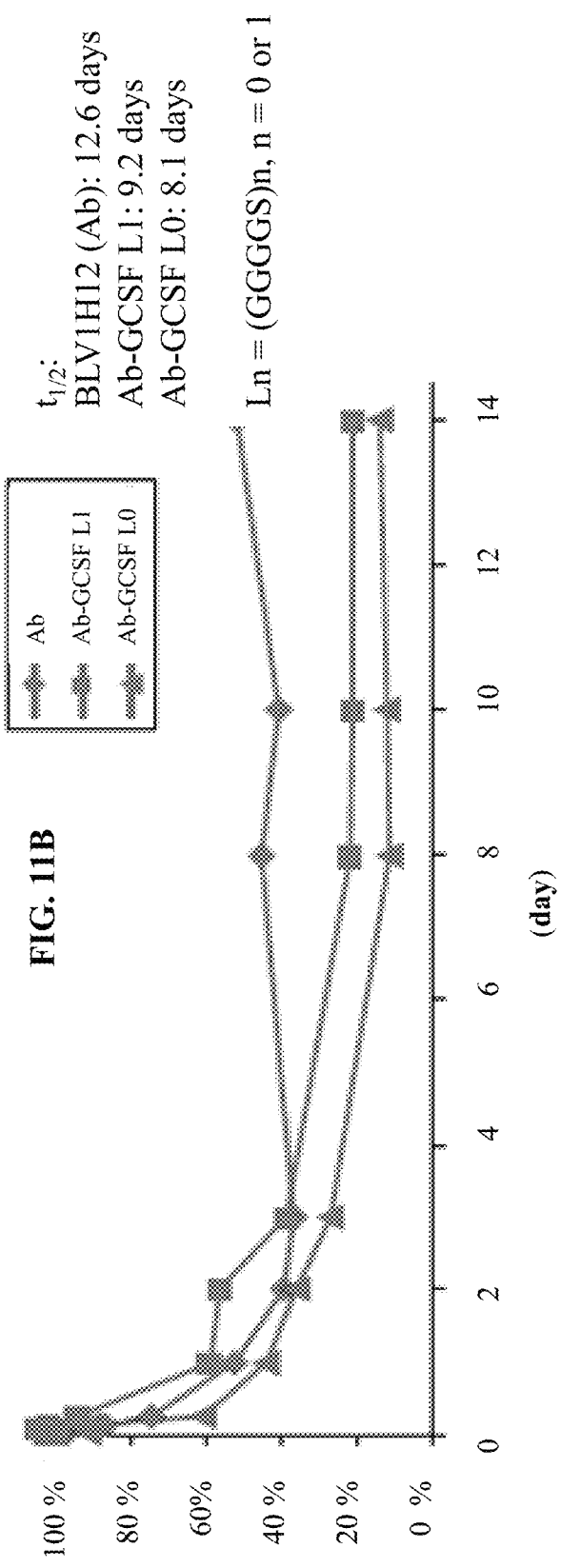

For PK study in mice, 70 μg of the immunoglobulin constructs described herein were injected into 3 BALB/c mice per group. Blood samples were drawn from time 0 to 14 days with extended intervals and analyzed by ELISA using anti-human IgG Fc antibody with horseradish peroxidase (HRP) labeled (KPL) and anti-6×His antibody ("6× His" disclosed as SEQ ID NO: 511) with HRP labeled (Clontech). Data were normalized by taking maximal concentration at the first time point (30 min). As seen in FIGS. 11A-11B and Table 11, the half-life for bovine G-CSF was significantly increased when provided in the form of an immunoglobulin construct described herein.

TABLE 11

| bGCSF | | Ab | | Ab-GCSF L1 | | Ab-GCSF L0 | |
|---|---|---|---|---|---|---|---|
| hour | Percentage | day | Percentage | day | Percentage | day | Percentage |
| 0.5 | 100.00% | 0.021 | 100.00% | 0.021 | 100.00% | 0.021 | 100.00% |
| 1 | 79.52% | 0.042 | 106.09% | 0.042 | 102.12% | 0.042 | 91.12% |
| 3 | 56.81% | 0.083 | 95.88% | 0.083 | 104.03% | 0.083 | 91.24% |
| 6 | 14.94% | 0.125 | 86.54% | 0.125 | 101.71% | 0.125 | 91.56% |
| 24 | 4.08% | 0.250 | 74.26% | 0.250 | 93.90% | 0.250 | 61.22% |
| 48 | 0.00% | 1.000 | 52.43% | 1.000 | 59.26% | 1.000 | 44.22% |

TABLE 11-continued

| bGCSF | | Ab | | Ab-GCSF L1 | | Ab-GCSF L0 | |
|---|---|---|---|---|---|---|---|
| hour | Percentage | day | Percentage | day | Percentage | day | Percentage |
| 72 | 0.00% | 2.000 | 39.46% | 2.000 | 56.66% | 2.000 | 36.36% |
| | | 3.000 | 36.97% | 3.000 | 39.09% | 3.000 | 27.38% |
| | | 8.000 | 45.44% | 8.000 | 22.21% | 8.000 | 11.53% |
| | | 10.000 | 40.98% | 10.000 | 21.15% | 10.000 | 12.44% |
| | | 14.000 | 51.96% | 14.000 | 21.41% | 14.000 | 14.35% |

Example 9

Neutrophils Counts in Mice

On the 10$^{th}$ day after injection of BLV1H12-bGCSF fusion antibodies into mice for PK study, blood samples were drawn from the mice and stained using the Diff Quick Staining Kit (Thermo Fisher Scientific, IL). Neutrophils and white blood cells were counted under microscope and the percentages of neutrophils were analyzed. FIGS. 12A-12B and Table 12 show proliferative activities of BLV1H12-bGCSF fusion antibodies on mice neutrophils that are blood stained and counted at the 10th day post-injection.

TABLE 12

| | Percentage of Neutrophil |
|---|---|
| N.C | 16.07 |
| Ab | 18.81 |
| Ab-GCSF L1 | 25.32 |
| Ab-GCSF L0 | 25.05 |
| bGCSF | 16.48 |

Example 10

Construction of Vectors of BLV1H12-bGCSF Fusion Proteins for Expression in Pichia Pastoris Gene fragments encoding BLV1H12-bGCSF chain heavy chain and BLV1H12 light chain were amplified from the pFuse expression vectors and subsequently ligated into the same pPICZα vector (Invitrogen). The expressions of the heavy and light chains were under the control of AOX1 promoter.

Example 11

Expression and Purification of BLV1H12-bGCSF Fusion Antibodies in Pichia

Figure 13A:
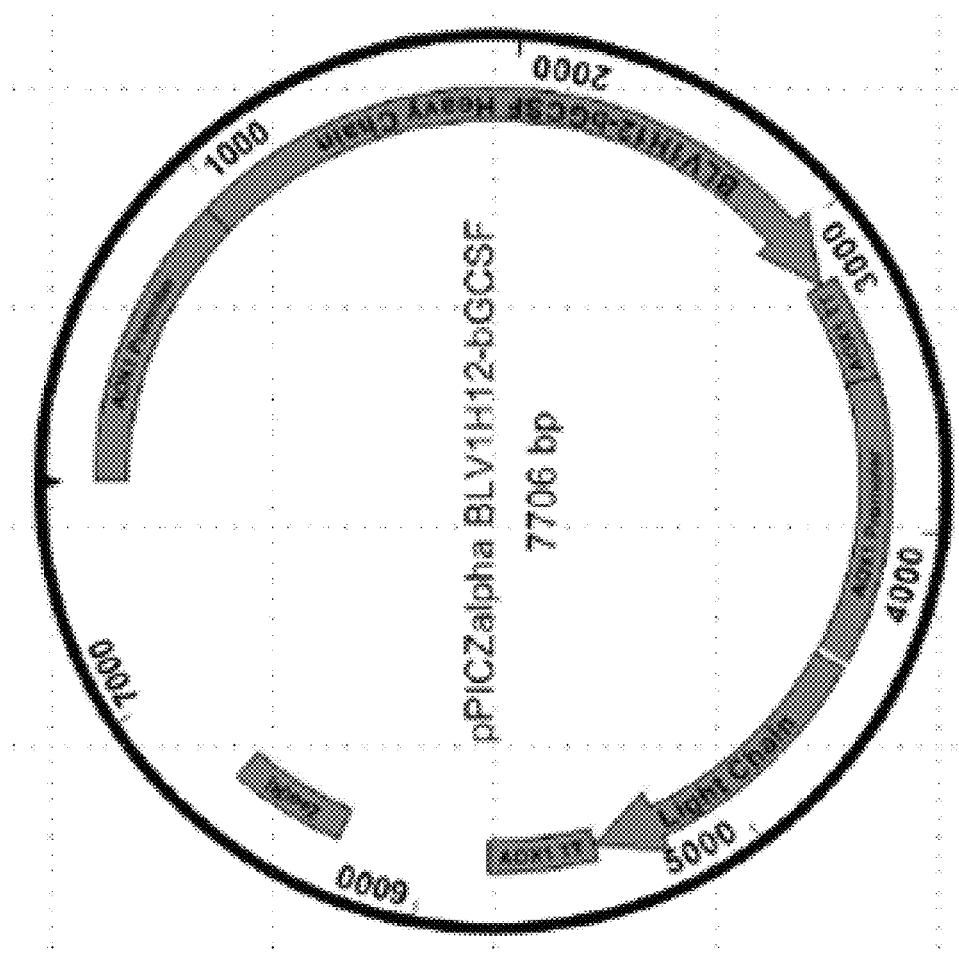
Figure 13C:
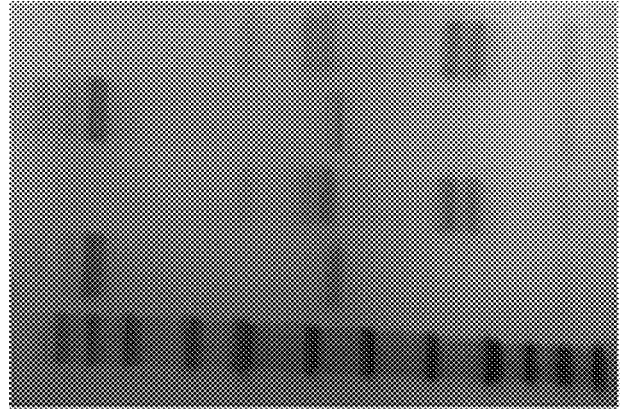
Figure 13B:
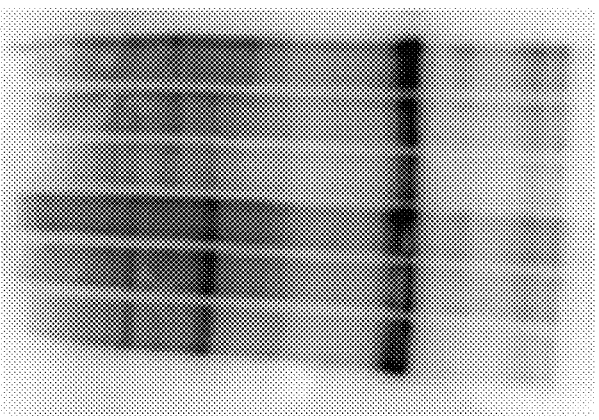
Figure 14B:
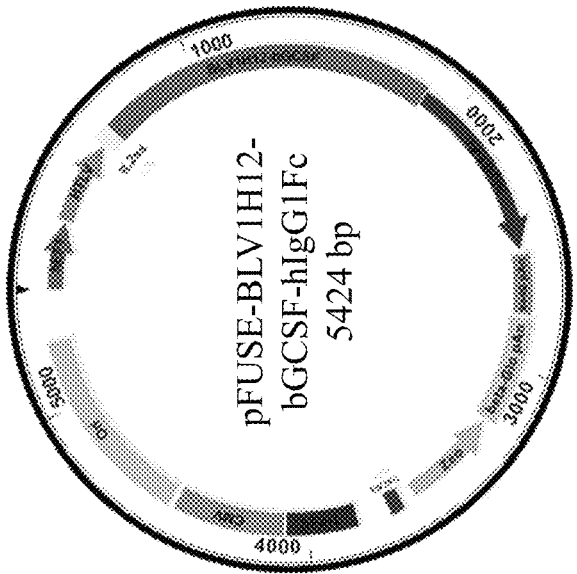
Figure 14C:
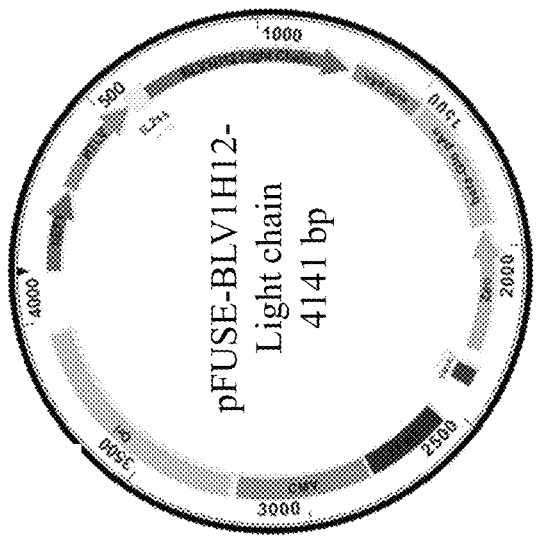
Figure 14A:
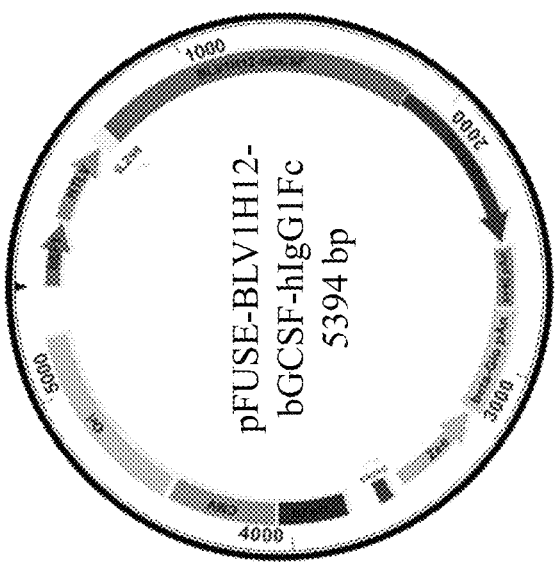

The Pichia GS190 cells were transformed with the pPICZα vectors encoding immunoglobulin construct heavy and light chains by electroporation. Positive transformants were selected based on zeocin resistance and confirmed by PCR. Pichia cells with integrated BLV1H12-bGCSF fusion genes were grown in BMGY medium till $OD_{600}$=2-6. The cells were then transferred into BMMY medium in ⅕ of its original volume for induction of the proteins expression. For every 24 hours, a final concentration of 0.5% methanol was added into the medium to maintain the induction. Medium containing the secreted immunoglobulin constructs were harvested after 96-hour induction. The BLV1H12-bGCSF fusion antibodies were purified by Protein A/G chromatography (Thermo Fisher Scientific, IL) and analyzed by SDS-PAGE gel. FIGS. 13A-13C show expression and purification of BLV1H12-bGCSF fusion antibodies in Pichia pastoris.

Example 12

Figure 8C:
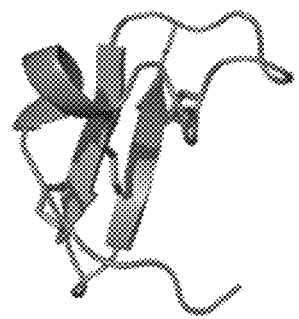
FIGS. 8A-8J depict schemes showing attachment of bovine G-CSF onto the knob domain of a heavy chain region of bovine BLV1H12 antibody to design an immunoglobulin construct described herein.
Figure 8E:
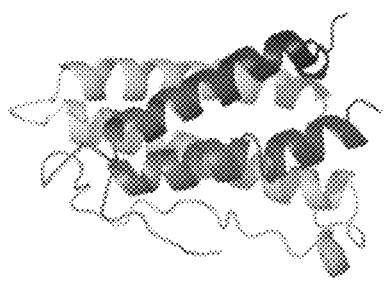
Figure 8B:
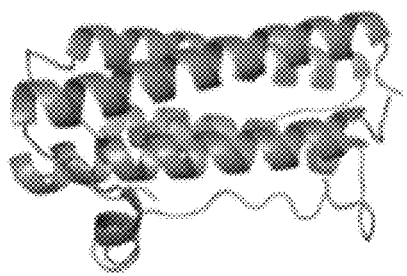
Figure 8D:
Figure 8A:
Figure 8H:
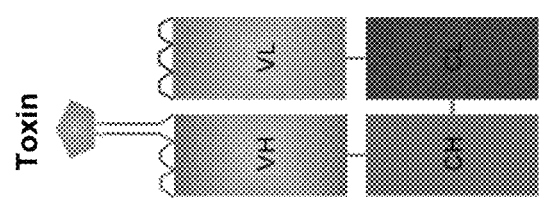
Figure 8J:
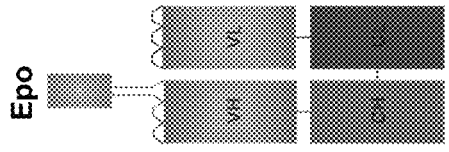
Figure 8G:
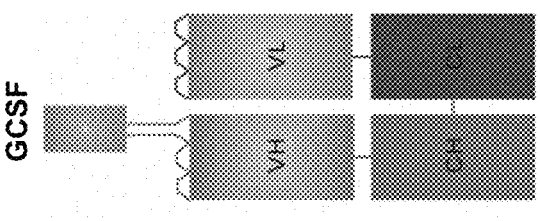
Figure 8I:
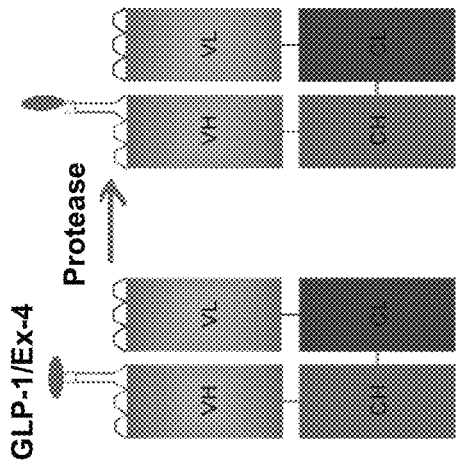
Figure 8F:
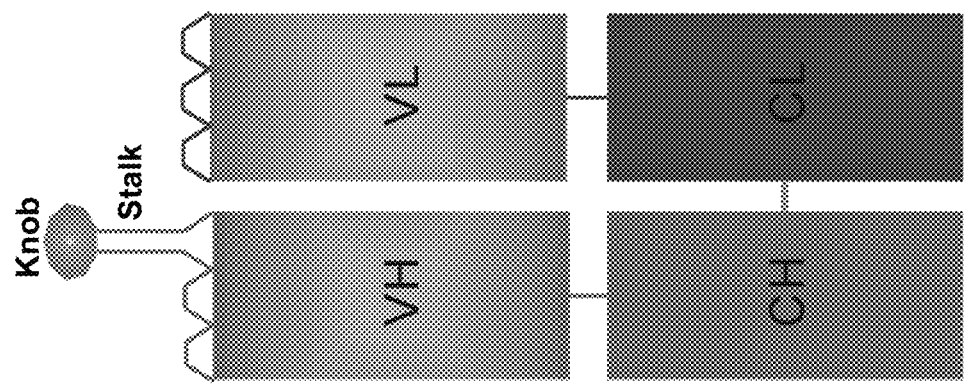
Figures 10A, 10B, 10C, 10D, 10E:
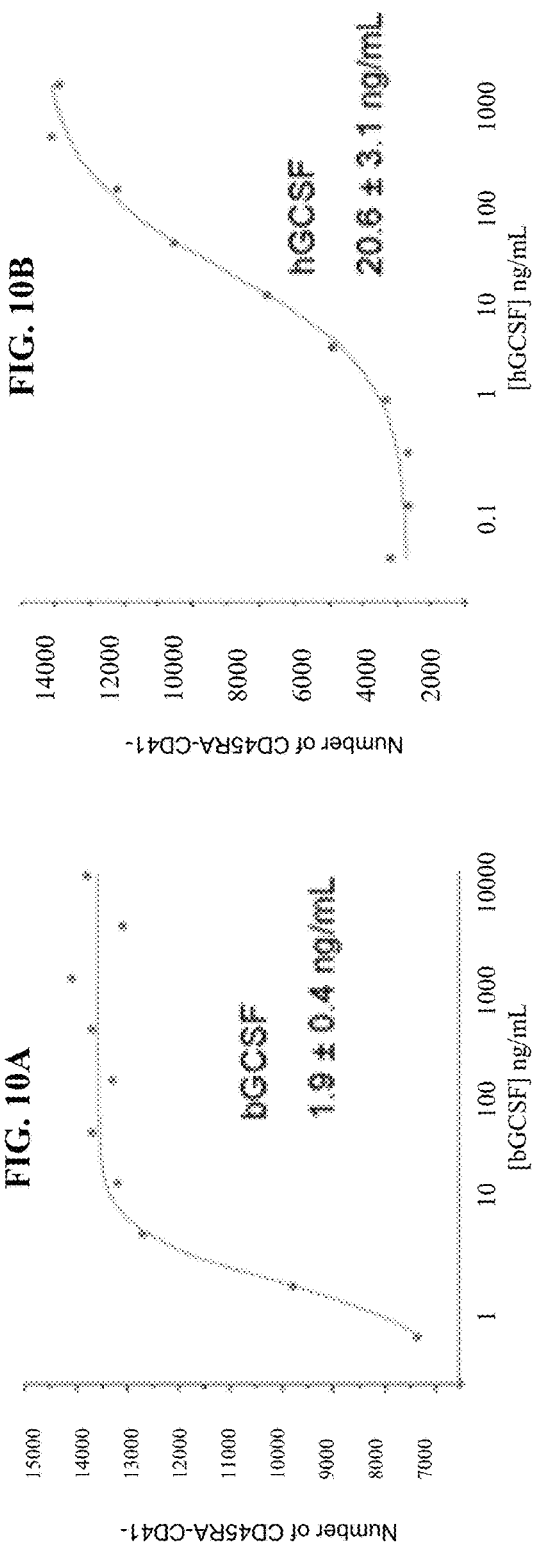
FIGS. 10A-10E present human granulocyte progenitor cell proliferative activities of the Ab-GCSF fusion proteins.

Constructing Vectors of BLV1H12-Moka1 Fusion Proteins for Expression in Mammalian Cells A gene encoding Moka1 was synthesized by Genscript or IDT, and amplified by polymerase chain reaction (PCR). To optimize the folding and stability of fusion proteins, flexible linkers of (GGGGS)n (SEQ ID NO: 509) (n=0, 1) were added on both ends of the Moka1 fragment. Subsequently, PCR fragments of Moka1 with and without the linker were grafted into the complementarity determining region 3 of the heavy chain (CDR3H) of BLV1H12 antibody by exploiting overlap extension PCR, to replace the 'knob' domain as shown in the crystal structure of BLV1H12. The expression vectors of BLV1H12-Moka1 fusion proteins were generated by in-frame ligation of the amplified BLV1H12-Moka1 fusion genes to the pFuse-hIgG1-Fc backbone vector (InvivoGen, CA). Similarly, the gene encoding the light chain of BLV1H12 antibody was cloned into the pFuse vector without hIgG1 Fc fragment. The obtained expression vectors were confirmed by sequencing. FIG. 8F and FIG. 8H provide depictions of a Moka1 peptide inserted into or replacing at least a portion of the knob domain of a heavy chain region of bovine BLV1H12 antibody.

Example 13

Expression and Purification of BLV1H12 Ab-Moka1 Fusion Antibodies

Figure 16B:
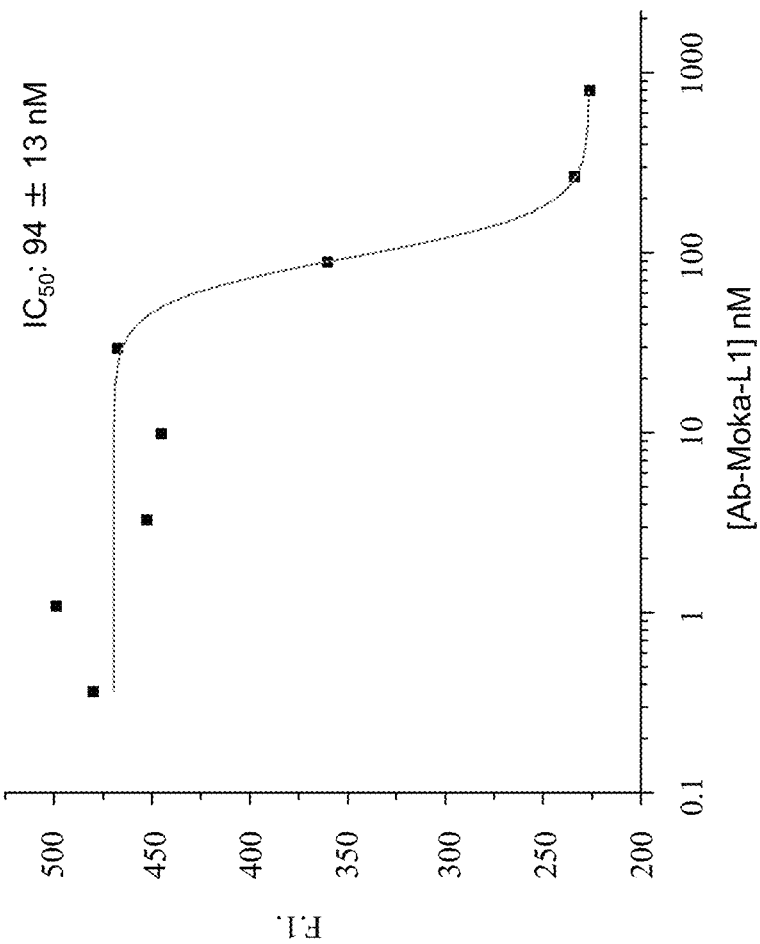
Figure 16A:
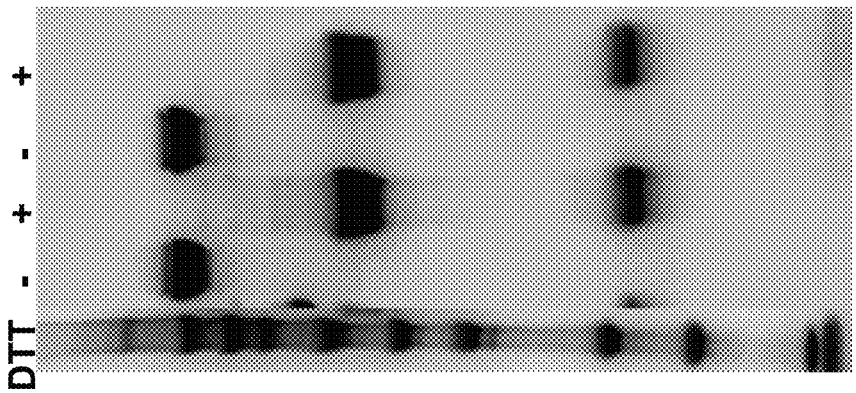

BLV1H12-Moka1 fusion antibodies were expressed through transient transfections of free style HEK 293 cells with vectors encoding BLV1H12-Moka1 fusion heavy chain and the BLV1H12 light chain. BLV1H12-Moka1 fusion antibodies were secreted into the culture medium and harvested at 48 hours and 96 hours after transfection. The BLV1H12-Moka1 fusion antibodies were purified by Protein A/G chromatography (Thermo Fisher Scientific, IL), and analyzed by SDS-PAGE gel. FIG. 16A shows a SDS PAGE of the immunoglobulin fusion antibodies Ab-Moka1 L0 (n=0) (SEQ ID NO: 26) and Ab-Moka1 L1 (n=1) (SEQ ID NO: 27).

Example 14

Figure 17:
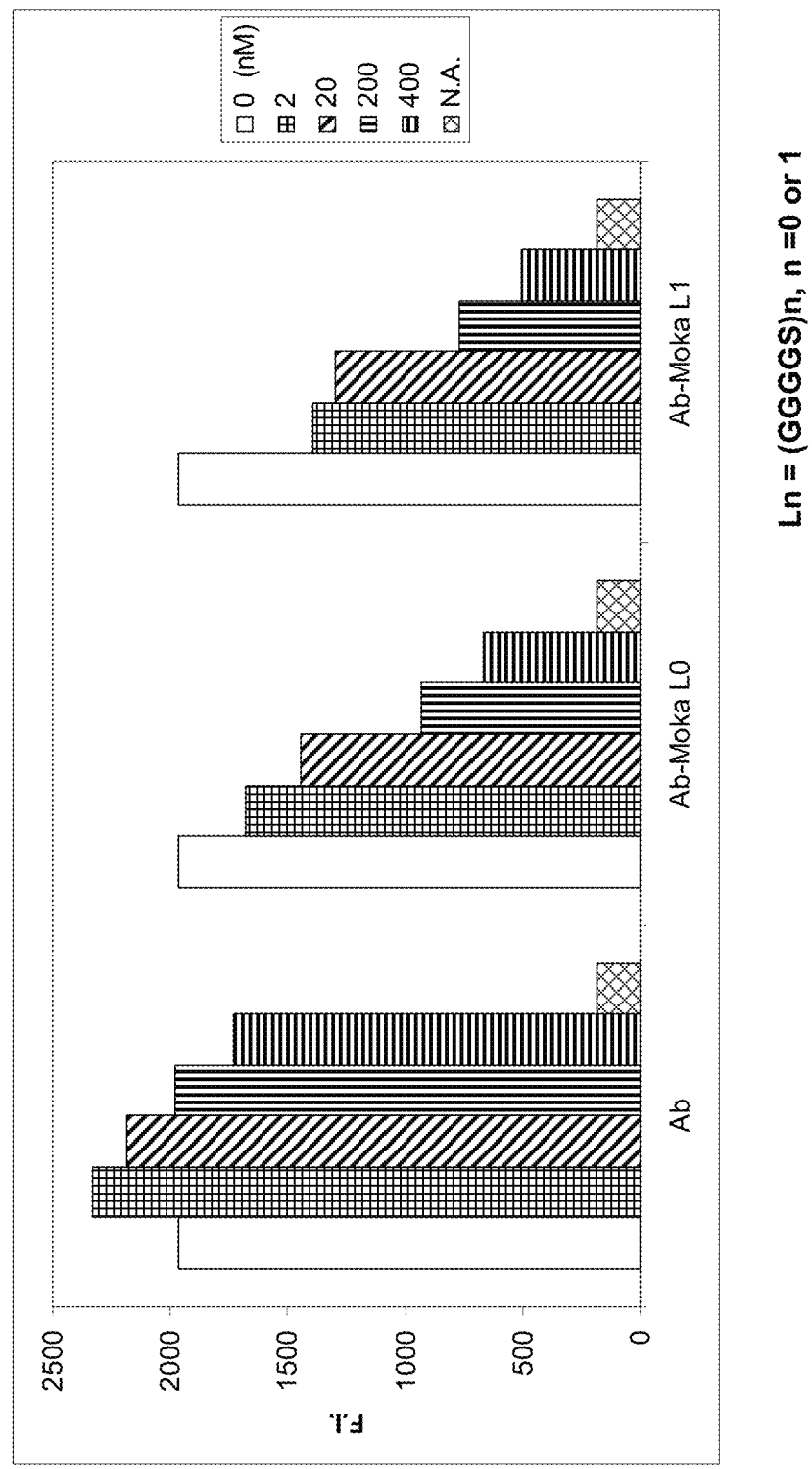

In Vitro Study of BLV1H12-Moka1 Fusion Antibodies Inhibitory Activities on Human Peripheral Blood Mononuclear Cells (PBMCs)/T Cells Activation Human PBMCs were isolated from fresh venous blood of healthy donors through ficoll gradient centrifugation, followed by resuspension in RPMI1640 medium with 10% FBS and plating in 96-well plates at a density of 1×10⁶ cells/mL. Human T cells were purified from the isolated PBMCs using T cell enrichment kit. Purified PBMCs and T cells were pretreated for 1 h at 37° C. with 5% $CO_2$ with various concentrations of purified BLV1H12-Moka1 fusion antibodies and then activated by anti-CD3 and CD28 antibodies. After 24 h treatment, supernatant was collected for measurement of the levels of secreted TNF-α using ELISA kit. FIG. 17 and Table 13 shows BLV1H12-Moka1 fusion antibodies inhibitory activities on human peripheral blood mononuclear cells (PBMCs). FIG. 16B and Table 14 shows BLV1H12-Moka1 fusion antibodies inhibitory activities on T cells activation.

TABLE 13

| Concentration (nM) | Ab F.I. | Ab-Moka L0 F.I. | Ab-Moka L1 F.I. |
|---|---|---|---|
| 0 | 1966.657 | 1966.657 | 1966.657 |
| 2 | 2333.599333 | 1679.371333 | 1394.048 |
| 20 | 2186.372667 | 1441.220667 | 1294.799333 |
| 200 | 1981.540333 | 928.0533333 | 773.3666667 |
| 400 | 1732.831333 | 664.9696667 | 505.102 |
| N.A. | 183.3106667 | 183.3106667 | 183.3106667 |

TABLE 14

| [Ab-Moka-L1] nM | F.I. |
|---|---|
| 0.3658 | 479.8675 |
| 1.09739 | 498.558 |
| 3.29218 | 452.342 |
| 9.87654 | 445.013 |
| 29.62963 | 467.268 |
| 88.88889 | 360.2535 |
| 266.66667 | 233.809 |
| 800 | 226.155 |

Example 15

Constructing Vectors of BLV1H12-VM24 Fusion Proteins for Expression in Mammalian Cells A gene encoding Vm24 was synthesized by Genscript or IDT, and amplified by polymerase chain reaction (PCR). To optimize the folding and stability of BLV1H12-VM24 fusion proteins, flexible linkers of GGGGS (SEQ ID NO: 509) or GGGSGGGGS (SEQ ID NO: 337) were added on both ends of the Vm24 fragment. Subsequently, PCR fragments of VM24 with varied lengths of linkers were grafted into the complementarity determining region 3 of the heavy chain (CDR3H) of BLV1H12 antibody by exploiting overlap extension PCR, to replace the 'knob' domain as shown in the crystal structure of BLV1H12. The expression vectors of BLV1H12-VM24 fusion proteins were generated by in-frame ligation of the amplified BLV1H12-VM24 fusion genes to the pFuse-hIgG1-Fc backbone vector (InvivoGen, CA). Similarly, the gene encoding the light chain of BLV1H12 antibody was cloned into the pFuse vector without hIgG1 Fc fragment. The obtained expression vectors were confirmed by sequencing. FIG. 8F and FIG. 8H provide depictions of a VM24 peptide inserted into or replacing at least a portion of the knob domain of a heavy chain region of bovine BLV1H12 antibody.

Example 16

Expression and Purification of BLV1H12-VM24 Fusion Antibodies

Figure 18:
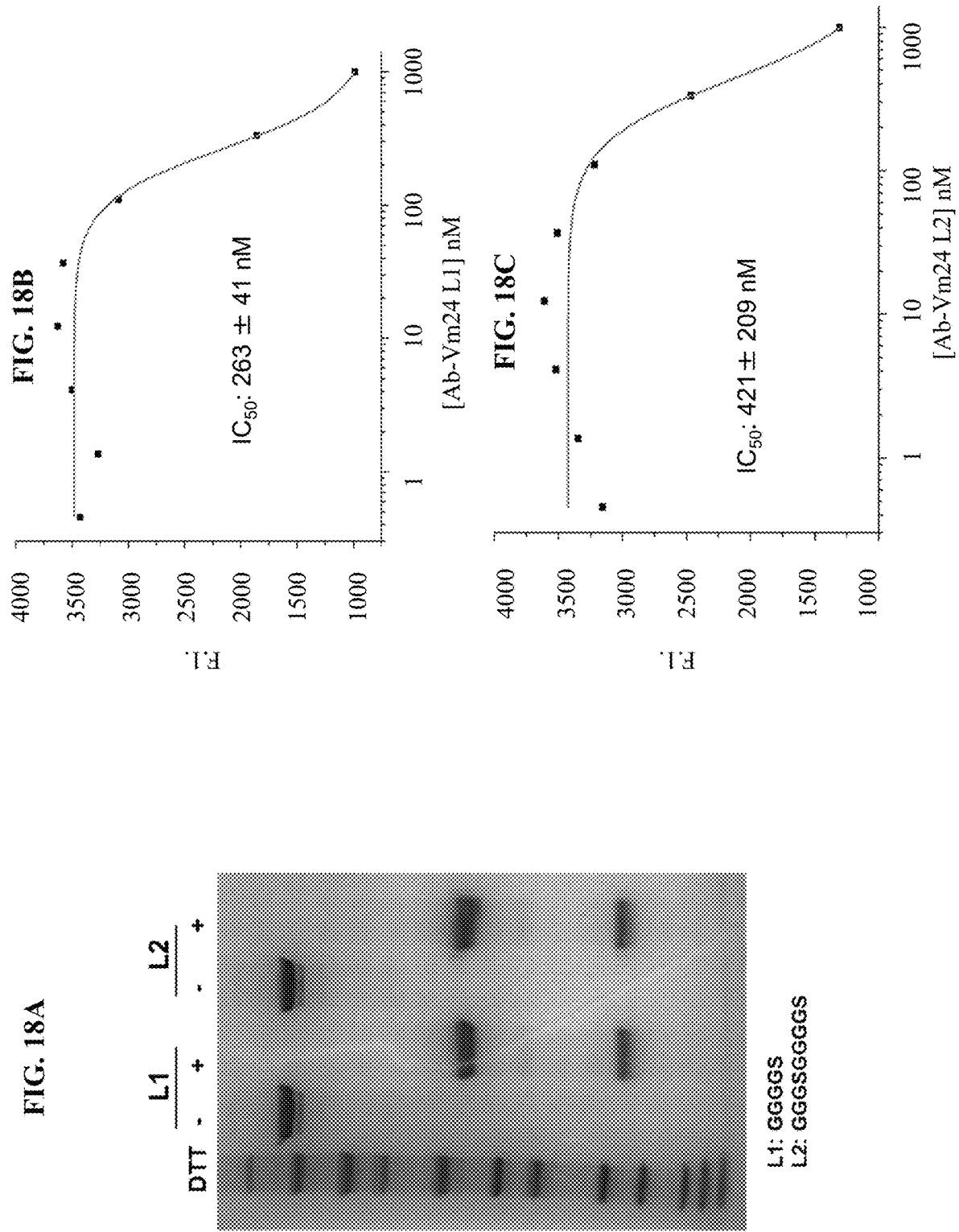

BLV1H12-VM24 fusion antibodies were expressed through transient transfections of free style HEK 293 cells with vectors encoding BLV1H12-VM24 fusion heavy chain and the BLV1H12 light chain. Expressed BLV1H12-VM24 fusion antibodies were secreted into the culture medium and harvested every 48 hours for twice after transfection. The BLV1H12-VM24 fusion antibodies were purified by Protein A/G chromatography (Thermo Fisher Scientific, IL), and analyzed by SDS-PAGE gel. FIG. 18A shows a SDS PAGE of the immunoglobulin constructs Ab-VM24 L1 (linker=GGGGS (SEQ ID NO: 509)) (SEQ ID NO: 35) and Ab-VM24 L2 (first linker=GGGSGGGGS (SEQ ID NO: 337) and second linker=GGGGSGGGS (SEQ ID NO: 338)) (SEQ ID NO: 36).

Example 17

In Vitro Study of BLV1H12-Vm24 Fusion Antibodies Inhibitory Activities on T Cells Activation Human T cells were purified from the isolated PBMCs using T cell enrichment kit. Purified T cells were pretreated for 1 h at 37° C. with 5% $CO_2$ with various concentrations of purified BLV1H12-VM24 fusion antibodies and then activated by anti-CD3 and CD28 antibodies. After 24 h treatment, supernatant was collected for measurement of the levels of secreted TNF-α using ELISA kit. FIGS. 18B-18C and Table 15 show the BLV1H12-VM24 fusion antibodies inhibitory activities on T cells activation.

TABLE 15

| [Ab-VM24 L1] nM | F.I. | [Ab-VM24-L2] nM | F.I. |
|---|---|---|---|
| 0.45725 | 3427.004 | 0.45725 | 3156.626 |
| 1.37174 | 3265.969 | 1.37174 | 3345.846 |
| 4.11523 | 3499.82 | 4.11523 | 3518.316 |
| 12.34568 | 3627.431 | 12.34568 | 3607.5755 |
| 37.03704 | 3575.4815 | 37.03704 | 3508.0475 |
| 111.11111 | 3085.439 | 111.11111 | 3220.2475 |
| 333.33333 | 1853.645 | 333.33333 | 2465.838 |
| 1000 | 990.818 | 1000 | 1306.0215 |

Example 18

Constructing Vectors of BLV1H12-Ex-4 Fusion Proteins for Expression in Mammalian Cells A gene encoding Exendin-4 (Ex-4) was synthesized by Genscript or IDT, and amplified by polymerase chain reaction (PCR). A cleavage site of Factor Xa was placed in front of the N-terminal of Exendin-4. In addition to this protease cleavage site, GGGGS linker (SEQ ID NO: 501) followed with a cysteine were also added on both ends of the Exendin-4 fragment. Subsequently, PCR fragments of Exendin-4 were grafted into the complementarity determining region 3 of the heavy chain (CDR3H) of BLV1H12 antibody by exploiting overlap extension PCR, to replace the 'knob' domain as shown in the crystal structure of BLV1H12. The expression vectors of BLV1H12-Ex-4 clip fusion proteins were generated by in-frame ligation of the amplified BLV1H12-fusion genes to the pFuse-hIgG1-Fc backbone vector (InvivoGen, CA). Similarly, the gene encoding the light chain of BLV1H12 antibody was cloned into the pFuse vector without hIgG1 Fc fragment. The obtained expression vectors were confirmed by sequencing. FIG. 8F and FIG. 8I show cartoons depicting Exendin-4 peptide inserted into or replacing at least a portion of the knob domain of an immunoglobulin heavy chain region. FIG. 8I also depicts the clipped version of the BLV1H12-Exendin-4 fusion protein, wherein Exendin-4 has a free N-terminus.

Example 19

Expression and Purification of BLV1H12-Ex-4 Clip Fusion Proteins

Figure 19:
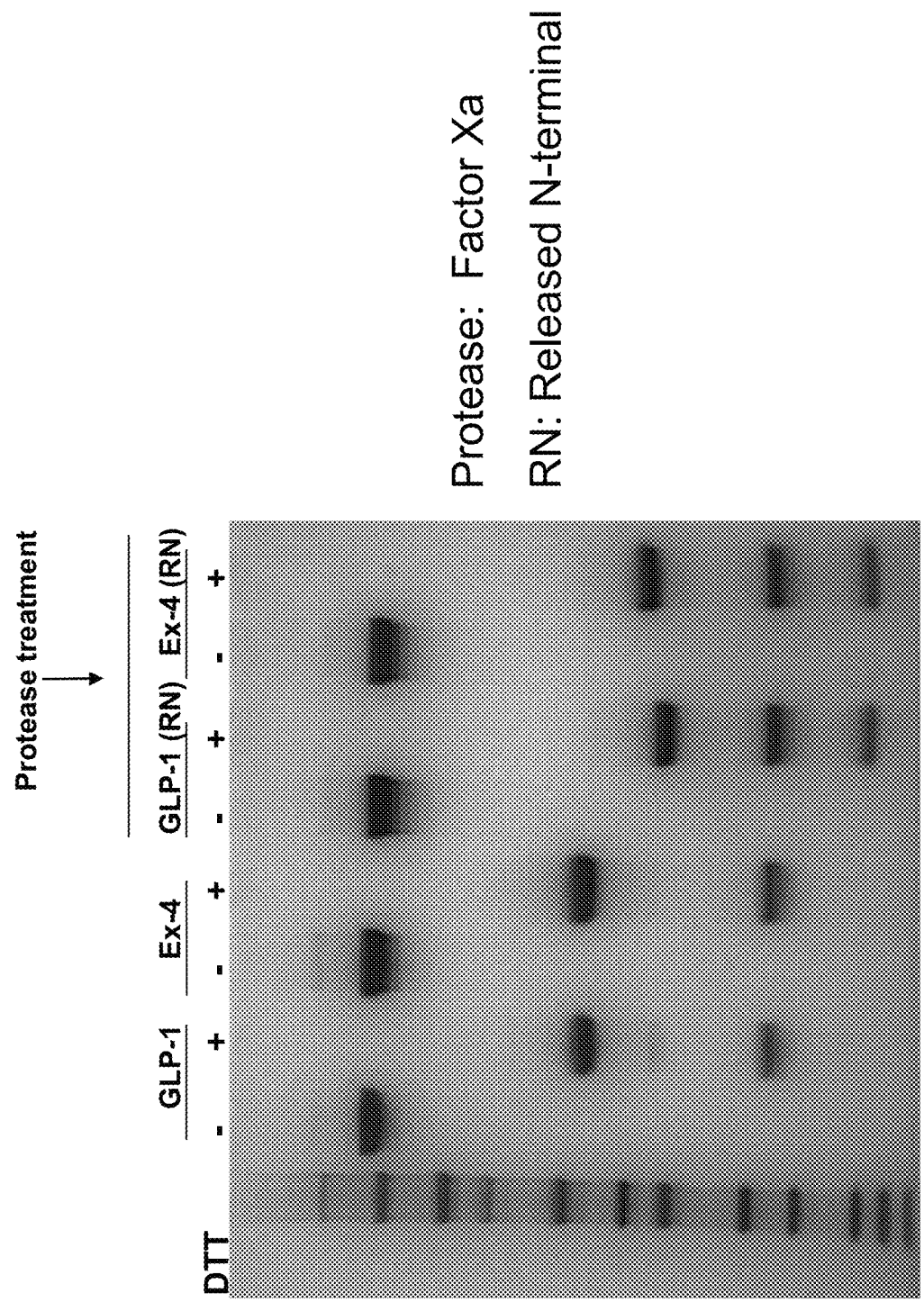

BLV1H12-Ex-4 fusion antibodies were expressed through transient transfections of free style HEK 293 cells with vectors encoding BLV1H12-Ex-4 fusion heavy chain and the BLV1H12 light chain. Expressed BLV1H12-Ex-4 fusion antibodies were secreted into the culture medium and harvested at 48 hours and 96 hours after transfection. The BLV1H12-Ex-4 fusion antibodies were purified by Protein A/G chromatography (Thermo Fisher Scientific, IL). BLV1H12-Ex-4 fusion antibodies were further treated with Factor Xa protease (GE Healthcare) following manufacture's protocol to release N-terminal of Ex-4 peptides fused to the BLV1H12 antibody. After treatment, BLV1H12-Ex-4 fusion antibodies were re-purified by Protein A/G affinity column to remove protease and analyzed by SDS-PAGE gel. FIG. 19 shows a western blot of expression of the immunoglobulin construct Ab-Exendin-4.

Example 20

In Vitro Study of BLV1H12-Ex-4 Clip Fusion Antibodies Activation Activities on GLP-1 Receptor (GLP-1R)

Figure 20:
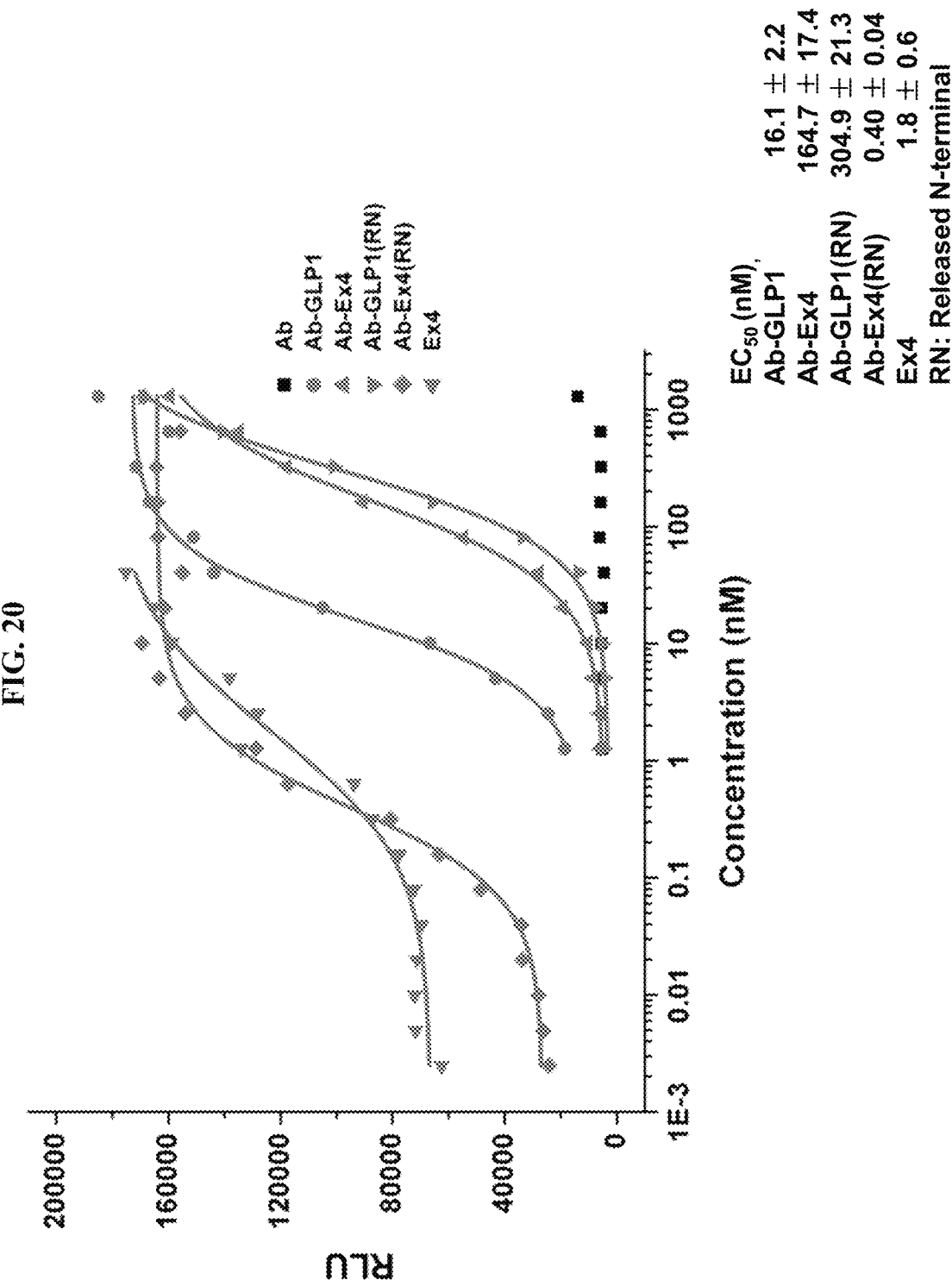

HEK293 cells expressing surface GLP-1R and cAMP responsive luciferase reporter gene were seeded in 384 well plates at a density of 5000 cells per well. After 24 h incubation at 37° C. with 5% $CO_2$, cells were treated with various concentrations of Exendin-4 peptides and BLV1H12-Ex-4 clip fusion antibodies and incubated for another 24 h. Subsequently, luciferase assay was performed using One-Glo luciferase reagent according manufacture's instruction (Promega). FIG. 20 and Tables 16-17 show the activity of Ab-Ex4 fusion antibodies on HEK293 cells expressing GLP-1 receptor.

TABLE 16

| Ab (nM) | RLU | Ab-GLP1 (nM) | RLU | Ab-Ex4 (nM) | RLU | Ab-GLP1(RN) (nM) | RLU |
|---|---|---|---|---|---|---|---|
| 1.26953 | 5200 | 1.26953 | 18600 | 1.26953 | 6120 | 1.26953 | 4740 |
| 2.53906 | 5000 | 2.53906 | 24500 | 2.53906 | 6360 | 2.53906 | 5800 |
| 5.07813 | 5600 | 5.07813 | 43200 | 5.07813 | 8500 | 5.07813 | 4400 |
| 10.15625 | 5500 | 10.15625 | 66560 | 10.15625 | 10420 | 10.15625 | 5200 |
| 20.3125 | 5380 | 20.3125 | 105040 | 20.3125 | 19340 | 20.3125 | 7780 |
| 40.625 | 4600 | 40.625 | 143780 | 40.625 | 27960 | 40.625 | 13600 |
| 81.25 | 6140 | 81.25 | 151060 | 81.25 | 54800 | 81.25 | 33760 |
| 162.5 | 5760 | 162.5 | 166640 | 162.5 | 90660 | 162.5 | 65800 |
| 325 | 5600 | 325 | 171400 | 325 | 117900 | 325 | 100920 |
| 650 | 5800 | 650 | 159780 | 650 | 134760 | 650 | 140640 |
| 1300 | 14000 | 1300 | 184960 | 1300 | 159660 | 1300 | 169060 |

TABLE 17

| Ab-Ex4(RN) (nM) | RLU | Ex4 (nM) | RLU |
|---|---|---|---|
| 0.00248 | 24120 | 0.00248 | 62500 |
| 0.00496 | 26320 | 0.00496 | 71840 |
| 0.00992 | 28140 | 0.00992 | 72160 |
| 0.01984 | 33500 | 0.01984 | 71360 |
| 0.03967 | 34180 | 0.03967 | 69720 |
| 0.07935 | 48860 | 0.07935 | 72380 |
| 0.15869 | 63460 | 0.15869 | 77680 |
| 0.31738 | 80740 | 0.31738 | 87220 |
| 0.63477 | 117240 | 0.63477 | 93760 |
| 1.26953 | 128740 | 1.26953 | 134100 |
| 2.53906 | 153820 | 2.53906 | 128120 |
| 5.07813 | 163020 | 5.07813 | 138220 |
| 10.15625 | 169360 | 10.15625 | 158700 |
| 20.3125 | 161380 | 20.3125 | 165300 |
| 40.625 | 154920 | 40.625 | 175200 |
| 81.25 | 163700 | | |
| 162.5 | 163860 | | |
| 325 | 164160 | | |
| 650 | 155700 | | |
| 1300 | 168740 | | |

Example 21

Constructing Vectors of BLV1H12-GLP-1 Clip Fusion Proteins for Expression in Mammalian Cells A gene encoding GLP-1 was synthesized by Genscript or IDT, and amplified by polymerase chain reaction (PCR). To optimize the folding and stability of fusion proteins, flexible linkers of (GGGGS)n (SEQ ID NO: 509) (n=0, 1) were added on both ends of the Moka1 fragment. Linkers of GGGGS (SEQ ID NO: 501) or GGGSGGGGS (SEQ ID NO: 337) were added on both ends of the GLP-1 fragment. A cleavage site of Factor Xa was placed in front of the N-terminal of GLP-1. In addition to this protease cleavage site, GGGGS linker (SEQ ID NO: 501) followed with a cysteine were also added on both ends of the GLP-1 fragment. Subsequently, PCR fragments of GLP-1 were grafted into the complementarity determining region 3 of the heavy chain (CDR3H) of BLV1H12 antibody by exploiting overlap extension PCR, to replace the 'knob' domain as shown in the crystal structure of BLV1H12. The expression vectors of BLV1H12-GLP-1 clip fusion proteins were generated by in-frame ligation of the amplified BLV1H12-GLP-1 fusion genes to the pFuse-hIgG1-Fc backbone vector (InvivoGen, CA). Similarly, the gene encoding the light chain of BLV1H12 antibody was cloned into the pFuse vector without hIgG1 Fc fragment. The obtained expression vectors were confirmed by sequencing. FIG. 8F and FIG. 8I show cartoons depicting a GLP1 peptide inserted into or replacing at least a portion of the knob domain of an immunoglobulin heavy chain region. FIG. 8I also shows a clipped version of the BLV1H12-GLP-1 fusion protein, wherein GLP-1 has a free N-terminus.

Example 22

Expression and Purification of BLV1H12-GLP-1 Clip Fusion Antibodies

BLV1H12-GLP-1 fusion antibodies were expressed through transient transfections of free style HEK 293 cells with vectors encoding BLV1H12-GLP-1 fusion heavy chain and the BLV1H12 light chain. Expressed BLV1H12-GLP-1 fusion antibodies were secreted into the culture medium and harvested at 48 hours and 96 hours after transfection. The BLV1H12-GLP-1 fusion antibodies were purified by Protein A/G chromatography (Thermo Fisher Scientific, IL). BLV1H12-GLP-1 fusion antibodies were further treated with Factor Xa protease (GE Healthcare) following manufacture's protocol to release N-terminal of GLP-1 peptide fused to the BLV1H12 antibody. After treatment, BLV1H12-GLP-1 clip fusion antibodies were re-purified by Protein A/G affinity column to remove protease and analyzed by SDS-PAGE gel. FIG. 19 provides a western blot of expression of the immunoglobulin construct Ab-GLP-1.

Example 23

In Vitro Study of BLV1H12-GLP-1 Clip Fusion Antibodies Activation Activities on GLP-1 Recepto (GLP-1R)

HEK293 cells expressing surface GLP-1R and cAMP responsive luciferase reporter gene were seeded in 384 well plates at a density of 5000 cells per well. After 24 h incubation at 37° C. with 5% $CO_2$, cells were treated with various concentrations of peptides and BLV1H12-GLP-1 clip fusion proteins and incubated for another 24 h. Subsequently, luciferase assay was performed using One-Glo luciferase reagent according manufacture's instruction (Promega). FIG. 20 and Table 16 show the activity of Ab-GLP-1 f fusion antibodies on HEK293 cells expressing GLP-1 receptor.

Example 24

Constructing Vectors of BLV1H12-hEPO Fusion Proteins for Expression in Mammalian Cells A gene encoding human EPO was synthesized by Genscript or IDT, and amplified by polymerase chain reaction (PCR). To optimize the folding and stability of fusion proteins, flexible linkers of (GGGGS (SEQ ID NO: 501)) were added on both ends of human EPO. Subsequently, PCR fragments of hEPO were grafted into the complementarity determining region 3 of the heavy chain (CDR3H) of BLV1H12 antibody by exploiting overlap extension PCR, to replace the 'knob' domain as shown in the crystal structure of BLV1H12. The expression vectors of BLV1H12-hEPO fusion proteins were generated by in-frame ligation of the amplified BLV1H12-fusion genes to the pFuse-hIgG1-Fc backbone vector (InvivoGen, CA). Similarly, the gene encoding the light chain of BLV1H12 antibody was cloned into the pFuse vector without hIgG1 Fc fragment. The obtained expression vectors were confirmed by sequencing. FIG. 8F and FIG. 8J show cartoons depicting hEPO peptide attached to the knob domain of an immunoglobulin heavy chain region.

Example 25

Expression and Purification of BLV1H12-hEPO Fusion Antibodies

BLV1H12-hEPO fusion antibodies were expressed through transient transfections of free style HEK 293 cells with vectors encoding BLV1H12-hEPO fusion heavy chain and the BLV1H12 light chain. Expressed BLV1H12-hEPO fusion antibodies were secreted into the culture medium and harvested at 48 hours and 96 hours after transfection. The BLV1H12-hEPO fusion antibodies were purified by Protein A/G chromatography (Thermo Fisher Scientific, IL), and analyzed by SDS-PAGE gel.

Example 26

Figure 21:
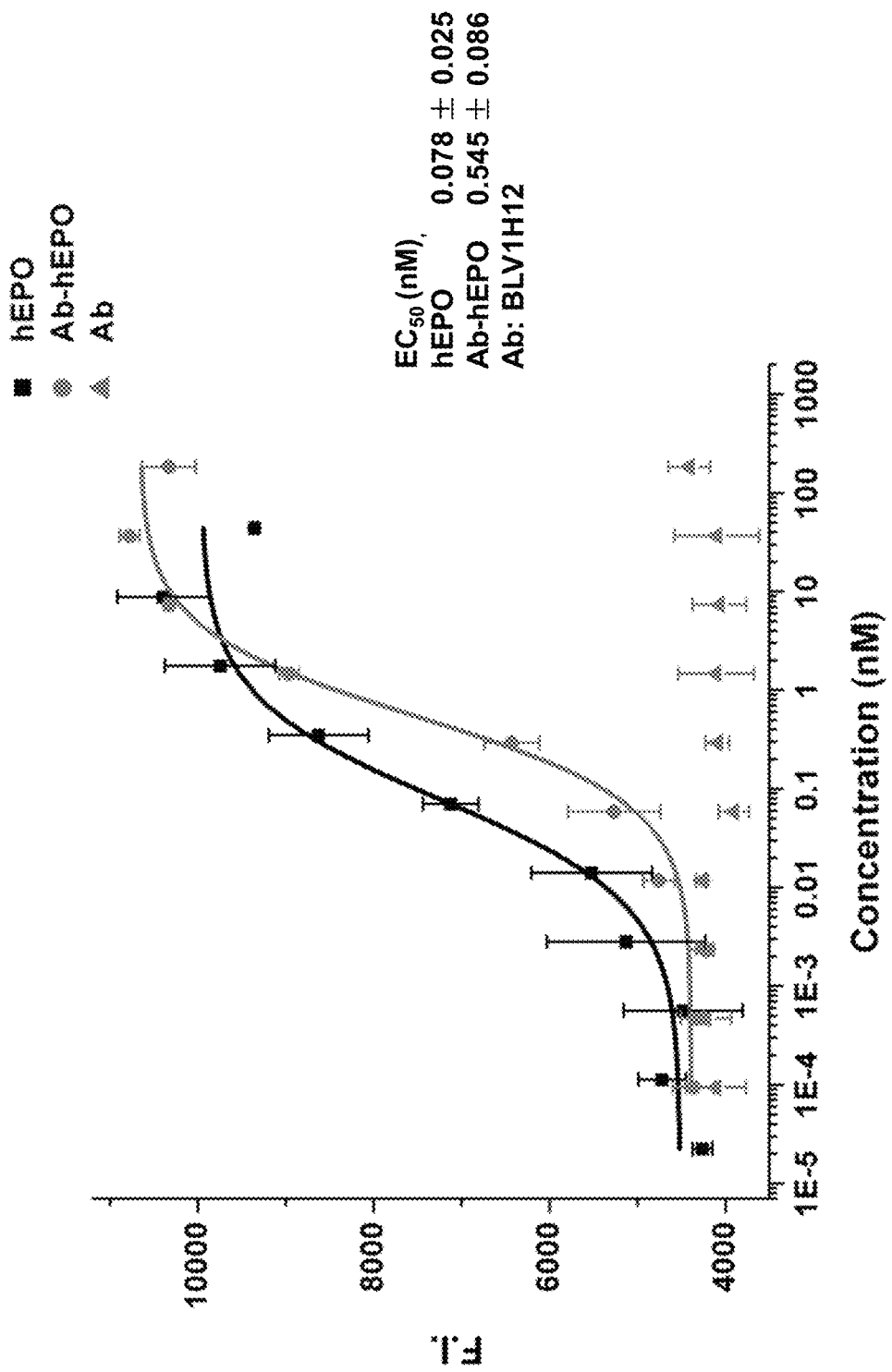

In Vitro Study of BLV1H12-hEPO Fusion Antibody Proliferative Activities on TF-1 Cells TF-1 cells were obtained from American Type Culture Collection (ATCC), VA, and cultured in RPMI-1640 medium supplemented with 10% fetal bovine serum (FBS), penicillin, streptomycin and 2 ng/mL granulocyte-macrophage colony-stimulating factor (GM-CSF). For proliferation assay, TF-1 cells were washed three times with RPMI-1640 medium and resuspended in RPMI-1640 medium with 10% FBS and penicillin and streptomycin at a density of $1.5 \times 10^5$ cells/ml. Cells were plated in 96-well plates and treated with varied concentrations of BLV1H12-hEPO fusion antibodies. After 72 h of incubation at 37° C. with 5% $CO_2$, cells viabilities were measured using AlamarBlue (Invitrogen) assay following manufacture's instruction. FIG. 21 and Table 18 show the proliferative activity of Ab-hEPO fusion antibodies on TF1 cells.

TABLE 18

| hEPO (nM) | F.I. | Ab-hEPO (nM) | F.I. | Ab (nM) | F.I. |
|---|---|---|---|---|---|
| 2.25E−05 | 4261.364 | 9.42E−05 | 4361.92 | 9.42E−05 | 4108.119 |
| 1.13E−04 | 4722.771 | 4.71E−04 | 4324.037 | 4.71E−04 | 4223.257 |
| 5.63E−04 | 4481.459 | 0.00236 | 4198.65 | 0.00236 | 4274.07 |
| 0.00282 | 5128.302 | 0.01178 | 4757.196 | 0.01178 | 4267.586 |
| 0.01408 | 5522.459 | 0.05888 | 5265.069 | 0.05888 | 3905.529 |
| 0.0704 | 7125.093 | 0.2944 | 6430.723 | 0.2944 | 4091.452 |
| 0.352 | 8629.194 | 1.472 | 8963.889 | 1.472 | 4109.106 |
| 1.76 | 9748.017 | 7.36 | 10330.18 | 7.36 | 4071.234 |
| 8.8 | 10392.97 | 36.8 | 10776.73 | 36.8 | 4100.011 |
| 44 | 9357.346 | 184 | 10330.44 | 184 | 4413.497 |

Example 27

Constructing Vectors of BLV1H12-hFGF21 Fusion Proteins for Expression in Mammalian Cells A gene encoding human FGF21 (hFGF21) was synthesized by Genscript or IDT, and amplified by polymerase chain reaction (PCR). To optimize the folding and stability of fusion proteins, flexible linkers of (GGGGS (SEQ ID NO:

501)) were added on both ends of human FGF21. Subsequently, PCR fragments of hFGF21 were grafted into the complementarity determining region 3 of the heavy chain (CDR3H) of BLV1H12 antibody by exploiting overlap extension PCR, to replace the 'knob' domain as shown in the crystal structure of BLV1H12. The expression vectors of BLV1H12-hFGF21 fusion proteins were generated by in-frame ligation of the amplified BLV1H12-fusion genes to the pFuse-hIgG1-Fc backbone vector (InvivoGen, CA). Similarly, the gene encoding the light chain of BLV1H12 antibody was cloned into the pFuse vector without hIgG1 Fc fragment. The obtained expression vectors were confirmed by sequencing.

Example 28

Expression and Purification of BLV1H12-hFGF21 Fusion Antibody

BLV1H12-hFGF21 fusion antibodies were expressed through transient transfections of free style HEK 293 cells with vectors encoding BLV1H12-hFGF21 fusion heavy chain and the BLV1H12 light chain. Expressed BLV1H12-hFGF21 fusion antibodies were secreted into the culture medium and harvested every 48 hours for twice after transfection. The BLV1H12-hFGF21 fusion antibodies were purified by Protein A/G chromatography (Thermo Fisher Scientific, IL), and analyzed by SDS-PAGE gel.

Example 29

Constructing Vectors of BLV1H12-hGMCSF Fusion Proteins for Expression in Mammalian Cells A gene encoding human GMCSF (hGMCSF) was synthesized by Genscript or IDT, and amplified by polymerase chain reaction (PCR). To optimize the folding and stability of fusion proteins, flexible linkers of (GGGGS (SEQ ID NO: 501)) were added on both ends of human GMCSF. Subsequently, PCR fragments of hGMCSF were grafted into the complementarity determining region 3 of the heavy chain (CDR3H) of BLV1H12 antibody by exploiting overlap extension PCR, to replace the 'knob' domain as shown in the crystal structure of BLV1H12. The expression vectors of BLV1H12-hGMCSF fusion proteins were generated by in-frame ligation of the amplified BLV1H12-hGMCSF fusion genes to the pFuse-hIgG1-Fc backbone vector (InvivoGen, CA). Similarly, the gene encoding the light chain of BLV1H12 antibody was cloned into the pFuse vector without hIgG1 Fc fragment. The obtained expression vectors were confirmed by sequencing.

Example 30

Expression and Purification of BLV1H12-hGMCSF Fusion Antibodies

BLV1H12-hGMCSF fusion antibodies can be expressed through transient transfections of free style HEK 293 cells with vectors encoding BLV1H12-hGMCSF fusion heavy chain and the BLV1H12 light chain. Expressed BLV1H12-hGMCSF fusion antibodies can be secreted into the culture medium and harvested at 48 hours and 96 hours after transfection. The BLV1H12-hGMCSF fusion antibodies can be purified by Protein A/G chromatography (Thermo Fisher Scientific, IL), and analyzed by SDS-PAGE gel.

Example 31

Constructing Vectors of BLV1H12-hIFN-b Proteins for Expression in Mammalian Cells A gene encoding human interferon-beta (hIFN-b) was synthesized by Genscript or IDT, and amplified by polymerase chain reaction (PCR). To optimize the folding and stability of fusion proteins, flexible linkers of (GGGGS (SEQ ID NO: 501)) were added on both ends of human interferon-beta. Subsequently, PCR fragments of hIFN-b were grafted into the complementarity determining region 3 of the heavy chain (CDR3H) of BLV1H12 antibody by exploiting overlap extension PCR, to replace the 'knob' domain as shown in the crystal structure of BLV1H12. The expression vectors of BLV1H12-hIFN-b fusion proteins were generated by in-frame ligation of the amplified BLV1H12-hIFN-b fusion genes to the pFuse-hIgG1-Fc backbone vector (InvivoGen, CA). Similarly, the gene encoding the light chain of BLV1H12 antibody was cloned into the pFuse vector without hIgG1 Fc fragment. The obtained expression vectors were confirmed by sequencing.

Example 32

Expression and Purification of BLV1H12-hIFN-b Fusion Antibodies

BLV1H12-hIFN-b fusion antibodies can be expressed through transient transfections of free style HEK 293 cells with vectors encoding BLV1H12-hIFN-b fusion heavy chain and the BLV1H12 light chain. Expressed BLV1H12-hIFN-b fusion antibodies can be secreted into the culture medium and harvested at 48 hours and 96 hours after transfection. The BLV1H12-hIFN-b fusion antibodies can be purified by Protein A/G chromatography (Thermo Fisher Scientific, IL), and analyzed by SDS-PAGE gel.

Example 33

Constructing Vectors of BLV1H12-fusion Proteins for Expression in Mammalian Cells Genes encoding encoding various genes were synthesized by Genscript (NJ, USA) and amplified by polymerase chain reaction (PCR). To optimize the folding and stability of the immunoglobulin constructs, one or more flexible linkers of (GGGGS)n (SEQ ID NO: 509) (n=0, 1), GGGSGGGGS (SEQ ID NO: 337), and/or GGGGSGGGS (SEQ ID NO: 338) were added on both ends of the gene fragment. Subsequently, PCR fragments of the genes with varied lengths of linkers were grafted into the complementarity determining region 3 of the heavy chain (CDR3H) of BLV1H12 antibody by exploiting overlap extension PCR, to replace at least a portion of the 'knob' domain as shown in the crystal structure of BLV1H12 (FIGS. 8A-8J). The expression vectors of BLV1H12-fusion proteins were generated by in-frame ligation of the amplified BLV1H12-fusion genes to the pFuse-hIgG1-Fc backbone vector (InvivoGen, CA). Similarly, the gene encoding the light chain of BLV1H12 antibody was cloned into the pFuse vector without hIgG1 Fc fragment. The obtained expression vectors were confirmed by sequencing.

Nucleic acid sequences of the BLV1H12-fusion proteins are displayed in Table 19 (SEQ ID NOS: 1-15). Peptide sequences of the BLVH12-fusion proteins are displayed in Table 21 (SEQ ID NOS: 23-37). As shown in the Table 19 and Table 21, the bovine heavy chain sequence is in bold font; the human heavy chain sequence is highlighted with a dashed underline; the non-antibody sequence is in italicized font; the stalk domain is in bold font and underlined; the knob domain is in bold font and double underlined; the linker sequence is in *italicized font and squiggly underlined*.

Example 34

Constructing Vectors of BLV1H12-IL8 Fusion Proteins for Expression in Mammalian Cells Gene encoding a human IL-8 sequence (see, e.g., SEQ ID NO: 317 corresponding to amino acids 26-99 of IL-8, designated IL8 herein) was amplified from cDNA (OriGene) by polymerase chain reaction (PCR). In some constructs, a linker (e.g., GSG or repeats of GSG ("GSG" disclosed as SEQ ID NO: 342)) may be added on one or both ends of the IL8 fragment. Subsequently, PCR fragments of IL8 with or without a linker were grafted into the complementarity determining region 3 of the heavy chain (CDR3H) of BLV1H12 antibody by PCR, to replace the 'knob' domain as shown in the crystal structure of BLV1H12. The expression vectors of BLV1H12-IL8 fusion proteins were generated by in-frame ligation of the amplified BLV1H12-IL8 fusion genes to CH1-CH2-CH3 in a pFuse-backbone vector (InvivoGen, CA). The BLV1H12-IL8 heavy chain variable region sequence is shown as SEQ ID NO: 16 (nucleotide) and SEQ ID NO: 38 (amino acid). Similarly, the gene encoding the light chain of BLV1H12 antibody was cloned into a pFuse vector without hIgG1 Fc fragment. The obtained expression vectors were confirmed by sequencing.

Example 35

Expression of BLV1H12-IL8 Fusion Proteins

BLV1H12-IL8 fusion proteins were expressed through transient transfections of 293T cells or Freestyle™ 293-F cells with vectors encoding BLV1H12-IL8 heavy and light chains. Expressed fusion proteins were secreted into the culture medium and culture supernatants obtained after 2 days of cell culture. The expression of BLV1H12-IL8 fusion proteins in the supernatants was determined by ELISA to be 37.2 nM Example 36

In Vitro Study of Activities of the BLV1H12-IL8 Fusion Proteins on CXCR1 Expressing Cells Briefly, a cell line expressing functionally validated CXCR1 derived from U2OS cells was obtained from DiscoveRx and cultured per manufacturer's instructions (Cat#93-0226C3, DiscoveRx Corporation, Freemont, Calif.). The parental cell line U2OS was obtained from ATCC and cultured under the same conditions as the CXCR1 cells. Cell culture supernatants from Example 2 above were then tested for binding to cells by flow cytometry. The adherent U2OS or CXCR1-U2OS cells were dissociated with Accutase (Innovative Cell Technologies, Inc., San Diego, Calif.), neutralized with an equal volume of media containing 10% serum, centrifuged at 1000 g, and resuspended in PBS with 2% BSA. Next, cells were dispensed into microtiter plates to achieve between 30,000 to 300,000 cells per well, centrifuged again, and resuspended in cell culture supernatant containing expressed IgG, or a dilution of IgG-containing cell culture supernatant. A fluorescent-conjugated anti-Human Fc antibody was used to detect binding of the expressedBLV1H12-IL8 fusion proteins to cells. Subsequently, cell fluorescence was measured by flow cytometry (e.g., FACS), and median Arbitrary Fluorescence Units (AFU) were calculated, revealing the extent of IgG binding to those cells. The ratio of median fluorescence (IgG binding) of CXCR1-U2OS cells versus U2OS parental cells shows that the BLV1H12-IL8 fusion protein has specificity for CXCR1 (Table 27).

TABLE 27

| | BLV1H12 (Median Arbitrary Fluorescence Units (AFU)) | BLV1H12-IL8 (Median Arbitrary Fluorescence Units (AFU)) |
|---|---|---|
| Parental U2OS | 4 | 76 |
| CXCR1-U2OS | 4 | 707 |

Example 37

Constructing Vectors of BLV1H12-ziconotide Fusion Proteins for Expression in Mammalian Cells Gene encoding a ziconotide sequence (see, e.g., SEQ ID NO: 318) was prepared from multiple oligonucleotides and then amplified by polymerase chain reaction (PCR). In some constructs, a linker (e.g., GSG or repeats of GSG ("GSG" disclosed as SEQ ID NO: 342)) may be added on one or both ends of the ziconotide fragment. Subsequently, PCR fragments of ziconotide with or without a linker were grafted into the complementarity determining region 3 of the heavy chain (CDR3H) of BLV1H12 antibody by PCR, to replace the 'knob' domain as shown in the crystal structure of BLV1H12. The expression vectors of BLV1H12-ziconotide fusion proteins were generated by in-frame ligation of the amplified BLV1H12-ziconotide fusion genes to CH1-CH2-CH3 in a pFuse-backbone vector (InvivoGen, CA). The BLV1H12-ziconotide heavy chain variable region sequence is shown as SEQ ID NO: 17 (nucleotide) and SEQ ID NO: 39 (amino acid). Similarly, the gene encoding the light chain of BLV1H12 antibody was cloned into a pFuse vector without hIgG1 Fc fragment. The obtained expression vectors were confirmed by sequencing.

Example 38

Expression of BLV1H12-ziconotide Fusion Proteins

BLV1H12-ziconotide fusion proteins were expressed through transient transfections of 293T cells or Freestyle™ 293-F cells with vectors encoding BLV1H12-ziconotide heavy and light chains. Expressed fusion proteins were secreted into the culture medium and culture supernatants obtained after 2 days of cell culture. The expression of BLV1H12-ziconotide fusion proteins in the supernatants was determined by ELISA and normalized as compared to the IL8 construct in Example 35 above to be 94.7% of the IL8 construct.

Example 39

Constructing Vectors of BLV1H12-somatostatin Fusion Proteins for Expression in Mammalian Cells Gene encoding a somatostatin sequence (see, e.g., SEQ ID NO: 319) was prepared from multiple oligonucleotides and then amplified by polymerase chain reaction (PCR). In some constructs, a linker (e.g., GSG or repeats of GSG ("GSG" disclosed as SEQ ID NO: 342)) may be added on one or both ends of the somatostatin fragment. Subsequently, PCR fragments of somatostatin with or without a linker were grafted into the complementarity determining region 3 of the heavy chain (CDR3H) of BLV1H12 antibody by PCR, to replace the 'knob' domain as shown in the crystal structure of BLV1H12. The expression vectors of BLV1H12-somatostatin fusion proteins were generated by in-frame ligation of the amplified BLV1H12-somatostatin fusion genes to CH1-CH2-CH3 in a pFuse-backbone vector (InvivoGen, CA). The BLV1H12-somatostatin heavy chain variable region sequence is shown as SEQ ID NO: 18 (nucleotide) and SEQ ID NO: 40 (amino acid). Similarly, the gene encoding the light chain of BLV1H12 antibody was cloned into a pFuse vector without hIgG1 Fc fragment. The obtained expression vectors were confirmed by sequencing.

Example 40

Expression of BLV1H12-Somatostatin Fusion Proteins

BLV1H12-somatostatin fusion proteins were expressed through transient transfections of 293T cells or Freestyle™ 293-F cells with vectors encoding BLV1H12-somatostatin heavy and light chains. Expressed fusion proteins were secreted into the culture medium and culture supernatants obtained after 2 days of cell culture. The expression of BLV1H12-somatostatin fusion proteins in the supernatants was determined by ELISA and normalized as compared to the IL8 construct in Example 35 above to be 46.5% of the IL8 construct.

Example 41

Constructing Vectors of BLV1H12-Chlorotoxin Fusion Proteins for Expression in Mammalian Cells Gene encoding a chlorotoxin sequence (see, e.g., SEQ ID NO: 320) was prepared from multiple oligonucleotides and then amplified by polymerase chain reaction (PCR). In some constructs, a linker (e.g., GSG or repeats of GSG ("GSG" disclosed as SEQ ID NO: 342)) may be added on one or both ends of the chlorotoxin fragment. Subsequently, PCR fragments of chlorotoxin with or without a linker were grafted into the complementarity determining region 3 of the heavy chain (CDR3H) of BLV1H12 antibody by PCR, to replace the 'knob' domain as shown in the crystal structure of BLV1H12. The expression vectors of BLV1H12-chlorotoxin fusion proteins were generated by in-frame ligation of the amplified BLV1H12-chlorotoxin fusion genes to CH1-CH2-CH3 in a pFuse-backbone vector (InvivoGen, CA). The BLV1H12-chlorotoxin heavy chain variable region sequence is shown as SEQ ID NO: 19 (nucleotide) and SEQ ID NO: 41 (amino acid). Similarly, the gene encoding the light chain of BLV1H12 antibody was cloned into a pFuse vector without hIgG1 Fc fragment. The obtained expression vectors were confirmed by sequencing.

Example 42

Expression of BLV1H12-Chlorotoxin Fusion Proteins

BLV1H12-chlorotoxin fusion proteins were expressed through transient transfections of 293T cells or Freestyle™ 293-F cells with vectors encoding BLV1H12-chlorotoxin heavy and light chains. Expressed fusion proteins were secreted into the culture medium and culture supernatants obtained after 2 days of cell culture. The expression of BLV1H12-chlorotoxin fusion proteins in the supernatants was determined by ELISA and normalized as compared to the IL8 construct in Example 35 above to be 39.7% of the IL8 construct.

Example 43

Constructing Vectors of BLV1H12-SDF-1 (Alpha) Fusion Proteins for Expression in Mammalian Cells Gene encoding a SDF-1 alpha sequence (see, e.g., SEQ ID NO: 321) was amplified from cDNA (OriGene) by polymerase chain reaction (PCR). In some constructs, a linker (e.g., GSG or repeats of GSG ("GSG" disclosed as SEQ ID NO: 342)) may be added on one or both ends of the SDF-1 (alpha) fragment. Subsequently, PCR fragments of SDF-1 (alpha) with or without a linker were grafted into the complementarity determining region 3 of the heavy chain (CDR3H) of BLV1H12 antibody by PCR, to replace the 'knob' domain as shown in the crystal structure of BLV1H12. The expression vectors of BLV1H12-SDF-1 (alpha) fusion proteins were generated by in-frame ligation of the amplified BLV1H12-SDF-1 (alpha) fusion genes to CH1-CH2-CH3 in a pFuse-backbone vector (InvivoGen, CA). The BLV1H12-SDF-1 (alpha) heavy chain variable region sequence is shown as SEQ ID NO: 20 (nucleotide) and SEQ ID NO: 42 (amino acid). Similarly, the gene encoding the light chain of BLV1H12 antibody was cloned into a pFuse vector without hIgG1 Fc fragment. The obtained expression vectors were confirmed by sequencing.

Example 44

Expression of BLV1H12-SDF-1 (Alpha) Fusion Proteins

BLV1H12-SDF-1 (alpha) fusion proteins were expressed through transient transfections of 293T cells or Freestyle™ 293-F cells with vectors encoding BLV1H12-SDF-1 (alpha) heavy and light chains. Expressed fusion proteins were secreted into the culture medium and culture supernatants obtained after 2 days of cell culture. The expression of BLV1H12-SDF-1 (alpha) fusion proteins in the supernatants was determined by ELISA and normalized as compared to the IL8 construct in Example 35 above to be 38.9% of the IL8 construct.

Example 45

Constructing Vectors of BLV1H12-IL21 Fusion Proteins for Expression in Mammalian Cells Gene encoding an IL21 sequence (see, e.g., SEQ ID NO: 322) was amplified from cDNA (OriGene) by polymerase chain reaction (PCR). In some constructs, a linker (e.g., GSG or repeats of GSG ("GSG" disclosed as SEQ ID NO: 342)) may be added on one or both ends of the IL21 fragment. Subsequently, PCR fragments of IL21 with or without a linker were grafted into the complementarity determining region 3 of the heavy chain (CDR3H) of BLV1H12 antibody by PCR, to replace the 'knob' domain as shown in the crystal structure of BLV1H12. The expression vectors of BLV1H12-IL21 fusion proteins were generated by in-frame ligation of the amplified BLV1H12-IL21 fusion genes to CH1-CH2-CH3 in a pFuse-backbone vector (InvivoGen, CA). The BLV1H12-IL21 heavy chain variable region sequence is shown as SEQ ID NO: 21 (nucleotide) and SEQ ID NO: 43 (amino acid). Similarly, the gene encoding the light chain of BLV1H12 antibody was cloned into a pFuse vector without hIgG1 Fc fragment. The obtained expression vectors were confirmed by sequencing.

Example 46

Expression of BLV1H12-IL21 Fusion Proteins

BLV1H12-IL21 fusion proteins were expressed through transient transfections of 293T cells or Freestyle™ 293-F cells with vectors encoding BLV1H12-IL21 heavy and light chains. Expressed fusion proteins were secreted into the culture medium and culture supernatants obtained after 2 days of cell culture. The expression of BLV1H12-IL21 fusion proteins in the supernatants was determined by ELISA and normalized as compared to the IL8 construct in Example 35 above to be 32.3% of the IL8 construct.

Example 47

Constructing Vectors of BLV1H12-Protoxin2 Fusion Proteins for Expression in Mammalian Cells Gene encoding protoxin2 was synthesized by Genscript or IDT, and amplified by polymerase chain reaction (PCR). To optimize the folding and stability of fusion proteins, flexible linkers of GGGGS (SEQ ID NO: 501) were added on both ends of protoxin2 fragments. Subsequently, PCR fragments of protoxin2 (called protoxin2-L1) were grafted into the complementarity determining region 3 of the heavy chain (CDR3H) of BLV1H12 antibody by exploiting overlap extension PCR, to replace the 'knob' domain as shown in the crystal structure of BLV1H12. The expression vectors of BLV1H12-fusion proteins were generated by in-frame ligation of the amplified BLV1H12-protoxin2-L1 fusion genes (SEQ ID NO: 15) to the pFuse-hIgG1-Fc backbone vector (InvivoGen, CA). Similarly, the gene encoding the light chain of BLV1H12 antibody was cloned into the pFuse vector without hIgG1 Fc fragment. The obtained expression vectors were confirmed by sequencing.

Example 48

Expression and Purification of BLV1H12-Protoxin2-L1 Fusion Proteins

BLV1H12-protoxin2-L1 fusion antibodies were expressed through transient transfections of free style HEK 293 cells with vectors encoding BLV1H12-protoxin2 fusion heavy chain and the BLV1H12 light chain. Expressed BLV1H12-protoxin2-L1 fusion antibodies were secreted into the culture medium and harvested at 48 hours and 96 hours after transfection. The BLV1H12-protoxin2-L1 fusion antibodies were purified by Protein A/G chromatography (Thermo Fisher Scientific, IL), and analyzed by SDS-PAGE gel (FIG. 15B).

Example 49

Constructing Vectors of BLV1H12-ProTxII Fusion Proteins for Expression in Mammalian Cells Gene encoding a ProTxII sequence (see, e.g., SEQ ID NO: 323) was prepared from multiple oligonucleotides and then amplified by polymerase chain reaction (PCR). In some constructs, a linker (e.g., GSG or repeats of GSG ("GSG" disclosed as SEQ ID NO: 342)) may be added on one or both ends of the ProTxII fragment. Subsequently, PCR fragments of ProTxII with or without a linker were grafted into the complementarity determining region 3 of the heavy chain (CDR3H) of BLV1H12 antibody by PCR, to replace the 'knob' domain as shown in the crystal structure of BLV1H12. The expression vectors of BLV1H12-ProTxII fusion proteins were generated by in-frame ligation of the amplified BLV1H12-ProTxII fusion genes to CH1-CH2-CH3 in a pFuse-backbone vector (InvivoGen, CA). The BLV1H12-ProTxII heavy chain variable region sequence is shown as SEQ ID NO: 22 (nucleotide) and SEQ ID NO: 44 (amino acid). Similarly, the gene encoding the light chain of BLV1H12 antibody was cloned into a pFuse vector without hIgG1 Fc fragment. The obtained expression vectors were confirmed by sequencing.

Example 50

Expression of BLV1H12-ProTxII Fusion Proteins

BLV1H12-ProTxII fusion proteins were expressed through transient transfections of 293T cells or Freestyle™ 293-F cells with vectors encoding BLV1H12-ProTxII heavy and light chains. Expressed fusion proteins were secreted into the culture medium and culture supernatants obtained after 2 days of cell culture. The expression of BLV1H12-ProTxII fusion proteins in the supernatants was determined by ELISA and normalized as compared to the IL8 construct in Example 35 above to be 2.1% of the IL8 construct.

For the disclosure herein, the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

TABLE 19

| Description | SEQ ID NO: | Sequence |
|---|---|---|
| Light Chain | 1 | CAGGCCGTCCTGAACCAGCCAAGCAGCGTCTCCGGGTCTCTGG |
| | | GGCAGCGGGTCTCAATCACCTGTAGCGGGTCTTCCTCCAATGTC |

TABLE 19-continued

| Description | SEQ ID NO: | Sequence |
|---|---|---|
| | | GGCAACGGCTACGTGTCTTGGTATCAGCTGATCCCTGGCAGTGC |
| | | CCCACGAACCCTGATCTACGGCGACACATCCAGAGCTTCTGGG |
| | | GTCCCCGATCGGTTCTCAGGGAGCAGATCCGGAAACACAGCTA |
| | | CTCTGACCATCAGCTCCCTGCAGGCTGAGGACGAAGCAGATTA |
| | | TTTCTGCGCATCTGCCGAGGACTCTAGTTCAAATGCCGTGTTTG |
| | | GAAGCGGCACCACACTGACAGTCCTGGGGCAGCCCAAGAGTCC |
| | | CCCTTCAGTGACTCTGTTCCCACCCTCTACCGAGGAACTGAACG |
| | | GAAACAAGGCCACACTGGTGTGTCTGATCAGCGACTTTTACCCT |
| | | GGATCCGTCACTGTGGTCTGGAAGGCAGATGGCAGCACAATTA |
| | | CTAGGAACGTGGAAACTACCCGCGCCTCCAAGCAGTCTAATAG |
| | | TAAATACGCCGCCAGCTCCTATCTGAGCCTGACCTCTAGTGATT |
| | | GGAAGTCCAAAGGGTCATATAGCTGCGAAGTGACCCATGAAGG |
| | | CTCAACCGTGACTAAGACTGTGAAACCATCCGAGTGCTCC |
| Heavy Chain- no insertion | 2 | CAGGTCCAGCTGAGAGAGAGCGGCCCTTCACTGGTCAAGC |
| | | CATCCCAGACACTGAGCCTGACATGCACAGCAAGCGGGTTT |
| | | TCACTGAGCGACAAGGCAGTGGGATGGGTCCGACAGGCAC |
| | | CAGGAAAAGCCCTGGAATGGCTGGGCAGCATCGATACCGG |
| | | CGGGAACACAGGGTACAATCCCGGACTGAAGAGCAGACTG |
| | | TCCATTACCAAGGACAACTCTAAAAGTCAGGTGTCACTGAG |
| | | CGTGAGCTCCGTCACCACAGAGGATAGTGCAACTTACTATT |
| | | GCACCTCTGTGCACCAGGAAACTAAGAAATACCAG<u>AGCTGT</u> |
| | | <u>CCTGACGGCTATCGGGAGAGATCTGATTGCAGTAATAGGCC</u> |
| | | <u>AGCTTGTGGCACATCCGACTGCTGTCGCGTGTCTGTCTTCG</u> |
| | | <u>GGAACTGCCTGACTACCCTGCCTGTGTCCTACTCTTATACC</u> |
| | | <u>TACAATTATGAATGGCATGTGGATGTCTGGGGACAGGGCCT</u> |
| | | GCTGGTGACAGTCTCTAGT |
| IFN-beta | 3 | CAGGTCCAGCTGAGAGAGAGCGGCCCTTCACTGGTCAAGC |
| | | CATCCCAGACACTGAGCCTGACATGCACAGCAAGCGGGTTT |
| | | TCACTGAGCGACAAGGCAGTGGGATGGGTCCGACAGGCAC |
| | | CAGGAAAAGCCCTGGAATGGCTGGGCAGCATCGATACCGG |
| | | CGGGAACACAGGGTACAATCCCGGACTGAAGAGCAGACTG |
| | | TCCATTACCAAGGACAACTCTAAAAGTCAGGTGTCACTGAG |
| | | CGTGAGCTCCGTCACCACAGAGGATAGTGCAACTTACTATT |
| | | GCACCTCTGTGCACCAGGAAACTAAGAAATACCAG<u>AGCGGG</u> |
| | | <u>GGTGGCGGAAGC</u>*ATGAGCTACAACTTGCTTGGATTCCTACAAAGAA* |
| | | *GCAGCAATTTTCAGTGTCAGAAGCTCCTGTGGCAATTGAATGGGAG* |
| | | *GCTTGAATACTGCCTCAAGGACAGGATGAACTTTGACATCCCTGAG* |

TABLE 19-continued

| Description | SEQ ID NO: | Sequence |
|---|---|---|
| | | *GAGATTAAGCAGCTGCAGCAGTTCCAGAAGGAGGACGCCGCATTGA* |
| | | *CCATCTATGAGATGCTCCAGAACATCTTTGCTATTTTCAGACAAGATT* |
| | | *CATCTAGCACTGGCTGGAATGAGACTATTGTTGAGAACCTCCTGGCT* |
| | | *AATGTCTATCATCAGATAAACCATCTGAAGACAGTCCTGGAAGAAAA* |
| | | *ACTGGAGAAAGAAGATTTCACCAGGGGAAAACTCATGAGCAGTCTG* |
| | | *CACCTGAAAAGATATTATGGGAGGATTCTGCATTACCTGAAGGCCAA* |
| | | *GGAGTACAGTCACTGTGCCTGGACCATAGTCAGAGTGGAAATCCTA* |
| | | *AGGAACTTTTACTTCATTAACAGACTTACAGGTTACCTCCGAAACGG* |
| | | *CGGAGGTGGGAGT*<u>TCTTATACCTACAATTATGAATGG</u>CATGT |
| | | GGATGTCTGGGGACAGGGCCTGCTGGTGACAGTCTCTAGT |
| | | GCTTCCACAACTGCACCAAAGGTGTACCCCCTGTCAAGCTG |
| | | CTGTGGGGACAAATCCTCTAGTACCGTGACACTGGGATGCC |
| | | TGGTCTCAAGCTATATGCCCGAGCCTGTGACTGTCACCTGG |
| | | AACTCAGGAGCCCTGAAAAGCGGAGTGCACACCTTCCCAGC |
| | | TGTGCTGCAGTCCTCTGGCCTGTATAGCCTGAGTTCAATGG |
| | | TGACAGTCCCCGGCAGTACTTCAGGGCAGACCTTCACCTGTAA |
| | | TGTGGCCCATCCTGCCAGCTCCACCAAAGTGGACAAAGCAGTG |
| | | GAACCCAAATCTTGC<u>GACAAAACTCACACATGCCCACCGTGCC</u> |
| | | <u>CAGCACCTGAACTCCTGGGGGGACCGTCAGTCTTCCTCTTCCCC</u> |
| | | <u>CCAAAACCCAAGGACACCCTCATGATCTCCCGGACCCCTGAGG</u> |
| | | <u>TCACATGCGTGGTGGTGGACGTGAGCCACGAAGACCCTGAGGT</u> |
| | | <u>CAAGTTCAACTGGTACGTGGACGGCGTGGAGGTGCATAATGCC</u> |
| | | <u>AAGACAAAGCCGCGGGAGGAGCAGTACAACAGCACGTACCGT</u> |
| | | <u>GTGGTCAGCGTCCTCACCGTCCTGCACCAGGACTGGCTGAATG</u> |
| | | <u>GCAAGGAGTACAAGTGCAAGGTCTCCAACAAAGCCCTCCCAGC</u> |
| | | <u>CCCCATCGAGAAAACCATCTCCAAAGCCAAAGGGCAGCCCCGA</u> |
| | | <u>GAACCACAGGTGTACACCCTGCCCCCATCCCGGGATGAGCTGA</u> |
| | | <u>CCAAGAACCAGGTCAGCCTGACCTGCCTGGTCAAAGGCTTCTA</u> |
| | | <u>TCCCAGCGACATCGCCGTGGAGTGGGAGAGCAATGGGCAGCCG</u> |
| | | <u>GAGAACAACTACAAGACCACGCCTCCCGTGCTGGACTCCGACG</u> |
| | | <u>GCTCCTTCTTCCTCTACAGCAAGCTCACCGTGGACAAGAGCAGG</u> |

TABLE 19-continued

| Description | SEQ ID NO: | Sequence |
|---|---|---|
| | | TGGCAGCAGGGGAACGTCTTCTCATGCTCCGTGATGCATGAGG |
| | | CTCTGCACAACCACTACACGCAGAAGAGCCTCTCCCTGTCTCCG |
| | | GGTAAA |
| bGCSF-L0 | 4 | CAGGTCCAGCTGAGAGAGAGCGGCCCTTCACTGGTCAAGC |
| | | CATCCCAGACACTGAGCCTGACATGCACAGCAAGCGGGTTT |
| | | TCACTGAGCGACAAGGCAGTGGGATGGGTCCGACAGGCAC |
| | | CAGGAAAAGCCCTGGAATGGCTGGGCAGCATCGATACCGG |
| | | CGGGAACACAGGGTACAATCCCGGACTGAAGAGCAGACTG |
| | | TCCATTACCAAGGACAACTCTAAAAGTCAGGTGTCACTGAG |
| | | CGTGAGCTCCGTCACCACAGAGGATAGTGCAACTTACTATT |
| | | GCACCTCTGTGCACCAGGAAACTAAGAAATACCAGAGCACC |
| | | CCCCTTGGCCCTGCCCGATCCCTGCCCCAGAGCTTCCTGCTCAAGT |
| | | GCTTAGAGCAAGTGAGGAAAATCCAGGCTGATGGCGCCGAGCTGC |
| | | AGGAGAGGCTGTGTGCCGCCCACAAGCTGTGCCACCCGGAGGAGC |
| | | TGATGCTGCTCAGGCACTCTCTGGGCATCCCCCAGGCTCCCCTAAG |
| | | CAGCTGCTCCAGCCAGTCCCTGCAGCTGACGAGCTGCCTGAACCAA |
| | | CTACACGGCGGCCTCTTTCTCTACCAGGGCCTCCTGCAGGCCCTGG |
| | | CGGGCATCTCCCCAGAGCTGGCCCCCACCTTGGACACACTGCAGC |
| | | TGGACGTCACTGACTTTGCCACGAACATCTGGCTGCAGATGGAGGA |
| | | CCTGGGGGCGGCCCCCGCTGTGCAGCCCACCCAGGGCGCCATGC |
| | | CGACCTTCACTTCAGCCTTCCAACGCAGAGCAGGAGGGGTCCTGGT |
| | | TGCTTCCCAGCTGCATCGTTTCCTGGAGCTGGCATACCGTGGCCTG |
| | | CGCTACCTTGCTGAGCCCTCTTATACCTACAATTATGAATGGC |
| | | ATGTGGATGTCTGGGGACAGGGCCTGCTGGTGACAGTCTCT |
| | | AGTGCTTCCACAACTGCACCAAAGGTGTACCCCCTGTCAAG |
| | | CTGCTGTGGGGACAAATCCTCTAGTACCGTGACACTGGGAT |
| | | GCCTGGTCTCAAGCTATATGCCCGAGCCTGTGACTGTCACC |
| | | TGGAACTCAGGAGCCCTGAAAAGCGGAGTGCACACCTTCCC |
| | | AGCTGTGCTGCAGTCCTCTGGCCTGTATAGCCTGAGTTCAA |
| | | TGGTGACAGTCCCCGGCAGTACTTCAGGGCAGACCTTCACC |
| | | TGTAATGTGGCCCATCCTGCCAGCTCCACCAAAGTGGACAA |
| | | AGCAGTGGAACCCAAATCTTGCGACAAAACTCACACATGCCC |
| | | ACCGTGCCCAGCACCTGAACTCCTGGGGGGACCGTCAGTCTTCC |
| | | TCTTCCCCCCAAAACCCAAGGACACCCTCATGATCTCCCGGACC |
| | | CCTGAGGTCACATGCGTGGTGGTGGACGTGAGCCACGAAGACC |

TABLE 19-continued

| Description | SEQ ID NO: | Sequence |
|---|---|---|
| | | CTGAGGTCAAGTTCAACTGGTACGTGGACGGCGTGGAGGTGCA |
| | | TAATGCCAAGACAAAGCCGCGGGAGGAGCAGTACAACAGCAC |
| | | GTACCGTGTGGTCAGCGTCCTCACCGTCCTGCACCAGGACTGGC |
| | | TGAATGGCAAGGAGTACAAGTGCAAGGTCTCCAACAAAGCCCT |
| | | CCCAGCCCCCATCGAGAAAACCATCTCCAAAGCCAAAGGGCAG |
| | | CCCCGAGAACCACAGGTGTACACCCTGCCCCCATCCCGGGATG |
| | | AGCTGACCAAGAACCAGGTCAGCCTGACCTGCCTGGTCAAAGG |
| | | CTTCTATCCCAGCGACATCGCCGTGGAGTGGGAGAGCAATGGG |
| | | CAGCCGGAGAACAACTACAAGACCACGCCTCCCGTGCTGGACT |
| | | CCGACGGCTCCTTCTTCCTCTACAGCAAGCTCACCGTGGACAAG |
| | | AGCAGGTGGCAGCAGGGGAACGTCTTCTCATGCTCCGTGATGC |
| | | ATGAGGCTCTGCACAACCACTACACGCAGAAGAGCCTCTCCCT |
| | | GTCTCCGGGTAAA |
| bGCSF-L1 | 5 | CAGGTCCAGCTGAGAGAGAGCGGCCCTTCACTGGTCAAGC |
| | | CATCCCAGACACTGAGCCTGACATGCACAGCAAGCGGGTTT |
| | | TCACTGAGCGACAAGGCAGTGGGATGGGTCCGACAGGCAC |
| | | CAGGAAAAGCCCTGGAATGGCTGGGCAGCATCGATACCGG |
| | | CGGGAACACAGGGTACAATCCCGGACTGAAGAGCAGACTG |
| | | TCCATTACCAAGGACAACTCTAAAAGTCAGGTGTCACTGAG |
| | | CGTGAGCTCCGTCACCACAGAGGATAGTGCAACTTACTATT |
| | | GCACCTCTGTGCACCAGGAAACTAAGAAATACCAGAGC_GGT_ |
| | | _GGCGGAGGATCTACCCCCTTGGCCCTGCCCGATCCCTGCCCAG_ |
| | | _AGCTTCCTGCTCAAGTGCTTAGAGCAAGTGAGGAAAATCCAGGCTG_ |
| | | _ATGGCGCCGAGCTGCAGGAGAGGCTGTGTGCCGCCCACAAGCTGT_ |
| | | _GCCACCCGGAGGAGCTGATGCTGCTCAGGCACTCTCTGGGCATCC_ |
| | | _CCCAGGCTCCCCTAAGCAGCTGCTCCAGCCAGTCCCTGCAGCTGA_ |
| | | _CGAGCTGCCTGAACCAACTACACGGCGGCCTCTTTCTCTACCAGGG_ |
| | | _CCTCCTGCAGGCCCTGGCGGGCATCTCCCCAGAGCTGGCCCCCAC_ |
| | | _CTTGGACACACTGCAGCTGGACGTCACTGACTTTGCCACGAACATC_ |
| | | _TGGCTGCAGATGGAGGACCTGGGGGCGGCCCCCGCTGTGCAGCC_ |
| | | _CACCCAGGGCGCCATGCCGACCTTCACTTCAGCCTTCCAACGCAGA_ |
| | | _GCAGGAGGGGTCCTGGTTGCTTCCCAGCTGCATCGTTTCCTGGAGC_ |

TABLE 19-continued

| Description | SEQ ID NO: | Sequence |
|---|---|---|
| | | *TGGCATACCGTGGCCTGCGCTACCTTGCTGAGCCCGGTGGCGGAG* |
| | | *GATCT*TCTTATACCTACAATTATGAATGGCATGTGGATGTCT |
| | | GGGGACAGGGCCTGCTGGTGACAGTCTCTAGTGCTTCCACA |
| | | ACTGCACCAAAGGTGTACCCCCTGTCAAGCTGCTGTGGGGA |
| | | CAAATCCTCTAGTACCGTGACACTGGGATGCCTGGTCTCAA |
| | | GCTATATGCCCGAGCCTGTGACTGTCACCTGGAACTCAGGA |
| | | GCCCTGAAAAGCGGAGTGCACACCTTCCCAGCTGTGCTGCA |
| | | GTCCTCTGGCCTGTATAGCCTGAGTTCAATGGTGACAGTCC |
| | | CCGGCAGTACTTCAGGGCAGACCTTCACCTGTAATGTGGCC |
| | | CATCCTGCCAGCTCCACCAAAGTGGACAAAGCAGTGGAACC |
| | | CAAATCTTGCGACAAAACTCACACATGCCCACCGTGCCCAGCA |
| | | CCTGAACTCCTGGGGGGACCGTCAGTCTTCCTCTTCCCCCCAAA |
| | | ACCCAAGGACACCCTCATGATCTCCCGGACCCCTGAGGTCACA |
| | | TGCGTGGTGGTGGACGTGAGCCACGAAGACCCTGAGGTCAAGT |
| | | TCAACTGGTACGTGGACGGCGTGGAGGTGCATAATGCCAAGAC |
| | | AAAGCCGCGGGAGGAGCAGTACAACAGCACGTACCGTGTGGTC |
| | | AGCGTCCTCACCGTCCTGCACCAGGACTGGCTGAATGGCAAGG |
| | | AGTACAAGTGCAAGGTCTCCAACAAAGCCCTCCCAGCCCCCAT |
| | | CGAGAAAACCATCTCCAAAGCCAAAGGGCAGCCCCGAGAACC |
| | | ACAGGTGTACACCCTGCCCCCATCCCGGGATGAGCTGACCAAG |
| | | AACCAGGTCAGCCTGACCTGCCTGGTCAAAGGCTTCTATCCCAG |
| | | CGACATCGCCGTGGAGTGGGAGAGCAATGGGCAGCCGGAGAA |
| | | CAACTACAAGACCACGCCTCCGTGCTGGACTCCGACGGCTCCT |
| | | TCTTCCTCTACAGCAAGCTCACCGTGGACAAGAGCAGGTGGCA |
| | | GCAGGGGAACGTCTTCTCATGCTCCGTGATGCATGAGGCTCTGC |
| | | ACAACCACTACACGCAGAAGAGCCTCTCCCTGTCTCCGGGTAA |
| | | A |
| GMCSF | 6 | CAGGTCCAGCTGAGAGAGAGCGGCCCTTCACTGGTCAAGC |
| | | CATCCCAGACACTGAGCCTGACATGCACAGCAAGCGGGTTT |
| | | TCACTGAGCGACAAGGCAGTGGGATGGGTCCGACAGGCAC |

TABLE 19-continued

| Description | SEQ ID NO: | Sequence |
|---|---|---|
| | | CAGGAAAAGCCCTGGAATGGCTGGGCAGCATCGATACCGG |
| | | CGGGAACACAGGGTACAATCCCGGACTGAAGAGCAGACTG |
| | | TCCATTACCAAGGACAACTCTAAAAGTCAGGTGTCACTGAG |
| | | CGTGAGCTCCGTCACCACAGAGGATAGTGCAACTTACTATT |
| | | GCACCTCTGTGCACCAGGAAACTAAGAAATACCAGAGC_GGG_ |
| | | _GGTGGCGGAAGCGCACCCGCCCGCTCGCCCAGCCCCAGCACGCA_ |
| | | _GCCCTGGGAGCATGTGAATGCCATCCAGGAGGCCCGGCGTCTCCT_ |
| | | _GAACCTGAGTAGAGACACTGCTGCTGAGATGAATGAAACAGTAGAA_ |
| | | _GTCATCTCAGAAATGTTTGACCTCCAGGAGCCGACCTGCCTACAGA_ |
| | | _CCCGCCTGGAGCTGTACAAGCAGGGCCTGCGGGGCAGCCTCACCA_ |
| | | _AGCTCAAGGGCCCCTTGACCATGATGGCCAGCCACTACAAGCAGCA_ |
| | | _CTGCCCTCCAACCCCGGAAACTTCCTGTGCAACCCAGATTATCACCT_ |
| | | _TTGAAAGTTTCAAAGAGAACCTGAAGGACTTTCTGCTTGTCATCCCC_ |
| | | _TTTGACTGCTGGGAGCCAGTCCAGGAGGGCGGAGGTGGGAGT_TCT |
| | | TATACCTACAATTATGAATGGCATGTGGATGTCTGGGACA |
| | | GGGCCTGCTGGTGACAGTCTCTAGTGCTTCCACAACTGCAC |
| | | CAAAGGTGTACCCCCTGTCAAGCTGCTGTGGGGACAAATCC |
| | | TCTAGTACCGTGACACTGGGATGCCTGGTCTCAAGCTATAT |
| | | GCCCGAGCCTGTGACTGTCACCTGGAACTCAGGAGCCCTGA |
| | | AAAGCGGAGTGCACACCTTCCCAGCTGTGCTGCAGTCCTCT |
| | | GGCCTGTATAGCCTGAGTTCAATGGTGACAGTCCCCGGCAG |
| | | TACTTCAGGGCAGACCTTCACCTGTAATGTGGCCCATCCTG |
| | | CCAGCTCCACCAAAGTGGACAAAGCAGTGGAACCCAAATCT |
| | | TGCGACAAAACTCACACATGCCCACCGTGCCCAGCACCTGAAC |
| | | TCCTGGGGGGACCGTCAGTCTTCCTCTTCCCCCCAAAACCCAAG |
| | | GACACCCTCATGATCTCCCGGACCCCTGAGGTCACATGCGTGGT |
| | | GGTGGACGTGAGCCACGAAGACCCTGAGGTCAAGTTCAACTGG |
| | | TACGTGGACGGCGTGGAGGTGCATAATGCCAAGACAAAGCCGC |
| | | GGGAGGAGCAGTACAACAGCACGTACCGTGTGGTCAGCGTCCT |
| | | CACCGTCCTGCACCAGGACTGGCTGAATGGCAAGGAGTACAAG |
| | | TGCAAGGTCTCCAACAAAGCCCTCCCAGCCCCCATCGAGAAAA |
| | | CCATCTCCAAAGCCAAAGGGCAGCCCCGAGAACCACAGGTGTA |
| | | CACCCTGCCCCCATCCCGGGATGAGCTGACCAAGAACCAGGTC |

TABLE 19-continued

| Description | SEQ ID NO: | Sequence |
|---|---|---|
| | | <u>AGCCTGACCTGCCTGGTCAAAGGCTTCTATCCCAGCGACATCGC</u> |
| | | <u>CGTGGAGTGGGAGAGCAATGGGCAGCCGGAGAACAACTACAA</u> |
| | | <u>GACCACGCCTCCCGTGCTGGACTCCGACGGCTCCTTCTTCCTCT</u> |
| | | <u>ACAGCAAGCTCACCGTGGACAAGAGCAGGTGGCAGCAGGGGA</u> |
| | | <u>ACGTCTTCTCATGCTCCGTGATGCATGAGGCTCTGCACAACCAC</u> |
| | | <u>TACACGCAGAAGAGCCTCTCCCTGTCTCCGGGTAAA</u> |
| hFGF21 | 7 | CAGGTCCAGCTGAGAGAGAGCGGCCCTTCACTGGTCAAGC |
| | | CATCCCAGACACTGAGCCTGACATGCACAGCAAGCGGGTTT |
| | | TCACTGAGCGACAAGGCAGTGGGATGGGTCCGACAGGCAC |
| | | CAGGAAAAGCCCTGGAATGGCTGGGCAGCATCGATACCGG |
| | | CGGGAACACAGGGTACAATCCCGGACTGAAGAGCAGACTG |
| | | TCCATTACCAAGGACAACTCTAAAAGTCAGGTGTCACTGAG |
| | | CGTGAGCTCCGTCACCACAGAGGATAGTGCAACTTACTATT |
| | | GCACCTCTGTGCACCAGGAAACTAAGAAATACCAGAGC_GGG_ |
| | | _GGTGGCGGAAGCC_ACCCCATCCCTGACTCCAGTCCTCTCCTGCAAT |
| | | _TCGGGGCCAAGTCCGGCAGCGGTACCTCTACACAGATGATGCCC_ |
| | | _AGCAGACAGAAGCCCACCTGGAGATCAGGGAGGATGGGACGGTGG_ |
| | | _GGGGCGCTGCTGACCAGAGCCCCGAAAGTCTCCTGCAGCTGAAAG_ |
| | | _CCTTGAAGCCGGGAGTTATTCAAATCTTGGGAGTCAAGACATCCAG_ |
| | | _GTTCCTGTGCCAGCGGCCAGATGGGGCCCTGTATGGATCGCTCCA_ |
| | | _CTTTGACCCTGAGGCCTGCAGCTTCCGGGAGCTGCTTCTTGAGGAC_ |
| | | _GGATACAATGTTTACCAGTCCGAAGCCCACGGCCTCCCGCTGCACC_ |
| | | _TGCCAGGGAACAAGTCCCCACACCGGGACCCTGCACCCCGAGGAC_ |
| | | _CAGCTCGCTTCCTGCCACTACCAGGCCTGCCCCCCGCACCCCCGG_ |
| | | _AGCCACCCGGAATCCTGGCCCCCAGCCCCCCGATGTGGGCTCCT_ |
| | | _CGGACCCTCTGAGCATGGTGGGACCTTCCCAGGGCCGAAGCCCCA_ |
| | | _GCTACGCTTCCGGCGGAGGTGGGAGT_TCTTATACCTACAATTAT |
| | | GAATGGCATGTGGATGTCTGGGACAGGGCCTGCTGGTGA |
| | | CAGTCTCTAGTGCTTCCACAACTGCACCAAAGGTGTACCCC |
| | | CTGTCAAGCTGCTGTGGGGACAAATCCTCTAGTACCGTGAC |
| | | ACTGGGATGCCTGGTCTCAAGCTATATGCCCGAGCCTGTGA |
| | | CTGTCACCTGGAACTCAGGAGCCCTGAAAAGCGGAGTGCAC |
| | | ACCTTCCCAGCTGTGCTGCAGTCCTCTGGCCTGTATAGCCT |
| | | GAGTTCAATGGTGACAGTCCCCGGCAGTACTTCAGGGCAGA |
| | | CCTTCACCTGTAATGTGGCCCATCCTGCCAGCTCCACCAAA |

TABLE 19-continued

| Description | SEQ ID NO: | Sequence |
|---|---|---|
| | | GTGGACAAAGCAGTGGAACCCAAATCTTGCGACAAAACTCA |
| | | CACATGCCCACCGTGCCCAGCACCTGAACTCCTGGGGGACCG |
| | | TCAGTCTTCCTCTTCCCCCAAAACCCAAGGACACCCTCATGAT |
| | | CTCCCGGACCCCTGAGGTCACATGCGTGGTGGTGGACGTGAGC |
| | | CACGAAGACCCTGAGGTCAAGTTCAACTGGTACGTGGACGGCG |
| | | TGGAGGTGCATAATGCCAAGACAAAGCCGCGGGAGGAGCAGT |
| | | ACAACAGCACGTACCGTGTGGTCAGCGTCCTCACCGTCCTGCAC |
| | | CAGGACTGGCTGAATGGCAAGGAGTACAAGTGCAAGGTCTCCA |
| | | ACAAAGCCCTCCCAGCCCCCATCGAGAAAACCATCTCCAAAGC |
| | | CAAAGGGCAGCCCCGAGAACCACAGGTGTACACCCTGCCCCCA |
| | | TCCCGGGATGAGCTGACCAAGAACCAGGTCAGCCTGACCTGCC |
| | | TGGTCAAAGGCTTCTATCCCAGCGACATCGCCGTGGAGTGGGA |
| | | GAGCAATGGGCAGCCGGAGAACAACTACAAGACCACGCCTCCC |
| | | GTGCTGGACTCCGACGGCTCCTTCTTCCTCTACAGCAAGCTCAC |
| | | CGTGGACAAGAGCAGGTGGCAGCAGGGGAACGTCTTCTCATGC |
| | | TCCGTGATGCATGAGGCTCTGCACAACCACTACACGCAGAAGA |
| | | GCCTCTCCCTGTCTCCGGGTAAA |
| Ex-4 | 8 | CAGGTCCAGCTGAGAGAGAGCGGCCCTTCACTGGTCAAGC |
| | | CATCCCAGACACTGAGCCTGACATGCACAGCAAGCGGGTTT |
| | | TCACTGAGCGACAAGGCAGTGGGATGGGTCCGACAGGCAC |
| | | CAGGAAAAGCCCTGGAATGGCTGGGCAGCATCGATACCGG |
| | | CGGGAACACAGGGTACAATCCCGGACTGAAGAGCAGACTG |
| | | TCCATTACCAAGGACAACTCTAAAAGTCAGGTGTCACTGAG |
| | | CGTGAGCTCCGTCACCACAGAGGATAGTGCAACTTACTATT |
| | | GCACCTCTGTGCACCAGGAAACTAAGAAATACCAGAGCTGC |
| | | *GGGGGTGGCGGAAGCATCGAAGGTCGTCACGCTGAGGGAACATTC* |
| | | *ACTTCCGATGTGTCCTCCTACCTGGAGGGCCAGGCTGCCAAAGAGT* |
| | | *TCATCGCTTGGCTCGTCAAGGGCAGGGGCGGAGGTGGGAGT*TGC |
| | | TCTTATACCTACAATTATGAATGGCATGTGGATGTCTGGGG |

TABLE 19-continued

| Description | SEQ ID NO: | Sequence |
|---|---|---|
| | | ACAGGGCCTGCTGGTGACAGTCTCTAGTGCTTCCACAACTG |
| | | CACCAAAGGTGTACCCCCTGTCAAGCTGCTGTGGGGACAAA |
| | | TCCTCTAGTACCGTGACACTGGGATGCCTGGTCTCAAGCTA |
| | | TATGCCCGAGCCTGTGACTGTCACCTGGAACTCAGGAGCCC |
| | | TGAAAAGCGGAGTGCACACCTTCCCAGCTGTGCTGCAGTCC |
| | | TCTGGCCTGTATAGCCTGAGTTCAATGGTGACAGTCCCCGG |
| | | CAGTACTTCAGGGCAGACCTTCACCTGTAATGTGGCCCATC |
| | | CTGCCAGCTCCACCAAAGTGGACAAAGCAGTGGAACCCAAA |
| | | TCTTGCGACAAAACTCACACATGCCCACCGTGCCCAGCACCTG |
| | | AACTCCTGGGGGACCGTCAGTCTTCCTCTTCCCCCCAAAACCC |
| | | AAGGACACCCTCATGATCTCCCGGACCCCTGAGGTCACATGCG |
| | | TGGTGGTGGACGTGAGCCACGAAGACCCTGAGGTCAAGTTCAA |
| | | CTGGTACGTGGACGGCGTGGAGGTGCATAATGCCAAGACAAAG |
| | | CCGCGGGAGGAGCAGTACAACAGCACGTACCGTGTGGTCAGCG |
| | | TCCTCACCGTCCTGCACCAGGACTGGCTGAATGGCAAGGAGTA |
| | | CAAGTGCAAGGTCTCCAACAAAGCCCTCCCAGCCCCCATCGAG |
| | | AAAACCATCTCCAAAGCCAAAGGGCAGCCCCGAGAACCACAG |
| | | GTGTACACCCTGCCCCCATCCCGGGATGAGCTGACCAAGAACC |
| | | AGGTCAGCCTGACCTGCCTGGTCAAAGGCTTCTATCCCAGCGAC |
| | | ATCGCCGTGGAGTGGGAGAGCAATGGGCAGCCGGAGAACAAC |
| | | TACAAGACCACGCCTCCCGTGCTGGACTCCGACGGCTCCTTCTT |
| | | CCTCTACAGCAAGCTCACCGTGGACAAGAGCAGGTGGCAGCAG |
| | | GGGAACGTCTTCTCATGCTCCGTGATGCATGAGGCTCTGCACAA |
| | | CCACTACACGCAGAAGAGCCTCTCCCTGTCTCCGGGTAAA |
| hGLP-1 | 9 | CAGGTCCAGCTGAGAGAGAGCGGCCCTTCACTGGTCAAGC |
| | | CATCCCAGACACTGAGCCTGACATGCACAGCAAGCGGGTTT |
| | | TCACTGAGCGACAAGGCAGTGGGATGGGTCCGACAGGCAC |
| | | CAGGAAAAGCCCTGGAATGGCTGGGCAGCATCGATACCGG |
| | | CGGGAACACAGGGTACAATCCCGGACTGAAGAGCAGACTG |
| | | TCCATTACCAAGGACAACTCTAAAAGTCAGGTGTCACTGAG |
| | | CGTGAGCTCCGTCAGCCACAGAGGATAGTGCAACTTACTATT |

TABLE 19-continued

| Description | SEQ ID NO: | Sequence |
|---|---|---|
| | | GCACCTCTGTGCACCAGGAAACTAAGAAATACCAGAGCTGC |
| | | GGGGGTGGCGGAAGCATCGAAGGTCGTCACGCTGAGGGAACATTC |
| | | ACTTCCGATGTGTCCTCCTACCTGGAGGGCCAGGCTGCCAAAGAGT |
| | | TCATCGCTTGGCTCGTCAAGGGCAGGGGCGGAGGTGGGAGTTGC |
| | | TCTTATACCTACAATTATGAATGGCATGTGGATGTCTGGGG |
| | | ACAGGGCCTGCTGGTGACAGTCTCTAGTGCTTCCACAACTG |
| | | CACCAAAGGTGTACCCCCTGTCAAGCTGCTGTGGGGACAAA |
| | | TCCTCTAGTACCGTGACACTGGGATGCCTGGTCTCAAGCTA |
| | | TATGCCCGAGCCTGTGACTGTCACCTGGAACTCAGGAGCCC |
| | | TGAAAAGCGGAGTGCACACCTTCCCAGCTGTGCTGCAGTCC |
| | | TCTGGCCTGTATAGCCTGAGTTCAATGGTGACAGTCCCCGG |
| | | CAGTACTTCAGGGCAGACCTTCACCTGTAATGTGGCCCATC |
| | | CTGCCAGCTCCACCAAAGTGGACAAAGCAGTGGAACCCAAA |
| | | TCTTGCGACAAAACTCACACATGCCCACCGTGCCCAGCACCTG |
| | | AACTCCTGGGGGACCGTCAGTCTTCCTCTTCCCCCCAAAACCC |
| | | AAGGACACCCTCATGATCTCCCGGACCCCTGAGGTCACATGCG |
| | | TGGTGGTGGACGTGAGCCACGAAGACCCTGAGGTCAAGTTCAA |
| | | CTGGTACGTGGACGGCGTGGAGGTGCATAATGCCAAGACAAAG |
| | | CCGCGGGAGGAGCAGTACAACAGCACGTACCGTGTGGTCAGCG |
| | | TCCTCACCGTCCTGCACCAGGACTGGCTGAATGGCAAGGAGTA |
| | | CAAGTGCAAGGTCTCCAACAAAGCCCTCCCAGCCCCCATCGAG |
| | | AAAACCATCTCCAAAGCCAAAGGGCAGCCCCGAGAACCACAG |
| | | GTGTACACCCTGCCCCCATCCCGGGATGAGCTGACCAAGAACC |
| | | AGGTCAGCCTGACCTGCCTGGTCAAAGGCTTCTATCCCAGCGAC |
| | | ATCGCCGTGGAGTGGGAGAGCAATGGGCAGCCGGAGAACAAC |
| | | TACAAGACCACGCCTCCCGTGCTGGACTCCGACGGCTCCTTCTT |
| | | CCTCTACAGCAAGCTCACCGTGGACAAGAGCAGGTGGCAGCAG |
| | | GGGAACGTCTTCTCATGCTCCGTGATGCATGAGGCTCTGCACAA |
| | | CCACTACACGCAGAAGAGCCTCTCCCTGTCTCCGGGTAAA |
| hEPO | 10 | CAGGTCCAGCTGAGAGAGAGCGGCCCTTCACTGGTCAAGC |
| | | CATCCCAGACACTGAGCCTGACATGCACAGCAAGCGGGTTT |

TABLE 19-continued

| Description | SEQ ID NO: | Sequence |
|---|---|---|
| | | TCACTGAGCGACAAGGCAGTGGGATGGGTCCGACAGGCAC |
| | | CAGGAAAAGCCCTGGAATGGCTGGGCAGCATCGATACCGG |
| | | CGGGAACACAGGGTACAATCCCGGACTGAAGAGCAGACTG |
| | | TCCATTACCAAGGACAACTCTAAAAGTCAGGTGTCACTGAG |
| | | CGTGAGCTCCGTCACCACAGAGGATAGTGCAACTTACTATT |
| | | GCACCTCTGTGCACCAGGAAACTAAGAAATACCAGAGCGGG |
| | | GGTGGCGGAAGCGCCCCACCACGCCTCATCTGTGACAGCCGAGTC |
| | | CTGGAGAGGTACCTCTTGGAGGCCAAGGAGGCCGAGAATATCACG |
| | | ACGGGCTGTGCTGAACACTGCAGCTTGAATGAGAATATCACTGTCC |
| | | CAGACACCAAAGTTAATTTCTATGCCTGGAAGAGGATGGAGGTCGG |
| | | GCAGCAGGCCGTAGAAGTCTGGCAGGGCCTGGCCCTGCTGTCGGA |
| | | AGCTGTCCTGCGGGGCCAGGCCCTGTTGGTCAACTCTTCCCAGCC |
| | | GTGGGAGCCCCTGCAGCTGCATGTGGATAAAGCCGTCAGTGGCCT |
| | | TCGCAGCCTCACCACTCTGCTTCGGGCTCTGGGAGCCCAGAAGGA |
| | | AGCCATCTCCCCTCCAGATGCGGCCTCAGCTGCTCCACTCCGAACA |
| | | ATCACTGCTGACACTTTCCGCAAACTCTTCCGAGTCTACTCCAATTT |
| | | CCTCCGGGGAAAGCTGAAGCTGTACACAGGGGAGGCCTGCAGGAC |
| | | AGGGGACAGAGGCGGAGGTGGGAGTTCTTATACCTACAATTAT |
| | | GAATGGCATGTGGATGTCTGGGGACAGGGCCTGCTGGTGA |
| | | CAGTCTCTAGTGCTTCCACAACTGCACCAAAGGTGTACCCC |
| | | CTGTCAAGCTGCTGTGGGGACAAATCCTCTAGTACCGTGAC |
| | | ACTGGGATGCCTGGTCTCAAGCTATATGCCCGAGCCTGTGA |
| | | CTGTCACCTGGAACTCAGGAGCCCTGAAAAGCGGAGTGCAC |
| | | ACCTTCCCAGCTGTGCTGCAGTCCTCTGGCCTGTATAGCCT |
| | | GAGTTCAATGGTGACAGTCCCCGGCAGTACTTCAGGGCAGA |
| | | CCTTCACCTGTAATGTGGCCCATCCTGCCAGCTCCACCAAA |
| | | GTGGACAAAGCAGTGGAACCCAAATCTTGCGACAAAACTCA |
| | | CACATGCCCACCGTGCCCAGCACCTGAACTCCTGGGGGGACCG |
| | | TCAGTCTTCCTCTTCCCCCCAAAACCCAAGGACACCCTCATGAT |
| | | CTCCCGGACCCCTGAGGTCACATGCGTGGTGGTGGACGTGAGC |
| | | CACGAAGACCCTGAGGTCAAGTTCAACTGGTACGTGGACGGCG |
| | | TGGAGGTGCATAATGCCAAGACAAAGCCGCGGGAGGAGCAGT |
| | | ACAACAGCACGTACCGTGTGGTCAGCGTCCTCACCGTCCTGCAC |

TABLE 19-continued

| Description | SEQ ID NO: | Sequence |
|---|---|---|
| | | CAGGACTGGCTGAATGGCAAGGAGTACAAGTGCAAGGTCTCCA |
| | | ACAAAGCCCTCCCAGCCCCATCGAGAAAACCATCTCCAAAGC |
| | | CAAAGGGCAGCCCCGAGAACCACAGGTGTACACCCTGCCCCCA |
| | | TCCCGGGATGAGCTGACCAAGAACCAGGTCAGCCTGACCTGCC |
| | | TGGTCAAAGGCTTCTATCCCAGCGACATCGCCGTGGAGTGGGA |
| | | GAGCAATGGGCAGCCGGAGAACAACTACAAGACCACGCCTCCC |
| | | GTGCTGGACTCCGACGGCTCCTTCTTCCTCTACAGCAAGCTCAC |
| | | CGTGGACAAGAGCAGGTGGCAGCAGGGGAACGTCTTCTCATGC |
| | | TCCGTGATGCATGAGGCTCTGCACAACCACTACACGCAGAAGA |
| | | GCCTCTCCCTGTCTCCGGGTAAA |
| Moka-L0 | 11 | CAGGTCCAGCTGAGAGAGAGCGGCCCTTCACTGGTCAAGC |
| | | CATCCCAGACACTGAGCCTGACATGCACAGCAAGCGGGTTT |
| | | TCACTGAGCGACAAGGCAGTGGGATGGGTCCGACAGGCAC |
| | | CAGGAAAAGCCCTGGAATGGCTGGGCAGCATCGATACCGG |
| | | CGGGAACACAGGGTACAATCCCGGACTGAAGAGCAGACTG |
| | | TCCATTACCAAGGACAACTCTAAAAGTCAGGTGTCACTGAG |
| | | CGTGAGCTCCGTCACCACAGAGGATAGTGCAACTTACTATT |
| | | GCACCTCTGTGCACCAGGAAACTAAGAAATACCAGAGCATC |
| | | AACGTGAAGTGCAGCCTGCCCCAGCAGTGCATCAAGCCCTGCAAG |
| | | GACGCCGGCATGCGGTTCGGCAAGTGCATGAACAAGAAGTGCAGG |
| | | TGCTACAGCTCTTATACCTACAATTATGAATGGCATGTGGAT |
| | | GTCTGGGGACAGGGCCTGCTGGTGACAGTCTCTAGTGCTTC |
| | | CACAACTGCACCAAAGGTGTACCCCCTGTCAAGCTGCTGTG |
| | | GGGACAAATCCTCTAGTACCGTGACACTGGGATGCCTGGTC |
| | | TCAAGCTATATGCCCGAGCCTGTGACTGTCACCTGGAACTC |
| | | AGGAGCCCTGAAAAGCGGAGTGCACACCTTCCCAGCTGTGC |
| | | TGCAGTCCTCTGGCCTGTATAGCCTGAGTTCAATGGTGACA |
| | | GTCCCCGGCAGTACTTCAGGGCAGACCTTCACCTGTAATGT |
| | | GGCCCATCCTGCCAGCTCCACCAAAGTGGACAAAGCAGTGG |
| | | AACCCAAATCTTGCGACAAAACTCACACATGCCCACCGTGCCC |
| | | AGCACCTGAACTCCTGGGGGGACCGTCAGTCTTCCTCTTCCCCC |
| | | CAAAACCCAAGGACACCCTCATGATCTCCCGGACCCCTGAGGT |

TABLE 19-continued

| Description | SEQ ID NO: | Sequence |
|---|---|---|
| | | CACATGCGTGGTGGTGGACGTGAGCCACGAAGACCCTGAGGTC |
| | | AAGTTCAACTGGTACGTGGACGGCGTGGAGGTGCATAATGCCA |
| | | AGACAAAGCCGCGGGAGGAGCAGTACAACAGCACGTACCGTG |
| | | TGGTCAGCGTCCTCACCGTCCTGCACCAGGACTGGCTGAATGGC |
| | | AAGGAGTACAAGTGCAAGGTCTCCAACAAAGCCCTCCCAGCCC |
| | | CCATCGAGAAAACCATCTCCAAAGCCAAAGGGCAGCCCCGAGA |
| | | ACCACAGGTGTACACCCTGCCCCCATCCCGGGATGAGCTGACC |
| | | AAGAACCAGGTCAGCCTGACCTGCCTGGTCAAAGGCTTCTATC |
| | | CCAGCGACATCGCCGTGGAGTGGGAGAGCAATGGGCAGCCGG |
| | | AGAACAACTACAAGACCACGCCTCCCGTGCTGGACTCCGACGG |
| | | CTCCTTCTTCCTCTACAGCAAGCTCACCGTGGACAAGAGCAGGT |
| | | GGCAGCAGGGGAACGTCTTCTCATGCTCCGTGATGCATGAGGC |
| | | TCTGCACAACCACTACACGCAGAAGAGCCTCTCCCTGTCTCCGG |
| | | GTAAA |
| Moka-L1 | 12 | CAGGTCCAGCTGAGAGAGAGCGGCCCTTCACTGGTCAAGC |
| | | CATCCCAGACACTGAGCCTGACATGCACAGCAAGCGGGTTT |
| | | TCACTGAGCGACAAGGCAGTGGGATGGGTCCGACAGGCAC |
| | | CAGGAAAAGCCCTGGAATGGCTGGGCAGCATCGATACCGG |
| | | CGGGAACACAGGGTACAATCCCGGACTGAAGAGCAGACTG |
| | | TCCATTACCAAGGACAACTCTAAAAGTCAGGTGTCACTGAG |
| | | CGTGAGCTCCGTCACCACAGAGGATAGTGCAACTTACTATT |
| | | GCACCTCTGTGCACCAGGAAACTAAGAAATACCAGAGCGGT |
| | | GGCGGAGGATCTATCAACGTGAAGTGCAGCCTGCCCCAGCAGTGC |
| | | ATCAAGCCCTGCAAGGACGCCGGCATGCGGTTCGGCAAGTGCATG |
| | | AACAAGAAGTGCAGGTGCTACAGCGGAGGTGGTGGTTCATCTTAT |
| | | ACCTACAATTATGAATGGCATGTGGATGTCTGGGGACAGGG |
| | | CCTGCTGGTGACAGTCTCTAGTGCTTCCACAACTGCACCAA |
| | | AGGTGTACCCCCTGTCAAGCTGCTGTGGGACAAATCCTCT |
| | | AGTACCGTGACACTGGGATGCCTGGTCTCAAGCTATATGCC |
| | | CGAGCCTGTGACTGTCACCTGGAACTCAGGAGCCCTGAAAA |
| | | GCGGAGTGCACACCTTCCCAGCTGTGCTGCAGTCCTCTGGC |

TABLE 19-continued

| Description | SEQ ID NO: | Sequence |
|---|---|---|
| | | CTGTATAGCCTGAGTTCAATGGTGACAGTCCCCGGCAGTAC |
| | | TTCAGGGCAGACCTTCACCTGTAATGTGGCCCATCCTGCCA |
| | | GCTCCACCAAAGTGGACAAAGCAGTGGAACCCAAATCTTGC |
| | | GACAAAACTCACACATGCCCACCGTGCCCAGCACCTGAACTCC |
| | | TGGGGGACCGTCAGTCTTCCTCTTCCCCCCAAAACCCAAGGAC |
| | | ACCCTCATGATCTCCCGGACCCCTGAGGTCACATGCGTGGTGGT |
| | | GGACGTGAGCCACGAAGACCCTGAGGTCAAGTTCAACTGGTAC |
| | | GTGGACGGCGTGGAGGTGCATAATGCCAAGACAAAGCCGCGG |
| | | GAGGAGCAGTACAACAGCACGTACCGTGTGGTCAGCGTCCTCA |
| | | CCGTCCTGCACCAGGACTGGCTGAATGGCAAGGAGTACAAGTG |
| | | CAAGGTCTCCAACAAAGCCCTCCCAGCCCCCATCGAGAAAACC |
| | | ATCTCCAAAGCCAAAGGGCAGCCCCGAGAACCACAGGTGTACA |
| | | CCCTGCCCCCATCCCGGGATGAGCTGACCAAGAACCAGGTCAG |
| | | CCTGACCTGCCTGGTCAAAGGCTTCTATCCCAGCGACATCGCCG |
| | | TGGAGTGGGAGAGCAATGGGCAGCCGGAGAACAACTACAAGA |
| | | CCACGCCTCCCGTGCTGGACTCCGACGGCTCCTTCTTCCTCTAC |
| | | AGCAAGCTCACCGTGGACAAGAGCAGGTGGCAGCAGGGGAAC |
| | | GTCTTCTCATGCTCCGTGATGCATGAGGCTCTGCACAACCACTA |
| | | CACGCAGAAGAGCCTCTCCCTGTCTCCGGGTAAA |
| VM-24-L1 | 13 | CAGGTCCAGCTGAGAGAGAGCGGCCCTTCACTGGTCAAGC |
| | | CATCCCAGACACTGAGCCTGACATGCACAGCAAGCGGGTTT |
| | | TCACTGAGCGACAAGGCAGTGGGATGGGTCCGACAGGCAC |
| | | CAGGAAAAGCCCTGGAATGGCTGGGCAGCATCGATACCGG |
| | | CGGGAACACAGGGTACAATCCCGGACTGAAGAGCAGACTG |
| | | TCCATTACCAAGGACAACTCTAAAAGTCAGGTGTCACTGAG |
| | | CGTGAGCTCCGTCACCACAGAGGATAGTGCAACTTACTATT |
| | | GCACCTCTGTGCACCAGGAAACTAAGAAATACCAGAGCGGG |
| | | GGTGGCGGAAGCGCCGCTGCAATCTCCTGCGTCGGCAGCCCCGAA |
| | | TGTCCTCCCAAGTGCCGGGCTCAGGGATGCAAGAACGGCAAGTGT |
| | | ATGAACCGGAAGTGCAAGTGCTACTATTGCGGCGGAGGTGGGAGT |

TABLE 19-continued

| Description | SEQ ID NO: | Sequence |
|---|---|---|
| | | TCTTATACCTACAATTATGAATGGCATGTGGATGTCTGGGG |
| | | ACAGGGCCTGCTGGTGACAGTCTCTAGTGCTTCCACAACTG |
| | | CACCAAAGGTGTACCCCCTGTCAAGCTGCTGTGGGGACAAA |
| | | TCCTCTAGTACCGTGACACTGGGATGCCTGGTCTCAAGCTA |
| | | TATGCCCGAGCCTGTGACTGTCACCTGGAACTCAGGAGCCC |
| | | TGAAAAGCGGAGTGCACACCTTCCCAGCTGTGCTGCAGTCC |
| | | TCTGGCCTGTATAGCCTGAGTTCAATGGTGACAGTCCCCGG |
| | | CAGTACTTCAGGGCAGACCTTCACCTGTAATGTGGCCCATC |
| | | CTGCCAGCTCCACCAAAGTGGACAAAGCAGTGGAACCCAAA |
| | | TCTTGCGACAAAACTCACACATGCCCACCGTGCCCAGCACCTG |
| | | AACTCCTGGGGGGACCGTCAGTCTTCCTCTTCCCCCCAAAACCC |
| | | AAGGACACCCTCATGATCTCCCGGACCCCTGAGGTCACATGCG |
| | | TGGTGGTGGACGTGAGCCACGAAGACCCTGAGGTCAAGTTCAA |
| | | CTGGTACGTGGACGGCGTGGAGGTGCATAATGCCAAGACAAAG |
| | | CCGCGGGAGGAGCAGTACAACAGCACGTACCGTGTGGTCAGCG |
| | | TCCTCACCGTCCTGCACCAGGACTGGCTGAATGGCAAGGAGTA |
| | | CAAGTGCAAGGTCTCCAACAAAGCCCTCCCAGCCCCCATCGAG |
| | | AAAACCATCTCCAAAGCCAAAGGGCAGCCCCGAGAACCACAG |
| | | GTGTACACCCTGCCCCCATCCCGGGATGAGCTGACCAAGAACC |
| | | AGGTCAGCCTGACCTGCCTGGTCAAAGGCTTCTATCCCAGCGAC |
| | | ATCGCCGTGGAGTGGGAGAGCAATGGGCAGCCGGAGAACAAC |
| | | TACAAGACCACGCCTCCCGTGCTGGACTCCGACGGCTCCTTCTT |
| | | CCTCTACAGCAAGCTCACCGTGGACAAGAGCAGGTGGCAGCAG |
| | | GGGAACGTCTTCTCATGCTCCGTGATGCATGAGGCTCTGCACAA |
| | | CCACTACACGCAGAAGAGCCTCTCCCTGTCTCCGGGTAAA |
| VM-24-L2 | 14 | CAGGTCCAGCTGAGAGAGAGCGGCCCTTCACTGGTCAAGC |
| | | CATCCCAGACACTGAGCCTGACATGCACAGCAAGCGGGTTT |
| | | TCACTGAGCGACAAGGCAGTGGGATGGGTCCGACAGGCAC |
| | | CAGGAAAAGCCCTGGAATGGCTGGGCAGCATCGATACCGG |
| | | CGGGAACACAGGGTACAATCCCGGACTGAAGAGCAGACTG |
| | | TCCATTACCAAGGACAACTCTAAAAGTCAGGTGTCACTGAG |

TABLE 19-continued

| Description | SEQ ID NO: | Sequence |
|---|---|---|
| | | CGTGAGCTCCGTCACCACAGAGGATAGTGCAACTTACTATT |
| | | GCACCTCTGTGCACCAGGAAACTAAGAAATACCAGAGCGGC |
| | | *GGTGGATCTGGGGGTGGCGGAAGCGCCGCTGCAATCTCCTGCGTC* |
| | | *GGCAGCCCCGAATGTCCTCCCAAGTGCCGGGCTCAGGGATGCAAG* |
| | | *AACGGCAAGTGTATGAACCGGAAGTGCAAGTGCTACTATTGCGGCG* |
| | | *GAGGTGGGAGTGGAGGCGGTAGC*TCTTATACCTACAATTATGA |
| | | ATGGCATGTGGATGTCTGGGGACAGGGCCTGCTGGTGACA |
| | | GTCTCTAGTGCTTCCACAACTGCACCAAAGGTGTACCCCCT |
| | | GTCAAGCTGCTGTGGGACAAATCCTCTAGTACCGTGACAC |
| | | TGGGATGCCTGGTCTCAAGCTATATGCCCGAGCCTGTGACT |
| | | GTCACCTGGAACTCAGGAGCCCTGAAAAGCGGAGTGCACA |
| | | CCTTCCCAGCTGTGCTGCAGTCCTCTGGCCTGTATAGCCTG |
| | | AGTTCAATGGTGACAGTCCCCGGCAGTACTTCAGGGCAGAC |
| | | CTTCACCTGTAATGTGGCCCATCCTGCCAGCTCCACCAAAG |
| | | TGGACAAAGCAGTGGAACCCAAATCTTGCGACAAAACTCAC |
| | | ACATGCCCACCGTGCCCAGCACCTGAACTCCTGGGGGGACCGT |
| | | CAGTCTTCCTCTTCCCCCCAAAACCCAAGGACACCCTCATGATC |
| | | TCCCGGACCCCTGAGGTCACATGCGTGGTGGTGGACGTGAGCC |
| | | ACGAAGACCCTGAGGTCAAGTTCAACTGGTACGTGGACGGCGT |
| | | GGAGGTGCATAATGCCAAGACAAAGCCGCGGGAGGAGCAGTA |
| | | CAACAGCACGTACCGTGTGGTCAGCGTCCTCACCGTCCTGCACC |
| | | AGGACTGGCTGAATGGCAAGGAGTACAAGTGCAAGGTCTCCAA |
| | | CAAAGCCCTCCCAGCCCCCATCGAGAAAACCATCTCCAAAGCC |
| | | AAAGGGCAGCCCCGAGAACCACAGGTGTACACCCTGCCCCCAT |
| | | CCCGGGATGAGCTGACCAAGAACCAGGTCAGCCTGACCTGCCT |
| | | GGTCAAAGGCTTCTATCCCAGCGACATCGCCGTGGAGTGGGAG |
| | | AGCAATGGGCAGCCGGAGAACAACTACAAGACCACGCCTCCCG |
| | | TGCTGGACTCCGACGGCTCCTTCTTCCTCTACAGCAAGCTCACC |
| | | GTGGACAAGAGCAGGTGGCAGCAGGGGAACGTCTTCTCATGCT |
| | | CCGTGATGCATGAGGCTCTGCACAACCACTACACGCAGAAGAG |

TABLE 19-continued

| Description | SEQ ID NO: | Sequence |
|---|---|---|
| | | CCTCTCCCTGTCTCCGGGTAAA |
| Protoxin2-L1 | 15 | CAGGTCCAGCTGAGAGAGAGCGGCCCTTCACTGGTCAAGC<br>CATCCCAGACACTGAGCCTGACATGCACAGCAAGCGGGTTT<br>TCACTGAGCGACAAGGCAGTGGGATGGGTCCGACAGGCAC<br>CAGGAAAAGCCCTGGAATGGCTGGGCAGCATCGATACCGG<br>CGGGAACACAGGGTACAATCCCGGACTGAAGAGCAGACTG<br>TCCATTACCAAGGACAACTCTAAAAGTCAGGTGTCACTGAG<br>CGTGAGCTCCGTCACCACAGAGGATAGTGCAACTTACTATT<br>GCACCTCTGTGCACCAGGAAACTAAGAAATACCAGAGCGGG<br>GGTGGCGGAAGCTACTGCCAGAAATGGATGTGGACCTGCGACTCT<br>GAACGTAAATGCTGCGAAGGTATGGTTTGCCGTCTGTGGTGCAAAA<br>AAAAACTGTGGGGCGGAGGTGGGAGTTCTTATACCTACAATTAT<br>GAATGGCATGTGGATGTCTGGGGACAGGGCCTGCTGGTGA<br>CAGTCTCTAGTGCTTCCACAACTGCACCAAAGGTGTACCCC<br>CTGTCAAGCTGCTGTGGGGACAAATCCTCTAGTACCGTGAC<br>ACTGGGATGCCTGGTCTCAAGCTATATGCCCGAGCCTGTGA<br>CTGTCACCTGGAACTCAGGAGCCCTGAAAAGCGGAGTGCAC<br>ACCTTCCCAGCTGTGCTGCAGTCCTCTGGCCTGTATAGCCT<br>GAGTTCAATGGTGACAGTCCCCGGCAGTACTTCAGGGCAGA<br>CCTTCACCTGTAATGTGGCCCATCCTGCCAGCTCCACCAAA<br>GTGGACAAAGCAGTGGAACCCAAATCTTGCGACAAAACTCA<br>CACATGCCCACCGTGCCCAGCACCTGAACTCCTGGGGGGACCG<br>TCAGTCTTCCTCTTCCCCCCAAAACCCAAGGACACCCTCATGAT<br>CTCCCGGACCCCTGAGGTCACATGCGTGGTGGTGGACGTGAGC<br>CACGAAGACCCTGAGGTCAAGTTCAACTGGTACGTGGACGGCG<br>TGGAGGTGCATAATGCCAAGACAAAGCCGCGGGAGGAGCAGT<br>ACAACAGCACGTACCGTGTGGTCAGCGTCCTCACCGTCCTGCAC<br>CAGGACTGGCTGAATGGCAAGGAGTACAAGTGCAAGGTCTCCA<br>ACAAAGCCCTCCCAGCCCCCATCGAGAAAACCATCTCCAAAGC<br>CAAAGGGCAGCCCCGAGAACCACAGGTGTACACCCTGCCCCCA<br>TCCCGGGATGAGCTGACCAAGAACCAGGTCAGCCTGACCTGCC<br>TGGTCAAAGGCTTCTATCCCAGCGACATCGCCGTGGAGTGGGA |

TABLE 19-continued

| Description | SEQ ID NO: | Sequence |
|---|---|---|
| | | GAGCAATGGGCAGCCGGAGAACAACTACAAGACCACGCCTCCC |
| | | GTGCTGGACTCCGACGGCTCCTTCTTCCTCTACAGCAAGCTCAC |
| | | CGTGGACAAGAGCAGGTGGCAGCAGGGGAACGTCTTCTCATGC |
| | | TCCGTGATGCATGAGGCTCTGCACAACCACTACACGCAGAAGA |
| | | GCCTCTCCCTGTCTCCGGGTAAA |

For SEQ ID NOS: 2-15
bovine heavy chain sequence = bold
human heavy chain sequence = dashed underline
non-antibody sequence = *italic*
Stalk = bold, underline; knob = bold, double underline; linker = *italic, squiggly underline*

TABLE 20

| Description | SEQ ID NO: | Sequence |
|---|---|---|
| BLV1H12-IL8 | 16 | CAGGTCCAGCTGAGAGAGAGCGGCCCTTCACTGGTCAAGCCATCCCAGACACTGAGCCTGACATGCACAGCAAGCGGGTTTTCACTGAGCGACAAGGCAGTGGGATGGGTCCGACAGGCACCAGGAAAAGCCCTGGAATGGCTGGGCAGCATCGATACCGGCGGGAACACAGGGTACAATCCCGGACTGAAGAGCAGACTGTCCATTACCAAGGACAACTCTAAAAGTCAGGTGTCACTGAGCGTGAGCTCCGTCACCACAGAGGATAGTGCAACTTACTATTGCACCTCTGTGCACCAGGAAACTAAGAAATACCAGAGCCCAAGGAGTGCTAAAGAACTTAGATGTCAGTGCATAAAGACATACTCCAAACCTTTTCCACCCCAAGTTCATCAAGGAGCTGAGAGTGATTGAGAGTGGACCACACTGCGCCAACACAGAGATTATTGTAAAGCTTTCTGATGGGAGAGAGCTCTGCCTGGACCCCAAGGAAAACTGGGTGCAGAGGGTCGTGGAGAAGTTCTTGAAGAGGGCTGAGAACTCAGGCAGCGGTTCTTATACCTACAATTATGAATGGCATGTGGATGTCTGGGGACAGGGCCTGCTGGTGACAGTC |
| BLV1H12-Ziconotide | 17 | CAGGTCCAGCTGAGAGAGAGCGGCCCTTCACTGGTCAAGCCATCCCAGACACTGAGCCTGACATGCACAGCAAGCGGGTTTTCACTGAGCGACAAGGCAGTGGGATGGGTCCGACAGGCACCAGGAAAAGCCCTGGAATGGCTGGGCAGCATCGATACCGGCGGGAACACAGGGTACAATCCCGGACTGAAGAGCAGACTGTCCATTACCAAGGACAACTCTAAAAGTCAGGTGTCACTGAGCGTGAGCTCCGTCACCACAGAGGATAGTGCAACTTACTATTGCACCTCTGTGCACCAGGAAACTAAGAAATACCAGAGCTGCAAGGGCAAAGGTGCGAAATGCAGCCGCCTGATGTATGATTGCTGTACCGGGTCCTGCCGCAGTGGCAAGTGCTCTTATACCTACAATTATGAATGGCATGTGGATGTCTGGGGACAGGGCCTGCTGGTGACAGTC |
| BLV1H12-Somatostatin | 18 | CAGGTCCAGCTGAGAGAGAGCGGCCCTTCACTGGTCAAGCCATCCCAGACACTGAGCCTGACATGCACAGCAAGCGGGTTTTCACTGAGCGACAAGGCAGTGGGATGGGTCCGACAGGCACCAGGAAAAGCCCTGGAATGGCTGGGCAGCATCGATACCGGCGGGAACACAGGGTACAATCCCGGACTGAAGAGCAGACTGTCCATTACCAAGGACAACTCTAAAAGTCAGGTGTCACTGAGCGTGAGCTCCGTCACCACAGAGGATAGTGCAACTTACTATTGCACCTCTGTGCACCAGGAAACTAAGAAATACCAGAGCGCTGGCTGCAAGAATTTCTTCTGGAAGACTTTCACATCCTGTGGTTCTTATACCTACAATTATGAATGGCATGTGGATGTCTGGGGACAGGGCCTGCTGGTGACAGTC |
| BLV1H12-Chlorotoxin | 19 | CAGGTCCAGCTGAGAGAGAGCGGCCCTTCACTGGTCAAGCCATCCCAGACACTGAGCCTGACATGCACAGCAAGCGGGTTTTCACTGAGCGACAAGGCAGTGGGATGGGTCCGACAGGCACCAGGAAAAGCCCTGGAATGGCTGGGCAGCATCGATACCGGCGGGAACACAGGGTACAATCCCGGACTGAAGAGCAGACTGTCCATTACCAAGGACAACTCTAAAAGTCAGGTGTCACTGAGCGTGAGCTCCGTCACCACAGAGGATAGTGCAACTTACTATTGCACCTCTGTGCACCAGGAAACTAAGAAATACCAGAGCATGTGTATGCCCTGCTTCACGACCGATCACCAGATGGCGCGCAAATGCGATGACTGTTGCGGCGGTAAAGGTCGCGGAAAGTGCTATGGCCCGCAGTGTCTGTCTTATACCTACAATTATGAATGGCATGTGGATGTCTGGGGACAGGGCCTGCTGGTGACAGTC |
| BLV1H12-SDF1(alpha) | 20 | CAGGTCCAGCTGAGAGAGAGCGGCCCTTCACTGGTCAAGCCATCCCAGACACTGAGCCTGACATGCACAGCAAGCGGGTTTTCACTGAGCGACAAGGCAGTGGGATGGGTCCGACAGGCACCAGGAAAAGCCCTGGAATGGCTGGGCAGCATCGATACCGGCGGGAACACAGGGTACAATCCCGGACTGAAGAGCAGACTGTCCATTACCAAGGACAACTCTAAAAGTCAGGTGTCACTGAGCGTGAGCTCCGTCACCACAGAGGATAGTGCAACTTACTATTGCACCTCTGTGCACCAGGAAACTAAGAAATACCAGACAAGCCCGTCAGCCTGAGCTACAGATGCCCATGCCGATTCTTCGAAAGCCATGTTGCCAGAGCCAACGTCAAGCATCTCAAAATTCTCAACACTCCAAACTGTGCCCTTCAGATTGTAGCCCGGCTGAAGAACAACAGACAAGTGTGCATTGACCCGAAGCTAAAGTGGATTCAGGAGTACCTGGAGAAAGCTTTAAACAAGGGCAGCGGTTCTTATACCTACAATTATGAATGGCATGTGGATGTCTGGGGACAGGGCCTGCTGGTGACAGTC |
| BLV1H12-IL21 | 21 | CAGGTCCAGCTGAGAGAGAGCGGCCCTTCACTGGTCAAGCCATCCCAGACACTGAGCCTGACATGCACAGCAAGCGGGTTTTCACTGAGCGACAAGGCAGTGGGATGGGTCCGACAGGCACCAGGAAAAGCCCTGGAATGGCTGGGCAGCATCGATACCGGCGGGAACACAGGGTACAATCCCGGACTGAAGAGCAGACTGTCCATTACCAAGGACAACTCTAAAAGTCAGGTGTCACTGAGCGTGAGCTCCGTCACCACAGAGGATAGTGC |

TABLE 20-continued

| Description | SEQ ID NO: | Sequence |
|---|---|---|
| | | AACTTACTATTGCACCTCTGTGCACCAGGAAACT AAGAAATACCAGAGCCAAGGTCAAGATCGCCACA TGATCAGAATGCGTCAGCTCATAGATATTGTTGA TCAGCTGAAGAACTACGTGAACGACTTGGTCCCT GAATTTCTGCCAGCTCCCGAAGATGTAGAGACAA ACTGTGAGTGGTCAGCCTTCTCCTGCTTTCAGAA GGCCCAACTAAAGTCAGCAAATACCGGCAACAAC GAGAGGATAATCAATGTATCAATCAAAAGCTGA AGAGGAAGCCACCTTCCACAAATGCAGGGAGACG GCAGAAACACCGCCTGACATGCCCTTCATGTGAT TCTTACGAGAAGAAGCCACCCAAAGAGTTCCTAG AGCGGTTCAAGTCACTTCTCCAAAAGATGATTCA TCAGCATCCTGTCCTCTCGCACACAGGAAGTGAA GATTCCTCTTATACCTACAATTATGAATGGCATG TGGATGTCTGGGGACAGGGCCTGCTGGTGACAGT C |

TABLE 20-continued

| Description | SEQ ID NO: | Sequence |
|---|---|---|
| BLV1H12-ProTxII | 22 | CAGGTCCAGCTGAGAGAGAGCGGCCCTTCACTGG TCAAGCCATCCCAGACACTGAGCCTGACATGCAC AGCAAGCGGGTTTTCACTGAGCGACAAGGCAGTG GGATGGGTCCGACAGGCACCAGGAAAAGCCCTGG AATGGCTGGGCAGCATCGATACCGGCGGGAACAC AGGGTACAATCCCGGACTGAAGAGCAGACTGTCC ATTACCAAGGACAACTCTAAAAGTCAGGTGTCAC TGAGCGTGAGCTCCGTCACCACAGAGGATAGTGC AACTTACTATTGCACCTCTGTGCACCAGGAAACT AAGAAATACCAGAGCTATTGCCAGAAGTGGATGT GGACCTGCGATAGCGAACGGAAATGTTGCGAAGG CATGGTGTGCCGCCTGTGGTGCAAGAAGAAACTC TGGTCTTATACCTACAATTATGAATGGCATGTGG ATGTCTGGGGACAGGGCCTGCTGGTGACAGTC |

TABLE 21

| Name | SEQ ID NO | Sequence |
|---|---|---|
| Light Chain | 23 | QAVLNQPSSVSGSLGQRVSITCSGSSSNVGNGYVSWYQLIPGSAPRTLIY GDTSRASGVPDRFSGSRSGNTATLTISSLQAEDEADYFCASAEDSSSNAV FGSGTTLTVLGQPKSPPSVTLFPPSTEELNGNKATLVCLISDFYPGSVTVV WKADGSTITRNVETTRASKQSNSKYAASSYLSLTSSDWKSKGSYSCEVT HEGSTVTKTVKPSECS |
| Heavy Chain | 24 | QVQLRESGPSLVKPSQTLSLTCTASGFSLSDKAVGWVRQAPGKALE WLGSIDTGGNTGYNPGLKSRLSITKDNSKSQVSLSVSSVTTEDSATYY CTSVHQETKKYQ<u>*SCPDGYRERSDCSNRPACGTSDCCRVSVFGNCLTTL PVSYS*</u>YTYNYEWHVDVWGQGLLVTVSS |
| IFN-beta | 25 | QVQLRESGPSLVKPSQTLSLTCTASGFSLSDKAVGWVRQAPGKALE WLGSIDTGGNTGYNPGLKSRLSITKDNSKSQVSLSVSSVTTEDSATYY CTSVHQETKKYQS<u>GGGGS</u>*MSYNLLGFLQRSSNFQCQKLLWQLNGRLEYC LKDRMNFDIPEEIKQLQQFQKEDAALTIYEMLQNIFAIFRQDSSSTGWNETIV ENLLANVYHQINHLKTVLEEKLEKEDFTRGKLMSSLHLKRYYGRILHYLKAKE YSHCAWTIVRVEILRNFYFINRLTGYLRN*<u>GGGGS</u>SYTYNYEWHVDVWGQG LLVTVSSASTTAPKVYPLSSCCGDKSSSTVTLGCLVSSYMPEPVTVTW NSGALKSGVHTFPAVLQSSGLYSLSSMVTVPGSTSGQTFTCNVAHPA SSTKVDKAVEPKSCDKTHTCPPCPAPELLGGPSVFLFPPKPKDTLMISRT PEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPP SRDELTKNQVSLTCLVKGFYPSDIAVEWESNGQPENNYKTTPPVLDSDGS FFLYSKLTVDKSRWQQGNVFSCSVMHEALHNHYTQKSLSLSPGK |

TABLE 21-continued

| Name | SEQ ID NO | Sequence |
| --- | --- | --- |
| bGCSF-L0 | 26 | QVQLRESGPSLVKPSQTLSLTCTASGFSLSDKAVGWVRQAPGKALE WLGSIDTGGNTGYNPGLKSRLSITKDNSKSQVSLSVSSVTTEDSATYY CTSVHQETKKYQSTPLGPARSLPQSFLLKCLEQVRKIQADGAELQERLCAA HKLCHPEELMLLRHSLGIPQAPLSSCSSQSLQLTSCLNQLHGGLFLYQGLLQA LAGISPELAPTLDTLQLDVTDFATNIWLQMEDLGAAPAVQPTQGAMPTFTSA FQRRAGGVLVASQLHRFLELAYRGLRYLAEPSYTYNYEWHDVWGQGLL VTVSSASTTAPKVYPLSSCCGDKSSSTVTLGCLVSSYMPEPVTVTWNS GALKSGVHTFPAVLQSSGLYSLSSMVTVPGSTSGQTFTCNVAHPASS TKVDKAVEPKSCDKTHTCPPCPAPELLGGPSVFLFPPKPKDTLMISRTPE VTCVVVDVSHEDPEVKFNWYVDGVEVHNAKTKPREEQYNSTYRVVSV LTVLHQDWLNGKEYKCKVSNKALPAPIEKTISKAKGQPREPQVYTLPPSR DELTKNQVSLTCLVKGFYPSDIAVEWESNGQPENNYKTTPPVLDSDGSFF LYSKLTVDKSRWQQGNVFSCSVMHELHNHYTQKSLSLSPGK |
| bGCSF-L1 | 27 | QVQLRESGPSLVKPSQTLSLTCTASGFSLSDKAVGWVRQAPGKALE WLGSIDTGGNTGYNPGLKSRLSITKDNSKSQVSLSVSSVTTEDSATYY CTSVHQETKKYQSGGGGSTPLGPARSLPQSFLLKCLEQVRKIQADGAELQ ERLCAAHKLCHPEELMLLRHSLGIPQAPLSSCSSQSLQLTSCLNQLHGGLFLY QGLLQALAGISPELAPTLDTLQLDVTDFATVIWLQMEDLGAAPAVQPTQGAM PTFTSAFQRRAGGVLVASQLHRFLELAYRGLRYLAEPGGGGSSYTYNYEWH VDVWGQGLLVTVSSASTTAPKVYPLSSCCGDKSSSTVTLGCLVSSYM PEPVTVTWNSGALKSGVHTFPAVLQSSGLYSLSSMVTVPGSTSGQTF TCNVAHPASSTKVDKAVEPKSCDKTHTCPPCPAPELLGGPSVFLFPPKP KDTLMISRTPEVTCVVVDVSHEDPEVKFNWYVDGVEVHNAKTKPREEQ YNSTYRVVSVLTVLHQDWLNGKEYKCKVSNKALPAPIEKTISKAKGQPR EPQVYTLPPSRDELTKNQVSLTCLVKGFYPSDIAVEWESNGQPENNYKTT PPVLDSDGSFFLYSKLTVDKSRWQQGNVFSCSVMHEALHNHYTQKSLSL SPGK |
| GMCSF | 28 | QVQLRESGPSLVKPSQTLSLTCTASGFSLSDKAVGWVRQAPGKALE WLGSIDTGGNTGYNPGLKSRLSITKDNSKSQVSLSVSSVTTEDSATYY CTSVHQETKKYQSGGGGSAPARSPSPSTQPWEHVNAIQEARRLLNLSRDTA AEMNETVEVISEMFDLQEPTCLQTRLELYKQGLRGSLTKLKGPLTMMASHYK |

TABLE 21-continued

| Name | SEQ ID NO | Sequence |
|---|---|---|
| | | *QHCPPTPETSCATQIITFESFKENLKDFLLVIPFDCWEPVQEGGGGS*__SYTYN__ |
| | | __YEWHVDVWGQGLLVTSSASTTAPKVYPLSSCCGDKSSSTVTLGCL__ |
| | | __VSSYMPEPVTVTWNSGALKSGVHTFPAVLQSSGLYSLSSMVTVPGST__ |
| | | __SGQTFTCNVAHPASSTKVDKAVEPKSC__DKTHTCPPCPAPELLGGPSVFL |
| | | FPPKPKDTLMISRTPEVTCVVVDVSHEDPEVKFNWYVDGVEVHNAKTKP |
| | | REEQYNSTYRVVSVLTVLHQDWLNGKEYKCKVSNKALPAPIEKTISKAK |
| | | GQPREPQVYTLPPSRDELTKNQVSLTCLVKGFYPSDIAVEWESNGQPENN |
| | | YKTTPPVLDSDGSFFLYSKLTVDKSRWQQGNVFSCSVMHEALHNHYTQ |
| | | KSLSLSPGK |
| hFGF21 | 29 | QVQLRESGPSLVKPSQTLSLTCTASGFSLSDKAVGWVRQAPGKALE |
| | | WLGSIDTGGNTGYNPGLKSRLSITKDNSKSQVSLSVSSVTTEDSATYY |
| | | CTSVHQETKKYQS*GGGGS*HPIPDSSPLLQFGGQVRQRYLYTDDAQQTEAH |
| | | *LEIREDGTVGGAADQSPESLLQLKALKPGVIQILGVKTSRFLCQRPDGALYGS* |
| | | *LHFDPEACSFRELLLEDGYNVYQSEAHGLPHLPGNKSPHRDPAPRGPARFL* |
| | | *PLPGLPPAPPEPPGILAPQPPDVGSSDPLSMVGPSQGRSPSYASGGGGS*__SYT__ |
| | | __YNYEWHVDVWGQGLLVTSSASTTAPKVYPLSSCCGDKSSSTVTLG__ |
| | | __CLVSSYMPEPVTVTWNSGALKSGVHTFPAVLQSSGLYSLSSMVTVPG__ |
| | | __STSGQTFTCNVAHPASSTKVDKAVEPKSC__DKTHTCPPCPAPELLGGPSV |
| | | FLFPPKPKDTLMISRTPEVTCVVVDVSHEDPEVKFNWYVDGVEVHNAKT |
| | | KPREEQYNSTYRVVSVLTVLHQDWLNGKEYKCKVSNKALPAPIEKTISK |
| | | AKGQPREPQVYTLPPSRDELTKNQVSLTCLVKGFYPSDIAVEWESNGQPE |
| | | NNYKTTPPVLDSDGSFFLYSKLTVDKSRWQQGNVFSCSVMHEALHNHY |
| | | TQKSLSLSPGK |
| Ex-4 | 30 | QVQLRESGPSLVKPSQTLSLTCTASGFSLSDKAVGWVRQAPGKALE |
| | | WLGSIDTGGNTGYNPGLKSRLSITKDNSKSQVSLSVSSVTTEDSATYY |
| | | __CTSVHQETKKYQSC__*GGGGS*IEGRHGEGTFTSDLSKQMEEEAVRLFIEWLK |
| | | *NGGPSSGAPPPSGGGGS*__CSYTYNYEWHVDVWGQGLLVTSSASTTAP__ |
| | | __KVYPLSSCCGDKSSSTVTLGCLVSSYMPEPVTVTWNSGALKSGVHTF__ |
| | | __PAVLQSSGLYSLSSMVTVPGSTSGQTFTCNVAHPASSTKVDKAVEPK__ |
| | | __SC__DKTHTCPPCPAPELLGGPSVFLFPPKPKDTLMISRTPEVTCVVVDVSHE |
| | | DPEVKFNWYVDGVEVHNAKTKPREEQYNSTYRVVSVLTVLHQDWLNG |

TABLE 21-continued

| Name | SEQ ID NO | Sequence |
|---|---|---|
| | | KEYKCKVSNKALPAPIEKTISKAKGQPREPQVYTLPPSRDELTKNQVSLT |
| | | CLVKGFYPSDIAVEWESNGQPENNYKTTPPVLDSDGSFFLYSKLTVDKSR |
| | | WQQGNVFSCSVMHEALHNHYTQKSLSLSPGK |
| hGLP-1 | 31 | QVQLRESGPSLVKPSQTLSLTCTASGFSLSDKAVGWVRQAPGKALE |
| | | WLGSIDTGGNTGYNPGLKSRLSITKDNSKSQVSLSVSSVTTEDSATYY |
| | | CTSVHQETKKYQSCGGGGSIEGRHAEGTFTSDVSSYLEGQAAKEFIAWLVK |
| | | GRGGGGSCSYTYNYEWHVDVWGQGLLVTVSSASTTAPKVYPLSSCC |
| | | GDKSSSTVTLGCLVSSYMPEPVTVTWNSGALKSGVHTFPAVLQSSGL |
| | | YSLSSMVTVPGSTSGQTFTCNVAHPASSTKVDKAVEPKSCDKTHTCPP |
| | | CPAPELLGGPSVFLFPPKPKDTLMISRTPEVTCVVVDVSHEDPEVKFNWY |
| | | VDGVEVHNAKTKPREEQYNSTYRVVSVLTVLHQDWLNGKEYKCKVSN |
| | | KALPAPIEKTISKAKGQPREPQVYTLPPSRDELTKNQVSLTCLVKGFYPSD |
| | | IAVEWESNGQPENNYKTTPPVLDSDGSFFLYSKLTVDKSRWQQGNVFSC |
| | | SVMHEALHNHYTQKSLSLSPGK |
| hEPO | 32 | QVQLRESGPSLVKPSQTLSLTCTASGFSLSDKAVGWVRQAPGKALE |
| | | WLGSIDTGGNTGYNPGLKSRLSITKDNSKSQVSLSVSSVTTEDSATYY |
| | | CTSVHQETKKYQSGGGGSAPPRLICDSRVLERYLLEAKEAENITTGCAEHC |
| | | SLNENITVPDTKVNFYAWKRMEVGQQAVEVWQGLALLSEAVLRGQALLVNSS |
| | | QPWEPLQLHVDKAVSGLRSLTTLLRALGAQKEAISPPDAASAAPLRTITADTFR |
| | | KLFRVYSNFLRGKLKLYTGEACRTGDRGGGGSSYTYNYEWHVDVWGQG |
| | | LLVTVSSASTTAPKVYPLSSCCGDKSSSTVTLGCLVSSYMPEPVTVTW |
| | | NSGALKSGVHTFPAVLQSSGLYSLSSMVTVPGSTSGQTFTCNVAHPA |
| | | SSTKVDKAVEPKSCDKTHTCPPCPAPELLGGPSVFLFPPKPKDTLMISRT |
| | | PEVTCVVVDVSHEDPEVKFNWYVDGVEVHNAKTKPREEQYNSTYRVVS |
| | | VLTVLHQDWLNGKEYKCKVSNKALPAPIEKTISKAKGQPREPQVYTLPP |
| | | SRDELTKNQVSLTCLVKGFYPSDIAVEWESNGQPENNYKTTPPVLDSDGS |
| | | FFLYSKLTVDKSRWQQGNVFSCSVMHEALHNHYTQKSLSLSPGK |
| Moka-L0 | 33 | QVQLRESGPSLVKPSQTLSLTCTASGFSLSDKAVGWVRQAPGKALE |
| | | WLGSIDTGGNTGYNPGLKSRLSITKDNSKSQVSLSVSSVTTEDSATYY |
| | | CTSVHQETKKYQSINVKCSLPQQCIKPCKDAGMRFGKCMNKKCRCYSSY |
| | | TYNYEWHVDVWGQGLLVTVSSASTTAPKVGYPLSSCCGDKSSSTVTL |

TABLE 21-continued

| Name | SEQ ID NO | Sequence |
|---|---|---|
| | | GCLVSSYMPEPVTVTWNSGALKSGVHTFPAVLQSSGLYSLSSMVTVP |
| | | GSTSGQTFTCNVAHPASSTKVDKAVEPKSCDKTHTCPPCPAPELLGGP |
| | | SVFLFPPKPKDTLMISRTPEVTCVVVDVSHEDPEVKFNWYVDGVEVHNA |
| | | KTKPREEQYNSTYRVVSVLTVLHQDWLNGKEYKCKVSNKALPAPIEKT |
| | | SKAKGQPREPQVYTLPPSRDELTKNQVSLTCLVKGFYPSDIAVEWESNG |
| | | QPENNYKTTPPVLDSDGSFFLYSKLTVDKSRWQQGNVFSCSVMHEALH |
| | | NHYTQKSLSLSPGK |
| Moka-L1 | 34 | QVQLRESGPSLVKPSQTLSLTCTASGFSLSDKAVGWVRQAPGKALE |
| | | WLGSIDTGGNTGYNPGLKSRLSITDKNSKSQVSLSVSSVTTEDSATYY |
| | | CTSVHQETKKYQSGGGGSINVKCSLPQQCIKPCKDAGMRFGKCMNKKCR |
| | | CYSGGGGSSYTYNYEWHVDVWGQGLLVTVSSASTTAPKVYPLSSCCG |
| | | DKSSSTVTLGCLVSSYMPEPVTVTWNSGALKSGVHTFPAVLQSSGLY |
| | | SLSSMVTVPGSTSGQTFTCNVAHPASSTKVDKAVEPKSCDKTHTCPPC |
| | | PAPELLGGPSVFLFPPKPKDTLMISRTPEVTCVVVDVSHEDPEVKFNWYV |
| | | DGVEVHNAKTKPREEQYNSTYRVVSVLTVLHQDWLNGKEYKCKVSNK |
| | | ALPAPIEKTISKAKGQPREPQVYTLPPSRDELTKNQVSLTCLVKGFYPSDI |
| | | AVEWESNGQPENNYKTTPPVLDSDGSFFLYSKLTVDKSRWQQGNVFSCS |
| | | VMHEALHNHYTQKSLSLSPGK |
| VM-24-L1 | 35 | QVQLRESGPSLVKPSQTLSLTCTASGFSLSDKAVGWVRQAPGKALE |
| | | WLGSIDTGGNTGYNPGLKSRLSITKDNSKSQVSLSVSSVTTEDSATYY |
| | | CTSVHQETKKYQSGGGGSAAAISCVGSPECPPKCRAQGCKNGKCMNRKC |
| | | KCYYCGGGGSSYTYNYEWHVDVWGQGLLVTVSSASTTAPKVYPLSSC |
| | | CGDKSSSTVTLGCLVSSYMPEPVTVTWNSGALKSGVHTFPAVLQSSG |
| | | LYSLSSMVTVPGSTSGQTFTCNVAHPASSTKVDKAVEPKSCDKTHTCP |
| | | PCPAPELLGGPSVFLFPPKPKDTLMISRTPEVTCVVVDVSHEDPEVKFNW |
| | | YVDGVEVHNAKTKPREEQYNSTYRVVSVLTVLHQDWLNGKEYKCKVS |
| | | NKALPAPIEKTISKAKGQPREPQVYTLPPSRDELTKNQVSLTCLVKGFYPS |
| | | DIAVEWESNGQPENNYKTTPPVLDSDGSFFLYSKLTVDKSRWQQGNVFS |
| | | CSVMHEALHNHYTQKSLSLSPGK |

TABLE 21-continued

| Name | SEQ ID NO | Sequence |
|---|---|---|
| VM-24-L2 | 36 | QVQLRESGPSLVKPSQTLSLTCTASGFSLSDKAVGWVRQAPGKALE<br>WLGSIDTGGNTGYNPGLKSRLSITKDNSKSQVSLSVSSVTTEDSATYY<br>CTSVHQETKKYQS*GGGSGGGGS*AAAISCVGSPECPPKCRAQGCKNGKCM<br>*NRKCKCYYCGGGGSGGGS*SYTYNYEWHVDVWGQGLLVTVSSASTTAP<br>KVYPLSSCCGDKSSSTVTLGCLVSSYMPEPVTVTWNSGALKSGVHTF<br>PAVLQSSGLYSLSSMVTVPGSTSGQTFTCNVAHPASSTKVDKAVEPK<br>SCDKTHTCPPCPAPELLGGPSVFLFPPKPKDTLMISRTPEVTCVVVDVSHE<br>DPEVKFNWYVDGVEVHNAKTKPREEQYNSTYRVVSVLTVLHQDWLNG<br>KEYKCKVSNKALPAPIEKTISKAKGQPREPQVYTLPPSRDELTKNQVSLT<br>CLVKGFYPSDIAVEWESNGQPENNYKTTPPVLDSDGSFFLYSKLTVDKSR<br>WQQGNVFSCSVMHEALHNHYTQKSLSLSPGK |
| Protoxin 2-L1 | 37 | QVQLRESGPSLVKPSQTLSLTCTASGFSLSDKAVGWVRQAPGKALE<br>WLGSIDTGGNTGYNPGLKSRLSITKDNSKSQVSLSVSSVTTEDSATYY<br>CTSVHQETKKYQS*GGGGS*YCQKWMWTCDSERKCCEGMVCRLWCKKKL<br>*WGGGGSS*YTYNYEWHVDVWGQGLLVTVSSASTTAPKVYPLSSCCGD<br>KSSSTVTLGCLVSSYMPEPVTVTWNSGALKSGVHTFPAVLQSSGLYS<br>LSSMVTVPGSTSGQTFTCNVAHPASSTKVDKAVEPKSCDKTHTCPPCP<br>APELLGGPSVFLFPPKPKDTLMISRTPEVTCVVVDVSHEDPEVKFNWYVD<br>GVEVHNAKTKPREEQYNSTYRVVSVLTVLHQDWLNGKEYKCKVSNKA<br>LPAPIEKTISKAKGQPREPQVYTLPPSRDELTKNQVSLTCLVKGFYPSDIA<br>VEWESNGQPENNYKTTPPVLDSDGSFFLYSKLTVDKSRWQQGNVFSCSV<br>MHEALHNHYTQKSLSLSPGK |

For SEQ ID NOS: 24-37
bovine heavy chain sequence = bold
human heavy chain sequence = dashed underline
non-antibody sequence = *italic*
Stalk = bold, underline; knob = bold, double underline; linker = *italic, squiggly underline*

TABLE 22

| Name | SEQ ID NO | SEQUENCE (bold font = non-antibody sequence) |
|---|---|---|
| BLV1H1 2-IL8 | 38 | QVQLRESGPSLVKPSQTLSLTCTASGFSLSDKAVGWVRQAPGKALEWLG<br>SIDTGGNTGYNPGLKSRLSITKDNSKSQVSLSVSSVTTEDSATYYCTSVH<br>QETKKYQSPRSAKELRCQCIKTYSKPFHPKFIKELRVIESGPHCANTEI |

TABLE 22-continued

| Name | SEQ ID NO | SEQUENCE (bold font = non-antibody sequence) |
|---|---|---|
| | | IVKLSDGRELCLDPKENWVQRVVEKFLKRAENSGSGSYTYNYEWHV DVWGQGLLVTV |
| BLV1H12-Ziconotide | 39 | QVQLRESGPSLVKPSQTLSLTCTASGFSLSDKAVGWVRQAPGKALEWLG SIDTGGNTGYNPGLKSRLSITKDNSKSQVSLSVSSVTTEDSATYYCTSVH QETKKYQSCKGKGAKCSRLMYDCCTGSCRSGKCSYTYNYEWHVDV WGQGLLVTV |
| BLV1H12-Somatostatin | 40 | QVQLRESGPSLVKPSQTLSLTCTASGFSLSDKAVGWVRQAPGKALEWLG SIDTGGNTGYNPGLKSRLSITKDNSKSQVSLSVSSVTTEDSATYYCTSVH QETKKYQSAGCKNFFWKTFTSCGSYTYNYEWHVDVWGQGLLVTV |
| BLV1H12-Chlorotoxin | 41 | QVQLRESGPSLVKPSQTLSLTCTASGFSLSDKAVGWVRQAPGKALEWLG SIDTGGNTGYNPGLKSRLSITKDNSKSQVSLSVSSVTTEDSATYYCTSVH QETKKYQSMCMPCFTTDHQMARKCDDCCGGKGRGKCYGPQCLSYT YNYEWHVDVWGQGLLVTV |
| BLV1H12-SDF1(alpha) | 42 | QVQLRESGPSLVKPSQTLSLTCTASGFSLSDKAVGWVRQAPGKALEWLG SIDTGGNTGYNPGLKSRLSITKDNSKSQVSLSVSSVTTEDSATYYCTSVH QETKKYQSKPVSLSYRCPCRFFESHVARANVKHLKILNTPNCALQIVA RLKNNNRQVCIDPKLKWIQEYLEKALNKGSGSYTYNYEWHVDVWG QGLLVTV |
| BLV1H12-IL21 | 43 | QVQLRESGPSLVKPSQTLSLTCTASGFSLSDKAVGWVRQAPGKALEWLG SIDTGGNTGYNPGLKSRLSITKDNSKSQVSLSVSSVTTEDSATYYCTSVH QETKKYQSQGQDRHMIRMRQLIDIVDQLKNYVNDLVPEFLPAPEDVE TNCEWSAFSCFQKAQLKSANTGNNERIINVSIKKLKRKPPSTNAGRR QKHRLTCPSCDSYEKKPPKEFLERFKSLLQKMIHQHLSSRTHGSEDSSYTYNYEWHVDVWGQGLLVTV |
| BLV1H12-ProTxII | 44 | QVQLRESGPSLVKPSQTLSLTCTASGFSLSDKAVGWVRQAPGKALEWLG SIDTGGNTGYNPGLKSRLSITKDNSKSQVSLSVSSVTTEDSATYYCTSVH QETKKYQSYCQKWMWTCDSERKCCEGMVCRLWCKKKLWSYTYNY EWHVDVWGQGLLVTV |
| BLV5B8 VHCH1 | 340 | QVQLRESGPSLVQPSQTLSLTCTASGFSLSRLSGYNPGLKSRLSITKDNSKSQVSLSVSSVTTEDSATYYCTTVHQ ETRKTCSDGYIAVDSCGRGQSDGCVNDCNSCYYGWRNCRRQPAIHSYEF HVDAWGRGLLVTVSSASTTAPKVYPLSSCCGDKSSSTVTLGCLVSSYMP EPVTVTWNSGALKSGVHTFPAVLQSSGLYSLSSMVTVPGSTSGQTFTCN VAHPASSTKVDKAVEPKSCDGS |
| BLV5B8 VLCL | 341 | QAVLNQPSSVSGSLGQRVSITCSGSSSNVGNGYVSWYQLIPGSAPRTLIY GDTSRASGVPDRFSGSRSGNTATLTISSLQAEDEADYFCASAEDSSSNAV FGSGTTLTVLGQPKSPPSVTLFPPSTEELNGNKATLVCLISDFYPGSVTVV WKADGSTITRNVETTRASKQSNSKYAASSYLSLTSSDWKSKGSYSCEVT HEGSTVTKTVKPSECS |

TABLE 23

Exemplary cysteine motifs

| SEQ ID NO: | Sequence |
|---|---|
| 45 | $CX_{10}CX_5CX_5CXCX_7C$ |
| 46 | $CX_{10}CX_6CX_5CXCX_{15}C$ |
| 47 | $CX_{11}CXCX_5C$ |
| 48 | $CX_{11}CX_5CX_5CXCX_7C$ |
| 49 | $CX_{10}CX_6CX_5CXCX_{13}C$ |
| 50 | $CX_{10}CX_5CXCX_4CX_8C$ |
| 51 | $CX_{10}CX_6CX_6CXCX_7C$ |
| 52 | $CX_{10}CX_4CX_7CXCX_8C$ |
| 53 | $CX_{10}CX_4CX_7CXCX_7C$ |
| 54 | $CX_{13}CX_8CX_8C$ |
| 55 | $CX_{10}CX_6CX_5CXCX_7C$ |
| 56 | $CX_{10}CX_5CX_5C$ |
| 57 | $CX_{10}CX_5CX_6CXCX_7C$ |
| 58 | $CX_{10}CX_6CX_5CX_7CX_9C$ |
| 59 | $CX_9CX_7CX_5CXCX_7C$ |
| 60 | $CX_{10}CX_6CX_5CXCX_9C$ |

TABLE 23-continued

Exemplary cysteine motifs

| SEQ ID NO: | Sequence |
|---|---|
| 61 | $CX_{10}CXCX_4CX_5CX_{11}C$ |
| 62 | $CX_7CX_3CX_6CX_5CXCX_5CX_{10}C$ |
| 63 | $CX_{10}CXCX_4CX_5CXCX_2CX_3C$ |
| 64 | $CX_{16}CX_5CXC$ |
| 65 | $CX_6CX_4CXCX_4CX_5C$ |
| 66 | $CX_{11}CX_4CX_5CX_6CX_3C$ |
| 67 | $CX_8CX_2CX_6CX_5C$ |
| 68 | $CX_{10}CX_5CX_5CXCX_{10}C$ |
| 69 | $CX_{10}CXCX_6CX_4CXC$ |
| 70 | $CX_{10}CX_5CX_5CXCX_2C$ |
| 71 | $CX_{14}CX_2CX_3CXCXC$ |
| 72 | $CX_{15}CX_5CXC$ |
| 73 | $CX_4CX_6CX_9CX_2CX_{11}C$ |
| 74 | $CX_6CX_4CX_5CX_5CX_{12}C$ |
| 75 | $CX_7CX_3CXCXCX_4CX_5CX_9C$ |
| 76 | $CX_{10}CX_6CX_5C$ |
| 77 | $CX_7CX_3CX_5CX_5CX_9C$ |
| 78 | $CX_7CX_5CXCX_2C$ |
| 79 | $CX_{10}CXCX_6C$ |
| 80 | $CX_{10}CX_3CX_3CX_5CX_7CXCX_6C$ |
| 81 | $CX_{10}CX_4CX_5CX_{12}CX_2C$ |
| 82 | $CX_{12}CX_4CX_5CXCXCX_9CX_3C$ |
| 83 | $CX_{12}CX_4CX_5CX_{12}CX_2C$ |
| 84 | $CX_{10}CX_6CX_5CXCX_{11}C$ |
| 85 | $CX_{16}CX_5CXCXCX_{14}C$ |
| 86 | $CX_{10}CX_5CXCX_8CX_6C$ |
| 87 | $CX_{12}CX_4CX_5CX_8CX_2C$ |
| 88 | $CX_{12}CX_5CX_5CXCX_8C$ |
| 89 | $CX_{10}CX_6CX_5CXCX_4CXCX_9C$ |
| 90 | $CX_{11}CX_4CX_5CX_8CX_2C$ |
| 91 | $CX_{10}CX_6CX_5CX_8CX_2C$ |
| 92 | $CX_{10}CX_6CX_5CXCX_8C$ |
| 93 | $CX_{10}CX_6CX_5CXCX_3CX_8CX_2C$ |
| 94 | $CX_{10}CX_6CX_5CXCX_2CX_6CX_5C$ |
| 95 | $CX_{10}CX_6CX_5CX_3CX_8C$ |
| 96 | $CX_7CX_6CX_3CX_3CX_9C$ |
| 97 | $CX_9CX_8CX_5CX_6CX_5C$ |
| 98 | $CX_{10}CX_2CX_2CX_7CXCX_{11}CX_5C$ |
| 99 | $CX_{10}CX_6CX_5CXCX_2CX_8CX_4C$ |
| 100 | $CCX_3CXCX_3CX_2CCXCX_5CX_9CX_5CXC$ |
| 101 | $CX_6CX_2CX_5CX_4CCXCX_4CX_6CXC$ |
| 102 | $CX_6CX_2CX_5CX_4CCXCX_4CX_6CXC$ |
| 103 | $CX_9CX_3CXCX_2CXCCCX_6CX_4C$ |
| 104 | $CX_5CX_3CXCX_4CX_4CCX_{10}CX_2CC$ |
| 105 | $CX_5CXCX_1CXCX_3CCX_3CX_4CX_{10}C$ |
| 106 | $CX_9CCCX_3CX_4CCCX_5CX_6C$ |
| 107 | $CCX_8CX_5CX_4CX_3CX_4CCXCX_1C$ |
| 108 | $CCX_6CCX_5CCCX_4CX_4CX_{12}C$ |
| 109 | $CX_6CX_2CX_3CCCX_4CX_5CX_3CX_3C$ |
| 110 | $CX_3CX_5CX_6CX_4CCXCX_5CX_4CXC$ |
| 111 | $CX_4CX_4CCX_4CX_4CXCX_{11}CX_2CXC$ |
| 112 | $CX_5CX_2CCX_5CX_4CCX_3CCX_7C$ |
| 113 | $CX_5CX_5CX_3CX_2CXCCX_4CX_7CXC$ |
| 114 | $CX_3CX_7CX_3CX_4CCXCX_2CX_5CX_2C$ |
| 115 | $CX_9CX_3CXCX_4CCX_5CCCX_6C$ |
| 116 | $CX_9CX_3CXCX_2CXCCX_6CX_3CX_3C$ |
| 117 | $CX_8CCXCX_3CCX_3CXCX_3CX_4C$ |
| 118 | $CX_9CCX_4CX_2CXCCXCX_4CX_3C$ |
| 119 | $CX_{10}CXCX_3CX_2CXCCX_4CX_5CXC$ |
| 120 | $CX_9CXCX_3CX_2CXCCX_4CX_5CXC$ |
| 121 | $CX_6CCXCX_5CX_4CXCX_5CX_2C$ |
| 122 | $CX_6CCXCX_3CXCCX_3CX_4CC$ |
| 123 | $CX_6CCXCX_3CXCX_2CXCX_4CX_8C$ |
| 124 | $CX_4CX_2CCX_3CXCX_4CCX_2CX_3C$ |
| 125 | $CX_3CX_5CX_3CCCX_4CX_9C$ |
| 126 | $CCX_9CX_3CXCCX_3CX_5C$ |
| 127 | $CX_9CX_2CX_3CX_4CCX_4CX_5C$ |
| 128 | $CX_9CX_7CX_4CCXCX_7CX_3C$ |
| 129 | $CX_9CX_3CCCX_{10}CX_2CX_3C$ |
| 130 | $CX_3CX_5CX_5CX_4CCX_{10}CX_6C$ |
| 131 | $CX_9CX_5CX_4CCXCX_5CX_4C$ |
| 132 | $CX_7CXCX_6CX_4CCCX_{10}C$ |
| 133 | $CX_8CX_2CX_4CCX_4CX_3CX_3C$ |
| 134 | $CX_7CX_5CXCX_4CCX_7CX_4C$ |

TABLE 23-continued

Exemplary cysteine motifs

| SEQ ID NO: | Sequence |
|---|---|
| 135 | $CX_{11}CX_3CX_4CCCX_8CX_2C$ |
| 136 | $CX_2CX_3CX_4CCX_4CX_5CX_{15}C$ |
| 137 | $CX_9CX_5CX_4CCX_7C$ |
| 138 | $CX_9CX_7CX_3CX_2CX_6C$ |
| 139 | $CX_9CX_5CX_4CCX_{14}C$ |
| 140 | $CX_9CX_5CX_4CCX_8C$ |
| 141 | $CX_9CX_6CX_4CCXC$ |
| 142 | $CX_5CCX_7CX_4CX_{12}$ |
| 143 | $CX_{10}CX_3CX_4CCX_4C$ |
| 144 | $CX_9CX_4CCX_5CX_4C$ |
| 145 | $CX_{10}CX_3CX_4CX_7CXC$ |
| 146 | $CX_7CX_7CX_2CX_2CX_3C$ |
| 147 | $CX_9CX_4CX_4CCX_6C$ |
| 148 | $CX_7CXCX_3CXCX_6C$ |
| 149 | $CX_7CXCX_4CXCX_4C$ |
| 150 | $CX_9CX_5CX_4C$ |
| 151 | $CX_3CX_6CX_8C$ |
| 152 | $CX_{10}CXCX_4C$ |
| 153 | $CX_{10}CCX_4C$ |
| 154 | $CX_{15}C$ |
| 155 | $CX_{10}C$ |
| 156 | $CX_9C$ |

TABLE 24

Exemplary conserved motifs with the stalk domain

| SEQ ID NO: | Sequence |
|---|---|
| 157 | TSVHQETKKYQ |
| 158 | VHQETKKYQ |
| 159 | TTVHQ |
| 160 | TSVHQ |
| 161 | SSVTQ |
| 162 | STVHQ |
| 163 | ATVRQ |
| 164 | TTVYQ |
| 165 | SPVHQ |
| 166 | ATVYQ |
| 167 | TAVYQ |
| 168 | TNVHQ |
| 169 | ATVHQ |
| 170 | STVYQ |
| 171 | TIVHQ |
| 172 | AIVYQ |
| 173 | TTVFQ |
| 174 | AAVFQ |
| 175 | GTVHQ |
| 176 | ASVHQ |
| 177 | TAVFQ |
| 178 | ATVFQ |
| 179 | AAAHQ |
| 180 | VVVYQ |
| 181 | GTVFQ |
| 182 | TAVHQ |
| 183 | ITVHQ |
| 184 | ITAHQ |
| 185 | VTVHQ |
| 186 | AAVHQ |
| 187 | GTVYQ |
| 188 | TTVLQ |
| 189 | TTTHQ |
| 190 | TTDYQ |
| 191 | TTDYQ |
| 192 | CTSVHQ |
| 193 | CSSVTQ |
| 194 | CSTVHQ |
| 195 | CATVRQ |
| 196 | CTTVYQ |
| 197 | CSPVHQ |
| 198 | CATVYQ |
| 199 | CTAVYQ |
| 200 | CTNVHQ |
| 201 | CATVHQ |
| 202 | CSTVYQ |

TABLE 24-continued

Exemplary conserved motifs with the stalk domain

| SEQ ID NO: | Sequence |
|---|---|
| 203 | CTIVHQ |
| 204 | CAIVYQ |
| 205 | CTTVFQ |
| 206 | CAAVFQ |
| 207 | CGTVHQ |
| 208 | CASVHQ |
| 209 | CTAVFQ |
| 210 | CATVFQ |
| 211 | CAAAHQ |
| 212 | CVVVYQ |
| 213 | CGTVFQ |
| 214 | CTAVHQ |
| 215 | CITVHQ |
| 216 | CITAHQ |
| 217 | CVTVHQ |
| 218 | CAAVHQ |
| 219 | CGTVYQ |
| 220 | CTTVLQ |
| 221 | CTTTHQ |
| 222 | CTTDYQ |
| 223 | CTTVHQ$X_n$ |
| 224 | CTSVHQ$X_n$ |
| 225 | VHQ |
| 226 | KKQ |
| 227 | VYQ |
| 228 | C$X^1X^2X^3X^4$Q |
| 229 | $X^1X^2$VHQ |
| 230 | C$X^1X^2$VHQ |
| 231 | $X^1X^2$V$X^3$Q |
| 232 | C$X^1X^2$V$X^3$Q |
| 233 | $X^1X^2$KKQ |
| 234 | C$X^1X^2$KKQ |
| 235 | YTYNYEW |
| 236 | YTYNYE |
| 237 | YLYTYEH |
| 238 | YLYTYE |

TABLE 24-continued

Exemplary conserved motifs with the stalk domain

| SEQ ID NO: | Sequence |
|---|---|
| 239 | CYTYNYEF |
| 240 | HYTYTYDF |
| 241 | HYTYTYEW |
| 242 | KHRYTYEW |
| 243 | NYIYKYSF |
| 244 | PYIYTYQF |
| 245 | SFTYTYEW |
| 246 | SYIYIYQW |
| 247 | SYNYTYSW |
| 248 | SYSYSYEY |
| 249 | SYTYNYDF |
| 250 | SYTYNYEW |
| 251 | SYTYNYQF |
| 252 | SYVWTHNF |
| 253 | TYKYVYEW |
| 254 | TYTYTYEF |
| 255 | TYTYTYEW |
| 256 | VFTYTYEF |
| 257 | AYTYEW |
| 258 | DYIYTY |
| 259 | IHSYEF |
| 260 | SFTYEF |
| 261 | SHSYEF |
| 262 | THTYEF |
| 263 | TWTYEF |
| 264 | TYNYEW |
| 265 | TYSYEF |
| 266 | TYSYEH |
| 267 | TYTYDF |
| 268 | TYTYEF |
| 269 | TYTYEW |
| 270 | AYEF |
| 271 | AYSF |
| 272 | AYSY |
| 273 | CYSF |
| 274 | DYTY |
| 275 | KYEH |

TABLE 24-continued

Exemplary conserved motifs with the stalk domain

| SEQ ID NO: | Sequence |
|---|---|
| 276 | KYEW |
| 277 | MYEF |
| 278 | NWIY |
| 279 | NYDY |
| 280 | NYQW |
| 281 | NYSF |
| 282 | PYEW |
| 283 | RYNW |
| 284 | RYTY |
| 285 | SYEF |
| 286 | SYEH |
| 287 | SYEW |
| 288 | SYKW |
| 289 | SYTY |
| 290 | TYDF |
| 291 | TYEF |
| 292 | TYEW |
| 293 | TYQW |
| 294 | TYTY |
| 295 | VYEW |
| 296 | YX$^1$YX$^2$ |
| 297 | YX$^1$YX$^2$Y |
| 298 | YX$^1$YX$^2$YX$^3$ |
| 299 | YX$^1$YX$^2$YX$^3$X$^4$ |
| 300 | YEX |
| 301 | YDX |
| 302 | XYE |
| 303 | XYD |
| 304 | YEX$^1$X$_n$W |
| 305 | YDX$^1$X$_n$W |
| 306 | YEX$^1$X$^2$X$^3$X$^4$X$^5$W |
| 307 | YDX$^1$X$^2$X$^3$X$^4$X$^5$W |
| 333 | YEXXXW |
| 334 | YEXXXXW |
| 335 | YDXXXW |
| 336 | YDXXXXW |

TABLE 25

Exemplary Linker Sequences

| SEQ ID NO: | Sequence |
|---|---|
| 337 | GGGSGGGGS |
| 338 | GGGGSGGGS |
| 339 | (GGGGS)n |
| 342 | (GSG)n |

TABLE 26

Exemplary non-antibody sequences

| Description | SEQ ID NO: | Sequence |
|---|---|---|
| IL8 | 317 | PRSAKELRCQCIKTYSKPFHPKFIKELRVIESGPHCANTEIIVKLSDGRELCLDPKENWVQRVVEKFLKRAENS |
| ziconotide | 318 | CKGKGAKCSRLMYDCCTGSCRSGKC |
| somatostatin | 319 | AGCKNFFWKTFTSCG |
| chlorotoxin | 320 | MCMPCFTTDHQMARKCDDCCGGKGRGKCYGPQCL |
| SDF1(alpha) | 321 | KPVSLSYRCPCRFFESHVARANVKHLKILNTPNCALQIVARLKNNNRQVCIDPKLKWIQEYLEKALNK |
| IL21 | 322 | QGQDRHMIRMRQLIDIVDQLKNYVNDLVPEFLPAPEDVETNCEWSAFSCFQKAQLKSANTGNNERIINVSIKKLKRKPPSTNAGRRQKHRLTCPSCDSYEKKPPKEFLERFKSLLQKMIHQHLSSRTHGSEDS |
| Protoxin2 | 323 | YCQKWMWTCDSERKCCEGMVCRLWCKKKLW |
| IFN-beta | 324 | MSYNLLGFLQRSSNFQCQKLLWQLNGRLEYCLKDRMNFDIPEEIKQLQQFQKEDAALTIYEMLQNIFAIFRQDSSSTGWNETIVENLLANVYHQINHLKTVLEEKLEKEDFTRGKLMSSLHLKRYYGRILHYLKAKEYSHCAWTIVRVEILRNFYFINRLTGYLRN |
| bGCSF | 325 | TPLGPARSLPQSFLLKCLEQVRKIQADGAELQERLCAAHKLCHPEELMLLRHSLGIPQAPLSSCSSQSLQLTSCLNQLHGGLFLYQGLLQALAGISPELAPTLDTLQLDVTDFATNIWLQMEDLGAAPAVQPTGAMPTFTSAFQRRAGGVLVASQLHRFLELAYRGLRYLAEP |
| GMCSF | 326 | APARSPSPSTQPWEHVNAIQEARRLLNLSRDTAAEMNETVEVISEMFDLQEPTCLQTRLELYKQGLRGSLTKLKGPLTMMASHYKQHCPPTPETSCATQIITFESFKENLKDFLLVIPFDCWEPVQE |
| hFGF21 | 327 | HPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGARFLPLPGLPPAPPEPPGILAPQPPDVGSSDPLSMVGPSQGRSPSYAS |
| Ex-4 | 328 | HGEGTFTSDLSKQMEEEAVRLFIEWLKNGGPSSGAPPPS |
| hGLP-1 | 329 | HAEGTFTSDVSSYLEGQAAKEFIAWLVKGR |

TABLE 26-continued

Exemplary non-antibody sequences

| Description | SEQ ID NO: | Sequence |
| --- | --- | --- |
| hEPO | 330 | PPRLICDSRVLERYLLEAKEAENITTGCAE HCSLNENITVPDTKVNFYAWKRMEVGQQAV EVWQGLALLSEAVLRGQALLVNSSQPWEPL QLHVDKAVSGLRSLTTLLRALGAQKEAISP PDAASAAPLRTITADTFRKLFRVYSNFLRG KLKLYTGEACRTGDR |
| Moka | 331 | INVKCSLPQQCIKPCKDAGMRFGKCMNKKCRCYS |
| VM-24 | 332 | AAAISCVGSPECPPKCRAQGCKNGKCMNRKCKCY YC |

What is claimed:

1. A polynucleotide encoding a fusion antibody or antigen-binding fragment thereof, wherein the fusion antibody or antigen-binding fragment thereof comprises a heavy chain comprising a heavy chain variable domain wherein the heavy chain variable domain comprises a complementarity determining region 3 (CDRH3) comprising from N- to C-terminus (i) a first stalk domain comprising SEQ ID NO: 159 or 160, (ii) a knob domain, wherein at least a portion of the knob domain is replaced by a toxin, and (iii) a second stalk domain comprising SEQ ID NO: 236.

2. The polynucleotide of claim 1, wherein the polynucleotide comprises a nucleic acid sequence encoding a linker sequence selected from (GGGGS)n (SEQ ID NO: 339) wherein n is an integer between 1 and 5, GGGSGGGGS (SEQ ID NO: 337), GGGGSGGGS (SEQ ID NO: 338), or (GSG)n (SEQ ID NO: 342) wherein n is greater than or equal to one, or a combination thereof, wherein the linker is linked to a C-terminus, an N-terminus, or both C-terminus and N-terminus of the non-antibody sequence.

3. The polynucleotide of claim 1, wherein the polynucleotide further comprises a coding sequence for a light chain.

4. The polynucleotide of claim 3, wherein the heavy chain and light chain are encoded in the same vector.

5. A vector comprising the polynucleotide of claim 3.

6. A host cell comprising the vector of claim 5.

7. A method of producing a fusion antibody or antigen-binding fragment thereof comprising an ultralong CDR3 or fragment thereof comprising culturing the host cell of claim 5 under conditions wherein the polynucleotide sequence is expressed and the fusion antibody or antigen-binding fragment thereof comprising the ultralong CDR3 or fragment thereof is produced.

8. The method of claim 7, further comprising recovering the fusion antibody or antigen-binding fragment thereof comprising the ultralong CDR3 or fragment thereof from the host cell culture.

9. The polynucleotide of claim 1, wherein the fusion antibody or antigen-binding fragment thereof is selected from a chimeric antibody, a human engineered antibody, a humanized antibody, a bovine antibody, a bovinized antibody, a bovine engineered antibody, and a fully bovine antibody.

10. The polynucleotide of claim 1, wherein the fusion antibody or antigen-binding fragment thereof comprises a Fab, a scFv, dsFv, diabody, (dsFv)2, minibody, flex minibody or bi-specific fragment.

11. A vector comprising the polynucleotide of claim 1.

12. A host cell comprising the vector of claim 11.

* * * * *

SEQUENCE LISTING

<160> NUMBER OF SEQ ID NOS: 511

<210> SEQ ID NO 1
<211> LENGTH: 648
<212> TYPE: DNA
<213> ORGANISM: Artificial Sequence
<220> FEATURE:
<223> OTHER INFORMATION: Description of Artificial Sequence: Synthetic
      Light Chain fusion polynucleotide

<400> SEQUENCE: 1

```
caggccgtcc tgaaccagcc aagcagcgtc tccgggtctc tggggcagcg ggtctcaatc    60
acctgtagcg gtcttcctc caatgtcggc aacggctacg tgtcttggta tcagctgatc    120
cctggcagtg ccccacgaac cctgatctac ggcgacacat ccagagcttc tggggtcccc    180
gatcggttct cagggagcag atccggaaac acagctactc tgaccatcag ctccctgcag    240
gctgaggacg aagcagatta tttctgcgca tctgccgagg actctagttc aaatgccgtg    300
tttggaagcg gcaccacact gacagtcctg ggcagccca agagtccccc ttcagtgact    360
ctgttcccac cctctaccga ggaactgaac ggaaacaagg ccacactggt gtgtctgatc    420
agcgactttt accctggatc cgtcactgtg gtctggaagg cagatggcag cacaattact    480
aggaacgtgg aaactacccg cgcctccaag cagtctaata gtaaatacgc cgccagctcc    540
tatctgagcc tgacctctag tgattggaag tccaaagggt catatagctg cgaagtgacc    600
catgaaggct caaccgtgac taagactgtg aaaccatccg agtgctcc                648
```

<210> SEQ ID NO 2
<211> LENGTH: 507
<212> TYPE: DNA
<213> ORGANISM: Artificial Sequence
<220> FEATURE:
<223> OTHER INFORMATION: Description of Artificial Sequence: Synthetic
      Heavy Chain -no insertion fusion polynucleotide

<400> SEQUENCE: 2

```
caggtccagc tgagagagag cggcccttca ctggtcaagc catcccagac actgagcctg    60
acatgcacag caagcgggtt ttcactgagc gacaaggcag tgggatgggt ccgacaggca    120
ccaggaaaag ccctggaatg gctgggcagc atcgataccg gcgggaacac agggtacaat    180
cccggactga gagcagact gtccattacc aaggacaact ctaaaagtca ggtgtcactg    240
agcgtgagct ccgtcaccac agaggatagt gcaacttact attgcacctc tgtgcaccag    300
gaaactaaga ataccagag ctgtcctgac ggctatcggg agagatctga ttgcagtaat    360
aggccagctt gtgcacatc cgactgctgt cgcgtgtctg tcttcgggaa ctgcctgact    420
accctgcctg tgtcctactc ttataccttac aattatgaat ggcatgtgga tgtctgggga   480
```

```
cagggcctgc tggtgacagt ctctagt                                       507
```

<210> SEQ ID NO 3
<211> LENGTH: 1905
<212> TYPE: DNA
<213> ORGANISM: Artificial Sequence
<220> FEATURE:
<223> OTHER INFORMATION: Description of Artificial Sequence: Synthetic
      IFN-beta fusion polynucleotide

<400> SEQUENCE: 3

```
caggtccagc tgagagagag cggcccttca ctggtcaagc catcccagac actgagcctg   60
acatgcacag caagcgggtt ttcactgagc gacaaggcag tgggatgggt ccgacaggca  120
ccaggaaaag ccctggaatg gctgggcagc atcgataccg gcgggaacac agggtacaat  180
cccggactga agagcagact gtccattacc aaggacaact ctaaaagtca ggtgtcactg  240
agcgtgagct ccgtcaccac agaggatagt gcaacttact attgcacctc tgtgcaccag  300
gaaactaaga ataccagag cggggtggc ggaagcatga gctacaactt gcttggattc  360
ctacaaagaa gcagcaattt tcagtgtcag aagctcctgt ggcaattgaa tgggaggctt  420
gaatactgcc tcaaggacag gatgaacttt gacatccctg aggagattaa gcagctgcag  480
cagttccaga aggaggacgc cgcattgacc atctatgaga tgctccagaa catctttgct  540
attttcagac aagattcatc tagcactggc tggaatgaga ctattgttga aacctcctg  600
gctaatgtct atcatcagat aaaccatctg aagacagtcc tggaagaaaa actggagaaa  660
gaagatttca ccagggaaa actcatgagc agtctgcacc tgaaaagata ttatgggagg  720
attctgcatt acctgaaggc caaggagtac agtcactgtg cctggaccat agtcagagtg  780
gaaatcctaa ggaactttta cttcattaac agacttacag gttacctccg aaacggcgga  840
ggtgggagtt cttataccta caattatgaa tggcatgtgg atgtctgggg acagggcctg  900
ctggtgacag tctctagtgc ttccacaact gcaccaaagg tgtaccccct gtcaagctgc  960
tgtgggaca atcctctag taccgtgaca ctgggatgcc tggtctcaag ctatatgccc 1020
gagcctgtga ctgtcacctg gaactcagga gccctgaaaa gcggagtgca caccttccca 1080
gctgtgctgc agtcctctgg cctgtatagc ctgagttcaa tggtgacagt ccccggcagt 1140
acttcagggc agaccttcac ctgtaatgtg gccatcctg ccagtccac caaagtggac 1200
aaagcagtgg aacccaaatc ttgcgacaaa actcacacat gcccaccgtg cccagcacct 1260
gaactcctgg gggaccgtc agtcttcctc ttccccccaa acccaagga cacctcatg 1320
atctccgga cccctgaggt cacatgcgtg gtggtggacg tgagccacga agaccctgag 1380
gtcaagttca actggtacgt ggacggcgtg gaggtgcata atgccaagac aaagccgcgg 1440
gaggagcagt acaacagcac gtaccgtgtg gtcagcgtcc tcaccgtcct gcaccaggac 1500
tggctgaatg gcaaggagta caagtgcaag gtctccaaca aagccctccc agcccccatc 1560
gagaaaacca tctccaaagc caaagggcag ccccgagaac cacaggtgta caccctgccc 1620
ccatcccggg atgagctgac caagaaccag gtcagcctga cctgcctggt caaaggcttc 1680
tatcccagcg acatcgccgt ggagtgggag agcaatgggc agccggagaa caactacaag 1740
accacgcctc ccgtgctgga ctccgacggc tccttcttcc tctacagcaa gctcaccgtg 1800
gacaagagca ggtggcagca ggggaacgtc ttctcatgct ccgtgatgca tgaggctctg 1860
cacaaccact acacgcagaa gagcctctcc ctgtctccgg gtaaa            1905
```

<210> SEQ ID NO 4
<211> LENGTH: 1899
<212> TYPE: DNA
<213> ORGANISM: Artificial Sequence
<220> FEATURE:
<223> OTHER INFORMATION: Description of Artificial Sequence: Synthetic bGCSF-L0 fusion polynucleotide

<400> SEQUENCE: 4

```
caggtccagc tgagagagag cggcccttca ctggtcaagc catcccagac actgagcctg      60
acatgcacag caagcgggtt ttcactgagc gacaaggcag tgggatgggt ccgacaggca     120
ccaggaaaag ccctggaatg gctgggcagc atcgataccg gcgggaacac agggtacaat     180
cccggactga agagcagact gtccattacc aaggacaact ctaaaagtca ggtgtcactg     240
agcgtgagct ccgtcaccac agaggatagt gcaacttact attgcaccta tgtgcaccag     300
gaaactaaga ataccagag caccccccctt ggccctgccc gatccctgcc ccagagcttc     360
ctgctcaagt gcttagagca agtgaggaaa atccaggctg atggcgccga gctgcaggag     420
aggctgtgtg ccgcccacaa gctgtgccac ccggaggagc tgatgctgct caggcactct     480
ctgggcatcc cccaggctcc cctaagcagc tgctccagcc agtccctgca gctgacgagc     540
tgcctgaacc aactacacgg cggcctcttt ctctaccagg cctcctgca ggccctggcg     600
ggcatctccc cagagctggc ccccaccttg acacactgc agctggacgt cactgacttt     660
gccacgaaca tctggctgca gatggaggac ctggggccgg ccccgctgt gcagcccacc     720
cagggcgcca tgccgacctt cacttcagcc ttccaacgca gagcaggagg ggtcctggtt     780
gcttccagc tgcatcgttt cctggagctg gcataccgtg gcctgcgcta ccttgctgag     840
ccctcttata cctacaatta tgaatggcat gtggatgtct ggggacaggg cctgctggtg     900
acagtctcta gtgcttccac aactgcacca aaggtgtacc ccctgtcaag ctgctgtggg     960
gacaaatcct ctagtaccgt gacactggga tgcctggtct caagctatat gcccgagcct    1020
gtgactgtca cctggaactc aggagccctg aaaagcggag tgcacacctt cccagctgtg    1080
ctgcagtcct ctggcctgta tagcctgagt tcaatggtga cagtccccgg cagtacttca    1140
gggcagacct tcacctgtaa tgtggcccat cctgccagct ccaccaaagt ggacaaagca    1200
gtggaaccca atcttgcga caaaactcac acatgcccac cgtgcccagc acctgaactc    1260
ctgggggac cgtcagtctt cctcttcccc ccaaaaccca aggacaccct catgatctcc    1320
cggaccectg aggtcacatg cgtggtggtg gacgtgagcc acgaagaccc tgaggtcaag    1380
ttcaactggt acgtggacgg cgtggaggtg cataatgcca agacaaagcc gcgggaggag    1440
cagtacaaca gcacgtaccg tgtggtcagc gtcctcaccg tcctgcacca ggactggctg    1500
aatggcaagg agtacaagtg caaggtctcc aacaaagccc tcccagcccc catcgagaaa    1560
accatctcca aagccaaagg gcagccccga gaaccacagg tgtacaccct gcccccatcc    1620
cgggatgagc tgaccaagaa ccaggtcagc ctgacctgcc tggtcaaagg cttctatccc    1680
agcgacatcg ccgtggagtg ggagagcaat gggcagccgg agaacaacta caagaccacg    1740
cctcccgtgc tggactccga cggctccttc ttcctctaca gcaagctcac cgtggacaag    1800
agcaggtggc agcaggggaa cgtcttctca tgctccgtga tgcatgaggc tctgcacaac    1860
cactacacgc agaagagcct ctccctgtct ccgggtaaa                           1899
```

<210> SEQ ID NO 5
<211> LENGTH: 1929
<212> TYPE: DNA
<213> ORGANISM: Artificial Sequence
<220> FEATURE:
<223> OTHER INFORMATION: Description of Artificial Sequence: Synthetic bGCSF-L1 fusion polynucleotide

<400> SEQUENCE: 5

```
caggtccagc tgagagagag cggcccttca ctggtcaagc catcccagac actgagcctg        60
acatgcacag caagcgggtt ttcactgagc gacaaggcag tgggatgggt ccgacaggca       120
ccaggaaaag ccctggaatg gctgggcagc atcgataccg gcgggaacac agggtacaat       180
cccggactga agagcagact gtccattacc aaggacaact ctaaaagtca ggtgtcactg       240
agcgtgagct ccgtcaccac agaggatagt gcaacttact attgcacctc tgtgcaccag       300
gaaactaaga ataccagag cggtggcgga ggatctaccc cccttggccc tgcccgatcc       360
ctgccccaga gcttcctgct caagtgctta gagcaagtga ggaaaatcca ggctgatggc       420
gccgagctgc aggagaggct gtgtgccgcc cacaagctgt gccacccgga ggagctgatg       480
ctgctcaggc actctctggg catccccag gctcccctaa gcagctgctc cagccagtcc       540
ctgcagctga cgagctgcct gaaccaacta cacggcggcc tctttctcta ccagggcctc       600
ctgcaggccc tggcgggcat ctccccagag ctggccccca ccttggacac actgcagctg       660
gacgtcactg actttgccac gaacatctgg ctgcagatgg aggacctggg ggcggccccc       720
gctgtgcagc ccacccaggg cgccatgccg accttcactt cagccttcca acgcagagca       780
ggaggggtcc tggttgcttc ccagctgcat cgtttcctgg agctggcata ccgtggcctg       840
cgctaccttg ctgagcccgg tggcggagga tcttcttata cctacaatta tgaatggcat       900
gtggatgtct ggggacaggg cctgctggtg acagtctcta gtgcttccac aactgcacca       960
aaggtgtacc ccctgtcaag ctgctgtggg acaaatcct ctagtaccgt gacactggga      1020
tgcctggtct caagctatat gcccgagcct gtgactgtca cctggaactc aggagccctg      1080
aaaagcggag tgcacacctt cccagctgtg ctgcagtcct ctggcctgta gcctgagt       1140
tcaatggtga cagtccccgg cagtacttca gggcagacct tcacctgtaa cgtgccccat      1200
cctgccagct ccaccaaagt ggacaaagca gtggaaccca atcttgcga caaaactcac      1260
acatgcccac cgtgcccagc acctgaactc ctggggggac cgtcagtctt cctcttcccc      1320
ccaaaaccca aggacaccct catgatctcc cggacccctg aggtcacatg cgtggtggtg      1380
gacgtgagcc acgaagaccc tgaggtcaag ttcaactggt acgtggacgg cgtggaggtg      1440
cataatgcca agacaaagcc gcgggaggag cagtacaaca gcacgtaccg tgtggtcagc      1500
gtcctcaccg tcctgcacca ggactggctg aatggcaagg agtacaagtg caaggtctcc      1560
aacaaagccc tcccagcccc catcgagaaa accatctcca aagccaaagg gcagccccga      1620
gaaccacagg tgtacaccct gcccccatcc cgggatgagc tgaccaagaa ccaggtcagc      1680
ctgacctgcc tggtcaaagg cttctatccc agcgacatcg ccgtggagtg ggagagcaat      1740
gggcagccgg agaacaacta caagaccacg cctcccgtgc tggactccga cggctccttc      1800
ttcctctaca gcaagctcac cgtggacaag agcaggtggc agcaggggaa cgtcttctca      1860
tgctccgtga tgcatgaggc tctgcacaac cactacacgc agaagagcct ctccctgtct      1920
ccgggtaaa                                                              1929
```

<210> SEQ ID NO 6
<211> LENGTH: 1788
<212> TYPE: DNA
<213> ORGANISM: Artificial Sequence
<220> FEATURE:
<223> OTHER INFORMATION: Description of Artificial Sequence: Synthetic GMCSF fusion polynucleotide

<400> SEQUENCE: 6

```
caggtccagc tgagagagag cggcccttca ctggtcaagc catcccagac actgagcctg      60
acatgcacag caagcgggtt ttcactgagc gacaaggcag tgggatgggt ccgacaggca     120
ccaggaaaag ccctggaatg gctgggcagc atcgataccg gcgggaacac agggtacaat     180
cccggactga gagcagact gtccattacc aaggacaact ctaaaagtca ggtgtcactg      240
agcgtgagct ccgtcaccac agaggatagt gcaacttact attgcacctc tgtgcaccag     300
gaaactaaga ataccagag cggggtggc ggaagcgcac ccgcccgctc gcccagcccc       360
agcacgcagc cctgggagca tgtgaatgcc atccaggagg cccggcgtct cctgaacctg     420
agtagagaca ctgctgctga gatgaatgaa acagtagaag tcatctcaga aatgtttgac     480
ctccaggagc cgacctgcct acagacccgc ctggagctgt acaagcaggg cctgcggggc     540
agcctcacca agctcaaggg ccccttgacc atgatggcca gccactacaa gcagcactgc     600
cctccaaccc cggaaacttc ctgtgcaacc cagattatca cctttgaaag tttcaaagag     660
aacctgaagg actttctgct tgtcatcccc tttgactgct gggagccagt ccaggagggc     720
ggaggtggga gttcttatac ctacaattat gaatggcatg tggatgtctg gggacagggc     780
ctgctggtga cagtctctag tgcttccaca actgcaccaa aggtgtaccc cctgtcaagc     840
tgctgtgggg acaaatcctc tagtaccgtg acactgggat gcctggtctc aagctatatg     900
cccgagcctg tgactgtcac ctggaactca ggagccctga aaagcggagt gcacaccttc     960
ccagctgtgc tgcagtcctc tggcctgtat agcctgagtt caatggtgac agtccccggc    1020
agtacttcag ggcagacctt cacctgtaat gtggcccatc ctgccagctc caccaaagtg    1080
gacaaagcag tggaacccaa atcttgcgac aaaactcaca catgcccacc gtgcccagca    1140
cctgaactcc tggggggacc gtcagtcttc ctcttccccc caaaacccaa ggacaccctc    1200
atgatctccc ggacccctga ggtcacatgc gtggtggtgg acgtgagcca cgaagaccct    1260
gaggtcaagt tcaactggta cgtggacggc gtggaggtgc ataatgccaa gacaaagccg    1320
cgggaggagc agtacaacag cacgtaccgt gtggtcagcg tcctcaccgt cctgcaccag    1380
gactggctga atggcaagga gtacaagtgc aaggtctcca acaaagccct cccagccccc    1440
atcgagaaaa ccatctccaa agccaaaggg cagccccgag aaccacaggt gtacaccctg    1500
cccccatccc gggatgagct gaccaagaac caggtcagcc tgacctgcct ggtcaaaggc    1560
ttctatccca gcgacatcgc cgtggagtgg gagagcaatg ggcagccgga gaacaactac    1620
aagaccacgc ctcccgtgct ggactccgac ggctccttct tcctctacag caagctcacc    1680
gtggacaaga gcaggtggca gcaggggaac gtcttctcat gctccgtgat gcatgaggct    1740
ctgcacaacc actacacgca gaagagcctc tccctgtctc cgggtaaa               1788
```

<210> SEQ ID NO 7
<211> LENGTH: 1950
<212> TYPE: DNA
<213> ORGANISM: Artificial Sequence
<220> FEATURE:
<223> OTHER INFORMATION: Description of Artificial Sequence: Synthetic hFGF21 fusion polynucleotide

<400> SEQUENCE: 7

```
caggtccagc tgagagagag cggcccttca ctggtcaagc catcccagac actgagcctg      60
acatgcacag caagcgggtt ttcactgagc gacaaggcag tgggatgggt ccgacaggca     120
```

```
ccaggaaaag ccctggaatg gctgggcagc atcgataccg gcgggaacac agggtacaat    180
cccggactga agagcagact gtccattacc aaggacaact ctaaaagtca ggtgtcactg    240
agcgtgagct ccgtcaccac agaggatagt gcaacttact attgcacctc tgtgcaccag    300
gaaactaaga ataccagag cggggtggc ggaagccacc ccatccctga ctccagtcct    360
ctcctgcaat tcgggggcca agtccggcag cggtacctct acacagatga tgcccagcag    420
acagaagccc acctggagat cagggaggat gggacggtgg ggggcgctgc tgaccagagc    480
cccgaaagtc tcctgcagct gaaagccttg aagccgggag ttattcaaat cttgggagtc    540
aagacatcca ggttcctgtg ccagcggcca gatgggggcc tgtatggatc gctccacttt    600
gaccctgagg cctgcagctt ccgggagctg cttcttgagg acggatacaa tgtttaccag    660
tccgaagccc acggcctccc gctgcacctg ccagggaaca agtccccaca ccggaccct    720 gcaccccgag gaccagctcg cttcctgcca ctaccaggcc tgccccccgc accccggag    780 ccaccccggaa tcctgccccc ccagccccc gatgtgggct cctcggaccc tctgagcatg    840 gtgggaccctt cccagggccg aagccccagc tacgcttccg gcggaggtgg gagttcttat    900
acctacaatt atgaatgcca tgtggatgtc tggggacagg gcctgctggt gacagtctct    960
agtgcttcca caactgcacc aaaggtgtac cccctgtcaa gctgctgtgg ggacaaatcc    1020
tctagtaccg tgacactggg atgcctggtc tcaagctata tgcccgagcc tgtgactgtc    1080
acctggaact caggagccct gaaaagcgga gtgcacacct tcccagctgt gctgcagtcc    1140
tctggcctgt atagcctgag ttcaatggtg acagtccccg gcagtacttc agggcagacc    1200
ttcacctgta atgtggccca tcctgccagc tccaccaaag tggacaaagc agtggaaccc    1260
aaatcttgcg acaaaactca cacatgccca ccgtgcccag cacctgaact cctgggggga    1320
ccgtcagtct tcctcttccc cccaaaaccc aaggacaccc tcatgatctc ccggaccct    1380 gaggtcacat gcgtggtggt ggacgtgagc cacgaagacc ctgaggtcaa gttcaactgg    1440
tacgtggacg gcgtggaggt gcataatgcc aagacaaagc cgcgggagga gcagtacaac    1500
agcacgtacc gtgtggtcag cgtcctcacc gtcctgcacc aggactggct gaatggcaag    1560
gagtacaagt gcaaggtctc caacaaagcc ctcccagccc ccatcgagaa aaccatctcc    1620
aaagccaaag gcagccccg agaaccacag gtgtacaccc tgcccccatc ccgggatgag    1680
ctgaccaaga accaggtcag cctgacctgc ctggtcaaag gcttctatcc cagcgacatc    1740
gccgtggagt gggagagcaa tgggcagccg gagaacaact acaagaccac gcctcccgtg    1800
ctggactccg acggctcctt cttcctctac agcaagctca ccgtggacaa gagcaggtgg    1860
cagcagggga acgtcttctc atgctccgtg atgcatgagg ctctgcacaa ccactacacg    1920
cagaagagcc tctccctgtc tccgggtaaa                                    1950
```

<210> SEQ ID NO 8
<211> LENGTH: 1515
<212> TYPE: DNA
<213> ORGANISM: Artificial Sequence
<220> FEATURE:
<223> OTHER INFORMATION: Description of Artificial Sequence: Synthetic
      Ex-4 fusion polynucleotide

<400> SEQUENCE: 8

```
caggtccagc tgagagagag cggcccttca ctggtcaagc catcccagac actgagcctg     60
acatgcacag caagcgggtt ttcactgagc gacaaggcag tgggatgggt ccgacaggca    120
ccaggaaaag ccctggaatg gctgggcagc atcgataccg gcgggaacac agggtacaat    180
```

```
cccggactga agagcagact gtccattacc aaggacaact ctaaaagtca ggtgtcactg      240
agcgtgagct ccgtcaccac agaggatagt gcaacttact attgcacctc tgtgcaccag      300
gaaactaaga ataccagag ctgcggggt ggcggaagca tcgaaggtcg tcacgctgag        360
ggaacattca cttccgatgt gtcctcctac ctggagggcc aggctgccaa agagttcatc      420
gcttggctcg tcaagggcag gggcggaggt gggagttgct cttataccta caattatgaa     480
tggcatgtgg atgtctgggg acagggcctg ctggtgacag tctctagtgc ttccacaact     540
gcaccaaagg tgtaccccct gtcaagctgc tgtggggaca atcctctag taccgtgaca      600 ctgggatgcc tggtctcaag ctatatgccc gagcctgtga ctgtcacctg gaactcagga     660
gccctgaaaa gcggagtgca caccttccca gctgtgctgc agtcctctgg cctgtatagc     720
ctgagttcaa tggtgacagt ccccggcagt acttcagggc agaccttcac ctgtaatgtg     780
gcccatcctg ccagctccac caaagtggac aaagcagtgg aacccaaatc ttgcgacaaa     840
actcacacat gcccaccgtg cccagcacct gaactcctgg ggggaccgtc agtcttcctc     900 ttcccccaa aacccaagga caccctcatg atctcccgga cccctgaggt cacatgcgtg      960
gtggtggacg tgagccacga agaccctgag gtcaagttca actggtacgt ggacggcgtg     1020
gaggtgcata atgccaagac aaagccgcgg gaggagcagt acaacagcac gtaccgtgtg     1080
gtcagcgtcc tcaccgtcct gcaccaggac tggctgaatg gcaaggagta caagtgcaag     1140
gtctccaaca aagccctccc agcccccatc gagaaaacca tctccaaagc caagggcag      1200 ccccgagaac cacaggtgta caccctgccc ccatcccggg atgagctgac caagaaccag     1260
gtcagcctga cctgcctggt caaaggcttc tatcccagcg acatcgccgt ggagtgggag     1320
agcaatgggc agccggagaa caactacaag accacgcctc ccgtgctgga ctccgacggc     1380
tccttcttcc tctacagcaa gctcaccgtg gacaagagca ggtggcagca ggggaacgtc     1440
ttctcatgct ccgtgatgca tgaggctctg cacaaccact acacgcagaa gagcctctcc     1500
ctgtctccgg gtaaa                                                      1515

<210> SEQ ID NO 9
<211> LENGTH: 1515
<212> TYPE: DNA
<213> ORGANISM: Artificial Sequence
<220> FEATURE:
<223> OTHER INFORMATION: Description of Artificial Sequence: Synthetic
      hGLP-1 fusion polynucleotide

<400> SEQUENCE: 9
caggtccagc tgagagagag cggcccttca ctggtcaagc catcccagac actgagcctg       60
acatgcacag caagcgggtt ttcactgagc gacaaggcag tgggatgggt ccgacaggca      120
ccaggaaaag ccctggaatg gctgggcagc atcgataccg gcgggaacac agggtacaat     180
cccggactga agagcagact gtccattacc aaggacaact ctaaaagtca ggtgtcactg      240
agcgtgagct ccgtcaccac agaggatagt gcaacttact attgcacctc tgtgcaccag      300
gaaactaaga ataccagag ctgcggggt ggcggaagca tcgaaggtcg tcacgctgag        360
ggaacattca cttccgatgt gtcctcctac ctggagggcc aggctgccaa agagttcatc      420
gcttggctcg tcaagggcag gggcggaggt gggagttgct cttataccta caattatgaa     480
tggcatgtgg atgtctgggg acagggcctg ctggtgacag tctctagtgc ttccacaact     540
gcaccaaagg tgtaccccct gtcaagctgc tgtggggaca atcctctag taccgtgaca      600 ctgggatgcc tggtctcaag ctatatgccc gagcctgtga ctgtcacctg gaactcagga     660
```

```
gccctgaaaa gcggagtgca caccttccca gctgtgctgc agtcctctgg cctgtatagc      720
ctgagttcaa tggtgacagt ccccggcagt acttcagggc agaccttcac ctgtaatgtg      780
gcccatcctg ccagctccac caaagtggac aaagcagtgg aacccaaatc ttgcgacaaa      840
actcacacat gcccaccgtg cccagcacct gaactcctgg ggggaccgtc agtcttcctc      900
ttccccccaa acccaagga caccctcatg atctcccgga cccctgaggt cacatgcgtg      960
gtggtggacg tgagccacga agaccctgag gtcaagttca actggtacgt ggacggcgtg     1020
gaggtgcata atgccaagac aaagccgcgg gaggagcagt acaacagcac gtaccgtgtg     1080
gtcagcgtcc tcaccgtcct gcaccaggac tggctgaatg gcaaggagta caagtgcaag     1140
gtctccaaca aagccctccc agcccccatc gagaaaacca tctccaaagc caagggcag      1200 ccccgagaac cacaggtgta caccctgccc ccatcccggg atgagctgac caagaaccag     1260
gtcagcctga cctgcctggt caaaggcttc tatcccagcg acatcgccgt ggagtgggag     1320
agcaatgggc agccggagaa caactacaag accacgcctc ccgtgctgga ctccgacggc     1380
tccttcttcc tctacagcaa gctcaccgtg gacaagagca ggtggcagca ggggaacgtc     1440
ttctcatgct ccgtgatgca tgaggctctg cacaaccact acacgcagaa gagcctctcc     1500
ctgtctccgg gtaaa                                                      1515

<210> SEQ ID NO 10
<211> LENGTH: 1905
<212> TYPE: DNA
<213> ORGANISM: Artificial Sequence
<220> FEATURE:
<223> OTHER INFORMATION: Description of Artificial Sequence: Synthetic
      hEPO fusion polynucleotide

<400> SEQUENCE: 10
caggtccagc tgagagagag cggcccttca ctggtcaagc catcccagac actgagcctg       60
acatgcacag caagcgggtt ttcactgagc gacaaggcag tgggatgggt ccgacaggca      120
ccaggaaaag ccctggaatg gctgggcagc atcgataccg gcgggaacac agggtacaat      180
cccggactga gagcagact gtccattacc aaggacaact ctaaaagtca ggtgtcactg       240
agcgtgagct ccgtcaccac agaggatagt gcaacttact attgcaccct ctgtgcaccag     300 gaaactaaga ataccagag cggggtggc ggaagcgccc caccacgcct catctgtgac        360
agccgagtcc tggagaggta cctcttggag gccaaggagg ccgagaatat cacgacgggc      420
tgtgctgaac actgcagctt gaatgagaat atcactgtcc cagacaccaa agttaatttc      480
tatgcctgga gaggatgga ggtcgggcag caggccgtag aagtctggca gggcctggcc       540
ctgctgtcgg aagctgtcct gcggggccag gccctgttgg tcaactcttc ccagccgtgg      600
gagcccctgc agctgcatgt ggataaagcc gtcagtggcc ttcgcagcct caccactctg      660
cttcgggctc tgggagccca gaaggaagcc atctcccctc agatgcggc ctcagctgct       720 ccactccgaa caatcactgc tgacactttc cgcaaactct ccgagtcta ctccaatttc      780 ctccggggaa agctgaagct gtacacaggg gaggcctgca ggacagggga cagaggcgga      840
ggtgggagtt cttataccta caattatgaa tggcatgtgg atgtctgggg acagggcctg      900
ctggtgacag tctctagtgc ttccacaact gcaccaaagg tgtaccccct gtcaagctgc     960 tgtgggaca atcctctag taccgtgaca ctgggatgcc tggtctcaag ctatatgccc       1020
gagcctgtga ctgtcacctg gaactcagga gccctgaaaa gcggagtgca caccttccca     1080
gctgtgctgc agtcctctgg cctgtatagc ctgagttcaa tggtgacagt ccccggcagt     1140
```

-continued

```
acttcagggc agaccttcac ctgtaatgtg gcccatcctg ccagctccac caaagtggac      1200
aaagcagtgg aacccaaatc ttgcgacaaa actcacacat gcccaccgtg cccagcacct      1260
gaactcctgg ggggaccgtc agtcttcctc ttccccccaa aacccaagga caccctcatg      1320
atctcccgga cccctgaggt cacatgcgtg gtggtggacg tgagccacga agaccctgag      1380
gtcaagttca actggtacgt ggacggcgtg gaggtgcata atgccaagac aaagccgcgg      1440
gaggagcagt acaacagcac gtaccgtgtg gtcagcgtcc tcaccgtcct gcaccaggac      1500
tggctgaatg gcaaggagta caagtgcaag gtctccaaca aagccctccc agcccccatc      1560
gagaaaacca tctccaaagc caagggcag ccccgagaac acaggtgta caccctgccc      1620 ccatcccggg atgagctgac caagaaccag gtcagcctga cctgcctggt caaaggcttc      1680
tatcccagcg acatcgccgt ggagtgggag agcaatgggc agccggagaa caactacaag      1740
accacgcctc ccgtgctgga ctccgacggc tccttcttcc tctacagcaa gctcaccgtg      1800
gacaagagca ggtggcagca ggggaacgtc ttctcatgct ccgtgatgca tgaggctctg      1860
cacaaccact acacgcagaa gagcctctcc ctgtctccgg gtaaa                     1905
```

<210> SEQ ID NO 11
<211> LENGTH: 1479
<212> TYPE: DNA
<213> ORGANISM: Artificial Sequence
<220> FEATURE:
<223> OTHER INFORMATION: Description of Artificial Sequence: Synthetic
    Moka-L0 fusion polynucleotide

<400> SEQUENCE: 11

```
caggtccagc tgagagagag cggcccttca ctggtcaagc catcccagac actgagcctg        60
acatgcacag caagcgggtt ttcactgagc gacaaggcag tgggatgggt ccgacaggca       120
ccaggaaaag ccctggaatg gctgggcagc atcgataccg gcgggaacac agggtacaat       180
cccggactga agagcagact gtccattacc aaggacaact ctaaaagtca ggtgtcactg       240
agcgtgagct ccgtcaccac agaggatagt gcaacttact attgcacctc tgtgcaccag       300
gaaactaaga ataccagag catcaacgtg aagtgcagcc tgccccagca gtgcatcaag       360
ccctgcaagg acgccggcat gcggttcggc aagtgcatga acaagaagtg caggtgctac       420
agctcttata cctacaatta tgaatggcat gtggatgtct ggggacaggg cctgctggtg       480
acagtctcta gtgcttccac aactgcacca aaggtgtacc ccctgtcaag ctgctgtggg       540
gacaaatcct ctagtaccgt gacactggga tgcctggtct caagctatat gcccgagcct       600
gtgactgtca cctggaactc aggagccctg aaaagcggag tgcacacctt cccagctgtg       660
ctgcagtcct ctggcctgta tagcctgagt tcaatggtga cagtccccgg cagtacttca       720
gggcagacct tcacctgtaa tgtggcccat cctgccagct ccaccaaagt ggacaaagca       780
gtggaaccca atcttgcga caaaactcac acatgcccac cgtgcccagc acctgaactc       840 ctgggggac cgtcagtctt cctcttcccc ccaaaaccca aggacaccct catgatctcc       900
cggacccctg aggtcacatg cgtggtggtg gacgtgagcc acgaagaccc tgaggtcaag       960
ttcaactggt acgtggacgg cgtggaggtg cataatgcca agacaaagcc gcgggaggag      1020
cagtacaaca gcacgtaccg tgtggtcagc gtcctcaccg tcctgcacca ggactggctg      1080
aatggcaagg agtacaagtg caaggtctcc aacaaagccc tcccagcccc catcgagaaa      1140
accatctcca aagccaaagg gcagcccga gaaccacagg tgtacaccct gcccccatcc      1200
cgggatgagc tgaccaagaa ccaggtcagc ctgacctgcc tggtcaaagg cttctatccc      1260
```

```
agcgacatcg ccgtggagtg ggagagcaat gggcagccgg agaacaacta caagaccacg    1320
cctcccgtgc tggactccga cggctccttc ttcctctaca gcaagctcac cgtggacaag    1380
agcaggtggc agcagggaa cgtcttctca tgctccgtga tgcatgaggc tctgcacaac    1440
cactacacgc agaagagcct ctccctgtct ccgggtaaa                            1479
```

<210> SEQ ID NO 12
<211> LENGTH: 1509
<212> TYPE: DNA
<213> ORGANISM: Artificial Sequence
<220> FEATURE:
<223> OTHER INFORMATION: Description of Artificial Sequence: Synthetic
      Moka-L1 fusion polynucleotide

<400> SEQUENCE: 12

```
caggtccagc tgagagagag cggcccttca ctggtcaagc catcccagac actgagcctg      60
acatgcacag caagcgggtt ttcactgagc gacaaggcag tgggatgggt ccgacaggca     120
ccaggaaaag ccctggaatg gctgggcagc atcgataccg gcgggaacac agggtacaat     180
cccggactga agagcagact gtccattacc aaggacaact ctaaaagtca ggtgtcactg     240
agcgtgagct ccgtcaccac agaggatagt gcaacttact attgcacctc tgtgcaccag     300
gaaactaaga ataccagag cggtggcgga ggatctatca acgtgaagtg cagcctgccc     360
cagcagtgca tcaagccctg caaggacgcc ggcatgcgtg tcggcaagtg catgaacaag     420
aagtgcaggt gctacagcgg aggtggtggt tcatcttata cctacaatta tgaatggcat     480
gtggatgtct ggggacaggg cctgctggtg acagtctcta gtgcttccac aactgcacca     540
aaggtgtacc ccctgtcaag ctgctgtggg acaaatcct ctagtaccgt gacactggga     600
tgcctggtct caagctatat gcccgagcct gtgactgtca cctggaactc aggagccctg     660
aaaagcggag tgcacacctt cccagctgtg ctgcagtcct ctggcctgta tagcctgagt     720
tcaatggtga cagtccccgg cagtacttca gggcagacct tcacctgtaa tgtgcccat      780 cctgccagct ccaccaaagt ggacaaagca gtggaaccca atcttgcga caaaactcac     840 acatgcccac cgtgcccagc acctgaactc ctggggggac cgtcagtctt cctcttcccc     900
ccaaaaccca aggacaccct catgatctcc cggacccctg aggtcacatg cgtggtggtg     960
gacgtgagcc acgaagaccc tgaggtcaag ttcaactggt acgtggacgg cgtggaggtg    1020
cataatgcca agacaaagcc gcgggaggag cagtacaaca gcacgtaccg tgtggtcagc    1080
gtcctcaccg tcctgcacca ggactggctg aatggcaagg agtacaagtg caaggtctcc    1140
aacaaagccc tcccagcccc catcgagaaa accatctcca agccaaagg gcagccccga    1200 gaaccacagg tgtacaccct gcccccatcc cgggatgagc tgaccaagaa ccaggtcagc    1260
ctgacctgcc tggtcaaagg cttctatccc agcgacatcg ccgtggagtg ggagagcaat    1320
gggcagccgg agaacaacta caagaccacg cctcccgtgc tggactccga cggctccttc    1380
ttcctctaca gcaagctcac cgtggacaag agcaggtggc agcagggaa cgtcttctca    1440 tgctccgtga tgcatgaggc tctgcacaac cactacacgc agaagagcct ctccctgtct    1500
ccgggtaaa                                                             1509
```

<210> SEQ ID NO 13
<211> LENGTH: 1515
<212> TYPE: DNA
<213> ORGANISM: Artificial Sequence
<220> FEATURE:
<223> OTHER INFORMATION: Description of Artificial Sequence: Synthetic
      VM-24-L1 fusion polynucleotide

<400> SEQUENCE: 13

```
caggtccagc tgagagagag cggcccttca ctggtcaagc catcccagac actgagcctg    60
acatgcacag caagcgggtt ttcactgagc gacaaggcag tgggatgggt ccgacaggca   120
ccaggaaaag ccctggaatg gctgggcagc atcgataccg cgggaacac agggtacaat    180 cccggactga agagcagact gtccattacc aaggacaact ctaaaagtca ggtgtcactg   240
agcgtgagct ccgtcaccac agaggatagt gcaacttact attgcacctc tgtgcaccag   300
gaaactaaga ataccagag cggggtggc ggaagcgccg ctgcaatctc ctgcgtcggc     360
agccccgaat gtcctcccaa gtgccgggct caggatgca agaacggcaa gtgtatgaac   420
cggaagtgca agtgctacta ttgcggcgga ggtgggagtt cttataccta caattatgaa   480
tggcatgtgg atgtctgggg acagggcctg ctggtgacag tctctagtgc ttccacaact   540
gcaccaaagg tgtaccccct gtcaagctgc tgtggggaca atcctctag taccgtgaca    600 ctgggatgcc tggtctcaag ctatatgccc gagcctgtga ctgtcacctg aactcagga    660 gccctgaaaa gcggagtgca caccttccca gctgtgctgc agtcctctgg cctgtatagc   720
ctgagttcaa tggtgacagt ccccggcagt acttcagggc agaccttcac ctgtaatgtg   780
gcccatcctg ccagctccac caaagtggac aaagcagtgg aacccaaatc ttgcgacaaa   840
actcacacat gcccaccgtg cccagcacct gaactcctgg ggggaccgtc agtcttcctc   900 ttcccccaa acccaagga caccctcatg atctcccgga cccctgaggt cacatgcgtg     960
gtggtggacg tgagccacga agaccctgag gtcaagttca actggtacgt ggacggcgtg  1020
gaggtgcata atgccaagac aaagccgcgg gaggagcagt acaacagcac gtaccgtgtg  1080
gtcagcgtcc tcaccgtcct gcaccaggac tggctgaatg caaggagta caagtgcaag   1140 gtctccaaca agcccctccc agcccccatc gagaaaacca tctccaaagc caagggcag    1200 ccccgagaac cacaggtgta caccctgccc ccatcccggg atgagctgac caagaaccag   1260
gtcagcctga cctgcctggt caaaggcttc tatcccagcg acatcgccgt ggagtgggag   1320
agcaatgggc agccggagaa caactacaag accacgcctc ccgtgctgga ctccgacggc   1380
tccttcttcc tctacagcaa gctcaccgtg gacaagagca ggtggcagca ggggaacgtc  1440
ttctcatgct ccgtgatgca tgaggctctg cacaaccact acacgcagaa gagcctctcc  1500
ctgtctccgg gtaaa                                                    1515
```

<210> SEQ ID NO 14
<211> LENGTH: 1539
<212> TYPE: DNA
<213> ORGANISM: Artificial Sequence
<220> FEATURE:
<223> OTHER INFORMATION: Description of Artificial Sequence: Synthetic VM-24-L2 fusion polynucleotide

<400> SEQUENCE: 14

```
caggtccagc tgagagagag cggcccttca ctggtcaagc catcccagac actgagcctg    60
acatgcacag caagcgggtt ttcactgagc gacaaggcag tgggatgggt ccgacaggca   120
ccaggaaaag ccctggaatg gctgggcagc atcgataccg cgggaacac agggtacaat    180 cccggactga agagcagact gtccattacc aaggacaact ctaaaagtca ggtgtcactg   240
agcgtgagct ccgtcaccac agaggatagt gcaacttact attgcacctc tgtgcaccag   300
gaaactaaga ataccagag cggcggtgga tctggggtg cggaagcgc cgctgcaatc     360 tcctgcgtcg gcagccccga atgtcctccc aagtgccggg ctcagggatg caagaacggc   420
```
aagtgtatga accggaagtg caagtgctac tattgcggcg gaggtgggag tggaggcggt 480
agctcttata cctacaatta tgaatggcat gtggatgtct ggggacaggg cctgctggtg 540
acagtctcta gtgcttccac aactgcacca aaggtgtacc ccctgtcaag ctgctgtggg 600
gacaaatcct ctagtaccgt gacactggga tgcctggtct caagctatat gcccgagcct 660
gtgactgtca cctggaactc aggagccctg aaaagcggag tgcacacctt cccagctgtg 720
ctgcagtcct ctggcctgta tagcctgagt tcaatggtga cagtccccgg cagtacttca 780
gggcagacct tcacctgtaa tgtggcccat cctgccagct ccaccaaagt ggacaaagca 840
gtggaaccca aatcttgcga caaaactcac acatgcccac cgtgcccagc acctgaactc 900
ctggggggac cgtcagtctt cctcttcccc ccaaaaccca aggacaccct catgatctcc 960
cggacccctg aggtcacatg cgtggtggtg gacgtgagcc acgaagaccc tgaggtcaag 1020
ttcaactggt acgtggacgg cgtggaggtg cataatgcca agacaaagcc gcgggaggag 1080
cagtacaaca gcacgtaccg tgtggtcagc gtcctcaccg tcctgcacca ggactggctg 1140
aatggcaagg agtacaagtg caaggtctcc aacaaagccc tcccagcccc catcgagaaa 1200
accatctcca aagccaaagg gcagccccga gaaccacagg tgtacaccct gcccccatcc 1260
cgggatgagc tgaccaagaa ccaggtcagc ctgacctgcc tggtcaaagg cttctatccc 1320
agcgacatcg ccgtggagtg ggagagcaat gggcagccgg agaacaacta caagaccacg 1380
cctcccgtgc tggactccga cggctccttc ttcctctaca gcaagctcac cgtggacaag 1440
agcaggtggc agcaggggaa cgtcttctca tgctccgtga tgcatgaggc tctgcacaac 1500
cactacacgc agaagagcct ctccctgtct ccgggtaaa 1539

<210> SEQ ID NO 15
<211> LENGTH: 1497
<212> TYPE: DNA
<213> ORGANISM: Artificial Sequence
<220> FEATURE:
<223> OTHER INFORMATION: Description of Artificial Sequence: Synthetic
Protoxin2-L1 fusion polynucleotide

<400> SEQUENCE: 15
caggtccagc tgagagagag cggcccttca ctggtcaagc catcccagac actgagcctg 60
acatgcacag caagcgggtt ttcactgagc gacaaggcag tgggatgggt ccgacaggca 120
ccaggaaaag ccctggaatg gctgggcagc atcgataccg gcgggaacac agggtacaat 180
cccggactga agagcagact gtccattacc aaggacaact ctaaaagtca ggtgtcactg 240
agcgtgagct ccgtcaccac agaggatagt gcaacttact attgcacctc tgtgcaccag 300
gaaactaaga aataccagag cgggggtggc ggaagctact gccagaaatg gatgtggacc 360
tgcgactctg aacgtaaatg ctgcgaaggt atggtttgcc gtctgtggtg caaaaaaaaa 420
ctgtggggcg gaggtgggag ttcttatacc tacaattatg aatggcatgt ggatgtctgg 480
ggacagggcc tgctggtgac agtctctagt gcttccacaa ctgcaccaaa ggtgtacccc 540
ctgtcaagct gctgtgggga caaatcctct agtaccgtga cactgggatg cctggtctca 600
agctatatgc ccgagcctgt gactgtcacc tggaactcag gagccctgaa aagcggagtg 660
cacaccttcc cagctgtgct gcagtcctct ggcctgtata gcctgagttc aatggtgaca 720
gtccccggca gtacttcagg gcagaccttc acctgtaatg tggcccatcc tgccagctcc 780
accaaagtgg acaaagcagt ggaacccaaa tcttgcgaca aaactcacac atgcccaccg 840
tgcccagcac ctgaactcct ggggggaccg tcagtcttcc tcttcccccc aaaacccaag 900

```
gacaccctca tgatctcccg gacccctgag gtcacatgcg tggtggtgga cgtgagccac    960
gaagaccctg aggtcaagtt caactggtac gtggacggcg tggaggtgca taatgccaag   1020
acaaagccgc gggaggagca gtacaacagc acgtaccgtg tggtcagcgt cctcaccgtc   1080
ctgcaccagg actggctgaa tggcaaggag tacaagtgca aggtctccaa caaagccctc   1140
ccagccccca tcgagaaaac catctccaaa gccaagggc agccccgaga ccacaggtg    1200 tacaccctgc ccccatcccg ggatgagctg accaagaacc aggtcagcct gacctgcctg   1260
gtcaaaggct tctatcccag cgacatcgcc gtggagtggg agagcaatgg gcagccggag   1320
aacaactaca agaccacgcc tcccgtgctg gactccgacg gctccttctt cctctacagc   1380
aagctcaccg tggacaagag caggtggcag caggggaacg tcttctcatg ctccgtgatg   1440
catgaggctc tgcacaacca ctacacgcag aagagcctct ccctgtctcc gggtaaa      1497
```

<210> SEQ ID NO 16
<211> LENGTH: 615
<212> TYPE: DNA
<213> ORGANISM: Artificial Sequence
<220> FEATURE:
<223> OTHER INFORMATION: Description of Artificial Sequence: Synthetic
      BLV1H12-IL8 fusion polynucleotide

<400> SEQUENCE: 16

```
caggtccagc tgagagagag cggcccttca ctggtcaagc catcccagac actgagcctg     60
acatgcacag caagcgggtt ttcactgagc gacaaggcag tgggatgggt ccgacaggca    120
ccaggaaaag ccctggaatg gctgggcagc atcgataccg gcgggaacac agggtacaat    180
cccggactga agagcagact gtccattacc aaggacaact ctaaaagtca ggtgtcactg    240
agcgtgagct ccgtcaccac agaggatagt gcaacttact attgcacctc tgtgcaccag    300
gaaactaaga ataccagag cccaaggagt gctaagaac ttagatgtca gtgcataaag     360
acatactcca aacctttcca ccccaagttc atcaaggagc tgagagtgat tgagagtgga    420
ccacactgcg ccaacacaga gattattgta aagctttctg atgggagaga gctctgcctg    480 gacccccaagg aaaactgggt gcagagggtc gtggagaagt tcttgaagag ggctgagaac    540
tcaggcagcg gttcttatac ctacaattat gaatggcatg tggatgtctg gggacagggc    600
ctgctggtga cagtc                                                    615
```

<210> SEQ ID NO 17
<211> LENGTH: 459
<212> TYPE: DNA
<213> ORGANISM: Artificial Sequence
<220> FEATURE:
<223> OTHER INFORMATION: Description of Artificial Sequence: Synthetic
      BLV1H12-Ziconotide fusion polynucleotide

<400> SEQUENCE: 17

```
caggtccagc tgagagagag cggcccttca ctggtcaagc catcccagac actgagcctg     60
acatgcacag caagcgggtt ttcactgagc gacaaggcag tgggatgggt ccgacaggca    120
ccaggaaaag ccctggaatg gctgggcagc atcgataccg gcgggaacac agggtacaat    180
cccggactga agagcagact gtccattacc aaggacaact ctaaaagtca ggtgtcactg    240
agcgtgagct ccgtcaccac agaggatagt gcaacttact attgcacctc tgtgcaccag    300
gaaactaaga ataccagag ctgcaagggc aaaggtgcga atgcagccg cctgatgtat    360 gattgctgta ccgggtcctg ccgcagtggc aagtgctctt atacctacaa ttatgaatgg    420
```
catgtggatg tctggggaca gggcctgctg gtgacagtc 459

<210> SEQ ID NO 18
<211> LENGTH: 429
<212> TYPE: DNA
<213> ORGANISM: Artificial Sequence
<220> FEATURE:
<223> OTHER INFORMATION: Description of Artificial Sequence: Synthetic
BLV1H12-Somatostatin fusion polynucleotide

<400> SEQUENCE: 18
caggtccagc tgagagagag cggcccttca ctggtcaagc catcccagac actgagcctg 60
acatgcacag caagcgggtt ttcactgagc gacaaggcag tgggatgggt ccgacaggca 120
ccaggaaaag ccctggaatg gctgggcagc atcgataccg gcgggaacac agggtacaat 180
cccggactga agagcagact gtccattacc aaggacaact ctaaaagtca ggtgtcactg 240
agcgtgagct ccgtcaccac agaggatagt gcaacttact attgcacctc tgtgcaccag 300
gaaactaaga aataccagag cgctggctgc aagaatttct tctggaagac tttcacatcc 360
tgtggttctt atacctacaa ttatgaatgg catgtggatg tctggggaca gggcctgctg 420
gtgacagtc 429

<210> SEQ ID NO 19
<211> LENGTH: 486
<212> TYPE: DNA
<213> ORGANISM: Artificial Sequence
<220> FEATURE:
<223> OTHER INFORMATION: Description of Artificial Sequence: Synthetic
BLV1H12-Chlorotoxin fusion polynucleotide

<400> SEQUENCE: 19
caggtccagc tgagagagag cggcccttca ctggtcaagc catcccagac actgagcctg 60
acatgcacag caagcgggtt ttcactgagc gacaaggcag tgggatgggt ccgacaggca 120
ccaggaaaag ccctggaatg gctgggcagc atcgataccg gcgggaacac agggtacaat 180
cccggactga agagcagact gtccattacc aaggacaact ctaaaagtca ggtgtcactg 240
agcgtgagct ccgtcaccac agaggatagt gcaacttact attgcacctc tgtgcaccag 300
gaaactaaga aataccagag catgtgtatg ccctgcttca cgaccgatca ccagatggcg 360
cgcaaatgcg atgactgttg cggcggtaaa ggtcgcggaa agtgctatgg cccgcagtgt 420
ctgtcttata cctacaatta tgaatggcat gtggatgtct ggggacaggg cctgctggtg 480
acagtc 486

<210> SEQ ID NO 20
<211> LENGTH: 597
<212> TYPE: DNA
<213> ORGANISM: Artificial Sequence
<220> FEATURE:
<223> OTHER INFORMATION: Description of Artificial Sequence: Synthetic
BLV1H12-SDF1(alpha) fusion polynucleotide

<400> SEQUENCE: 20
caggtccagc tgagagagag cggcccttca ctggtcaagc catcccagac actgagcctg 60
acatgcacag caagcgggtt ttcactgagc gacaaggcag tgggatgggt ccgacaggca 120
ccaggaaaag ccctggaatg gctgggcagc atcgataccg gcgggaacac agggtacaat 180
cccggactga agagcagact gtccattacc aaggacaact ctaaaagtca ggtgtcactg 240
agcgtgagct ccgtcaccac agaggatagt gcaacttact attgcacctc tgtgcaccag 300

```
gaaactaaga aataccagag caagcccgtc agcctgagct acagatgccc atgccgattc    360
ttcgaaagcc atgttgccag agccaacgtc aagcatctca aaattctcaa cactccaaac    420
tgtgcccttc agattgtagc ccggctgaag aacaacaaca gacaagtgtg cattgacccg    480
aagctaaagt ggattcagga gtacctggag aaagctttaa acaagggcag cggttcttat    540
acctacaatt atgaatggca tgtggatgtc tggggacagg gcctgctggt gacagtc       597
```

<210> SEQ ID NO 21
<211> LENGTH: 783
<212> TYPE: DNA
<213> ORGANISM: Artificial Sequence
<220> FEATURE:
<223> OTHER INFORMATION: Description of Artificial Sequence: Synthetic
      BLV1H12-IL21 fusion polynucleotide

<400> SEQUENCE: 21

```
caggtccagc tgagagagag cggccccttca ctggtcaagc catcccagac actgagcctg    60
acatgcacag caagcgggtt ttcactgagc gacaaggcag tgggatgggt ccgacaggca    120
ccaggaaaag ccctggaatg gctgggcagc atcgataccg gcgggaacac agggtacaat    180
cccggactga gagcagact gtccattacc aaggacaact ctaaaagtca ggtgtcactg     240
agcgtgagct ccgtcaccac agaggatagt gcaacttact attgcaccctc tgtgcaccag   300 gaaactaaga ataccagag ccaaggtcaa gatcgccaca tgatcagaat gcgtcagctc     360
atagatattg ttgatcagct gaagaactac gtgaacgact tggtccctga atttctgcca    420
gctcccgaag atgtagagac aaactgtgag tggtcagcct ctcctgctt tcagaaggcc     480 caactaaagt cagcaaatac cggcaacaac gagaggataa tcaatgtatc aatcaaaaag    540
ctgaagagga agccaccttc cacaaatgca gggagacggc agaaacaccg cctgacatgc    600
ccttcatgtg attcttacga agaagccca cccaaagagt tcctagagcg gttcaagtca     660
cttctccaaa agatgattca tcagcatctg tcctctcgca cacacggaag tgaagattcc    720
tcttatacct acaattatga atggcatgtg gatgtctggg gacagggcct gctggtgaca    780
gtc                                                                  783
```

<210> SEQ ID NO 22
<211> LENGTH: 474
<212> TYPE: DNA
<213> ORGANISM: Artificial Sequence
<220> FEATURE:
<223> OTHER INFORMATION: Description of Artificial Sequence: Synthetic
      BLV1H12-ProTxII fusion polynucleotide

<400> SEQUENCE: 22

```
caggtccagc tgagagagag cggccccttca ctggtcaagc catcccagac actgagcctg    60
acatgcacag caagcgggtt ttcactgagc gacaaggcag tgggatgggt ccgacaggca    120
ccaggaaaag ccctggaatg gctgggcagc atcgataccg gcgggaacac agggtacaat    180
cccggactga gagcagact gtccattacc aaggacaact ctaaaagtca ggtgtcactg     240
agcgtgagct ccgtcaccac agaggatagt gcaacttact attgcaccctc tgtgcaccag   300 gaaactaaga ataccagag ctattgccag aagtggatgt ggacctgcga tagcgaacgg     360
aaatgttgcg aaggcatggt gtgccgcctg tggtgcaaga agaaactctg gtcttatacc    420
tacaattatg aatggcatgt ggatgtctgg ggacagggcc tgctggtgac agtc          474
```

<210> SEQ ID NO 23
<211> LENGTH: 216

```
<212> TYPE: PRT
<213> ORGANISM: Artificial Sequence
<220> FEATURE:
<223> OTHER INFORMATION: Description of Artificial Sequence: Synthetic
      Light Chain fusion polypeptide

<400> SEQUENCE: 23

Gln Ala Val Leu Asn Gln Pro Ser Ser Val Ser Gly Ser Leu Gly Gln
1               5                   10                  15

Arg Val Ser Ile Thr Cys Ser Gly Ser Ser Asn Val Gly Asn Gly
            20                  25                  30

Tyr Val Ser Trp Tyr Gln Leu Ile Pro Gly Ser Ala Pro Arg Thr Leu
        35                  40                  45

Ile Tyr Gly Asp Thr Ser Arg Ala Ser Gly Val Pro Asp Arg Phe Ser
50                  55                  60

Gly Ser Arg Ser Gly Asn Thr Ala Thr Leu Thr Ile Ser Ser Leu Gln
65                  70                  75                  80

Ala Glu Asp Glu Ala Asp Tyr Phe Cys Ala Ser Ala Glu Asp Ser Ser
                85                  90                  95

Ser Asn Ala Val Phe Gly Ser Gly Thr Thr Leu Thr Val Leu Gly Gln
            100                 105                 110

Pro Lys Ser Pro Pro Ser Val Thr Leu Phe Pro Pro Ser Thr Glu Glu
        115                 120                 125

Leu Asn Gly Asn Lys Ala Thr Leu Val Cys Leu Ile Ser Asp Phe Tyr
130                 135                 140

Pro Gly Ser Val Thr Val Val Trp Lys Ala Asp Gly Ser Thr Ile Thr
145                 150                 155                 160

Arg Asn Val Glu Thr Thr Arg Ala Ser Lys Gln Ser Asn Ser Lys Tyr
                165                 170                 175

Ala Ala Ser Ser Tyr Leu Ser Leu Thr Ser Ser Asp Trp Lys Ser Lys
            180                 185                 190

Gly Ser Tyr Ser Cys Glu Val Thr His Glu Gly Ser Thr Val Thr Lys
        195                 200                 205

Thr Val Lys Pro Ser Glu Cys Ser
    210                 215

<210> SEQ ID NO 24
<211> LENGTH: 169
<212> TYPE: PRT
<213> ORGANISM: Artificial Sequence
<220> FEATURE:
<223> OTHER INFORMATION: Description of Artificial Sequence: Synthetic
      Heavy Chain fusion polypeptide

<400> SEQUENCE: 24

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Thr Gly Tyr Asn Pro Gly Leu Lys
50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
                85                  90                  95
```

Ser Val His Gln Glu Thr Lys Lys Tyr Gln Ser Cys Pro Asp Gly Tyr
            100                 105                 110

Arg Glu Arg Ser Asp Cys Ser Asn Arg Pro Ala Cys Gly Thr Ser Asp
        115                 120                 125

Cys Cys Arg Val Ser Val Phe Gly Asn Cys Leu Thr Thr Leu Pro Val
    130                 135                 140

Ser Tyr Ser Tyr Thr Tyr Asn Tyr Glu Trp His Val Asp Val Trp Gly
145                 150                 155                 160

Gln Gly Leu Leu Val Thr Val Ser Ser
                165

<210> SEQ ID NO 25
<211> LENGTH: 635
<212> TYPE: PRT
<213> ORGANISM: Artificial Sequence
<220> FEATURE:
<223> OTHER INFORMATION: Description of Artificial Sequence: Synthetic
      IFN-beta fusion polypeptide

<400> SEQUENCE: 25

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Thr Gly Tyr Asn Pro Gly Leu Lys
    50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
                85                  90                  95

Ser Val His Gln Glu Thr Lys Lys Tyr Gln Ser Gly Gly Gly Gly Ser
            100                 105                 110

Met Ser Tyr Asn Leu Leu Gly Phe Leu Gln Arg Ser Ser Asn Phe Gln
        115                 120                 125

Cys Gln Lys Leu Leu Trp Gln Leu Asn Gly Arg Leu Glu Tyr Cys Leu
    130                 135                 140

Lys Asp Arg Met Asn Phe Asp Ile Pro Glu Glu Ile Lys Gln Leu Gln
145                 150                 155                 160

Gln Phe Gln Lys Glu Asp Ala Ala Leu Thr Ile Tyr Glu Met Leu Gln
                165                 170                 175

Asn Ile Phe Ala Ile Phe Arg Gln Asp Ser Ser Ser Thr Gly Trp Asn
            180                 185                 190

Glu Thr Ile Val Glu Asn Leu Leu Ala Asn Val Tyr His Gln Ile Asn
        195                 200                 205

His Leu Lys Thr Val Leu Glu Glu Lys Leu Glu Lys Glu Asp Phe Thr
    210                 215                 220

Arg Gly Lys Leu Met Ser Ser Leu His Leu Lys Arg Tyr Tyr Gly Arg
225                 230                 235                 240

Ile Leu His Tyr Leu Lys Ala Lys Glu Tyr Ser His Cys Ala Trp Thr
                245                 250                 255

Ile Val Arg Val Glu Ile Leu Arg Asn Phe Tyr Phe Ile Asn Arg Leu
            260                 265                 270

Thr Gly Tyr Leu Arg Asn Gly Gly Gly Ser Ser Tyr Thr Tyr Asn
        275                 280                 285

Tyr Glu Trp His Val Asp Val Trp Gly Gln Gly Leu Leu Val Thr Val
            290                 295                 300

Ser Ser Ala Ser Thr Thr Ala Pro Lys Val Tyr Pro Leu Ser Ser Cys
305                 310                 315                 320

Cys Gly Asp Lys Ser Ser Thr Val Thr Leu Gly Cys Leu Val Ser
                325                 330                 335

Ser Tyr Met Pro Glu Pro Val Thr Val Thr Trp Asn Ser Gly Ala Leu
            340                 345                 350

Lys Ser Gly Val His Thr Phe Pro Ala Val Leu Gln Ser Ser Gly Leu
            355                 360                 365

Tyr Ser Leu Ser Ser Met Val Thr Val Pro Gly Ser Thr Ser Gly Gln
            370                 375                 380

Thr Phe Thr Cys Asn Val Ala His Pro Ala Ser Ser Thr Lys Val Asp
385                 390                 395                 400

Lys Ala Val Glu Pro Lys Ser Cys Asp Lys Thr His Thr Cys Pro Pro
                405                 410                 415

Cys Pro Ala Pro Glu Leu Leu Gly Gly Pro Ser Val Phe Leu Phe Pro
            420                 425                 430

Pro Lys Pro Lys Asp Thr Leu Met Ile Ser Arg Thr Pro Glu Val Thr
            435                 440                 445

Cys Val Val Val Asp Val Ser His Glu Asp Pro Glu Val Lys Phe Asn
450                 455                 460

Trp Tyr Val Asp Gly Val Glu Val His Asn Ala Lys Thr Lys Pro Arg
465                 470                 475                 480

Glu Glu Gln Tyr Asn Ser Thr Tyr Arg Val Val Ser Val Leu Thr Val
                485                 490                 495

Leu His Gln Asp Trp Leu Asn Gly Lys Glu Tyr Lys Cys Lys Val Ser
            500                 505                 510

Asn Lys Ala Leu Pro Ala Pro Ile Glu Lys Thr Ile Ser Lys Ala Lys
            515                 520                 525

Gly Gln Pro Arg Glu Pro Gln Val Tyr Thr Leu Pro Pro Ser Arg Asp
            530                 535                 540

Glu Leu Thr Lys Asn Gln Val Ser Leu Thr Cys Leu Val Lys Gly Phe
545                 550                 555                 560

Tyr Pro Ser Asp Ile Ala Val Glu Trp Glu Ser Asn Gly Gln Pro Glu
                565                 570                 575

Asn Asn Tyr Lys Thr Thr Pro Pro Val Leu Asp Ser Asp Gly Ser Phe
            580                 585                 590

Phe Leu Tyr Ser Lys Leu Thr Val Asp Lys Ser Arg Trp Gln Gln Gly
            595                 600                 605

Asn Val Phe Ser Cys Ser Val Met His Glu Ala Leu His Asn His Tyr
            610                 615                 620

Thr Gln Lys Ser Leu Ser Leu Ser Pro Gly Lys
625                 630                 635

<210> SEQ ID NO 26
<211> LENGTH: 633
<212> TYPE: PRT
<213> ORGANISM: Artificial Sequence
<220> FEATURE:
<223> OTHER INFORMATION: Description of Artificial Sequence: Synthetic
      bGCSF-L0 fusion polypeptide

<400> SEQUENCE: 26

Gln Val Gln Leu Arg Glu Ser Gly Pro Ser Leu Val Lys Pro Ser Gln

-continued

```
1               5                   10                  15
Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
            35                  40                  45

Gly Ser Ile Asp Thr Gly Gly Asn Thr Gly Tyr Asn Pro Gly Leu Lys
            50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
                    85                  90                  95

Ser Val His Gln Glu Thr Lys Lys Tyr Gln Ser Thr Pro Leu Gly Pro
                100                 105                 110

Ala Arg Ser Leu Pro Gln Ser Phe Leu Leu Lys Cys Leu Glu Gln Val
                115                 120                 125

Arg Lys Ile Gln Ala Asp Gly Ala Glu Leu Gln Glu Arg Leu Cys Ala
            130                 135                 140

Ala His Lys Leu Cys His Pro Glu Glu Leu Met Leu Leu Arg His Ser
145                 150                 155                 160

Leu Gly Ile Pro Gln Ala Pro Leu Ser Ser Cys Ser Ser Gln Ser Leu
                    165                 170                 175

Gln Leu Thr Ser Cys Leu Asn Gln Leu His Gly Gly Leu Phe Leu Tyr
                180                 185                 190

Gln Gly Leu Leu Gln Ala Leu Ala Gly Ile Ser Pro Glu Leu Ala Pro
            195                 200                 205

Thr Leu Asp Thr Leu Gln Leu Asp Val Thr Asp Phe Ala Thr Asn Ile
            210                 215                 220

Trp Leu Gln Met Glu Asp Leu Gly Ala Ala Pro Ala Val Gln Pro Thr
225                 230                 235                 240

Gln Gly Ala Met Pro Thr Phe Thr Ser Ala Phe Gln Arg Arg Ala Gly
                    245                 250                 255

Gly Val Leu Val Ala Ser Gln Leu His Arg Phe Leu Glu Leu Ala Tyr
                260                 265                 270

Arg Gly Leu Arg Tyr Leu Ala Glu Pro Ser Tyr Thr Tyr Asn Tyr Glu
            275                 280                 285

Trp His Val Asp Val Trp Gly Gln Gly Leu Leu Val Thr Val Ser Ser
            290                 295                 300

Ala Ser Thr Thr Ala Pro Lys Val Tyr Pro Leu Ser Ser Cys Cys Gly
305                 310                 315                 320

Asp Lys Ser Ser Ser Thr Val Thr Leu Gly Cys Leu Val Ser Ser Tyr
                    325                 330                 335

Met Pro Glu Pro Val Thr Val Thr Trp Asn Ser Gly Ala Leu Lys Ser
                340                 345                 350

Gly Val His Thr Phe Pro Ala Val Leu Gln Ser Ser Gly Leu Tyr Ser
            355                 360                 365

Leu Ser Ser Met Val Thr Val Pro Gly Ser Thr Ser Gly Gln Thr Phe
            370                 375                 380

Thr Cys Asn Val Ala His Pro Ala Ser Ser Thr Lys Val Asp Lys Ala
385                 390                 395                 400

Val Glu Pro Lys Ser Cys Asp Lys Thr His Thr Cys Pro Pro Cys Pro
                    405                 410                 415

Ala Pro Glu Leu Leu Gly Gly Pro Ser Val Phe Leu Phe Pro Pro Lys
                420                 425                 430
```

```
Pro Lys Asp Thr Leu Met Ile Ser Arg Thr Pro Glu Val Thr Cys Val
        435                 440                 445

Val Val Asp Val Ser His Glu Asp Pro Glu Val Lys Phe Asn Trp Tyr
        450                 455                 460

Val Asp Gly Val Glu Val His Asn Ala Lys Thr Lys Pro Arg Glu Glu
465                 470                 475                 480

Gln Tyr Asn Ser Thr Tyr Arg Val Val Ser Val Leu Thr Val Leu His
                485                 490                 495

Gln Asp Trp Leu Asn Gly Lys Glu Tyr Lys Cys Lys Val Ser Asn Lys
            500                 505                 510

Ala Leu Pro Ala Pro Ile Glu Lys Thr Ile Ser Lys Ala Lys Gly Gln
        515                 520                 525

Pro Arg Glu Pro Gln Val Tyr Thr Leu Pro Pro Ser Arg Asp Glu Leu
        530                 535                 540

Thr Lys Asn Gln Val Ser Leu Thr Cys Leu Val Lys Gly Phe Tyr Pro
545                 550                 555                 560

Ser Asp Ile Ala Val Glu Trp Glu Ser Asn Gly Gln Pro Glu Asn Asn
                565                 570                 575

Tyr Lys Thr Thr Pro Pro Val Leu Asp Ser Asp Gly Ser Phe Phe Leu
            580                 585                 590

Tyr Ser Lys Leu Thr Val Asp Lys Ser Arg Trp Gln Gln Gly Asn Val
        595                 600                 605

Phe Ser Cys Ser Val Met His Glu Ala Leu His Asn His Tyr Thr Gln
        610                 615                 620

Lys Ser Leu Ser Leu Ser Pro Gly Lys
625                 630

<210> SEQ ID NO 27
<211> LENGTH: 643
<212> TYPE: PRT
<213> ORGANISM: Artificial Sequence
<220> FEATURE:
<223> OTHER INFORMATION: Description of Artificial Sequence: Synthetic
      bGCSF-L1 fusion polypeptide

<400> SEQUENCE: 27

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Thr Gly Tyr Asn Pro Gly Leu Lys
    50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
                85                  90                  95

Ser Val His Gln Glu Thr Lys Lys Tyr Gln Ser Gly Gly Gly Gly Ser
            100                 105                 110

Thr Pro Leu Gly Pro Ala Arg Ser Leu Pro Gln Ser Phe Leu Leu Lys
        115                 120                 125

Cys Leu Glu Gln Val Arg Lys Ile Gln Ala Asp Gly Ala Glu Leu Gln
    130                 135                 140

Glu Arg Leu Cys Ala Ala His Lys Leu Cys His Pro Glu Glu Leu Met
```

```
            145                 150                 155                 160
Leu Leu Arg His Ser Leu Gly Ile Pro Gln Ala Pro Leu Ser Ser Cys
                165                 170                 175
Ser Ser Gln Ser Leu Gln Leu Thr Ser Cys Leu Asn Gln Leu His Gly
                180                 185                 190
Gly Leu Phe Leu Tyr Gln Gly Leu Gln Ala Leu Ala Gly Ile Ser
                195                 200                 205
Pro Glu Leu Ala Pro Thr Leu Asp Thr Leu Gln Leu Asp Val Thr Asp
    210                 215                 220
Phe Ala Thr Asn Ile Trp Leu Gln Met Glu Asp Leu Gly Ala Ala Pro
225                 230                 235                 240
Ala Val Gln Pro Thr Gln Gly Ala Met Pro Thr Phe Thr Ser Ala Phe
                245                 250                 255
Gln Arg Arg Ala Gly Gly Val Leu Val Ala Ser Gln Leu His Arg Phe
                260                 265                 270
Leu Glu Leu Ala Tyr Arg Gly Leu Arg Tyr Leu Ala Glu Pro Gly Gly
                275                 280                 285
Gly Gly Ser Ser Tyr Thr Tyr Asn Tyr Glu Trp His Val Asp Val Trp
    290                 295                 300
Gly Gln Gly Leu Leu Val Thr Val Ser Ser Ala Ser Thr Thr Ala Pro
305                 310                 315                 320
Lys Val Tyr Pro Leu Ser Ser Cys Cys Gly Asp Lys Ser Ser Ser Thr
                325                 330                 335
Val Thr Leu Gly Cys Leu Val Ser Ser Tyr Met Pro Glu Pro Val Thr
                340                 345                 350
Val Thr Trp Asn Ser Gly Ala Leu Lys Ser Gly Val His Thr Phe Pro
                355                 360                 365
Ala Val Leu Gln Ser Ser Gly Leu Tyr Ser Leu Ser Ser Met Val Thr
                370                 375                 380
Val Pro Gly Ser Thr Ser Gly Gln Thr Phe Thr Cys Asn Val Ala His
385                 390                 395                 400
Pro Ala Ser Ser Thr Lys Val Asp Lys Ala Val Glu Pro Lys Ser Cys
                405                 410                 415
Asp Lys Thr His Thr Cys Pro Pro Cys Pro Ala Pro Glu Leu Leu Gly
                420                 425                 430
Gly Pro Ser Val Phe Leu Phe Pro Pro Lys Pro Lys Asp Thr Leu Met
                435                 440                 445
Ile Ser Arg Thr Pro Glu Val Thr Cys Val Val Val Asp Val Ser His
                450                 455                 460
Glu Asp Pro Glu Val Lys Phe Asn Trp Tyr Val Asp Gly Val Glu Val
465                 470                 475                 480
His Asn Ala Lys Thr Lys Pro Arg Glu Glu Gln Tyr Asn Ser Thr Tyr
                485                 490                 495
Arg Val Val Ser Val Leu Thr Val Leu His Gln Asp Trp Leu Asn Gly
                500                 505                 510
Lys Glu Tyr Lys Cys Lys Val Ser Asn Lys Ala Leu Pro Ala Pro Ile
                515                 520                 525
Glu Lys Thr Ile Ser Lys Ala Lys Gly Gln Pro Arg Glu Pro Gln Val
                530                 535                 540
Tyr Thr Leu Pro Pro Ser Arg Asp Glu Leu Thr Lys Asn Gln Val Ser
545                 550                 555                 560
Leu Thr Cys Leu Val Lys Gly Phe Tyr Pro Ser Asp Ile Ala Val Glu
                565                 570                 575
```

```
Trp Glu Ser Asn Gly Gln Pro Glu Asn Asn Tyr Lys Thr Thr Pro Pro
            580                 585                 590

Val Leu Asp Ser Asp Gly Ser Phe Phe Leu Tyr Ser Lys Leu Thr Val
        595                 600                 605

Asp Lys Ser Arg Trp Gln Gln Gly Asn Val Phe Ser Cys Ser Val Met
    610                 615                 620

His Glu Ala Leu His Asn His Tyr Thr Gln Lys Ser Leu Ser Leu Ser
625                 630                 635                 640

Pro Gly Lys

<210> SEQ ID NO 28
<211> LENGTH: 596
<212> TYPE: PRT
<213> ORGANISM: Artificial Sequence
<220> FEATURE:
<223> OTHER INFORMATION: Description of Artificial Sequence: Synthetic
      GMCSF fusion polypeptide

<400> SEQUENCE: 28

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Thr Gly Tyr Asn Pro Gly Leu Lys
    50                  55                  60

Ser Arg Leu Ser Ile Thr Lys Asp Asn Ser Lys Ser Gln Val Ser Leu
65                  70                  75                  80

Ser Val Ser Val Thr Thr Glu Asp Ser Ala Thr Tyr Tyr Cys Thr
                85                  90                  95

Ser Val His Gln Glu Thr Lys Lys Tyr Gln Ser Gly Gly Gly Ser
                100                 105                 110

Ala Pro Ala Arg Ser Pro Ser Pro Ser Thr Gln Pro Trp Glu His Val
        115                 120                 125

Asn Ala Ile Gln Glu Ala Arg Arg Leu Leu Asn Leu Ser Arg Asp Thr
    130                 135                 140

Ala Ala Glu Met Asn Glu Thr Val Glu Val Ile Ser Glu Met Phe Asp
145                 150                 155                 160

Leu Gln Glu Pro Thr Cys Leu Gln Thr Arg Leu Glu Leu Tyr Lys Gln
                165                 170                 175

Gly Leu Arg Gly Ser Leu Thr Lys Leu Lys Gly Pro Leu Thr Met Met
            180                 185                 190

Ala Ser His Tyr Lys Gln His Cys Pro Pro Thr Pro Glu Thr Ser Cys
        195                 200                 205

Ala Thr Gln Ile Ile Thr Phe Glu Ser Phe Lys Glu Asn Leu Lys Asp
    210                 215                 220

Phe Leu Leu Val Ile Pro Phe Asp Cys Trp Glu Pro Val Gln Glu Gly
225                 230                 235                 240

Gly Gly Gly Ser Ser Tyr Thr Tyr Asn Tyr Glu Trp His Val Asp Val
                245                 250                 255

Trp Gly Gln Gly Leu Leu Val Thr Val Ser Ser Ala Ser Thr Thr Ala
            260                 265                 270

Pro Lys Val Tyr Pro Leu Ser Ser Cys Cys Gly Asp Lys Ser Ser Ser
        275                 280                 285
```

```
Thr Val Thr Leu Gly Cys Leu Val Ser Ser Tyr Met Pro Glu Pro Val
    290                 295                 300
Thr Val Thr Trp Asn Ser Gly Ala Leu Lys Ser Gly Val His Thr Phe
305                 310                 315                 320
Pro Ala Val Leu Gln Ser Ser Gly Leu Tyr Ser Leu Ser Ser Met Val
                325                 330                 335
Thr Val Pro Gly Ser Thr Ser Gly Gln Thr Phe Thr Cys Asn Val Ala
            340                 345                 350
His Pro Ala Ser Ser Thr Lys Val Asp Lys Ala Val Glu Pro Lys Ser
        355                 360                 365
Cys Asp Lys Thr His Thr Cys Pro Pro Cys Pro Ala Pro Glu Leu Leu
370                 375                 380
Gly Gly Pro Ser Val Phe Leu Phe Pro Pro Lys Pro Lys Asp Thr Leu
385                 390                 395                 400
Met Ile Ser Arg Thr Pro Glu Val Thr Cys Val Val Val Asp Val Ser
                405                 410                 415
His Glu Asp Pro Glu Val Lys Phe Asn Trp Tyr Val Asp Gly Val Glu
            420                 425                 430
Val His Asn Ala Lys Thr Lys Pro Arg Glu Glu Gln Tyr Asn Ser Thr
        435                 440                 445
Tyr Arg Val Val Ser Val Leu Thr Val Leu His Gln Asp Trp Leu Asn
450                 455                 460
Gly Lys Glu Tyr Lys Cys Lys Val Ser Asn Lys Ala Leu Pro Ala Pro
465                 470                 475                 480
Ile Glu Lys Thr Ile Ser Lys Ala Lys Gly Gln Pro Arg Glu Pro Gln
                485                 490                 495
Val Tyr Thr Leu Pro Pro Ser Arg Asp Glu Leu Thr Lys Asn Gln Val
            500                 505                 510
Ser Leu Thr Cys Leu Val Lys Gly Phe Tyr Pro Ser Asp Ile Ala Val
        515                 520                 525
Glu Trp Glu Ser Asn Gly Gln Pro Glu Asn Asn Tyr Lys Thr Thr Pro
530                 535                 540
Pro Val Leu Asp Ser Asp Gly Ser Phe Phe Leu Tyr Ser Lys Leu Thr
545                 550                 555                 560
Val Asp Lys Ser Arg Trp Gln Gln Gly Asn Val Phe Ser Cys Ser Val
                565                 570                 575
Met His Glu Ala Leu His Asn His Tyr Thr Gln Lys Ser Leu Ser Leu
            580                 585                 590
Ser Pro Gly Lys
        595

<210> SEQ ID NO 29
<211> LENGTH: 650
<212> TYPE: PRT
<213> ORGANISM: Artificial Sequence
<220> FEATURE:
<223> OTHER INFORMATION: Description of Artificial Sequence: Synthetic
      hFGF21 fusion polypeptide

<400> SEQUENCE: 29

Gln Val Gln Leu Arg Glu Ser Gly Pro Ser Leu Val Lys Pro Ser Gln
1               5                   10                  15
Thr Leu Ser Leu Thr Cys Thr Ala Ser Gly Phe Ser Leu Ser Asp Lys
            20                  25                  30
Ala Val Gly Trp Val Arg Gln Ala Pro Gly Lys Ala Leu Glu Trp Leu
```

```
            35                  40                  45
Gly Ser Ile Asp Thr Gly Asn Thr Gly Tyr Asn Pro Gly Leu Lys
 50                  55                  60

Ser Arg Leu Ser Ile Thr Lys Asp Asn Ser Lys Ser Gln Val Ser Leu
 65                  70                  75                  80

Ser Val Ser Ser Val Thr Thr Glu Asp Ser Ala Thr Tyr Tyr Cys Thr
                     85                  90                  95

Ser Val His Gln Glu Thr Lys Lys Tyr Gln Ser Gly Gly Gly Gly Ser
                100                 105                 110

His Pro Ile Pro Asp Ser Ser Pro Leu Leu Gln Phe Gly Gln Val
            115                 120                 125

Arg Gln Arg Tyr Leu Tyr Thr Asp Ala Gln Gln Thr Glu Ala His
        130                 135                 140

Leu Glu Ile Arg Glu Asp Gly Thr Val Gly Gly Ala Ala Asp Gln Ser
145                 150                 155                 160

Pro Glu Ser Leu Leu Gln Leu Lys Ala Leu Lys Pro Gly Val Ile Gln
                165                 170                 175

Ile Leu Gly Val Lys Thr Ser Arg Phe Leu Cys Gln Arg Pro Asp Gly
                180                 185                 190

Ala Leu Tyr Gly Ser Leu His Phe Asp Pro Glu Ala Cys Ser Phe Arg
            195                 200                 205

Glu Leu Leu Leu Glu Asp Gly Tyr Asn Val Tyr Gln Ser Glu Ala His
        210                 215                 220

Gly Leu Pro Leu His Leu Pro Gly Asn Lys Ser Pro His Arg Asp Pro
225                 230                 235                 240

Ala Pro Arg Gly Pro Ala Arg Phe Leu Pro Leu Pro Gly Leu Pro Pro
                245                 250                 255

Ala Pro Pro Glu Pro Pro Gly Ile Leu Ala Pro Gln Pro Pro Asp Val
            260                 265                 270

Gly Ser Ser Asp Pro Leu Ser Met Val Gly Pro Ser Gln Gly Arg Ser
        275                 280                 285

Pro Ser Tyr Ala Ser Gly Gly Gly Ser Ser Tyr Thr Tyr Asn Tyr
290                 295                 300

Glu Trp His Val Asp Val Trp Gly Gln Gly Leu Leu Val Thr Val Ser
305                 310                 315                 320

Ser Ala Ser Thr Thr Ala Pro Lys Val Tyr Pro Leu Ser Ser Cys Cys
                325                 330                 335

Gly Asp Lys Ser Ser Ser Thr Val Thr Leu Gly Cys Leu Val Ser Ser
            340                 345                 350

Tyr Met Pro Glu Pro Val Thr Val Thr Trp Asn Ser Gly Ala Leu Lys
        355                 360                 365

Ser Gly Val His Thr Phe Pro Ala Val Leu Gln Ser Ser Gly Leu Tyr
    370                 375                 380

Ser Leu Ser Ser Met Val Thr Val Pro Gly Ser Thr Ser Gly Gln Thr
385                 390                 395                 400

Phe Thr Cys Asn Val Ala His Pro Ala Ser Ser Thr Lys Val Asp Lys
                405                 410                 415

Ala Val Glu Pro Lys Ser Cys Asp Lys Thr His Thr Cys Pro Pro Cys
            420                 425                 430

Pro Ala Pro Glu Leu Leu Gly Gly Pro Ser Val Phe Leu Phe Pro Pro
        435                 440                 445

Lys Pro Lys Asp Thr Leu Met Ile Ser Arg Thr Pro Glu Val Thr Cys
    450                 455                 460
```

```
Val Val Val Asp Val Ser His Glu Asp Pro Glu Val Lys Phe Asn Trp
465                 470                 475                 480

Tyr Val Asp Gly Val Glu Val His Asn Ala Lys Thr Lys Pro Arg Glu
                485                 490                 495

Glu Gln Tyr Asn Ser Thr Tyr Arg Val Val Ser Val Leu Thr Val Leu
            500                 505                 510

His Gln Asp Trp Leu Asn Gly Lys Glu Tyr Lys Cys Lys Val Ser Asn
            515                 520                 525

Lys Ala Leu Pro Ala Pro Ile Glu Lys Thr Ile Ser Lys Ala Lys Gly
530                 535                 540

Gln Pro Arg Glu Pro Gln Val Tyr Thr Leu Pro Pro Ser Arg Asp Glu
545                 550                 555                 560

Leu Thr Lys Asn Gln Val Ser Leu Thr Cys Leu Val Lys Gly Phe Tyr
                565                 570                 575

Pro Ser Asp Ile Ala Val Glu Trp Glu Ser Asn Gly Gln Pro Glu Asn
            580                 585                 590

Asn Tyr Lys Thr Thr Pro Pro Val Leu Asp Ser Asp Gly Ser Phe Phe
            595                 600                 605

Leu Tyr Ser Lys Leu Thr Val Asp Lys Ser Arg Trp Gln Gln Gly Asn
            610                 615                 620

Val Phe Ser Cys Ser Val Met His Glu Ala Leu His Asn His Tyr Thr
625                 630                 635                 640

Gln Lys Ser Leu Ser Leu Ser Pro Gly Lys
                645                 650

<210> SEQ ID NO 30
<211> LENGTH: 514
<212> TYPE: PRT
<213> ORGANISM: Artificial Sequence
<220> FEATURE:
<223> OTHER INFORMATION: Description of Artificial Sequence: Synthetic
      Ex-4 fusion polypeptide

<400> SEQUENCE: 30

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Thr Gly Tyr Asn Pro Gly Leu Lys
    50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
                85                  90                  95

Ser Val His Gln Glu Thr Lys Lys Tyr Gln Ser Cys Gly Gly Gly Gly
            100                 105                 110

Ser Ile Glu Gly Arg His Gly Glu Gly Thr Phe Thr Ser Asp Leu Ser
        115                 120                 125

Lys Gln Met Glu Glu Glu Ala Val Arg Leu Phe Ile Glu Trp Leu Lys
    130                 135                 140

Asn Gly Gly Pro Ser Ser Gly Ala Pro Pro Ser Gly Gly Gly Gly
145                 150                 155                 160

Ser Cys Ser Tyr Thr Tyr Asn Tyr Glu Trp His Val Asp Val Trp Gly
```

```
                     165                 170                 175

Gln Gly Leu Leu Val Thr Val Ser Ser Ala Ser Thr Thr Ala Pro Lys
            180                 185                 190

Val Tyr Pro Leu Ser Ser Cys Cys Gly Asp Lys Ser Ser Ser Thr Val
        195                 200                 205

Thr Leu Gly Cys Leu Val Ser Ser Tyr Met Pro Glu Pro Val Thr Val
    210                 215                 220

Thr Trp Asn Ser Gly Ala Leu Lys Ser Gly Val His Thr Phe Pro Ala
225                 230                 235                 240

Val Leu Gln Ser Ser Gly Leu Tyr Ser Leu Ser Ser Met Val Thr Val
                245                 250                 255

Pro Gly Ser Thr Ser Gly Gln Thr Phe Thr Cys Asn Val Ala His Pro
            260                 265                 270

Ala Ser Ser Thr Lys Val Asp Lys Ala Val Glu Pro Lys Ser Cys Asp
        275                 280                 285

Lys Thr His Thr Cys Pro Pro Cys Pro Ala Pro Glu Leu Leu Gly Gly
    290                 295                 300

Pro Ser Val Phe Leu Phe Pro Pro Lys Pro Lys Asp Thr Leu Met Ile
305                 310                 315                 320

Ser Arg Thr Pro Glu Val Thr Cys Val Val Val Asp Val Ser His Glu
                325                 330                 335

Asp Pro Glu Val Lys Phe Asn Trp Tyr Val Asp Gly Val Glu Val His
            340                 345                 350

Asn Ala Lys Thr Lys Pro Arg Glu Glu Gln Tyr Asn Ser Thr Tyr Arg
        355                 360                 365

Val Val Ser Val Leu Thr Val Leu His Gln Asp Trp Leu Asn Gly Lys
    370                 375                 380

Glu Tyr Lys Cys Lys Val Ser Asn Lys Ala Leu Pro Ala Pro Ile Glu
385                 390                 395                 400

Lys Thr Ile Ser Lys Ala Lys Gly Gln Pro Arg Glu Pro Gln Val Tyr
                405                 410                 415

Thr Leu Pro Pro Ser Arg Asp Glu Leu Thr Lys Asn Gln Val Ser Leu
            420                 425                 430

Thr Cys Leu Val Lys Gly Phe Tyr Pro Ser Asp Ile Ala Val Glu Trp
        435                 440                 445

Glu Ser Asn Gly Gln Pro Glu Asn Asn Tyr Lys Thr Thr Pro Pro Val
    450                 455                 460

Leu Asp Ser Asp Gly Ser Phe Phe Leu Tyr Ser Lys Leu Thr Val Asp
465                 470                 475                 480

Lys Ser Arg Trp Gln Gln Gly Asn Val Phe Ser Cys Ser Val Met His
                485                 490                 495

Glu Ala Leu His Asn His Tyr Thr Gln Lys Ser Leu Ser Leu Ser Pro
            500                 505                 510

Gly Lys

<210> SEQ ID NO 31
<211> LENGTH: 505
<212> TYPE: PRT
<213> ORGANISM: Artificial Sequence
<220> FEATURE:
<223> OTHER INFORMATION: Description of Artificial Sequence: Synthetic
      hGLP-1 fusion polypeptide

<400> SEQUENCE: 31

Gln Val Gln Leu Arg Glu Ser Gly Pro Ser Leu Val Lys Pro Ser Gln
```

-continued

```
1               5                   10                  15
Thr Leu Ser Leu Thr Cys Thr Ala Ser Gly Phe Ser Leu Ser Asp Lys
                20                  25                  30

Ala Val Gly Trp Val Arg Gln Ala Pro Gly Lys Ala Leu Glu Trp Leu
                35                  40                  45

Gly Ser Ile Asp Thr Gly Gly Asn Thr Gly Tyr Asn Pro Gly Leu Lys
                50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
                85                  90                  95

Ser Val His Gln Glu Thr Lys Lys Tyr Gln Ser Cys Gly Gly Gly Gly
                100                 105                 110

Ser Ile Glu Gly Arg His Ala Glu Gly Thr Phe Thr Ser Asp Val Ser
                115                 120                 125

Ser Tyr Leu Glu Gly Gln Ala Ala Lys Glu Phe Ile Ala Trp Leu Val
                130                 135                 140

Lys Gly Arg Gly Gly Gly Ser Cys Ser Tyr Thr Tyr Asn Tyr Glu
145                 150                 155                 160

Trp His Val Asp Val Trp Gly Gln Gly Leu Leu Val Thr Val Ser Ser
                165                 170                 175

Ala Ser Thr Thr Ala Pro Lys Val Tyr Pro Leu Ser Ser Cys Cys Gly
                180                 185                 190

Asp Lys Ser Ser Ser Thr Val Thr Leu Gly Cys Leu Val Ser Ser Tyr
                195                 200                 205

Met Pro Glu Pro Val Thr Val Thr Trp Asn Ser Gly Ala Leu Lys Ser
210                 215                 220

Gly Val His Thr Phe Pro Ala Val Leu Gln Ser Ser Gly Leu Tyr Ser
225                 230                 235                 240

Leu Ser Ser Met Val Thr Val Pro Gly Ser Thr Ser Gly Gln Thr Phe
                245                 250                 255

Thr Cys Asn Val Ala His Pro Ala Ser Ser Thr Lys Val Asp Lys Ala
                260                 265                 270

Val Glu Pro Lys Ser Cys Asp Lys Thr His Thr Cys Pro Pro Cys Pro
                275                 280                 285

Ala Pro Glu Leu Leu Gly Gly Pro Ser Val Phe Leu Phe Pro Pro Lys
                290                 295                 300

Pro Lys Asp Thr Leu Met Ile Ser Arg Thr Pro Glu Val Thr Cys Val
305                 310                 315                 320

Val Val Asp Val Ser His Glu Asp Pro Glu Val Lys Phe Asn Trp Tyr
                325                 330                 335

Val Asp Gly Val Glu Val His Asn Ala Lys Thr Lys Pro Arg Glu Glu
                340                 345                 350

Gln Tyr Asn Ser Thr Tyr Arg Val Val Ser Val Leu Thr Val Leu His
                355                 360                 365

Gln Asp Trp Leu Asn Gly Lys Glu Tyr Lys Cys Lys Val Ser Asn Lys
                370                 375                 380

Ala Leu Pro Ala Pro Ile Glu Lys Thr Ile Ser Lys Ala Lys Gly Gln
385                 390                 395                 400

Pro Arg Glu Pro Gln Val Tyr Thr Leu Pro Pro Ser Arg Asp Glu Leu
                405                 410                 415

Thr Lys Asn Gln Val Ser Leu Thr Cys Leu Val Lys Gly Phe Tyr Pro
                420                 425                 430
```

```
Ser Asp Ile Ala Val Glu Trp Glu Ser Asn Gly Gln Pro Glu Asn Asn
        435                 440                 445

Tyr Lys Thr Thr Pro Pro Val Leu Asp Ser Asp Gly Ser Phe Phe Leu
    450                 455                 460

Tyr Ser Lys Leu Thr Val Asp Lys Ser Arg Trp Gln Gln Gly Asn Val
465                 470                 475                 480

Phe Ser Cys Ser Val Met His Glu Ala Leu His Asn His Tyr Thr Gln
                485                 490                 495

Lys Ser Leu Ser Leu Ser Pro Gly Lys
            500                 505

<210> SEQ ID NO 32
<211> LENGTH: 635
<212> TYPE: PRT
<213> ORGANISM: Artificial Sequence
<220> FEATURE:
<223> OTHER INFORMATION: Description of Artificial Sequence: Synthetic
      hEPO fusion polypeptide

<400> SEQUENCE: 32

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Thr Gly Tyr Asn Pro Gly Leu Lys
    50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
                85                  90                  95

Ser Val His Gln Glu Thr Lys Lys Tyr Gln Ser Gly Gly Gly Gly Ser
            100                 105                 110

Ala Pro Pro Arg Leu Ile Cys Asp Ser Arg Val Leu Glu Arg Tyr Leu
        115                 120                 125

Leu Glu Ala Lys Glu Ala Glu Asn Ile Thr Thr Gly Cys Ala Glu His
    130                 135                 140

Cys Ser Leu Asn Glu Asn Ile Thr Val Pro Asp Thr Lys Val Asn Phe
145                 150                 155                 160

Tyr Ala Trp Lys Arg Met Glu Val Gly Gln Gln Ala Val Glu Val Trp
                165                 170                 175

Gln Gly Leu Ala Leu Leu Ser Glu Ala Val Leu Arg Gly Gln Ala Leu
            180                 185                 190

Leu Val Asn Ser Ser Gln Pro Trp Glu Pro Leu Gln Leu His Val Asp
        195                 200                 205

Lys Ala Val Ser Gly Leu Arg Ser Leu Thr Thr Leu Leu Arg Ala Leu
    210                 215                 220

Gly Ala Gln Lys Glu Ala Ile Ser Pro Pro Asp Ala Ala Ser Ala Ala
225                 230                 235                 240

Pro Leu Arg Thr Ile Thr Ala Asp Thr Phe Arg Lys Leu Phe Arg Val
                245                 250                 255

Tyr Ser Asn Phe Leu Arg Gly Lys Leu Lys Leu Tyr Thr Gly Glu Ala
            260                 265                 270

Cys Arg Thr Gly Asp Arg Gly Gly Gly Ser Ser Tyr Thr Tyr Asn
```

```
                275                 280                 285
Tyr Glu Trp His Val Asp Val Trp Gly Gln Gly Leu Leu Val Thr Val
290                 295                 300
Ser Ser Ala Ser Thr Thr Ala Pro Lys Val Tyr Pro Leu Ser Ser Cys
305                 310                 315                 320
Cys Gly Asp Lys Ser Ser Thr Val Thr Leu Gly Cys Leu Val Ser
                325                 330                 335
Ser Tyr Met Pro Glu Pro Val Thr Val Thr Trp Asn Ser Gly Ala Leu
                340                 345                 350
Lys Ser Gly Val His Thr Phe Pro Ala Val Leu Gln Ser Ser Gly Leu
                355                 360                 365
Tyr Ser Leu Ser Ser Met Val Thr Val Pro Gly Ser Thr Ser Gly Gln
                370                 375                 380
Thr Phe Thr Cys Asn Val Ala His Pro Ala Ser Ser Thr Lys Val Asp
385                 390                 395                 400
Lys Ala Val Glu Pro Lys Ser Cys Asp Lys Thr His Thr Cys Pro Pro
                405                 410                 415
Cys Pro Ala Pro Glu Leu Leu Gly Gly Pro Ser Val Phe Leu Phe Pro
                420                 425                 430
Pro Lys Pro Lys Asp Thr Leu Met Ile Ser Arg Thr Pro Glu Val Thr
                435                 440                 445
Cys Val Val Val Asp Val Ser His Glu Asp Pro Glu Val Lys Phe Asn
450                 455                 460
Trp Tyr Val Asp Gly Val Glu Val His Asn Ala Lys Thr Lys Pro Arg
465                 470                 475                 480
Glu Glu Gln Tyr Asn Ser Thr Tyr Arg Val Val Ser Val Leu Thr Val
                485                 490                 495
Leu His Gln Asp Trp Leu Asn Gly Lys Glu Tyr Lys Cys Lys Val Ser
                500                 505                 510
Asn Lys Ala Leu Pro Ala Pro Ile Glu Lys Thr Ile Ser Lys Ala Lys
                515                 520                 525
Gly Gln Pro Arg Glu Pro Gln Val Tyr Thr Leu Pro Pro Ser Arg Asp
                530                 535                 540
Glu Leu Thr Lys Asn Gln Val Ser Leu Thr Cys Leu Val Lys Gly Phe
545                 550                 555                 560
Tyr Pro Ser Asp Ile Ala Val Glu Trp Glu Ser Asn Gly Gln Pro Glu
                565                 570                 575
Asn Asn Tyr Lys Thr Thr Pro Pro Val Leu Asp Ser Asp Gly Ser Phe
                580                 585                 590
Phe Leu Tyr Ser Lys Leu Thr Val Asp Lys Ser Arg Trp Gln Gln Gly
                595                 600                 605
Asn Val Phe Ser Cys Ser Val Met His Glu Ala Leu His Asn His Tyr
                610                 615                 620
Thr Gln Lys Ser Leu Ser Leu Ser Pro Gly Lys
625                 630                 635

<210> SEQ ID NO 33
<211> LENGTH: 493
<212> TYPE: PRT
<213> ORGANISM: Artificial Sequence
<220> FEATURE:
<223> OTHER INFORMATION: Description of Artificial Sequence: Synthetic
      Moka-L0 fusion polypeptide

<400> SEQUENCE: 33
```

-continued

```
Gln Val Gln Leu Arg Glu Ser Gly Pro Ser Leu Val Lys Pro Ser Gln
  1               5                  10                  15
Thr Leu Ser Leu Thr Cys Thr Ala Ser Gly Phe Ser Leu Ser Asp Lys
             20                  25                  30
Ala Val Gly Trp Val Arg Gln Ala Pro Gly Lys Ala Leu Glu Trp Leu
         35                  40                  45
Gly Ser Ile Asp Thr Gly Asn Thr Gly Tyr Asn Pro Gly Leu Lys
 50                  55                  60
Ser Arg Leu Ser Ile Thr Lys Asp Asn Ser Lys Ser Gln Val Ser Leu
 65                  70                  75                  80
Ser Val Ser Ser Val Thr Thr Glu Asp Ser Ala Thr Tyr Tyr Cys Thr
             85                  90                  95
Ser Val His Gln Glu Thr Lys Lys Tyr Gln Ser Ile Asn Val Lys Cys
        100                 105                 110
Ser Leu Pro Gln Gln Cys Ile Lys Pro Cys Lys Asp Ala Gly Met Arg
        115                 120                 125
Phe Gly Lys Cys Met Asn Lys Lys Cys Arg Cys Tyr Ser Ser Tyr Thr
        130                 135                 140
Tyr Asn Tyr Glu Trp His Val Asp Val Trp Gly Gln Gly Leu Leu Val
145                 150                 155                 160
Thr Val Ser Ser Ala Ser Thr Thr Ala Pro Lys Val Tyr Pro Leu Ser
            165                 170                 175
Ser Cys Cys Gly Asp Lys Ser Ser Thr Val Thr Leu Gly Cys Leu
            180                 185                 190
Val Ser Ser Tyr Met Pro Glu Pro Val Thr Val Thr Trp Asn Ser Gly
        195                 200                 205
Ala Leu Lys Ser Gly Val His Thr Phe Pro Ala Val Leu Gln Ser Ser
        210                 215                 220
Gly Leu Tyr Ser Leu Ser Ser Met Val Thr Val Pro Gly Ser Thr Ser
225                 230                 235                 240
Gly Gln Thr Phe Thr Cys Asn Val Ala His Pro Ala Ser Ser Thr Lys
            245                 250                 255
Val Asp Lys Ala Val Glu Pro Lys Ser Cys Asp Lys Thr His Thr Cys
        260                 265                 270
Pro Pro Cys Pro Ala Pro Glu Leu Leu Gly Gly Pro Ser Val Phe Leu
        275                 280                 285
Phe Pro Pro Lys Pro Lys Asp Thr Leu Met Ile Ser Arg Thr Pro Glu
        290                 295                 300
Val Thr Cys Val Val Val Asp Val Ser His Glu Asp Pro Glu Val Lys
305                 310                 315                 320
Phe Asn Trp Tyr Val Asp Gly Val Glu Val His Asn Ala Lys Thr Lys
            325                 330                 335
Pro Arg Glu Glu Gln Tyr Asn Ser Thr Tyr Arg Val Val Ser Val Leu
        340                 345                 350
Thr Val Leu His Gln Asp Trp Leu Asn Gly Lys Glu Tyr Lys Cys Lys
        355                 360                 365
Val Ser Asn Lys Ala Leu Pro Ala Pro Ile Glu Lys Thr Ile Ser Lys
        370                 375                 380
Ala Lys Gly Gln Pro Arg Glu Pro Gln Val Tyr Thr Leu Pro Pro Ser
385                 390                 395                 400
Arg Asp Glu Leu Thr Lys Asn Gln Val Ser Leu Thr Cys Leu Val Lys
            405                 410                 415
Gly Phe Tyr Pro Ser Asp Ile Ala Val Glu Trp Glu Ser Asn Gly Gln
```

```
                     420                 425                 430
Pro Glu Asn Asn Tyr Lys Thr Thr Pro Pro Val Leu Asp Ser Asp Gly
            435                 440                 445

Ser Phe Phe Leu Tyr Ser Lys Leu Thr Val Asp Lys Ser Arg Trp Gln
450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys
            485                 490

<210> SEQ ID NO 34
<211> LENGTH: 503
<212> TYPE: PRT
<213> ORGANISM: Artificial Sequence
<220> FEATURE:
<223> OTHER INFORMATION: Description of Artificial Sequence: Synthetic
      Moka-L1 fusion polypeptide

<400> SEQUENCE: 34

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Thr Gly Tyr Asn Pro Gly Leu Lys
    50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
                85                  90                  95

Ser Val His Gln Glu Thr Lys Lys Tyr Gln Ser Gly Gly Gly Gly Ser
            100                 105                 110

Ile Asn Val Lys Cys Ser Leu Pro Gln Gln Cys Ile Lys Pro Cys Lys
        115                 120                 125

Asp Ala Gly Met Arg Phe Gly Lys Cys Met Asn Lys Lys Cys Arg Cys
    130                 135                 140

Tyr Ser Gly Gly Gly Gly Ser Ser Tyr Thr Tyr Asn Tyr Glu Trp His
145                 150                 155                 160

Val Asp Val Trp Gly Gln Gly Leu Leu Val Thr Val Ser Ser Ala Ser
                165                 170                 175

Thr Thr Ala Pro Lys Val Tyr Pro Leu Ser Ser Cys Cys Gly Asp Lys
            180                 185                 190

Ser Ser Ser Thr Val Thr Leu Gly Cys Leu Val Ser Ser Tyr Met Pro
        195                 200                 205

Glu Pro Val Thr Val Thr Trp Asn Ser Gly Ala Leu Lys Ser Gly Val
    210                 215                 220

His Thr Phe Pro Ala Val Leu Gln Ser Ser Gly Leu Tyr Ser Leu Ser
225                 230                 235                 240

Ser Met Val Thr Val Pro Gly Ser Thr Ser Gly Gln Thr Phe Thr Cys
                245                 250                 255

Asn Val Ala His Pro Ala Ser Ser Thr Lys Val Asp Lys Ala Val Glu
            260                 265                 270

Pro Lys Ser Cys Asp Lys Thr His Thr Cys Pro Pro Cys Pro Ala Pro
        275                 280                 285
```

```
Glu Leu Leu Gly Gly Pro Ser Val Phe Leu Phe Pro Pro Lys Pro Lys
290                 295                 300

Asp Thr Leu Met Ile Ser Arg Thr Pro Glu Val Thr Cys Val Val Val
305                 310                 315                 320

Asp Val Ser His Glu Asp Pro Glu Val Lys Phe Asn Trp Tyr Val Asp
            325                 330                 335

Gly Val Glu Val His Asn Ala Lys Thr Lys Pro Arg Glu Glu Gln Tyr
            340                 345                 350

Asn Ser Thr Tyr Arg Val Val Ser Val Leu Thr Val Leu His Gln Asp
        355                 360                 365

Trp Leu Asn Gly Lys Glu Tyr Lys Cys Lys Val Ser Asn Lys Ala Leu
370                 375                 380

Pro Ala Pro Ile Glu Lys Thr Ile Ser Lys Ala Lys Gly Gln Pro Arg
385                 390                 395                 400

Glu Pro Gln Val Tyr Thr Leu Pro Pro Ser Arg Asp Glu Leu Thr Lys
            405                 410                 415

Asn Gln Val Ser Leu Thr Cys Leu Val Lys Gly Phe Tyr Pro Ser Asp
            420                 425                 430

Ile Ala Val Glu Trp Glu Ser Asn Gly Gln Pro Glu Asn Asn Tyr Lys
        435                 440                 445

Thr Thr Pro Pro Val Leu Asp Ser Asp Gly Ser Phe Phe Leu Tyr Ser
450                 455                 460

Lys Leu Thr Val Asp Lys Ser Arg Trp Gln Gln Gly Asn Val Phe Ser
465                 470                 475                 480

Cys Ser Val Met His Glu Ala Leu His Asn His Tyr Thr Gln Lys Ser
            485                 490                 495

Leu Ser Leu Ser Pro Gly Lys
            500

<210> SEQ ID NO 35
<211> LENGTH: 505
<212> TYPE: PRT
<213> ORGANISM: Artificial Sequence
<220> FEATURE:
<223> OTHER INFORMATION: Description of Artificial Sequence: Synthetic
      VM-24-L1 fusion polypeptide

<400> SEQUENCE: 35

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Thr Gly Tyr Asn Pro Gly Leu Lys
    50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
                85                  90                  95

Ser Val His Gln Glu Thr Lys Lys Tyr Gln Ser Gly Gly Gly Gly Ser
            100                 105                 110

Ala Ala Ala Ile Ser Cys Val Gly Ser Pro Glu Cys Pro Pro Lys Cys
        115                 120                 125

Arg Ala Gln Gly Cys Lys Asn Gly Lys Cys Met Asn Arg Lys Cys Lys
    130                 135                 140
```

Cys Tyr Tyr Cys Gly Gly Gly Ser Ser Tyr Thr Tyr Asn Tyr Glu
145                 150                 155                 160

Trp His Val Asp Val Trp Gly Gln Gly Leu Val Thr Val Ser Ser
            165                 170                 175

Ala Ser Thr Thr Ala Pro Lys Val Tyr Pro Leu Ser Ser Cys Cys Gly
        180                 185                 190

Asp Lys Ser Ser Ser Thr Val Thr Leu Gly Cys Leu Val Ser Ser Tyr
        195                 200                 205

Met Pro Glu Pro Val Thr Val Thr Trp Asn Ser Gly Ala Leu Lys Ser
    210                 215                 220

Gly Val His Thr Phe Pro Ala Val Leu Gln Ser Ser Gly Leu Tyr Ser
225                 230                 235                 240

Leu Ser Ser Met Val Thr Val Pro Gly Ser Thr Ser Gly Gln Thr Phe
            245                 250                 255

Thr Cys Asn Val Ala His Pro Ala Ser Ser Thr Lys Val Asp Lys Ala
        260                 265                 270

Val Glu Pro Lys Ser Cys Asp Lys Thr His Thr Cys Pro Pro Cys Pro
    275                 280                 285

Ala Pro Glu Leu Leu Gly Gly Pro Ser Val Phe Leu Phe Pro Pro Lys
    290                 295                 300

Pro Lys Asp Thr Leu Met Ile Ser Arg Thr Pro Glu Val Thr Cys Val
305                 310                 315                 320

Val Val Asp Val Ser His Glu Asp Pro Glu Val Lys Phe Asn Trp Tyr
            325                 330                 335

Val Asp Gly Val Glu Val His Asn Ala Lys Thr Lys Pro Arg Glu Glu
        340                 345                 350

Gln Tyr Asn Ser Thr Tyr Arg Val Val Ser Val Leu Thr Val Leu His
    355                 360                 365

Gln Asp Trp Leu Asn Gly Lys Glu Tyr Lys Cys Lys Val Ser Asn Lys
370                 375                 380

Ala Leu Pro Ala Pro Ile Glu Lys Thr Ile Ser Lys Ala Lys Gly Gln
385                 390                 395                 400

Pro Arg Glu Pro Gln Val Tyr Thr Leu Pro Pro Ser Arg Asp Glu Leu
            405                 410                 415

Thr Lys Asn Gln Val Ser Leu Thr Cys Leu Val Lys Gly Phe Tyr Pro
        420                 425                 430

Ser Asp Ile Ala Val Glu Trp Glu Ser Asn Gly Gln Pro Glu Asn Asn
        435                 440                 445

Tyr Lys Thr Thr Pro Pro Val Leu Asp Ser Asp Gly Ser Phe Phe Leu
    450                 455                 460

Tyr Ser Lys Leu Thr Val Asp Lys Ser Arg Trp Gln Gln Gly Asn Val
465                 470                 475                 480

Phe Ser Cys Ser Val Met His Glu Ala Leu His Asn His Tyr Thr Gln
            485                 490                 495

Lys Ser Leu Ser Leu Ser Pro Gly Lys
        500                 505

<210> SEQ ID NO 36
<211> LENGTH: 513
<212> TYPE: PRT
<213> ORGANISM: Artificial Sequence
<220> FEATURE:
<223> OTHER INFORMATION: Description of Artificial Sequence: Synthetic
      VM-24-L2 fusion polypeptide

```
<400> SEQUENCE: 36

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Thr Gly Tyr Asn Pro Gly Leu Lys
    50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
                85                  90                  95

Ser Val His Gln Glu Thr Lys Lys Tyr Gln Ser Gly Gly Gly Ser Gly
            100                 105                 110

Gly Gly Gly Ser Ala Ala Ala Ile Ser Cys Val Gly Ser Pro Glu Cys
        115                 120                 125

Pro Pro Lys Cys Arg Ala Gln Gly Cys Lys Asn Gly Lys Cys Met Asn
    130                 135                 140

Arg Lys Cys Lys Cys Tyr Tyr Cys Gly Gly Gly Ser Gly Gly Gly
145                 150                 155                 160

Ser Ser Tyr Thr Tyr Asn Tyr Glu Trp His Val Asp Val Trp Gly Gln
                165                 170                 175

Gly Leu Leu Val Thr Val Ser Ser Ala Ser Thr Thr Ala Pro Lys Val
            180                 185                 190

Tyr Pro Leu Ser Ser Cys Cys Gly Asp Lys Ser Ser Ser Thr Val Thr
        195                 200                 205

Leu Gly Cys Leu Val Ser Ser Tyr Met Pro Glu Pro Val Thr Val Thr
    210                 215                 220

Trp Asn Ser Gly Ala Leu Lys Ser Gly Val His Thr Phe Pro Ala Val
225                 230                 235                 240

Leu Gln Ser Ser Gly Leu Tyr Ser Leu Ser Ser Met Val Thr Val Pro
                245                 250                 255

Gly Ser Thr Ser Gly Gln Thr Phe Thr Cys Asn Val Ala His Pro Ala
            260                 265                 270

Ser Ser Thr Lys Val Asp Lys Ala Val Glu Pro Lys Ser Cys Asp Lys
        275                 280                 285

Thr His Thr Cys Pro Pro Cys Pro Ala Pro Glu Leu Leu Gly Gly Pro
    290                 295                 300

Ser Val Phe Leu Phe Pro Pro Lys Pro Lys Asp Thr Leu Met Ile Ser
305                 310                 315                 320

Arg Thr Pro Glu Val Thr Cys Val Val Val Asp Val Ser His Glu Asp
                325                 330                 335

Pro Glu Val Lys Phe Asn Trp Tyr Val Asp Gly Val Glu Val His Asn
            340                 345                 350

Ala Lys Thr Lys Pro Arg Glu Glu Gln Tyr Asn Ser Thr Tyr Arg Val
        355                 360                 365

Val Ser Val Leu Thr Val Leu His Gln Asp Trp Leu Asn Gly Lys Glu
    370                 375                 380

Tyr Lys Cys Lys Val Ser Asn Lys Ala Leu Pro Ala Pro Ile Glu Lys
385                 390                 395                 400

Thr Ile Ser Lys Ala Lys Gly Gln Pro Arg Glu Pro Gln Val Tyr Thr
                405                 410                 415
```

```
Leu Pro Pro Ser Arg Asp Glu Leu Thr Lys Asn Gln Val Ser Leu Thr
            420                 425                 430

Cys Leu Val Lys Gly Phe Tyr Pro Ser Asp Ile Ala Val Glu Trp Glu
            435                 440                 445

Ser Asn Gly Gln Pro Glu Asn Asn Tyr Lys Thr Thr Pro Pro Val Leu
            450                 455                 460

Asp Ser Asp Gly Ser Phe Phe Leu Tyr Ser Lys Leu Thr Val Asp Lys
465                 470                 475                 480

Ser Arg Trp Gln Gln Gly Asn Val Phe Ser Cys Ser Val Met His Glu
                    485                 490                 495

Ala Leu His Asn His Tyr Thr Gln Lys Ser Leu Ser Leu Ser Pro Gly
            500                 505                 510

Lys

<210> SEQ ID NO 37
<211> LENGTH: 499
<212> TYPE: PRT
<213> ORGANISM: Artificial Sequence
<220> FEATURE:
<223> OTHER INFORMATION: Description of Artificial Sequence: Synthetic
      Protoxin2-L1 fusion polypeptide

<400> SEQUENCE: 37

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
            35                  40                  45

Gly Ser Ile Asp Thr Gly Gly Asn Thr Gly Tyr Asn Pro Gly Leu Lys
        50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
                85                  90                  95

Ser Val His Gln Glu Thr Lys Lys Tyr Gln Ser Gly Gly Gly Gly Ser
            100                 105                 110

Tyr Cys Gln Lys Trp Met Trp Thr Cys Asp Ser Glu Arg Lys Cys Cys
            115                 120                 125

Glu Gly Met Val Cys Arg Leu Trp Cys Lys Lys Lys Leu Trp Gly Gly
            130                 135                 140

Gly Gly Ser Ser Tyr Thr Tyr Asn Tyr Glu Trp His Val Asp Val Trp
145                 150                 155                 160

Gly Gln Gly Leu Leu Val Thr Val Ser Ser Ala Ser Thr Thr Ala Pro
                165                 170                 175

Lys Val Tyr Pro Leu Ser Ser Cys Cys Gly Asp Lys Ser Ser Ser Thr
            180                 185                 190

Val Thr Leu Gly Cys Leu Val Ser Ser Tyr Met Pro Glu Pro Val Thr
            195                 200                 205

Val Thr Trp Asn Ser Gly Ala Leu Lys Ser Gly Val His Thr Phe Pro
            210                 215                 220

Ala Val Leu Gln Ser Ser Gly Leu Tyr Ser Leu Ser Ser Met Val Thr
225                 230                 235                 240

Val Pro Gly Ser Thr Ser Gly Gln Thr Phe Thr Cys Asn Val Ala His
                245                 250                 255
```

```
Pro Ala Ser Ser Thr Lys Val Asp Lys Ala Val Glu Pro Lys Ser Cys
            260                 265                 270

Asp Lys Thr His Thr Cys Pro Pro Cys Pro Ala Pro Glu Leu Leu Gly
            275                 280                 285

Gly Pro Ser Val Phe Leu Phe Pro Pro Lys Pro Lys Asp Thr Leu Met
        290                 295                 300

Ile Ser Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335

His Asn Ala Lys Thr Lys Pro Arg Glu Glu Gln Tyr Asn Ser Thr Tyr
            340                 345                 350

Arg Val Val Ser Val Leu Thr Val Leu His Gln Asp Trp Leu Asn Gly
        355                 360                 365

Lys Glu Tyr Lys Cys Lys Val Ser Asn Lys Ala Leu Pro Ala Pro Ile
    370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
                405                 410                 415

Leu Thr Cys Leu Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
        435                 440                 445

Val Leu Asp Ser Asp Gly Ser Phe Phe Leu Tyr Ser Lys Leu Thr Val
    450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Pro Gly Lys

<210> SEQ ID NO 38
<211> LENGTH: 205
<212> TYPE: PRT
<213> ORGANISM: Artificial Sequence
<220> FEATURE:
<223> OTHER INFORMATION: Description of Artificial Sequence: Synthetic
      BLV1H12-IL8 fusion polypeptide

<400> SEQUENCE: 38

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Thr Gly Tyr Asn Pro Gly Leu Lys
    50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
                85                  90                  95

Ser Val His Gln Glu Thr Lys Lys Tyr Gln Ser Pro Arg Ser Ala Lys
            100                 105                 110
```

Glu Leu Arg Cys Gln Cys Ile Lys Thr Tyr Ser Lys Pro Phe His Pro
            115                 120                 125

Lys Phe Ile Lys Glu Leu Arg Val Ile Glu Ser Gly Pro His Cys Ala
        130                 135                 140

Asn Thr Glu Ile Ile Val Lys Leu Ser Asp Gly Arg Glu Leu Cys Leu
145                 150                 155                 160

Asp Pro Lys Glu Asn Trp Val Gln Arg Val Glu Lys Phe Leu Lys
                165                 170                 175

Arg Ala Glu Asn Ser Gly Ser Gly Ser Tyr Thr Tyr Asn Tyr Glu Trp
                180                 185                 190

His Val Asp Val Trp Gly Gln Gly Leu Leu Val Thr Val
                195                 200                 205

<210> SEQ ID NO 39
<211> LENGTH: 153
<212> TYPE: PRT
<213> ORGANISM: Artificial Sequence
<220> FEATURE:
<223> OTHER INFORMATION: Description of Artificial Sequence: Synthetic
      BLV1H12-Ziconotide fusion polypeptide

<400> SEQUENCE: 39

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Thr Gly Tyr Asn Pro Gly Leu Lys
    50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
                85                  90                  95

Ser Val His Gln Glu Thr Lys Lys Tyr Gln Ser Cys Lys Gly Lys Gly
            100                 105                 110

Ala Lys Cys Ser Arg Leu Met Tyr Asp Cys Cys Thr Gly Ser Cys Arg
        115                 120                 125

Ser Gly Lys Cys Ser Tyr Thr Tyr Asn Tyr Glu Trp His Val Asp Val
    130                 135                 140

Trp Gly Gln Gly Leu Leu Val Thr Val
145                 150

<210> SEQ ID NO 40
<211> LENGTH: 143
<212> TYPE: PRT
<213> ORGANISM: Artificial Sequence
<220> FEATURE:
<223> OTHER INFORMATION: Description of Artificial Sequence: Synthetic
      BLV1H12-Somatostatin fusion polypeptide

<400> SEQUENCE: 40

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

```
Gly Ser Ile Asp Thr Gly Gly Asn Thr Gly Tyr Asn Pro Gly Leu Lys
        50                  55                  60

Ser Arg Leu Ser Ile Thr Lys Asp Asn Ser Lys Ser Gln Val Ser Leu
 65                  70                  75                  80

Ser Val Ser Ser Val Thr Thr Glu Asp Ser Ala Thr Tyr Tyr Cys Thr
                85                  90                  95

Ser Val His Gln Glu Thr Lys Lys Tyr Gln Ser Ala Gly Cys Lys Asn
            100                 105                 110

Phe Phe Trp Lys Thr Phe Thr Ser Cys Gly Ser Tyr Thr Tyr Asn Tyr
        115                 120                 125

Glu Trp His Val Asp Val Trp Gly Gln Gly Leu Leu Val Thr Val
    130                 135                 140

<210> SEQ ID NO 41
<211> LENGTH: 162
<212> TYPE: PRT
<213> ORGANISM: Artificial Sequence
<220> FEATURE:
<223> OTHER INFORMATION: Description of Artificial Sequence: Synthetic
      BLV1H12-Chlorotoxin fusion polypeptide

<400> SEQUENCE: 41

Gln Val Gln Leu Arg Glu Ser Gly Pro Ser Leu Val Lys Pro Ser Gln
 1               5                   10                  15

Thr Leu Ser Leu Thr Cys Thr Ala Ser Gly Phe Ser Leu Ser Asp Lys
                20                  25                  30

Ala Val Gly Trp Val Arg Gln Ala Pro Gly Lys Ala Leu Glu Trp Leu
            35                  40                  45

Gly Ser Ile Asp Thr Gly Gly Asn Thr Gly Tyr Asn Pro Gly Leu Lys
        50                  55                  60

Ser Arg Leu Ser Ile Thr Lys Asp Asn Ser Lys Ser Gln Val Ser Leu
 65                  70                  75                  80

Ser Val Ser Ser Val Thr Thr Glu Asp Ser Ala Thr Tyr Tyr Cys Thr
                85                  90                  95

Ser Val His Gln Glu Thr Lys Lys Tyr Gln Ser Met Cys Met Pro Cys
            100                 105                 110

Phe Thr Thr Asp His Gln Met Ala Arg Lys Cys Asp Asp Cys Cys Gly
        115                 120                 125

Gly Lys Gly Arg Gly Lys Cys Tyr Gly Pro Gln Cys Leu Ser Tyr Thr
    130                 135                 140

Tyr Asn Tyr Glu Trp His Val Asp Val Trp Gly Gln Gly Leu Leu Val
145                 150                 155                 160

Thr Val

<210> SEQ ID NO 42
<211> LENGTH: 199
<212> TYPE: PRT
<213> ORGANISM: Artificial Sequence
<220> FEATURE:
<223> OTHER INFORMATION: Description of Artificial Sequence: Synthetic
      BLV1H12-SDF1(alpha) fusion polypeptide

<400> SEQUENCE: 42

Gln Val Gln Leu Arg Glu Ser Gly Pro Ser Leu Val Lys Pro Ser Gln
 1               5                   10                  15

Thr Leu Ser Leu Thr Cys Thr Ala Ser Gly Phe Ser Leu Ser Asp Lys
                20                  25                  30
```

Ala Val Gly Trp Val Arg Gln Ala Pro Gly Lys Ala Leu Glu Trp Leu
           35                  40                  45

Gly Ser Ile Asp Thr Gly Gly Asn Thr Gly Tyr Asn Pro Gly Leu Lys
 50                  55                  60

Ser Arg Leu Ser Ile Thr Lys Asp Asn Ser Lys Ser Gln Val Ser Leu
65                   70                  75                  80

Ser Val Ser Ser Val Thr Thr Glu Asp Ser Ala Thr Tyr Tyr Cys Thr
                 85                  90                  95

Ser Val His Gln Glu Thr Lys Lys Tyr Gln Ser Lys Pro Val Ser Leu
            100                 105                 110

Ser Tyr Arg Cys Pro Cys Arg Phe Phe Glu Ser His Val Ala Arg Ala
            115                 120                 125

Asn Val Lys His Leu Lys Ile Leu Asn Thr Pro Asn Cys Ala Leu Gln
130                 135                 140

Ile Val Ala Arg Leu Lys Asn Asn Asn Arg Gln Val Cys Ile Asp Pro
145                 150                 155                 160

Lys Leu Lys Trp Ile Gln Glu Tyr Leu Glu Lys Ala Leu Asn Lys Gly
                165                 170                 175

Ser Gly Ser Tyr Thr Tyr Asn Tyr Glu Trp His Val Asp Val Trp Gly
            180                 185                 190

Gln Gly Leu Leu Val Thr Val
            195

<210> SEQ ID NO 43
<211> LENGTH: 261
<212> TYPE: PRT
<213> ORGANISM: Artificial Sequence
<220> FEATURE:
<223> OTHER INFORMATION: Description of Artificial Sequence: Synthetic
      BLV1H12-IL21 fusion polypeptide

<400> SEQUENCE: 43

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
           35                  40                  45

Gly Ser Ile Asp Thr Gly Gly Asn Thr Gly Tyr Asn Pro Gly Leu Lys
 50                  55                  60

Ser Arg Leu Ser Ile Thr Lys Asp Asn Ser Lys Ser Gln Val Ser Leu
65                   70                  75                  80

Ser Val Ser Ser Val Thr Thr Glu Asp Ser Ala Thr Tyr Tyr Cys Thr
                 85                  90                  95

Ser Val His Gln Glu Thr Lys Lys Tyr Gln Ser Gln Gly Gln Asp Arg
            100                 105                 110

His Met Ile Arg Met Arg Gln Leu Ile Asp Ile Val Asp Gln Leu Lys
            115                 120                 125

Asn Tyr Val Asn Asp Leu Val Pro Glu Phe Leu Pro Ala Pro Glu Asp
130                 135                 140

Val Glu Thr Asn Cys Glu Trp Ser Ala Phe Ser Cys Phe Gln Lys Ala
145                 150                 155                 160

Gln Leu Lys Ser Ala Asn Thr Gly Asn Asn Glu Arg Ile Ile Asn Val
                165                 170                 175

Ser Ile Lys Lys Leu Lys Arg Lys Pro Pro Ser Thr Asn Ala Gly Arg
            180                 185                 190

```
Arg Gln Lys His Arg Leu Thr Cys Pro Ser Cys Asp Ser Tyr Glu Lys
        195                 200                 205

Lys Pro Pro Lys Glu Phe Leu Glu Arg Phe Lys Ser Leu Leu Gln Lys
    210                 215                 220

Met Ile His Gln His Leu Ser Ser Arg Thr His Gly Ser Glu Asp Ser
225                 230                 235                 240

Ser Tyr Thr Tyr Asn Tyr Glu Trp His Val Asp Val Trp Gly Gln Gly
            245                 250                 255

Leu Leu Val Thr Val
            260

<210> SEQ ID NO 44
<211> LENGTH: 158
<212> TYPE: PRT
<213> ORGANISM: Artificial Sequence
<220> FEATURE:
<223> OTHER INFORMATION: Description of Artificial Sequence: Synthetic
      BLV1H12-ProTxII fusion polypeptide

<400> SEQUENCE: 44

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Thr Gly Tyr Asn Pro Gly Leu Lys
    50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
                85                  90                  95

Ser Val His Gln Glu Thr Lys Lys Tyr Gln Ser Tyr Cys Gln Lys Trp
            100                 105                 110

Met Trp Thr Cys Asp Ser Glu Arg Lys Cys Cys Glu Gly Met Val Cys
        115                 120                 125

Arg Leu Trp Cys Lys Lys Leu Trp Ser Tyr Thr Tyr Asn Tyr Glu
    130                 135                 140

Trp His Val Asp Val Trp Gly Gln Gly Leu Leu Val Thr Val
145                 150                 155

<210> SEQ ID NO 45
<211> LENGTH: 34
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(17)
<223> OTHER INFORMATION: Any amino acid
<220> FEATURE:
<221> NAME/KEY: MOD_RES
<222> LOCATION: (19)..(23)
<223> OTHER INFORMATION: Any amino acid
<220> FEATURE:
<221> NAME/KEY: MOD_RES
```

<222> LOCATION: (25)..(25)
<223> OTHER INFORMATION: Any amino acid
<220> FEATURE:
<221> NAME/KEY: MOD_RES
<222> LOCATION: (27)..(33)
<223> OTHER INFORMATION: Any amino acid

<400> SEQUENCE: 45

Cys Xaa Xaa Xaa Xaa Xaa Xaa Xaa Xaa Xaa Cys Xaa Xaa Xaa Xaa
1               5                   10                  15

Xaa Cys Xaa Xaa Xaa Xaa Xaa Cys Xaa Cys Xaa Xaa Xaa Xaa Xaa
            20                  25                  30

Xaa Cys

<210> SEQ ID NO 46
<211> LENGTH: 43
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(42)
<223> OTHER INFORMATION: Any amino acid

<400> SEQUENCE: 46

Cys Xaa Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Cys Xaa Xaa Xaa Xaa Xaa
            20                  25                  30

Xaa Xaa Xaa Xaa Xaa Xaa Xaa Xaa Xaa Xaa Cys
            35                  40

<210> SEQ ID NO 47
<211> LENGTH: 21
<212> TYPE: PRT
<213> ORGANISM: Artificial Sequence
<220> FEATURE:
<223> OTHER INFORMATION: Description of Artificial Sequence: Synthetic
      Cysteine motif peptide
<220> FEATURE:
<221> NAME/KEY: MOD_RES
<222> LOCATION: (2)..(12)
<223> OTHER INFORMATION: Any amino acid
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (16)..(20)
<223> OTHER INFORMATION: Any amino acid

<400> SEQUENCE: 47

```
Cys Xaa Xaa Xaa Xaa Xaa Xaa Xaa Xaa Xaa Xaa Cys Xaa Cys Xaa
1               5                   10                  15

Xaa Xaa Xaa Xaa Cys
            20
```

<210> SEQ ID NO 48
<211> LENGTH: 35
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(12)
<223> OTHER INFORMATION: Any amino acid
<220> FEATURE:
<221> NAME/KEY: MOD_RES
<222> LOCATION: (14)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(34)
<223> OTHER INFORMATION: Any amino acid

<400> SEQUENCE: 48

```
Cys Xaa Xaa Xaa Xaa Xaa Xaa Xaa Xaa Xaa Xaa Xaa Cys Xaa Xaa
1               5                   10                  15

Xaa Xaa Cys Xaa Xaa Xaa Xaa Xaa Cys Xaa Cys Xaa Xaa Xaa Xaa
            20                  25                  30

Xaa Xaa Cys
        35
```

<210> SEQ ID NO 49
<211> LENGTH: 41
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(40)
<223> OTHER INFORMATION: Any amino acid

<400> SEQUENCE: 49

```
Cys Xaa Xaa Xaa Xaa Xaa Xaa Xaa Xaa Xaa Xaa Cys Xaa Xaa Xaa Xaa
```

```
                1               5                  10                  15
Xaa Xaa Cys Xaa Xaa Xaa Xaa Cys Xaa Cys Xaa Xaa Xaa Xaa Xaa
            20                  25                  30
Xaa Xaa Xaa Xaa Xaa Xaa Xaa Xaa Cys
            35                  40

<210> SEQ ID NO 50
<211> LENGTH: 34
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(17)
<223> OTHER INFORMATION: Any amino acid
<220> FEATURE:
<221> NAME/KEY: MOD_RES
<222> LOCATION: (19)..(19)
<223> OTHER INFORMATION: Any amino acid
<220> FEATURE:
<221> NAME/KEY: MOD_RES
<222> LOCATION: (21)..(24)
<223> OTHER INFORMATION: Any amino acid
<220> FEATURE:
<221> NAME/KEY: MOD_RES
<222> LOCATION: (26)..(33)
<223> OTHER INFORMATION: Any amino acid

<400> SEQUENCE: 50

Cys Xaa Xaa Xaa Xaa Xaa Xaa Xaa Xaa Xaa Xaa Cys Xaa Xaa Xaa Xaa
1               5                  10                  15
Xaa Cys Xaa Cys Xaa Xaa Xaa Xaa Cys Xaa Xaa Xaa Xaa Xaa Xaa Xaa
            20                  25                  30
Xaa Cys

<210> SEQ ID NO 51
<211> LENGTH: 36
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(25)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (29)..(35)
<223> OTHER INFORMATION: Any amino acid

<400> SEQUENCE: 51

Cys Xaa Xaa Xaa Xaa Xaa Xaa Xaa Xaa Xaa Xaa Cys Xaa Xaa Xaa Xaa
```

```
                1               5                   10                  15
Xaa Xaa Cys Xaa Xaa Xaa Xaa Xaa Cys Xaa Cys Xaa Xaa Xaa Xaa
                        20                  25                  30
Xaa Xaa Xaa Cys
        35
```

<210> SEQ ID NO 52
<211> LENGTH: 36
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(35)
<223> OTHER INFORMATION: Any amino acid

<400> SEQUENCE: 52

```
Cys Xaa Xaa Xaa Xaa Xaa Xaa Xaa Xaa Xaa Cys Xaa Xaa Xaa Xaa
1               5                   10                  15
Cys Xaa Xaa Xaa Xaa Xaa Xaa Xaa Cys Xaa Cys Xaa Xaa Xaa Xaa
                        20                  25                  30
Xaa Xaa Xaa Cys
        35
```

<210> SEQ ID NO 53
<211> LENGTH: 35
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(34)
<223> OTHER INFORMATION: Any amino acid

<400> SEQUENCE: 53

```
Cys Xaa Xaa Xaa Xaa Xaa Xaa Xaa Xaa Cys Xaa Xaa Xaa Xaa
1               5                   10                  15

Cys Xaa Xaa Xaa Xaa Xaa Xaa Xaa Cys Xaa Cys Xaa Xaa Xaa Xaa
            20                  25              30

Xaa Xaa Cys
        35

<210> SEQ ID NO 54
<211> LENGTH: 33
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(14)
<223> OTHER INFORMATION: Any amino acid
<220> FEATURE:
<221> NAME/KEY: MOD_RES
<222> LOCATION: (16)..(23)
<223> OTHER INFORMATION: Any amino acid
<220> FEATURE:
<221> NAME/KEY: MOD_RES
<222> LOCATION: (25)..(32)
<223> OTHER INFORMATION: Any amino acid

<400> SEQUENCE: 54

Cys Xaa Xaa Xaa Xaa Xaa Xaa Xaa Xaa Xaa Xaa Xaa Xaa Cys Xaa
1               5                   10                  15

Xaa Xaa Xaa Xaa Xaa Xaa Xaa Cys Xaa Xaa Xaa Xaa Xaa Xaa Xaa
            20                  25                  30

Cys

<210> SEQ ID NO 55
<211> LENGTH: 35
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(34)
<223> OTHER INFORMATION: Any amino acid

<400> SEQUENCE: 55

Cys Xaa Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Cys Xaa Xaa Xaa Xaa Xaa
            20                  25                  30

Xaa Xaa Cys
        35
```

```
<210> SEQ ID NO 56
<211> LENGTH: 24
<212> TYPE: PRT
<213> ORGANISM: Artificial Sequence
<220> FEATURE:
<223> OTHER INFORMATION: Description of Artificial Sequence: Synthetic
      Cysteine motif peptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(17)
<223> OTHER INFORMATION: Any amino acid
<220> FEATURE:
<221> NAME/KEY: MOD_RES
<222> LOCATION: (19)..(23)
<223> OTHER INFORMATION: Any amino acid

<400> SEQUENCE: 56

Cys Xaa Xaa Xaa Xaa Xaa Xaa Xaa Xaa Xaa Xaa Cys Xaa Xaa Xaa Xaa
1               5                   10                  15

Xaa Cys Xaa Xaa Xaa Xaa Xaa Cys
            20

<210> SEQ ID NO 57
<211> LENGTH: 35
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(17)
<223> OTHER INFORMATION: Any amino acid
<220> FEATURE:
<221> NAME/KEY: MOD_RES
<222> LOCATION: (19)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(34)
<223> OTHER INFORMATION: Any amino acid

<400> SEQUENCE: 57

Cys Xaa Xaa Xaa Xaa Xaa Xaa Xaa Xaa Xaa Xaa Cys Xaa Xaa Xaa Xaa
1               5                   10                  15

Xaa Cys Xaa Xaa Xaa Xaa Xaa Cys Xaa Cys Xaa Xaa Xaa Xaa Xaa Xaa
            20                  25                  30

Xaa Xaa Cys
        35

<210> SEQ ID NO 58
<211> LENGTH: 43
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
```

```
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(32)
<223> OTHER INFORMATION: Any amino acid
<220> FEATURE:
<221> NAME/KEY: MOD_RES
<222> LOCATION: (34)..(42)
<223> OTHER INFORMATION: Any amino acid

<400> SEQUENCE: 58

Cys Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Xaa Xaa Xaa Xaa Xaa
            20                  25                  30

Cys Xaa Xaa Xaa Xaa Xaa Xaa Xaa Xaa Xaa Cys
        35                  40

<210> SEQ ID NO 59
<211> LENGTH: 35
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(10)
<223> OTHER INFORMATION: Any amino acid
<220> FEATURE:
<221> NAME/KEY: MOD_RES
<222> LOCATION: (12)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(34)
<223> OTHER INFORMATION: Any amino acid

<400> SEQUENCE: 59

Cys Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Cys Xaa Xaa Xaa Xaa
            20                  25                  30

Xaa Xaa Cys
        35

<210> SEQ ID NO 60
<211> LENGTH: 37
<212> TYPE: PRT
<213> ORGANISM: Artificial Sequence
<220> FEATURE:
<223> OTHER INFORMATION: Description of Artificial Sequence: Synthetic
      Cysteine motif polypeptide
```

```
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(36)
<223> OTHER INFORMATION: Any amino acid

<400> SEQUENCE: 60

Cys Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Cys Xaa Xaa Xaa Xaa
            20                  25                  30

Xaa Xaa Xaa Xaa Cys
        35

<210> SEQ ID NO 61
<211> LENGTH: 37
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (15)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(36)
<223> OTHER INFORMATION: Any amino acid

<400> SEQUENCE: 61

Cys Xaa Xaa Xaa Xaa Xaa Xaa Xaa Xaa Xaa Xaa Cys Xaa Cys Xaa Xaa
1               5                   10                  15

Xaa Xaa Cys Xaa Xaa Xaa Xaa Xaa Cys Xaa Xaa Xaa Xaa Xaa Xaa
            20                  25                  30

Xaa Xaa Xaa Xaa Cys
        35

<210> SEQ ID NO 62
<211> LENGTH: 45
<212> TYPE: PRT
<213> ORGANISM: Artificial Sequence
<220> FEATURE:
<223> OTHER INFORMATION: Description of Artificial Sequence: Synthetic
```

```
        Cysteine motif polypeptide
<220> FEATURE:
<221> NAME/KEY: MOD_RES
<222> LOCATION: (2)..(8)
<223> OTHER INFORMATION: Any amino acid
<220> FEATURE:
<221> NAME/KEY: MOD_RES
<222> LOCATION: (10)..(12)
<223> OTHER INFORMATION: Any amino acid
<220> FEATURE:
<221> NAME/KEY: MOD_RES
<222> LOCATION: (14)..(19)
<223> OTHER INFORMATION: Any amino acid
<220> FEATURE:
<221> NAME/KEY: MOD_RES
<222> LOCATION: (21)..(25)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (29)..(33)
<223> OTHER INFORMATION: Any amino acid
<220> FEATURE:
<221> NAME/KEY: MOD_RES
<222> LOCATION: (35)..(44)
<223> OTHER INFORMATION: Any amino acid

<400> SEQUENCE: 62

Cys Xaa Xaa Xaa Xaa Xaa Xaa Xaa Cys Xaa Xaa Xaa Cys Xaa Xaa Xaa
1               5                   10                  15

Xaa Xaa Xaa Cys Xaa Xaa Xaa Xaa Xaa Cys Xaa Cys Xaa Xaa Xaa Xaa
            20                  25                  30

Xaa Cys Xaa Xaa Xaa Xaa Xaa Xaa Xaa Xaa Xaa Xaa Cys
        35                  40                  45

<210> SEQ ID NO 63
<211> LENGTH: 34
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (15)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(29)
<223> OTHER INFORMATION: Any amino acid
<220> FEATURE:
<221> NAME/KEY: MOD_RES
<222> LOCATION: (31)..(33)
<223> OTHER INFORMATION: Any amino acid

<400> SEQUENCE: 63
```

Cys Xaa Xaa Xaa Xaa Xaa Xaa Xaa Xaa Xaa Cys Xaa Cys Xaa Xaa
1               5                   10                  15

Xaa Xaa Cys Xaa Xaa Xaa Xaa Cys Xaa Cys Xaa Xaa Cys Xaa Xaa
            20                  25                  30

Xaa Cys

<210> SEQ ID NO 64
<211> LENGTH: 26
<212> TYPE: PRT
<213> ORGANISM: Artificial Sequence
<220> FEATURE:
<223> OTHER INFORMATION: Description of Artificial Sequence: Synthetic
      Cysteine motif peptide
<220> FEATURE:
<221> NAME/KEY: MOD_RES
<222> LOCATION: (2)..(17)
<223> OTHER INFORMATION: Any amino acid
<220> FEATURE:
<221> NAME/KEY: MOD_RES
<222> LOCATION: (19)..(23)
<223> OTHER INFORMATION: Any amino acid
<220> FEATURE:
<221> NAME/KEY: MOD_RES
<222> LOCATION: (25)..(25)
<223> OTHER INFORMATION: Any amino acid

<400> SEQUENCE: 64

Cys Xaa Xaa Xaa Xaa Xaa Xaa Xaa Xaa Xaa Xaa Xaa Xaa Xaa Xaa
1               5                   10                  15

Xaa Cys Xaa Xaa Xaa Xaa Xaa Cys Xaa Cys
            20                  25

<210> SEQ ID NO 65
<211> LENGTH: 26
<212> TYPE: PRT
<213> ORGANISM: Artificial Sequence
<220> FEATURE:
<223> OTHER INFORMATION: Description of Artificial Sequence: Synthetic
      Cysteine motif peptide
<220> FEATURE:
<221> NAME/KEY: MOD_RES
<222> LOCATION: (2)..(7)
<223> OTHER INFORMATION: Any amino acid
<220> FEATURE:
<221> NAME/KEY: MOD_RES
<222> LOCATION: (9)..(12)
<223> OTHER INFORMATION: Any amino acid
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (16)..(19)
<223> OTHER INFORMATION: Any amino acid
<220> FEATURE:
<221> NAME/KEY: MOD_RES
<222> LOCATION: (21)..(25)
<223> OTHER INFORMATION: Any amino acid

<400> SEQUENCE: 65

Cys Xaa Xaa Xaa Xaa Xaa Xaa Cys Xaa Xaa Xaa Xaa Cys Xaa Cys Xaa
1               5                   10                  15

Xaa Xaa Xaa Cys Xaa Xaa Xaa Xaa Xaa Cys
            20                  25

<210> SEQ ID NO 66
<211> LENGTH: 35
<212> TYPE: PRT

```
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(12)
<223> OTHER INFORMATION: Any amino acid
<220> FEATURE:
<221> NAME/KEY: MOD_RES
<222> LOCATION: (14)..(17)
<223> OTHER INFORMATION: Any amino acid
<220> FEATURE:
<221> NAME/KEY: MOD_RES
<222> LOCATION: (19)..(23)
<223> OTHER INFORMATION: Any amino acid
<220> FEATURE:
<221> NAME/KEY: MOD_RES
<222> LOCATION: (25)..(30)
<223> OTHER INFORMATION: Any amino acid
<220> FEATURE:
<221> NAME/KEY: MOD_RES
<222> LOCATION: (32)..(34)
<223> OTHER INFORMATION: Any amino acid

<400> SEQUENCE: 66

Cys Xaa Xaa Xaa Xaa Xaa Xaa Xaa Xaa Xaa Xaa Cys Xaa Xaa Xaa
1               5                   10                  15

Xaa Cys Xaa Xaa Xaa Xaa Xaa Cys Xaa Xaa Xaa Xaa Xaa Xaa Cys Xaa
            20                  25                  30

Xaa Xaa Cys
        35

<210> SEQ ID NO 67
<211> LENGTH: 26
<212> TYPE: PRT
<213> ORGANISM: Artificial Sequence
<220> FEATURE:
<223> OTHER INFORMATION: Description of Artificial Sequence: Synthetic
      Cysteine motif peptide
<220> FEATURE:
<221> NAME/KEY: MOD_RES
<222> LOCATION: (2)..(9)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (14)..(19)
<223> OTHER INFORMATION: Any amino acid
<220> FEATURE:
<221> NAME/KEY: MOD_RES
<222> LOCATION: (21)..(25)
<223> OTHER INFORMATION: Any amino acid

<400> SEQUENCE: 67

Cys Xaa Xaa Xaa Xaa Xaa Xaa Xaa Xaa Cys Xaa Xaa Cys Xaa Xaa Xaa
1               5                   10                  15

Xaa Xaa Xaa Cys Xaa Xaa Xaa Xaa Xaa Cys
            20                  25

<210> SEQ ID NO 68
<211> LENGTH: 37
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
```

```
<222> LOCATION: (2)..(11)
<223> OTHER INFORMATION: Any amino acid
<220> FEATURE:
<221> NAME/KEY: MOD_RES
<222> LOCATION: (13)..(17)
<223> OTHER INFORMATION: Any amino acid
<220> FEATURE:
<221> NAME/KEY: MOD_RES
<222> LOCATION: (19)..(23)
<223> OTHER INFORMATION: Any amino acid
<220> FEATURE:
<221> NAME/KEY: MOD_RES
<222> LOCATION: (25)..(25)
<223> OTHER INFORMATION: Any amino acid
<220> FEATURE:
<221> NAME/KEY: MOD_RES
<222> LOCATION: (27)..(36)
<223> OTHER INFORMATION: Any amino acid

<400> SEQUENCE: 68

Cys Xaa Xaa Xaa Xaa Xaa Xaa Xaa Xaa Xaa Xaa Cys Xaa Xaa Xaa Xaa
1               5                   10                  15

Xaa Cys Xaa Xaa Xaa Xaa Xaa Cys Xaa Cys Xaa Xaa Xaa Xaa Xaa Xaa
            20                  25                  30

Xaa Xaa Xaa Xaa Cys
        35

<210> SEQ ID NO 69
<211> LENGTH: 28
<212> TYPE: PRT
<213> ORGANISM: Artificial Sequence
<220> FEATURE:
<223> OTHER INFORMATION: Description of Artificial Sequence: Synthetic
      Cysteine motif peptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (15)..(20)
<223> OTHER INFORMATION: Any amino acid
<220> FEATURE:
<221> NAME/KEY: MOD_RES
<222> LOCATION: (22)..(25)
<223> OTHER INFORMATION: Any amino acid
<220> FEATURE:
<221> NAME/KEY: MOD_RES
<222> LOCATION: (27)..(27)
<223> OTHER INFORMATION: Any amino acid

<400> SEQUENCE: 69

Cys Xaa Xaa Xaa Xaa Xaa Xaa Xaa Xaa Xaa Xaa Cys Xaa Cys Xaa Xaa
1               5                   10                  15

Xaa Xaa Xaa Xaa Cys Xaa Xaa Xaa Xaa Cys Xaa Cys
            20                  25

<210> SEQ ID NO 70
<211> LENGTH: 29
<212> TYPE: PRT
<213> ORGANISM: Artificial Sequence
<220> FEATURE:
<223> OTHER INFORMATION: Description of Artificial Sequence: Synthetic
      Cysteine motif peptide
<220> FEATURE:
<221> NAME/KEY: MOD_RES
<222> LOCATION: (2)..(11)
<223> OTHER INFORMATION: Any amino acid
```

<220> FEATURE:
<221> NAME/KEY: MOD_RES
<222> LOCATION: (13)..(17)
<223> OTHER INFORMATION: Any amino acid
<220> FEATURE:
<221> NAME/KEY: MOD_RES
<222> LOCATION: (19)..(23)
<223> OTHER INFORMATION: Any amino acid
<220> FEATURE:
<221> NAME/KEY: MOD_RES
<222> LOCATION: (25)..(25)
<223> OTHER INFORMATION: Any amino acid
<220> FEATURE:
<221> NAME/KEY: MOD_RES
<222> LOCATION: (27)..(28)
<223> OTHER INFORMATION: Any amino acid

<400> SEQUENCE: 70

Cys Xaa Xaa Xaa Xaa Xaa Xaa Xaa Xaa Xaa Cys Xaa Xaa Xaa Xaa
1               5                   10                  15

Xaa Cys Xaa Xaa Xaa Xaa Xaa Cys Xaa Cys Xaa Xaa Cys
            20                  25

<210> SEQ ID NO 71
<211> LENGTH: 27
<212> TYPE: PRT
<213> ORGANISM: Artificial Sequence
<220> FEATURE:
<223> OTHER INFORMATION: Description of Artificial Sequence: Synthetic
      Cysteine motif peptide
<220> FEATURE:
<221> NAME/KEY: MOD_RES
<222> LOCATION: (2)..(15)
<223> OTHER INFORMATION: Any amino acid
<220> FEATURE:
<221> NAME/KEY: MOD_RES
<222> LOCATION: (17)..(18)
<223> OTHER INFORMATION: Any amino acid
<220> FEATURE:
<221> NAME/KEY: MOD_RES
<222> LOCATION: (20)..(22)
<223> OTHER INFORMATION: Any amino acid
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid

<400> SEQUENCE: 71

Cys Xaa Xaa Xaa Xaa Xaa Xaa Xaa Xaa Xaa Xaa Xaa Xaa Xaa Xaa Cys
1               5                   10                  15

Xaa Xaa Cys Xaa Xaa Xaa Cys Xaa Cys Xaa Cys
            20                  25

<210> SEQ ID NO 72
<211> LENGTH: 25
<212> TYPE: PRT
<213> ORGANISM: Artificial Sequence
<220> FEATURE:
<223> OTHER INFORMATION: Description of Artificial Sequence: Synthetic
      Cysteine motif peptide
<220> FEATURE:
<221> NAME/KEY: MOD_RES
<222> LOCATION: (2)..(16)
<223> OTHER INFORMATION: Any amino acid
<220> FEATURE:
<221> NAME/KEY: MOD_RES
<222> LOCATION: (18)..(22)
<223> OTHER INFORMATION: Any amino acid
<220> FEATURE:

```
<221> NAME/KEY: MOD_RES
<222> LOCATION: (24)..(24)
<223> OTHER INFORMATION: Any amino acid

<400> SEQUENCE: 72

Cys Xaa Xaa Xaa Xaa Xaa Xaa Xaa Xaa Xaa Xaa Xaa Xaa Xaa Xaa
1               5                   10                  15

Cys Xaa Xaa Xaa Xaa Xaa Cys Xaa Cys
            20                  25

<210> SEQ ID NO 73
<211> LENGTH: 38
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(5)
<223> OTHER INFORMATION: Any amino acid
<220> FEATURE:
<221> NAME/KEY: MOD_RES
<222> LOCATION: (7)..(12)
<223> OTHER INFORMATION: Any amino acid
<220> FEATURE:
<221> NAME/KEY: MOD_RES
<222> LOCATION: (14)..(22)
<223> OTHER INFORMATION: Any amino acid
<220> FEATURE:
<221> NAME/KEY: MOD_RES
<222> LOCATION: (24)..(25)
<223> OTHER INFORMATION: Any amino acid
<220> FEATURE:
<221> NAME/KEY: MOD_RES
<222> LOCATION: (27)..(37)
<223> OTHER INFORMATION: Any amino acid

<400> SEQUENCE: 73

Cys Xaa Xaa Xaa Xaa Cys Xaa Xaa Xaa Xaa Xaa Xaa Cys Xaa Xaa
1               5                   10                  15

Xaa Xaa Xaa Xaa Xaa Xaa Cys Xaa Xaa Cys Xaa Xaa Xaa Xaa Xaa
            20                  25                  30

Xaa Xaa Xaa Xaa Xaa Cys
        35

<210> SEQ ID NO 74
<211> LENGTH: 38
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(7)
<223> OTHER INFORMATION: Any amino acid
<220> FEATURE:
<221> NAME/KEY: MOD_RES
<222> LOCATION: (9)..(12)
<223> OTHER INFORMATION: Any amino acid
<220> FEATURE:
<221> NAME/KEY: MOD_RES
<222> LOCATION: (14)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(37)
```

```
<223> OTHER INFORMATION: Any amino acid

<400> SEQUENCE: 74

Cys Xaa Xaa Xaa Xaa Xaa Xaa Cys Xaa Xaa Xaa Xaa Cys Xaa Xaa Xaa
1               5                   10                  15

Xaa Xaa Cys Xaa Xaa Xaa Xaa Xaa Cys Xaa Xaa Xaa Xaa Xaa Xaa Xaa
                20                  25                  30

Xaa Xaa Xaa Xaa Xaa Cys
        35

<210> SEQ ID NO 75
<211> LENGTH: 38
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(8)
<223> OTHER INFORMATION: Any amino acid
<220> FEATURE:
<221> NAME/KEY: MOD_RES
<222> LOCATION: (10)..(12)
<223> OTHER INFORMATION: Any amino acid
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (18)..(21)
<223> OTHER INFORMATION: Any amino acid
<220> FEATURE:
<221> NAME/KEY: MOD_RES
<222> LOCATION: (23)..(27)
<223> OTHER INFORMATION: Any amino acid
<220> FEATURE:
<221> NAME/KEY: MOD_RES
<222> LOCATION: (29)..(37)
<223> OTHER INFORMATION: Any amino acid

<400> SEQUENCE: 75

Cys Xaa Xaa Xaa Xaa Xaa Xaa Xaa Cys Xaa Xaa Xaa Cys Xaa Cys Xaa
1               5                   10                  15

Cys Xaa Xaa Xaa Xaa Cys Xaa Xaa Xaa Xaa Xaa Cys Xaa Xaa Xaa Xaa
                20                  25                  30

Xaa Xaa Xaa Xaa Xaa Cys
        35

<210> SEQ ID NO 76
<211> LENGTH: 25
<212> TYPE: PRT
<213> ORGANISM: Artificial Sequence
<220> FEATURE:
<223> OTHER INFORMATION: Description of Artificial Sequence: Synthetic
      Cysteine motif peptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
```

<222> LOCATION: (20)..(24)
<223> OTHER INFORMATION: Any amino acid

<400> SEQUENCE: 76

Cys Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys
            20                  25

<210> SEQ ID NO 77
<211> LENGTH: 35
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(8)
<223> OTHER INFORMATION: Any amino acid
<220> FEATURE:
<221> NAME/KEY: MOD_RES
<222> LOCATION: (10)..(12)
<223> OTHER INFORMATION: Any amino acid
<220> FEATURE:
<221> NAME/KEY: MOD_RES
<222> LOCATION: (14)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(34)
<223> OTHER INFORMATION: Any amino acid

<400> SEQUENCE: 77

Cys Xaa Xaa Xaa Xaa Xaa Xaa Xaa Cys Xaa Xaa Xaa Cys Xaa Xaa
1               5                   10                  15

Xaa Xaa Cys Xaa Xaa Xaa Xaa Xaa Cys Xaa Xaa Xaa Xaa Xaa Xaa
            20                  25                  30

Xaa Xaa Cys
        35

<210> SEQ ID NO 78
<211> LENGTH: 20
<212> TYPE: PRT
<213> ORGANISM: Artificial Sequence
<220> FEATURE:
<223> OTHER INFORMATION: Description of Artificial Sequence: Synthetic
      Cysteine motif peptide
<220> FEATURE:
<221> NAME/KEY: MOD_RES
<222> LOCATION: (2)..(8)
<223> OTHER INFORMATION: Any amino acid
<220> FEATURE:
<221> NAME/KEY: MOD_RES
<222> LOCATION: (10)..(14)
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (18)..(19)
<223> OTHER INFORMATION: Any amino acid

<400> SEQUENCE: 78

Cys Xaa Xaa Xaa Xaa Xaa Xaa Xaa Cys Xaa Xaa Xaa Xaa Xaa Cys Xaa

Cys Xaa Xaa Cys
            20

<210> SEQ ID NO 79
<211> LENGTH: 21
<212> TYPE: PRT
<213> ORGANISM: Artificial Sequence
<220> FEATURE:
<223> OTHER INFORMATION: Description of Artificial Sequence: Synthetic
      Cysteine motif peptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (15)..(20)
<223> OTHER INFORMATION: Any amino acid

<400> SEQUENCE: 79

Cys Xaa Xaa Xaa Xaa Xaa Xaa Xaa Xaa Xaa Xaa Cys Xaa Cys Xaa Xaa
1               5                   10                  15

Xaa Xaa Xaa Xaa Cys
            20

<210> SEQ ID NO 80
<211> LENGTH: 43
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(15)
<223> OTHER INFORMATION: Any amino acid
<220> FEATURE:
<221> NAME/KEY: MOD_RES
<222> LOCATION: (17)..(19)
<223> OTHER INFORMATION: Any amino acid
<220> FEATURE:
<221> NAME/KEY: MOD_RES
<222> LOCATION: (21)..(25)
<223> OTHER INFORMATION: Any amino acid
<220> FEATURE:
<221> NAME/KEY: MOD_RES
<222> LOCATION: (27)..(33)
<223> OTHER INFORMATION: Any amino acid
<220> FEATURE:
<221> NAME/KEY: MOD_RES
<222> LOCATION: (35)..(35)
<223> OTHER INFORMATION: Any amino acid
<220> FEATURE:
<221> NAME/KEY: MOD_RES
<222> LOCATION: (37)..(42)
<223> OTHER INFORMATION: Any amino acid

<400> SEQUENCE: 80

Cys Xaa Xaa Xaa Xaa Xaa Xaa Xaa Xaa Xaa Xaa Cys Xaa Xaa Xaa Cys
1               5                   10                  15

Xaa Xaa Xaa Cys Xaa Xaa Xaa Xaa Xaa Cys Xaa Xaa Xaa Xaa Xaa Xaa
            20                  25                  30

Xaa Cys Xaa Cys Xaa Xaa Xaa Xaa Xaa Xaa Cys
         35                  40

<210> SEQ ID NO 81
<211> LENGTH: 39
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(22)
<223> OTHER INFORMATION: Any amino acid
<220> FEATURE:
<221> NAME/KEY: MOD_RES
<222> LOCATION: (24)..(35)
<223> OTHER INFORMATION: Any amino acid
<220> FEATURE:
<221> NAME/KEY: MOD_RES
<222> LOCATION: (37)..(38)
<223> OTHER INFORMATION: Any amino acid

<400> SEQUENCE: 81

Cys Xaa Xaa Xaa Xaa Xaa Xaa Xaa Xaa Xaa Xaa Cys Xaa Xaa Xaa Xaa
1               5                   10                  15

Cys Xaa Xaa Xaa Xaa Cys Xaa Xaa Xaa Xaa Xaa Xaa Xaa Xaa Xaa Xaa
            20                  25                  30

Xaa Xaa Xaa Cys Xaa Xaa Cys
        35

<210> SEQ ID NO 82
<211> LENGTH: 43
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(13)
<223> OTHER INFORMATION: Any amino acid
<220> FEATURE:
<221> NAME/KEY: MOD_RES
<222> LOCATION: (15)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(28)
<223> OTHER INFORMATION: Any amino acid
<220> FEATURE:
<221> NAME/KEY: MOD_RES
<222> LOCATION: (30)..(38)
<223> OTHER INFORMATION: Any amino acid
<220> FEATURE:
<221> NAME/KEY: MOD_RES
<222> LOCATION: (40)..(42)
<223> OTHER INFORMATION: Any amino acid

<400> SEQUENCE: 82

Cys Xaa Xaa Xaa Xaa Xaa Xaa Xaa Xaa Xaa Xaa Xaa Cys Xaa Xaa
1               5                   10                  15

Xaa Xaa Cys Xaa Xaa Xaa Xaa Xaa Cys Xaa Cys Xaa Cys Xaa Xaa Xaa
            20                  25                  30

Xaa Xaa Xaa Xaa Xaa Xaa Cys Xaa Xaa Xaa Cys
        35                  40

<210> SEQ ID NO 83
<211> LENGTH: 41
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(13)
<223> OTHER INFORMATION: Any amino acid
<220> FEATURE:
<221> NAME/KEY: MOD_RES
<222> LOCATION: (15)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(37)
<223> OTHER INFORMATION: Any amino acid
<220> FEATURE:
<221> NAME/KEY: MOD_RES
<222> LOCATION: (39)..(40)
<223> OTHER INFORMATION: Any amino acid

<400> SEQUENCE: 83

Cys Xaa Xaa Xaa Xaa Xaa Xaa Xaa Xaa Xaa Xaa Xaa Cys Xaa Xaa
1               5                   10                  15

Xaa Xaa Cys Xaa Xaa Xaa Xaa Xaa Cys Xaa Xaa Xaa Xaa Xaa Xaa Xaa
            20                  25                  30

Xaa Xaa Xaa Xaa Xaa Cys Xaa Xaa Cys
        35                  40

<210> SEQ ID NO 84
<211> LENGTH: 39
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(38)

<223> OTHER INFORMATION: Any amino acid

<400> SEQUENCE: 84

Cys Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Cys Xaa Xaa Xaa Xaa Xaa
            20                  25                  30

Xaa Xaa Xaa Xaa Xaa Xaa Cys
        35

<210> SEQ ID NO 85
<211> LENGTH: 43
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(17)
<223> OTHER INFORMATION: Any amino acid
<220> FEATURE:
<221> NAME/KEY: MOD_RES
<222> LOCATION: (19)..(23)
<223> OTHER INFORMATION: Any amino acid
<220> FEATURE:
<221> NAME/KEY: MOD_RES
<222> LOCATION: (25)..(25)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (29)..(42)
<223> OTHER INFORMATION: Any amino acid

<400> SEQUENCE: 85

Cys Xaa Xaa Xaa Xaa Xaa Xaa Xaa Xaa Xaa Xaa Xaa Xaa Xaa Xaa Xaa
1               5                   10                  15

Xaa Cys Xaa Xaa Xaa Xaa Xaa Cys Xaa Cys Xaa Cys Xaa Xaa Xaa Xaa
            20                  25                  30

Xaa Xaa Xaa Xaa Xaa Xaa Xaa Xaa Xaa Xaa Cys
        35                  40

<210> SEQ ID NO 86
<211> LENGTH: 36
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(17)
<223> OTHER INFORMATION: Any amino acid
<220> FEATURE:
<221> NAME/KEY: MOD_RES
<222> LOCATION: (19)..(19)
<223> OTHER INFORMATION: Any amino acid
<220> FEATURE:
<221> NAME/KEY: MOD_RES
<222> LOCATION: (21)..(28)
<223> OTHER INFORMATION: Any amino acid
<220> FEATURE:
<221> NAME/KEY: MOD_RES

```
<222> LOCATION: (30)..(35)
<223> OTHER INFORMATION: Any amino acid

<400> SEQUENCE: 86

Cys Xaa Xaa Xaa Xaa Xaa Xaa Xaa Xaa Xaa Cys Xaa Xaa Xaa Xaa
1               5                   10                  15

Xaa Cys Xaa Cys Xaa Xaa Xaa Xaa Xaa Xaa Xaa Cys Xaa Xaa Xaa
            20                  25                  30

Xaa Xaa Xaa Cys
        35

<210> SEQ ID NO 87
<211> LENGTH: 37
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(13)
<223> OTHER INFORMATION: Any amino acid
<220> FEATURE:
<221> NAME/KEY: MOD_RES
<222> LOCATION: (15)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(33)
<223> OTHER INFORMATION: Any amino acid
<220> FEATURE:
<221> NAME/KEY: MOD_RES
<222> LOCATION: (35)..(36)
<223> OTHER INFORMATION: Any amino acid

<400> SEQUENCE: 87

Cys Xaa Xaa Xaa Xaa Xaa Xaa Xaa Xaa Xaa Xaa Xaa Cys Xaa Xaa
1               5                   10                  15

Xaa Xaa Cys Xaa Xaa Xaa Xaa Xaa Cys Xaa Xaa Xaa Xaa Xaa Xaa
            20                  25                  30

Xaa Cys Xaa Xaa Cys
        35

<210> SEQ ID NO 88
<211> LENGTH: 37
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(13)
<223> OTHER INFORMATION: Any amino acid
<220> FEATURE:
<221> NAME/KEY: MOD_RES
<222> LOCATION: (15)..(19)
<223> OTHER INFORMATION: Any amino acid
<220> FEATURE:
<221> NAME/KEY: MOD_RES
<222> LOCATION: (21)..(25)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
```

```
<221> NAME/KEY: MOD_RES
<222> LOCATION: (29)..(36)
<223> OTHER INFORMATION: Any amino acid

<400> SEQUENCE: 88

Cys Xaa Xaa Xaa Xaa Xaa Xaa Xaa Xaa Xaa Xaa Xaa Cys Xaa Xaa
1               5                   10                  15

Xaa Xaa Xaa Cys Xaa Xaa Xaa Xaa Cys Xaa Cys Xaa Xaa Xaa Xaa
                20                  25                  30

Xaa Xaa Xaa Xaa Cys
        35

<210> SEQ ID NO 89
<211> LENGTH: 44
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(31)
<223> OTHER INFORMATION: Any amino acid
<220> FEATURE:
<221> NAME/KEY: MOD_RES
<222> LOCATION: (33)..(33)
<223> OTHER INFORMATION: Any amino acid
<220> FEATURE:
<221> NAME/KEY: MOD_RES
<222> LOCATION: (35)..(43)
<223> OTHER INFORMATION: Any amino acid

<400> SEQUENCE: 89

Cys Xaa Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Cys Xaa Xaa Xaa Xaa Cys
                20                  25                  30

Xaa Cys Xaa Xaa Xaa Xaa Xaa Xaa Xaa Xaa Xaa Cys
        35                  40

<210> SEQ ID NO 90
<211> LENGTH: 36
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(12)
<223> OTHER INFORMATION: Any amino acid
<220> FEATURE:
<221> NAME/KEY: MOD_RES
<222> LOCATION: (14)..(17)
<223> OTHER INFORMATION: Any amino acid
```

-continued

```
<220> FEATURE:
<221> NAME/KEY: MOD_RES
<222> LOCATION: (19)..(23)
<223> OTHER INFORMATION: Any amino acid
<220> FEATURE:
<221> NAME/KEY: MOD_RES
<222> LOCATION: (25)..(32)
<223> OTHER INFORMATION: Any amino acid
<220> FEATURE:
<221> NAME/KEY: MOD_RES
<222> LOCATION: (34)..(35)
<223> OTHER INFORMATION: Any amino acid

<400> SEQUENCE: 90

Cys Xaa Xaa Xaa Xaa Xaa Xaa Xaa Xaa Xaa Xaa Cys Xaa Xaa Xaa
1               5                   10                  15

Xaa Cys Xaa Xaa Xaa Xaa Xaa Cys Xaa Xaa Xaa Xaa Xaa Xaa Xaa
            20                  25                  30

Cys Xaa Xaa Cys
        35

<210> SEQ ID NO 91
<211> LENGTH: 37
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(33)
<223> OTHER INFORMATION: Any amino acid
<220> FEATURE:
<221> NAME/KEY: MOD_RES
<222> LOCATION: (35)..(36)
<223> OTHER INFORMATION: Any amino acid

<400> SEQUENCE: 91

Cys Xaa Xaa Xaa Xaa Xaa Xaa Xaa Xaa Xaa Xaa Cys Xaa Xaa Xaa
1               5                   10                  15

Xaa Xaa Cys Xaa Xaa Xaa Xaa Xaa Cys Xaa Xaa Xaa Xaa Xaa Xaa
            20                  25                  30

Xaa Cys Xaa Xaa Cys
        35

<210> SEQ ID NO 92
<211> LENGTH: 36
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
```

<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(35)
<223> OTHER INFORMATION: Any amino acid

<400> SEQUENCE: 92

Cys Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Cys Xaa Xaa Xaa Xaa
            20                  25                  30

Xaa Xaa Xaa Cys
        35

<210> SEQ ID NO 93
<211> LENGTH: 43
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(30)
<223> OTHER INFORMATION: Any amino acid
<220> FEATURE:
<221> NAME/KEY: MOD_RES
<222> LOCATION: (32)..(39)
<223> OTHER INFORMATION: Any amino acid
<220> FEATURE:
<221> NAME/KEY: MOD_RES
<222> LOCATION: (41)..(42)
<223> OTHER INFORMATION: Any amino acid

<400> SEQUENCE: 93

Cys Xaa Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Cys Xaa Xaa Xaa Cys Xaa
            20                  25                  30

Xaa Xaa Xaa Xaa Xaa Xaa Xaa Cys Xaa Xaa Cys
        35                  40

<210> SEQ ID NO 94
<211> LENGTH: 43
<212> TYPE: PRT
<213> ORGANISM: Artificial Sequence
<220> FEATURE:

```
<223> OTHER INFORMATION: Description of Artificial Sequence: Synthetic
      Cysteine motif polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(29)
<223> OTHER INFORMATION: Any amino acid
<220> FEATURE:
<221> NAME/KEY: MOD_RES
<222> LOCATION: (31)..(36)
<223> OTHER INFORMATION: Any amino acid
<220> FEATURE:
<221> NAME/KEY: MOD_RES
<222> LOCATION: (38)..(42)
<223> OTHER INFORMATION: Any amino acid

<400> SEQUENCE: 94

Cys Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Cys Xaa Xaa Cys Xaa Xaa
            20                  25                  30

Xaa Xaa Xaa Xaa Cys Xaa Xaa Xaa Xaa Xaa Cys
        35                  40

<210> SEQ ID NO 95
<211> LENGTH: 38
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(28)
<223> OTHER INFORMATION: Any amino acid
<220> FEATURE:
<221> NAME/KEY: MOD_RES
<222> LOCATION: (30)..(37)
<223> OTHER INFORMATION: Any amino acid

<400> SEQUENCE: 95

Cys Xaa Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Xaa Xaa Cys Xaa Xaa Xaa
            20                  25                  30
```

Xaa Xaa Xaa Xaa Xaa Cys
        35

<210> SEQ ID NO 96
<211> LENGTH: 34
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(8)
<223> OTHER INFORMATION: Any amino acid
<220> FEATURE:
<221> NAME/KEY: MOD_RES
<222> LOCATION: (10)..(15)
<223> OTHER INFORMATION: Any amino acid
<220> FEATURE:
<221> NAME/KEY: MOD_RES
<222> LOCATION: (17)..(19)
<223> OTHER INFORMATION: Any amino acid
<220> FEATURE:
<221> NAME/KEY: MOD_RES
<222> LOCATION: (21)..(23)
<223> OTHER INFORMATION: Any amino acid
<220> FEATURE:
<221> NAME/KEY: MOD_RES
<222> LOCATION: (25)..(33)
<223> OTHER INFORMATION: Any amino acid

<400> SEQUENCE: 96

Cys Xaa Xaa Xaa Xaa Xaa Xaa Xaa Cys Xaa Xaa Xaa Xaa Xaa Xaa Cys
1               5                   10                  15

Xaa Xaa Xaa Cys Xaa Xaa Xaa Cys Xaa Xaa Xaa Xaa Xaa Xaa Xaa Xaa
            20                  25                  30

Xaa Cys

<210> SEQ ID NO 97
<211> LENGTH: 39
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(10)
<223> OTHER INFORMATION: Any amino acid
<220> FEATURE:
<221> NAME/KEY: MOD_RES
<222> LOCATION: (12)..(19)
<223> OTHER INFORMATION: Any amino acid
<220> FEATURE:
<221> NAME/KEY: MOD_RES
<222> LOCATION: (21)..(25)
<223> OTHER INFORMATION: Any amino acid
<220> FEATURE:
<221> NAME/KEY: MOD_RES
<222> LOCATION: (27)..(32)
<223> OTHER INFORMATION: Any amino acid
<220> FEATURE:
<221> NAME/KEY: MOD_RES
<222> LOCATION: (34)..(38)
<223> OTHER INFORMATION: Any amino acid

<400> SEQUENCE: 97

Cys Xaa Xaa Xaa Xaa Xaa Xaa Xaa Xaa Xaa Cys Xaa Xaa Xaa Xaa Xaa
1               5                   10                  15

Xaa Xaa Xaa Cys Xaa Xaa Xaa Xaa Xaa Cys Xaa Xaa Xaa Xaa Xaa Xaa
            20                  25                  30

Cys Xaa Xaa Xaa Xaa Xaa Cys
          35

<210> SEQ ID NO 98
<211> LENGTH: 46
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(14)
<223> OTHER INFORMATION: Any amino acid
<220> FEATURE:
<221> NAME/KEY: MOD_RES
<222> LOCATION: (16)..(17)
<223> OTHER INFORMATION: Any amino acid
<220> FEATURE:
<221> NAME/KEY: MOD_RES
<222> LOCATION: (19)..(25)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (29)..(39)
<223> OTHER INFORMATION: Any amino acid
<220> FEATURE:
<221> NAME/KEY: MOD_RES
<222> LOCATION: (41)..(45)
<223> OTHER INFORMATION: Any amino acid

<400> SEQUENCE: 98

Cys Xaa Xaa Xaa Xaa Xaa Xaa Xaa Xaa Xaa Xaa Cys Xaa Xaa Cys Xaa
1               5                   10                  15

Xaa Cys Xaa Xaa Xaa Xaa Xaa Xaa Xaa Cys Xaa Cys Xaa Xaa Xaa Xaa
            20                  25                  30

Xaa Xaa Xaa Xaa Xaa Xaa Xaa Cys Xaa Xaa Xaa Xaa Xaa Cys
          35                  40                  45

<210> SEQ ID NO 99
<211> LENGTH: 44
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(29)
<223> OTHER INFORMATION: Any amino acid
<220> FEATURE:
<221> NAME/KEY: MOD_RES
<222> LOCATION: (31)..(38)
<223> OTHER INFORMATION: Any amino acid
<220> FEATURE:
<221> NAME/KEY: MOD_RES
<222> LOCATION: (40)..(43)
<223> OTHER INFORMATION: Any amino acid

<400> SEQUENCE: 99

Cys Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Cys Xaa Xaa Cys Xaa Xaa
            20                  25                  30

Xaa Xaa Xaa Xaa Xaa Xaa Cys Xaa Xaa Xaa Xaa Cys
        35                  40

<210> SEQ ID NO 100
<211> LENGTH: 42
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (3)..(5)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (9)..(11)
<223> OTHER INFORMATION: Any amino acid
<220> FEATURE:
<221> NAME/KEY: MOD_RES
<222> LOCATION: (13)..(14)
<223> OTHER INFORMATION: Any amino acid
<220> FEATURE:
<221> NAME/KEY: MOD_RES
<222> LOCATION: (17)..(17)
<223> OTHER INFORMATION: Any amino acid
<220> FEATURE:
<221> NAME/KEY: MOD_RES
<222> LOCATION: (19)..(23)
<223> OTHER INFORMATION: Any amino acid
<220> FEATURE:
<221> NAME/KEY: MOD_RES
<222> LOCATION: (25)..(33)
<223> OTHER INFORMATION: Any amino acid
<220> FEATURE:
<221> NAME/KEY: MOD_RES
<222> LOCATION: (35)..(39)
<223> OTHER INFORMATION: Any amino acid
<220> FEATURE:
<221> NAME/KEY: MOD_RES
<222> LOCATION: (41)..(41)
<223> OTHER INFORMATION: Any amino acid

<400> SEQUENCE: 100

Cys Cys Xaa Xaa Xaa Cys Xaa Cys Xaa Xaa Xaa Cys Xaa Xaa Cys Cys
1               5                   10                  15

Xaa Cys Xaa Xaa Xaa Xaa Xaa Cys Xaa Xaa Xaa Xaa Xaa Xaa Xaa Xaa
            20                  25                  30

Xaa Cys Xaa Xaa Xaa Xaa Xaa Cys Xaa Cys
        35                  40

<210> SEQ ID NO 101
<211> LENGTH: 39

```
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(7)
<223> OTHER INFORMATION: Any amino acid
<220> FEATURE:
<221> NAME/KEY: MOD_RES
<222> LOCATION: (9)..(10)
<223> OTHER INFORMATION: Any amino acid
<220> FEATURE:
<221> NAME/KEY: MOD_RES
<222> LOCATION: (12)..(16)
<223> OTHER INFORMATION: Any amino acid
<220> FEATURE:
<221> NAME/KEY: MOD_RES
<222> LOCATION: (18)..(21)
<223> OTHER INFORMATION: Any amino acid
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (26)..(29)
<223> OTHER INFORMATION: Any amino acid
<220> FEATURE:
<221> NAME/KEY: MOD_RES
<222> LOCATION: (31)..(36)
<223> OTHER INFORMATION: Any amino acid
<220> FEATURE:
<221> NAME/KEY: MOD_RES
<222> LOCATION: (38)..(38)
<223> OTHER INFORMATION: Any amino acid

<400> SEQUENCE: 101

Cys Xaa Xaa Xaa Xaa Xaa Xaa Cys Xaa Xaa Cys Xaa Xaa Xaa Xaa Xaa
1               5                   10                  15

Cys Xaa Xaa Xaa Xaa Cys Xaa Xaa Cys Xaa Xaa Xaa Cys Xaa Xaa
            20                  25                  30

Xaa Xaa Xaa Xaa Cys Xaa Cys
        35

<210> SEQ ID NO 102
<211> LENGTH: 38
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(8)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (12)..(16)
<223> OTHER INFORMATION: Any amino acid
<220> FEATURE:
<221> NAME/KEY: MOD_RES
<222> LOCATION: (18)..(21)
<223> OTHER INFORMATION: Any amino acid
<220> FEATURE:
<221> NAME/KEY: MOD_RES
<222> LOCATION: (25)..(28)
<223> OTHER INFORMATION: Any amino acid
<220> FEATURE:
<221> NAME/KEY: MOD_RES
```

```
<222> LOCATION: (30)..(35)
<223> OTHER INFORMATION: Any amino acid
<220> FEATURE:
<221> NAME/KEY: MOD_RES
<222> LOCATION: (37)..(37)
<223> OTHER INFORMATION: Any amino acid

<400> SEQUENCE: 102

Cys Xaa Xaa Xaa Xaa Xaa Xaa Xaa Cys Xaa Cys Xaa Xaa Xaa Xaa
1               5                   10                  15

Cys Xaa Xaa Xaa Xaa Cys Cys Cys Xaa Xaa Xaa Cys Xaa Xaa
            20                  25                  30

Xaa Xaa Xaa Cys Xaa Cys
        35

<210> SEQ ID NO 103
<211> LENGTH: 36
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(10)
<223> OTHER INFORMATION: Any amino acid
<220> FEATURE:
<221> NAME/KEY: MOD_RES
<222> LOCATION: (12)..(14)
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (18)..(19)
<223> OTHER INFORMATION: Any amino acid
<220> FEATURE:
<221> NAME/KEY: MOD_RES
<222> LOCATION: (21)..(21)
<223> OTHER INFORMATION: Any amino acid
<220> FEATURE:
<221> NAME/KEY: MOD_RES
<222> LOCATION: (25)..(30)
<223> OTHER INFORMATION: Any amino acid
<220> FEATURE:
<221> NAME/KEY: MOD_RES
<222> LOCATION: (32)..(35)
<223> OTHER INFORMATION: Any amino acid

<400> SEQUENCE: 103

Cys Xaa Xaa Xaa Xaa Xaa Xaa Xaa Xaa Xaa Cys Xaa Xaa Xaa Cys Xaa
1               5                   10                  15

Cys Xaa Xaa Cys Xaa Cys Cys Cys Xaa Xaa Xaa Xaa Xaa Cys Xaa
            20                  25                  30

Xaa Xaa Xaa Cys
        35

<210> SEQ ID NO 104
<211> LENGTH: 39
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(6)
<223> OTHER INFORMATION: Any amino acid
<220> FEATURE:
```

<221> NAME/KEY: MOD_RES
<222> LOCATION: (8)..(10)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (14)..(17)
<223> OTHER INFORMATION: Any amino acid
<220> FEATURE:
<221> NAME/KEY: MOD_RES
<222> LOCATION: (19)..(22)
<223> OTHER INFORMATION: Any amino acid
<220> FEATURE:
<221> NAME/KEY: MOD_RES
<222> LOCATION: (25)..(34)
<223> OTHER INFORMATION: Any amino acid
<220> FEATURE:
<221> NAME/KEY: MOD_RES
<222> LOCATION: (36)..(37)
<223> OTHER INFORMATION: Any amino acid

<400> SEQUENCE: 104

Cys Xaa Xaa Xaa Xaa Xaa Cys Xaa Xaa Xaa Cys Xaa Cys Xaa Xaa Xaa
1               5                   10                  15

Xaa Cys Xaa Xaa Xaa Xaa Cys Cys Xaa Xaa Xaa Xaa Xaa Xaa Xaa Xaa
                20                  25                  30

Xaa Xaa Cys Xaa Xaa Cys Cys
            35

<210> SEQ ID NO 105
<211> LENGTH: 38
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (14)..(16)
<223> OTHER INFORMATION: Any amino acid
<220> FEATURE:
<221> NAME/KEY: MOD_RES
<222> LOCATION: (19)..(21)
<223> OTHER INFORMATION: Any amino acid
<220> FEATURE:
<221> NAME/KEY: MOD_RES
<222> LOCATION: (23)..(26)
<223> OTHER INFORMATION: Any amino acid
<220> FEATURE:
<221> NAME/KEY: MOD_RES
<222> LOCATION: (28)..(37)
<223> OTHER INFORMATION: Any amino acid

<400> SEQUENCE: 105

Cys Xaa Xaa Xaa Xaa Xaa Cys Xaa Cys Xaa Cys Xaa Cys Xaa Xaa Xaa

```
                1               5                  10                 15
Cys Cys Xaa Xaa Xaa Cys Xaa Xaa Xaa Cys Xaa Xaa Xaa Xaa Xaa
                        20                 25                 30
Xaa Xaa Xaa Xaa Xaa Cys
        35

<210> SEQ ID NO 106
<211> LENGTH: 37
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(10)
<223> OTHER INFORMATION: Any amino acid
<220> FEATURE:
<221> NAME/KEY: MOD_RES
<222> LOCATION: (14)..(16)
<223> OTHER INFORMATION: Any amino acid
<220> FEATURE:
<221> NAME/KEY: MOD_RES
<222> LOCATION: (18)..(21)
<223> OTHER INFORMATION: Any amino acid
<220> FEATURE:
<221> NAME/KEY: MOD_RES
<222> LOCATION: (25)..(29)
<223> OTHER INFORMATION: Any amino acid
<220> FEATURE:
<221> NAME/KEY: MOD_RES
<222> LOCATION: (31)..(36)
<223> OTHER INFORMATION: Any amino acid

<400> SEQUENCE: 106

Cys Xaa Xaa Xaa Xaa Xaa Xaa Xaa Xaa Cys Cys Cys Xaa Xaa Xaa
1               5                  10                 15
Cys Xaa Xaa Xaa Xaa Cys Cys Cys Xaa Xaa Xaa Xaa Xaa Cys Xaa Xaa
                        20                 25                 30
Xaa Xaa Xaa Xaa Cys
        35

<210> SEQ ID NO 107
<211> LENGTH: 36
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (3)..(10)
<223> OTHER INFORMATION: Any amino acid
<220> FEATURE:
<221> NAME/KEY: MOD_RES
<222> LOCATION: (12)..(16)
<223> OTHER INFORMATION: Any amino acid
<220> FEATURE:
<221> NAME/KEY: MOD_RES
<222> LOCATION: (18)..(21)
<223> OTHER INFORMATION: Any amino acid
<220> FEATURE:
<221> NAME/KEY: MOD_RES
<222> LOCATION: (23)..(25)
<223> OTHER INFORMATION: Any amino acid
<220> FEATURE:
<221> NAME/KEY: MOD_RES
<222> LOCATION: (27)..(30)
<223> OTHER INFORMATION: Any amino acid
<220> FEATURE:
<221> NAME/KEY: MOD_RES
<222> LOCATION: (33)..(33)
```

-continued

```
<223> OTHER INFORMATION: Any amino acid
<220> FEATURE:
<221> NAME/KEY: MOD_RES
<222> LOCATION: (35)..(35)
<223> OTHER INFORMATION: Any amino acid

<400> SEQUENCE: 107

Cys Cys Xaa Xaa Xaa Xaa Xaa Xaa Cys Xaa Xaa Xaa Xaa Xaa
1               5                   10                  15

Cys Xaa Xaa Xaa Xaa Cys Xaa Xaa Xaa Cys Xaa Xaa Xaa Xaa Cys Cys
            20                  25                  30

Xaa Cys Xaa Cys
        35

<210> SEQ ID NO 108
<211> LENGTH: 41
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (3)..(8)
<223> OTHER INFORMATION: Any amino acid
<220> FEATURE:
<221> NAME/KEY: MOD_RES
<222> LOCATION: (11)..(15)
<223> OTHER INFORMATION: Any amino acid
<220> FEATURE:
<221> NAME/KEY: MOD_RES
<222> LOCATION: (19)..(22)
<223> OTHER INFORMATION: Any amino acid
<220> FEATURE:
<221> NAME/KEY: MOD_RES
<222> LOCATION: (24)..(27)
<223> OTHER INFORMATION: Any amino acid
<220> FEATURE:
<221> NAME/KEY: MOD_RES
<222> LOCATION: (29)..(40)
<223> OTHER INFORMATION: Any amino acid

<400> SEQUENCE: 108

Cys Cys Xaa Xaa Xaa Xaa Xaa Xaa Cys Cys Xaa Xaa Xaa Xaa Xaa Cys
1               5                   10                  15

Cys Cys Xaa Xaa Xaa Xaa Cys Xaa Xaa Xaa Xaa Cys Xaa Xaa Xaa Xaa
            20                  25                  30

Xaa Xaa Xaa Xaa Xaa Xaa Xaa Xaa Cys
        35                  40

<210> SEQ ID NO 109
<211> LENGTH: 36
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(7)
<223> OTHER INFORMATION: Any amino acid
<220> FEATURE:
<221> NAME/KEY: MOD_RES
<222> LOCATION: (9)..(10)
<223> OTHER INFORMATION: Any amino acid
<220> FEATURE:
<221> NAME/KEY: MOD_RES
<222> LOCATION: (12)..(14)
<223> OTHER INFORMATION: Any amino acid
<220> FEATURE:
<221> NAME/KEY: MOD_RES
```

```
<222> LOCATION: (18)..(21)
<223> OTHER INFORMATION: Any amino acid
<220> FEATURE:
<221> NAME/KEY: MOD_RES
<222> LOCATION: (23)..(27)
<223> OTHER INFORMATION: Any amino acid
<220> FEATURE:
<221> NAME/KEY: MOD_RES
<222> LOCATION: (29)..(31)
<223> OTHER INFORMATION: Any amino acid
<220> FEATURE:
<221> NAME/KEY: MOD_RES
<222> LOCATION: (33)..(35)
<223> OTHER INFORMATION: Any amino acid

<400> SEQUENCE: 109

Cys Xaa Xaa Xaa Xaa Xaa Xaa Cys Xaa Xaa Cys Xaa Xaa Xaa Cys Cys
 1               5                  10                  15

Cys Xaa Xaa Xaa Xaa Cys Xaa Xaa Xaa Xaa Xaa Cys Xaa Xaa Xaa Cys
                20                  25                  30

Xaa Xaa Xaa Cys
        35

<210> SEQ ID NO 110
<211> LENGTH: 39
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(4)
<223> OTHER INFORMATION: Any amino acid
<220> FEATURE:
<221> NAME/KEY: MOD_RES
<222> LOCATION: (6)..(10)
<223> OTHER INFORMATION: Any amino acid
<220> FEATURE:
<221> NAME/KEY: MOD_RES
<222> LOCATION: (12)..(17)
<223> OTHER INFORMATION: Any amino acid
<220> FEATURE:
<221> NAME/KEY: MOD_RES
<222> LOCATION: (19)..(22)
<223> OTHER INFORMATION: Any amino acid
<220> FEATURE:
<221> NAME/KEY: MOD_RES
<222> LOCATION: (25)..(25)
<223> OTHER INFORMATION: Any amino acid
<220> FEATURE:
<221> NAME/KEY: MOD_RES
<222> LOCATION: (27)..(31)
<223> OTHER INFORMATION: Any amino acid
<220> FEATURE:
<221> NAME/KEY: MOD_RES
<222> LOCATION: (33)..(36)
<223> OTHER INFORMATION: Any amino acid
<220> FEATURE:
<221> NAME/KEY: MOD_RES
<222> LOCATION: (38)..(38)
<223> OTHER INFORMATION: Any amino acid

<400> SEQUENCE: 110

Cys Xaa Xaa Xaa Cys Xaa Xaa Xaa Xaa Xaa Cys Xaa Xaa Xaa Xaa Xaa
 1               5                  10                  15

Xaa Cys Xaa Xaa Xaa Xaa Cys Xaa Cys Xaa Xaa Xaa Xaa Xaa Cys Xaa Cys
                20                  25                  30

Xaa Xaa Xaa Xaa Cys Xaa Cys
        35
```

```
<210> SEQ ID NO 111
<211> LENGTH: 41
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(5)
<223> OTHER INFORMATION: Any amino acid
<220> FEATURE:
<221> NAME/KEY: MOD_RES
<222> LOCATION: (7)..(10)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(21)
<223> OTHER INFORMATION: Any amino acid
<220> FEATURE:
<221> NAME/KEY: MOD_RES
<222> LOCATION: (23)..(23)
<223> OTHER INFORMATION: Any amino acid
<220> FEATURE:
<221> NAME/KEY: MOD_RES
<222> LOCATION: (25)..(35)
<223> OTHER INFORMATION: Any amino acid
<220> FEATURE:
<221> NAME/KEY: MOD_RES
<222> LOCATION: (37)..(38)
<223> OTHER INFORMATION: Any amino acid
<220> FEATURE:
<221> NAME/KEY: MOD_RES
<222> LOCATION: (40)..(40)
<223> OTHER INFORMATION: Any amino acid

<400> SEQUENCE: 111

Cys Xaa Xaa Xaa Xaa Cys Xaa Xaa Xaa Xaa Cys Cys Xaa Xaa Xaa Xaa
1               5                   10                  15

Cys Xaa Xaa Xaa Xaa Cys Xaa Cys Xaa Xaa Xaa Xaa Xaa Xaa Xaa Xaa
            20                  25                  30

Xaa Xaa Xaa Cys Xaa Xaa Cys Xaa Cys
        35                  40

<210> SEQ ID NO 112
<211> LENGTH: 36
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(6)
<223> OTHER INFORMATION: Any amino acid
<220> FEATURE:
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (12)..(16)
<223> OTHER INFORMATION: Any amino acid
<220> FEATURE:
<221> NAME/KEY: MOD_RES
<222> LOCATION: (18)..(21)
<223> OTHER INFORMATION: Any amino acid
<220> FEATURE:
<221> NAME/KEY: MOD_RES
<222> LOCATION: (24)..(26)
<223> OTHER INFORMATION: Any amino acid
```

```
<220> FEATURE:
<221> NAME/KEY: MOD_RES
<222> LOCATION: (29)..(35)
<223> OTHER INFORMATION: Any amino acid

<400> SEQUENCE: 112

Cys Xaa Xaa Xaa Xaa Xaa Cys Xaa Xaa Cys Cys Xaa Xaa Xaa Xaa
1               5                   10                  15

Cys Xaa Xaa Xaa Xaa Cys Cys Xaa Xaa Cys Cys Xaa Xaa Xaa Xaa
                20                  25                  30

Xaa Xaa Xaa Cys
        35

<210> SEQ ID NO 113
<211> LENGTH: 38
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(6)
<223> OTHER INFORMATION: Any amino acid
<220> FEATURE:
<221> NAME/KEY: MOD_RES
<222> LOCATION: (8)..(12)
<223> OTHER INFORMATION: Any amino acid
<220> FEATURE:
<221> NAME/KEY: MOD_RES
<222> LOCATION: (14)..(16)
<223> OTHER INFORMATION: Any amino acid
<220> FEATURE:
<221> NAME/KEY: MOD_RES
<222> LOCATION: (18)..(19)
<223> OTHER INFORMATION: Any amino acid
<220> FEATURE:
<221> NAME/KEY: MOD_RES
<222> LOCATION: (21)..(21)
<223> OTHER INFORMATION: Any amino acid
<220> FEATURE:
<221> NAME/KEY: MOD_RES
<222> LOCATION: (24)..(27)
<223> OTHER INFORMATION: Any amino acid
<220> FEATURE:
<221> NAME/KEY: MOD_RES
<222> LOCATION: (29)..(35)
<223> OTHER INFORMATION: Any amino acid
<220> FEATURE:
<221> NAME/KEY: MOD_RES
<222> LOCATION: (37)..(37)
<223> OTHER INFORMATION: Any amino acid

<400> SEQUENCE: 113

Cys Xaa Xaa Xaa Xaa Xaa Cys Xaa Xaa Xaa Xaa Xaa Cys Xaa Xaa
1               5                   10                  15

Cys Xaa Xaa Cys Xaa Cys Cys Xaa Xaa Xaa Xaa Cys Xaa Xaa Xaa
                20                  25                  30

Xaa Xaa Xaa Cys Xaa Cys
        35

<210> SEQ ID NO 114
<211> LENGTH: 37
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(4)
```

```
<223> OTHER INFORMATION: Any amino acid
<220> FEATURE:
<221> NAME/KEY: MOD_RES
<222> LOCATION: (6)..(12)
<223> OTHER INFORMATION: Any amino acid
<220> FEATURE:
<221> NAME/KEY: MOD_RES
<222> LOCATION: (14)..(16)
<223> OTHER INFORMATION: Any amino acid
<220> FEATURE:
<221> NAME/KEY: MOD_RES
<222> LOCATION: (18)..(21)
<223> OTHER INFORMATION: Any amino acid
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (26)..(27)
<223> OTHER INFORMATION: Any amino acid
<220> FEATURE:
<221> NAME/KEY: MOD_RES
<222> LOCATION: (29)..(33)
<223> OTHER INFORMATION: Any amino acid
<220> FEATURE:
<221> NAME/KEY: MOD_RES
<222> LOCATION: (35)..(36)
<223> OTHER INFORMATION: Any amino acid

<400> SEQUENCE: 114

Cys Xaa Xaa Xaa Cys Xaa Xaa Xaa Xaa Xaa Xaa Xaa Cys Xaa Xaa Xaa
1               5                   10                  15

Cys Xaa Xaa Xaa Xaa Cys Cys Xaa Cys Xaa Xaa Cys Xaa Xaa Xaa Xaa
            20                  25                  30

Xaa Cys Xaa Xaa Cys
        35

<210> SEQ ID NO 115
<211> LENGTH: 38
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(10)
<223> OTHER INFORMATION: Any amino acid
<220> FEATURE:
<221> NAME/KEY: MOD_RES
<222> LOCATION: (12)..(14)
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (18)..(21)
<223> OTHER INFORMATION: Any amino acid
<220> FEATURE:
<221> NAME/KEY: MOD_RES
<222> LOCATION: (24)..(28)
<223> OTHER INFORMATION: Any amino acid
<220> FEATURE:
<221> NAME/KEY: MOD_RES
<222> LOCATION: (32)..(37)
<223> OTHER INFORMATION: Any amino acid

<400> SEQUENCE: 115

Cys Xaa Xaa Xaa Xaa Xaa Xaa Xaa Xaa Xaa Cys Xaa Xaa Xaa Cys Xaa
1               5                   10                  15
```

```
Cys Xaa Xaa Xaa Xaa Cys Cys Xaa Xaa Xaa Cys Cys Cys Xaa
            20                  25                  30

Xaa Xaa Xaa Xaa Xaa Cys
        35
```

<210> SEQ ID NO 116
<211> LENGTH: 38
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(10)
<223> OTHER INFORMATION: Any amino acid
<220> FEATURE:
<221> NAME/KEY: MOD_RES
<222> LOCATION: (12)..(14)
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (18)..(19)
<223> OTHER INFORMATION: Any amino acid
<220> FEATURE:
<221> NAME/KEY: MOD_RES
<222> LOCATION: (21)..(21)
<223> OTHER INFORMATION: Any amino acid
<220> FEATURE:
<221> NAME/KEY: MOD_RES
<222> LOCATION: (24)..(29)
<223> OTHER INFORMATION: Any amino acid
<220> FEATURE:
<221> NAME/KEY: MOD_RES
<222> LOCATION: (31)..(33)
<223> OTHER INFORMATION: Any amino acid
<220> FEATURE:
<221> NAME/KEY: MOD_RES
<222> LOCATION: (35)..(37)
<223> OTHER INFORMATION: Any amino acid

<400> SEQUENCE: 116

```
Cys Xaa Xaa Xaa Xaa Xaa Xaa Xaa Xaa Xaa Cys Xaa Xaa Xaa Cys Xaa
1               5                   10                  15

Cys Xaa Xaa Cys Xaa Cys Cys Xaa Xaa Xaa Xaa Xaa Cys Xaa Xaa
            20                  25                  30

Xaa Cys Xaa Xaa Xaa Cys
        35
```

<210> SEQ ID NO 117
<211> LENGTH: 33
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(9)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (14)..(16)
<223> OTHER INFORMATION: Any amino acid
<220> FEATURE:

```
<221> NAME/KEY: MOD_RES
<222> LOCATION: (19)..(21)
<223> OTHER INFORMATION: Any amino acid
<220> FEATURE:
<221> NAME/KEY: MOD_RES
<222> LOCATION: (23)..(23)
<223> OTHER INFORMATION: Any amino acid
<220> FEATURE:
<221> NAME/KEY: MOD_RES
<222> LOCATION: (25)..(27)
<223> OTHER INFORMATION: Any amino acid
<220> FEATURE:
<221> NAME/KEY: MOD_RES
<222> LOCATION: (29)..(32)
<223> OTHER INFORMATION: Any amino acid

<400> SEQUENCE: 117

Cys Xaa Xaa Xaa Xaa Xaa Xaa Xaa Cys Cys Xaa Cys Xaa Xaa Xaa
1               5                   10                  15

Cys Cys Xaa Xaa Xaa Cys Xaa Cys Xaa Xaa Xaa Cys Xaa Xaa Xaa Xaa
            20                  25                  30

Cys

<210> SEQ ID NO 118
<211> LENGTH: 34
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(10)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(19)
<223> OTHER INFORMATION: Any amino acid
<220> FEATURE:
<221> NAME/KEY: MOD_RES
<222> LOCATION: (21)..(21)
<223> OTHER INFORMATION: Any amino acid
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (26)..(29)
<223> OTHER INFORMATION: Any amino acid
<220> FEATURE:
<221> NAME/KEY: MOD_RES
<222> LOCATION: (31)..(33)
<223> OTHER INFORMATION: Any amino acid

<400> SEQUENCE: 118

Cys Xaa Xaa Xaa Xaa Xaa Xaa Xaa Xaa Xaa Cys Cys Xaa Xaa Xaa Xaa
1               5                   10                  15

Cys Xaa Xaa Cys Xaa Cys Cys Xaa Cys Xaa Xaa Xaa Xaa Cys Xaa Xaa
            20                  25                  30

Xaa Cys

<210> SEQ ID NO 119
<211> LENGTH: 37
<212> TYPE: PRT
<213> ORGANISM: Artificial Sequence
<220> FEATURE:
```

```
<223> OTHER INFORMATION: Description of Artificial Sequence: Synthetic
      Cysteine motif polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (15)..(17)
<223> OTHER INFORMATION: Any amino acid
<220> FEATURE:
<221> NAME/KEY: MOD_RES
<222> LOCATION: (19)..(20)
<223> OTHER INFORMATION: Any amino acid
<220> FEATURE:
<221> NAME/KEY: MOD_RES
<222> LOCATION: (22)..(22)
<223> OTHER INFORMATION: Any amino acid
<220> FEATURE:
<221> NAME/KEY: MOD_RES
<222> LOCATION: (25)..(28)
<223> OTHER INFORMATION: Any amino acid
<220> FEATURE:
<221> NAME/KEY: MOD_RES
<222> LOCATION: (30)..(34)
<223> OTHER INFORMATION: Any amino acid
<220> FEATURE:
<221> NAME/KEY: MOD_RES
<222> LOCATION: (36)..(36)
<223> OTHER INFORMATION: Any amino acid

<400> SEQUENCE: 119

Cys Xaa Xaa Xaa Xaa Xaa Xaa Xaa Xaa Xaa Xaa Cys Xaa Cys Xaa Xaa
1               5                   10                  15

Xaa Cys Xaa Xaa Cys Xaa Cys Cys Xaa Xaa Xaa Xaa Cys Xaa Xaa Xaa
            20                  25                  30

Xaa Xaa Cys Xaa Cys
        35

<210> SEQ ID NO 120
<211> LENGTH: 36
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(10)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (14)..(16)
<223> OTHER INFORMATION: Any amino acid
<220> FEATURE:
<221> NAME/KEY: MOD_RES
<222> LOCATION: (18)..(19)
<223> OTHER INFORMATION: Any amino acid
<220> FEATURE:
<221> NAME/KEY: MOD_RES
<222> LOCATION: (21)..(21)
<223> OTHER INFORMATION: Any amino acid
<220> FEATURE:
<221> NAME/KEY: MOD_RES
<222> LOCATION: (24)..(27)
<223> OTHER INFORMATION: Any amino acid
<220> FEATURE:
```

```
<221> NAME/KEY: MOD_RES
<222> LOCATION: (29)..(33)
<223> OTHER INFORMATION: Any amino acid
<220> FEATURE:
<221> NAME/KEY: MOD_RES
<222> LOCATION: (35)..(35)
<223> OTHER INFORMATION: Any amino acid

<400> SEQUENCE: 120

Cys Xaa Xaa Xaa Xaa Xaa Xaa Xaa Xaa Cys Xaa Cys Xaa Xaa Xaa
1               5                   10                  15

Cys Xaa Xaa Cys Xaa Cys Cys Xaa Xaa Xaa Cys Xaa Xaa Xaa Xaa
            20                  25                  30

Xaa Cys Xaa Cys
        35

<210> SEQ ID NO 121
<211> LENGTH: 34
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(7)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (12)..(16)
<223> OTHER INFORMATION: Any amino acid
<220> FEATURE:
<221> NAME/KEY: MOD_RES
<222> LOCATION: (18)..(21)
<223> OTHER INFORMATION: Any amino acid
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (26)..(30)
<223> OTHER INFORMATION: Any amino acid
<220> FEATURE:
<221> NAME/KEY: MOD_RES
<222> LOCATION: (32)..(33)
<223> OTHER INFORMATION: Any amino acid

<400> SEQUENCE: 121

Cys Xaa Xaa Xaa Xaa Xaa Xaa Cys Cys Xaa Cys Xaa Xaa Xaa Xaa
1               5                   10                  15

Cys Xaa Xaa Xaa Xaa Cys Cys Xaa Cys Xaa Xaa Xaa Xaa Cys Xaa
            20                  25                  30

Xaa Cys

<210> SEQ ID NO 122
<211> LENGTH: 28
<212> TYPE: PRT
<213> ORGANISM: Artificial Sequence
<220> FEATURE:
<223> OTHER INFORMATION: Description of Artificial Sequence: Synthetic
      Cysteine motif peptide
<220> FEATURE:
<221> NAME/KEY: MOD_RES
<222> LOCATION: (2)..(7)
<223> OTHER INFORMATION: Any amino acid
<220> FEATURE:
```

```
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (12)..(14)
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (19)..(21)
<223> OTHER INFORMATION: Any amino acid
<220> FEATURE:
<221> NAME/KEY: MOD_RES
<222> LOCATION: (23)..(26)
<223> OTHER INFORMATION: Any amino acid

<400> SEQUENCE: 122

Cys Xaa Xaa Xaa Xaa Xaa Xaa Cys Cys Xaa Cys Xaa Xaa Xaa Cys Xaa
1               5                   10                  15

Cys Cys Xaa Xaa Xaa Cys Xaa Xaa Xaa Xaa Cys Cys
            20                  25

<210> SEQ ID NO 123
<211> LENGTH: 36
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(7)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (12)..(14)
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (18)..(19)
<223> OTHER INFORMATION: Any amino acid
<220> FEATURE:
<221> NAME/KEY: MOD_RES
<222> LOCATION: (21)..(21)
<223> OTHER INFORMATION: Any amino acid
<220> FEATURE:
<221> NAME/KEY: MOD_RES
<222> LOCATION: (23)..(26)
<223> OTHER INFORMATION: Any amino acid
<220> FEATURE:
<221> NAME/KEY: MOD_RES
<222> LOCATION: (28)..(35)
<223> OTHER INFORMATION: Any amino acid

<400> SEQUENCE: 123

Cys Xaa Xaa Xaa Xaa Xaa Xaa Cys Cys Xaa Cys Xaa Xaa Xaa Cys Xaa
1               5                   10                  15

Cys Xaa Xaa Cys Xaa Cys Xaa Xaa Xaa Xaa Cys Xaa Xaa Xaa Xaa Xaa
            20                  25                  30

Xaa Xaa Xaa Cys
            35
```

```
<210> SEQ ID NO 124
<211> LENGTH: 29
<212> TYPE: PRT
<213> ORGANISM: Artificial Sequence
<220> FEATURE:
<223> OTHER INFORMATION: Description of Artificial Sequence: Synthetic
      Cysteine motif peptide
<220> FEATURE:
<221> NAME/KEY: MOD_RES
<222> LOCATION: (2)..(5)
<223> OTHER INFORMATION: Any amino acid
<220> FEATURE:
<221> NAME/KEY: MOD_RES
<222> LOCATION: (7)..(8)
<223> OTHER INFORMATION: Any amino acid
<220> FEATURE:
<221> NAME/KEY: MOD_RES
<222> LOCATION: (11)..(13)
<223> OTHER INFORMATION: Any amino acid
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (17)..(20)
<223> OTHER INFORMATION: Any amino acid
<220> FEATURE:
<221> NAME/KEY: MOD_RES
<222> LOCATION: (23)..(24)
<223> OTHER INFORMATION: Any amino acid
<220> FEATURE:
<221> NAME/KEY: MOD_RES
<222> LOCATION: (26)..(28)
<223> OTHER INFORMATION: Any amino acid

<400> SEQUENCE: 124

Cys Xaa Xaa Xaa Xaa Cys Xaa Xaa Cys Cys Xaa Xaa Xaa Cys Xaa Cys
1               5                   10                  15

Xaa Xaa Xaa Xaa Cys Cys Xaa Xaa Cys Xaa Xaa Xaa Cys
            20                  25

<210> SEQ ID NO 125
<211> LENGTH: 32
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(4)
<223> OTHER INFORMATION: Any amino acid
<220> FEATURE:
<221> NAME/KEY: MOD_RES
<222> LOCATION: (6)..(10)
<223> OTHER INFORMATION: Any amino acid
<220> FEATURE:
<221> NAME/KEY: MOD_RES
<222> LOCATION: (12)..(14)
<223> OTHER INFORMATION: Any amino acid
<220> FEATURE:
<221> NAME/KEY: MOD_RES
<222> LOCATION: (18)..(21)
<223> OTHER INFORMATION: Any amino acid
<220> FEATURE:
<221> NAME/KEY: MOD_RES
<222> LOCATION: (23)..(31)
<223> OTHER INFORMATION: Any amino acid

<400> SEQUENCE: 125

Cys Xaa Xaa Xaa Cys Xaa Xaa Xaa Xaa Xaa Cys Xaa Xaa Xaa Cys Cys
1               5                   10                  15
```

```
Cys Xaa Xaa Xaa Xaa Cys Xaa Xaa Xaa Xaa Xaa Xaa Xaa Xaa Cys
            20                  25                  30
```

<210> SEQ ID NO 126
<211> LENGTH: 29
<212> TYPE: PRT
<213> ORGANISM: Artificial Sequence
<220> FEATURE:
<223> OTHER INFORMATION: Description of Artificial Sequence: Synthetic
      Cysteine motif peptide
<220> FEATURE:
<221> NAME/KEY: MOD_RES
<222> LOCATION: (3)..(11)
<223> OTHER INFORMATION: Any amino acid
<220> FEATURE:
<221> NAME/KEY: MOD_RES
<222> LOCATION: (13)..(15)
<223> OTHER INFORMATION: Any amino acid
<220> FEATURE:
<221> NAME/KEY: MOD_RES
<222> LOCATION: (17)..(17)
<223> OTHER INFORMATION: Any amino acid
<220> FEATURE:
<221> NAME/KEY: MOD_RES
<222> LOCATION: (20)..(22)
<223> OTHER INFORMATION: Any amino acid
<220> FEATURE:
<221> NAME/KEY: MOD_RES
<222> LOCATION: (24)..(28)
<223> OTHER INFORMATION: Any amino acid

<400> SEQUENCE: 126

```
Cys Cys Xaa Xaa Xaa Xaa Xaa Xaa Xaa Xaa Xaa Cys Xaa Xaa Xaa Cys
1               5                   10                  15

Xaa Cys Cys Xaa Xaa Xaa Cys Xaa Xaa Xaa Xaa Xaa Cys
            20                  25
```

<210> SEQ ID NO 127
<211> LENGTH: 35
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(10)
<223> OTHER INFORMATION: Any amino acid
<220> FEATURE:
<221> NAME/KEY: MOD_RES
<222> LOCATION: (12)..(13)
<223> OTHER INFORMATION: Any amino acid
<220> FEATURE:
<221> NAME/KEY: MOD_RES
<222> LOCATION: (15)..(17)
<223> OTHER INFORMATION: Any amino acid
<220> FEATURE:
<221> NAME/KEY: MOD_RES
<222> LOCATION: (19)..(22)
<223> OTHER INFORMATION: Any amino acid
<220> FEATURE:
<221> NAME/KEY: MOD_RES
<222> LOCATION: (25)..(28)
<223> OTHER INFORMATION: Any amino acid
<220> FEATURE:
<221> NAME/KEY: MOD_RES
<222> LOCATION: (30)..(34)
<223> OTHER INFORMATION: Any amino acid

<400> SEQUENCE: 127

```
Cys Xaa Xaa Xaa Xaa Xaa Xaa Xaa Xaa Xaa Cys Xaa Xaa Cys Xaa Xaa
1               5                   10                  15
```

Xaa Cys Xaa Xaa Xaa Xaa Cys Cys Xaa Xaa Xaa Cys Xaa Xaa Xaa
            20                  25                  30

Xaa Xaa Cys
        35

<210> SEQ ID NO 128
<211> LENGTH: 39
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(10)
<223> OTHER INFORMATION: Any amino acid
<220> FEATURE:
<221> NAME/KEY: MOD_RES
<222> LOCATION: (12)..(18)
<223> OTHER INFORMATION: Any amino acid
<220> FEATURE:
<221> NAME/KEY: MOD_RES
<222> LOCATION: (20)..(23)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(34)
<223> OTHER INFORMATION: Any amino acid
<220> FEATURE:
<221> NAME/KEY: MOD_RES
<222> LOCATION: (36)..(38)
<223> OTHER INFORMATION: Any amino acid

<400> SEQUENCE: 128

Cys Xaa Xaa Xaa Xaa Xaa Xaa Xaa Xaa Cys Xaa Xaa Xaa Xaa Xaa
1               5                   10                  15

Xaa Xaa Cys Xaa Xaa Xaa Xaa Cys Cys Xaa Cys Xaa Xaa Xaa Xaa
            20                  25                  30

Xaa Xaa Cys Xaa Xaa Xaa Cys
        35

<210> SEQ ID NO 129
<211> LENGTH: 35
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(10)
<223> OTHER INFORMATION: Any amino acid
<220> FEATURE:
<221> NAME/KEY: MOD_RES
<222> LOCATION: (12)..(14)
<223> OTHER INFORMATION: Any amino acid
<220> FEATURE:
<221> NAME/KEY: MOD_RES
<222> LOCATION: (18)..(27)
<223> OTHER INFORMATION: Any amino acid
<220> FEATURE:
<221> NAME/KEY: MOD_RES
<222> LOCATION: (29)..(30)
<223> OTHER INFORMATION: Any amino acid
<220> FEATURE:
<221> NAME/KEY: MOD_RES
<222> LOCATION: (32)..(34)
<223> OTHER INFORMATION: Any amino acid

<400> SEQUENCE: 129

Cys Xaa Xaa Xaa Xaa Xaa Xaa Xaa Xaa Cys Xaa Xaa Xaa Cys Cys
1               5                   10                  15

Cys Xaa Xaa Xaa Xaa Xaa Xaa Xaa Xaa Xaa Cys Xaa Xaa Cys Xaa
                20                  25                  30

Xaa Xaa Cys
        35

<210> SEQ ID NO 130
<211> LENGTH: 41
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(4)
<223> OTHER INFORMATION: Any amino acid
<220> FEATURE:
<221> NAME/KEY: MOD_RES
<222> LOCATION: (6)..(10)
<223> OTHER INFORMATION: Any amino acid
<220> FEATURE:
<221> NAME/KEY: MOD_RES
<222> LOCATION: (12)..(16)
<223> OTHER INFORMATION: Any amino acid
<220> FEATURE:
<221> NAME/KEY: MOD_RES
<222> LOCATION: (18)..(21)
<223> OTHER INFORMATION: Any amino acid
<220> FEATURE:
<221> NAME/KEY: MOD_RES
<222> LOCATION: (24)..(33)
<223> OTHER INFORMATION: Any amino acid
<220> FEATURE:
<221> NAME/KEY: MOD_RES
<222> LOCATION: (35)..(40)
<223> OTHER INFORMATION: Any amino acid

<400> SEQUENCE: 130

Cys Xaa Xaa Xaa Cys Xaa Xaa Xaa Xaa Xaa Cys Xaa Xaa Xaa Xaa
1               5                   10                  15

Cys Xaa Xaa Xaa Xaa Cys Cys Xaa Xaa Xaa Xaa Xaa Xaa Xaa Xaa
                20                  25                  30

Xaa Cys Xaa Xaa Xaa Xaa Xaa Xaa Cys
        35                  40

<210> SEQ ID NO 131
<211> LENGTH: 36
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(10)
<223> OTHER INFORMATION: Any amino acid
<220> FEATURE:
<221> NAME/KEY: MOD_RES
<222> LOCATION: (12)..(16)
<223> OTHER INFORMATION: Any amino acid
<220> FEATURE:
<221> NAME/KEY: MOD_RES
<222> LOCATION: (18)..(21)
<223> OTHER INFORMATION: Any amino acid
<220> FEATURE:
<221> NAME/KEY: MOD_RES
<222> LOCATION: (24)..(24)
<223> OTHER INFORMATION: Any amino acid

```
<220> FEATURE:
<221> NAME/KEY: MOD_RES
<222> LOCATION: (26)..(30)
<223> OTHER INFORMATION: Any amino acid
<220> FEATURE:
<221> NAME/KEY: MOD_RES
<222> LOCATION: (32)..(35)
<223> OTHER INFORMATION: Any amino acid

<400> SEQUENCE: 131

Cys Xaa Xaa Xaa Xaa Xaa Xaa Xaa Xaa Cys Xaa Xaa Xaa Xaa Xaa
1               5                   10                  15

Cys Xaa Xaa Xaa Xaa Cys Cys Xaa Cys Xaa Xaa Xaa Xaa Cys Xaa
                20                  25                  30

Xaa Xaa Xaa Cys
        35

<210> SEQ ID NO 132
<211> LENGTH: 36
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(8)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (12)..(17)
<223> OTHER INFORMATION: Any amino acid
<220> FEATURE:
<221> NAME/KEY: MOD_RES
<222> LOCATION: (19)..(22)
<223> OTHER INFORMATION: Any amino acid
<220> FEATURE:
<221> NAME/KEY: MOD_RES
<222> LOCATION: (26)..(35)
<223> OTHER INFORMATION: Any amino acid

<400> SEQUENCE: 132

Cys Xaa Xaa Xaa Xaa Xaa Xaa Xaa Cys Xaa Cys Xaa Xaa Xaa Xaa
1               5                   10                  15

Xaa Cys Xaa Xaa Xaa Xaa Cys Cys Cys Xaa Xaa Xaa Xaa Xaa Xaa
                20                  25                  30

Xaa Xaa Xaa Cys
        35

<210> SEQ ID NO 133
<211> LENGTH: 32
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(9)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (14)..(17)
```

```
<223> OTHER INFORMATION: Any amino acid
<220> FEATURE:
<221> NAME/KEY: MOD_RES
<222> LOCATION: (20)..(23)
<223> OTHER INFORMATION: Any amino acid
<220> FEATURE:
<221> NAME/KEY: MOD_RES
<222> LOCATION: (25)..(27)
<223> OTHER INFORMATION: Any amino acid
<220> FEATURE:
<221> NAME/KEY: MOD_RES
<222> LOCATION: (29)..(31)
<223> OTHER INFORMATION: Any amino acid

<400> SEQUENCE: 133

Cys Xaa Xaa Xaa Xaa Xaa Xaa Xaa Xaa Cys Xaa Xaa Cys Xaa Xaa Xaa
1               5                   10                  15

Xaa Cys Cys Xaa Xaa Xaa Xaa Cys Xaa Xaa Xaa Cys Xaa Xaa Xaa Cys
            20                  25                  30

<210> SEQ ID NO 134
<211> LENGTH: 36
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(8)
<223> OTHER INFORMATION: Any amino acid
<220> FEATURE:
<221> NAME/KEY: MOD_RES
<222> LOCATION: (10)..(14)
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (18)..(21)
<223> OTHER INFORMATION: Any amino acid
<220> FEATURE:
<221> NAME/KEY: MOD_RES
<222> LOCATION: (24)..(30)
<223> OTHER INFORMATION: Any amino acid
<220> FEATURE:
<221> NAME/KEY: MOD_RES
<222> LOCATION: (32)..(35)
<223> OTHER INFORMATION: Any amino acid

<400> SEQUENCE: 134

Cys Xaa Xaa Xaa Xaa Xaa Xaa Xaa Cys Xaa Xaa Xaa Xaa Xaa Cys Xaa
1               5                   10                  15

Cys Xaa Xaa Xaa Xaa Cys Cys Xaa Xaa Xaa Xaa Xaa Xaa Cys Xaa
            20                  25                  30

Xaa Xaa Xaa Cys
        35

<210> SEQ ID NO 135
<211> LENGTH: 36
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(12)
<223> OTHER INFORMATION: Any amino acid
<220> FEATURE:
```

```
<221> NAME/KEY: MOD_RES
<222> LOCATION: (14)..(16)
<223> OTHER INFORMATION: Any amino acid
<220> FEATURE:
<221> NAME/KEY: MOD_RES
<222> LOCATION: (18)..(21)
<223> OTHER INFORMATION: Any amino acid
<220> FEATURE:
<221> NAME/KEY: MOD_RES
<222> LOCATION: (25)..(32)
<223> OTHER INFORMATION: Any amino acid
<220> FEATURE:
<221> NAME/KEY: MOD_RES
<222> LOCATION: (34)..(35)
<223> OTHER INFORMATION: Any amino acid

<400> SEQUENCE: 135

Cys Xaa Xaa Xaa Xaa Xaa Xaa Xaa Xaa Xaa Xaa Cys Xaa Xaa
1               5                   10                  15

Cys Xaa Xaa Xaa Xaa Cys Cys Cys Xaa Xaa Xaa Xaa Xaa Xaa
            20                  25                  30

Cys Xaa Xaa Cys
        35

<210> SEQ ID NO 136
<211> LENGTH: 41
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(7)
<223> OTHER INFORMATION: Any amino acid
<220> FEATURE:
<221> NAME/KEY: MOD_RES
<222> LOCATION: (9)..(12)
<223> OTHER INFORMATION: Any amino acid
<220> FEATURE:
<221> NAME/KEY: MOD_RES
<222> LOCATION: (15)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(40)
<223> OTHER INFORMATION: Any amino acid

<400> SEQUENCE: 136

Cys Xaa Xaa Cys Xaa Xaa Xaa Cys Xaa Xaa Xaa Xaa Cys Cys Xaa Xaa
1               5                   10                  15

Xaa Xaa Cys Xaa Xaa Xaa Xaa Xaa Cys Xaa Xaa Xaa Xaa Xaa Xaa
            20                  25                  30

Xaa Xaa Xaa Xaa Xaa Xaa Xaa Xaa Cys
        35                  40

<210> SEQ ID NO 137
<211> LENGTH: 31
<212> TYPE: PRT
<213> ORGANISM: Artificial Sequence
<220> FEATURE:
<223> OTHER INFORMATION: Description of Artificial Sequence: Synthetic
      Cysteine motif polypeptide
```

<220> FEATURE:
<221> NAME/KEY: MOD_RES
<222> LOCATION: (2)..(10)
<223> OTHER INFORMATION: Any amino acid
<220> FEATURE:
<221> NAME/KEY: MOD_RES
<222> LOCATION: (12)..(16)
<223> OTHER INFORMATION: Any amino acid
<220> FEATURE:
<221> NAME/KEY: MOD_RES
<222> LOCATION: (18)..(21)
<223> OTHER INFORMATION: Any amino acid
<220> FEATURE:
<221> NAME/KEY: MOD_RES
<222> LOCATION: (24)..(30)
<223> OTHER INFORMATION: Any amino acid

<400> SEQUENCE: 137

Cys Xaa Xaa Xaa Xaa Xaa Xaa Xaa Xaa Cys Xaa Xaa Xaa Xaa Xaa
1               5                   10                  15

Cys Xaa Xaa Xaa Xaa Cys Cys Xaa Xaa Xaa Xaa Xaa Xaa Xaa Cys
                20                  25                  30

<210> SEQ ID NO 138
<211> LENGTH: 33
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(10)
<223> OTHER INFORMATION: Any amino acid
<220> FEATURE:
<221> NAME/KEY: MOD_RES
<222> LOCATION: (12)..(18)
<223> OTHER INFORMATION: Any amino acid
<220> FEATURE:
<221> NAME/KEY: MOD_RES
<222> LOCATION: (20)..(22)
<223> OTHER INFORMATION: Any amino acid
<220> FEATURE:
<221> NAME/KEY: MOD_RES
<222> LOCATION: (24)..(25)
<223> OTHER INFORMATION: Any amino acid
<220> FEATURE:
<221> NAME/KEY: MOD_RES
<222> LOCATION: (27)..(32)
<223> OTHER INFORMATION: Any amino acid

<400> SEQUENCE: 138

Cys Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Cys Xaa Xaa Cys Xaa Xaa Xaa Xaa Xaa
                20                  25                  30

Cys

<210> SEQ ID NO 139
<211> LENGTH: 38
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(10)
<223> OTHER INFORMATION: Any amino acid
<220> FEATURE:
<221> NAME/KEY: MOD_RES
<222> LOCATION: (12)..(16)

-continued

```
<223> OTHER INFORMATION: Any amino acid
<220> FEATURE:
<221> NAME/KEY: MOD_RES
<222> LOCATION: (18)..(21)
<223> OTHER INFORMATION: Any amino acid
<220> FEATURE:
<221> NAME/KEY: MOD_RES
<222> LOCATION: (24)..(37)
<223> OTHER INFORMATION: Any amino acid

<400> SEQUENCE: 139

Cys Xaa Xaa Xaa Xaa Xaa Xaa Xaa Xaa Cys Xaa Xaa Xaa Xaa Xaa
1               5                   10                  15

Cys Xaa Xaa Xaa Xaa Cys Cys Xaa Xaa Xaa Xaa Xaa Xaa Xaa Xaa
            20                  25                  30

Xaa Xaa Xaa Xaa Xaa Cys
        35

<210> SEQ ID NO 140
<211> LENGTH: 32
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(10)
<223> OTHER INFORMATION: Any amino acid
<220> FEATURE:
<221> NAME/KEY: MOD_RES
<222> LOCATION: (12)..(16)
<223> OTHER INFORMATION: Any amino acid
<220> FEATURE:
<221> NAME/KEY: MOD_RES
<222> LOCATION: (18)..(21)
<223> OTHER INFORMATION: Any amino acid
<220> FEATURE:
<221> NAME/KEY: MOD_RES
<222> LOCATION: (24)..(31)
<223> OTHER INFORMATION: Any amino acid

<400> SEQUENCE: 140

Cys Xaa Xaa Xaa Xaa Xaa Xaa Xaa Xaa Xaa Cys Xaa Xaa Xaa Xaa Xaa
1               5                   10                  15

Cys Xaa Xaa Xaa Xaa Cys Cys Xaa Xaa Xaa Xaa Xaa Xaa Xaa Xaa Cys
            20                  25                  30

<210> SEQ ID NO 141
<211> LENGTH: 26
<212> TYPE: PRT
<213> ORGANISM: Artificial Sequence
<220> FEATURE:
<223> OTHER INFORMATION: Description of Artificial Sequence: Synthetic
      Cysteine motif peptide
<220> FEATURE:
<221> NAME/KEY: MOD_RES
<222> LOCATION: (2)..(10)
<223> OTHER INFORMATION: Any amino acid
<220> FEATURE:
<221> NAME/KEY: MOD_RES
<222> LOCATION: (12)..(17)
<223> OTHER INFORMATION: Any amino acid
<220> FEATURE:
<221> NAME/KEY: MOD_RES
<222> LOCATION: (19)..(22)
<223> OTHER INFORMATION: Any amino acid
<220> FEATURE:
<221> NAME/KEY: MOD_RES
<222> LOCATION: (25)..(25)
<223> OTHER INFORMATION: Any amino acid
```

<400> SEQUENCE: 141

Cys Xaa Xaa Xaa Xaa Xaa Xaa Xaa Xaa Cys Xaa Xaa Xaa Xaa Xaa
1               5                   10                  15

Xaa Cys Xaa Xaa Xaa Xaa Cys Cys Xaa Cys
            20                  25

<210> SEQ ID NO 142
<211> LENGTH: 33
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(6)
<223> OTHER INFORMATION: Any amino acid
<220> FEATURE:
<221> NAME/KEY: MOD_RES
<222> LOCATION: (9)..(15)
<223> OTHER INFORMATION: Any amino acid
<220> FEATURE:
<221> NAME/KEY: MOD_RES
<222> LOCATION: (17)..(20)
<223> OTHER INFORMATION: Any amino acid
<220> FEATURE:
<221> NAME/KEY: MOD_RES
<222> LOCATION: (22)..(33)
<223> OTHER INFORMATION: Any amino acid

<400> SEQUENCE: 142

Cys Xaa Xaa Xaa Xaa Xaa Cys Cys Xaa Xaa Xaa Xaa Xaa Xaa Xaa Cys
1               5                   10                  15

Xaa Xaa Xaa Xaa Cys Xaa Xaa Xaa Xaa Xaa Xaa Xaa Xaa Xaa Xaa Xaa
            20                  25                  30

Xaa

<210> SEQ ID NO 143
<211> LENGTH: 27
<212> TYPE: PRT
<213> ORGANISM: Artificial Sequence
<220> FEATURE:
<223> OTHER INFORMATION: Description of Artificial Sequence: Synthetic
      Cysteine motif peptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(15)
<223> OTHER INFORMATION: Any amino acid
<220> FEATURE:
<221> NAME/KEY: MOD_RES
<222> LOCATION: (17)..(20)
<223> OTHER INFORMATION: Any amino acid
<220> FEATURE:
<221> NAME/KEY: MOD_RES
<222> LOCATION: (23)..(26)
<223> OTHER INFORMATION: Any amino acid

<400> SEQUENCE: 143

Cys Xaa Xaa Xaa Xaa Xaa Xaa Xaa Xaa Xaa Xaa Cys Xaa Xaa Xaa Cys
1               5                   10                  15

Xaa Xaa Xaa Xaa Cys Cys Xaa Xaa Xaa Xaa Cys
            20                  25

<210> SEQ ID NO 144
<211> LENGTH: 28

```
<212> TYPE: PRT
<213> ORGANISM: Artificial Sequence
<220> FEATURE:
<223> OTHER INFORMATION: Description of Artificial Sequence: Synthetic
      Cysteine motif peptide
<220> FEATURE:
<221> NAME/KEY: MOD_RES
<222> LOCATION: (2)..(10)
<223> OTHER INFORMATION: Any amino acid
<220> FEATURE:
<221> NAME/KEY: MOD_RES
<222> LOCATION: (12)..(15)
<223> OTHER INFORMATION: Any amino acid
<220> FEATURE:
<221> NAME/KEY: MOD_RES
<222> LOCATION: (18)..(22)
<223> OTHER INFORMATION: Any amino acid
<220> FEATURE:
<221> NAME/KEY: MOD_RES
<222> LOCATION: (24)..(27)
<223> OTHER INFORMATION: Any amino acid

<400> SEQUENCE: 144

Cys Xaa Xaa Xaa Xaa Xaa Xaa Xaa Xaa Cys Xaa Xaa Xaa Xaa Cys
1               5                   10                  15

Cys Xaa Xaa Xaa Xaa Xaa Cys Xaa Xaa Xaa Xaa Cys
            20                  25

<210> SEQ ID NO 145
<211> LENGTH: 31
<212> TYPE: PRT
<213> ORGANISM: Artificial Sequence
<220> FEATURE:
<223> OTHER INFORMATION: Description of Artificial Sequence: Synthetic
      Cysteine motif polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(15)
<223> OTHER INFORMATION: Any amino acid
<220> FEATURE:
<221> NAME/KEY: MOD_RES
<222> LOCATION: (17)..(20)
<223> OTHER INFORMATION: Any amino acid
<220> FEATURE:
<221> NAME/KEY: MOD_RES
<222> LOCATION: (22)..(28)
<223> OTHER INFORMATION: Any amino acid
<220> FEATURE:
<221> NAME/KEY: MOD_RES
<222> LOCATION: (30)..(30)
<223> OTHER INFORMATION: Any amino acid

<400> SEQUENCE: 145

Cys Xaa Xaa Xaa Xaa Xaa Xaa Xaa Xaa Xaa Xaa Cys Xaa Xaa Xaa Cys
1               5                   10                  15

Xaa Xaa Xaa Xaa Cys Xaa Xaa Xaa Xaa Xaa Xaa Xaa Cys Xaa Cys
            20                  25                  30

<210> SEQ ID NO 146
<211> LENGTH: 27
<212> TYPE: PRT
<213> ORGANISM: Artificial Sequence
<220> FEATURE:
<223> OTHER INFORMATION: Description of Artificial Sequence: Synthetic
      Cysteine motif peptide
<220> FEATURE:
<221> NAME/KEY: MOD_RES
<222> LOCATION: (2)..(8)
<223> OTHER INFORMATION: Any amino acid
```

<220> FEATURE:
<221> NAME/KEY: MOD_RES
<222> LOCATION: (10)..(16)
<223> OTHER INFORMATION: Any amino acid
<220> FEATURE:
<221> NAME/KEY: MOD_RES
<222> LOCATION: (18)..(19)
<223> OTHER INFORMATION: Any amino acid
<220> FEATURE:
<221> NAME/KEY: MOD_RES
<222> LOCATION: (21)..(22)
<223> OTHER INFORMATION: Any amino acid
<220> FEATURE:
<221> NAME/KEY: MOD_RES
<222> LOCATION: (24)..(26)
<223> OTHER INFORMATION: Any amino acid

<400> SEQUENCE: 146

Cys Xaa Xaa Xaa Xaa Xaa Xaa Cys Xaa Xaa Xaa Xaa Xaa Xaa Xaa
1               5                   10                  15

Cys Xaa Xaa Cys Xaa Xaa Cys Xaa Xaa Xaa Cys
            20                  25

<210> SEQ ID NO 147
<211> LENGTH: 29
<212> TYPE: PRT
<213> ORGANISM: Artificial Sequence
<220> FEATURE:
<223> OTHER INFORMATION: Description of Artificial Sequence: Synthetic
      Cysteine motif peptide
<220> FEATURE:
<221> NAME/KEY: MOD_RES
<222> LOCATION: (2)..(10)
<223> OTHER INFORMATION: Any amino acid
<220> FEATURE:
<221> NAME/KEY: MOD_RES
<222> LOCATION: (12)..(15)
<223> OTHER INFORMATION: Any amino acid
<220> FEATURE:
<221> NAME/KEY: MOD_RES
<222> LOCATION: (17)..(20)
<223> OTHER INFORMATION: Any amino acid
<220> FEATURE:
<221> NAME/KEY: MOD_RES
<222> LOCATION: (23)..(28)
<223> OTHER INFORMATION: Any amino acid

<400> SEQUENCE: 147

Cys Xaa Xaa Xaa Xaa Xaa Xaa Xaa Xaa Xaa Cys Xaa Xaa Xaa Xaa Cys
1               5                   10                  15

Xaa Xaa Xaa Xaa Cys Cys Xaa Xaa Xaa Xaa Xaa Xaa Cys
            20                  25

<210> SEQ ID NO 148
<211> LENGTH: 24
<212> TYPE: PRT
<213> ORGANISM: Artificial Sequence
<220> FEATURE:
<223> OTHER INFORMATION: Description of Artificial Sequence: Synthetic
      Cysteine motif peptide
<220> FEATURE:
<221> NAME/KEY: MOD_RES
<222> LOCATION: (2)..(8)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (12)..(14)
<223> OTHER INFORMATION: Any amino acid
<220> FEATURE:

```
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (18)..(23)
<223> OTHER INFORMATION: Any amino acid

<400> SEQUENCE: 148

Cys Xaa Xaa Xaa Xaa Xaa Xaa Cys Xaa Cys Xaa Xaa Xaa Cys Xaa
1               5                   10                  15

Cys Xaa Xaa Xaa Xaa Xaa Xaa Cys
            20

<210> SEQ ID NO 149
<211> LENGTH: 23
<212> TYPE: PRT
<213> ORGANISM: Artificial Sequence
<220> FEATURE:
<223> OTHER INFORMATION: Description of Artificial Sequence: Synthetic
      Cysteine motif peptide
<220> FEATURE:
<221> NAME/KEY: MOD_RES
<222> LOCATION: (2)..(8)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (12)..(15)
<223> OTHER INFORMATION: Any amino acid
<220> FEATURE:
<221> NAME/KEY: MOD_RES
<222> LOCATION: (17)..(17)
<223> OTHER INFORMATION: Any amino acid
<220> FEATURE:
<221> NAME/KEY: MOD_RES
<222> LOCATION: (19)..(22)
<223> OTHER INFORMATION: Any amino acid

<400> SEQUENCE: 149

Cys Xaa Xaa Xaa Xaa Xaa Xaa Xaa Cys Xaa Cys Xaa Xaa Xaa Xaa Cys
1               5                   10                  15

Xaa Cys Xaa Xaa Xaa Xaa Cys
            20

<210> SEQ ID NO 150
<211> LENGTH: 22
<212> TYPE: PRT
<213> ORGANISM: Artificial Sequence
<220> FEATURE:
<223> OTHER INFORMATION: Description of Artificial Sequence: Synthetic
      Cysteine motif peptide
<220> FEATURE:
<221> NAME/KEY: MOD_RES
<222> LOCATION: (2)..(10)
<223> OTHER INFORMATION: Any amino acid
<220> FEATURE:
<221> NAME/KEY: MOD_RES
<222> LOCATION: (12)..(16)
<223> OTHER INFORMATION: Any amino acid
<220> FEATURE:
<221> NAME/KEY: MOD_RES
<222> LOCATION: (18)..(21)
<223> OTHER INFORMATION: Any amino acid

<400> SEQUENCE: 150

Cys Xaa Xaa Xaa Xaa Xaa Xaa Xaa Xaa Xaa Cys Xaa Xaa Xaa Xaa Xaa
1               5                   10                  15
```

Cys Xaa Xaa Xaa Xaa Cys
            20

<210> SEQ ID NO 151
<211> LENGTH: 21
<212> TYPE: PRT
<213> ORGANISM: Artificial Sequence
<220> FEATURE:
<223> OTHER INFORMATION: Description of Artificial Sequence: Synthetic
      Cysteine motif peptide
<220> FEATURE:
<221> NAME/KEY: MOD_RES
<222> LOCATION: (2)..(4)
<223> OTHER INFORMATION: Any amino acid
<220> FEATURE:
<221> NAME/KEY: MOD_RES
<222> LOCATION: (6)..(11)
<223> OTHER INFORMATION: Any amino acid
<220> FEATURE:
<221> NAME/KEY: MOD_RES
<222> LOCATION: (13)..(20)
<223> OTHER INFORMATION: Any amino acid

<400> SEQUENCE: 151

Cys Xaa Xaa Xaa Cys Xaa Xaa Xaa Xaa Xaa Xaa Cys Xaa Xaa Xaa Xaa
1               5                   10                  15

Xaa Xaa Xaa Xaa Cys
            20

<210> SEQ ID NO 152
<211> LENGTH: 19
<212> TYPE: PRT
<213> ORGANISM: Artificial Sequence
<220> FEATURE:
<223> OTHER INFORMATION: Description of Artificial Sequence: Synthetic
      Cysteine motif peptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (15)..(18)
<223> OTHER INFORMATION: Any amino acid

<400> SEQUENCE: 152

Cys Xaa Xaa Xaa Xaa Xaa Xaa Xaa Xaa Xaa Xaa Cys Xaa Cys Xaa Xaa
1               5                   10                  15

Xaa Xaa Cys

<210> SEQ ID NO 153
<211> LENGTH: 18
<212> TYPE: PRT
<213> ORGANISM: Artificial Sequence
<220> FEATURE:
<223> OTHER INFORMATION: Description of Artificial Sequence: Synthetic
      Cysteine motif peptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (14)..(17)
<223> OTHER INFORMATION: Any amino acid

<400> SEQUENCE: 153

-continued

Cys Xaa Xaa Xaa Xaa Xaa Xaa Xaa Xaa Xaa Cys Cys Xaa Xaa Xaa
1               5                   10                  15

Xaa Cys

<210> SEQ ID NO 154
<211> LENGTH: 17
<212> TYPE: PRT
<213> ORGANISM: Artificial Sequence
<220> FEATURE:
<223> OTHER INFORMATION: Description of Artificial Sequence: Synthetic
      Cysteine motif peptide
<220> FEATURE:
<221> NAME/KEY: MOD_RES
<222> LOCATION: (2)..(16)
<223> OTHER INFORMATION: Any amino acid

<400> SEQUENCE: 154

Cys Xaa Xaa Xaa Xaa Xaa Xaa Xaa Xaa Xaa Xaa Xaa Xaa Xaa Xaa
1               5                   10                  15

Cys

<210> SEQ ID NO 155
<211> LENGTH: 12
<212> TYPE: PRT
<213> ORGANISM: Artificial Sequence
<220> FEATURE:
<223> OTHER INFORMATION: Description of Artificial Sequence: Synthetic
      Cysteine motif peptide
<220> FEATURE:
<221> NAME/KEY: MOD_RES
<222> LOCATION: (2)..(11)
<223> OTHER INFORMATION: Any amino acid

<400> SEQUENCE: 155

Cys Xaa Xaa Xaa Xaa Xaa Xaa Xaa Xaa Xaa Xaa Cys
1               5                   10

<210> SEQ ID NO 156
<211> LENGTH: 11
<212> TYPE: PRT
<213> ORGANISM: Artificial Sequence
<220> FEATURE:
<223> OTHER INFORMATION: Description of Artificial Sequence: Synthetic
      Cysteine motif peptide
<220> FEATURE:
<221> NAME/KEY: MOD_RES
<222> LOCATION: (2)..(10)
<223> OTHER INFORMATION: Any amino acid

<400> SEQUENCE: 156

Cys Xaa Xaa Xaa Xaa Xaa Xaa Xaa Xaa Cys
1               5                   10

<210> SEQ ID NO 157
<211> LENGTH: 11
<212> TYPE: PRT
<213> ORGANISM: Bos taurus
<220> FEATURE:
<223> OTHER INFORMATION: Stalk motif 1

<400> SEQUENCE: 157

Thr Ser Val His Gln Glu Thr Lys Lys Tyr Gln
1               5                   10

<210> SEQ ID NO 158
<211> LENGTH: 9
<212> TYPE: PRT
<213> ORGANISM: Bos taurus

```
<220> FEATURE:
<223> OTHER INFORMATION: Stalk motif 1

<400> SEQUENCE: 158

Val His Gln Glu Thr Lys Lys Tyr Gln
1               5

<210> SEQ ID NO 159
<211> LENGTH: 5
<212> TYPE: PRT
<213> ORGANISM: Bos taurus
<220> FEATURE:
<223> OTHER INFORMATION: Stalk motif 1

<400> SEQUENCE: 159

Thr Thr Val His Gln
1               5

<210> SEQ ID NO 160
<211> LENGTH: 5
<212> TYPE: PRT
<213> ORGANISM: Bos taurus
<220> FEATURE:
<223> OTHER INFORMATION: Stalk motif 1

<400> SEQUENCE: 160

Thr Ser Val His Gln
1               5

<210> SEQ ID NO 161
<211> LENGTH: 5
<212> TYPE: PRT
<213> ORGANISM: Bos taurus
<220> FEATURE:
<223> OTHER INFORMATION: Stalk motif 1

<400> SEQUENCE: 161

Ser Ser Val Thr Gln
1               5

<210> SEQ ID NO 162
<211> LENGTH: 5
<212> TYPE: PRT
<213> ORGANISM: Bos taurus
<220> FEATURE:
<223> OTHER INFORMATION: Stalk motif 1

<400> SEQUENCE: 162

Ser Thr Val His Gln
1               5

<210> SEQ ID NO 163
<211> LENGTH: 5
<212> TYPE: PRT
<213> ORGANISM: Bos taurus
<220> FEATURE:
<223> OTHER INFORMATION: Stalk motif 1

<400> SEQUENCE: 163

Ala Thr Val Arg Gln
1               5

<210> SEQ ID NO 164
<211> LENGTH: 5
<212> TYPE: PRT
<213> ORGANISM: Bos taurus
<220> FEATURE:
```

```
<223> OTHER INFORMATION: Stalk motif 1

<400> SEQUENCE: 164

Thr Thr Val Tyr Gln
1               5

<210> SEQ ID NO 165
<211> LENGTH: 5
<212> TYPE: PRT
<213> ORGANISM: Bos taurus
<220> FEATURE:
<223> OTHER INFORMATION: Stalk motif 1

<400> SEQUENCE: 165

Ser Pro Val His Gln
1               5

<210> SEQ ID NO 166
<211> LENGTH: 5
<212> TYPE: PRT
<213> ORGANISM: Bos taurus
<220> FEATURE:
<223> OTHER INFORMATION: Stalk motif 1

<400> SEQUENCE: 166

Ala Thr Val Tyr Gln
1               5

<210> SEQ ID NO 167
<211> LENGTH: 5
<212> TYPE: PRT
<213> ORGANISM: Bos taurus
<220> FEATURE:
<223> OTHER INFORMATION: Stalk motif 1

<400> SEQUENCE: 167

Thr Ala Val Tyr Gln
1               5

<210> SEQ ID NO 168
<211> LENGTH: 5
<212> TYPE: PRT
<213> ORGANISM: Bos taurus
<220> FEATURE:
<223> OTHER INFORMATION: Stalk motif 1

<400> SEQUENCE: 168

Thr Asn Val His Gln
1               5

<210> SEQ ID NO 169
<211> LENGTH: 5
<212> TYPE: PRT
<213> ORGANISM: Bos taurus
<220> FEATURE:
<223> OTHER INFORMATION: Stalk motif 1

<400> SEQUENCE: 169

Ala Thr Val His Gln
1               5

<210> SEQ ID NO 170
<211> LENGTH: 5
<212> TYPE: PRT
<213> ORGANISM: Bos taurus
<220> FEATURE:
<223> OTHER INFORMATION: Stalk motif 1
```

```
<400> SEQUENCE: 170

Ser Thr Val Tyr Gln
1               5

<210> SEQ ID NO 171
<211> LENGTH: 5
<212> TYPE: PRT
<213> ORGANISM: Bos taurus
<220> FEATURE:
<223> OTHER INFORMATION: Stalk motif 1

<400> SEQUENCE: 171

Thr Ile Val His Gln
1               5

<210> SEQ ID NO 172
<211> LENGTH: 5
<212> TYPE: PRT
<213> ORGANISM: Bos taurus
<220> FEATURE:
<223> OTHER INFORMATION: Stalk motif 1

<400> SEQUENCE: 172

Ala Ile Val Tyr Gln
1               5

<210> SEQ ID NO 173
<211> LENGTH: 5
<212> TYPE: PRT
<213> ORGANISM: Bos taurus
<220> FEATURE:
<223> OTHER INFORMATION: Stalk motif 1

<400> SEQUENCE: 173

Thr Thr Val Phe Gln
1               5

<210> SEQ ID NO 174
<211> LENGTH: 5
<212> TYPE: PRT
<213> ORGANISM: Bos taurus
<220> FEATURE:
<223> OTHER INFORMATION: Stalk motif 1

<400> SEQUENCE: 174

Ala Ala Val Phe Gln
1               5

<210> SEQ ID NO 175
<211> LENGTH: 5
<212> TYPE: PRT
<213> ORGANISM: Bos taurus
<220> FEATURE:
<223> OTHER INFORMATION: Stalk motif 1

<400> SEQUENCE: 175

Gly Thr Val His Gln
1               5

<210> SEQ ID NO 176
<211> LENGTH: 5
<212> TYPE: PRT
<213> ORGANISM: Bos taurus
<220> FEATURE:
<223> OTHER INFORMATION: Stalk motif 1
```

```
<400> SEQUENCE: 176

Ala Ser Val His Gln
1               5

<210> SEQ ID NO 177
<211> LENGTH: 5
<212> TYPE: PRT
<213> ORGANISM: Bos taurus
<220> FEATURE:
<223> OTHER INFORMATION: Stalk motif 1

<400> SEQUENCE: 177

Thr Ala Val Phe Gln
1               5

<210> SEQ ID NO 178
<211> LENGTH: 5
<212> TYPE: PRT
<213> ORGANISM: Bos taurus
<220> FEATURE:
<223> OTHER INFORMATION: Stalk motif 1

<400> SEQUENCE: 178

Ala Thr Val Phe Gln
1               5

<210> SEQ ID NO 179
<211> LENGTH: 5
<212> TYPE: PRT
<213> ORGANISM: Bos taurus
<220> FEATURE:
<223> OTHER INFORMATION: Stalk motif 1

<400> SEQUENCE: 179

Ala Ala Ala His Gln
1               5

<210> SEQ ID NO 180
<211> LENGTH: 5
<212> TYPE: PRT
<213> ORGANISM: Bos taurus
<220> FEATURE:
<223> OTHER INFORMATION: Stalk motif 1

<400> SEQUENCE: 180

Val Val Val Tyr Gln
1               5

<210> SEQ ID NO 181
<211> LENGTH: 5
<212> TYPE: PRT
<213> ORGANISM: Bos taurus
<220> FEATURE:
<223> OTHER INFORMATION: Stalk motif 1

<400> SEQUENCE: 181

Gly Thr Val Phe Gln
1               5

<210> SEQ ID NO 182
<211> LENGTH: 5
<212> TYPE: PRT
<213> ORGANISM: Bos taurus
<220> FEATURE:
<223> OTHER INFORMATION: Stalk motif 1

<400> SEQUENCE: 182
```

Thr Ala Val His Gln
1               5

<210> SEQ ID NO 183
<211> LENGTH: 5
<212> TYPE: PRT
<213> ORGANISM: Bos taurus
<220> FEATURE:
<223> OTHER INFORMATION: Stalk motif 1

<400> SEQUENCE: 183

Ile Thr Val His Gln
1               5

<210> SEQ ID NO 184
<211> LENGTH: 5
<212> TYPE: PRT
<213> ORGANISM: Bos taurus
<220> FEATURE:
<223> OTHER INFORMATION: Stalk motif 1

<400> SEQUENCE: 184

Ile Thr Ala His Gln
1               5

<210> SEQ ID NO 185
<211> LENGTH: 5
<212> TYPE: PRT
<213> ORGANISM: Bos taurus
<220> FEATURE:
<223> OTHER INFORMATION: Stalk motif 1

<400> SEQUENCE: 185

Val Thr Val His Gln
1               5

<210> SEQ ID NO 186
<211> LENGTH: 5
<212> TYPE: PRT
<213> ORGANISM: Bos taurus
<220> FEATURE:
<223> OTHER INFORMATION: Stalk motif 1

<400> SEQUENCE: 186

Ala Ala Val His Gln
1               5

<210> SEQ ID NO 187
<211> LENGTH: 5
<212> TYPE: PRT
<213> ORGANISM: Bos taurus
<220> FEATURE:
<223> OTHER INFORMATION: Stalk motif 1

<400> SEQUENCE: 187

Gly Thr Val Tyr Gln
1               5

<210> SEQ ID NO 188
<211> LENGTH: 5
<212> TYPE: PRT
<213> ORGANISM: Bos taurus
<220> FEATURE:
<223> OTHER INFORMATION: Stalk motif 1

<400> SEQUENCE: 188

```
Thr Thr Val Leu Gln
1               5

<210> SEQ ID NO 189
<211> LENGTH: 5
<212> TYPE: PRT
<213> ORGANISM: Bos taurus
<220> FEATURE:
<223> OTHER INFORMATION: Stalk motif 1

<400> SEQUENCE: 189

Thr Thr Thr His Gln
1               5

<210> SEQ ID NO 190
<211> LENGTH: 5
<212> TYPE: PRT
<213> ORGANISM: Bos taurus
<220> FEATURE:
<223> OTHER INFORMATION: Stalk motif 1

<400> SEQUENCE: 190

Thr Thr Asp Tyr Gln
1               5

<210> SEQ ID NO 191
<211> LENGTH: 5
<212> TYPE: PRT
<213> ORGANISM: Bos taurus
<220> FEATURE:
<223> OTHER INFORMATION: Stalk motif 1

<400> SEQUENCE: 191

Thr Thr Asp Tyr Gln
1               5

<210> SEQ ID NO 192
<211> LENGTH: 6
<212> TYPE: PRT
<213> ORGANISM: Bos taurus
<220> FEATURE:
<223> OTHER INFORMATION: Stalk motif 1

<400> SEQUENCE: 192

Cys Thr Ser Val His Gln
1               5

<210> SEQ ID NO 193
<211> LENGTH: 6
<212> TYPE: PRT
<213> ORGANISM: Bos taurus
<220> FEATURE:
<223> OTHER INFORMATION: Stalk motif 1

<400> SEQUENCE: 193

Cys Ser Ser Val Thr Gln
1               5

<210> SEQ ID NO 194
<211> LENGTH: 6
<212> TYPE: PRT
<213> ORGANISM: Bos taurus
<220> FEATURE:
<223> OTHER INFORMATION: Stalk motif 1

<400> SEQUENCE: 194

Cys Ser Thr Val His Gln
```

```
1               5

<210> SEQ ID NO 195
<211> LENGTH: 6
<212> TYPE: PRT
<213> ORGANISM: Bos taurus
<220> FEATURE:
<223> OTHER INFORMATION: Stalk motif 1

<400> SEQUENCE: 195

Cys Ala Thr Val Arg Gln
1               5

<210> SEQ ID NO 196
<211> LENGTH: 6
<212> TYPE: PRT
<213> ORGANISM: Bos taurus
<220> FEATURE:
<223> OTHER INFORMATION: Stalk motif 1

<400> SEQUENCE: 196

Cys Thr Thr Val Tyr Gln
1               5

<210> SEQ ID NO 197
<211> LENGTH: 6
<212> TYPE: PRT
<213> ORGANISM: Bos taurus
<220> FEATURE:
<223> OTHER INFORMATION: Stalk motif 1

<400> SEQUENCE: 197

Cys Ser Pro Val His Gln
1               5

<210> SEQ ID NO 198
<211> LENGTH: 6
<212> TYPE: PRT
<213> ORGANISM: Bos taurus
<220> FEATURE:
<223> OTHER INFORMATION: Stalk motif 1

<400> SEQUENCE: 198

Cys Ala Thr Val Tyr Gln
1               5

<210> SEQ ID NO 199
<211> LENGTH: 6
<212> TYPE: PRT
<213> ORGANISM: Bos taurus
<220> FEATURE:
<223> OTHER INFORMATION: Stalk motif 1

<400> SEQUENCE: 199

Cys Thr Ala Val Tyr Gln
1               5

<210> SEQ ID NO 200
<211> LENGTH: 6
<212> TYPE: PRT
<213> ORGANISM: Bos taurus
<220> FEATURE:
<223> OTHER INFORMATION: Stalk motif 1

<400> SEQUENCE: 200

Cys Thr Asn Val His Gln
1               5
```

<210> SEQ ID NO 201
<211> LENGTH: 6
<212> TYPE: PRT
<213> ORGANISM: Bos taurus
<220> FEATURE:
<223> OTHER INFORMATION: Stalk motif 1

<400> SEQUENCE: 201

Cys Ala Thr Val His Gln
1               5

<210> SEQ ID NO 202
<211> LENGTH: 6
<212> TYPE: PRT
<213> ORGANISM: Bos taurus
<220> FEATURE:
<223> OTHER INFORMATION: Stalk motif 1

<400> SEQUENCE: 202

Cys Ser Thr Val Tyr Gln
1               5

<210> SEQ ID NO 203
<211> LENGTH: 6
<212> TYPE: PRT
<213> ORGANISM: Bos taurus
<220> FEATURE:
<223> OTHER INFORMATION: Stalk motif 1

<400> SEQUENCE: 203

Cys Thr Ile Val His Gln
1               5

<210> SEQ ID NO 204
<211> LENGTH: 6
<212> TYPE: PRT
<213> ORGANISM: Bos taurus
<220> FEATURE:
<223> OTHER INFORMATION: Stalk motif 1

<400> SEQUENCE: 204

Cys Ala Ile Val Tyr Gln
1               5

<210> SEQ ID NO 205
<211> LENGTH: 6
<212> TYPE: PRT
<213> ORGANISM: Bos taurus
<220> FEATURE:
<223> OTHER INFORMATION: Stalk motif 1

<400> SEQUENCE: 205

Cys Thr Thr Val Phe Gln
1               5

<210> SEQ ID NO 206
<211> LENGTH: 6
<212> TYPE: PRT
<213> ORGANISM: Bos taurus
<220> FEATURE:
<223> OTHER INFORMATION: Stalk motif 1

<400> SEQUENCE: 206

Cys Ala Ala Val Phe Gln
1               5

<210> SEQ ID NO 207
<211> LENGTH: 6
<212> TYPE: PRT
<213> ORGANISM: Bos taurus
<220> FEATURE:
<223> OTHER INFORMATION: Stalk motif 1

<400> SEQUENCE: 207

Cys Gly Thr Val His Gln
1               5

<210> SEQ ID NO 208
<211> LENGTH: 6
<212> TYPE: PRT
<213> ORGANISM: Bos taurus
<220> FEATURE:
<223> OTHER INFORMATION: Stalk motif 1

<400> SEQUENCE: 208

Cys Ala Ser Val His Gln
1               5

<210> SEQ ID NO 209
<211> LENGTH: 6
<212> TYPE: PRT
<213> ORGANISM: Bos taurus
<220> FEATURE:
<223> OTHER INFORMATION: Stalk motif 1

<400> SEQUENCE: 209

Cys Thr Ala Val Phe Gln
1               5

<210> SEQ ID NO 210
<211> LENGTH: 6
<212> TYPE: PRT
<213> ORGANISM: Bos taurus
<220> FEATURE:
<223> OTHER INFORMATION: Stalk motif 1

<400> SEQUENCE: 210

Cys Ala Thr Val Phe Gln
1               5

<210> SEQ ID NO 211
<211> LENGTH: 6
<212> TYPE: PRT
<213> ORGANISM: Bos taurus
<220> FEATURE:
<223> OTHER INFORMATION: Stalk motif 1

<400> SEQUENCE: 211

Cys Ala Ala Ala His Gln
1               5

<210> SEQ ID NO 212
<211> LENGTH: 6
<212> TYPE: PRT
<213> ORGANISM: Bos taurus
<220> FEATURE:
<223> OTHER INFORMATION: Stalk motif 1

<400> SEQUENCE: 212

Cys Val Val Val Tyr Gln
1               5

<210> SEQ ID NO 213
<211> LENGTH: 6
<212> TYPE: PRT
<213> ORGANISM: Bos taurus
<220> FEATURE:
<223> OTHER INFORMATION: Stalk motif 1

<400> SEQUENCE: 213

Cys Gly Thr Val Phe Gln
1               5

<210> SEQ ID NO 214
<211> LENGTH: 6
<212> TYPE: PRT
<213> ORGANISM: Bos taurus
<220> FEATURE:
<223> OTHER INFORMATION: Stalk motif 1

<400> SEQUENCE: 214

Cys Thr Ala Val His Gln
1               5

<210> SEQ ID NO 215
<211> LENGTH: 6
<212> TYPE: PRT
<213> ORGANISM: Bos taurus
<220> FEATURE:
<223> OTHER INFORMATION: Stalk motif 1

<400> SEQUENCE: 215

Cys Ile Thr Val His Gln
1               5

<210> SEQ ID NO 216
<211> LENGTH: 6
<212> TYPE: PRT
<213> ORGANISM: Bos taurus
<220> FEATURE:
<223> OTHER INFORMATION: Stalk motif 1

<400> SEQUENCE: 216

Cys Ile Thr Ala His Gln
1               5

<210> SEQ ID NO 217
<211> LENGTH: 6
<212> TYPE: PRT
<213> ORGANISM: Bos taurus
<220> FEATURE:
<223> OTHER INFORMATION: Stalk motif 1

<400> SEQUENCE: 217

Cys Val Thr Val His Gln
1               5

<210> SEQ ID NO 218
<211> LENGTH: 6
<212> TYPE: PRT
<213> ORGANISM: Bos taurus
<220> FEATURE:
<223> OTHER INFORMATION: Stalk motif 1

<400> SEQUENCE: 218

Cys Ala Ala Val His Gln
1               5

<210> SEQ ID NO 219

```
<211> LENGTH: 6
<212> TYPE: PRT
<213> ORGANISM: Bos taurus
<220> FEATURE:
<223> OTHER INFORMATION: Stalk motif 1

<400> SEQUENCE: 219

Cys Gly Thr Val Tyr Gln
1               5

<210> SEQ ID NO 220
<211> LENGTH: 6
<212> TYPE: PRT
<213> ORGANISM: Bos taurus
<220> FEATURE:
<223> OTHER INFORMATION: Stalk motif 1

<400> SEQUENCE: 220

Cys Thr Thr Val Leu Gln
1               5

<210> SEQ ID NO 221
<211> LENGTH: 6
<212> TYPE: PRT
<213> ORGANISM: Bos taurus
<220> FEATURE:
<223> OTHER INFORMATION: Stalk motif 1

<400> SEQUENCE: 221

Cys Thr Thr Thr His Gln
1               5

<210> SEQ ID NO 222
<211> LENGTH: 6
<212> TYPE: PRT
<213> ORGANISM: Bos taurus
<220> FEATURE:
<223> OTHER INFORMATION: Stalk motif 1

<400> SEQUENCE: 222

Cys Thr Thr Asp Tyr Gln
1               5

<210> SEQ ID NO 223
<211> LENGTH: 7
<212> TYPE: PRT
<213> ORGANISM: Bos taurus
<220> FEATURE:
<223> OTHER INFORMATION: Stalk motif 1
<220> FEATURE:
<221> NAME/KEY: MOD_RES
<222> LOCATION: (7)..(7)
<223> OTHER INFORMATION: Any amino acid

<400> SEQUENCE: 223

Cys Thr Thr Val His Gln Xaa
1               5

<210> SEQ ID NO 224
<211> LENGTH: 14
<212> TYPE: PRT
<213> ORGANISM: Bos taurus
<220> FEATURE:
<223> OTHER INFORMATION: Stalk motif 1
<220> FEATURE:
<221> NAME/KEY: MOD_RES
<222> LOCATION: (7)..(14)
<223> OTHER INFORMATION: Any amino acid and this region may encompass
      1-8 residues
```

```
<400> SEQUENCE: 224

Cys Thr Ser Val His Gln Xaa Xaa Xaa Xaa Xaa Xaa Xaa Xaa
1               5                   10

<210> SEQ ID NO 225
<211> LENGTH: 3
<212> TYPE: PRT
<213> ORGANISM: Bos taurus
<220> FEATURE:
<223> OTHER INFORMATION: Stalk motif 1

<400> SEQUENCE: 225

Val His Gln
1

<210> SEQ ID NO 226
<211> LENGTH: 3
<212> TYPE: PRT
<213> ORGANISM: Bos taurus
<220> FEATURE:
<223> OTHER INFORMATION: Stalk motif 1

<400> SEQUENCE: 226

Lys Lys Gln
1

<210> SEQ ID NO 227
<211> LENGTH: 3
<212> TYPE: PRT
<213> ORGANISM: Bos taurus
<220> FEATURE:
<223> OTHER INFORMATION: Stalk motif 1

<400> SEQUENCE: 227

Val Tyr Gln
1

<210> SEQ ID NO 228
<211> LENGTH: 6
<212> TYPE: PRT
<213> ORGANISM: Bos taurus
<220> FEATURE:
<223> OTHER INFORMATION: Stalk motif 1
<220> FEATURE:
<221> NAME/KEY: MOD_RES
<222> LOCATION: (2)..(2)
<223> OTHER INFORMATION: Thr, Ser, Ala or Gly
<220> FEATURE:
<221> NAME/KEY: MOD_RES
<222> LOCATION: (3)..(3)
<223> OTHER INFORMATION: Thr, Ser, Ala, Pro or Ile
<220> FEATURE:
<221> NAME/KEY: MOD_RES
<222> LOCATION: (4)..(4)
<223> OTHER INFORMATION: Val or Lys
<220> FEATURE:
<221> NAME/KEY: MOD_RES
<222> LOCATION: (5)..(5)
<223> OTHER INFORMATION: His, Lys or Tyr

<400> SEQUENCE: 228

Cys Xaa Xaa Xaa Xaa Gln
1               5

<210> SEQ ID NO 229
<211> LENGTH: 5
<212> TYPE: PRT
<213> ORGANISM: Bos taurus
```

```
<220> FEATURE:
<223> OTHER INFORMATION: Stalk motif 1
<220> FEATURE:
<221> NAME/KEY: MOD_RES
<222> LOCATION: (1)..(1)
<223> OTHER INFORMATION: Thr, Ser, Ala or Gly
<220> FEATURE:
<221> NAME/KEY: MOD_RES
<222> LOCATION: (2)..(2)
<223> OTHER INFORMATION: Thr, Ser, Ala, Pro or Ile

<400> SEQUENCE: 229

Xaa Xaa Val His Gln
1               5

<210> SEQ ID NO 230
<211> LENGTH: 6
<212> TYPE: PRT
<213> ORGANISM: Bos taurus
<220> FEATURE:
<223> OTHER INFORMATION: Stalk motif 1
<220> FEATURE:
<221> NAME/KEY: MOD_RES
<222> LOCATION: (2)..(2)
<223> OTHER INFORMATION: Thr, Ser, Ala or Gly
<220> FEATURE:
<221> NAME/KEY: MOD_RES
<222> LOCATION: (3)..(3)
<223> OTHER INFORMATION: Thr, Ser, Ala, Pro or Ile

<400> SEQUENCE: 230

Cys Xaa Xaa Val His Gln
1               5

<210> SEQ ID NO 231
<211> LENGTH: 5
<212> TYPE: PRT
<213> ORGANISM: Bos taurus
<220> FEATURE:
<223> OTHER INFORMATION: Stalk motif 1
<220> FEATURE:
<221> NAME/KEY: MOD_RES
<222> LOCATION: (1)..(1)
<223> OTHER INFORMATION: Thr, Ser, Ala or Gly
<220> FEATURE:
<221> NAME/KEY: MOD_RES
<222> LOCATION: (2)..(2)
<223> OTHER INFORMATION: Thr, Ser, Ala, Pro or Ile
<220> FEATURE:
<221> NAME/KEY: MOD_RES
<222> LOCATION: (4)..(4)
<223> OTHER INFORMATION: His, Tyr or Lys

<400> SEQUENCE: 231

Xaa Xaa Val Xaa Gln
1               5

<210> SEQ ID NO 232
<211> LENGTH: 6
<212> TYPE: PRT
<213> ORGANISM: Bos taurus
<220> FEATURE:
<223> OTHER INFORMATION: Stalk motif 1
<220> FEATURE:
<221> NAME/KEY: MOD_RES
<222> LOCATION: (2)..(2)
<223> OTHER INFORMATION: Thr, Ser, Ala or Gly
<220> FEATURE:
<221> NAME/KEY: MOD_RES
<222> LOCATION: (3)..(3)
<223> OTHER INFORMATION: Thr, Ser, Ala, Pro or Ile
<220> FEATURE:
<221> NAME/KEY: MOD_RES
```

```
<222> LOCATION: (5)..(5)
<223> OTHER INFORMATION: His, Tyr or Lys

<400> SEQUENCE: 232

Cys Xaa Xaa Val Xaa Gln
1               5

<210> SEQ ID NO 233
<211> LENGTH: 5
<212> TYPE: PRT
<213> ORGANISM: Bos taurus
<220> FEATURE:
<223> OTHER INFORMATION: Stalk motif 1
<220> FEATURE:
<221> NAME/KEY: MOD_RES
<222> LOCATION: (1)..(1)
<223> OTHER INFORMATION: Thr, Ser, Ala or Gly
<220> FEATURE:
<221> NAME/KEY: MOD_RES
<222> LOCATION: (2)..(2)
<223> OTHER INFORMATION: Thr, Ser, Ala, Pro or Ile

<400> SEQUENCE: 233

Xaa Xaa Lys Lys Gln
1               5

<210> SEQ ID NO 234
<211> LENGTH: 6
<212> TYPE: PRT
<213> ORGANISM: Bos taurus
<220> FEATURE:
<223> OTHER INFORMATION: Stalk motif 1
<220> FEATURE:
<221> NAME/KEY: MOD_RES
<222> LOCATION: (2)..(2)
<223> OTHER INFORMATION: Thr, Ser, Ala or Gly
<220> FEATURE:
<221> NAME/KEY: MOD_RES
<222> LOCATION: (3)..(3)
<223> OTHER INFORMATION: Thr, Ser, Ala, Pro or Ile

<400> SEQUENCE: 234

Cys Xaa Xaa Lys Lys Gln
1               5

<210> SEQ ID NO 235
<211> LENGTH: 7
<212> TYPE: PRT
<213> ORGANISM: Bos taurus
<220> FEATURE:
<223> OTHER INFORMATION: Stalk motif 2

<400> SEQUENCE: 235

Tyr Thr Tyr Asn Tyr Glu Trp
1               5

<210> SEQ ID NO 236
<211> LENGTH: 6
<212> TYPE: PRT
<213> ORGANISM: Bos taurus
<220> FEATURE:
<223> OTHER INFORMATION: Stalk motif 2

<400> SEQUENCE: 236

Tyr Thr Tyr Asn Tyr Glu
1               5

<210> SEQ ID NO 237
<211> LENGTH: 7
```

```
<212> TYPE: PRT
<213> ORGANISM: Bos taurus
<220> FEATURE:
<223> OTHER INFORMATION: Stalk motif 2

<400> SEQUENCE: 237

Tyr Leu Tyr Thr Tyr Glu His
1               5

<210> SEQ ID NO 238
<211> LENGTH: 6
<212> TYPE: PRT
<213> ORGANISM: Bos taurus
<220> FEATURE:
<223> OTHER INFORMATION: Stalk motif 2

<400> SEQUENCE: 238

Tyr Leu Tyr Thr Tyr Glu
1               5

<210> SEQ ID NO 239
<211> LENGTH: 8
<212> TYPE: PRT
<213> ORGANISM: Bos taurus
<220> FEATURE:
<223> OTHER INFORMATION: Stalk motif 2

<400> SEQUENCE: 239

Cys Tyr Thr Tyr Asn Tyr Glu Phe
1               5

<210> SEQ ID NO 240
<211> LENGTH: 8
<212> TYPE: PRT
<213> ORGANISM: Bos taurus
<220> FEATURE:
<223> OTHER INFORMATION: Stalk motif 2

<400> SEQUENCE: 240

His Tyr Thr Tyr Thr Tyr Asp Phe
1               5

<210> SEQ ID NO 241
<211> LENGTH: 8
<212> TYPE: PRT
<213> ORGANISM: Bos taurus
<220> FEATURE:
<223> OTHER INFORMATION: Stalk motif 2

<400> SEQUENCE: 241

His Tyr Thr Tyr Thr Tyr Glu Trp
1               5

<210> SEQ ID NO 242
<211> LENGTH: 8
<212> TYPE: PRT
<213> ORGANISM: Bos taurus
<220> FEATURE:
<223> OTHER INFORMATION: Stalk motif 2

<400> SEQUENCE: 242

Lys His Arg Tyr Thr Tyr Glu Trp
1               5

<210> SEQ ID NO 243
<211> LENGTH: 8
<212> TYPE: PRT
```

```
<213> ORGANISM: Bos taurus
<220> FEATURE:
<223> OTHER INFORMATION: Stalk motif 2

<400> SEQUENCE: 243

Asn Tyr Ile Tyr Lys Tyr Ser Phe
1               5

<210> SEQ ID NO 244
<211> LENGTH: 8
<212> TYPE: PRT
<213> ORGANISM: Bos taurus
<220> FEATURE:
<223> OTHER INFORMATION: Stalk motif 2

<400> SEQUENCE: 244

Pro Tyr Ile Tyr Thr Tyr Gln Phe
1               5

<210> SEQ ID NO 245
<211> LENGTH: 8
<212> TYPE: PRT
<213> ORGANISM: Bos taurus
<220> FEATURE:
<223> OTHER INFORMATION: Stalk motif 2

<400> SEQUENCE: 245

Ser Phe Thr Tyr Thr Tyr Glu Trp
1               5

<210> SEQ ID NO 246
<211> LENGTH: 8
<212> TYPE: PRT
<213> ORGANISM: Bos taurus
<220> FEATURE:
<223> OTHER INFORMATION: Stalk motif 2

<400> SEQUENCE: 246

Ser Tyr Ile Tyr Ile Tyr Gln Trp
1               5

<210> SEQ ID NO 247
<211> LENGTH: 8
<212> TYPE: PRT
<213> ORGANISM: Bos taurus
<220> FEATURE:
<223> OTHER INFORMATION: Stalk motif 2

<400> SEQUENCE: 247

Ser Tyr Asn Tyr Thr Tyr Ser Trp
1               5

<210> SEQ ID NO 248
<211> LENGTH: 8
<212> TYPE: PRT
<213> ORGANISM: Bos taurus
<220> FEATURE:
<223> OTHER INFORMATION: Stalk motif 2

<400> SEQUENCE: 248

Ser Tyr Ser Tyr Ser Tyr Glu Tyr
1               5

<210> SEQ ID NO 249
<211> LENGTH: 8
<212> TYPE: PRT
<213> ORGANISM: Bos taurus
```

```
<220> FEATURE:
<223> OTHER INFORMATION: Stalk motif 2

<400> SEQUENCE: 249

Ser Tyr Thr Tyr Asn Tyr Asp Phe
1               5

<210> SEQ ID NO 250
<211> LENGTH: 8
<212> TYPE: PRT
<213> ORGANISM: Bos taurus
<220> FEATURE:
<223> OTHER INFORMATION: Stalk motif 2

<400> SEQUENCE: 250

Ser Tyr Thr Tyr Asn Tyr Glu Trp
1               5

<210> SEQ ID NO 251
<211> LENGTH: 8
<212> TYPE: PRT
<213> ORGANISM: Bos taurus
<220> FEATURE:
<223> OTHER INFORMATION: Stalk motif 2

<400> SEQUENCE: 251

Ser Tyr Thr Tyr Asn Tyr Gln Phe
1               5

<210> SEQ ID NO 252
<211> LENGTH: 8
<212> TYPE: PRT
<213> ORGANISM: Bos taurus
<220> FEATURE:
<223> OTHER INFORMATION: Stalk motif 2

<400> SEQUENCE: 252

Ser Tyr Val Trp Thr His Asn Phe
1               5

<210> SEQ ID NO 253
<211> LENGTH: 8
<212> TYPE: PRT
<213> ORGANISM: Bos taurus
<220> FEATURE:
<223> OTHER INFORMATION: Stalk motif 2

<400> SEQUENCE: 253

Thr Tyr Lys Tyr Val Tyr Glu Trp
1               5

<210> SEQ ID NO 254
<211> LENGTH: 8
<212> TYPE: PRT
<213> ORGANISM: Bos taurus
<220> FEATURE:
<223> OTHER INFORMATION: Stalk motif 2

<400> SEQUENCE: 254

Thr Tyr Thr Tyr Thr Tyr Glu Phe
1               5

<210> SEQ ID NO 255
<211> LENGTH: 8
<212> TYPE: PRT
<213> ORGANISM: Bos taurus
<220> FEATURE:
```

<223> OTHER INFORMATION: Stalk motif 2

<400> SEQUENCE: 255

Thr Tyr Thr Tyr Thr Tyr Glu Trp
1               5

<210> SEQ ID NO 256
<211> LENGTH: 8
<212> TYPE: PRT
<213> ORGANISM: Bos taurus
<220> FEATURE:
<223> OTHER INFORMATION: Stalk motif 2

<400> SEQUENCE: 256

Val Phe Thr Tyr Thr Tyr Glu Phe
1               5

<210> SEQ ID NO 257
<211> LENGTH: 6
<212> TYPE: PRT
<213> ORGANISM: Bos taurus
<220> FEATURE:
<223> OTHER INFORMATION: Stalk motif 2

<400> SEQUENCE: 257

Ala Tyr Thr Tyr Glu Trp
1               5

<210> SEQ ID NO 258
<211> LENGTH: 6
<212> TYPE: PRT
<213> ORGANISM: Bos taurus
<220> FEATURE:
<223> OTHER INFORMATION: Stalk motif 2

<400> SEQUENCE: 258

Asp Tyr Ile Tyr Thr Tyr
1               5

<210> SEQ ID NO 259
<211> LENGTH: 6
<212> TYPE: PRT
<213> ORGANISM: Bos taurus
<220> FEATURE:
<223> OTHER INFORMATION: Stalk motif 2

<400> SEQUENCE: 259

Ile His Ser Tyr Glu Phe
1               5

<210> SEQ ID NO 260
<211> LENGTH: 6
<212> TYPE: PRT
<213> ORGANISM: Bos taurus
<220> FEATURE:
<223> OTHER INFORMATION: Stalk motif 2

<400> SEQUENCE: 260

Ser Phe Thr Tyr Glu Phe
1               5

<210> SEQ ID NO 261
<211> LENGTH: 6
<212> TYPE: PRT
<213> ORGANISM: Bos taurus
<220> FEATURE:
<223> OTHER INFORMATION: Stalk motif 2

<400> SEQUENCE: 261

Ser His Ser Tyr Glu Phe
1               5

<210> SEQ ID NO 262
<211> LENGTH: 6
<212> TYPE: PRT
<213> ORGANISM: Bos taurus
<220> FEATURE:
<223> OTHER INFORMATION: Stalk motif 2

<400> SEQUENCE: 262

Thr His Thr Tyr Glu Phe
1               5

<210> SEQ ID NO 263
<211> LENGTH: 6
<212> TYPE: PRT
<213> ORGANISM: Bos taurus
<220> FEATURE:
<223> OTHER INFORMATION: Stalk motif 2

<400> SEQUENCE: 263

Thr Trp Thr Tyr Glu Phe
1               5

<210> SEQ ID NO 264
<211> LENGTH: 6
<212> TYPE: PRT
<213> ORGANISM: Bos taurus
<220> FEATURE:
<223> OTHER INFORMATION: Stalk motif 2

<400> SEQUENCE: 264

Thr Tyr Asn Tyr Glu Trp
1               5

<210> SEQ ID NO 265
<211> LENGTH: 6
<212> TYPE: PRT
<213> ORGANISM: Bos taurus
<220> FEATURE:
<223> OTHER INFORMATION: Stalk motif 2

<400> SEQUENCE: 265

Thr Tyr Ser Tyr Glu Phe
1               5

<210> SEQ ID NO 266
<211> LENGTH: 6
<212> TYPE: PRT
<213> ORGANISM: Bos taurus
<220> FEATURE:
<223> OTHER INFORMATION: Stalk motif 2

<400> SEQUENCE: 266

Thr Tyr Ser Tyr Glu His
1               5

<210> SEQ ID NO 267
<211> LENGTH: 6
<212> TYPE: PRT
<213> ORGANISM: Bos taurus
<220> FEATURE:
<223> OTHER INFORMATION: Stalk motif 2

```
<400> SEQUENCE: 267

Thr Tyr Thr Tyr Asp Phe
1               5

<210> SEQ ID NO 268
<211> LENGTH: 6
<212> TYPE: PRT
<213> ORGANISM: Bos taurus
<220> FEATURE:
<223> OTHER INFORMATION: Stalk motif 2

<400> SEQUENCE: 268

Thr Tyr Thr Tyr Glu Phe
1               5

<210> SEQ ID NO 269
<211> LENGTH: 6
<212> TYPE: PRT
<213> ORGANISM: Bos taurus
<220> FEATURE:
<223> OTHER INFORMATION: Stalk motif 2

<400> SEQUENCE: 269

Thr Tyr Thr Tyr Glu Trp
1               5

<210> SEQ ID NO 270
<211> LENGTH: 4
<212> TYPE: PRT
<213> ORGANISM: Bos taurus
<220> FEATURE:
<223> OTHER INFORMATION: Stalk motif 2

<400> SEQUENCE: 270

Ala Tyr Glu Phe
1

<210> SEQ ID NO 271
<211> LENGTH: 4
<212> TYPE: PRT
<213> ORGANISM: Bos taurus
<220> FEATURE:
<223> OTHER INFORMATION: Stalk motif 2

<400> SEQUENCE: 271

Ala Tyr Ser Phe
1

<210> SEQ ID NO 272
<211> LENGTH: 4
<212> TYPE: PRT
<213> ORGANISM: Bos taurus
<220> FEATURE:
<223> OTHER INFORMATION: Stalk motif 2

<400> SEQUENCE: 272

Ala Tyr Ser Tyr
1

<210> SEQ ID NO 273
<211> LENGTH: 4
<212> TYPE: PRT
<213> ORGANISM: Bos taurus
<220> FEATURE:
<223> OTHER INFORMATION: Stalk motif 2

<400> SEQUENCE: 273
```

```
<210> SEQ ID NO 274
<211> LENGTH: 4
<212> TYPE: PRT
<213> ORGANISM: Bos taurus
<220> FEATURE:
<223> OTHER INFORMATION: Stalk motif 2

<400> SEQUENCE: 274

Asp Tyr Thr Tyr
1

<210> SEQ ID NO 275
<211> LENGTH: 4
<212> TYPE: PRT
<213> ORGANISM: Bos taurus
<220> FEATURE:
<223> OTHER INFORMATION: Stalk motif 2

<400> SEQUENCE: 275

Lys Tyr Glu His
1

<210> SEQ ID NO 276
<211> LENGTH: 4
<212> TYPE: PRT
<213> ORGANISM: Bos taurus
<220> FEATURE:
<223> OTHER INFORMATION: Stalk motif 2

<400> SEQUENCE: 276

Lys Tyr Glu Trp
1

<210> SEQ ID NO 277
<211> LENGTH: 4
<212> TYPE: PRT
<213> ORGANISM: Bos taurus
<220> FEATURE:
<223> OTHER INFORMATION: Stalk motif 2

<400> SEQUENCE: 277

Met Tyr Glu Phe
1

<210> SEQ ID NO 278
<211> LENGTH: 4
<212> TYPE: PRT
<213> ORGANISM: Bos taurus
<220> FEATURE:
<223> OTHER INFORMATION: Stalk motif 2

<400> SEQUENCE: 278

Asn Trp Ile Tyr
1

<210> SEQ ID NO 279
<211> LENGTH: 4
<212> TYPE: PRT
<213> ORGANISM: Bos taurus
<220> FEATURE:
<223> OTHER INFORMATION: Stalk motif 2

<400> SEQUENCE: 279
```

(preceded by:)

```
Cys Tyr Ser Phe
1
```

Asn Tyr Asp Tyr
1

<210> SEQ ID NO 280
<211> LENGTH: 4
<212> TYPE: PRT
<213> ORGANISM: Bos taurus
<220> FEATURE:
<223> OTHER INFORMATION: Stalk motif 2

<400> SEQUENCE: 280

Asn Tyr Gln Trp
1

<210> SEQ ID NO 281
<211> LENGTH: 4
<212> TYPE: PRT
<213> ORGANISM: Bos taurus
<220> FEATURE:
<223> OTHER INFORMATION: Stalk motif 2

<400> SEQUENCE: 281

Asn Tyr Ser Phe
1

<210> SEQ ID NO 282
<211> LENGTH: 4
<212> TYPE: PRT
<213> ORGANISM: Bos taurus
<220> FEATURE:
<223> OTHER INFORMATION: Stalk motif 2

<400> SEQUENCE: 282

Pro Tyr Glu Trp
1

<210> SEQ ID NO 283
<211> LENGTH: 4
<212> TYPE: PRT
<213> ORGANISM: Bos taurus
<220> FEATURE:
<223> OTHER INFORMATION: Stalk motif 2

<400> SEQUENCE: 283

Arg Tyr Asn Trp
1

<210> SEQ ID NO 284
<211> LENGTH: 4
<212> TYPE: PRT
<213> ORGANISM: Bos taurus
<220> FEATURE:
<223> OTHER INFORMATION: Stalk motif 2

<400> SEQUENCE: 284

Arg Tyr Thr Tyr
1

<210> SEQ ID NO 285
<211> LENGTH: 4
<212> TYPE: PRT
<213> ORGANISM: Bos taurus
<220> FEATURE:
<223> OTHER INFORMATION: Stalk motif 2

<400> SEQUENCE: 285

Ser Tyr Glu Phe

```
<210> SEQ ID NO 286
<211> LENGTH: 4
<212> TYPE: PRT
<213> ORGANISM: Bos taurus
<220> FEATURE:
<223> OTHER INFORMATION: Stalk motif 2

<400> SEQUENCE: 286

Ser Tyr Glu His
1

<210> SEQ ID NO 287
<211> LENGTH: 4
<212> TYPE: PRT
<213> ORGANISM: Bos taurus
<220> FEATURE:
<223> OTHER INFORMATION: Stalk motif 2

<400> SEQUENCE: 287

Ser Tyr Glu Trp
1

<210> SEQ ID NO 288
<211> LENGTH: 4
<212> TYPE: PRT
<213> ORGANISM: Bos taurus
<220> FEATURE:
<223> OTHER INFORMATION: Stalk motif 2

<400> SEQUENCE: 288

Ser Tyr Lys Trp
1

<210> SEQ ID NO 289
<211> LENGTH: 4
<212> TYPE: PRT
<213> ORGANISM: Bos taurus
<220> FEATURE:
<223> OTHER INFORMATION: Stalk motif 2

<400> SEQUENCE: 289

Ser Tyr Thr Tyr
1

<210> SEQ ID NO 290
<211> LENGTH: 4
<212> TYPE: PRT
<213> ORGANISM: Bos taurus
<220> FEATURE:
<223> OTHER INFORMATION: Stalk motif 2

<400> SEQUENCE: 290

Thr Tyr Asp Phe
1

<210> SEQ ID NO 291
<211> LENGTH: 4
<212> TYPE: PRT
<213> ORGANISM: Bos taurus
<220> FEATURE:
<223> OTHER INFORMATION: Stalk motif 2

<400> SEQUENCE: 291

Thr Tyr Glu Phe
1
```

```
<210> SEQ ID NO 292
<211> LENGTH: 4
<212> TYPE: PRT
<213> ORGANISM: Bos taurus
<220> FEATURE:
<223> OTHER INFORMATION: Stalk motif 2

<400> SEQUENCE: 292

Thr Tyr Glu Trp
1

<210> SEQ ID NO 293
<211> LENGTH: 4
<212> TYPE: PRT
<213> ORGANISM: Bos taurus
<220> FEATURE:
<223> OTHER INFORMATION: Stalk motif 2

<400> SEQUENCE: 293

Thr Tyr Gln Trp
1

<210> SEQ ID NO 294
<211> LENGTH: 4
<212> TYPE: PRT
<213> ORGANISM: Bos taurus
<220> FEATURE:
<223> OTHER INFORMATION: Stalk motif 2

<400> SEQUENCE: 294

Thr Tyr Thr Tyr
1

<210> SEQ ID NO 295
<211> LENGTH: 4
<212> TYPE: PRT
<213> ORGANISM: Bos taurus
<220> FEATURE:
<223> OTHER INFORMATION: Stalk motif 2

<400> SEQUENCE: 295

Val Tyr Glu Trp
1

<210> SEQ ID NO 296
<211> LENGTH: 4
<212> TYPE: PRT
<213> ORGANISM: Bos taurus
<220> FEATURE:
<223> OTHER INFORMATION: Stalk motif 2
<220> FEATURE:
<221> NAME/KEY: MOD_RES
<222> LOCATION: (2)..(2)
<223> OTHER INFORMATION: Thr, Ser, Asn or Ile
<220> FEATURE:
<221> NAME/KEY: MOD_RES
<222> LOCATION: (4)..(4)
<223> OTHER INFORMATION: Glu or Asp

<400> SEQUENCE: 296

Tyr Xaa Tyr Xaa
1

<210> SEQ ID NO 297
<211> LENGTH: 5
<212> TYPE: PRT
<213> ORGANISM: Bos taurus
```

```
<220> FEATURE:
<223> OTHER INFORMATION: Stalk motif 2
<220> FEATURE:
<221> NAME/KEY: MOD_RES
<222> LOCATION: (2)..(2)
<223> OTHER INFORMATION: Leu, Ser, Thr or Arg
<220> FEATURE:
<221> NAME/KEY: MOD_RES
<222> LOCATION: (4)..(4)
<223> OTHER INFORMATION: Thr, Ser, Asn or Ile

<400> SEQUENCE: 297

Tyr Xaa Tyr Xaa Tyr
1               5

<210> SEQ ID NO 298
<211> LENGTH: 6
<212> TYPE: PRT
<213> ORGANISM: Bos taurus
<220> FEATURE:
<223> OTHER INFORMATION: Stalk motif 2
<220> FEATURE:
<221> NAME/KEY: MOD_RES
<222> LOCATION: (2)..(2)
<223> OTHER INFORMATION: Leu, Ser, Thr or Arg
<220> FEATURE:
<221> NAME/KEY: MOD_RES
<222> LOCATION: (4)..(4)
<223> OTHER INFORMATION: Thr, Ser, Asn or Ile
<220> FEATURE:
<221> NAME/KEY: MOD_RES
<222> LOCATION: (6)..(6)
<223> OTHER INFORMATION: Glu or Asp

<400> SEQUENCE: 298

Tyr Xaa Tyr Xaa Tyr Xaa
1               5

<210> SEQ ID NO 299
<211> LENGTH: 7
<212> TYPE: PRT
<213> ORGANISM: Bos taurus
<220> FEATURE:
<223> OTHER INFORMATION: Stalk motif 2
<220> FEATURE:
<221> NAME/KEY: MOD_RES
<222> LOCATION: (2)..(2)
<223> OTHER INFORMATION: Leu, Ser, Thr or Arg
<220> FEATURE:
<221> NAME/KEY: MOD_RES
<222> LOCATION: (4)..(4)
<223> OTHER INFORMATION: Thr, Ser, Asn or Ile
<220> FEATURE:
<221> NAME/KEY: MOD_RES
<222> LOCATION: (6)..(6)
<223> OTHER INFORMATION: Glu or Asp
<220> FEATURE:
<221> NAME/KEY: MOD_RES
<222> LOCATION: (7)..(7)
<223> OTHER INFORMATION: His, Trp, Asn, Phe, Ile or Tyr

<400> SEQUENCE: 299

Tyr Xaa Tyr Xaa Tyr Xaa Xaa
1               5

<210> SEQ ID NO 300
<211> LENGTH: 3
<212> TYPE: PRT
<213> ORGANISM: Bos taurus
<220> FEATURE:
<223> OTHER INFORMATION: Stalk motif 2
<220> FEATURE:
<221> NAME/KEY: MOD_RES
```

```
<222> LOCATION: (3)..(3)
<223> OTHER INFORMATION: His, Trp, Asn, Phe, Ile or Tyr

<400> SEQUENCE: 300

Tyr Glu Xaa
1

<210> SEQ ID NO 301
<211> LENGTH: 3
<212> TYPE: PRT
<213> ORGANISM: Bos taurus
<220> FEATURE:
<223> OTHER INFORMATION: Stalk motif 2
<220> FEATURE:
<221> NAME/KEY: MOD_RES
<222> LOCATION: (3)..(3)
<223> OTHER INFORMATION: His, Trp, Asn, Phe, Ile or Tyr

<400> SEQUENCE: 301

Tyr Asp Xaa
1

<210> SEQ ID NO 302
<211> LENGTH: 3
<212> TYPE: PRT
<213> ORGANISM: Bos taurus
<220> FEATURE:
<223> OTHER INFORMATION: Stalk motif 2
<220> FEATURE:
<221> NAME/KEY: MOD_RES
<222> LOCATION: (1)..(1)
<223> OTHER INFORMATION: Thr, Ser, Asn or Ile

<400> SEQUENCE: 302

Xaa Tyr Glu
1

<210> SEQ ID NO 303
<211> LENGTH: 3
<212> TYPE: PRT
<213> ORGANISM: Bos taurus
<220> FEATURE:
<223> OTHER INFORMATION: Stalk motif 2
<220> FEATURE:
<221> NAME/KEY: MOD_RES
<222> LOCATION: (1)..(1)
<223> OTHER INFORMATION: Thr, Ser, Asn or Ile

<400> SEQUENCE: 303

Xaa Tyr Asp
1

<210> SEQ ID NO 304
<211> LENGTH: 5
<212> TYPE: PRT
<213> ORGANISM: Bos taurus
<220> FEATURE:
<223> OTHER INFORMATION: Stalk motif 2
<220> FEATURE:
<221> NAME/KEY: MOD_RES
<222> LOCATION: (3)..(3)
<223> OTHER INFORMATION: His, Trp, Asn, Phe, Ile or Tyr
<220> FEATURE:
<221> NAME/KEY: MOD_RES
<222> LOCATION: (4)..(4)
<223> OTHER INFORMATION: Any amino acid

<400> SEQUENCE: 304

Tyr Glu Xaa Xaa Trp
1               5
```

```
<210> SEQ ID NO 305
<211> LENGTH: 5
<212> TYPE: PRT
<213> ORGANISM: Bos taurus
<220> FEATURE:
<223> OTHER INFORMATION: Stalk motif 2
<220> FEATURE:
<221> NAME/KEY: MOD_RES
<222> LOCATION: (3)..(3)
<223> OTHER INFORMATION: His, Trp, Asn, Phe, Ile or Tyr
<220> FEATURE:
<221> NAME/KEY: MOD_RES
<222> LOCATION: (4)..(4)
<223> OTHER INFORMATION: Any amino acid

<400> SEQUENCE: 305

Tyr Asp Xaa Xaa Trp
1               5

<210> SEQ ID NO 306
<211> LENGTH: 8
<212> TYPE: PRT
<213> ORGANISM: Bos taurus
<220> FEATURE:
<223> OTHER INFORMATION: Stalk motif 2
<220> FEATURE:
<221> NAME/KEY: MOD_RES
<222> LOCATION: (3)..(7)
<223> OTHER INFORMATION: Any amino acid

<400> SEQUENCE: 306

Tyr Glu Xaa Xaa Xaa Xaa Xaa Trp
1               5

<210> SEQ ID NO 307
<211> LENGTH: 8
<212> TYPE: PRT
<213> ORGANISM: Bos taurus
<220> FEATURE:
<223> OTHER INFORMATION: Stalk motif 2
<220> FEATURE:
<221> NAME/KEY: MOD_RES
<222> LOCATION: (3)..(7)
<223> OTHER INFORMATION: Any amino acid

<400> SEQUENCE: 307

Tyr Asp Xaa Xaa Xaa Xaa Xaa Trp
1               5

<210> SEQ ID NO 308
<211> LENGTH: 63
<212> TYPE: DNA
<213> ORGANISM: Artificial Sequence
<220> FEATURE:
<223> OTHER INFORMATION: Description of Artificial Sequence: Synthetic
      MID1 FW primer

<400> SEQUENCE: 308
cctatcccct gtgtgccttg gcagtctcag acgagtgcgt ttgagcgaca aggctgtagg      60
ctg                                                                    63

<210> SEQ ID NO 309
<211> LENGTH: 62
<212> TYPE: DNA
<213> ORGANISM: Artificial Sequence
<220> FEATURE:
<223> OTHER INFORMATION: Description of Artificial Sequence: Synthetic
      MID1 RV primer
```

<400> SEQUENCE: 309
ccatctcatc cctgcgtgtc tccgactcag acgagtgcgt ctttcggggc tgtggtggag    60
gc    62

<210> SEQ ID NO 310
<211> LENGTH: 63
<212> TYPE: DNA
<213> ORGANISM: Artificial Sequence
<220> FEATURE:
<223> OTHER INFORMATION: Description of Artificial Sequence: Synthetic
      MID10 FW primer

<400> SEQUENCE: 310
cctatcccct gtgtgccttg gcagtctcag tctctatgcg ttgagcgaca aggctgtagg    60
ctg    63

<210> SEQ ID NO 311
<211> LENGTH: 66
<212> TYPE: DNA
<213> ORGANISM: Artificial Sequence
<220> FEATURE:
<223> OTHER INFORMATION: Description of Artificial Sequence: Synthetic
      MID10 RV primer

<400> SEQUENCE: 311
ccatctcatc cctgcgtgtc tccgactcag tctctatgcg agtgaagact ctcgggtgtg    60
attcac    66

<210> SEQ ID NO 312
<211> LENGTH: 63
<212> TYPE: DNA
<213> ORGANISM: Artificial Sequence
<220> FEATURE:
<223> OTHER INFORMATION: Description of Artificial Sequence: Synthetic
      MID11 FW primer

<400> SEQUENCE: 312
cctatcccct gtgtgccttg gcagtctcag tgatacgtct ttgagcgaca aggctgtagg    60
ctg    63

<210> SEQ ID NO 313
<211> LENGTH: 66
<212> TYPE: DNA
<213> ORGANISM: Artificial Sequence
<220> FEATURE:
<223> OTHER INFORMATION: Description of Artificial Sequence: Synthetic
      MID11 RV primer

<400> SEQUENCE: 313
ccatctcatc cctgcgtgtc tccgactcag tgatacgtct agtgaagact ctcgggtgtg    60
attcac    66

<210> SEQ ID NO 314
<211> LENGTH: 23
<212> TYPE: DNA
<213> ORGANISM: Artificial Sequence
<220> FEATURE:
<223> OTHER INFORMATION: Description of Artificial Sequence: Synthetic
      primer A

<400> SEQUENCE: 314
ttgagcgaca aggctgtagg ctg    23

<210> SEQ ID NO 315
<211> LENGTH: 22
<212> TYPE: DNA
<213> ORGANISM: Artificial Sequence
<220> FEATURE:
<223> OTHER INFORMATION: Description of Artificial Sequence: Synthetic
      primer B

<400> SEQUENCE: 315
ctttcggggc tgtggtggag gc                                              22

<210> SEQ ID NO 316
<211> LENGTH: 20
<212> TYPE: DNA
<213> ORGANISM: Artificial Sequence
<220> FEATURE:
<223> OTHER INFORMATION: Description of Artificial Sequence: Synthetic
      primer C

<400> SEQUENCE: 316
agatccaagc tgtgaccggc                                                 20

<210> SEQ ID NO 317
<211> LENGTH: 74
<212> TYPE: PRT
<213> ORGANISM: Homo sapiens
<220> FEATURE:
<223> OTHER INFORMATION: IL8

<400> SEQUENCE: 317

Pro Arg Ser Ala Lys Glu Leu Arg Cys Gln Cys Ile Lys Thr Tyr Ser
1               5                   10                  15

Lys Pro Phe His Pro Lys Phe Ile Lys Glu Leu Arg Val Ile Glu Ser
            20                  25                  30

Gly Pro His Cys Ala Asn Thr Glu Ile Ile Val Lys Leu Ser Asp Gly
        35                  40                  45

Arg Glu Leu Cys Leu Asp Pro Lys Glu Asn Trp Val Gln Arg Val Val
    50                  55                  60

Glu Lys Phe Leu Lys Arg Ala Glu Asn Ser
65                  70

<210> SEQ ID NO 318
<211> LENGTH: 25
<212> TYPE: PRT
<213> ORGANISM: Unknown
<220> FEATURE:
<223> OTHER INFORMATION: Description of Unknown: Ziconotide peptide

<400> SEQUENCE: 318

Cys Lys Gly Lys Gly Ala Lys Cys Ser Arg Leu Met Tyr Asp Cys Cys
1               5                   10                  15

Thr Gly Ser Cys Arg Ser Gly Lys Cys
            20                  25

<210> SEQ ID NO 319
<211> LENGTH: 15
<212> TYPE: PRT
<213> ORGANISM: Unknown
<220> FEATURE:
<223> OTHER INFORMATION: Description of Unknown: Somatostatin peptide

<400> SEQUENCE: 319

Ala Gly Cys Lys Asn Phe Phe Trp Lys Thr Phe Thr Ser Cys Gly

-continued

```
1               5               10              15
```

<210> SEQ ID NO 320
<211> LENGTH: 34
<212> TYPE: PRT
<213> ORGANISM: Unknown
<220> FEATURE:
<223> OTHER INFORMATION: Description of Unknown: Chlorotoxin polypeptide

<400> SEQUENCE: 320

```
Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu
```

<210> SEQ ID NO 321
<211> LENGTH: 68
<212> TYPE: PRT
<213> ORGANISM: Unknown
<220> FEATURE:
<223> OTHER INFORMATION: Description of Unknown: SDF1(alpha) polypeptide

<400> SEQUENCE: 321

```
Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys
65
```

<210> SEQ ID NO 322
<211> LENGTH: 133
<212> TYPE: PRT
<213> ORGANISM: Homo sapiens
<220> FEATURE:
<223> OTHER INFORMATION: IL21

<400> SEQUENCE: 322

```
Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125
```

Gly Ser Glu Asp Ser
        130

<210> SEQ ID NO 323
<211> LENGTH: 30
<212> TYPE: PRT
<213> ORGANISM: Unknown
<220> FEATURE:
<223> OTHER INFORMATION: Description of Unknown: Protoxin2 polypeptide

<400> SEQUENCE: 323

Tyr Cys Gln Lys Trp Met Trp Thr Cys Asp Ser Glu Arg Lys Cys Cys
1               5                   10                  15

Glu Gly Met Val Cys Arg Leu Trp Cys Lys Lys Lys Leu Trp
            20                  25                  30

<210> SEQ ID NO 324
<211> LENGTH: 166
<212> TYPE: PRT
<213> ORGANISM: Homo sapiens
<220> FEATURE:
<223> OTHER INFORMATION: IFN-beta

<400> SEQUENCE: 324

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 325
<211> LENGTH: 174
<212> TYPE: PRT
<213> ORGANISM: Bos taurus
<220> FEATURE:
<223> OTHER INFORMATION: bGCSF

<400> SEQUENCE: 325

Thr Pro Leu Gly Pro Ala Arg Ser Leu Pro Gln Ser Phe Leu Leu Lys
1               5                   10                  15

Cys Leu Glu Gln Val Arg Lys Ile Gln Ala Asp Gly Ala Glu Leu Gln
            20                  25                  30

Glu Arg Leu Cys Ala Ala His Lys Leu Cys His Pro Glu Glu Leu Met

-continued

```
                35                  40                  45
Leu Leu Arg His Ser Leu Gly Ile Pro Gln Ala Pro Leu Ser Ser Cys
 50                  55                  60
Ser Ser Gln Ser Leu Gln Leu Thr Ser Cys Leu Asn Gln Leu His Gly
 65                  70                  75                  80
Gly Leu Phe Leu Tyr Gln Gly Leu Leu Gln Ala Leu Ala Gly Ile Ser
                 85                  90                  95
Pro Glu Leu Ala Pro Thr Leu Asp Thr Leu Gln Leu Asp Val Thr Asp
            100                 105                 110
Phe Ala Thr Asn Ile Trp Leu Gln Met Glu Asp Leu Gly Ala Ala Pro
        115                 120                 125
Ala Val Gln Pro Thr Gln Gly Ala Met Pro Thr Phe Thr Ser Ala Phe
    130                 135                 140
Gln Arg Arg Ala Gly Gly Val Leu Val Ala Ser Gln Leu His Arg Phe
145                 150                 155                 160
Leu Glu Leu Ala Tyr Arg Gly Leu Arg Tyr Leu Ala Glu Pro
                165                 170
```

<210> SEQ ID NO 326
<211> LENGTH: 127
<212> TYPE: PRT
<213> ORGANISM: Homo sapiens
<220> FEATURE:
<223> OTHER INFORMATION: GMCSF

<400> SEQUENCE: 326

```
Ala Pro Ala Arg Ser Pro Ser Pro Ser Thr Gln Pro Trp Glu His Val
 1               5                  10                  15
Asn Ala Ile Gln Glu Ala Arg Arg Leu Leu Asn Leu Ser Arg Asp Thr
             20                  25                  30
Ala Ala Glu Met Asn Glu Thr Val Glu Val Ile Ser Glu Met Phe Asp
         35                  40                  45
Leu Gln Glu Pro Thr Cys Leu Gln Thr Arg Leu Glu Leu Tyr Lys Gln
 50                  55                  60
Gly Leu Arg Gly Ser Leu Thr Lys Leu Lys Gly Pro Leu Thr Met Met
 65                  70                  75                  80
Ala Ser His Tyr Lys Gln His Cys Pro Pro Thr Pro Glu Thr Ser Cys
                 85                  90                  95
Ala Thr Gln Ile Ile Thr Phe Glu Ser Phe Lys Glu Asn Leu Lys Asp
            100                 105                 110
Phe Leu Leu Val Ile Pro Phe Asp Cys Trp Glu Pro Val Gln Glu
        115                 120                 125
```

<210> SEQ ID NO 327
<211> LENGTH: 181
<212> TYPE: PRT
<213> ORGANISM: Homo sapiens
<220> FEATURE:
<223> OTHER INFORMATION: hFGF21

<400> SEQUENCE: 327

```
His Pro Ile Pro Asp Ser Ser Pro Leu Leu Gln Phe Gly Gly Gln Val
 1               5                  10                  15
Arg Gln Arg Tyr Leu Tyr Thr Asp Asp Ala Gln Gln Thr Glu Ala His
             20                  25                  30
Leu Glu Ile Arg Glu Asp Gly Thr Val Gly Gly Ala Ala Asp Gln Ser
         35                  40                  45
```

Pro Glu Ser Leu Leu Gln Leu Lys Ala Leu Lys Pro Gly Val Ile Gln
         50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Glu Asp Gly Tyr Asn Val Tyr Gln Ser Glu Ala His
             100                 105                 110

Gly Leu Pro Leu His Leu Pro Gly Asn Lys Ser Pro His Arg Asp Pro
             115                 120                 125

Ala Pro Arg Gly Pro Ala Arg Phe Leu Pro Leu Pro Gly Leu Pro Pro
130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                 165                 170                 175

Pro Ser Tyr Ala Ser
            180

<210> SEQ ID NO 328
<211> LENGTH: 39
<212> TYPE: PRT
<213> ORGANISM: Homo sapiens
<220> FEATURE:
<223> OTHER INFORMATION: Ex-4

<400> SEQUENCE: 328

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
                 20                  25                  30

Ser Gly Ala Pro Pro Ser
             35

<210> SEQ ID NO 329
<211> LENGTH: 30
<212> TYPE: PRT
<213> ORGANISM: Homo sapiens
<220> FEATURE:
<223> OTHER INFORMATION: hGLP-1

<400> SEQUENCE: 329

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
                 20                  25                  30

<210> SEQ ID NO 330
<211> LENGTH: 165
<212> TYPE: PRT
<213> ORGANISM: Homo sapiens
<220> FEATURE:
<223> OTHER INFORMATION: hEPO

<400> SEQUENCE: 330

Pro Pro Arg Leu Ile Cys Asp Ser Arg Val Leu Glu Arg Tyr Leu Leu
 1               5                  10                  15

Glu Ala Lys Glu Ala Glu Asn Ile Thr Thr Gly Cys Ala Glu His Cys
                 20                  25                  30

Ser Leu Asn Glu Asn Ile Thr Val Pro Asp Thr Lys Val Asn Phe Tyr

```
              35                  40                  45
Ala Trp Lys Arg Met Glu Val Gly Gln Gln Ala Val Glu Val Trp Gln
 50                  55                  60

Gly Leu Ala Leu Leu Ser Glu Ala Val Leu Arg Gly Gln Ala Leu Leu
 65                  70                  75                  80

Val Asn Ser Ser Gln Pro Trp Glu Pro Leu Gln Leu His Val Asp Lys
                 85                  90                  95

Ala Val Ser Gly Leu Arg Ser Leu Thr Thr Leu Leu Arg Ala Leu Gly
            100                 105                 110

Ala Gln Lys Glu Ala Ile Ser Pro Pro Asp Ala Ala Ser Ala Ala Pro
        115                 120                 125

Leu Arg Thr Ile Thr Ala Asp Thr Phe Arg Lys Leu Phe Arg Val Tyr
130                 135                 140

Ser Asn Phe Leu Arg Gly Lys Leu Lys Leu Tyr Thr Gly Glu Ala Cys
145                 150                 155                 160

Arg Thr Gly Asp Arg
                165

<210> SEQ ID NO 331
<211> LENGTH: 34
<212> TYPE: PRT
<213> ORGANISM: Unknown
<220> FEATURE:
<223> OTHER INFORMATION: Description of Unknown: Moka toxin polypeptide

<400> SEQUENCE: 331

Ile Asn Val Lys Cys Ser Leu Pro Gln Gln Cys Ile Lys Pro Cys Lys
 1               5                  10                  15

Asp Ala Gly Met Arg Phe Gly Lys Cys Met Asn Lys Lys Cys Arg Cys
                20                  25                  30

Tyr Ser

<210> SEQ ID NO 332
<211> LENGTH: 36
<212> TYPE: PRT
<213> ORGANISM: Unknown
<220> FEATURE:
<223> OTHER INFORMATION: Description of Unknown: VM-24 polypeptide

<400> SEQUENCE: 332

Ala Ala Ala Ile Ser Cys Val Gly Ser Pro Glu Cys Pro Pro Lys Cys
 1               5                  10                  15

Arg Ala Gln Gly Cys Lys Asn Gly Lys Cys Met Asn Arg Lys Cys Lys
                20                  25                  30

Cys Tyr Tyr Cys
         35

<210> SEQ ID NO 333
<211> LENGTH: 6
<212> TYPE: PRT
<213> ORGANISM: Bos taurus
<220> FEATURE:
<223> OTHER INFORMATION: Stalk motif 2
<220> FEATURE:
<221> NAME/KEY: MOD_RES
<222> LOCATION: (3)..(5)
<223> OTHER INFORMATION: Any amino acid

<400> SEQUENCE: 333

Tyr Glu Xaa Xaa Xaa Trp
 1               5
```

```
<210> SEQ ID NO 334
<211> LENGTH: 7
<212> TYPE: PRT
<213> ORGANISM: Bos taurus
<220> FEATURE:
<223> OTHER INFORMATION: Stalk motif 2
<220> FEATURE:
<221> NAME/KEY: MOD_RES
<222> LOCATION: (3)..(6)
<223> OTHER INFORMATION: Any amino acid

<400> SEQUENCE: 334

Tyr Glu Xaa Xaa Xaa Xaa Trp
1               5

<210> SEQ ID NO 335
<211> LENGTH: 6
<212> TYPE: PRT
<213> ORGANISM: Bos taurus
<220> FEATURE:
<223> OTHER INFORMATION: Stalk motif 2
<220> FEATURE:
<221> NAME/KEY: MOD_RES
<222> LOCATION: (3)..(5)
<223> OTHER INFORMATION: Any amino acid

<400> SEQUENCE: 335

Tyr Asp Xaa Xaa Xaa Trp
1               5

<210> SEQ ID NO 336
<211> LENGTH: 7
<212> TYPE: PRT
<213> ORGANISM: Bos taurus
<220> FEATURE:
<223> OTHER INFORMATION: Stalk motif 2
<220> FEATURE:
<221> NAME/KEY: MOD_RES
<222> LOCATION: (3)..(6)
<223> OTHER INFORMATION: Any amino acid

<400> SEQUENCE: 336

Tyr Asp Xaa Xaa Xaa Xaa Trp
1               5

<210> SEQ ID NO 337
<211> LENGTH: 9
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 337

Gly Gly Gly Ser Gly Gly Gly Gly Ser
1               5

<210> SEQ ID NO 338
<211> LENGTH: 9
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 338

Gly Gly Gly Gly Ser Gly Gly Gly Ser
1               5
```

<210> SEQ ID NO 339
<211> LENGTH: 25
<212> TYPE: PRT
<213> ORGANISM: Artificial Sequence
<220> FEATURE:
<223> OTHER INFORMATION: Description of Artificial Sequence: Synthetic
linker peptide
<220> FEATURE:
<221> NAME/KEY: misc_feature
<222> LOCATION: (1)..(25)
<223> OTHER INFORMATION: This sequence may encompass 0-5 "Gly Gly Gly
Gly Ser" repeating units

<400> SEQUENCE: 339

Gly Gly Gly Gly Ser Gly Gly Gly Gly Ser Gly Gly Gly Gly Ser Gly
1               5                  10                  15

Gly Gly Gly Ser Gly Gly Gly Gly Ser
            20                  25

<210> SEQ ID NO 340
<211> LENGTH: 269
<212> TYPE: PRT
<213> ORGANISM: Bos taurus
<220> FEATURE:
<223> OTHER INFORMATION: BLV5B8 VHCH1

<400> SEQUENCE: 340

Gln Val Gln Leu Arg Glu Ser Gly Pro Ser Leu Val Gln Pro Ser Gln
1               5                  10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Ser Thr Gly Tyr Asn Pro Gly Leu Lys
    50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
                85                  90                  95

Thr Val His Gln Glu Thr Arg Lys Thr Cys Ser Asp Gly Tyr Ile Ala
            100                 105                 110

Val Asp Ser Cys Gly Arg Gly Gln Ser Asp Gly Cys Val Asn Asp Cys
        115                 120                 125

Asn Ser Cys Tyr Tyr Gly Trp Arg Asn Cys Arg Arg Gln Pro Ala Ile
    130                 135                 140

His Ser Tyr Glu Phe His Val Asp Ala Trp Gly Arg Gly Leu Leu Val
145                 150                 155                 160

Thr Val Ser Ser Ala Ser Thr Thr Ala Pro Lys Val Tyr Pro Leu Ser
                165                 170                 175

Ser Cys Cys Gly Asp Lys Ser Ser Thr Val Thr Leu Gly Cys Leu
            180                 185                 190

Val Ser Ser Tyr Met Pro Glu Pro Val Thr Val Thr Trp Asn Ser Gly
        195                 200                 205

Ala Leu Lys Ser Gly Val His Thr Phe Pro Ala Val Leu Gln Ser Ser
    210                 215                 220

Gly Leu Tyr Ser Leu Ser Ser Met Val Thr Val Pro Gly Ser Thr Ser
225                 230                 235                 240

Gly Gln Thr Phe Thr Cys Asn Val Ala His Pro Ala Ser Ser Thr Lys

```
                      245                 250                 255
Val Asp Lys Ala Val Glu Pro Lys Ser Cys Asp Gly Ser
            260                 265

<210> SEQ ID NO 341
<211> LENGTH: 216
<212> TYPE: PRT
<213> ORGANISM: Bos taurus
<220> FEATURE:
<223> OTHER INFORMATION: BLV5B8 VLCL

<400> SEQUENCE: 341

Gln Ala Val Leu Asn Gln Pro Ser Ser Val Ser Gly Ser Leu Gly Gln
1               5                   10                  15

Arg Val Ser Ile Thr Cys Ser Gly Ser Ser Asn Val Gly Asn Gly
            20                  25                  30

Tyr Val Ser Trp Tyr Gln Leu Ile Pro Gly Ser Ala Pro Arg Thr Leu
        35                  40                  45

Ile Tyr Gly Asp Thr Ser Arg Ala Ser Gly Val Pro Asp Arg Phe Ser
    50                  55                  60

Gly Ser Arg Ser Gly Asn Thr Ala Thr Leu Thr Ile Ser Ser Leu Gln
65                  70                  75                  80

Ala Glu Asp Glu Ala Asp Tyr Phe Cys Ala Ser Ala Glu Asp Ser Ser
                85                  90                  95

Ser Asn Ala Val Phe Gly Ser Gly Thr Thr Leu Thr Val Leu Gly Gln
            100                 105                 110

Pro Lys Ser Pro Pro Ser Val Thr Leu Phe Pro Pro Ser Thr Glu Glu
        115                 120                 125

Leu Asn Gly Asn Lys Ala Thr Leu Val Cys Leu Ile Ser Asp Phe Tyr
    130                 135                 140

Pro Gly Ser Val Thr Val Val Trp Lys Ala Asp Gly Ser Thr Ile Thr
145                 150                 155                 160

Arg Asn Val Glu Thr Thr Arg Ala Ser Lys Gln Ser Asn Ser Lys Tyr
                165                 170                 175

Ala Ala Ser Ser Tyr Leu Ser Leu Thr Ser Ser Asp Trp Lys Ser Lys
            180                 185                 190

Gly Ser Tyr Ser Cys Glu Val Thr His Glu Gly Ser Thr Val Thr Lys
        195                 200                 205

Thr Val Lys Pro Ser Glu Cys Ser
    210                 215

<210> SEQ ID NO 342
<211> LENGTH: 3
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 342

Gly Ser Gly
1

<210> SEQ ID NO 343
<211> LENGTH: 11
<212> TYPE: PRT
<213> ORGANISM: Mus sp.
<220> FEATURE:
<223> OTHER INFORMATION: D44.1
```

<400> SEQUENCE: 343

Cys Ala Arg Gly Asp Gly Asn Tyr Gly Tyr Trp
1               5                   10

<210> SEQ ID NO 344
<211> LENGTH: 13
<212> TYPE: PRT
<213> ORGANISM: Mus sp.
<220> FEATURE:
<223> OTHER INFORMATION: 93F3

<400> SEQUENCE: 344

Cys Ala Lys His Thr Tyr Gly Gly Pro Gly Asp Ser Trp
1               5                   10

<210> SEQ ID NO 345
<211> LENGTH: 14
<212> TYPE: PRT
<213> ORGANISM: Mus sp.
<220> FEATURE:
<223> OTHER INFORMATION: OKT3

<400> SEQUENCE: 345

Cys Ala Arg Tyr Tyr Asp Asp His Tyr Cys Leu Asp Tyr Trp
1               5                   10

<210> SEQ ID NO 346
<211> LENGTH: 14
<212> TYPE: PRT
<213> ORGANISM: Homo sapiens
<220> FEATURE:
<223> OTHER INFORMATION: Yvo

<400> SEQUENCE: 346

Cys Ala Arg Thr Ser Gly Trp Asp Ile Glu Phe Glu Tyr Trp
1               5                   10

<210> SEQ ID NO 347
<211> LENGTH: 16
<212> TYPE: PRT
<213> ORGANISM: Homo sapiens
<220> FEATURE:
<223> OTHER INFORMATION: CR6261

<400> SEQUENCE: 347

Cys Ala Lys His Met Gly Tyr Gln Val Arg Glu Thr Met Asp Val Trp
1               5                   10                  15

<210> SEQ ID NO 348
<211> LENGTH: 32
<212> TYPE: PRT
<213> ORGANISM: Homo sapiens
<220> FEATURE:
<223> OTHER INFORMATION: PG9

<400> SEQUENCE: 348

Cys Val Arg Glu Ala Gly Gly Pro Asp Tyr Arg Asn Gly Tyr Asn Tyr
1               5                   10                  15

Tyr Asp Phe Tyr Asp Gly Tyr Tyr Asn Tyr His Tyr Met Asp Val Trp
                20                  25                  30

<210> SEQ ID NO 349
<211> LENGTH: 20
<212> TYPE: PRT
<213> ORGANISM: Bos taurus
<220> FEATURE:

<223> OTHER INFORMATION: B-S1

<400> SEQUENCE: 349

Cys Ala Lys Ser Ser Gly Thr Asn Phe Ala Val Ala Thr Trp Asp Val
1               5                   10                  15

Ile Asp Ala Trp
            20

<210> SEQ ID NO 350
<211> LENGTH: 26
<212> TYPE: PRT
<213> ORGANISM: Bos taurus
<220> FEATURE:
<223> OTHER INFORMATION: B-S2

<400> SEQUENCE: 350

Cys Ala Lys Ser Ser Gly Asn Val Gly Phe Tyr Gln Ser Tyr Asn Ser
1               5                   10                  15

Arg Ser Trp Lys Gln Tyr Val Asp Ala Trp
            20                  25

<210> SEQ ID NO 351
<211> LENGTH: 27
<212> TYPE: PRT
<213> ORGANISM: Bos taurus
<220> FEATURE:
<223> OTHER INFORMATION: B-S3

<400> SEQUENCE: 351

Cys Ala Lys His Phe Ala Gly Ala Asn Ile Ile Cys Asp Leu Asn His
1               5                   10                  15

Asp Ala Trp Gly Ser Gly Ser Leu Asp Ala Trp
            20                  25

<210> SEQ ID NO 352
<211> LENGTH: 30
<212> TYPE: PRT
<213> ORGANISM: Bos taurus
<220> FEATURE:
<223> OTHER INFORMATION: B-S4

<400> SEQUENCE: 352

Cys Thr Lys Glu Thr Trp Thr Gly Pro Gly Tyr Asn Ala Asn Gly Cys
1               5                   10                  15

Tyr Cys Val Gly Gly Arg Gly Glu Cys Tyr Val Asp Ala Trp
            20                  25                  30

<210> SEQ ID NO 353
<211> LENGTH: 60
<212> TYPE: PRT
<213> ORGANISM: Bos taurus
<220> FEATURE:
<223> OTHER INFORMATION: BF4E9

<400> SEQUENCE: 353

Cys Thr Thr Val His Gln Ile Phe Cys Pro Asp Gly Tyr Ser Tyr Gly
1               5                   10                  15

Tyr Gly Cys Gly Tyr Gly Tyr Gly Cys Ser Gly Tyr Cys Tyr Gly
            20                  25                  30

Tyr Gly Gly Tyr Gly Tyr Gly Gly Tyr Gly Tyr Ser Ser Tyr Ser
        35                  40                  45

Tyr Ser Tyr Ser Tyr Glu Tyr Tyr Gly Asp Ala Trp
    50                  55                  60

```
<210> SEQ ID NO 354
<211> LENGTH: 60
<212> TYPE: PRT
<213> ORGANISM: Bos taurus
<220> FEATURE:
<223> OTHER INFORMATION: BLV5B8

<400> SEQUENCE: 354

Cys Thr Thr Val His Gln Glu Thr Arg Lys Thr Cys Ser Asp Gly Tyr
1               5                   10                  15

Ile Ala Val Asp Ser Cys Gly Arg Gly Gln Ser Asp Gly Cys Val Asn
            20                  25                  30

Asp Cys Asn Ser Cys Tyr Tyr Gly Trp Arg Asn Cys Arg Arg Gln Pro
        35                  40                  45

Ala Ile His Ser Tyr Glu Phe His Val Asp Ala Trp
    50                  55                  60

<210> SEQ ID NO 355
<211> LENGTH: 61
<212> TYPE: PRT
<213> ORGANISM: Bos taurus
<220> FEATURE:
<223> OTHER INFORMATION: BLV5D3

<400> SEQUENCE: 355

Cys Ser Ser Val Thr Gln Arg Thr His Val Ser Arg Ser Cys Pro Asp
1               5                   10                  15

Gly Cys Ser Asp Gly Asp Gly Cys Val Asp Gly Cys Cys Cys Ser Ala
            20                  25                  30

Tyr Arg Cys Tyr Thr Pro Gly Val Arg Asp Leu Ser Cys Thr Ser Tyr
        35                  40                  45

Ser Ile Thr Tyr Thr Tyr Glu Trp Asn Val Asp Ala Trp
    50                  55                  60

<210> SEQ ID NO 356
<211> LENGTH: 62
<212> TYPE: PRT
<213> ORGANISM: Bos taurus
<220> FEATURE:
<223> OTHER INFORMATION: BLV8C11

<400> SEQUENCE: 356

Cys Thr Thr Val His Gln Lys Thr Thr Arg Lys Thr Cys Cys Ser Asp
1               5                   10                  15

Ala Tyr Arg Tyr Asp Ser Gly Cys Gly Ser Gly Cys Asp Cys Cys Gly
            20                  25                  30

Ala Asp Cys Tyr Val Phe Gly Ala Cys Thr Phe Gly Leu Asp Ser Ser
        35                  40                  45

Tyr Ser Tyr Ile Tyr Ile Tyr Gln Trp Tyr Val Asp Ala Trp
    50                  55                  60

<210> SEQ ID NO 357
<211> LENGTH: 63
<212> TYPE: PRT
<213> ORGANISM: Bos taurus
<220> FEATURE:
<223> OTHER INFORMATION: B-L2

<400> SEQUENCE: 357

Cys Ala Thr Val Arg Gln Thr Thr Leu Arg Asp Cys Pro Gly Gly Tyr
1               5                   10                  15
```

```
Thr Glu Asp Arg Ser Cys Val Asn Thr Tyr Ser Cys Gly Ala Asp Asp
            20                  25                  30

Cys Cys Gly Arg Gly Asp Val Gly Tyr Pro Ala Leu Tyr Gly Tyr Arg
        35                  40                  45

Cys Ala Ala His Ile Gln Arg Tyr Asn Trp His Ala Asp Ala Trp
    50                  55                  60

<210> SEQ ID NO 358
<211> LENGTH: 65
<212> TYPE: PRT
<213> ORGANISM: Bos taurus
<220> FEATURE:
<223> OTHER INFORMATION: BLV1H12

<400> SEQUENCE: 358

Cys Thr Ser Val His Gln Glu Thr Lys Lys Tyr Gln Ser Cys Pro Asp
1               5                   10                  15

Gly Tyr Arg Glu Arg Ser Asp Cys Ser Asn Arg Pro Ala Cys Gly Thr
            20                  25                  30

Ser Asp Cys Cys Arg Val Ser Val Phe Gly Asn Cys Leu Thr Thr Leu
        35                  40                  45

Pro Val Ser Tyr Ser Tyr Thr Tyr Asn Tyr Glu Trp His Val Asp Val
    50                  55                  60

Trp
65

<210> SEQ ID NO 359
<211> LENGTH: 70
<212> TYPE: PRT
<213> ORGANISM: Bos taurus
<220> FEATURE:
<223> OTHER INFORMATION: B-L1

<400> SEQUENCE: 359

Cys Ser Thr Val His Gln Lys Thr Arg Thr Thr Gln Gly Asn Thr Cys
1               5                   10                  15

Pro Asp Gly Tyr Thr Leu Lys Asp Asp Cys Pro Arg Cys Arg Gly Gly
            20                  25                  30

Cys Asp Gly Tyr Asp Cys Cys Trp Gly Asp Ala Cys Arg Ser Ser Gly
        35                  40                  45

Leu Cys Trp Gly His Asn Pro Leu Val Thr Glu Thr Tyr Thr Tyr Glu
    50                  55                  60

Phe Tyr Ile Asp Ala Trp
65                  70

<210> SEQ ID NO 360
<211> LENGTH: 48
<212> TYPE: PRT
<213> ORGANISM: Bos taurus
<220> FEATURE:
<223> OTHER INFORMATION: BLV1H12 (2)

<400> SEQUENCE: 360

Ser Cys Pro Asp Gly Tyr Arg Glu Arg Ser Asp Cys Ser Asn Arg Pro
1               5                   10                  15

Ala Cys Gly Thr Ser Asp Cys Cys Arg Val Ser Val Phe Gly Asn Cys
            20                  25                  30

Leu Thr Thr Leu Pro Val Ser Tyr Ser Tyr Thr Tyr Asn Tyr Glu Trp
        35                  40                  45
```

<210> SEQ ID NO 361
<211> LENGTH: 44
<212> TYPE: PRT
<213> ORGANISM: Bos taurus
<220> FEATURE:
<223> OTHER INFORMATION: BLV5B8 (2)

<400> SEQUENCE: 361

```
Cys Ser Asp Gly Tyr Ile Ala Val Asp Ser Cys Gly Arg Gly Gln Ser
1               5                   10                  15

Asp Gly Cys Val Asn Asp Cys Asn Ser Cys Tyr Tyr Gly Trp Arg Asn
            20                  25                  30

Cys Arg Arg Gln Pro Ala Ile His Ser Tyr Glu Phe
        35                  40
```

<210> SEQ ID NO 362
<211> LENGTH: 133
<212> TYPE: PRT
<213> ORGANISM: Bos taurus
<220> FEATURE:
<223> OTHER INFORMATION: VHBUL

<400> SEQUENCE: 362

```
Leu Lys Arg Leu Val Gly Val Val Thr Leu Ile Cys Ser Lys Met Asn
1               5                   10                  15

Pro Leu Trp Thr Leu Leu Phe Val Leu Ser Ala Pro Arg Gly Val Leu
            20                  25                  30

Ser Gln Val Gln Leu Arg Glu Ser Gly Pro Ser Leu Val Lys Pro Ser
        35                  40                  45

Gln Thr Leu Ser Leu Thr Cys Thr Ala Ser Gly Phe Ser Leu Ser Asp
    50                  55                  60

Lys Ala Val Gly Trp Val Arg Gln Ala Pro Gly Lys Ala Leu Glu Trp
65                  70                  75                  80

Leu Gly Gly Ile Asp Thr Gly Gly Ser Thr Gly Tyr Asn Pro Gly Leu
                85                  90                  95

Lys Ser Arg Leu Ser Ile Thr Lys Asp Asn Ser Lys Ser Gln Val Ser
            100                 105                 110

Leu Ser Val Ser Ser Val Thr Thr Glu Asp Ser Ala Thr Tyr Tyr Cys
        115                 120                 125

Thr Thr Val His Gln
    130
```

<210> SEQ ID NO 363
<211> LENGTH: 521
<212> TYPE: DNA
<213> ORGANISM: Bos taurus
<220> FEATURE:
<223> OTHER INFORMATION: VHBUL
<220> FEATURE:
<221> NAME/KEY: CDS
<222> LOCATION: (1)..(90)
<220> FEATURE:
<221> NAME/KEY: CDS
<222> LOCATION: (173)..(481)

<400> SEQUENCE: 363

```
ttg aag aga ctt gtg gga gtg gtg act ctc atc tgc tcc aag atg aac      48
Leu Lys Arg Leu Val Gly Val Val Thr Leu Ile Cys Ser Lys Met Asn
1               5                   10                  15 cca ctg tgg acc ctc ctc ttt gtg ctc tca gcc ccc aga ggt              90
Pro Leu Trp Thr Leu Leu Phe Val Leu Ser Ala Pro Arg Gly
            20                  25                  30
```

```
gagtgtctct gggtcagaca taggcacgtg gggaagctgc ctctgagccc acgggtcacc      150
gtgcttctct ctctccacag gg gtc ctg tcc cag gtg cag ctg cgg gag tcg      202
                         Val Leu Ser Gln Val Gln Leu Arg Glu Ser
                                      35                  40 ggc ccc agc ctg gtg aag ccc tca cag acc ctc tcg ctc acc tgc acg      250
Gly Pro Ser Leu Val Lys Pro Ser Gln Thr Leu Ser Leu Thr Cys Thr
                45                  50                  55 gcc tct gga ttc tca ttg agc gac aag gct gta ggc tgg gtc cgc cag      298
Ala Ser Gly Phe Ser Leu Ser Asp Lys Ala Val Gly Trp Val Arg Gln
            60                  65                  70 gct cca ggg aag gcg ctg gag tgg ctc ggt ggt ata gac act ggt gga      346
Ala Pro Gly Lys Ala Leu Glu Trp Leu Gly Gly Ile Asp Thr Gly Gly
        75                  80                  85 agc aca ggc tat aac cca ggc ctg aaa tcc cgg ctc agc atc acc aag      394
Ser Thr Gly Tyr Asn Pro Gly Leu Lys Ser Arg Leu Ser Ile Thr Lys
    90                  95                 100 gac aac tcc aag agc caa gtc tct ctg tca gtg agc agc gtg aca act      442
Asp Asn Ser Lys Ser Gln Val Ser Leu Ser Val Ser Ser Val Thr Thr
105                 110                 115                 120 gag gac tcg gcc aca tac tac tgt act act gtg cac cag acacagtgag      491
Glu Asp Ser Ala Thr Tyr Tyr Cys Thr Thr Val His Gln
                125                 130 gggaaatcag tgtgagccca gacaaaaacc                                      521

<210> SEQ ID NO 364
<211> LENGTH: 6
<212> TYPE: PRT
<213> ORGANISM: Bos taurus
<220> FEATURE:
<223> OTHER INFORMATION: VH germline

<400> SEQUENCE: 364

Cys Thr Thr Val His Gln
1               5

<210> SEQ ID NO 365
<211> LENGTH: 48
<212> TYPE: PRT
<213> ORGANISM: Bos taurus
<220> FEATURE:
<223> OTHER INFORMATION: DH2 germline

<400> SEQUENCE: 365

Ser Cys Pro Asp Gly Tyr Ser Tyr Gly Tyr Gly Cys Gly Tyr Gly Tyr
1               5                   10                  15

Gly Cys Ser Gly Tyr Asp Cys Tyr Gly Tyr Gly Gly Tyr Gly Gly Tyr
            20                  25                  30

Gly Gly Tyr Gly Tyr Ser Ser Tyr Ser Tyr Ser Tyr Thr Tyr Glu Tyr
        35                  40                  45

<210> SEQ ID NO 366
<211> LENGTH: 5
<212> TYPE: PRT
<213> ORGANISM: Bos taurus
<220> FEATURE:
<223> OTHER INFORMATION: JH1 germline

<400> SEQUENCE: 366

Tyr Val Asp Ala Trp
1               5
```

```
<210> SEQ ID NO 367
<211> LENGTH: 64
<212> TYPE: PRT
<213> ORGANISM: Bos taurus
<220> FEATURE:
<223> OTHER INFORMATION: BLV1H12

<400> SEQUENCE: 367

Cys Thr Ser Val His Gln Glu Thr Lys Lys Tyr Ser Cys Pro Asp Gly
1               5                   10                  15

Tyr Arg Glu Arg Ser Asp Cys Ser Asn Arg Pro Ala Cys Gly Thr Ser
            20                  25                  30

Asp Cys Cys Arg Val Ser Val Phe Gly Asn Cys Leu Thr Thr Leu Pro
        35                  40                  45

Val Ser Tyr Ser Tyr Thr Tyr Asn Tyr Glu Trp His Val Asp Val Trp
    50                  55                  60

<210> SEQ ID NO 368
<211> LENGTH: 60
<212> TYPE: PRT
<213> ORGANISM: Bos taurus
<220> FEATURE:
<223> OTHER INFORMATION: BLV5B8

<400> SEQUENCE: 368

Cys Thr Thr Val His Gln Glu Thr Arg Lys Thr Cys Ser Asp Gly Tyr
1               5                   10                  15

Ile Ala Val Asp Ser Cys Gly Arg Gly Gln Ser Asp Gly Cys Val Asn
            20                  25                  30

Asp Cys Asn Ser Cys Tyr Tyr Gly Trp Arg Asn Cys Arg Arg Gln Pro
        35                  40                  45

Ala Ile His Ser Tyr Glu Phe His Val Asp Ala Trp
    50                  55                  60

<210> SEQ ID NO 369
<211> LENGTH: 63
<212> TYPE: PRT
<213> ORGANISM: Bos taurus
<220> FEATURE:
<223> OTHER INFORMATION: Bovine VH CDRH3 (1)

<400> SEQUENCE: 369

Cys Ser Pro Val His Gln Glu Ile Arg Lys Cys Cys Pro Ala Gly Cys
1               5                   10                  15

Gln Cys Gly Arg Ser Cys Gly Ala Cys Cys Gly Cys Ala Gly Asp Glu
            20                  25                  30

Phe Cys Gly Ile Asn Val Tyr Gly Tyr Val Thr Cys Gly Gly Tyr Arg
        35                  40                  45

Thr Cys Ser Cys Ile Asp Thr Tyr Asp Phe Tyr Val Asp Ala Trp
    50                  55                  60

<210> SEQ ID NO 370
<211> LENGTH: 63
<212> TYPE: PRT
<213> ORGANISM: Bos taurus
<220> FEATURE:
<223> OTHER INFORMATION: Bovine VH CDRH3 (2)

<400> SEQUENCE: 370

Cys Thr Thr Val His Gln Lys Thr Lys Lys Leu Cys Pro Asn Gly Arg
1               5                   10                  15

Thr Cys Gly Cys Gly Cys Asp Cys Gly Ser Gly Cys Cys Thr Ser Tyr
```

20                  25                  30

Cys Asp Ser Phe Gly Cys Trp Gly Gly Arg Asp Thr Phe Gly Ser Ser
            35                  40                  45

Cys Thr Ser Ala Thr Tyr Thr Tyr Glu Trp Gly Val Asp Ala Trp
    50                  55                  60

<210> SEQ ID NO 371
<211> LENGTH: 64
<212> TYPE: PRT
<213> ORGANISM: Bos taurus
<220> FEATURE:
<223> OTHER INFORMATION: Bovine VH CDRH3 (3)

<400> SEQUENCE: 371

Cys Ala Thr Val His Gln His Thr Asn Lys Lys Arg Cys Pro Asp Gly
1               5                   10                  15

Tyr Glu Phe Ser Ala Gly Cys Cys Gly Glu Gly Cys Ser Gly Ser
            20                  25                  30

Asp Cys Cys Cys Asn Ser Arg Leu Arg Cys Ser Trp Tyr Glu Ile Tyr
            35                  40                  45

Cys Ser Val Ser Pro Ser Asp Thr Tyr Glu Phe His Val Asp Ala Trp
    50                  55                  60

<210> SEQ ID NO 372
<211> LENGTH: 70
<212> TYPE: PRT
<213> ORGANISM: Bos taurus
<220> FEATURE:
<223> OTHER INFORMATION: Bovine VH CDRH3 (4)

<400> SEQUENCE: 372

Cys Ser Thr Val His Gln Lys Thr Arg Thr Thr Gln Gly Asn Thr Cys
1               5                   10                  15

Pro Asp Gly Tyr Thr Leu Lys Asp Asp Cys Pro Arg Cys Arg Gly Gly
            20                  25                  30

Cys Asp Gly Tyr Asp Cys Cys Trp Gly Asp Ala Cys Arg Ser Ser Gly
            35                  40                  45

Leu Cys Trp Gly His Asn Pro Leu Val Thr Glu Thr Tyr Thr Tyr Glu
    50                  55                  60

Phe Tyr Ile Asp Ala Trp
65                  70

<210> SEQ ID NO 373
<211> LENGTH: 63
<212> TYPE: PRT
<213> ORGANISM: Bos taurus
<220> FEATURE:
<223> OTHER INFORMATION: Bovine VH CDRH3 (5)

<400> SEQUENCE: 373

Cys Thr Thr Val His Gln Glu Thr His Lys Arg Cys Pro Asp Gly Tyr
1               5                   10                  15

Thr Tyr Gly Tyr Tyr Cys Gly Tyr Ala Cys Thr Cys Ser Gly Asp Glu
            20                  25                  30

Cys Tyr Arg Tyr Asp Tyr Cys Ala Ala Tyr Gly Ser Leu Gly Cys Cys
            35                  40                  45

Thr Asn Asp His Thr Tyr Thr Tyr Glu Phe His Val Asp Ser Trp
    50                  55                  60

<210> SEQ ID NO 374

```
<211> LENGTH: 63
<212> TYPE: PRT
<213> ORGANISM: Bos taurus
<220> FEATURE:
<223> OTHER INFORMATION: Bovine VH CDRH3 (6)

<400> SEQUENCE: 374

Cys Thr Ala Val Tyr Gln Gln Thr Arg Lys Ser Cys Pro Asp Gly Tyr
1               5                   10                  15

Arg Ser Gly Asn Asp Cys Ser Ser Ala Cys Ser Cys Ser Asn Tyr Glu
            20                  25                  30

Cys Tyr Arg Tyr Gly Ser Tyr Gly Ser Asn Gly Lys Cys Gly Tyr Asp
        35                  40                  45

Ala His Ala Tyr Thr Tyr Thr Tyr Glu Ile His Ile Asp Ala Trp
    50                  55                  60

<210> SEQ ID NO 375
<211> LENGTH: 64
<212> TYPE: PRT
<213> ORGANISM: Bos taurus
<220> FEATURE:
<223> OTHER INFORMATION: Bovine VH CDRH3 (7)

<400> SEQUENCE: 375

Cys Gly Ala Val His Gln Lys Thr Ala Arg Ser Cys Pro Asn Ile Tyr
1               5                   10                  15

Ser Thr Tyr Tyr Gly Gly Arg Ser Gly Ser Val Gly Cys Ser Ala Tyr
            20                  25                  30

Asp Cys Glu Asn Cys Cys Thr Tyr Asp Gly Met Gly Arg Tyr Ser Val
        35                  40                  45

Ser Thr Cys Ser Gly Ser Val Ile Tyr Glu Phe Tyr Val Asp Thr Trp
    50                  55                  60

<210> SEQ ID NO 376
<211> LENGTH: 60
<212> TYPE: PRT
<213> ORGANISM: Bos taurus
<220> FEATURE:
<223> OTHER INFORMATION: Bovine VH CDRH3 (8)

<400> SEQUENCE: 376

Cys Ala Thr Lys Lys Gln Ile Cys Cys Pro Asp Asp Ser Ser Leu Glu
1               5                   10                  15

Val Ala Cys Ser His Gly Ala Gly Cys Ser Gly Cys Val Gly Tyr Thr
            20                  25                  30

Gly Gly Thr Trp Gly Thr Leu Ser Asp Tyr Phe His Gly Lys Tyr Thr
        35                  40                  45

Cys Thr Tyr Thr Tyr Glu His Asn Val Asp Ala Trp
    50                  55                  60

<210> SEQ ID NO 377
<211> LENGTH: 63
<212> TYPE: PRT
<213> ORGANISM: Bos taurus
<220> FEATURE:
<223> OTHER INFORMATION: Bovine VH CDRH3 (9)

<400> SEQUENCE: 377

Cys Thr Ile Val His Gln Gln Thr Thr Lys Arg Cys Pro Asp Asp
1               5                   10                  15

Asn Tyr Pro Tyr Trp Cys Ser Val Ala Asn Gly Gly Gly Ser Asp Ala
            20                  25                  30
```

```
Cys Tyr Gly Cys Ser Gly Arg Ser Ser Asp Thr Phe Trp Arg Cys Ser
            35                  40                  45

Thr Val Arg Tyr Arg Tyr Thr Tyr Glu Trp His Val Asp Ala Trp
        50                  55                  60

<210> SEQ ID NO 378
<211> LENGTH: 63
<212> TYPE: PRT
<213> ORGANISM: Bos taurus
<220> FEATURE:
<223> OTHER INFORMATION: Bovine VH CDRH3 (10)

<400> SEQUENCE: 378

Cys Ala Thr Val His Gln Leu Thr Arg Ala His Cys Pro Asp Asp Tyr
1               5                   10                  15

Ser Tyr Leu Tyr Thr Ser Arg Trp Asp Cys Ala Ser Cys Asp Asp Gly
            20                  25                  30

Cys Tyr Ala Ala Arg Asp Trp Arg Gly Cys Phe Asp Cys Glu Ser Ser
            35                  40                  45

Lys Thr Ser Val Ser Tyr Ile Tyr Glu His His Val Asn Ala Trp
        50                  55                  60

<210> SEQ ID NO 379
<211> LENGTH: 65
<212> TYPE: PRT
<213> ORGANISM: Bos taurus
<220> FEATURE:
<223> OTHER INFORMATION: Bovine VH CDRH3 (11)

<400> SEQUENCE: 379

Cys Ala Thr Val His Gln Arg Thr Glu Lys Ser Cys Ser Ala Gly His
1               5                   10                  15

Ile Asp Gly Val Gln Cys Cys Ser Gly Val Ala Cys Asp Gly Ala
            20                  25                  30

Gly Cys Val Arg Gly Cys Ser Tyr Gly Thr Asp Gly Trp Tyr Gly Trp
            35                  40                  45

Cys Asn Arg Tyr Ser Tyr Thr Ile Thr Tyr Glu Phe Tyr Val Thr Ala
        50                  55                  60

Trp
65

<210> SEQ ID NO 380
<211> LENGTH: 67
<212> TYPE: PRT
<213> ORGANISM: Bos taurus
<220> FEATURE:
<223> OTHER INFORMATION: Bovine VH CDRH3 (12)

<400> SEQUENCE: 380

Cys Thr Thr Val His Gln Arg Thr Lys Arg Ser Cys Pro Asp Asp Tyr
1               5                   10                  15

Thr Tyr Thr Tyr Thr Cys Val Ser Glu Ser Asp His Gln Ala Glu Arg
            20                  25                  30

Gly Cys Tyr Gly Pro Gly Gly Tyr Gly Trp Cys Asp Trp Thr Gly Ser
            35                  40                  45

Thr Thr Val Ser Arg Glu Gly Glu Arg Asn Asn Tyr Glu Phe His Ile
        50                  55                  60

Asp Ala Trp
65
```

```
<210> SEQ ID NO 381
<211> LENGTH: 63
<212> TYPE: PRT
<213> ORGANISM: Bos taurus
<220> FEATURE:
<223> OTHER INFORMATION: Bovine VH CDRH3 (13)

<400> SEQUENCE: 381
```

Cys Thr Thr Val His Gln Ile Thr His Lys Glu Cys Pro Asp Gly Tyr
1               5                   10                  15

Ser Asp Gly Cys Thr Cys Thr Arg Ser Trp Tyr Tyr Ser Gly Trp Asn
            20                  25                  30

Cys Tyr Pro Gly Glu Val Cys Trp Ser Arg Gly Gly Cys Gly Ile Ser
        35                  40                  45

Gly Val Thr Tyr Ser Asp Thr Tyr Glu Phe Tyr Ile Asp Ala Trp
    50                  55                  60

```
<210> SEQ ID NO 382
<211> LENGTH: 65
<212> TYPE: PRT
<213> ORGANISM: Bos taurus
<220> FEATURE:
<223> OTHER INFORMATION: Bovine VH CDRH3 (14)

<400> SEQUENCE: 382
```

Cys Gly Thr Val His Gln His Thr Thr Lys Asn Thr Cys Pro Asp
1               5                   10                  15

Gly Tyr Thr Phe Arg Ala Gly Cys Cys Cys Ser Ser Gly Cys Ile Ser
            20                  25                  30

Cys Asp Ser Ser Ile Cys Asp Asn Thr Ser Pro Ser Trp Phe Cys Ser
        35                  40                  45

Arg Thr Ser Pro Thr Tyr Thr Tyr Thr Tyr Glu Phe Tyr Ile Thr Ala
    50                  55                  60

Trp
65

```
<210> SEQ ID NO 383
<211> LENGTH: 62
<212> TYPE: PRT
<213> ORGANISM: Bos taurus
<220> FEATURE:
<223> OTHER INFORMATION: Bovine VH CDRH3 (15)

<400> SEQUENCE: 383
```

Cys Ala Thr Val His Gln Lys Thr Leu Glu Lys Thr Cys Pro Asp Gly
1               5                   10                  15

Tyr Ala Tyr Gly Asp Thr Asp Asn Gly His Cys Ser Ala Tyr Asp Cys
            20                  25                  30

Trp Arg Met Gly Thr Tyr Cys Thr Glu Asp Met Tyr Gly Cys Ser Cys
        35                  40                  45

Tyr Ser Gly Thr Thr Thr Tyr Glu Trp Tyr Val Glu Ala Trp
    50                  55                  60

```
<210> SEQ ID NO 384
<211> LENGTH: 64
<212> TYPE: PRT
<213> ORGANISM: Bos taurus
<220> FEATURE:
<223> OTHER INFORMATION: Bovine VH CDRH3 (16)

<400> SEQUENCE: 384
```

-continued

Cys Ala Thr Val His Gln Glu Val Gln Lys Thr Cys Pro Asp Gly
1               5                   10                  15

Tyr Ala His Leu Gly Phe Cys Asn Asp Asp Gly Arg Leu Gly Ser
            20                  25                  30

Ala Cys Cys Ser Gly Gly Ala Phe Gly Ser Asp Gly Asp Thr Asp Cys
            35                  40                  45

His Cys Tyr Ser Asp Ser Tyr Asn Tyr Glu Asn His Val Asp Glu Trp
50                  55                  60

<210> SEQ ID NO 385
<211> LENGTH: 59
<212> TYPE: PRT
<213> ORGANISM: Bos taurus
<220> FEATURE:
<223> OTHER INFORMATION: Bovine VH CDRH3 (17)

<400> SEQUENCE: 385

Cys Ser Thr Val His Gln Lys Thr Gln Arg Ser Cys Pro Asp Gly Tyr
1               5                   10                  15

Arg Thr Gly Tyr Gly Cys Asp Asp Gly Ser Cys Cys Ser Gly Ser Asn
            20                  25                  30

Cys Tyr Ser Tyr Leu Ser Arg Ile Asn Arg Gly Thr Cys Arg Thr Lys
            35                  40                  45

Ile Thr Thr Tyr Glu His His Ile Asp Ala Trp
    50                  55

<210> SEQ ID NO 386
<211> LENGTH: 67
<212> TYPE: PRT
<213> ORGANISM: Bos taurus
<220> FEATURE:
<223> OTHER INFORMATION: Bovine VH CDRH3 (18)

<400> SEQUENCE: 386

Cys Thr Thr Val His Gln Glu Thr Lys Thr Arg Ser Thr Cys Pro Asp
1               5                   10                  15

Gly Tyr Gly Cys Thr Val Gly Cys Tyr Tyr Gly Thr Tyr Ser Cys Ser
            20                  25                  30

Gly Ser Asp Cys Thr Cys Ser Arg Ile Arg Arg Val Tyr Gly Ala Thr
            35                  40                  45

Gly Gly Leu Ser Ile Cys Thr Ser Thr His Thr Tyr Glu Trp His Val
50                  55                  60

Asp Thr Trp
65

<210> SEQ ID NO 387
<211> LENGTH: 64
<212> TYPE: PRT
<213> ORGANISM: Bos taurus
<220> FEATURE:
<223> OTHER INFORMATION: Bovine VH CDRH3 (19)

<400> SEQUENCE: 387

Cys Thr Thr Val His Gln Arg Thr Thr Glu Arg Ser Cys Pro Glu
1               5                   10                  15

Gly Tyr Asn Trp Arg Tyr Gly Cys Asp Gly Trp Val Arg Gly Cys Ser
            20                  25                  30

Asp Ala Cys Trp Thr Gly Asp Thr Asp Gly Ala Arg Gly Glu Tyr Gly
            35                  40                  45

Gly Asp Gly Ser Val Arg Thr Ser Tyr Glu Trp Tyr Ala Asp Ala Trp

<210> SEQ ID NO 388
<211> LENGTH: 62
<212> TYPE: PRT
<213> ORGANISM: Bos taurus
<220> FEATURE:
<223> OTHER INFORMATION: Bovine VH CDRH3 (20)

<400> SEQUENCE: 388

```
Cys Thr Thr Val His Gln Lys Thr Gln Arg Thr Cys Pro Asp Gly Trp
1               5                   10                  15
Thr Asp Ile Trp Asp Cys Cys Arg Lys Ser Thr Cys Ser Gly Ser Asp
            20                  25                  30
Cys Pro Thr Asn Asp Asp Cys Arg Leu Ile Phe Pro Tyr Ala Trp Ser
        35                  40                  45
Thr Thr Tyr Leu Tyr Thr Tyr Glu His His Val Asp Thr Trp
    50                  55                  60
```

<210> SEQ ID NO 389
<211> LENGTH: 144
<212> TYPE: DNA
<213> ORGANISM: Bos taurus
<220> FEATURE:
<223> OTHER INFORMATION: DH2 germline

<400> SEQUENCE: 389

```
agttgtcctg atggttatag ttatggttat ggttgtggtt atggttatgg ttgtagtggt      60
tatgattgtt atggttatgg tggttatggt ggttatggtg ttatggttat tagtagttat     120
agttatagtt atacttacga atat                                            144
```

<210> SEQ ID NO 390
<211> LENGTH: 155
<212> TYPE: DNA
<213> ORGANISM: Bos taurus
<220> FEATURE:
<223> OTHER INFORMATION: MID10

<400> SEQUENCE: 390

```
tgtactactg tgcaccagaa aacacaaaaa gttgtcctga tggttatatg atgtgtatgt      60
gttgtgcgtg ttgtgtggtg gtgttgtgtt tggtgtatg gtttgtggta ctgtatgtag     120
tatacttata cttacgaatt cacgtcgatg cctgg                                155
```

<210> SEQ ID NO 391
<211> LENGTH: 155
<212> TYPE: DNA
<213> ORGANISM: Bos taurus
<220> FEATURE:
<223> OTHER INFORMATION: MID1

<400> SEQUENCE: 391

```
tgtactactg tgcaccagaa aacaacaaac agttgtcctg atggttatag tatggtatct      60
gtgtgtactt atggttgtgt gtgatgattg tgtgtagtta tggtcgtgtg gtatgtgtga     120
gttatatata cttacgaatt cacgtcgatg cctgg                                155
```

<210> SEQ ID NO 392
<211> LENGTH: 157
<212> TYPE: DNA
<213> ORGANISM: Bos taurus
<220> FEATURE:
<223> OTHER INFORMATION: MID11

<400> SEQUENCE: 392

```
tgtactactg tgcaccagaa acaaaaaag ttgtcctgat ggttatagta tgatgtgtgt      60
tgtggttgtg ttgtagtgat tgattgttgt gtgtggtgtg tggtgtgtag ttgtagttgt     120
attatactta tacttacgaa ttcacgtcga tgcctgg                             157
```

<210> SEQ ID NO 393
<211> LENGTH: 160
<212> TYPE: DNA
<213> ORGANISM: Artificial Sequence
<220> FEATURE:
<223> OTHER INFORMATION: Description of Artificial Sequence: Synthetic consensus sequence

<400> SEQUENCE: 393

```
tgtactactg tgcaccagaa acacaaaaa gttgtcctga tggttatagt atgrtgtgtg      60
tgtgtttrtg gttgtggtgt rgtgrttgtg tgtgttrtgg tgtgtggttt gtggtttggt    120
tgtattatac ttatacttac gaattcacgt cgatgcctgg                          160
```

<210> SEQ ID NO 394
<211> LENGTH: 148
<212> TYPE: DNA
<213> ORGANISM: Bos taurus
<220> FEATURE:
<223> OTHER INFORMATION: Bovine DH2
<220> FEATURE:
<221> NAME/KEY: CDS
<222> LOCATION: (3)..(146)

<400> SEQUENCE: 394

```
gt agt tgt cct gat ggt tat agt tat ggt tat ggt tgt ggt tat ggt       47
   Ser Cys Pro Asp Gly Tyr Ser Tyr Gly Tyr Gly Cys Gly Tyr Gly
   1               5                   10                  15 tat ggt tgt agt ggt tat gat tgt tat ggt tat ggt ggt tat ggt ggt      95
Tyr Gly Cys Ser Gly Tyr Asp Cys Tyr Gly Tyr Gly Gly Tyr Gly Gly
                20                  25                  30 tat ggt ggt tat ggt tat agt agt tat agt tat agt tat act tac gaa    143
Tyr Gly Gly Tyr Gly Tyr Ser Ser Tyr Ser Tyr Ser Tyr Thr Tyr Glu
            35                  40                  45 tat ac                                                              148
Tyr
```

<210> SEQ ID NO 395
<211> LENGTH: 48
<212> TYPE: PRT
<213> ORGANISM: Bos taurus
<220> FEATURE:
<223> OTHER INFORMATION: Bovine DH2

<400> SEQUENCE: 395

```
Ser Cys Pro Asp Gly Tyr Ser Tyr Gly Tyr Gly Cys Gly Tyr Gly Tyr
1               5                   10                  15

Gly Cys Ser Gly Tyr Asp Cys Tyr Gly Tyr Gly Gly Tyr Gly Gly Tyr
            20                  25                  30

Gly Gly Tyr Gly Tyr Ser Ser Tyr Ser Tyr Ser Tyr Thr Tyr Glu Tyr
        35                  40                  45
```

<210> SEQ ID NO 396
<211> LENGTH: 61
<212> TYPE: PRT
<213> ORGANISM: Bos taurus
<220> FEATURE:

<223> OTHER INFORMATION: UL CDRH3 (1)

<400> SEQUENCE: 396

Cys Thr Thr Val Tyr Gln Glu Thr His Lys Asn Cys Pro Glu Gly Trp
1               5                   10                  15

Met Ser Arg Asp Thr Cys Arg Ile Asp Ala Cys Ser Gly Asp Cys Cys
            20                  25                  30

Arg Val Tyr Asp Ala Ser Thr Gln Glu Arg Trp Arg Arg Gln Val Gln
        35                  40                  45

Ser Tyr Ile Tyr Thr Tyr Glu Leu His Val Asp Thr Trp
    50                  55                  60

<210> SEQ ID NO 397
<211> LENGTH: 61
<212> TYPE: PRT
<213> ORGANISM: Bos taurus
<220> FEATURE:
<223> OTHER INFORMATION: UL CDRH3 (2)

<400> SEQUENCE: 397

Cys Thr Ala Val Tyr Gln Glu Thr His Lys Asn Cys Pro Glu Gly Tyr
1               5                   10                  15

Met Asp Arg Gly Ser Cys Arg Ile Asp Ala Cys Ser Gly Ala Cys Cys
            20                  25                  30

Arg Val Tyr Asp Ala Arg Thr Gln Glu Cys Trp Arg Arg Asp Val Gln
        35                  40                  45

Ser Tyr Ile Tyr Thr Tyr Glu Leu His Val Asp Thr Trp
    50                  55                  60

<210> SEQ ID NO 398
<211> LENGTH: 58
<212> TYPE: PRT
<213> ORGANISM: Bos taurus
<220> FEATURE:
<223> OTHER INFORMATION: UL CDRH3 (3)

<400> SEQUENCE: 398

Cys Ile Thr Ala His Gln Glu Thr Gln Lys Ser Cys Ser Asp Asp Tyr
1               5                   10                  15

Thr Tyr Tyr Gly Asp Ala Thr Cys Ala Tyr Val Cys Ser Thr Asp Glu
            20                  25                  30

Cys Cys Cys Gly Arg Thr Trp Leu Ser Ala Gly Tyr Arg Pro Cys Arg
        35                  40                  45

Tyr Thr Tyr Asn Leu His Val Asp Ala Trp
    50                  55

<210> SEQ ID NO 399
<211> LENGTH: 58
<212> TYPE: PRT
<213> ORGANISM: Bos taurus
<220> FEATURE:
<223> OTHER INFORMATION: UL CDRH3 (4)

<400> SEQUENCE: 399

Cys Ile Thr Val His Gln Glu Thr Gln Lys Ser Cys Pro Asp Asp Tyr
1               5                   10                  15

Thr Tyr Tyr Gly Asp Gly Thr Cys Val Tyr Ile Cys Ser Ile Asp Lys
            20                  25                  30

Cys Cys Cys Gly Arg Thr Trp Leu Ser Ser Gly Cys His Pro Cys Arg
        35                  40                  45

-continued

Tyr Thr Tyr Asn Leu His Val Asp Ala Trp
        50                  55

<210> SEQ ID NO 400
<211> LENGTH: 58
<212> TYPE: PRT
<213> ORGANISM: Bos taurus
<220> FEATURE:
<223> OTHER INFORMATION: UL CDRH3 (5)

<400> SEQUENCE: 400

Cys Ile Thr Val His Gln Glu Thr Gln Lys Ser Cys Pro Asp Asp Tyr
1               5                   10                  15

Thr Tyr Tyr Gly Asp Gly Thr Cys Ala Tyr Val Cys Ser Ile Asp Asn
            20                  25                  30

Cys Cys Cys Gly Arg Thr Trp Leu Ser Ser Gly Cys Leu Pro Cys Arg
        35                  40                  45

Tyr Thr Tyr Asn Leu His Val Asp Ala Trp
        50                  55

<210> SEQ ID NO 401
<211> LENGTH: 58
<212> TYPE: PRT
<213> ORGANISM: Bos taurus
<220> FEATURE:
<223> OTHER INFORMATION: UL CDRH3 (6)

<400> SEQUENCE: 401

Cys Ile Thr Val His Gln Glu Thr Gln Lys Ser Cys Pro Asp Asp Tyr
1               5                   10                  15

Thr Ser Tyr Gly Asp Ala Thr Cys Ala Tyr Val Cys Ser Thr Asp Glu
            20                  25                  30

Cys Cys Cys Gly Arg Thr Trp Leu Ser Ala Gly Cys Arg Pro Cys Arg
        35                  40                  45

Tyr Thr Tyr Asn Leu His Val Asp Ala Trp
        50                  55

<210> SEQ ID NO 402
<211> LENGTH: 58
<212> TYPE: PRT
<213> ORGANISM: Bos taurus
<220> FEATURE:
<223> OTHER INFORMATION: UL CDRH3 (7)

<400> SEQUENCE: 402

Cys Ile Thr Val His Gln Glu Thr Gln Lys Ser Cys Phe Asp Asp Tyr
1               5                   10                  15

Thr Tyr Tyr Gly Asp Ala Ser Cys Ala Tyr Val Cys Ser Thr Asp Glu
            20                  25                  30

Cys Cys Cys Gly Arg Thr Trp Leu Ser Ala Gly Cys Arg Pro Cys Arg
        35                  40                  45

Tyr Thr Tyr Asn Leu His Val Asp Ala Trp
        50                  55

<210> SEQ ID NO 403
<211> LENGTH: 58
<212> TYPE: PRT
<213> ORGANISM: Bos taurus
<220> FEATURE:
<223> OTHER INFORMATION: UL CDRH3 (8)

<400> SEQUENCE: 403

-continued

Cys Ile Thr Val His Gln Glu Thr Gln Lys Ser Cys Pro Asp Asp Tyr
1               5                   10                  15

Thr Tyr Tyr Gly Asp Gly Thr Cys Ala Tyr Val Cys Ser Ile Asp Lys
            20                  25                  30

Cys Cys Cys Gly Arg Thr Trp Leu Ser Ser Gly Cys Leu Pro Cys Arg
        35                  40                  45

Tyr Thr Tyr Asn Leu His Val Asp Ala Trp
    50                  55

<210> SEQ ID NO 404
<211> LENGTH: 58
<212> TYPE: PRT
<213> ORGANISM: Bos taurus
<220> FEATURE:
<223> OTHER INFORMATION: UL CDRH3 (9)

<400> SEQUENCE: 404

Cys Ile Thr Val His Gln Glu Thr Gln Lys Ser Cys Pro Asp Asp Tyr
1               5                   10                  15

Thr Tyr Tyr Gly Asp Ala Thr Cys Ala Tyr Val Cys Ser Thr Asp Glu
            20                  25                  30

Cys Cys Cys Gly Arg Thr Trp Leu Ser Ala Gly Cys Arg Pro Cys Arg
        35                  40                  45

Tyr Thr Tyr Asn Leu His Val Asp Ala Trp
    50                  55

<210> SEQ ID NO 405
<211> LENGTH: 58
<212> TYPE: PRT
<213> ORGANISM: Bos taurus
<220> FEATURE:
<223> OTHER INFORMATION: UL CDRH3 (10)

<400> SEQUENCE: 405

Cys Ile Thr Val His Gln Glu Thr Gln Lys Ser Cys Pro Asp Asp Tyr
1               5                   10                  15

Thr Tyr Tyr Gly Asp Ala Ser Cys Ala Tyr Val Cys Ser Thr Asp Glu
            20                  25                  30

Cys Cys Cys Gly Arg Thr Trp Leu Ser Ala Gly Cys Arg Pro Cys Arg
        35                  40                  45

Tyr Thr Tyr Asn Leu His Val Asp Ala Trp
    50                  55

<210> SEQ ID NO 406
<211> LENGTH: 58
<212> TYPE: PRT
<213> ORGANISM: Bos taurus
<220> FEATURE:
<223> OTHER INFORMATION: UL CDRH3 (11)

<400> SEQUENCE: 406

Cys Ile Thr Ala His Gln Glu Thr Gln Lys Ser Cys Ser Asp Asp Tyr
1               5                   10                  15

Thr Tyr Tyr Gly Asp Ala Thr Cys Ala Tyr Val Cys Ser Thr Asp Glu
            20                  25                  30

Cys Cys Cys Gly Arg Thr Trp Leu Ser Ala Gly Cys Arg Pro Cys Arg
        35                  40                  45

Tyr Thr Tyr Asn Leu His Val Asp Ala Trp
    50                  55

```
<210> SEQ ID NO 407
<211> LENGTH: 58
<212> TYPE: PRT
<213> ORGANISM: Bos taurus
<220> FEATURE:
<223> OTHER INFORMATION: UL CDRH3 (12)

<400> SEQUENCE: 407

Cys Gly Thr Val Tyr Gln His Thr Lys Glu Ile Lys Thr Cys Pro Asp
1               5                   10                  15

Gly Tyr Ser Asp Cys Phe Thr Tyr Cys Pro Val Thr Cys Pro Gly Trp
            20                  25                  30

Asp Cys Cys Arg Arg Asn Asp Cys Gly Arg Thr Arg Tyr Thr Val Ala
        35                  40                  45

Tyr Ser Tyr Ala Leu His Val Asp Val Trp
    50                  55

<210> SEQ ID NO 408
<211> LENGTH: 58
<212> TYPE: PRT
<213> ORGANISM: Bos taurus
<220> FEATURE:
<223> OTHER INFORMATION: UL CDRH3 (13)

<400> SEQUENCE: 408

Cys Gly Thr Val Tyr Gln His Thr Lys Glu Ile Lys Thr Cys Pro Asp
1               5                   10                  15

Gly Tyr Ser Asp Val Phe Thr Tyr Cys Pro Val Ser Cys Pro Gly Trp
            20                  25                  30

Asp Cys Cys Arg Arg Ala Asp Cys Arg Arg Thr Arg Tyr Thr Val Ala
        35                  40                  45

Tyr Ser Tyr Ala Leu His Val Asp Val Trp
    50                  55

<210> SEQ ID NO 409
<211> LENGTH: 58
<212> TYPE: PRT
<213> ORGANISM: Bos taurus
<220> FEATURE:
<223> OTHER INFORMATION: UL CDRH3 (14)

<400> SEQUENCE: 409

Cys Gly Thr Val Tyr Gln His Thr Lys Glu Ile Lys Thr Cys Pro Asp
1               5                   10                  15

Gly Tyr Ser Asp Val Phe Thr Tyr Cys Pro Val Thr Cys Pro Gly Trp
            20                  25                  30

Asp Cys Cys Arg Arg Asn Asp Cys Gly Arg Thr Arg Tyr Thr Val Ala
        35                  40                  45

Tyr Ser Tyr Ala Leu His Val Asp Val Trp
    50                  55

<210> SEQ ID NO 410
<211> LENGTH: 58
<212> TYPE: PRT
<213> ORGANISM: Bos taurus
<220> FEATURE:
<223> OTHER INFORMATION: UL CDRH3 (15)

<400> SEQUENCE: 410

Cys Gly Thr Val Tyr Gln His Thr Lys Glu Ile Lys Thr Cys Pro Asp
1               5                   10                  15

Gly Tyr Ser Asp Val Phe Thr Tyr Cys Pro Val Ser Cys Pro Gly Trp
```

```
                20                  25                  30

Asp Cys Cys Arg Arg Asn Asp Cys Gly Arg Thr Arg Tyr Thr Val Ala
            35                  40                  45

Tyr Ser Tyr Ala Leu His Val Asp Val Trp
        50                  55

<210> SEQ ID NO 411
<211> LENGTH: 48
<212> TYPE: PRT
<213> ORGANISM: Bos taurus
<220> FEATURE:
<223> OTHER INFORMATION: DH2 germline

<400> SEQUENCE: 411

Ser Cys Pro Asp Gly Tyr Ser Tyr Gly Tyr Gly Cys Gly Tyr Gly Tyr
1               5                   10                  15

Gly Cys Ser Gly Tyr Asp Cys Tyr Gly Tyr Gly Tyr Gly Tyr Gly Tyr
            20                  25                  30

Gly Gly Tyr Gly Tyr Ser Ser Tyr Ser Tyr Thr Tyr Glu Tyr
            35                  40                  45

<210> SEQ ID NO 412
<211> LENGTH: 65
<212> TYPE: PRT
<213> ORGANISM: Bos taurus
<220> FEATURE:
<223> OTHER INFORMATION: BLV1H12

<400> SEQUENCE: 412

Cys Thr Ser Val His Gln Glu Thr Lys Lys Tyr Gln Ser Cys Pro Asp
1               5                   10                  15

Gly Tyr Arg Glu Arg Ser Asp Cys Ser Asn Arg Pro Ala Cys Gly Thr
            20                  25                  30

Ser Asp Cys Cys Arg Val Ser Val Phe Gly Asn Cys Leu Thr Thr Leu
            35                  40                  45

Pro Val Ser Tyr Ser Tyr Thr Tyr Asn Tyr Glu Trp His Val Asp Val
        50                  55                  60

Trp
65

<210> SEQ ID NO 413
<211> LENGTH: 63
<212> TYPE: PRT
<213> ORGANISM: Bos taurus
<220> FEATURE:
<223> OTHER INFORMATION: B08

<400> SEQUENCE: 413

Cys Ala Ala Val His Gln Gln Thr Thr Asn Arg Cys Pro Ala Gly Ser
1               5                   10                  15

Ser Val Arg Asn Gly Cys Cys Val Asn Pro Val Trp His Pro Asn Ser
            20                  25                  30

Cys Ala Arg Asn Val Val Tyr Thr Lys Asp Gln His Gly Val Cys Cys
            35                  40                  45

Ser Glu Arg Leu Ile Tyr Thr Tyr Glu His His Val Asp Thr Trp
        50                  55                  60

<210> SEQ ID NO 414
<211> LENGTH: 63
<212> TYPE: PRT
<213> ORGANISM: Bos taurus
```

```
<220> FEATURE:
<223> OTHER INFORMATION: B09

<400> SEQUENCE: 414

Cys Thr Ile Val Asn Gln Leu Thr Lys Lys Thr Cys Pro Asp Thr Tyr
1               5                   10                  15

Thr Asp Ala Glu Ser Cys Cys Gly Gly Ser Gly Cys Tyr Leu Asp Ser
            20                  25                  30

Cys Tyr Thr Ile Lys Lys Tyr Gly Cys Gly Arg Ile Gly Arg Trp Pro
        35                  40                  45

Thr Thr Thr Tyr Ser Tyr Thr Tyr Asp Arg Tyr Val Asp Ala Trp
    50                  55                  60

<210> SEQ ID NO 415
<211> LENGTH: 67
<212> TYPE: PRT
<213> ORGANISM: Bos taurus
<220> FEATURE:
<223> OTHER INFORMATION: H12

<400> SEQUENCE: 415

Cys Val Ile Val His Gln Lys Thr Thr Gln Gln Ser Ser Cys Pro Ala
1               5                   10                  15

Gly Phe Arg Asp Cys Val Ala Cys Thr Pro Gly Pro Glu Ser Cys Cys
            20                  25                  30

Arg Ser Gly Cys Asp Gly Ala Arg Arg Val Gly Leu Arg Tyr Phe
        35                  40                  45

Phe Asp Ser Thr Ser Pro Ile Thr Thr Tyr Tyr Glu His His Ile
    50                  55                  60

Asp Ala Trp
65

<210> SEQ ID NO 416
<211> LENGTH: 15
<212> TYPE: PRT
<213> ORGANISM: Bos taurus
<220> FEATURE:
<223> OTHER INFORMATION: JH1 germline

<400> SEQUENCE: 416

Tyr Val Asp Ala Trp Gly Gln Gly Leu Leu Val Thr Val Ser Ser
1               5                   10                  15

<210> SEQ ID NO 417
<211> LENGTH: 71
<212> TYPE: PRT
<213> ORGANISM: Bos taurus
<220> FEATURE:
<223> OTHER INFORMATION: UL1

<400> SEQUENCE: 417

Cys Ser Thr Val His Gln Lys Thr Arg Thr Thr Gln Gly Glu Tyr Leu
1               5                   10                  15

Ser Leu Met Val Thr Leu Leu Lys Asp Asp Cys Pro Arg Cys Arg Gly
            20                  25                  30

Gly Cys Asp Gly Tyr Asp Cys Cys Trp Gly Asp Ala Cys Arg Ser Ser
        35                  40                  45

Gly Leu Cys Trp Gly His Asn Pro Leu Val Thr Glu Thr Tyr Thr Tyr
    50                  55                  60

Glu Phe Tyr Ile Asp Ala Trp
65                  70
```

<210> SEQ ID NO 418
<211> LENGTH: 71
<212> TYPE: PRT
<213> ORGANISM: Bos taurus
<220> FEATURE:
<223> OTHER INFORMATION: UL2

<400> SEQUENCE: 418

```
Cys Ser Thr Val His Gln Lys Thr Arg Thr Gln Gly Asn Asn Leu
1               5                   10                  15

Ser Leu Met Val Thr Leu Leu Lys Asp Asp Cys Pro Arg Cys Arg Gly
            20                  25                  30

Gly Cys Asp Gly Tyr Asp Cys Cys Trp Gly Asp Ala Cys Arg Ser Ser
            35                  40                  45

Gly Leu Cys Trp Gly His Asn Pro Leu Val Thr Glu Thr Tyr Thr Tyr
        50                  55                  60

Glu Phe Tyr Ile Asp Ala Trp
65                  70
```

<210> SEQ ID NO 419
<211> LENGTH: 70
<212> TYPE: PRT
<213> ORGANISM: Bos taurus
<220> FEATURE:
<223> OTHER INFORMATION: UL3

<400> SEQUENCE: 419

```
Cys Ser Thr Val His Gln Lys Thr Arg Thr Gln Gly Asn Thr Cys
1               5                   10                  15

Pro Asp Gly Tyr Thr Leu Lys Asp Asp Cys Pro Arg Cys Arg Gly Gly
            20                  25                  30

Cys Asp Gly Tyr Asp Cys Cys Trp Gly Asp Ala Cys Arg Ser Ser Gly
            35                  40                  45

Leu Cys Trp Gly His Asn Pro Leu Val Thr Glu Thr Tyr Thr Tyr Glu
        50                  55                  60

Phe Tyr Ile Asp Ala Trp
65                  70
```

<210> SEQ ID NO 420
<211> LENGTH: 70
<212> TYPE: PRT
<213> ORGANISM: Bos taurus
<220> FEATURE:
<223> OTHER INFORMATION: UL4

<400> SEQUENCE: 420

```
Cys Ser Thr Val His Gln Lys Thr Arg Thr Gln Gly Asn Thr Cys
1               5                   10                  15

Pro Asp Gly Tyr Thr Phe Lys Asp Asp Cys Pro Arg Cys Arg Gly Gly
            20                  25                  30

Cys Asp Gly Tyr Asp Cys Cys Trp Gly Asp Ala Cys Arg Ser Ser Gly
            35                  40                  45

Leu Cys Trp Gly His Asn Pro Leu Val Thr Glu Thr Tyr Thr Tyr Glu
        50                  55                  60

Phe Tyr Ile Asp Ala Trp
65                  70
```

<210> SEQ ID NO 421
<211> LENGTH: 70

```
<212> TYPE: PRT
<213> ORGANISM: Bos taurus
<220> FEATURE:
<223> OTHER INFORMATION: UL5

<400> SEQUENCE: 421

Cys Thr Thr Val His Gln Lys Thr Arg Thr Thr Gln Gly Asn Thr Cys
1               5                   10                  15

Pro Asp Gly Tyr Thr Leu Lys Asp Asp Cys Pro Arg Cys Arg Gly Gly
                20                  25                  30

Cys Asp Gly Tyr Asp Cys Cys Trp Gly Asp Ala Cys Arg Ser Ser Gly
            35                  40                  45

Leu Cys Trp Gly His Asn Pro Leu Val Thr Glu Thr Tyr Thr Tyr Glu
        50                  55                  60

Phe Tyr Ile Asp Ala Trp
65                  70

<210> SEQ ID NO 422
<211> LENGTH: 70
<212> TYPE: PRT
<213> ORGANISM: Bos taurus
<220> FEATURE:
<223> OTHER INFORMATION: UL6

<400> SEQUENCE: 422

Cys Ser Thr Val His Gln Lys Thr Arg Thr Thr Gln Gly Asn Thr Cys
1               5                   10                  15

Pro Asp Gly Tyr Thr Leu Lys Asn Asp Cys Pro Arg Cys Arg Gly Gly
                20                  25                  30

Cys Asp Gly Tyr Asp Cys Cys Trp Gly Asp Ala Cys Arg Ser Ser Gly
            35                  40                  45

Leu Cys Trp Gly His Asn Pro Leu Val Thr Glu Thr Tyr Thr Tyr Glu
        50                  55                  60

Phe Tyr Ile Asp Ala Trp
65                  70

<210> SEQ ID NO 423
<211> LENGTH: 70
<212> TYPE: PRT
<213> ORGANISM: Bos taurus
<220> FEATURE:
<223> OTHER INFORMATION: UL7

<400> SEQUENCE: 423

Cys Thr Thr Val Tyr Gln Lys Thr Arg Thr Thr Gln Gly Asn Thr Cys
1               5                   10                  15

Pro Asp Gly Tyr Thr Leu Lys Asp Asp Cys Pro Arg Cys Arg Gly Gly
                20                  25                  30

Cys Asp Gly Tyr Asp Cys Cys Trp Gly Asp Ala Cys Arg Ser Ser Gly
            35                  40                  45

Leu Cys Trp Gly His Asn Pro Leu Val Thr Glu Thr Tyr Thr Tyr Glu
        50                  55                  60

Phe Tyr Ile Asp Ala Trp
65                  70

<210> SEQ ID NO 424
<211> LENGTH: 70
<212> TYPE: PRT
<213> ORGANISM: Bos taurus
<220> FEATURE:
<223> OTHER INFORMATION: UL8
```

-continued

<400> SEQUENCE: 424

Cys Ser Thr Val His Gln Lys Pro Gly Gln His Lys Gly Ile Leu Val
1               5                   10                  15

Leu Met Val Thr Leu Leu Lys Asp Asp Cys Pro Arg Cys Arg Gly Gly
            20                  25                  30

Cys Asp Gly Tyr Asp Cys Cys Trp Gly Asp Ala Cys Arg Ser Ser Gly
        35                  40                  45

Leu Cys Trp Gly His Asn Pro Leu Val Thr Glu Thr Tyr Thr Tyr Glu
    50                  55                  60

Phe Tyr Ile Asp Ala Trp
65                  70

<210> SEQ ID NO 425
<211> LENGTH: 70
<212> TYPE: PRT
<213> ORGANISM: Bos taurus
<220> FEATURE:
<223> OTHER INFORMATION: UL9

<400> SEQUENCE: 425

Cys Ser Thr Val His Gln Lys Thr Arg Thr Thr Gln Gly Ile Leu Val
1               5                   10                  15

Leu Met Val Thr Leu Leu Lys Asp Asp Cys Pro Arg Cys Arg Gly Gly
            20                  25                  30

Cys Asp Gly Tyr Asp Cys Cys Trp Gly Asp Ala Cys Arg Ser Ser Gly
        35                  40                  45

Leu Cys Trp Gly His Asn Pro Leu Val Thr Glu Thr Tyr Thr Tyr Glu
    50                  55                  60

Phe Tyr Ile Asp Ala Trp
65                  70

<210> SEQ ID NO 426
<211> LENGTH: 63
<212> TYPE: PRT
<213> ORGANISM: Bos taurus
<220> FEATURE:
<223> OTHER INFORMATION: UL10

<400> SEQUENCE: 426

Cys Ser Pro Val His Gln Glu Ile Arg Lys Cys Cys Pro Ala Gly Cys
1               5                   10                  15

Gln Cys Gly Arg Ser Cys Gly Ala Cys Cys Gly Cys Ala Gly Asp Glu
            20                  25                  30

Phe Cys Gly Ile Asn Val Tyr Gly Tyr Val Thr Cys Gly Gly Tyr Arg
        35                  40                  45

Thr Cys Ser Cys Ile Asp Thr Tyr Asp Phe Tyr Val Asp Ala Trp
    50                  55                  60

<210> SEQ ID NO 427
<211> LENGTH: 63
<212> TYPE: PRT
<213> ORGANISM: Bos taurus
<220> FEATURE:
<223> OTHER INFORMATION: UL11

<400> SEQUENCE: 427

Cys Ser Pro Val His Gln Gln Thr Arg Lys Cys Cys Pro Ala Gly Cys
1               5                   10                  15

Gln Cys Gly Arg Ser Cys Gly Ala Cys Cys Gly Cys Ala Gly Asp Glu

```
                    20                  25                  30

Phe Cys Gly Ile Asn Val Tyr Gly Tyr Ile Thr Cys Gly Gly Tyr Arg
            35                  40                  45

Thr Cys Ser Cys Ile Asp Thr Tyr Asp Phe Tyr Val Glu Ala Trp
        50                  55                  60

<210> SEQ ID NO 428
<211> LENGTH: 68
<212> TYPE: PRT
<213> ORGANISM: Bos taurus
<220> FEATURE:
<223> OTHER INFORMATION: UL12

<400> SEQUENCE: 428

Cys Ala Thr Val Tyr Gln Lys Thr Asn Gln Ser Lys Asn Cys Pro Glu
1               5                   10                  15

Gly Ser Ala Trp Cys Arg Ser Cys Asp Gly Ala Gly Cys Ala Asp
            20                  25                  30

Tyr Glu Cys Cys Arg Cys Gly Trp Ser Gly Cys Ser Trp Arg Asn Gly
            35                  40                  45

Ala Cys Glu Cys Ser Ser Leu Ser Ser Ser Tyr Thr Tyr Glu Leu His
        50                  55                  60

Val Asp Ala Trp
65

<210> SEQ ID NO 429
<211> LENGTH: 65
<212> TYPE: PRT
<213> ORGANISM: Bos taurus
<220> FEATURE:
<223> OTHER INFORMATION: UL13

<400> SEQUENCE: 429

Cys Ser Thr Val His Gln Thr His Gln Ile His Thr Cys Pro Asn
1               5                   10                  15

Gly Trp Thr Gly Gly Cys Val Cys Ser Ser Arg Phe Asn Cys Arg Gly
            20                  25                  30

Asn Asn Cys Cys Arg Thr Ala Tyr Cys Ser Val Asp Arg Tyr Val
        35                  40                  45

Cys Ala Cys Pro Thr Val Thr Tyr Thr Glu Phe Asn Val Asp Ser
        50                  55                  60

Trp
65

<210> SEQ ID NO 430
<211> LENGTH: 65
<212> TYPE: PRT
<213> ORGANISM: Bos taurus
<220> FEATURE:
<223> OTHER INFORMATION: UL14

<400> SEQUENCE: 430

Cys Thr Ala Val Tyr Gln Lys Thr Thr Ser Ile Arg Ser Cys Pro Gly
1               5                   10                  15

Gly Thr Leu Arg Asn Gly Cys Arg Ser Ala Cys Gly Cys Asn Asp
            20                  25                  30

Cys Asp Cys Cys Cys Gly Ser Ser Trp Asp Ile Cys Tyr Met Ser Lys
            35                  40                  45

Cys Thr Ser Ala Pro Glu Thr Tyr Thr Tyr Glu Leu His Ile Asp Ala
        50                  55                  60
```

-continued

Trp
65

<210> SEQ ID NO 431
<211> LENGTH: 65
<212> TYPE: PRT
<213> ORGANISM: Bos taurus
<220> FEATURE:
<223> OTHER INFORMATION: UL15

<400> SEQUENCE: 431

Cys Thr Asn Val His Gln Lys Thr Lys Lys Thr Cys Pro Asp Asp Tyr
1               5                   10                  15

Thr Cys Gly Val Ser Cys Ser Cys Ser Ser Gly Cys Ala Asp Tyr
            20                  25                  30

Gly Cys Cys Ser Tyr Ile Thr Tyr Gly Val Pro Gly Asp Cys Gly Gly
            35                  40                  45

Cys Cys Ser Tyr Lys His Arg Tyr Thr Tyr Glu Trp Asn Val Asp Ala
        50                  55                  60

Trp
65

<210> SEQ ID NO 432
<211> LENGTH: 63
<212> TYPE: PRT
<213> ORGANISM: Bos taurus
<220> FEATURE:
<223> OTHER INFORMATION: UL16

<400> SEQUENCE: 432

Cys Thr Thr Val His Gln Lys Thr Lys Lys Leu Cys Pro Asn Gly Arg
1               5                   10                  15

Thr Cys Gly Cys Gly Cys Asp Cys Gly Ser Gly Cys Cys Thr Ser Tyr
            20                  25                  30

Cys Asp Ser Phe Gly Cys Trp Gly Gly Arg Asp Thr Phe Gly Ser Ser
            35                  40                  45

Cys Thr Ser Ala Thr Tyr Thr Tyr Glu Trp Gly Val Asp Ala Trp
        50                  55                  60

<210> SEQ ID NO 433
<211> LENGTH: 64
<212> TYPE: PRT
<213> ORGANISM: Bos taurus
<220> FEATURE:
<223> OTHER INFORMATION: UL17

<400> SEQUENCE: 433

Cys Ala Thr Val His Gln His Thr Asn Lys Lys Arg Cys Pro Asp Gly
1               5                   10                  15

Tyr Glu Phe Ser Ala Gly Cys Cys Gly Glu Gly Cys Ser Gly Ser
            20                  25                  30

Asp Cys Cys Cys Asn Ser Arg Leu Arg Cys Ser Trp Tyr Glu Ile Tyr
            35                  40                  45

Cys Ser Val Ser Pro Ser Asp Thr Tyr Glu Phe His Val Asp Ala Trp
        50                  55                  60

<210> SEQ ID NO 434
<211> LENGTH: 64
<212> TYPE: PRT
<213> ORGANISM: Bos taurus
<220> FEATURE:

```
<223> OTHER INFORMATION: UL18

<400> SEQUENCE: 434

Cys Thr Thr Val His Gln His Thr Asn Lys Arg Cys Pro Asp Gly
1               5                   10                  15

Tyr Arg Phe Ser Ala Ala Cys Cys Gly Glu Gly Cys Ser Gly Asn
                20                  25                  30

Glu Cys Cys Cys Asn Thr Arg Leu Arg Cys Ser Trp Tyr Glu Ile Tyr
                35                  40                  45

Cys Ser Val Ser Pro Ser Asp Thr Tyr Glu Phe His Val Asp Ala Trp
            50                  55                  60

<210> SEQ ID NO 435
<211> LENGTH: 64
<212> TYPE: PRT
<213> ORGANISM: Bos taurus
<220> FEATURE:
<223> OTHER INFORMATION: UL19

<400> SEQUENCE: 435

Cys Thr Thr Val His Gln His Thr Asn Gln Asn Arg Cys Pro Thr Gly
1               5                   10                  15

Tyr Lys His Ser Ala Gly Cys Cys Cys Gly Val Gly Cys Ser Gly Asn
                20                  25                  30

Asp Cys Cys Cys Asn Ser Arg Leu Arg Cys Ser Trp Tyr Glu Thr Tyr
                35                  40                  45

Cys Ser Leu Ser Pro Thr Asp Met Tyr Glu Phe Tyr Val Asp Ala Trp
            50                  55                  60

<210> SEQ ID NO 436
<211> LENGTH: 64
<212> TYPE: PRT
<213> ORGANISM: Bos taurus
<220> FEATURE:
<223> OTHER INFORMATION: UL20

<400> SEQUENCE: 436

Cys Ser Thr Val His Gln His Thr Asn Gln Asn Arg Cys Pro Ala Gly
1               5                   10                  15

Tyr Lys His Ser Ala Gly Cys Cys Cys Gly Val Gly Cys Ser Gly Asn
                20                  25                  30

Asp Cys Cys Cys Asn Ser Arg Leu Arg Cys Ser Trp Tyr Glu Thr Tyr
                35                  40                  45

Cys Ser Leu Ser Pro Thr Asp Met Tyr Glu Phe Tyr Val Asp Ala Trp
            50                  55                  60

<210> SEQ ID NO 437
<211> LENGTH: 63
<212> TYPE: PRT
<213> ORGANISM: Bos taurus
<220> FEATURE:
<223> OTHER INFORMATION: UL21

<400> SEQUENCE: 437

Cys Thr Thr Val His Gln Lys Thr Asn Glu Arg Cys Cys Arg Val Val
1               5                   10                  15

Ser Asp Asp Gly Glu Cys Gly Asp Gly Asn Ser Cys His Arg Trp Leu
                20                  25                  30

Cys Ser Asp Tyr Cys Tyr Ser Gly Asp Cys Cys Ala Cys Gly Cys Arg
                35                  40                  45
```

Ala Tyr His Tyr Thr Tyr Thr Tyr Glu Trp Asn Ile Asp Ala Trp
    50                  55                  60

<210> SEQ ID NO 438
<211> LENGTH: 63
<212> TYPE: PRT
<213> ORGANISM: Bos taurus
<220> FEATURE:
<223> OTHER INFORMATION: UL22

<400> SEQUENCE: 438

Cys Thr Thr Val His Gln Lys Thr Asn Glu Arg Cys Cys Arg Val Val
1               5                   10                  15

Ser Asp Asp Gly Glu Cys Gly Asp Gly Asn Ser Cys His Arg Trp Leu
            20                  25                  30

Cys Ser Asp Tyr Cys Tyr Ser Gly Asp Cys Cys Ala Cys Gly Cys Arg
        35                  40                  45

Ala Tyr His Tyr Thr Tyr Thr Tyr Asp Phe Arg Ile Asp Val Trp
    50                  55                  60

<210> SEQ ID NO 439
<211> LENGTH: 64
<212> TYPE: PRT
<213> ORGANISM: Bos taurus
<220> FEATURE:
<223> OTHER INFORMATION: UL23

<400> SEQUENCE: 439

Cys Thr Thr Val His Gln Lys Thr Asn Arg Glu Arg Cys Cys Pro Asp
1               5                   10                  15

Gly Tyr Tyr Tyr Cys Cys Arg Ser Val Ser Asp Cys Cys Cys Ser Thr
            20                  25                  30

Arg Ala Cys Val Gly Asp Ser Cys Gly Trp Thr Asp Phe Gly Ser Thr
        35                  40                  45

His Asn Val Asp Cys Ser Phe Thr Tyr Glu Phe His Val Asp Ala Trp
    50                  55                  60

<210> SEQ ID NO 440
<211> LENGTH: 63
<212> TYPE: PRT
<213> ORGANISM: Bos taurus
<220> FEATURE:
<223> OTHER INFORMATION: UL24

<400> SEQUENCE: 440

Cys Thr Thr Val His Gln Gln Thr Arg Lys Ser Cys Pro Asp Gly Tyr
1               5                   10                  15

Thr Tyr Cys His Asp Cys Gly Tyr Gly Cys Cys Cys Gly Ala Ser Phe
            20                  25                  30

Cys Arg Asp Tyr Gly Gly Cys Gly Ser Leu Cys Gly Arg Tyr Cys Thr
        35                  40                  45

Ser Phe Asp Tyr Ile Tyr Thr Tyr Glu Asn Tyr Val Glu Thr Trp
    50                  55                  60

<210> SEQ ID NO 441
<211> LENGTH: 64
<212> TYPE: PRT
<213> ORGANISM: Bos taurus
<220> FEATURE:
<223> OTHER INFORMATION: UL25

<400> SEQUENCE: 441

```
Cys Thr Thr Val His Gln Glu Thr Lys Lys Asn Cys Pro Asp Asn Cys
1               5                   10                  15

Tyr Tyr Glu Asn Ser Cys Gly Asp Tyr Gly Ser Gly Cys Asn Gly Gly
                20                  25                  30

Asp Cys Cys Arg Cys Gly Thr Trp Leu Thr Cys Ser Val Ser Gly Cys
            35                  40                  45

Thr Cys Ile Arg Ala Thr Asn Thr Tyr Gln Trp Tyr Val Asn Ala Trp
        50                  55                  60
```

<210> SEQ ID NO 442
<211> LENGTH: 64
<212> TYPE: PRT
<213> ORGANISM: Bos taurus
<220> FEATURE:
<223> OTHER INFORMATION: UL26

<400> SEQUENCE: 442

```
Cys Thr Thr Val His Gln Ser Thr Asn Lys Lys Ser Cys Pro Asp Arg
1               5                   10                  15

Val Cys Trp Ala Val Gly Cys Cys Phe Gly Glu Asp Cys Thr Ser Ser
                20                  25                  30

Asp Cys Thr Cys Tyr Ala Ser Pro Gly Asn Pro Tyr Arg His Asp Cys
            35                  40                  45

Gly Asn Cys Asp Cys Arg Ser Ser Tyr Glu His His Val Asp Ala Trp
        50                  55                  60
```

<210> SEQ ID NO 443
<211> LENGTH: 63
<212> TYPE: PRT
<213> ORGANISM: Bos taurus
<220> FEATURE:
<223> OTHER INFORMATION: UL27

<400> SEQUENCE: 443

```
Cys Thr Thr Val Arg Gln Glu Thr Leu Ile Arg Cys Arg Asp Gly Pro
1               5                   10                  15

Ser Cys Ala Ala Cys Cys Arg Ser Gly Arg Arg Cys Ser Gly Tyr Gly
                20                  25                  30

Cys Cys Thr Asp Gly Cys Cys Ser Asp Asn Asp Tyr Ala Asp Cys Ile
            35                  40                  45

Arg Gly Glu Phe Val Asp Val Tyr Glu Trp Asn Val Asp Ala Trp
        50                  55                  60
```

<210> SEQ ID NO 444
<211> LENGTH: 63
<212> TYPE: PRT
<213> ORGANISM: Bos taurus
<220> FEATURE:
<223> OTHER INFORMATION: UL28

<400> SEQUENCE: 444

```
Cys Ser Thr Val Tyr Gln Lys Thr Arg Thr Thr Cys Pro Asp Gly Tyr
1               5                   10                  15

Thr Cys Gly Asp Gly Ala Arg Cys Glu Lys Ala Cys Arg Gly Cys Asp
                20                  25                  30

Cys Cys Arg Thr Thr Val Cys Asp Thr Val Trp Ser Ser Tyr Cys Ser
            35                  40                  45

Cys Tyr Ser Phe Thr Asp Ser Tyr Glu Phe Tyr Val Asp Ala Trp
        50                  55                  60
```

```
<210> SEQ ID NO 445
<211> LENGTH: 66
<212> TYPE: PRT
<213> ORGANISM: Bos taurus
<220> FEATURE:
<223> OTHER INFORMATION: UL29

<400> SEQUENCE: 445

Cys Ala Thr Val Tyr Gln Lys Thr Asn Arg Glu Met Ser Cys Pro Asp
1               5                   10                  15

Gly Cys Arg Ile His Asn Ala Arg Leu Cys Leu Ser Gly Cys Ser Gly
            20                  25                  30

Ser Asp Cys Cys Ser Cys Gly Asp Cys Val Ser Asp Ala Arg Cys Tyr
        35                  40                  45

Asn Cys Arg Ser Ala Val Phe Thr Tyr Thr Tyr Glu Phe His Val Asp
    50                  55                  60

Ala Trp
65

<210> SEQ ID NO 446
<211> LENGTH: 63
<212> TYPE: PRT
<213> ORGANISM: Bos taurus
<220> FEATURE:
<223> OTHER INFORMATION: UL30

<400> SEQUENCE: 446

Cys Thr Ile Val His Gln Glu Thr Lys Arg Ser Cys Pro Asp Gly Tyr
1               5                   10                  15

Asn Thr Gly Thr Arg Cys Phe Gly Ser Cys Gly Cys Ile Gly Ser Asn
            20                  25                  30

Cys Cys Arg Ser Thr Thr Ser Cys Cys Ala Gly Ile Tyr Ser Gln
        35                  40                  45

Cys Thr Thr Ser Thr Leu Thr Tyr Glu Trp His Ala Asp Val Trp
    50                  55                  60

<210> SEQ ID NO 447
<211> LENGTH: 63
<212> TYPE: PRT
<213> ORGANISM: Bos taurus
<220> FEATURE:
<223> OTHER INFORMATION: UL31

<400> SEQUENCE: 447

Cys Ala Ile Val Tyr Gln Arg Thr Arg Gln Arg Cys Pro Asp Gly Tyr
1               5                   10                  15

Asn Thr Gly Thr Arg Cys Phe Gly Thr Cys Gly Cys Asn Gly Ser Asn
            20                  25                  30

Cys Cys Arg Phe Thr Thr Ser Cys Cys Ala Gly Val Tyr Ser Gln
        35                  40                  45

Cys Thr Thr Ser Thr Leu Thr Tyr Glu Trp His Ala Asp Val Trp
    50                  55                  60

<210> SEQ ID NO 448
<211> LENGTH: 63
<212> TYPE: PRT
<213> ORGANISM: Bos taurus
<220> FEATURE:
<223> OTHER INFORMATION: UL32

<400> SEQUENCE: 448

Cys Thr Thr Val His Gln Lys Thr Glu Thr Arg Cys Pro Asp Gly Tyr
```

```
1               5                   10                  15
Ser Ser Thr Asn Gly Cys Asp Ala Arg Cys Gly Cys Ser Asp Cys Asp
                20                  25                  30

Cys Cys Asn Val Gly Arg Trp Gly Cys Pro Leu Ile Cys Ser Arg Asn
        35                  40                  45

Cys Arg Ser Phe Thr Tyr Thr Tyr Glu Trp Tyr Ala Asp Ala Trp
    50                  55                  60

<210> SEQ ID NO 449
<211> LENGTH: 63
<212> TYPE: PRT
<213> ORGANISM: Bos taurus
<220> FEATURE:
<223> OTHER INFORMATION: UL33

<400> SEQUENCE: 449

Cys Thr Thr Val His Gln Lys Thr Asn Lys Lys Glu Ser Cys Pro Asp
1               5                   10                  15

Gly Tyr Thr Met Asn Glu Cys Cys Gly Cys Gly Tyr Gly Cys Cys Arg
                20                  25                  30

Gly Gly Cys Val Cys Ser Ala Tyr Cys Ser Arg Pro Asn Cys Trp Arg
        35                  40                  45

Glu Leu Thr Tyr Thr Tyr Thr Tyr Glu Phe Tyr Val Asp Thr Trp
    50                  55                  60

<210> SEQ ID NO 450
<211> LENGTH: 63
<212> TYPE: PRT
<213> ORGANISM: Bos taurus
<220> FEATURE:
<223> OTHER INFORMATION: UL34

<400> SEQUENCE: 450

Cys Thr Thr Val Tyr Gln Lys Ser Arg Lys Glu Ser Ser Cys Pro Asn
1               5                   10                  15

Gly Trp Ile Tyr Gly Lys Asp Cys Cys Ser Trp Ser Tyr Cys Thr Asp
                20                  25                  30

Cys Asp Cys Cys Leu Cys Gly Asp Leu His Cys Tyr Asp Gly Cys Ser
        35                  40                  45

Ser Phe Gly Val Thr Trp Thr Tyr Glu Phe His Val Asp Ala Trp
    50                  55                  60

<210> SEQ ID NO 451
<211> LENGTH: 62
<212> TYPE: PRT
<213> ORGANISM: Bos taurus
<220> FEATURE:
<223> OTHER INFORMATION: UL35

<400> SEQUENCE: 451

Cys Thr Thr Val Phe Gln Glu Thr Arg Lys Ser Cys Pro Thr Gly Phe
1               5                   10                  15

Tyr Val Asp Gly Ser Thr Cys Gly Cys Ala Thr Tyr Cys Arg Thr Cys
                20                  25                  30

Asp Cys Cys Gly Gly Tyr Arg Cys Ser Gly Gly Ser Cys Ala Cys
        35                  40                  45

Ser Ser Tyr Thr Tyr Asn Tyr Asp Phe His Val Asp Ala Trp
    50                  55                  60

<210> SEQ ID NO 452
```

```
<211> LENGTH: 61
<212> TYPE: PRT
<213> ORGANISM: Bos taurus
<220> FEATURE:
<223> OTHER INFORMATION: UL36

<400> SEQUENCE: 452

Cys Ala Ala Val Phe Gln Glu Thr Arg Thr Asn Cys Pro Ser Gly Tyr
1               5                   10                  15

Gly Asn Ala Phe Ser Cys Gly Cys Pro Ile Ala Cys Arg Asp Cys Asp
            20                  25                  30

Cys Cys Gly Gly Tyr Trp Cys Ser Gly Gly Ala Asp Cys His Cys Val
        35                  40                  45

Ser Tyr Asn Tyr Thr Tyr Ser Trp His Val Asp Ala Trp
    50                  55                  60

<210> SEQ ID NO 453
<211> LENGTH: 62
<212> TYPE: PRT
<213> ORGANISM: Bos taurus
<220> FEATURE:
<223> OTHER INFORMATION: UL37

<400> SEQUENCE: 453

Cys Ala Thr Val Tyr Gln Lys Thr Glu Lys His Cys Pro Leu Phe His
1               5                   10                  15

Ser Ile Cys Cys His Cys Gly Glu Gly Val Gly Cys Ser Gly Gly Asp
            20                  25                  30

Cys Cys Gly Cys Glu Arg Arg Ser Gly Cys Val Val Cys Thr Met Arg
        35                  40                  45

Asn Ser Tyr Thr Tyr Asn Tyr Gln Phe His Val Asp Ala Trp
    50                  55                  60

<210> SEQ ID NO 454
<211> LENGTH: 63
<212> TYPE: PRT
<213> ORGANISM: Bos taurus
<220> FEATURE:
<223> OTHER INFORMATION: UL38

<400> SEQUENCE: 454

Cys Gly Thr Val His Gln Lys Thr Lys Glu Leu Cys Pro Asp Asp Ser
1               5                   10                  15

Thr Tyr Cys Cys Gly Cys Val Ser Gly Cys Ala Cys Thr Tyr Gly
            20                  25                  30

Cys Asp Gly Val Gly Cys Cys Arg Val Ser Leu Trp Thr Thr Tyr Ile
        35                  40                  45

Lys Asp Ile Val Gly Val Ser Tyr Glu Trp His Val Asp Ala Trp
    50                  55                  60

<210> SEQ ID NO 455
<211> LENGTH: 61
<212> TYPE: PRT
<213> ORGANISM: Bos taurus
<220> FEATURE:
<223> OTHER INFORMATION: UL39

<400> SEQUENCE: 455

Cys Ala Ser Val His Gln His Thr Glu Pro Thr Cys Pro Ala Gly Tyr
1               5                   10                  15

Thr Tyr Cys Cys Gly Cys Leu Tyr Lys Cys Asn Cys Gly Asp Cys Gly
            20                  25                  30
```

-continued

```
Cys Tyr Asn Val Gly Cys Gly Ser Gly Trp Leu Gly Lys Ala Cys Gly
            35                  40                  45

Asp Tyr Arg Glu Thr Tyr Glu Trp Tyr Val Asp Ala Trp
            50                  55                  60

<210> SEQ ID NO 456
<211> LENGTH: 61
<212> TYPE: PRT
<213> ORGANISM: Bos taurus
<220> FEATURE:
<223> OTHER INFORMATION: UL40

<400> SEQUENCE: 456

Cys Ala Ser Val His Gln His Thr Glu Pro Thr Cys Pro Ala Gly Tyr
1               5                   10                  15

Thr Tyr Cys Cys Gly Cys Leu Tyr Lys Cys Asn Cys Gly Asp Cys Gly
            20                  25                  30

Cys Tyr Asn Ala Gly Cys Gly Ser Gly Trp Leu Gly Lys Ala Cys Gly
            35                  40                  45

Asp Tyr Arg Glu Thr Tyr Glu Trp Tyr Val Asp Ala Trp
            50                  55                  60

<210> SEQ ID NO 457
<211> LENGTH: 61
<212> TYPE: PRT
<213> ORGANISM: Bos taurus
<220> FEATURE:
<223> OTHER INFORMATION: UL41

<400> SEQUENCE: 457

Cys Thr Thr Val Phe Gln Glu Thr Arg Lys Ser Cys Pro Ser Gly Phe
1               5                   10                  15

Arg Asp Arg Asp Ala Cys Gly Cys Ala Val Thr Cys Arg Asn Cys Asp
            20                  25                  30

Cys Cys Gly Gly Gly Pro Cys Asn Gly Gly Ser Cys Arg Cys Asn
            35                  40                  45

Asn Tyr Ile Tyr Lys Tyr Ser Phe His Val Asp Ala Trp
            50                  55                  60

<210> SEQ ID NO 458
<211> LENGTH: 61
<212> TYPE: PRT
<213> ORGANISM: Bos taurus
<220> FEATURE:
<223> OTHER INFORMATION: UL42

<400> SEQUENCE: 458

Cys Thr Ala Val Phe Gln Glu Thr Arg Lys Asp Cys Pro Ser Gly Tyr
1               5                   10                  15

Gly Ser Ala Phe Thr Cys Gly Cys Leu Ala Ala Cys His Gly Cys Asp
            20                  25                  30

Cys Cys Gly Gly Gly Trp Cys Ser Gly Gly Asp Cys Arg Cys Arg
            35                  40                  45

Ser Tyr Ser Thr Ala Tyr Ser Phe His Ile Asp Ala Trp
            50                  55                  60

<210> SEQ ID NO 459
<211> LENGTH: 61
<212> TYPE: PRT
<213> ORGANISM: Bos taurus
<220> FEATURE:
```

<223> OTHER INFORMATION: UL43

<400> SEQUENCE: 459

Cys Ala Thr Val Phe Gln Glu Thr Arg Lys Ser Cys Pro Ser Gly Tyr
1               5                   10                  15

Ala Asp Arg Phe Thr Cys Asp Cys Val Tyr Tyr Cys Gln Thr Cys Asp
            20                  25                  30

Cys Cys Gly Gly Asn Arg Cys Ser Gly Gly Pro Cys Arg Cys Ser
        35                  40                  45

Ser Tyr Ser Ile Asn Tyr Ser Phe His Val Asp Thr Trp
    50                  55                  60

<210> SEQ ID NO 460
<211> LENGTH: 58
<212> TYPE: PRT
<213> ORGANISM: Bos taurus
<220> FEATURE:
<223> OTHER INFORMATION: UL44

<400> SEQUENCE: 460

Cys Ala Ala Ala His Gln Glu Thr Lys Lys Ser Cys Pro Asp Gly Thr
1               5                   10                  15

Cys Arg Gln Cys Cys Gly Gly Val Cys Arg Cys His Ala Ser Gly Cys
            20                  25                  30

Cys Tyr Trp Cys Thr Thr Gly Cys Val Gly Arg Ala Leu Ser Glu Ser
        35                  40                  45

His Ser Tyr Glu Phe His Val Asp Thr Trp
    50                  55

<210> SEQ ID NO 461
<211> LENGTH: 70
<212> TYPE: PRT
<213> ORGANISM: Bos taurus
<220> FEATURE:
<223> OTHER INFORMATION: UL45

<400> SEQUENCE: 461

Cys Ser Thr Val His Gln Lys Thr Arg Thr Thr Gln Gly Asn Thr Cys
1               5                   10                  15

Pro Asp Gly Tyr Thr Leu Lys Asp Asp Cys Pro Arg Cys Arg Gly Gly
            20                  25                  30

Cys Asp Gly Tyr Asp Cys Cys Trp Gly Asp Ala Cys Arg Ser Ser Gly
        35                  40                  45

Leu Cys Trp Gly His Asn Pro Leu Val Thr Thr Tyr Thr Tyr Glu
    50                  55                  60

Phe Tyr Ile Asp Ala Trp
65                  70

<210> SEQ ID NO 462
<211> LENGTH: 68
<212> TYPE: PRT
<213> ORGANISM: Bos taurus
<220> FEATURE:
<223> OTHER INFORMATION: UL46

<400> SEQUENCE: 462

Cys Val Val Val Tyr Gln Lys Thr Asn Ser Gln Lys Ser Cys Pro Arg
1               5                   10                  15

Gly Tyr Thr Glu Arg Glu Thr Cys Asn Arg Arg Tyr Gly Trp Gly Cys
            20                  25                  30

Gly Arg Tyr Asp Cys Cys Asp Cys Asp Arg Trp Val Ser Gly Asn Cys
            35                  40                  45

Ala Asn Ile Cys Thr Asp Tyr Thr Asp Thr His Thr Tyr Glu Phe His
 50                  55                  60

Ala Asp Ala Trp
 65

<210> SEQ ID NO 463
<211> LENGTH: 64
<212> TYPE: PRT
<213> ORGANISM: Bos taurus
<220> FEATURE:
<223> OTHER INFORMATION: UL47

<400> SEQUENCE: 463

Cys Gly Thr Val Phe Gln Gln Thr His Lys Val Arg Asp Cys Pro Asp
 1               5                  10                  15

Gly Phe Thr Ala Ala Pro Arg Cys Gly Gly Glu Cys Cys Cys Ser Asn
            20                  25                  30

Val Asn Ser Arg Ser Gly Gly Trp Cys Arg Tyr Cys Gly Arg Asp Cys
            35                  40                  45

Thr Ala Pro Thr Glu Thr Ser Thr Tyr Glu Phe His Val Asp Ala Trp
 50                  55                  60

<210> SEQ ID NO 464
<211> LENGTH: 63
<212> TYPE: PRT
<213> ORGANISM: Bos taurus
<220> FEATURE:
<223> OTHER INFORMATION: UL48

<400> SEQUENCE: 464

Cys Thr Ala Val Tyr Gln Arg Thr Gly Gln Lys Cys Pro Glu Gly Cys
 1               5                  10                  15

Glu Ser Arg Asn Thr Cys Leu Tyr Ser Arg Asn Cys Gly Asp Tyr Thr
            20                  25                  30

Cys Cys Gly Gly Ser Arg Ala Ser Gly Ser Gly Ala Cys Gly Trp Asn
            35                  40                  45

Ser Val Asp Cys Lys Asn Lys Tyr Glu His His Val Asp Ala Trp
 50                  55                  60

<210> SEQ ID NO 465
<211> LENGTH: 63
<212> TYPE: PRT
<213> ORGANISM: Bos taurus
<220> FEATURE:
<223> OTHER INFORMATION: UL49

<400> SEQUENCE: 465

Cys Thr Thr Val Tyr Gln Lys Thr Lys Gln Asn Cys Pro Asp Gly Tyr
 1               5                  10                  15

Asp Phe Arg Asp Thr Cys Gly Ser Gln Ser Tyr Cys Ser Gly Tyr Asp
            20                  25                  30

Cys Cys Arg Cys Ser Arg Phe Gly Gly Cys Ser Ile Gly Thr Cys Ile
            35                  40                  45

Ser Tyr Ser Asp Ala Tyr Thr Tyr Glu Trp Tyr Val Asp Ala Trp
 50                  55                  60

<210> SEQ ID NO 466
<211> LENGTH: 63
<212> TYPE: PRT

<213> ORGANISM: Bos taurus
<220> FEATURE:
<223> OTHER INFORMATION: UL50

<400> SEQUENCE: 466

Cys Thr Thr Val His Gln Gln Thr His Glu Lys Arg Ser Cys Pro Glu
1               5                   10                  15

Ser Tyr Ser Tyr Ser Cys Ser Cys Ala Ser Gly Val Val Gly Cys Gly
                20                  25                  30

Pro Asp Asp Cys Cys Cys Thr Tyr Arg Ile Ser Ile Arg Gly Tyr Thr
            35                  40                  45

Cys Ser Ser Leu Ser Asn Ser Tyr Glu Trp Tyr Val Asp Ala Trp
    50                  55                  60

<210> SEQ ID NO 467
<211> LENGTH: 61
<212> TYPE: PRT
<213> ORGANISM: Bos taurus
<220> FEATURE:
<223> OTHER INFORMATION: UL51

<400> SEQUENCE: 467

Cys Thr Ala Val His Gln Gln Thr Lys Arg Lys Ser Gly Cys Pro Asp
1               5                   10                  15

Gly Tyr Ser Asp Glu Ser Cys Ser Tyr Cys Gly Ser Ser Trp Cys Cys
                20                  25                  30

Pro Val Tyr Trp Cys Gly Ser Pro Cys Ser Tyr Arg Cys Leu Arg His
            35                  40                  45

Thr Asp Thr Tyr Ser Tyr Glu His His Val Asp Ala Trp
    50                  55                  60

<210> SEQ ID NO 468
<211> LENGTH: 60
<212> TYPE: PRT
<213> ORGANISM: Bos taurus
<220> FEATURE:
<223> OTHER INFORMATION: UL52

<400> SEQUENCE: 468

Cys Ala Thr Val Tyr Gln Glu Thr Lys Arg Thr Cys Ala Gly Gly His
1               5                   10                  15

Ser Val Glu Cys Asp Ser Pro Tyr Asp Cys Asn Cys Arg Gly Gly Asp
                20                  25                  30

Cys Cys Arg Ser Pro Ile Phe Asn Asp Cys Trp Ala Ala Ser Cys Ser
            35                  40                  45

Ala Thr Lys Thr Tyr Glu Trp His Val Glu Ser Trp
    50                  55                  60

<210> SEQ ID NO 469
<211> LENGTH: 58
<212> TYPE: PRT
<213> ORGANISM: Bos taurus
<220> FEATURE:
<223> OTHER INFORMATION: UL53

<400> SEQUENCE: 469

Cys Ile Thr Val His Gln Glu Thr Gln Lys Ser Cys Pro Asp Asp Tyr
1               5                   10                  15

Thr Tyr Tyr Gly Asp Gly Thr Cys Ala Tyr Val Cys Ser Ile Asp Lys
                20                  25                  30

Cys Cys Cys Gly Arg Thr Trp Leu Ser Ser Gly Cys Leu Pro Cys Arg

-continued

```
                35                  40                  45

Tyr Thr Tyr Asn Leu His Val Asp Ala Trp
    50                  55

<210> SEQ ID NO 470
<211> LENGTH: 58
<212> TYPE: PRT
<213> ORGANISM: Bos taurus
<220> FEATURE:
<223> OTHER INFORMATION: UL54

<400> SEQUENCE: 470

Cys Ile Thr Val His Gln Glu Thr Gln Lys Ser Cys Pro Asp Asp Tyr
1               5                   10                  15

Thr Ser Tyr Gly Asp Ala Thr Cys Ala Tyr Val Cys Ser Thr Asp Glu
            20                  25                  30

Cys Cys Cys Gly Arg Thr Trp Leu Ser Ala Gly Cys Arg Pro Cys Arg
        35                  40                  45

Tyr Thr Tyr Asn Leu His Val Asp Ala Trp
    50                  55

<210> SEQ ID NO 471
<211> LENGTH: 58
<212> TYPE: PRT
<213> ORGANISM: Bos taurus
<220> FEATURE:
<223> OTHER INFORMATION: UL55

<400> SEQUENCE: 471

Cys Ile Thr Val His Gln Glu Thr Gln Lys Ser Cys Phe Asp Asp Tyr
1               5                   10                  15

Thr Tyr Tyr Gly Asp Ala Ser Cys Ala Tyr Val Cys Ser Thr Asp Glu
            20                  25                  30

Cys Cys Cys Gly Arg Thr Trp Leu Ser Ala Gly Cys Arg Pro Cys Arg
        35                  40                  45

Tyr Thr Tyr Asn Leu His Val Asp Ala Trp
    50                  55

<210> SEQ ID NO 472
<211> LENGTH: 58
<212> TYPE: PRT
<213> ORGANISM: Bos taurus
<220> FEATURE:
<223> OTHER INFORMATION: UL56

<400> SEQUENCE: 472

Cys Ile Thr Ala His Gln Glu Thr Gln Lys Ser Cys Ser Asp Asp Tyr
1               5                   10                  15

Thr Tyr Tyr Gly Asp Ala Thr Cys Ala Tyr Val Cys Ser Thr Asp Glu
            20                  25                  30

Cys Cys Cys Gly Arg Thr Trp Leu Ser Ala Gly Cys Arg Pro Cys Arg
        35                  40                  45

Tyr Thr Tyr Asn Leu His Val Asp Ala Trp
    50                  55

<210> SEQ ID NO 473
<211> LENGTH: 58
<212> TYPE: PRT
<213> ORGANISM: Bos taurus
<220> FEATURE:
<223> OTHER INFORMATION: UL57
```

-continued

```
<400> SEQUENCE: 473

Cys Ile Thr Val His Gln Glu Thr Gln Lys Ser Cys Pro Asp Asp Tyr
1               5                   10                  15

Thr Tyr Tyr Gly Asp Gly Thr Cys Ala Tyr Val Cys Ser Ile Asp Asn
            20                  25                  30

Cys Cys Cys Gly Arg Thr Trp Leu Ser Ser Gly Cys Leu Pro Cys Arg
        35                  40                  45

Tyr Thr Tyr Asn Leu His Val Asp Ala Trp
    50                  55

<210> SEQ ID NO 474
<211> LENGTH: 61
<212> TYPE: PRT
<213> ORGANISM: Bos taurus
<220> FEATURE:
<223> OTHER INFORMATION: UL58

<400> SEQUENCE: 474

Cys Val Thr Val His Gln Gln Thr His Ala Thr Arg Arg Cys Pro Asp
1               5                   10                  15

Gly Tyr Gly Asp Ser Tyr Ala Cys Lys Ser Asn Tyr Gly Cys Ser Ala
            20                  25                  30

Glu Gly Cys Cys Arg Trp Gly Pro Gly Ser Gly Ala Cys Thr Gly Ala
        35                  40                  45

Ile Tyr Thr Ser Pro Tyr Glu Trp Tyr Val Asp Ala Trp
    50                  55                  60

<210> SEQ ID NO 475
<211> LENGTH: 60
<212> TYPE: PRT
<213> ORGANISM: Bos taurus
<220> FEATURE:
<223> OTHER INFORMATION: UL59

<400> SEQUENCE: 475

Cys Ala Ala Val His Gln Arg Thr Glu Gly Gln Gln Ser Cys Pro Asp
1               5                   10                  15

Gly Tyr Leu Glu Thr Arg Val Cys Pro Tyr Arg Met Tyr Arg Cys Ile
            20                  25                  30

Gly Trp Asp Cys Cys Arg Cys Ser Asp Gly Ser Arg Asp Asn Tyr Ile
        35                  40                  45

Met Thr Tyr Ser Tyr Glu Phe His Val Asp Val Trp
    50                  55                  60

<210> SEQ ID NO 476
<211> LENGTH: 59
<212> TYPE: PRT
<213> ORGANISM: Bos taurus
<220> FEATURE:
<223> OTHER INFORMATION: UL60

<400> SEQUENCE: 476

Cys Thr Thr Val Tyr Gln Glu Thr Lys Thr Lys Ser Gly Cys Pro Asp
1               5                   10                  15

Gly Tyr Ser Cys Cys Tyr Asn Gly Arg Ser Arg Ser Cys Arg Pro Asn
            20                  25                  30

Asp Cys Ser Thr Tyr Gly Glu Val Arg Ser Leu Ser Arg Ser Cys Tyr
        35                  40                  45

Thr Tyr Asn Tyr Glu Phe Tyr Val Asp Ala Trp
    50                  55
```

<210> SEQ ID NO 477
<211> LENGTH: 58
<212> TYPE: PRT
<213> ORGANISM: Bos taurus
<220> FEATURE:
<223> OTHER INFORMATION: UL61

<400> SEQUENCE: 477

Cys Gly Thr Val Tyr Gln His Thr Lys Glu Ile Lys Thr Cys Pro Asp
1               5                   10                  15

Gly Tyr Ser Asp Val Phe Thr Tyr Cys Pro Val Thr Cys Pro Gly Trp
            20                  25                  30

Asp Cys Cys Arg Arg Asn Asp Cys Gly Arg Thr Arg Tyr Thr Val Ala
        35                  40                  45

Tyr Ser Tyr Ala Leu His Val Asp Val Trp
    50                  55

<210> SEQ ID NO 478
<211> LENGTH: 57
<212> TYPE: PRT
<213> ORGANISM: Bos taurus
<220> FEATURE:
<223> OTHER INFORMATION: UL62

<400> SEQUENCE: 478

Cys Thr Thr Val Leu Gln Glu Thr His Gln Gln Arg Gly Cys Pro Ala
1               5                   10                  15

Gly Tyr Gln Val Val Asp Gly Cys Pro Tyr Gly Asp Cys Cys Arg Thr
            20                  25                  30

Ser Tyr Val Cys Gly Pro Leu Thr Cys Thr Ser Asn Thr Ala Thr Arg
        35                  40                  45

Asn Tyr Gln Trp Tyr Val Asp Ala Trp
    50                  55

<210> SEQ ID NO 479
<211> LENGTH: 56
<212> TYPE: PRT
<213> ORGANISM: Bos taurus
<220> FEATURE:
<223> OTHER INFORMATION: UL63

<400> SEQUENCE: 479

Cys Ser Thr Val Tyr Gln Lys Thr Glu Lys Cys Pro Asp Gly Tyr
1               5                   10                  15

Thr Asp Arg Arg Asp Glu Cys Pro Asn Thr Cys Lys Asn Phe Asp Cys
            20                  25                  30

Glu Asn Glu Gly Gly Leu Arg Cys Leu Cys Ser Ala Tyr Ile Ser Ala
        35                  40                  45

Tyr Glu Phe His Val Asp Ala Trp
    50                  55

<210> SEQ ID NO 480
<211> LENGTH: 55
<212> TYPE: PRT
<213> ORGANISM: Bos taurus
<220> FEATURE:
<223> OTHER INFORMATION: UL64

<400> SEQUENCE: 480

Cys Thr Thr Thr His Gln Arg Thr Gln Lys Ser Cys Pro Asp Tyr Ala
1               5                   10                  15

Ser Tyr Asp Cys Gly Ser Pro Asp Glu Glu Cys Ser Ser Cys Arg
            20                  25                  30

Ser Cys Thr Arg Trp Cys Ala Pro Thr Ala Pro Tyr Ile Tyr Thr Tyr
            35                  40                  45

Gln Phe Tyr Ile Asp Ala Trp
        50                  55

<210> SEQ ID NO 481
<211> LENGTH: 54
<212> TYPE: PRT
<213> ORGANISM: Bos taurus
<220> FEATURE:
<223> OTHER INFORMATION: UL65

<400> SEQUENCE: 481

Cys Thr Thr Val His Gln Gln Thr Asn Lys Arg Cys Pro Thr Gly Tyr
1               5                   10                  15

Asn Ser Gly Thr Leu Cys Asn Met Ile Gly Cys Ser Gly Asp Glu Cys
            20                  25                  30

Cys Asn Tyr Gly Arg Val Glu Cys Thr Ser Tyr Val Trp Thr His Asn
        35                  40                  45

Phe Tyr Val Asp Ala Trp
    50

<210> SEQ ID NO 482
<211> LENGTH: 53
<212> TYPE: PRT
<213> ORGANISM: Bos taurus
<220> FEATURE:
<223> OTHER INFORMATION: UL66

<400> SEQUENCE: 482

Cys Thr Thr Val His Gln Glu Thr Gln Arg Thr Ser Cys Pro Ser Gly
1               5                   10                  15

Trp Thr Tyr Thr Cys Asn Cys Arg Asn Gly Cys Gly Cys Tyr Arg Pro
            20                  25                  30

Ser Gln Leu Cys Gly Ala Tyr Val Ala Val Thr His Thr Tyr Glu Phe
        35                  40                  45

His Val Asp Ala Trp
    50

<210> SEQ ID NO 483
<211> LENGTH: 53
<212> TYPE: PRT
<213> ORGANISM: Bos taurus
<220> FEATURE:
<223> OTHER INFORMATION: UL67

<400> SEQUENCE: 483

Cys Ala Thr Val His Gln Lys Asp Lys His Cys Pro Ala Gly Tyr Arg
1               5                   10                  15

Ser Gly Thr Leu Cys Arg Met Ile Gly Cys Thr Gly Asp Asp Cys Cys
            20                  25                  30

Asn Tyr Asp Arg Val Glu Cys Thr Asn Tyr Asp Tyr Thr Asn Asn Phe
        35                  40                  45

Tyr Val Asp Ala Trp
    50

<210> SEQ ID NO 484
<211> LENGTH: 52

```
<212> TYPE: PRT
<213> ORGANISM: Bos taurus
<220> FEATURE:
<223> OTHER INFORMATION: UL68

<400> SEQUENCE: 484

Cys Thr Ala Val His Gln Gln Thr Thr Glu Lys Gly Lys Thr Cys Pro
1               5                   10                  15

Pro Arg Ser Arg Asp Met Gly Thr Arg Cys Arg Asp Asp Arg Tyr Tyr
            20                  25                  30

Pro Trp Arg Tyr Ser Asp Tyr Thr Tyr Thr Tyr Thr Tyr Glu Trp His
        35                  40                  45

Val Asp Ala Trp
    50

<210> SEQ ID NO 485
<211> LENGTH: 51
<212> TYPE: PRT
<213> ORGANISM: Bos taurus
<220> FEATURE:
<223> OTHER INFORMATION: UL69

<400> SEQUENCE: 485

Cys Thr Ser Val His Gln Lys Thr Asp Val Thr Cys Pro Ser Gly Ala
1               5                   10                  15

Thr Tyr Arg Cys Asp Cys Gly Arg Gly Cys Gly Cys Tyr Asp Pro
            20                  25                  30

Trp Cys Ser Thr Thr Tyr Arg Gly Thr Tyr Thr Tyr Asp Phe His Val
        35                  40                  45

Glu Thr Trp
    50

<210> SEQ ID NO 486
<211> LENGTH: 50
<212> TYPE: PRT
<213> ORGANISM: Bos taurus
<220> FEATURE:
<223> OTHER INFORMATION: UL70

<400> SEQUENCE: 486

Cys Gly Thr Val His Gln Glu Thr His Thr Gln Arg Thr Cys Pro Asp
1               5                   10                  15

Ala Cys Asp Val Thr Gly Asp Asn Cys Lys Val Arg Arg Asn Gly Asp
            20                  25                  30

Trp Cys Gly Arg Ala Ser Lys Thr Asp Thr Tyr Asp Phe Tyr Val Asp
        35                  40                  45

Ala Trp
    50

<210> SEQ ID NO 487
<211> LENGTH: 49
<212> TYPE: PRT
<213> ORGANISM: Bos taurus
<220> FEATURE:
<223> OTHER INFORMATION: UL71

<400> SEQUENCE: 487

Cys Thr Thr Asp Tyr Gln Lys Thr Glu Lys Ser Cys Pro Glu Asn Tyr
1               5                   10                  15

Tyr Ala Glu Thr Gly Tyr Cys Met Cys Gly Ser Trp Arg Cys Gly Tyr
            20                  25                  30
```

-continued

Gly Ser Thr Thr Ser Leu Ile Val Ser Tyr Lys Trp Tyr Val Asp Ala
            35                  40                  45

Trp

<210> SEQ ID NO 488
<211> LENGTH: 49
<212> TYPE: PRT
<213> ORGANISM: Bos taurus
<220> FEATURE:
<223> OTHER INFORMATION: UL72

<400> SEQUENCE: 488

Cys Thr Thr Val His Gln Lys Thr Asn Gln Lys Trp Gly Cys Pro Asp
1               5                   10                  15

Gly Tyr Val His Met Ser Gly Ser Cys Cys Arg Gly Ser Ile Cys Thr
            20                  25                  30

Asn Gly Leu Phe Arg Asn Thr Tyr Thr Tyr Glu Phe Asn Val Glu Ala
            35                  40                  45

Trp

<210> SEQ ID NO 489
<211> LENGTH: 48
<212> TYPE: PRT
<213> ORGANISM: Bos taurus
<220> FEATURE:
<223> OTHER INFORMATION: UL73

<400> SEQUENCE: 489

Cys Thr Thr Val Tyr Gln Glu Thr Arg Thr Asn Cys Pro Asp Gly Tyr
1               5                   10                  15

Asn Tyr Arg Ser Gly Asp Cys Arg Arg Trp Asn His Trp Leu Gly Glu
            20                  25                  30

Gln Arg Val Ser Pro Thr Tyr Asn Tyr Glu Trp Tyr Val Asp Ser Trp
            35                  40                  45

<210> SEQ ID NO 490
<211> LENGTH: 47
<212> TYPE: PRT
<213> ORGANISM: Bos taurus
<220> FEATURE:
<223> OTHER INFORMATION: UL74

<400> SEQUENCE: 490

Cys Thr Thr Val Tyr Gln Lys Thr Thr Thr Thr Lys Ser Cys Pro Gly
1               5                   10                  15

Gly Phe Asp Asn Gly Arg Arg Cys Ile Met Gly Leu Gly Asp Leu Arg
            20                  25                  30

Asp Tyr Thr Tyr Phe Asn Lys Tyr Glu Trp Tyr Val Glu Thr Trp
            35                  40                  45

<210> SEQ ID NO 491
<211> LENGTH: 46
<212> TYPE: PRT
<213> ORGANISM: Bos taurus
<220> FEATURE:
<223> OTHER INFORMATION: UL75

<400> SEQUENCE: 491

Cys Ser Thr Val His Gln Lys Thr Glu Gln Arg Cys Leu Asp Gly Tyr
1               5                   10                  15

Asp Asp Arg Gly Ala Tyr Cys Tyr Asp Ser Val Arg Gly Leu Met Ser
            20                  25                  30

-continued

```
Trp Thr Tyr Lys Tyr Val Tyr Glu Trp Arg Val Asp Thr Trp
        35                  40                  45

<210> SEQ ID NO 492
<211> LENGTH: 45
<212> TYPE: PRT
<213> ORGANISM: Bos taurus
<220> FEATURE:
<223> OTHER INFORMATION: UL76

<400> SEQUENCE: 492

Cys Thr Asn Val His Gln Met Thr Ile Lys Thr Cys Pro Asp Gly Gly
1               5                   10                  15

Ser Tyr Gly Trp Tyr Trp Pro Tyr Gly Tyr Gly Cys Asn Gly Gly Val
            20                  25                  30

Ser Ala Thr Tyr Thr Tyr Glu Phe Tyr Val Asp Ala Trp
        35                  40                  45

<210> SEQ ID NO 493
<211> LENGTH: 44
<212> TYPE: PRT
<213> ORGANISM: Bos taurus
<220> FEATURE:
<223> OTHER INFORMATION: UL77

<400> SEQUENCE: 493

Cys Thr Thr Val Tyr Gln Lys Thr Glu Ser Val Arg Ser Cys Pro Asp
1               5                   10                  15

Gly Ser Met Asp Gly Trp Arg Cys Arg Leu Gly Thr Met Asn Trp Ile
            20                  25                  30

Tyr Ser Asn Thr Tyr Glu Phe Tyr Val Asp Ala Trp
        35                  40

<210> SEQ ID NO 494
<211> LENGTH: 59
<212> TYPE: PRT
<213> ORGANISM: Artificial Sequence
<220> FEATURE:
<223> OTHER INFORMATION: Description of Artificial Sequence: Synthetic
      ultralong CDR3 consensus motif polypeptide
<220> FEATURE:
<221> NAME/KEY: MOD_RES
<222> LOCATION: (1)..(1)
<223> OTHER INFORMATION: Thr, Gly, Ala, Ser or Val
<220> FEATURE:
<221> NAME/KEY: MOD_RES
<222> LOCATION: (2)..(2)
<223> OTHER INFORMATION: Ser, Thr, Pro, Ile, Ala, Val or Asn
<220> FEATURE:
<221> NAME/KEY: MOD_RES
<222> LOCATION: (3)..(3)
<223> OTHER INFORMATION: Val, Ala, Thr or Asp
<220> FEATURE:
<221> NAME/KEY: MOD_RES
<222> LOCATION: (4)..(4)
<223> OTHER INFORMATION: His, Thr, Arg, Tyr, Phe or Leu
<220> FEATURE:
<221> NAME/KEY: MOD_RES
<222> LOCATION: (6)..(59)
<223> OTHER INFORMATION: Any amino acid and this region may encompass
      27-54 residues

<400> SEQUENCE: 494

Xaa Xaa Xaa Xaa Gln Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30
```

```
Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa
        50                  55

<210> SEQ ID NO 495
<211> LENGTH: 5
<212> TYPE: PRT
<213> ORGANISM: Artificial Sequence
<220> FEATURE:
<223> OTHER INFORMATION: Description of Artificial Sequence: Synthetic
      ultralong CDR3 consensus motif peptide
<220> FEATURE:
<221> NAME/KEY: MOD_RES
<222> LOCATION: (1)..(1)
<223> OTHER INFORMATION: Thr, Gly, Ala, Ser or Val
<220> FEATURE:
<221> NAME/KEY: MOD_RES
<222> LOCATION: (2)..(2)
<223> OTHER INFORMATION: Ser, Thr, Pro, Ile, Ala, Val or Asn
<220> FEATURE:
<221> NAME/KEY: MOD_RES
<222> LOCATION: (3)..(3)
<223> OTHER INFORMATION: Val, Ala, Thr or Asp
<220> FEATURE:
<221> NAME/KEY: MOD_RES
<222> LOCATION: (4)..(4)
<223> OTHER INFORMATION: His, Thr, Arg, Tyr, Phe or Leu

<400> SEQUENCE: 495

Xaa Xaa Xaa Xaa Gln
1               5

<210> SEQ ID NO 496
<211> LENGTH: 8
<212> TYPE: PRT
<213> ORGANISM: Artificial Sequence
<220> FEATURE:
<223> OTHER INFORMATION: Description of Artificial Sequence: Synthetic
      ultralong CDR3 consensus motif peptide
<220> FEATURE:
<221> NAME/KEY: MOD_RES
<222> LOCATION: (1)..(1)
<223> OTHER INFORMATION: Tyr, Phe, Trp or His
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Tyr, Phe, Trp or His
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Tyr, Phe, Trp or His
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Tyr, Phe, Trp or His
<220> FEATURE:
<221> NAME/KEY: MOD_RES
<222> LOCATION: (8)..(8)
<223> OTHER INFORMATION: Any amino acid
<220> FEATURE:
<221> NAME/KEY: misc_feature
```

```
<222> LOCATION: (1)..(8)
<223> OTHER INFORMATION: This sequence may encompass 1-4 "Xaa Xaa"
      repeating units

<400> SEQUENCE: 496

Xaa Xaa Xaa Xaa Xaa Xaa Xaa Xaa
1               5

<210> SEQ ID NO 497
<211> LENGTH: 67
<212> TYPE: PRT
<213> ORGANISM: Artificial Sequence
<220> FEATURE:
<223> OTHER INFORMATION: Description of Artificial Sequence: Synthetic
      ultralong CDR3 consensus motif polypeptide
<220> FEATURE:
<221> NAME/KEY: MOD_RES
<222> LOCATION: (1)..(1)
<223> OTHER INFORMATION: Thr, Gly, Ala, Ser or Val
<220> FEATURE:
<221> NAME/KEY: MOD_RES
<222> LOCATION: (2)..(2)
<223> OTHER INFORMATION: Ser, Thr, Pro, Ile, Ala, Val or Asn
<220> FEATURE:
<221> NAME/KEY: MOD_RES
<222> LOCATION: (3)..(3)
<223> OTHER INFORMATION: Val, Ala, Thr or Asp
<220> FEATURE:
<221> NAME/KEY: MOD_RES
<222> LOCATION: (4)..(4)
<223> OTHER INFORMATION: His, Thr, Arg, Tyr, Phe or Leu
<220> FEATURE:
<221> NAME/KEY: MOD_RES
<222> LOCATION: (6)..(59)
<223> OTHER INFORMATION: Any amino acid and this region may encompass
      27-54 residues
<220> FEATURE:
<221> NAME/KEY: MOD_RES
<222> LOCATION: (60)..(60)
<223> OTHER INFORMATION: Tyr, Phe, Trp or His
<220> FEATURE:
<221> NAME/KEY: MOD_RES
<222> LOCATION: (61)..(61)
<223> OTHER INFORMATION: Any amino acid
<220> FEATURE:
<221> NAME/KEY: MOD_RES
<222> LOCATION: (62)..(62)
<223> OTHER INFORMATION: Tyr, Phe, Trp or His
<220> FEATURE:
<221> NAME/KEY: MOD_RES
<222> LOCATION: (63)..(63)
<223> OTHER INFORMATION: Any amino acid
<220> FEATURE:
<221> NAME/KEY: MOD_RES
<222> LOCATION: (64)..(64)
<223> OTHER INFORMATION: Tyr, Phe, Trp or His
<220> FEATURE:
<221> NAME/KEY: MOD_RES
<222> LOCATION: (65)..(65)
<223> OTHER INFORMATION: Any amino acid
<220> FEATURE:
<221> NAME/KEY: MOD_RES
<222> LOCATION: (66)..(66)
<223> OTHER INFORMATION: Tyr, Phe, Trp or His
<220> FEATURE:
<221> NAME/KEY: MOD_RES
<222> LOCATION: (67)..(67)
<223> OTHER INFORMATION: Any amino acid
<220> FEATURE:
<221> NAME/KEY: misc_feature
<222> LOCATION: (60)..(67)
<223> OTHER INFORMATION: This region may encompass 1-4 "Xaa Xaa"
      repeating units

<400> SEQUENCE: 497

Xaa Xaa Xaa Xaa Gln Xaa Xaa Xaa Xaa Xaa Xaa Xaa Xaa Xaa Xaa Xaa
```

-continued

```
                1               5                  10                  15
Xaa Xaa Xaa Xaa Xaa Xaa Xaa Xaa Xaa Xaa Xaa Xaa Xaa Xaa Xaa
            20                  25                  30
Xaa Xaa Xaa Xaa Xaa Xaa Xaa Xaa Xaa Xaa Xaa Xaa Xaa Xaa Xaa
            35                  40                  45
Xaa Xaa Xaa Xaa Xaa Xaa Xaa Xaa Xaa Xaa Xaa Xaa Xaa Xaa Xaa
            50                  55                  60
Xaa Xaa Xaa
65

<210> SEQ ID NO 498
<211> LENGTH: 8
<212> TYPE: PRT
<213> ORGANISM: Artificial Sequence
<220> FEATURE:
<223> OTHER INFORMATION: Description of Artificial Sequence: Synthetic
      ultralong CDR3 consensus motif peptide
<220> FEATURE:
<221> NAME/KEY: MOD_RES
<222> LOCATION: (2)..(2)
<223> OTHER INFORMATION: Glu or Asp
<220> FEATURE:
<221> NAME/KEY: MOD_RES
<222> LOCATION: (3)..(3)
<223> OTHER INFORMATION: His, Trp, Asn, Phe, Ile or Tyr
<220> FEATURE:
<221> NAME/KEY: MOD_RES
<222> LOCATION: (4)..(7)
<223> OTHER INFORMATION: Any amino acid and this region may encompass
      1-4 residues

<400> SEQUENCE: 498

Tyr Xaa Xaa Xaa Xaa Xaa Xaa Trp
1               5

<210> SEQ ID NO 499
<211> LENGTH: 25
<212> TYPE: PRT
<213> ORGANISM: Artificial Sequence
<220> FEATURE:
<223> OTHER INFORMATION: Description of Artificial Sequence: Synthetic
      linker peptide
<220> FEATURE:
<221> NAME/KEY: misc_feature
<222> LOCATION: (1)..(25)
<223> OTHER INFORMATION: This sequence may encompass 1-5 "Gly Gly Gly
      Gly Ser" repeating units

<400> SEQUENCE: 499

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 500
<211> LENGTH: 4
<212> TYPE: PRT
<213> ORGANISM: Bos taurus
<220> FEATURE:
<223> OTHER INFORMATION: Stalk motif

<400> SEQUENCE: 500

Cys Pro Asp Gly
1

<210> SEQ ID NO 501
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 501

Gly Gly Gly Gly Ser
1               5

<210> SEQ ID NO 502
<211> LENGTH: 6
<212> TYPE: PRT
<213> ORGANISM: Bos taurus
<220> FEATURE:
<223> OTHER INFORMATION: Stalk motif
<220> FEATURE:
<221> NAME/KEY: MOD_RES
<222> LOCATION: (3)..(3)
<223> OTHER INFORMATION: Thr or Ser

<400> SEQUENCE: 502

Cys Thr Xaa Val His Gln
1               5

<210> SEQ ID NO 503
<211> LENGTH: 14
<212> TYPE: PRT
<213> ORGANISM: Bos taurus
<220> FEATURE:
<223> OTHER INFORMATION: Stalk motif
<220> FEATURE:
<221> NAME/KEY: MOD_RES
<222> LOCATION: (3)..(3)
<223> OTHER INFORMATION: Thr or Ser
<220> FEATURE:
<221> NAME/KEY: MOD_RES
<222> LOCATION: (7)..(14)
<223> OTHER INFORMATION: Any amino acid and this region may encompass
      1-8, 1-7, 1-6, 1-5, 1-4, or 1-3 residues

<400> SEQUENCE: 503

Cys Thr Xaa Val His Gln Xaa Xaa Xaa Xaa Xaa Xaa Xaa Xaa
1               5                   10

<210> SEQ ID NO 504
<211> LENGTH: 3
<212> TYPE: PRT
<213> ORGANISM: Bos taurus
<220> FEATURE:
<223> OTHER INFORMATION: Stalk motif
<220> FEATURE:
<221> NAME/KEY: MOD_RES
<222> LOCATION: (2)..(2)
<223> OTHER INFORMATION: Glu or Asp
<220> FEATURE:
<221> NAME/KEY: MOD_RES
<222> LOCATION: (3)..(3)
<223> OTHER INFORMATION: His, Trp, Asn, Phe, Ile or Tyr

<400> SEQUENCE: 504

Tyr Xaa Xaa
1

<210> SEQ ID NO 505
<211> LENGTH: 3
<212> TYPE: PRT
<213> ORGANISM: Bos taurus
<220> FEATURE:
<223> OTHER INFORMATION: Stalk motif
<220> FEATURE:
```

```
<221> NAME/KEY: MOD_RES
<222> LOCATION: (1)..(1)
<223> OTHER INFORMATION: Thr, Ser, Asn or Ile
<220> FEATURE:
<221> NAME/KEY: MOD_RES
<222> LOCATION: (3)..(3)
<223> OTHER INFORMATION: Glu or Asp

<400> SEQUENCE: 505

Xaa Tyr Xaa
1

<210> SEQ ID NO 506
<211> LENGTH: 8
<212> TYPE: PRT
<213> ORGANISM: Bos taurus
<220> FEATURE:
<223> OTHER INFORMATION: Stalk motif
<220> FEATURE:
<221> NAME/KEY: MOD_RES
<222> LOCATION: (2)..(2)
<223> OTHER INFORMATION: Glu or Asp
<220> FEATURE:
<221> NAME/KEY: MOD_RES
<222> LOCATION: (3)..(3)
<223> OTHER INFORMATION: His, Trp, Asn, Phe, Ile or Tyr
<220> FEATURE:
<221> NAME/KEY: MOD_RES
<222> LOCATION: (4)..(4)
<223> OTHER INFORMATION: Tyr, His, Gly or Asn
<220> FEATURE:
<221> NAME/KEY: MOD_RES
<222> LOCATION: (5)..(5)
<223> OTHER INFORMATION: Val, Ile or Ala
<220> FEATURE:
<221> NAME/KEY: MOD_RES
<222> LOCATION: (6)..(6)
<223> OTHER INFORMATION: Asp, Asn, Thr or Glu
<220> FEATURE:
<221> NAME/KEY: MOD_RES
<222> LOCATION: (7)..(7)
<223> OTHER INFORMATION: Ala, Val, Ser or Thr

<400> SEQUENCE: 506

Tyr Xaa Xaa Xaa Xaa Xaa Xaa Trp
1               5

<210> SEQ ID NO 507
<211> LENGTH: 4
<212> TYPE: PRT
<213> ORGANISM: Bos taurus
<220> FEATURE:
<223> OTHER INFORMATION: knob domain
<220> FEATURE:
<221> NAME/KEY: MOD_RES
<222> LOCATION: (2)..(2)
<223> OTHER INFORMATION: Pro or Ser

<400> SEQUENCE: 507

Cys Xaa Asp Gly
1

<210> SEQ ID NO 508
<211> LENGTH: 5
<212> TYPE: PRT
<213> ORGANISM: Bos taurus
<220> FEATURE:
<223> OTHER INFORMATION: Stalk motif
<220> FEATURE:
<221> NAME/KEY: MOD_RES
<222> LOCATION: (2)..(2)
<223> OTHER INFORMATION: Ser or Thr
```

```
<400> SEQUENCE: 508

Thr Xaa Val His Gln
1               5

<210> SEQ ID NO 509
<211> LENGTH: 5
<212> TYPE: PRT
<213> ORGANISM: Artificial Sequence
<220> FEATURE:
<223> OTHER INFORMATION: Description of Artificial Sequence: Synthetic
      linker peptide
<220> FEATURE:
<221> NAME/KEY: misc_feature
<222> LOCATION: (1)..(5)
<223> OTHER INFORMATION: This sequence may encompass 0-1 "Gly Gly Gly
      Gly Ser" repeating units

<400> SEQUENCE: 509

Gly Gly Gly Gly Ser
1               5

<210> SEQ ID NO 510
<211> LENGTH: 4
<212> TYPE: PRT
<213> ORGANISM: Unknown
<220> FEATURE:
<223> OTHER INFORMATION: Description of Unknown: Cleavage site peptide

<400> SEQUENCE: 510

Ile Glu Gly Arg
1

<210> SEQ ID NO 511
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 511

His His His His His His
1               5
```